US011549146B2

(12) United States Patent
Mcgovern et al.

(10) Patent No.: US 11,549,146 B2
(45) Date of Patent: Jan. 10, 2023

(54) DIAGNOSIS OF INFLAMMATORY BOWEL DISEASE BASED ON GENES

(71) Applicant: CEDARS-SINAI MEDICAL CENTER, Los Angeles, CA (US)

(72) Inventors: Dermot P. Mcgovern, Los Angeles, CA (US); Dalin Li, Walnut, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 224 days.

(21) Appl. No.: 16/303,033

(22) PCT Filed: May 19, 2017

(86) PCT No.: PCT/US2017/033625

§ 371 (c)(1),
(2) Date: Nov. 19, 2018

(87) PCT Pub. No.: WO2017/201461

PCT Pub. Date: Nov. 23, 2017

(65) Prior Publication Data

US 2019/0194754 A1 Jun. 27, 2019

Related U.S. Application Data

(60) Provisional application No. 62/339,357, filed on May 20, 2016.

(51) Int. Cl.

| | |
|---|---|
| ***C12Q 1/68*** | (2018.01) |
| ***C12Q 1/6883*** | (2018.01) |
| ***G16B 20/20*** | (2019.01) |
| ***C12Q 1/6816*** | (2018.01) |

(52) U.S. Cl.

CPC ......... *C12Q 1/6883* (2013.01); *C12Q 1/6816* (2013.01); *G16B 20/20* (2019.02); *C12Q 2600/118* (2013.01); *C12Q 2600/156* (2013.01); *C12Q 2600/172* (2013.01)

(58) Field of Classification Search

None

See application file for complete search history.

(56) References Cited

U.S. PATENT DOCUMENTS

| | | | |
|---|---|---|---|
| 4,443,421 | A | 4/1984 | Hollifield et al. |
| 4,707,260 | A | 11/1987 | Nagayama et al. |
| 5,000,850 | A | 3/1991 | Berry |
| 7,708,996 | B2 | 5/2010 | Yu et al. |
| 8,017,122 | B2 | 9/2011 | Siadak et al. |
| 8,263,743 | B2 | 9/2012 | Smith et al. |
| 2006/0134663 | A1 | 6/2006 | Harkin et al. |
| 2009/0018031 | A1 | 1/2009 | Trinklein et al. |
| 2009/0317388 | A1 | 12/2009 | Burkly et al. |
| 2010/0240043 | A1 | 9/2010 | Rotter et al. |
| 2011/0045476 | A1 | 2/2011 | Barken et al. |
| 2011/0217310 | A1 | 9/2011 | Siegel et al. |
| 2012/0079611 | A1 | 3/2012 | Shih et al. |
| 2012/0208900 | A1 | 8/2012 | Dubinsky et al. |
| 2012/0315282 | A1 | 12/2012 | Bedinger et al. |
| 2013/0136720 | A1 | 5/2013 | Mcgovern et al. |
| 2014/0141983 | A1 | 5/2014 | Singh et al. |
| 2015/0008194 | A1 | 1/2015 | Davis et al. |
| 2015/0376707 | A1 | 12/2015 | Targan et al. |
| 2018/0030412 | A1 | 2/2018 | Walsh et al. |
| 2018/0110855 | A1 | 4/2018 | Bilsborough et al. |

FOREIGN PATENT DOCUMENTS

| | | | |
|---|---|---|---|
| CN | 104204230 | A | 12/2014 |
| CN | 104805198 | A | 7/2015 |
| JP | 2010088432 | A | 4/2010 |
| JP | 2015502740 | A | 1/2015 |
| WO | WO-0006768 | A1 | 2/2000 |
| WO | WO-2006048291 | A2 | 5/2006 |
| WO | WO-2008106451 | A2 | 9/2008 |
| WO | WO-2008106579 | A2 | 9/2008 |
| WO | WO-2010025340 | A2 | 3/2010 |
| WO | WO-2010062960 | A2 | 6/2010 |
| WO | WO-2010075579 | A2 | 7/2010 |
| WO | WO-2011088380 | A1 | 7/2011 |
| WO | WO-2012065143 | A1 | 5/2012 |
| WO | WO-2012156515 | A1 | 11/2012 |
| WO | WO-2013059732 | A1 | 4/2013 |
| WO | WO-2014186750 | A2 | 11/2014 |
| WO | WO-2015054529 | A1 | 4/2015 |
| WO | WO-2015138774 | A1 | 9/2015 |
| WO | WO-2016170348 | A2 | 10/2016 |
| WO | WO-2017147468 | A1 | 8/2017 |
| WO | WO-2017201461 | A1 | 11/2017 |

(Continued)

OTHER PUBLICATIONS

Barrett et al., Constitutive TL1A Expression under Colitogenic Condition Modulates the Severity and Location of Gut Mucosal Inflammation and Induces Fibrostenosis, American Journal of Pathology, 2012, vol. 180(2), pp. 636-649.

European Patent Application No. 17800279.6 Partial Supplemental Search Report dated Oct. 31, 2019.

European Patent Application No. 17800279.6 Extended European Search Report dated Feb. 4, 2020.

Fitzpatrick, LR, Novel Pharmacological Approaches for Inflammatory Bowel Disease: Targeting Key Intracellular Pathways and the IL-23/IL-17 Axis, International Journal of Inflammation, vol. 2012, pp. 1-8.

Koga et al., Transanal Delivery of Angiotensin Converting Enzyme Inhibitor Prevents Colonic Fibrosis in a Mouse Colitis Model: Development of a Unique Mode of Treatment, Surgery, 144(2):259-268, 2008.

(Continued)

*Primary Examiner* — Jehanne S Sitton

(74) *Attorney, Agent, or Firm* — Wilson Sonsini Goodrich & Rosati

(57) ABSTRACT

The present invention describes a method of prognosing high or low probability of developing an inflammatory bowel disease (IBD) in a subject and a method of diagnosing an inflammatory bowel disease (IBD) in a subject. The invention further provides for a method of identifying genes/genetic loci associated with a disease condition, such as IBD, CD and/or UC.

13 Claims, 27 Drawing Sheets

Specification includes a Sequence Listing.

(56) References Cited

FOREIGN PATENT DOCUMENTS

| | | | |
|---|---|---|---|
| WO | WO-2018204764 | A1 | 11/2018 |
| WO | WO-2020121618 | A1 | 6/2020 |

OTHER PUBLICATIONS

Takedatsu et al.: TL1A (TNFSF15) Regulates the Development of Chronic Colitis By Modulating both T helper (TH) 1 and TH17 Activation; Gastroenterology; HHS Public Access; 135(2): 552-567 (2008).

Parente et al., Bowel Ultrasound in Assessment of Crohn's Disease and Detection of Related Small Bowel Strictures: A Prospective Comparative Study Versus X Ray and Intraoperative Findings, Gut, 50: 490-495, 2002.

PCT/US2009/069541 International Search Report dated Mar. 4, 2010.

Pinchuk et al., Human Colonic Myofibroblast Promote Expansion of CD4+ CD25high Foxp3+ Regulatory T Cells, Gastroenterology, 140(7):2019-2030, pp. 1-19, and p. 8, 2011.

Shih et at, Constitutive TL1A (TNFSF15) Expression on Lymphoid or Myeloid Cells Leads to Mild Intestinal Inflammation and Fibrosis, PLOS One, 6(1), pp. 1-16, 2011.

Spinelli et al., Intestinal Fibrosis in Crohn's Disease: Medical Treatment or Surgery?, Current Drug Targets, 11(2):242-248, 2010.

Strober et at, Proinflammatoly Cytokines in Pathogenesis of Inflammatory Bowel Diseases, Gastroenterology, 140(6):1756-1767, 2011.

Prometheus Biosciences, Inc. Form S-1 Registration Statement as filed with the Securities and Exchange Commission on Feb. 19, 2021 (246 pages).

Shih et al. Reversal of murine colitis and fibrosis by neutralizing TL1A antibody: potential novel therapy to alter natural history of Crohn's disease. Gastroenterol 142(5):S84, Abstract #357, 2012.

Al et al.: Role of genetic and environmental factors in pathogenesis of inflammatory bowel disease. International Journal of Digestive Diseases 34(2):110-113 (2014) Machine English Translation of Abstract.

FIG. 4

| | | boundary | | | In IIBDGC cohort | | In Cedars Cohort | | |
|---|---|---|---|---|---|---|---|---|---|
| disease | chr | Lower | Upper | Locus/Major gene | n.snp | P.region | n.snp | p.region | p.meta |
| CD | 7 | 107255548 | 107453103 | SLC26A4 | 9 | 1.15E-09 | 8 | 0.00159 | 5.13E-11 |
| CD | 17 | 6996653 | 7077742 | DLG4 | 4 | 5.17E-05 | 4 | 0.00361 | 3.08E-06 |
| CD | 19 | 46133256 | 46346330 | GIPR | 25 | 2.73E-06 | 21 | 0.04411 | 2.04E-06 |
| CD | 20 | 39583952 | 39998520 | ZHX3 | 6 | 2.80E-09 | 5 | 0.01847 | 1.28E-09 |
| CD | 22 | 40288830 | 40797647 | TNRC6B | 10 | 1.91E-05 | 8 | 0.00048 | 1.80E-07 |
| UC | 7 | 92236164 | 92306993 | CDK6 | 4 | 1.83E-05 | 4 | 0.00721 | 2.22E-06 |
| UC | 11 | 36363575 | 36579932 | PRR5L | 35 | 5.62E-05 | 32 | 0.00044 | 4.63E-07 |
| IBD | 1 | 112869069 | 113313563 | WNT2B | 10 | 1.00E-05 | 9 | 0.00641 | 1.13E-06 |
| IBD | 6 | 25186512 | 25707171 | LRRC16A | 35 | 1.27E-09 | 31 | 0.01181 | 3.89E-10 |
| IBD | 6 | 26172219 | 27910708 | All Histone cluster1 gene | 155 | 2.94E-06 | 132 | 0.00603 | 3.34E-07 |
| IBD | 7 | 74455474 | 74509323 | GTF2IRD2B | 10 | 0.0001 | 9 | 7.78E-05 | 1.54E-07 |
| IBD | 11 | 128234772 | 128502496 | ETS1 | 449 | 1.07E-06 | 402 | 0.06996 | 1.30E-06 |
| IBD | 22 | 32339213 | 32616657 | SLC5A1 | 6 | 0.00139 | 2 | 4.12E-06 | 1.15E-07 |
| IBD | 4 | 106048291 | 106173199 | TET2 | 7 | 5.14E-08 | 6 | 0.10506 | 1.08E-07 |

FIG. 6B

| | | | | | Cedars | | | | IIBDGC | | | | Meta | |
|---|---|---|---|---|---|---|---|---|---|---|---|---|---|---|
| SNP | CHR | BP | Gene | PHRED | F_A | F_U | OR | P | F_A | F_U | OR | P | OR | P |
| rs10010325 | 4 | 1.06E+08 | TET2 | 3.696 | 0.47 | 0.48 | 0.95 | 0.127 | 0.48 | 0.50 | 0.93 | 8.95E-09 | 0.94 | 2.99E-09 |
| rs17035289 | 4 | 1.06E+08 | LOC643675 \| | 2.865 | 0.21 | 0.16 | 1.16 | 1.21E-03 | 0.18 | 0.17 | 1.07 | 8.28E-06 | 1.08 | 1.30E-07 |
| rs974801 | 4 | 1.06E+08 | TET2 | 2.56 | 0.36 | 0.36 | 0.99 | 0.727 | 0.36 | 0.38 | 0.94 | 5.73E-08 | 0.94 | 1.47E-07 |
| rs17035310 | 4 | 1.06E+08 | LOC643675 \| | 1.215 | 0.15 | 0.13 | 1.15 | 5.33E-03 | 0.14 | 0.13 | 1.06 | 1.70E-03 | 1.07 | 9.82E-05 |
| rs2189234 | 4 | 1.06E+08 | TET2 | 0.715 | 0.36 | 0.38 | 0.99 | 0.712 | 0.38 | 0.37 | 1.05 | 3.10E-04 | 1.04 | 1.09E-03 |
| rs7661349 | 4 | 1.06E+08 | LOC643675 \| | 9.167 | 0.32 | 0.37 | 0.96 | 0.232 | 0.36 | 0.34 | 1.05 | 2.49E-04 | 1.04 | 1.98E-03 |
| rs2726518 | 4 | 1.06E+08 | TET2 \| PPA2 | 0.968 | 0.52 | 0.46 | 1.08 | 0.473 | 0.44 | 0.45 | 0.98 | 0.060 | 0.98 | 0.07461 |

FIG. 6C

```
Call:
glm(formula = formu.final, family = binomial, data = dat.all)

Deviance Residuals:
    Min       1Q   Median       3Q      Max
-2.5478  -1.1799   0.4209   1.1563   2.2715

Coefficients:
            Estimate Std. Error z value Pr(>|z|)
(Intercept)  1.25452    0.16835   7.452 9.20e-14 ***
rs17035289   0.12122    0.02878   4.212 2.53e-05 ***
rs10010325  -0.06751    0.02496  -2.705  0.00683 **
rs17035310  -0.07844    0.03377  -2.323  0.02017 *
```

FIG. 7C

```
Call:
glm(formula = formu.final, family = binomial, data = dat.all)

Deviance Residuals:
    Min       1Q   Median       3Q      Max
-2.5663  -1.1808   0.4168   1.1532   2.3333

Coefficients:
            Estimate Std. Error z value Pr(>|z|)
(Intercept)  1.25350    0.16824   7.451 9.28e-14 ***
rs2690110    0.02487    0.01247   1.994 0.046101 *
rs7752195   -0.18875    0.02372  -7.957 1.76e-15 ***
rs6937918    0.04045    0.01205   3.357 0.000787 ***
rs9358858   -0.04254    0.01300  -3.273 0.001065 **
```

FIG. 8B

| rsnum | gene | feature | expression_gene_(population_and_p-value) |
|---|---|---|---|
| rs2690110 | LRRC16A | intron[NM_017640.4] | NA NA NA |
| rs7752195 | LRRC16A | intron[NM_017640.4] | BTN3A2 CEU 0.000000008<br>BTN3A2 CEU 0.0000006<br>BTN3A3 CEU 0.0000006<br>GNRHR2 YRI 0.000003<br>NEK2 YRI 0.00002<br>CACNA1E YRI 0.00004<br>TUBA1A YRI 0.00008<br>TUBA1B YRI 0.00008 |
| rs6937910 | LRRC16A | intron[NM_017640.4] | NA NA NA |
| rs9358858 | LRRC16A | intron[NM_017640.4] | OR56B1 YRI 0.00002<br>KISS1 YRI 0.00002 |

FIG. 9A

| | | | Cedars | | | IIBDGC | | | | |
|---|---|---|---|---|---|---|---|---|---|---|
| gene | chr | region | n.snp | p | | n.snp | p | | p.meta | Comments |
| KIAA1546(TET2) | 4 | 106267740 10639 | 6 | 0.019 | | 7 | 2.82E-09 | | 1.33E-09 | none |
| LRRC16 | 6 | 25400380 25715 | 26 | 1.55E-06 | | 30 | 0.00343 | | 1.19E-08 | none |
| HFE | 6 | 26180424 26212 | 5 | 2.86E-03 | | 5 | 3.84E-05 | | 1.87E-06 | none |
| HIST1H4H | 6 | 26384629 264274 | 6 | 1.08E-04 | | 7 | 0.002435 | | 4.24E-06 | none |
| LOC100132361 | 6 | 26397182 26473 | 15 | 2.89E-05 | | 18 | 0.003704 | | 1.82E-06 | none |
| HIST1H2BM | 6 | 27891338 27896 | 2 | 1.48E-04 | | 2 | 0.000103 | | 2.89E-07 | none |
| HIST1H4J | 6 | 27891338 27904 | 3 | 1.53E-04 | | 3 | 9.72E-05 | | 2.83E-07 | none |
| HIST1H4K | 6 | 27904914 27913 | 2 | 2.43E-04 | | 3 | 0.000429 | | 1.78E-06 | none |
| HIST1H2BN | 6 | 27914964 279244 | 9 | 3.28E-04 | | 9 | 0.000217 | | 1.24E-06 | none |
| HIST1H2AL | 6 | 27914964 27942 | 10 | 3.27E-04 | | 10 | 0.000221 | | 1.26E-06 | none |
| HIST1H1B | 6 | 27942064 27945 | 3 | 1.45E-04 | | 3 | 8.61E-05 | | 2.41E-07 | none |

FIG. 9C

```
Call:
glm(formula = IBD ~ PC1 + Source + PC2 + PC3 + PC4 + rs13198474 +
    rs198846 + rs198854 + PC1:Source + Source:PC2 + Source:PC3 +
    Source:PC4, family = binomial, data = dat.all)

Deviance Residuals:
    Min       1Q   Median       3Q      Max
-2.6098  -1.1802   0.4169   1.1534   2.3096

Coefficients:
            Estimate Std. Error z value Pr(>|z|)
(Intercept)  1.37511    0.16859   8.157 3.44e-16 ***
rs13198474  -0.25205    0.02420 -10.415  < 2e-16 ***
rs198846    -0.10895    0.01831  -5.952 2.65e-09 ***
rs198854    -0.06432    0.01362  -4.724 2.31e-06 ***
```

FIG. 10A

| rsnum | gene | feature | expression_gene_(population_and_p-value) |
|---|---|---|---|
| rs13198474 | SLC17A3 | utr-5[NM_001098486.1] | BTN3A2 CEU 0.0000000000005<br>BTN3A2 CEU 0.00000000002<br>BTN3A3 CEU 0.00000000002<br>SYT17 CEU 0.00002<br>HLA-DOA1 CEU 0.0001<br>HLA-DOA2 CEU 0.0001 |
| rs198846 | HIST1H1T | near-gene-3[NM_005323.3] | FAM20B CEU 0.000004<br>HLA-B CEU 0.000004<br>HLA-C CEU 0.000004<br>MICA CEU 0.000004<br>MICB CEU 0.000004<br>XXbac-BPG181B23.1 CEU 0.000004 |
| rs198854 | HIST1H4C | near-gene-5[NM_003542.3] | ZDHHC18 YRI 0.00005<br>PRDM15 YRI 0.00006 |

FIG. 10B

| P-value | SNP | Probe | Probe Chr. | Probe Chr. position | Gene name | FDR |
|---|---|---|---|---|---|---|
| 8.571049728721546E-6 | rs13198474 | 3890349 | 6 | 26212438 | HIST1H4C,HIST1H4A | 0.00 |
| 1.7045753691425042E-4 | rs13198474 | 3930377 | 6 | 26093147 | TRIM38 | 0.06 |

| P-value | SNP | Probe | Probe Chr. | Probe Chr. position | Gene name | FDR |
|---|---|---|---|---|---|---|
| 5.456307142692245E-21 | rs198846 | 7210333 | 6 | 26335240 | - | 0.00 |
| 4.107104411030292E-17 | rs198846 | 3930377 | 6 | 26093147 | TRIM38 | 0.00 |
| 0.00215064336881067 | rs198846 | 3890349 | 6 | 26212438 | HIST1H4C,HIST1H4A | 0.39 |
| 0.0023626413529773747 | rs198846 | 1030017 | 6 | 26265200 | HIST1H2AC,HIST1H4A,HIST1H1E | 0.41 |

| P-value | SNP | Probe | Probe Chr. | Probe Chr. position | Gene name | FDR |
|---|---|---|---|---|---|---|
| 1.935602569010773E-11 | rs198854 | 2970019 | 6 | 26393396 | HIST1H4H | 0.00 |
| 1.0360165606222519E-10 | rs198854 | 7210333 | 6 | 26335240 | - | 0.00 |
| 1.7834437343125703E-7 | rs198854 | 3930377 | 6 | 26093147 | TRIM38 | 0.00 |
| 1.4681254471856774E-4 | rs198854 | 6590594 | 6 | 26232467 | HIST1H2AC,HIST1H4A | 0.06 |
| 0.001193621305505144 | rs198854 | 1450484 | 6 | 26292370 | HIST1H2BE,HIST1H2AC,HIST1H4A | 0.27 |

FIG. 11A

| | | | Cedars | | | IIBDGC | | | | |
|---|---|---|---|---|---|---|---|---|---|---|
| gene | chr | region | n.snp | p | | n.snp | p | | p.meta | Comments |
| KIAA1546(TET2) | 4 | 106267740 10639 | 6 | 0.019 | | 7 | 2.82E-09 | | 1.33E-09 | none |
| LRRC16 | 6 | 25400380 25715 | 26 | 1.55E-06 | | 30 | 0.00343 | | 1.19E-08 | none |
| HFE | 6 | 26180424 26212 | 5 | 2.86E-03 | | 5 | 3.84E-05 | | 1.87E-06 | none |
| HIST1H4H | 6 | 26384629 264274 | 6 | 1.08E-04 | | 7 | 0.002435 | | 4.24E-06 | none |
| LOC100132361 | 6 | 26397182 26473 | 15 | 2.89E-05 | | 18 | 0.003704 | | 1.82E-06 | none |
| HIST1H2BM | 6 | 27891338 27896 | 2 | 1.48E-04 | | 2 | 0.000103 | | 2.89E-07 | none |
| HIST1H4J | 6 | 27891338 27904 | 3 | 1.53E-04 | | 3 | 9.72E-05 | | 2.83E-07 | none |
| HIST1H4K | 6 | 27904914 27913 | 2 | 2.43E-04 | | 3 | 0.000429 | | 1.78E-06 | none |
| HIST1H2BN | 6 | 27914964 27924 | 9 | 3.28E-04 | | 9 | 0.000217 | | 1.24E-06 | none |
| HIST1H2AL | 6 | 27914964 27942 | 10 | 3.27E-04 | | 10 | 0.000221 | | 1.26E-06 | none |
| HIST1H1B | 6 | 27942064 27945 | 3 | 1.45E-04 | | 3 | 8.61E-05 | | 2.41E-07 | none |

FIG. 11C

```
Call:
glm(formula = IBD ~ PC1 + Source + PC2 + PC3 + PC4 + rs200484 +
    rs9295740 + rs4713119 + rs9461412 + PC1:Source + Source:PC2 +
    Source:PC3 + Source:PC4, family = binomial, data = dat.all)

Deviance Residuals:
    Min       1Q   Median       3Q      Max
-2.5693  -1.1789   0.4111   1.1534   2.2937

Coefficients:
            Estimate Std. Error z value Pr(>|z|)
(Intercept)  1.26637    0.16764   7.554 4.21e-14 ***
rs200484    -0.35930    0.03202 -11.220  < 2e-16 ***
rs9295740    0.17719    0.02772   6.392 1.63e-10 ***
rs4713119   -0.08550    0.01784  -4.792 1.65e-06 ***
rs9461412   -0.14858    0.03876  -3.833 0.000126 ***
```

FIG. 12

| rsnum | gene | feature | expression_gene_(population_and_p-value) |
|---|---|---|---|
| rs200484 | HIST1H2AI<br>HIST1H2BL | near-gene-5[NM_003509.2]<br>reference[NM_003519.3] | BTN3A2 CEU 0.000000000000009<br>BTN3A2 CEU 0.0000000000002<br>BTN3A3 CEU 0.0000000000002<br>HLA-DOA1 CEU 0.0000002<br>HLA-DOA2 CEU 0.0000002<br>SYT17 CEU 0.000007<br>HIST1H4A CEU 0.00006<br>HIST1H4B CEU 0.00006<br>HIST1H4C CEU 0.00006<br>HIST1H4D CEU 0.00006<br>HIST1H4E CEU 0.00006<br>HIST1H4F CEU 0.00006<br>HIST1H4H CEU 0.00006<br>HIST1H4I CEU 0.00006<br>HIST1H4J CEU 0.00006<br>HIST1H4K CEU 0.00006<br>HIST1H4L CEU 0.00006<br>HIST2H4A CEU 0.00006<br>HIST2H4B CEU 0.00006<br>HIST4H4 CEU 0.00006 |
| rs9295740 | NA | NA | BTN3A2 CEU 0.00000000001<br>BTN3A3 CEU 0.00000000001<br>BTN3A2 CEU 0.0000000001<br>HLA-DOA1 CEU 0.000006<br>HLA-DOA2 CEU 0.000006<br>NTNG1 CEU 0.00002<br>C9orf139 CEU 0.00009 |
| rs4713119 | NA | NA | NA NA NA |
| rs9461412 | NA | NA | NA NA NA |

FIG. 13

```
Call:
glm(formula = IBD ~ PC1 + Source + PC2 + PC3 + PC4 + rs200484 +
    rs9295740 + rs4713119 + rs6937918 + rs198846 + rs7752195 +
    rs198854 + rs9358858 + rs9461412 + rs2690110 + rs13198474 +
    PC1:Source + Source:PC2 + Source:PC3 + Source:PC4, family = binomial,
    data = dat.all)

Deviance Residuals:
    Min       1Q   Median       3Q      Max
-2.6048  -1.1778   0.4082   1.1509   2.3377

Coefficients:
             Estimate Std. Error z value Pr(>|z|)
(Intercept)   1.32605    0.16916   7.839 4.54e-15 ***
rs200484     -0.29557    0.03555  -8.313  < 2e-16 ***
rs9295740     0.16562    0.02790   5.936 2.93e-09 ***
rs4713119    -0.08995    0.01796  -5.008 5.49e-07 ***
rs6937918     0.03534    0.01208   2.926  0.00343 **
rs198846     -0.10461    0.01847  -5.663 1.49e-08 ***
rs7752195    -0.08784    0.03802  -2.310  0.02087 *
rs198854     -0.06101    0.01380  -4.422 9.76e-06 ***
rs9358858    -0.03671    0.01311  -2.800  0.00511 **
rs9461412    -0.12768    0.03904  -3.271  0.00107 **
rs2690110     0.03136    0.01254   2.500  0.01241 *
rs13198474   -0.07282    0.04106  -1.774  0.07614 .
```

DIAGNOSIS OF INFLAMMATORY BOWEL DISEASE BASED ON GENES

CROSS REFERENCE TO RELATED APPLICATIONS

This application is a U.S. National Phase of International Application No. PCT/US2017/033625 filed May 19, 2017, which claims the benefit of U.S. Provisional Application Ser. No. 62/339,357 filed on May 20, 2016 which is incorporated by reference in its entirety.

STATEMENT REGARDING FEDERALLY-SPONSORED RESEARCH

This invention was made with government support under Grant Nos. DK108140 and DK062413 awarded by the National Institutes of Health. The government has certain rights in the invention.

FIELD OF THE INVENTION

The invention relates to genetics and medicine.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Crohn's disease (CD) and ulcerative colitis (UC), the two common forms of idiopathic inflammatory bowel disease (IBD), are chronic, relapsing inflammatory disorders of the gastrointestinal tract. Each has a peak age of onset in the second to fourth decades of life and prevalences in European ancestry populations that average approximately 100-150 per 100,000 (D. K. Podolsky, N Engl J Med 347, 417 (2002); E. V. Loftus, Jr., Gastroenterology 126, 1504 (2004)). Although the precise etiology of IBD remains to be elucidated, a widely accepted hypothesis is that ubiquitous, commensal intestinal bacteria trigger an inappropriate, overactive, and ongoing mucosal immune response that mediates intestinal tissue damage in genetically susceptible individuals (D. K. Podolsky, N Engl J Med 347, 417 (2002)). Genetic factors play an important role in IBD pathogenesis, as evidenced by the increased rates of IBD in Ashkenazi Jews, familial aggregation of IBD, and increased concordance for IBD in monozygotic compared to dizygotic twin pairs (S. Vermeire, P. Rutgeerts, Genes Immun 6, 637 (2005)). CD and UC are thought to be related disorders that share some genetic susceptibility loci but differ at others.

Thus, there is need in the art to determine other genes, allelic variants and/or haplotypes that may assist in explaining the genetic risk, diagnosing, and/or predicting susceptibility for or protection against inflammatory bowel disease including but not limited to CD and/or UC.

SUMMARY OF THE INVENTION

Various embodiments of the present invention provide for a method of prognosing high or low probability of developing an inflammatory bowel disease (IBD) in a subject, comprising: genotyping the subject for a risk allele at a gene/genetic locus; and upon detecting the risk allele, prognosing high probability of developing the IBD in the subject; or upon not detecting the risk allele, prognosing low probability of developing the IBD in the subject.

In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. In various embodiments, the gene/genetic locus comprise one or more of SEQ ID NO: 1-SEQ ID NO: 341.

In various other embodiments, genotyping the subject comprises: obtaining a sample from the subject; and genotyping the sample for the risk allele at the gene/genetic locus. In yet other embodiments, genotyping the sample comprises: contacting the sample with an oligonucleotide probe specific to the risk allele; generating an allele-specific hybridization complex between the oligonucleotide probe and the risk allele; and upon detecting the allele-specific hybridization complex, detecting the risk allele; or upon not detecting the allele-specific hybridization complex, not detecting the risk allele. In some embodiments, the oligonucleotide probe is labeled with a fluorescent dye, and wherein detecting the allele-specific hybridization complex comprises detecting fluorescence signal from the oligonucleotide probe. In other embodiments, the oligonucleotide probe comprises a reporter dye and a quencher dye.

In various embodiments, the method further comprises conducting PCR amplification after forming the allele-specific hybridization complex.

Various embodiments of the present invention provide for a method of diagnosing an inflammatory bowel disease (IBD) in a subject, comprising: genotyping a sample from the subject for a risk allele at a gene/genetic locus; upon detecting the risk allele, diagnosing IBD in the subject; and administering an IBD therapy to the subject diagnosed with IBD, thereby treating IBD in the subject. In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. In various embodiments, the gene/genetic locus comprise one or more of SEQ ID NO: 1-SEQ ID NO: 341. In various embodiments, the method further comprises providing an IBD therapy to the subject. In some embodiments, the IBD therapy comprises anti-TNF therapy, anti-TL1A therapy, colectomy, or a combination thereof.

Various embodiments of the present invention provide for a method, comprising: genotyping a sample from the subject for a risk allele at a gene/genetic locus; upon detecting the risk allele, diagnosing IBD in the subject; and administering the IBD therapy to the subject diagnosed with IBD, thereby treating IBD in the subject. In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. In various other embodiments, the gene/genetic locus comprise one or more of SEQ ID NO: 1-SEQ ID NO: 341. In various embodiments, the method further comprises providing an IBD therapy to the subject. In some embodiments, the IBD therapy comprises anti-TNF therapy, anti-TL1A therapy, colectomy, or a combination thereof.

Various embodiments of the present invention provide for a method of identifying genes/genetic loci associated with a condition, comprising: acquiring genetic data from samples of a cohort of the condition; performing a GLS transformation on the genetic data, thereby decorrelating the genetic data; conducting gene-based analysis on the GLS-transformed genetic data; and identifying genes/genetic loci associated with the condition. In various embodiments, the condition is IBD, CD, or UC, or a combination thereof. In some embodiments, the cohort comprises correlated subjects or family subjects. In other embodiments, the genetic data comprise SNP genotypes. In yet other embodiments, performing the GLS transformation comprises transforming the genetic data according to functions $G=\Sigma_o^{-1/2}$, $Gy=GX\beta+Ge$, $\hat{\beta}_{GLS}=(X'\Sigma_o^{-1}X)^{-1}X'\Sigma_o^{-1}y$, $var(\hat{\beta}_{GLS})=var((X'\Sigma_o^{-1}X)^{-1}X'\Sigma_o^{-1}y)=(X'\Sigma_o^{-1}X)^{-1}$, or a combination thereof.

In various embodiments, conducting gene-based analysis comprises applying a gene-based test based on the assumption of independent or uncorrelated subjects. In various embodiments, conducting gene-based analysis comprises applying C-alpha, SKAT, SKAT-CommonRare, CMC, WSS, Variable Threshold, or Comprehensive Approach, or a combination thereof.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 4 depicts, in accordance with various embodiments of the invention, a list of novel genes/regions identified in our analysis: SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, and TET2.

FIGS. 6A-6D depict, in accordance with various embodiments of the invention, detailed examination of TET2 region: local plot (A), SNPs (B), fine mapping (C), and function (D). rs17035289 is SEQ ID NO: 333 and rs2726518 is SEQ ID NO: 334. All other rs numbers are found in table 1.

FIGS. 7A-7C depict, in accordance with various embodiments of the invention, detailed examination of LRRC16 region: local plot (A), local plot (B), and fine mapping with four independent signals (C).

FIGS. 8A-8C depict, in accordance with various embodiments of the invention, eQTL results: SeeQTL (A), Scandb (B), and GeneVar (C). rs9358858 is SEQ ID NO: 335. All other rs numbers are found in table 1.

FIGS. 9A-9C depict, in accordance with various embodiments of the invention, detailed examination of a first portion in the HIST1 cluster: genes (A), local signals (B), and fine mapping with three independent signals (P=2.23E-25) (C). rs2071303 is SEQ ID NO: 336, rs13198474 is SEQ ID NO: 337, rs198846 is SEQ ID NO:338 and rs198854 is SEQ ID NO:339.

FIGS. 10A-10B depict, in accordance with various embodiments of the invention, eQTL analysis: SCANdb (A) and Blood eQTL (B). rs13198474 is SEQ ID NO: 337, rs198846 is SEQ ID NO:338 and rs198854 is SEQ ID NO:339.

FIGS. 11A-11C depict, in accordance with various embodiments of the invention, detailed examination of a second portion in the HIST1 cluster: genes (A), local signals (B), and fine mapping with four independent signals (P=3.25E-29) (C). rs9295740 is SEQ ID NO: 340 and rs9461412 is SEQ ID NO: 341.

FIG. 12 depicts, in accordance with various embodiments of the invention, eQTL analysis: SCANdb.

FIG. 13 depicts, in accordance with various embodiments of the invention, independent signals from 3 regions: LRRC16, first portion in the HIST1 cluster, and second portion in the HIST1 cluster.

DETAILED DESCRIPTION OF THE INVENTION

Figure 1B:
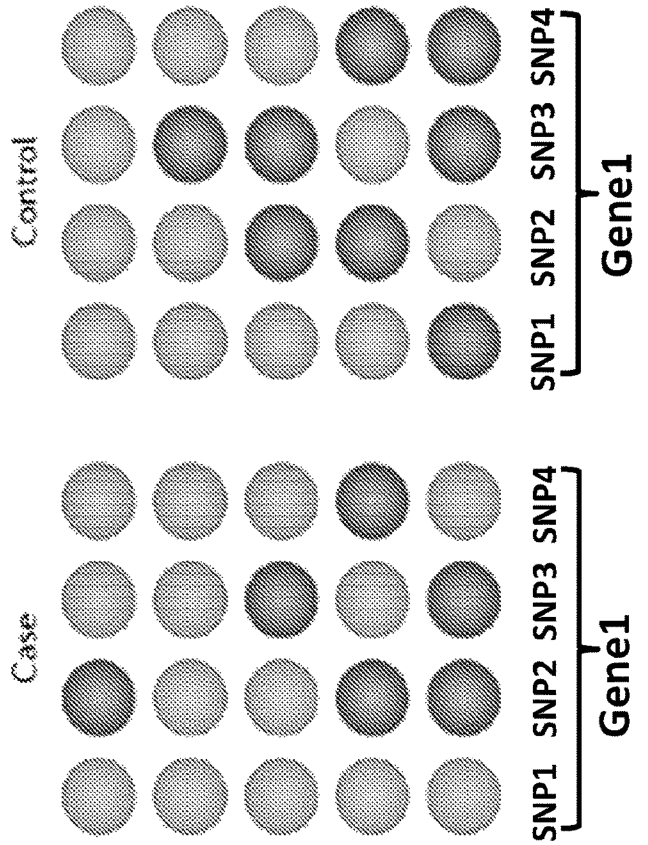
FIGS. 1A-1B depict, in accordance with various embodiments of the invention, Single-SNP based and gene-based analysis.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22*nd ed.*, Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3*rd ed., revised ed.*, J. Wiley & Sons (New York, N.Y. 2006); Smith, *March's Advanced Organic Chemistry Reactions, Mechanisms and Structure* 7*th ed.*, J. Wiley & Sons (New York, N.Y. 2013); Singleton, *Dictionary of DNA and Genome Technology* 3*rd ed.*, Wiley-Blackwell (Nov. 28, 2012); and Green and Sambrook, *Molecular Cloning: A Laboratory Manual* 4th *ed.*, Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2*nd ed.*, Cold Spring Harbor Press (Cold Spring Harbor N.Y., 2013);

Köhler and Milstein, *Derivation of specific antibody-producing tissue culture and tumor lines by cell fusion*, Eur. J. Immunol. 1976 Jul. 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of intestinal inflammation and/or fibrosis, delay or slowing of intestinal inflammation and/or fibrosis, and amelioration or palliation of symptoms associated with intestinal inflammation and/or fibrosis.

"Diseases", "conditions" and "disease conditions," as used herein may include, but are in no way limited to any form of intestinal inflammation or intestinal inflammation-related condition, disease or disorder, for example, intestinal inflammation, intestinal fibrosis, inflammatory bowel disease (IBD), Crohn's disease (CD), ulcerative colitis (UC), colitis, acute colitis, and chronic colitis.

method of prognosing high or low probability of developing an inflammatory bowel disease (IBD) in a subject, comprising: genotyping the subject for a risk allele at a gene/genetic locus; and upon detecting the risk allele, prognosing high probability of developing the IBD in the subject; or upon not detecting the risk allele, prognosing low probability of developing the IBD in the subject.

"Risk variant" as used herein refers to an allele, whose presence is associated with an increase in susceptibility to an inflammatory bowel disease, including but not limited to Crohn's Disease and ulcerative colitis, relative to an individual who does not have the risk variant.

"High probability", as used herein refers to an increase in susceptibility to an inflammatory bowel disease, when the risk variants are present in an individual, relative to an individual who does not have the risk variants.

"Low probability", as used herein refers to a decrease in susceptibility to an inflammatory bowel disease, when the risk variants are absent in an individual, relative to an individual who has the risk variants.

As used herein, the term "administering," refers to the placement an agent as disclosed herein into a subject by a method or route which results in at least partial localization of the agents at a desired site. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

The term "sample" or "biological sample" as used herein denotes a sample taken or isolated from a biological organism, e.g., a blood sample from a subject. Exemplary biological samples include, but are not limited to, cheek swab; mucus; whole blood, blood, serum; plasma; urine; saliva; semen; lymph; fecal extract; sputum; other body fluid or biofluid; cell sample; and/or tissue sample etc. The term also includes a mixture of the above-mentioned samples. The term "sample" also includes untreated or pretreated (or pre-processed) biological samples. In some embodiments, a sample can comprise one or more cells from the subject.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., intestinal inflammation and/or fibrosis, IBD, CD, UC, colitis, acute colitis, and chronic colitis) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "statistically significant" or "significantly" refers to statistical evidence that there is a difference. It is defined as the probability of making a decision to reject the null hypothesis when the null hypothesis is actually true. The decision is often made using the p-value.

As used herein, "a disease's Odds" or "Odds of a disease" in a certain population is defined as the ratio between disease probability and non-disease probability in such a population (i.e., a disease's Odds=disease probability/non-disease probability).

As used herein, "a risk allele's Odds Ratio (OR)" or "Odds Ratio (OR) of a risk allele" with respect to a disease is defined as the ratio between the disease's Odds in the risk allele's carrier population and the disease's Odds in the risk allele's non-carrier population. (i.e., a risk allele's OR=the disease's Odds in carriers/the disease's Odds in non-carriers).

METHODS OF THE INVENTION

This invention provides methods of identifying genes/genetic loci associated with a condition such as IBD. The identification of these genes/genetic loci can be used for risk stratification of a population with respect to IBD. We could use such a tool at birth to identify people at risk for IBD with the intent of impacting the population by delivering preventative interventions that could modulate environmental epigenetic factors. This invention also provides methods of diagnosing IBD and methods of individualizing IBD treatment plans as a precision medicine approach.

Prognosing

Various embodiments of the present invention provide for a method of prognosing high or low probability of developing an inflammatory bowel disease (IBD) in a subject, comprising: genotyping the subject for a risk allele at a gene/genetic locus; and upon detecting the risk allele, prognosing high probability of developing the IBD in the subject; or upon not detecting the risk allele, prognosing low probability of developing the IBD in the subject.

In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. In various embodiments, the gene/genetic locus comprise one or more of SEQ ID NO: 1-SEQ ID NO: 341.

In various other embodiments, genotyping the subject comprises: obtaining a sample from the subject; and genotyping the sample for the risk allele at the gene/genetic locus. In yet other embodiments, genotyping the sample comprises: contacting the sample with an oligonucleotide probe specific to the risk allele; generating an allele-specific hybridization complex between the oligonucleotide probe and the risk allele; and upon detecting the allele-specific hybridization complex, detecting the risk allele; or upon not detecting the allele-specific hybridization complex, not detecting the risk allele. In some embodiments, the oligonucleotide probe is labeled with a fluorescent dye, and wherein detecting the allele-specific hybridization complex comprises detecting fluorescence signal from the oligonucleotide probe. In other embodiments, the oligonucleotide probe comprises a reporter dye and a quencher dye.

In various embodiments, the method further comprises conducting PCR amplification after forming the allele-specific hybridization complex.

Various embodiments of the present invention provide a method of prognosing high or low probability of developing an inflammatory bowel disease (IBD) in a subject. The method comprises: genotyping the subject for a risk allele at a gene/genetic locus; and upon detecting the risk allele, prognosing high probability of developing the IBD in the subject; or upon not detecting the risk allele, prognosing low probability of developing the IBD in the subject.

Various embodiments of the present invention provide a method of prognosing high probability of developing an inflammatory bowel disease (IBD) in a subject. The method comprises: genotyping the subject for a risk allele at a gene/genetic locus; and upon detecting the risk allele, prognosing high probability of developing the IBD in the subject.

Various embodiments of the present invention provide a method of prognosing low probability of developing an inflammatory bowel disease (IBD) in a subject. The method comprises: genotyping the subject for a risk allele at a gene/genetic locus; and upon not detecting the risk allele, prognosing low probability of developing the IBD in the subject.

In accordance with the present invention, high or low probability of developing IBD means that a subject has more or less likelihood of developing IBD as compared to the general population which the subject belongs to.

Diagnosing

Various embodiments of the present invention provide for a method of diagnosing an inflammatory bowel disease (IBD) in a subject, comprising: genotyping a sample from the subject for a risk allele at a gene/genetic locus; upon detecting the risk allele, diagnosing IBD in the subject; and administering an IBD therapy to the subject diagnosed with IBD, thereby treating IBD in the subject. In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. In various embodiments, the gene/genetic locus comprise one or more of SEQ ID NO: 1-SEQ ID NO: 341. In some embodiments, the IBD therapy comprises anti-TNF therapy, anti-TL1A therapy, colectomy, or a combination thereof.

Various embodiments of the present invention provide for a method, comprising: genotyping a sample from the subject for a risk allele at a gene/genetic locus; upon detecting the risk allele, diagnosing IBD in the subject; and administering an IBD therapy to the subject diagnosed with IBD, thereby treating IBD in the subject. In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. In various other embodiments, the gene/genetic locus comprise one or more of SEQ ID NO: 1-SEQ ID NO: 341. In various embodiments, the method further comprises providing an IBD therapy to the subject. In some embodiments, the IBD therapy comprises anti-TNF therapy, anti-TL1A therapy, colectomy, or a combination thereof.

Various embodiments of the present invention provide a method of identifying susceptibility to or identifying protection against an inflammatory bowel disease (IBD) in a subject. The method comprises: genotyping the subject for a risk allele at a gene/genetic locus; and upon detecting the risk allele, identifying susceptibility to the IBD in the subject; or upon not detecting the risk allele, identifying protection against the IBD in the subject.

Various embodiments of the present invention provide a method of identifying susceptibility to an inflammatory bowel disease (IBD) in a subject. The method comprises: genotyping the subject for a risk allele at a gene/genetic locus; and upon detecting the risk allele, identifying susceptibility to the IBD in the subject.

Various embodiments of the present invention provide a method of identifying protection against an inflammatory bowel disease (IBD) in a subject. The method comprises: genotyping the subject for a risk allele at a gene/genetic locus; and upon not detecting the risk allele, identifying protection against the IBD in the subject.

In accordance with the present invention, susceptibility to IBD means that a subject has more likelihood of developing IBD as compared to the general population which the subject belongs to. In accordance with the present invention, protection against IBD means that a subject has less likelihood of developing IBD as compared to the general population which the subject belongs to.

Various embodiments of the present invention provide a method of diagnosing an inflammatory bowel disease (IBD) in a subject. The method comprises: genotyping the subject for a risk allele at a gene/genetic locus; and upon detecting the risk allele, diagnosing the IBD in the subject; or upon not detecting the risk allele, not diagnosing the IBD in the subject.

Various embodiments of the present invention provide a method of diagnosing an inflammatory bowel disease (IBD) in a subject. The method comprises: genotyping the subject for a risk allele at a gene/genetic locus; detecting the risk allele; and diagnosing the IBD in the subject.

Various embodiments of the present invention provide a method of treating an inflammatory bowel disease (IBD) in a subject. The method comprises: administering the IBD therapy to the subject, wherein the subject is diagnosed with the IBD according to a method as described herein, thereby treating the IBD in the subject. In various embodiments, the method further comprises providing an IBD therapy to the subject.

Various embodiments of the present invention provide a method of treating an inflammatory bowel disease (IBD) in a subject. The method comprises: genotyping the subject for a risk allele at a gene/genetic locus; and upon detecting the risk allele, administering the IBD therapy to the subject; or upon not detecting the risk allele, not administering the IBD therapy to the subject. In various embodiments, the method further comprises providing an IBD therapy to the subject.

Various embodiments of the present invention provide a method of treating an inflammatory bowel disease (IBD) in a subject. The method comprises: genotyping the subject for a risk allele at a gene/genetic locus; detecting the risk allele; and administering the IBD therapy to the subject, thereby treating the IBD in the subject. In various embodiments, the method further comprises providing an IBD therapy to the subject.

Various embodiments of the present invention provide a method of administering an inflammatory bowel disease (IBD) therapy to a subject. The method comprises: genotyping the subject for a risk allele at a gene/genetic locus; and upon detecting the risk allele, administering the IBD therapy to the subject; or upon not detecting the risk allele, not administering the IBD therapy to the subject.

Various embodiments of the present invention provide a method of administering an inflammatory bowel disease (IBD) therapy to a subject. The method comprises: genotyping the subject for a risk allele at a gene/genetic locus; detecting the risk allele; and administering the IBD therapy to the subject.

In various embodiments, the IBD therapy comprises anti-TNF therapy, anti-TL1A therapy, or colectomy, or a combination thereof. In some embodiments, the IBD therapy is an anti-TNF antibody. In some embodiments, the IBD therapy is an anti-TL1A antibody. In some embodiments, the IBD therapy is colectomy.

In various embodiments, the subject is a human. In some embodiments, the subject is a child. In some embodiments, the subject is a teenager. In other embodiments, the subject is an adult. In various embodiments, the IBD is Crohn's disease (CD) or ulcerative colitis (UC).

In various embodiments, the sample is cheek swab; mucus; whole blood; blood; serum; plasma; urine; saliva; semen; lymph; fecal extract; sputum; other body fluid or biofluid; cell sample; or tissue sample; or a combination thereof. In various embodiments, the sample comprises a nucleic acid from the individual. In some embodiments, the nucleic acid comprises genomic DNA. In various embodiments, the sample is a body fluid. In some embodiments, the body fluid is whole blood, plasma, saliva, mucus, or cheek swab. In various embodiments, the sample is a cell or tissue. In some embodiments, the cell is a blood cell. In some embodiments, the cell is a blood cell line (e.g., a lymphoblastoid cell line) obtained from the subject and transformed with an Epstein Barr virus.

In various embodiments, the gene/genetic locus comprises 1, 2, 3, 4, 5, 6, 7, 8, 9, 10, 11, 12, 13, 14, or more, or all of the genes/genetic loci listed in Table 1 as SEQ ID NOs: 1-341. In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. Each gene can comprise the following sequences: SLC26A4 (SEQ ID NOs: 1-6); DLG4 (SEQ ID NO: 7); GIPR (SEQ ID NOs: 8-27); ZHX3 (SEQ ID NOs: 28-30); TNRC6B (SEQ ID NOs: 31-38); CDK6 (SEQ ID NOs: 39-40); PRR5L (SEQ ID NOs: 41-54); WNT2B (SEQ ID NOs: 55-58); LRRC16A (SEQ ID NOs: 59-75, 335); HIST1 cluster (all Histone cluster 1 genes—SEQ ID NOs: 76-173, 338, 339); GTF2IRD2B (SEQ ID NOs: 174-180); ETS1 (SEQ ID NOs: 181-325); SLC5A1 (SEQ ID NOs: 326-327); and TET2 (SEQ ID NOs: 328-332, 334).

In various embodiments, the risk allele comprises 1, 2, 3, 4, 5, 6, 7, 8, 9, 10, or more, or all of the risk alleles listed in Table 1 as SEQ ID NOs: 1-341. In various embodiments, the risk allele comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 99, or 100, or more, or all of the risk alleles listed in Table 1 as SEQ ID NOs: 1-341. In various embodiments, the risk allele comprises N of the risk alleles listed in Table 1 as SEQ ID NOs: 1-341, and wherein N is a positive integer not more than 341 (i.e., $1 \leq N \leq 341$). In various embodiments, the risk allele comprises 1-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, or 95-100 of the risk alleles listed in Table 1 as SEQ ID NOs: 1-341. In various embodiments, the risk allele comprises 100-105, 105-110, 110-115, 115-120, 120-125, 125-130, 130-135, 135-140, 140-145, 145-150, 150-155, 155-160, 160-165, 165-170, 170-175, 175-180, 180-185, 185-190, 190-195, or 195-200 of the risk alleles listed in Table 1 as SEQ ID NOs: 1-341. In various embodiments, the risk allele comprises 200-205, 205-210, 210-215, 215-220, 220-225, 325-230, 230-235, 235-240, 240-245, 245-250, 250-255, 255-260, 260-265, 265-270, 270-275, 275-280, 280-285, 285-290, 290-295, or 295-300 of the risk alleles listed in Table 1 as SEQ ID NOs: 1-341. In various embodiments, the risk allele comprises 300-305, 305-310, 310-315, 315-320, 320-325, 325-330, or 330-341 of the risk alleles listed in Table 1 as SEQ ID NOs: 1-341.

In some embodiments, the subject's genotypes can be obtained from previous genetic or genomic tests performed on the subject and those previous tests were not performed with particular respect to IBD or any condition. For example, the subject's genotypes can be obtained from analyzing the subject's genome sequencing results, or obtained from a database storing the subject's personal genetic or genomic information. In these embodiments, genotyping the subject does not require conducting laboratory tests on the subject, as it involves acquiring and analyzing data already available. In other embodiments, for example, when personal genetic or genomic information is not available or when subject or physician desire new laboratory tests, genotyping the subject requires conducting laboratory tests on the subject.

In various embodiments of the present invention, genotyping the subject comprises: obtaining a sample from the subject; and genotyping the sample for the risk allele at the gene/genetic locus.

In some embodiments, genotyping the sample comprises: contacting the sample with an oligonucleotide probe specific to the risk allele; generating an allele-specific hybridization complex between the oligonucleotide probe and the risk allele; and upon detecting the allele-specific hybridization complex, detecting the risk allele; or upon not detecting the allele-specific hybridization complex, not detecting the risk allele. In various embodiments, the oligonucleotide probe is labeled with a fluorescent dye, and wherein detecting the allele-specific hybridization complex comprises detecting fluorescence signal from the oligonucleotide probe. In various embodiments, the oligonucleotide probe comprises a reporter dye and a quencher dye. In certain embodiments, the method further comprises conducting PCR amplification after forming the allele-specific hybridization complex. In various embodiments, detecting the allele-specific hybridization complex comprises detecting the electrophoretic mobility of the allele-specific hybridization complex.

In various embodiments, genotyping the sample comprises detecting a SNP's alleles in the sample by: contacting the sample with detection agents that specifically bind to the SNP's alleles; and detecting the binding levels between the detection agents and the SNP's alleles. Alleles can be detected by genotyping assays, PCR, Reverse transcription PCR, real-time PCR, microarray, DNA sequencing, and RNA sequencing techniques.

Various embodiments of the present invention provide a composition. In various embodiments, the composition comprises one or more detection agents that specifically bind to one or more alleles at one or more genes/genetic loci. This composition may be used to identify genes/genetic loci associated with a condition, and/or to prognose low or high probability of developing IBD, and/or to prognose susceptibility to or protection against IBD, and/or to diagnose IBD, and/or to treat IBD, and/or to direct administering an IBD therapy.

In various embodiments, the detection agents are oligonucleotide probes, nucleic acids, DNAs, RNAs, aptamers, peptides, proteins, antibodies, avimers, or small molecules, or a combination thereof. In some embodiments, the detection agents are allele-specific oligonucleotide probes targeting the SNP's alleles. In various embodiments, a SNP's alleles are detected by using a microarray. In some embodiments, the microarray is an oligonucleotide microarray, DNA microarray, cDNA microarrays, RNA microarray, peptide microarray, protein microarray, or antibody microarray, or a combination thereof.

In various embodiments, detecting a SNP's alleles comprises: contacting the sample with one or more allele-specific oligonucleotide probes targeting the SNP's alleles; generating double-stranded hybridization complex through allele-specific binding between the SNP's alleles and said allele-specific oligonucleotide probes; and detecting the double-stranded hybridization complex newly generated through allele-specific binding between the SNP's alleles and said allele-specific oligonucleotide probes. In some embodiments, the method further comprises conducting PCR amplification of the double-stranded hybridization complex.

In various embodiments, the present invention provides allele-specific oligonucleotide probes for each of the alleles (e.g., major alleles, minor alleles, risk alleles, and non-risk alleles listed Table 1. In accordance with the present invention, said allele-specific oligonucleotide probes may comprise about 10-15, 15-20, 20-25, 25-30, 30-35, 35-40, 40-45, or 45-50 nucleotides; they are either identical or complementary to a sequence segment encompassing the polymorphic position of a SNP as disclosed herein; and they are specific to one or the other allele at the polymorphic position. For a non-limiting example, rs10247487 has either T or C allele (in the context of forward strand) at its polymorphic position (e.g., "Y" at nucleotide 501 of the following exemplar sequence (SEQ ID NO: 1).

```
CCTAAGGAAG TTCTAGACTA GTGTTTCATG GAGCCCATTC TTTTAAATTA AAAGTAGCCA    60

TTTAAAAAAA TTAAAGTCCC AGAAAATGAC CATTAGAATA TGCAATTTAA AAATAGCAAA   120

TAAAACAAAC TAAGGTTTTT TTGAACAGAT ATATAGAAAC AAAATTTCAC TTAGTTTACA   180

ATATAAACAT GCATTTCACA TTAGCATTAA AATGCTATTG TGATTTATCT CTCTTTCAAA   240

TACTATTGCC TCTACTTACA CAATCATATT TGTCCTTTCG CCACAATCTG CCTATTTCAG   300

CAAACTGCAT CAGCATTCCC TTTAAGTTTC CCAATGCTAA AGCTGCCAGG ACGGACTGTG   360

AAAAACACAA ACATCAGATG TACTTTAAGT TAATGAAATA AACCACAGGG AAGCAAAGGT   420

GAAGGCTATA GATAAGTGTG TGCTTTAAAG GGCCTCAAAG CAAATCAAAG CATTACACCC   480

TTTTCCGGTG TGCGATGCCA YGCAAGACAC ACCAGAACTG GGACTCTGAC CTGTTCCTAT   540

GAATGACTTT GTCCCCACAA CAGTGACAAG GCCTAGGCTG CTCTTGTGAT TATGAGATAG   600

ATGATCTGAT GGCGTTTAGT AGCCTGCACC TTGGGACAGA GAAAGGCAGA CCTTCAGACC   660

TATGACAGAC TAACATTTGG AATAAATTCC TCCCAAGCAG AGACAGTCTA ATGTGTGTTT   720

GTTTATTGGA GTCAAGGAGA TGGGGGTTGC TCTTTGTTAA AAAAAAAAAT AGCTTGGGAA   780

GCTTGAGGTC CTGGAATGAG ATGACTTGAG GCGGGCTTTC TGGGACAGCA TGAAACATAT   840

CTATCTAGTT CCTGCTATAT CCCCAGAACC TACTATGTTA AATGCATACA GGAGGGGCTT   900
```

-continued

```
TAAAATTAGT CAGTGAATGA GTGGCTGAGC CAATGAATGA ATATTTCCCA GGCCAGTACT   960

AATCCCTACA GCCAAGCTTC AGACTTCCAA TTCTTCCACA G                      1001
```

Hence, an allele-specific oligonucleotide probe for the T allele at rs10247487 may comprise, for a non-limiting example, 21 nucleotides; and these 21 nucleotides are either identical or complementary to the sequence segment 481-501, 482-502, 483-503, 484-504, 485-505, 486-506, 487-507, 488-508, 489-509, 490-511, 491-511, 492-512, 493-513, 494-514, 495-515, 496-516, 497-517, 498-518, 499-519, 500-520, or 501-521 of the above exemplar sequence where nucleotide 501 is set as the T allele. Vice versa, an allele-specific oligonucleotide probe for the C allele at rs10247487 may comprise, for a non-limiting example, 21 nucleotides; and these 21 nucleotides are either identical or complementary to the sequence segment 481-501, 482-502, 483-503, 484-504, 485-505, 486-506, 487-507, 488-508, 489-509, 490-511, 491-511, 492-512, 493-513, 494-514, 495-515, 496-516, 497-517, 498-518, 499-519, 500-520, or 501-521 of the above exemplar sequence where nucleotide 501 is set as the C allele.

In various embodiments, said allele-specific oligonucleotide probes are labeled with one or more fluorescent dyes, and wherein detecting the double-stranded hybridization complex comprises detecting fluorescence signals from the fluorescent dyes. In some embodiments, said allele-specific oligonucleotide probes are labeled with a reporter dye and a quencher dye. In some embodiments, detecting the double-stranded hybridization complex comprises detecting the electrophoretic mobility of the double-stranded hybridization complex.

A variety of methods can be used to detect the presence or absence of a variant allele or haplotype. As an example, enzymatic amplification of nucleic acid from an individual may be used to obtain nucleic acid for subsequent analysis. The presence or absence of a variant allele or haplotype may also be determined directly from the individual's nucleic acid without enzymatic amplification.

Detecting the presence or absence of a variant allele or haplotype may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

Analysis of the nucleic acid from an individual, whether amplified or not, may be performed using any of various techniques. Useful techniques include, without limitation, polymerase chain reaction based analysis, sequence analysis and electrophoretic analysis. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

A TaqmanB allelic discrimination assay available from Applied Biosystems may be useful for determining the presence or absence of a variant allele. In a TaqmanB allelic discrimination assay, a specific, fluorescent, dye-labeled probe for each allele is constructed. The probes contain different fluorescent reporter dyes such as FAM and VICTM to differentiate the amplification of each allele. In addition, each probe has a quencher dye at one end which quenches fluorescence by fluorescence resonant energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MGB) group to a DNA probe as described, for example, in Kutyavin et al., "3'-minor groove binder-DNA probes increase sequence specificity at PCR extension temperature," Nucleic Acids Research 28:655-661 (2000)). Minor grove binders include, but are not limited to, compounds such as dihydrocyclopyrroloindole tripeptide (DPI).

Sequence analysis also may also be useful for determining the presence or absence of a variant allele or haplotype.

Restriction fragment length polymorphism (RFLP) analysis may also be useful for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization may also be used to detect a variant allele or haplotype. Allele-specific oligonucleotide hybridization is based on the use of a labeled oligonucleotide probe having a sequence perfectly complementary, for example, to the sequence encompassing a variant allele or haplotype. Under appropriate conditions, the allele-specific probe hybridizes to a nucleic acid containing the variant allele or haplotype but does not hybridize to the other alleles or haplotypes, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a variant allele or haplotype by using an allele-specific oligonucleotide primer that is perfectly complementary to the nucleotide sequence of the variant allele or haplotype but which has one or more mismatches as compared to other alleles or haplotypes (Mullis et al., supra, (1994)). One skilled in the art understands that the one or more nucleotide mismatches that distinguish between the variant allele or haplotype and the other alleles or haplotypes are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the variant allele or haplotype and the other alleles at the 3' end of the primer.

A heteroduplex mobility assay (HMA) is another well-known assay that may be used to detect a variant allele or haplotype. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

The technique of single strand conformational, polymorphism (SSCP) also may be used to detect the presence or absence of a variant allele or haplotype (see Hayashi, K., Methods Applic. 1:34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect a variant allele or haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of a variant allele or haplotype are known in the art and useful in the methods of the invention. Other well-known approaches for determining the presence or absence of a variant allele or haplotype include automated sequencing and RNAase mismatch techniques (Winter et al., Proc. Natl. Acad. Sci. 82:7575-7579 (1985)). Furthermore, one skilled in the art understands that, where the presence or absence of multiple alleles or haplotypes is to be determined, individual alleles or haplotypes can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that multiple alleles can be detected in individual reactions or in a single reaction (a "multiplex" assay). In view of the above, one skilled in the art realizes that the methods of the present invention may be practiced using one or any combination of the well-known assays described above or another art-recognized genetic assay.

Gene Identification

Various embodiments of the present invention provide for a method of identifying genes/genetic loci associated with a condition, comprising: acquiring genetic data from samples of a cohort of the condition; performing a GLS transformation on the genetic data, thereby decorrelating the genetic data; conducting gene-based analysis on the GLS-transformed genetic data; and identifying genes/genetic loci associated with the condition. In various embodiments, the condition is IBD, CD, or UC, or a combination thereof. In some embodiments, the cohort comprises correlated subjects or family subjects. In other embodiments, the genetic data comprise SNP genotypes. In yet other embodiments, performing the GLS transformation comprises transforming the genetic data according to functions $G=\Sigma_o^{-1/2}$, $Gy=GX\beta+Ge$, $\hat{\beta}_{GLS}=(X'\Sigma_o^{-1}X)^{-1}X'\Sigma_o^{-1}y$, $var(\hat{\beta}_{GLS})=var((X'\Sigma_o^{-1}X)^{-1}X'\Sigma_o^{-1}y)=(X'\Sigma_o^{-1}X)^{-1}$, or a combination thereof.

In various embodiments, conducting gene-based analysis comprises applying a gene-based test based on the assumption of independent or uncorrelated subjects. In various embodiments, conducting gene-based analysis comprises applying C-alpha, SKAT, SKAT-CommonRare, CMC, WSS, Variable Threshold, or Comprehensive Approach, or a combination thereof.

Various embodiments of the present invention provide a method of identifying genes/genetic loci associated with a condition. The method comprises: acquiring genetic data from samples of a cohort of the condition; performing a GLS transformation on the genetic data, thereby decorrelating the genetic data; conducting gene-based analysis on the GLS-transformed genetic data; and identifying genes/genetic loci associated with the condition. In various embodiments, the condition is IBD, CD, or UC, or a combination thereof.

In various embodiments, the cohort comprises correlated subjects or family subjects. In some embodiments, the cohort comprises cases subjects diagnosed with the condition. In some embodiments, the cohort comprises controls subjects who are healthy or not diagnosed with the condition. In various embodiments, the genetic data comprise SNP genotypes.

In various embodiments, performing the GLS transformation comprises transforming the genetic data according to functions (5)-(8), described above. In various embodiments, conducting gene-based analysis comprises applying a gene-based test based on the assumption of independent or uncorrelated subjects. In various embodiments, conducting gene-based analysis comprises applying C-alpha, SKAT, SKAT-CommonRare, CMC, WSS, Variable Threshold, or Comprehensive Approach, or a combination thereof.

Kits of the Invention

Various embodiments of the present invention also provide a kit. The kit may consist of or may consist essentially of or may comprise: one or more detection agents for detecting one or more alleles at one or more genes/genetic loci; instructions of using the agent to identify genes/genetic loci associated with a condition, and/or to prognose low or high probability of developing IBD, and/or to prognose susceptibility to or protection against IBD, and/or to diagnose IBD, and/or to treat IBD, and/or to direct administering an IBD therapy. In some embodiments, the one or more alleles are risk alleles associated with IBD.

Various embodiments of the present invention also provide a kit. The kit may consist of or may consist essentially of or may comprise: one or more detection agents for detecting one or more alleles at one or more genes/genetic loci; instructions of using the agent to identify genes/genetic loci associated with a condition. In various embodiments, the kit further comprises samples obtained from a cohort of the condition. In various embodiments, the condition is IBD, Crohn's disease (CD), or ulcerative colitis (UC).

Various embodiments of the present invention also provide a kit. The kit may consist of or may consist essentially of or may comprise: one or more detection agents for detecting one or more risk alleles at one or more genes/genetic loci; instructions of using the agent to prognose low or high probability of developing IBD, and/or to prognose susceptibility to or protection against IBD, and/or to diagnose IBD, and/or to treat IBD, and/or to direct administering an IBD therapy. In various embodiments, the risk alleles are associated with IBD. In various embodiments, the kit further comprises a sample obtained from a subject who desires prognosis, and/or diagnosis, and/or treatment of IBD. In various embodiments, the IBD is Crohn's disease (CD) or ulcerative colitis (UC).

In various embodiments, the one or more genes/genetic loci comprise 1, 2, 3, 4, 5, 6, 7, 8, 9, 10, 11, 12, 13, 14, or more, or all of the genes/genetic loci listed in Table 1 as SEQ ID NOs: 1-341. In various embodiments, the one or more genes/genetic loci comprise SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the one or more genes/genetic loci comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A.

In various embodiments, the kit further comprises an IBD therapy. Examples of the IBD therapy including but are not limited to anti-TNF therapy and anti-TL1A therapy. In some embodiments, the IBD therapy is an anti-TNF antibody. In some embodiments, the IBD therapy is an anti-TL1A antibody.

The kit is an assemblage of materials or components, including at least one of the inventive elements or modules. In various embodiments, the one or more detection agents specifically bind to one or more SNP's alleles. In some embodiments, the one or more SNP's alleles can be major alleles, minor alleles, or both. In some embodiments, the one or more SNP's alleles can be risk alleles, non-risk alleles, or protection alleles, or a combination thereof.

In some embodiments, the one or more detection agents specifically bind to one or more risk alleles listed in Table 1 as SEQ ID NOs: 1-341. In some embodiments, the one or more detection agents specifically bind to 1, 2, 3, 4, 5, 6, 7, 8, 9, 10, or more, or all of the risk alleles listed in Table 1 as SEQ ID NOs: 1-341. In various embodiments, the one or more detection agents specifically bind to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 99, or 100, or more, or all of the risk alleles listed in Table 1 as SEQ ID NOs: 1-341. In some embodiments, the one or more detection agents specifically bind to N of the risk alleles listed in Table 1, and wherein N is a positive integer not more than 341 (i.e., $1 \leq N \leq 341$). In various embodiments, the one or more detection agents specifically bind to 1-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, or 95-100 of the risk alleles listed in Table 1 as SEQ ID NOs: 1-341. In various embodiments, the one or more detection agents specifically bind to 100-105, 105-110, 110-115, 115-120, 120-125, 125-130, 130-135, 135-140, 140-145, 145-150, 150-155, 155-160, 160-165, 165-170, 170-175, 175-180, 180-185, 185-190, 190-195, or 195-200 of the risk alleles listed in Table 1 as SEQ ID NOs: 1-341. In various embodiments, the one or more detection agents specifically bind to 200-205, 205-210, 210-215, 215-220, 220-225, 325-230, 230-235, 235-240, 240-245, 245-250, 250-255, 255-260, 260-265, 265-270, 270-275, 275-280, 280-285, 285-290, 290-295, or 295-300 of the risk alleles listed in Table 1 as SEQ ID NOs: 1-341. In various embodiments, the one or more detection agents specifically bind to 300-305, 305-310, 310-315, 315-320, 320-325, 325-330, 330-335, 335-340, 340-341 of the risk alleles listed in Table 1 as SEQ ID NOs: 1-341.

In various embodiments, the one or more detection agents are applied to contact a biological sample obtained from the subject; and the level of binding between the one or more detection agents and the one or more alleles is detected. In some embodiments, the one or more detection agents are oligonucleotide probes, nucleic acids, DNAs, RNAs, peptides, proteins, antibodies, aptamers, or small molecules, or a combination thereof. In various embodiments, the level of binding is detected using a microarray. In some embodiments, the microarray is an oligonucleotide microarray, DNA microarray, cDNA microarrays, RNA microarray, peptide microarray, protein microarray, or antibody microarray, or a combination thereof.

In various embodiments, the one or detection agents are oligonucleotide probes specific to the one or more alleles. In various embodiments, the oligonucleotide probes are labeled with a fluorescent dye. In various embodiments, the oligonucleotide probes comprise reporter dyes and quencher dyes. In various embodiments, the kit further comprises a module configured to detecting fluorescence signal from the one or more detection agents. In various embodiments, the kit further comprises a module configured for conducting PCR amplification.

The exact nature of the components configured in the inventive kit depends on its intended purpose. Instructions for use may be included in the kit. "Instructions for use" typically include a tangible expression describing the technique to be employed in using the components of the kit to affect a desired outcome. Optionally, the kit also contains other useful components, such as, spray bottles or cans, diluents, buffers, pharmaceutically acceptable carriers, syringes, catheters, applicators (for example, applicators of cream, gel or lotion etc.), pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the detection agents can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in assays and therapies. As used herein, the term "package" refers to a suitable solid matrix or material such as glass, plastic, paper, foil, and the like, capable of holding the individual kit components. Thus, for example, a package can be a glass vial used to contain suitable quantities of a composition as described herein. The packaging material generally has an external label which indicates the contents and/or purpose of the kit and/or its components.

Novel Genes/Regions, SNPs and Risk Alleles

Table 1 provides information of genes/regions, SNPs, SEQ ID NOs (SEQ ID NO: 1-341) and risk alleles in accordance with various embodiments of the present invention. "Dis" stands for disease; "gene.i" stands for gene ID;

"SNP" stands for single nucleotide polymorphism; "rsID" stands for Reference SNP cluster ID (rs number); "chr" stands for chromosome; "pos_hg19" stands for position in human genome version 19; "pos_hg18" stands for position in human genome version 18; "A1" stands for minor allele; "A2" stands for major allele; "risk.allele" stands for the allele that leads to increased disease risk; "OR.risk.allele" stands for Odds Ratio in meta-analysis for the risk allele; "F_A_cedars" stands for minor allele frequency in Cedars affected cases; "F_U_cedars" stands for minor allele frequency in Cedars unaffected controls; "OR_cedars" stands for Odds Ratio in Cedars cohort; "SE_cedars" stands for Standard Error for log(OR) in Cedars cohort; "L95_cedars" stands for lower boundary of 95% Confidence Interval of OR in Cedars cohort; "U95_cedars" stands for upper boundary of 95% Confidence Interval of OR in Cedars cohort; "STAT_cedars" stands for test statistics (Z-value) in Cedars cohort; "P_cedars" stands for P-value in Cedars cohort; "F_A_iibdgc" stands for minor allele frequency in IIBDGC affected cases; "F_U_iibdgc" stands for minor allele frequency in IIBDGC unaffected controls; "OR_iibdgc" stands for Odds Ratio in IIBDGC cohort; "SE_iibdgc" stands for Standard Error for log(OR) in IIBDGC cohort; "L95_iibdgc" stands for lower boundary of 95% Confidence Interval of OR in IIBDGC cohort; "U95_iibdgc" stands for upper boundary of 95% Confidence Interval of OR in IIBDGC cohort; "STAT_iibdgc" stands for test statistics (Z statistics) in IIBDGC cohort; "P_iibdgc" stands for P-value in IIBDGC cohort; "beta_meta_fixed" stands for log(OR) in meta-analysis; "se_meta_fixed" stands for Standard Error of log(OR) in meta-analysis; and "P_meta_fixed" stands for P-value in meta-analysis.

TABLE 1

(part 1)

| dis | gene.i | SNP | rsID | SEQ ID NO | chr | pos_hg19 | pos_hg18 | A 1 | A 2 | risk allele | OR.risk. allele |
|---|---|---|---|---|---|---|---|---|---|---|---|
| CD | SLC26A4 | rs10247487 | rs10247487 | 1 | 7 | 107420354 | 107207590 | A | G | G | 1.060282 |
| CD | SLC26A4 | rs10263826 | rs10263826 | 2 | 7 | 107421072 | 107208308 | G | A | A | 1.065343 |
| CD | SLC26A4 | rs10273733 | rs10273733 | 3 | 7 | 107258121 | 107045357 | A | G | A | 1.064739 |
| CD | SLC26A4 | rs12539555 | rs12539555 | 4 | 7 | 107404473 | 107191709 | G | A | G | 1.03454 |
| CD | SLC26A4 | rs2248465 | rs2248465 | 5 | 7 | 107303628 | 107090864 | G | A | G | 1.06059 |
| CD | SLC26A4 | rs2808 | rs2808 | 6 | 7 | 107260856 | 107048092 | A | G | A | 1.074763 |
| CD | DLG4 | rs3785794 | rs3785794 | 7 | 17 | 7005915 | 6946639 | A | G | G | 1.11467 |
| CD | GIPR | chr19:50983512 | rs55681266 | 8 | 19 | 46291672 | 50983512 | A | C | C | 1.065155 |
| CD | GIPR | chr19:51014231 | rs56243424 | 9 | 19 | 46322391 | 51014231 | A | G | G | 1.069862 |
| CD | GIPR | chr19:51026971 | rs73047896 | 10 | 19 | 46335131 | 51026971 | G | A | A | 1.073444 |
| CD | GIPR | rs10401439 | rs10401439 | 11 | 19 | 46320780 | 51012620 | A | G | G | 1.077122 |
| CD | GIPR | rs10402263 | rs10402263 | 12 | 19 | 46313758 | 51005598 | C | G | G | 1.062002 |
| CD | GIPR | rs10421891 | rs10421891 | 13 | 19 | 46315809 | 51007649 | G | A | A | 1.067512 |
| CD | GIPR | rs10500292 | rs10500292 | 14 | 19 | 46327933 | 51019773 | A | G | G | 1.065373 |
| CD | GIPR | rs11883351 | rs11883351 | 15 | 19 | 46304400 | 50996240 | A | G | G | 1.068662 |
| CD | GIPR | rs12463359 | rs12463359 | 16 | 19 | 46304585 | 50996425 | A | C | C | 1.063059 |
| CD | GIPR | rs16980013 | rs16980013 | 17 | 19 | 46267453 | 50959293 | A | C | C | 1.066731 |
| CD | GIPR | rs16980051 | rs16980051 | 18 | 19 | 46345886 | 51037726 | A | G | G | 1.063307 |
| CD | GIPR | rs17878252 | rs17878252 | 19 | 19 | 46234155 | 50925995 | A | G | G | 1.066875 |
| CD | GIPR | rs2070736 | rs2070736 | 20 | 19 | 46286714 | 50978554 | C | A | A | 1.068257 |
| CD | GIPR | rs2334255 | rs2334255 | 21 | 19 | 46186150 | 50877990 | A | C | A | 1.051486 |
| CD | GIPR | rs4514788 | rs4514788 | 22 | 19 | 46317593 | 51009433 | C | A | A | 1.060853 |
| CD | GIPR | rs4802273 | rs4802273 | 23 | 19 | 46244060 | 50935900 | G | A | A | 1.068602 |
| CD | GIPR | rs4802274 | rs4802274 | 24 | 19 | 46251768 | 50943608 | G | A | A | 1.069354 |
| CD | GIPR | rs4803861 | rs4803861 | 25 | 19 | 46328179 | 51020019 | A | G | G | 1.071572 |
| CD | GIPR | rs8111071 | rs8111071 | 26 | 19 | 46307406 | 50999246 | G | A | G | 1.075838 |
| CD | GIPR | rs918490 | rs918490 | 27 | 19 | 46338729 | 51030569 | A | G | G | 1.073866 |
| CD | ZHX3 | rs6072275 | rs6072275 | 28 | 20 | 39743905 | 39177319 | A | G | A | 1.086747 |
| CD | ZHX3 | rs6072343 | rs6072343 | 29 | 20 | 39968188 | 39401602 | A | G | A | 1.100691 |
| CD | ZHX3 | rs6093462 | rs6093462 | 30 | 20 | 39908689 | 39342103 | A | G | G | 1.075153 |
| CD | TNRC6B | rs114607 | rs114607 | 31 | 22 | 40376383 | 38706329 | A | G | G | 1.04635 |
| CD | TNRC6B | rs137955 | rs137955 | 32 | 22 | 40291807 | 38621753 | A | G | A | 1.049438 |
| CD | TNRC6B | rs137956 | rs137956 | 33 | 22 | 40293463 | 38623409 | G | A | G | 1.053575 |
| CD | TNRC6B | rs137977 | rs137977 | 34 | 22 | 40320361 | 38650307 | A | C | C | 1.032278 |
| CD | TNRC6B | rs137981 | rs137981 | 35 | 22 | 40327206 | 38657152 | G | A | A | 1.055186 |
| CD | TNRC6B | rs138027 | rs138027 | 36 | 22 | 40616112 | 38946058 | G | A | A | 1.049378 |
| CD | TNRC6B | rs2958647 | rs2958647 | 37 | 22 | 40291139 | 38621085 | C | A | C | 1.050825 |
| CD | TNRC6B | rs713925 | rs713925 | 38 | 22 | 40299158 | 38629104 | C | A | A | 1.035056 |
| UC | CDK6 | rs2282978 | rs2282978 | 39 | 7 | 92264410 | 92102346 | G | A | A | 1.080458 |
| UC | CDK6 | rs4272 | rs4272 | 40 | 7 | 92236829 | 92074765 | G | A | A | 1.068931 |
| UC | PRR5L | rs11033597 | rs11033597 | 41 | 11 | 36429876 | 36386452 | A | G | A | 1.068317 |
| UC | PRR5L | rs11600757 | rs11600757 | 42 | 11 | 36473784 | 36430360 | A | G | A | 1.082739 |
| UC | PRR5L | rs11601211 | rs11601211 | 43 | 11 | 36465159 | 36421735 | G | A | G | 1.063202 |
| UC | PRR5L | rs12281565 | rs12281565 | 44 | 11 | 36471571 | 36428147 | G | A | G | 1.079272 |
| UC | PRR5L | rs1365120 | rs1365120 | 45 | 11 | 36438075 | 36394651 | G | A | G | 1.179 |
| UC | PRR5L | rs1895840 | rs1895840 | 46 | 11 | 36424277 | 36380853 | G | A | G | 1.061208 |
| UC | PRR5L | rs2303439 | rs2303439 | 47 | 11 | 36514290 | 36470866 | A | G | A | 1.071103 |
| UC | PRR5L | rs330260 | rs330260 | 48 | 11 | 36422172 | 36378748 | G | A | G | 1.054865 |
| UC | PRR5L | rs331485 | rs331485 | 49 | 11 | 36454231 | 36410807 | A | G | G | 1.064878 |
| UC | PRR5L | rs4077044 | rs4077044 | 50 | 11 | 36412655 | 36369231 | C | A | C | 1.038306 |
| UC | PRR5L | rs5030437 | rs5030437 | 51 | 11 | 36524755 | 36481331 | A | G | A | 1.066163 |
| UC | PRR5L | rs5030445 | rs5030445 | 52 | 11 | 36522260 | 36478836 | A | G | A | 1.064399 |
| UC | PRR5L | rs5030472 | rs5030472 | 53 | 11 | 36513786 | 36470362 | A | G | A | 1.081762 |
| UC | PRR5L | rs7929195 | rs35403761 | 54 | 11 | 36458586 | 36415162 | A | C | C | 1.051966 |

TABLE 1-continued

| | | | | | | | | | | | |
|---|---|---|---|---|---|---|---|---|---|---|---|
| IBD | WNT2B | rs10745330 | rs10745330 | 55 | 1 | 113083439 | 112884962 | A | G | A | 1.047821 |
| IBD | WNT2B | rs2999155 | rs2999155 | 56 | 1 | 113221658 | 113023181 | G | A | G | 1.045707 |
| IBD | WNT2B | rs3790609 | rs3790609 | 57 | 1 | 113056990 | 112858513 | A | G | A | 1.059618 |
| IBD | WNT2B | rs6682737 | rs6682737 | 58 | 1 | 113136229 | 112937752 | G | A | G | 1.046411 |
| IBD | LRRC16A | rs10456320 | rs10456320 | 59 | 6 | 25292401 | 25400380 | A | G | A | 1.071532 |
| IBD | LRRC16A | rs11755567 | rs11755567 | 60 | 6 | 25237288 | 25345267 | A | G | G | 1.049589 |
| IBD | LRRC16A | rs13191296 | rs13191296 | 61 | 6 | 25684606 | 25792585 | A | G | G | 1.094237 |
| IBD | LRRC16A | rs2690110 | rs2690110 | 62 | 6 | 25328567 | 25436546 | G | A | G | 1.060658 |
| IBD | LRRC16A | rs4712908 | rs4712908 | 63 | 6 | 25320920 | 25428899 | A | G | G | 1.038597 |
| IBD | LRRC16A | rs6921589 | rs6921589 | 64 | 6 | 25422369 | 25530348 | A | C | C | 1.06713 |
| IBD | LRRC16A | rs6937918 | rs6937918 | 65 | 6 | 25407295 | 25515274 | A | G | A | 1.035383 |
| IBD | LRRC16A | rs742132 | rs742132 | 66 | 6 | 25607571 | 25715550 | G | A | G | 1.03153 |
| IBD | LRRC16A | rs7752195 | rs7752195 | 67 | 6 | 25419094 | 25527073 | A | G | G | 1.106969 |
| IBD | LRRC16A | rs7752524 | rs7752524 | 68 | 6 | 25310585 | 25418564 | G | A | G | 1.088791 |
| IBD | LRRC16A | rs7762757 | rs7762757 | 69 | 6 | 25420992 | 25528971 | T | A | T | 1.032075 |
| IBD | LRRC16A | rs880226 | rs880226 | 70 | 6 | 25402303 | 25510282 | G | A | G | 1.033746 |
| IBD | LRRC16A | rs9295661 | rs9295661 | 71 | 6 | 25450026 | 25558005 | C | A | A | 1.105753 |
| IBD | LRRC16A | rs9358854 | rs9358854 | 72 | 6 | 25411464 | 25519443 | A | G | G | 1.038355 |
| IBD | LRRC16A | rs9461157 | rs9461157 | 73 | 6 | 25400323 | 25508302 | A | G | A | 1.035385 |
| IBD | LRRC16A | rs9461165 | rs9461165 | 74 | 6 | 25406932 | 25514911 | G | A | G | 1.036141 |
| IBD | LRRC16A | rs9467445 | rs9467445 | 75 | 6 | 25234884 | 25342863 | G | A | A | 1.054554 |
| IBD | All Histone cluster1 gene | rs10484399 | rs10484399 | 76 | 6 | 27534528 | 27642507 | G | A | A | 1.081187 |
| IBD | All Histone cluster1 gene | rs10484439 | rs10484439 | 77 | 6 | 26309908 | 26417887 | A | G | G | 1.077614 |
| IBD | All Histone cluster1 gene | rs12176317 | rs12176317 | 78 | 6 | 26372786 | 26480765 | G | A | A | 1.065838 |
| IBD | All Histone cluster1 gene | rs13194053 | rs13194053 | 79 | 6 | 27143883 | 27251862 | G | A | A | 1.055137 |
| IBD | All Histone cluster1 gene | rs13194491 | rs13194491 | 80 | 6 | 27037080 | 27145059 | A | G | A | 1.050167 |
| IBD | All Histone cluster1 gene | rs13194781 | rs13194781 | 81 | 6 | 27815639 | 27923618 | G | A | A | 1.080774 |
| IBD | All Histone cluster1 gene | rs13195040 | rs13195040 | 82 | 6 | 27413924 | 27521903 | G | A | A | 1.086088 |
| IBD | All Histone cluster1 gene | rs13199772 | rs13199772 | 83 | 6 | 27834085 | 27942064 | G | A | A | 1.080476 |
| IBD | All Histone cluster1 gene | rs13212651 | rs13212651 | 84 | 6 | 27806985 | 27914964 | G | A | A | 1.081515 |
| IBD | All Histone cluster1 gene | rs1321578 | rs1321578 | 85 | 6 | 27104783 | 27212762 | C | A | A | 1.073664 |
| IBD | All Histone cluster1 gene | rs13217599 | rs13217599 | 86 | 6 | 27586230 | 27694209 | G | A | G | 1.058743 |
| IBD | All Histone cluster1 gene | rs13218875 | rs13218875 | 87 | 6 | 27884012 | 27991991 | A | G | G | 1.081223 |
| IBD | All Histone cluster1 gene | rs13219354 | rs13219354 | 88 | 6 | 27185664 | 27293643 | G | A | A | 1.062354 |
| IBD | All Histone cluster1 gene | rs16867901 | rs16867901 | 89 | 6 | 27656076 | 27764055 | A | G | G | 1.199385 |

TABLE 1-continued

| | | | | | | | | | | | |
|---|---|---|---|---|---|---|---|---|---|---|---|
| IBD | All Histone cluster1 gene | rs16867911 | rs16867911 | 90 | 6 | 27662204 | 27770183 | A | C | C | 1.182881 |
| IBD | All Histone cluster1 gene | rs16891725 | rs16891725 | 91 | 6 | 26479150 | 26587129 | A | G | G | 1.064118 |
| IBD | All Histone cluster1 gene | rs175597 | rs175597 | 92 | 6 | 27810626 | 27918605 | G | A | A | 1.088234 |
| IBD | All Histone cluster1 gene | rs17693963 | rs17693963 | 93 | 6 | 27710165 | 27818144 | C | A | A | 1.06249 |
| IBD | All Histone cluster1 gene | rs17739310 | rs17739310 | 94 | 6 | 27296775 | 27404754 | A | G | A | 1.045616 |
| IBD | All Histone cluster1 gene | rs17750424 | rs17750424 | 95 | 6 | 27701122 | 27809101 | G | A | A | 1.10485 |
| IBD | All Histone cluster1 gene | rs1977 | rs1977 | 96 | 6 | 26377546 | 26485525 | G | A | A | 1.066601 |
| IBD | All Histone cluster1 gene | rs1985732 | rs1985732 | 97 | 6 | 26376161 | 26484140 | G | A | A | 1.028229 |
| IBD | All Histone cluster1 gene | rs200483 | rs200483 | 98 | 6 | 27774824 | 27882803 | A | G | G | 1.085554 |
| IBD | All Histone cluster1 gene | rs200484 | rs200484 | 99 | 6 | 27775674 | 27883653 | G | A | A | 1.085885 |
| IBD | All Histone cluster1 gene | rs200490 | rs200490 | 100 | 6 | 27796935 | 27904914 | A | C | C | 1.086946 |
| IBD | All Histone cluster1 gene | rs200501 | rs200501 | 101 | 6 | 27788942 | 27896921 | A | G | G | 1.082685 |
| IBD | All Histone cluster1 gene | rs200948 | rs200948 | 102 | 6 | 27835272 | 27943251 | G | A | A | 1.089064 |
| IBD | All Histone cluster1 gene | rs200953 | rs200953 | 103 | 6 | 27837267 | 27945246 | G | A | A | 1.08938 |
| IBD | All Histone cluster1 gene | rs200989 | rs200989 | 104 | 6 | 27816442 | 27924421 | G | A | A | 1.088773 |
| IBD | All Histone cluster1 gene | rs200990 | rs200990 | 105 | 6 | 27815823 | 27923802 | C | A | A | 1.090237 |
| IBD | All Histone cluster1 gene | rs200991 | rs200991 | 106 | 6 | 27815494 | 27923473 | A | C | C | 1.037049 |
| IBD | All Histone cluster1 gene | rs200995 | rs200995 | 107 | 6 | 27813694 | 27921673 | G | A | A | 1.088144 |
| IBD | All Histone cluster1 gene | rs201002 | rs201002 | 108 | 6 | 27808192 | 27916171 | G | A | A | 1.08662 |
| IBD | All Histone cluster1 gene | rs201004 | rs201004 | 109 | 6 | 27804934 | 27912913 | G | A | A | 1.032214 |

TABLE 1-continued

| | | | | | | | | | | | |
|---|---|---|---|---|---|---|---|---|---|---|---|
| IBD | All Histone cluster1 gene | rs2064092 | rs2064092 | 110 | 6 | 27511371 | 27619350 | A | C | A | 1.051684 |
| IBD | All Histone cluster1 gene | rs2072806 | rs2072806 | 111 | 6 | 26385093 | 26493072 | G | C | C | 1.051691 |
| IBD | All Histone cluster1 gene | rs2073529 | rs2073529 | 112 | 6 | 26375159 | 26483138 | G | A | A | 1.05463 |
| IBD | All Histone cluster1 gene | rs2093169 | rs2093169 | 113 | 6 | 26495099 | 26603078 | A | G | G | 1.040318 |
| IBD | All Histone cluster1 gene | rs2393997 | rs2393997 | 114 | 6 | 27670697 | 27778676 | A | C | C | 1.036294 |
| IBD | All Histone cluster1 gene | rs2494711 | rs2494711 | 115 | 6 | 26649421 | 26757400 | A | G | A | 1.031221 |
| IBD | All Histone cluster1 gene | rs2747054 | rs2747054 | 116 | 6 | 27783359 | 27891338 | G | A | A | 1.087876 |
| IBD | All Histone cluster1 gene | rs2893910 | rs2893910 | 117 | 6 | 27283254 | 27391233 | A | T | T | 1.043311 |
| IBD | All Histone cluster1 gene | rs34706883 | rs34706883 | 118 | 6 | 27805255 | 27913234 | C | A | A | 1.080478 |
| IBD | All Histone cluster1 gene | rs370155 | rs370155 | 119 | 6 | 27782031 | 27890010 | C | A | A | 1.086886 |
| IBD | All Histone cluster1 gene | rs3799378 | rs3799378 | 120 | 6 | 26404374 | 26512353 | G | A | A | 1.043914 |
| IBD | All Histone cluster1 gene | rs3799380 | rs3799380 | 121 | 6 | 26467182 | 26575161 | G | A | A | 1.038428 |
| IBD | All Histone cluster1 gene | rs3799383 | rs3799383 | 122 | 6 | 26510748 | 26618727 | A | G | G | 1.056523 |
| IBD | All Histone cluster1 gene | rs3800307 | rs3800307 | 123 | 6 | 27185792 | 27293771 | T | A | A | 1.048767 |
| IBD | All Histone cluster1 gene | rs3800316 | rs3800316 | 124 | 6 | 27256102 | 27364081 | C | A | A | 1.042094 |
| IBD | All Histone cluster1 gene | rs4452638 | rs4452638 | 125 | 6 | 27229265 | 27337244 | A | G | G | 1.059797 |
| IBD | All Histone cluster1 gene | rs4634439 | rs4634439 | 126 | 6 | 26598004 | 26705983 | G | A | A | 1.064038 |
| IBD | All Histone cluster1 gene | rs4712981 | rs4712981 | 127 | 6 | 26361430 | 26469409 | A | G | G | 1.030139 |
| IBD | All Histone cluster1 gene | rs4713119 | rs4713119 | 128 | 6 | 27712825 | 27820804 | G | A | A | 1.035871 |
| IBD | All Histone cluster1 gene | rs6456728 | rs6456728 | 129 | 6 | 26477779 | 26585758 | A | G | G | 1.038342 |

TABLE 1-continued

| | | | | | | | | | | | |
|---|---|---|---|---|---|---|---|---|---|---|---|
| IBD | All Histone cluster1 gene | rs6904071 | rs6904071 | 130 | 6 | 27047256 | 27155235 | A | G | G | 1.053969 |
| IBD | All Histone cluster1 gene | rs6904596 | rs6904596 | 131 | 6 | 27491299 | 27599278 | A | G | G | 1.092306 |
| IBD | All Histone cluster1 gene | rs6913660 | rs6913660 | 132 | 6 | 27091425 | 27199404 | A | C | C | 1.053669 |
| IBD | All Histone cluster1 gene | rs6915101 | rs6915101 | 133 | 6 | 27741682 | 27849661 | A | G | G | 1.107933 |
| IBD | All Histone cluster1 gene | rs6920256 | rs6920256 | 134 | 6 | 26537801 | 26645780 | A | G | G | 1.06397 |
| IBD | All Histone cluster1 gene | rs6923139 | rs6923139 | 135 | 6 | 26313348 | 26421327 | A | G | G | 1.082433 |
| IBD | All Histone cluster1 gene | rs6932590 | rs6932590 | 136 | 6 | 27248931 | 27356910 | G | A | A | 1.054939 |
| IBD | All Histone cluster1 gene | rs6933583 | rs6933583 | 137 | 6 | 26355283 | 26463262 | C | A | A | 1.029881 |
| IBD | All Histone cluster1 gene | rs6934794 | rs6934794 | 138 | 6 | 27519345 | 27627324 | A | G | A | 1.039168 |
| IBD | All Histone cluster1 gene | rs6938200 | rs6938200 | 139 | 6 | 27231150 | 27339129 | G | A | A | 1.055915 |
| IBD | All Histone cluster1 gene | rs721600 | rs721600 | 140 | 6 | 27298905 | 27406884 | A | G | A | 1.052598 |
| IBD | All Histone cluster1 gene | rs7745603 | rs7745603 | 141 | 6 | 27090404 | 27198383 | A | G | G | 1.03892 |
| IBD | All Histone cluster1 gene | rs7746199 | rs7746199 | 142 | 6 | 27261324 | 27369303 | A | G | G | 1.033691 |
| IBD | All Histone cluster1 gene | rs7749305 | rs7749305 | 143 | 6 | 27446566 | 27554545 | G | A | A | 1.091115 |
| IBD | All Histone cluster1 gene | rs7749319 | rs7749319 | 144 | 6 | 27126460 | 27234439 | A | G | G | 1.070772 |
| IBD | All Histone cluster1 gene | rs7756567 | rs7756567 | 145 | 6 | 26481642 | 26589621 | C | A | A | 1.039822 |
| IBD | All Histone cluster1 gene | rs7773938 | rs7773938 | 146 | 6 | 26474044 | 26582023 | A | G | G | 1.039994 |
| IBD | All Histone cluster1 gene | rs911186 | rs911186 | 147 | 6 | 27150599 | 27258578 | G | A | A | 1.07032 |
| IBD | All Histone cluster1 gene | rs9295739 | rs9295739 | 148 | 6 | 27662395 | 27770374 | A | G | G | 1.187594 |
| IBD | All Histone cluster1 gene | rs9295749 | rs9295749 | 149 | 6 | 27767395 | 27875374 | A | G | A | 1.051982 |

TABLE 1-continued

| | | | | | | | | | | | |
|---|---|---|---|---|---|---|---|---|---|---|---|
| IBD | All Histone cluster1 gene | rs9358944 | rs9358944 | 150 | 6 | 26469875 | 26577854 | C | A | A | 1.040086 |
| IBD | All Histone cluster1 gene | rs9358945 | rs9358945 | 151 | 6 | 26472114 | 26580093 | G | A | A | 1.040079 |
| IBD | All Histone cluster1 gene | rs9358946 | rs9358946 | 152 | 6 | 26478927 | 26586906 | A | G | G | 1.044383 |
| IBD | All Histone cluster1 gene | rs9366653 | rs9366653 | 153 | 6 | 26354247 | 26462226 | A | G | G | 1.062054 |
| IBD | All Histone cluster1 gene | rs9366658 | rs9366658 | 154 | 6 | 26469866 | 26577845 | A | G | G | 1.040086 |
| IBD | All Histone cluster1 gene | rs9379844 | rs9379844 | 155 | 6 | 26291527 | 26399506 | A | G | A | 1.023444 |
| IBD | All Histone cluster1 gene | rs9379851 | rs9379851 | 156 | 6 | 26354780 | 26462759 | C | A | A | 1.062436 |
| IBD | All Histone cluster1 gene | rs9379856 | rs9379856 | 157 | 6 | 26366836 | 26474815 | C | A | A | 1.058985 |
| IBD | All Histone cluster1 gene | rs9379858 | rs9379858 | 158 | 6 | 26367689 | 26475668 | G | A | A | 1.06275 |
| IBD | All Histone cluster1 gene | rs9379859 | rs9379859 | 159 | 6 | 26369549 | 26477528 | A | G | G | 1.06306 |
| IBD | All Histone cluster1 gene | rs9379870 | rs72402459 | 160 | 6 | 26374410 | 26482389 | G | A | A | 1.030307 |
| IBD | All Histone cluster1 gene | rs9379897 | rs9379897 | 161 | 6 | 26601526 | 26709505 | G | A | A | 1.064283 |
| IBD | All Histone cluster1 gene | rs9393691 | rs9393691 | 162 | 6 | 26272829 | 26380808 | G | A | G | 1.024334 |
| IBD | All Histone cluster1 gene | rs9393705 | rs9393705 | 163 | 6 | 26361011 | 26468990 | A | G | G | 1.06191 |
| IBD | All Histone cluster1 gene | rs9393708 | rs9393708 | 164 | 6 | 26362643 | 26470622 | G | A | A | 1.06285 |
| IBD | All Histone cluster1 gene | rs9393713 | rs9393713 | 165 | 6 | 26373678 | 26481657 | A | G | G | 1.065096 |
| IBD | All Histone cluster1 gene | rs9393714 | rs9393714 | 166 | 6 | 26373740 | 26481719 | A | C | C | 1.072207 |
| IBD | All Histone cluster1 gene | rs9393777 | rs9393777 | 167 | 6 | 26942027 | 27050006 | G | A | A | 1.053641 |
| IBD | All Histone cluster1 gene | rs9461362 | rs9461362 | 168 | 6 | 27303927 | 27411906 | A | G | A | 1.044123 |
| IBD | All Histone cluster1 gene | rs9467704 | rs9467704 | 169 | 6 | 26319486 | 26427465 | A | G | G | 1.078175 |

TABLE 1-continued

| | | | | | | | | | | | |
|---|---|---|---|---|---|---|---|---|---|---|---|
| IBD | All Histone cluster1 gene | rs9468152 | rs9468152 | 170 | 6 | 27492906 | 27600885 | C | A | C | 1.054429 |
| IBD | All Histone cluster1 gene | rs9468159 | rs9468159 | 171 | 6 | 27522374 | 27630353 | A | G | A | 1.054638 |
| IBD | All Histone cluster1 gene | rs9468202 | rs9468202 | 172 | 6 | 27688630 | 27796609 | G | A | A | 1.205805 |
| IBD | All Histone cluster1 gene | rs9468227 | rs9468227 | 173 | 6 | 27746342 | 27854321 | G | A | A | 1.12639 |
| IBD | GTF2IRD2B | imm_7_74094413 | rs138546574 | 174 | 7 | 74456477 | 74094413 | G | A | A | 1.152605 |
| IBD | GTF2IRD2B | imm_7_74108242 | rs200682695 | 175 | 7 | 74470306 | 74108242 | A | G | G | 1.046913 |
| IBD | GTF2IRD2B | imm_7_74117236 | rs111889192 | 176 | 7 | 74479300 | 74117236 | A | C | C | 1.139471 |
| IBD | GTF2IRD2B | imm_7_74118166 | rs4731019 | 177 | 7 | 74480230 | 74118166 | G | A | A | 1.040123 |
| IBD | GTF2IRD2B | imm_7_74120730 | rs111457769 | 178 | 7 | 74482794 | 74120730 | G | A | A | 1.07638 |
| IBD | GTF2IRD2B | imm_7_74133859 | rs801068 | 179 | 7 | 74495923 | 74133859 | G | A | A | 1.0382 |
| IBD | GTF2IRD2B | imm_7_74145400 | rs113516730 | 180 | 7 | 74507464 | 74145400 | A | T | T | 1.037022 |
| IBD | ETS1 | imm_11_127760024 | rs34271980 | 181 | 11 | 128254814 | 127760024 | T | A | T | 1.043861 |
| IBD | ETS1 | imm_11_127761269 | rs7118804 | 182 | 11 | 128256059 | 127761269 | G | A | G | 1.046577 |
| IBD | ETS1 | imm_11_127765567 | rs11600923 | 183 | 11 | 128260357 | 127765567 | A | G | A | 1.050849 |
| IBD | ETS1 | imm_11_127767721 | rs73025060 | 184 | 11 | 128262511 | 127767721 | G | A | A | 1.082772 |
| IBD | ETS1 | imm_11_127770666 | rs11824169 | 185 | 11 | 128265456 | 127770666 | A | C | A | 1.028063 |
| IBD | ETS1 | imm_11_127770668 | rs11824170 | 186 | 11 | 128265458 | 127770668 | A | G | A | 1.027116 |
| IBD | ETS1 | imm_11_127774308 | rs76299412 | 187 | 11 | 128269098 | 127774308 | A | G | A | 1.048341 |
| IBD | ETS1 | imm_11_127775128 | rs11605437 | 188 | 11 | 128269918 | 127775128 | G | A | G | 1.046927 |
| IBD | ETS1 | imm_11_127776527 | rs75500046 | 189 | 11 | 128271317 | 127776527 | A | G | G | 1.085488 |
| IBD | ETS1 | imm_11_127776913 | rs118033474 | 190 | 11 | 128271703 | 127776913 | A | G | G | 1.084318 |
| IBD | ETS1 | imm_11_127777217 | rs4937327 | 191 | 11 | 128272007 | 127777217 | C | G | G | 1.03851 |
| IBD | ETS1 | imm_11_127778327 | rs55781388 | 192 | 11 | 128273117 | 127778327 | G | C | G | 1.028 |
| IBD | ETS1 | imm_11_127778329 | rs201456100 | 193 | 11 | 128273119 | 127778329 | C | G | C | 1.032237 |
| IBD | ETS1 | imm_11_127779030 | rs74563193 | 194 | 11 | 128273820 | 127779030 | A | G | G | 1.078295 |
| IBD | ETS1 | imm_11_127780425 | rs74349003 | 195 | 11 | 128275215 | 127780425 | G | C | G | 1.07275 |
| IBD | ETS1 | imm_11_127780902 | rs9943540 | 196 | 11 | 128275692 | 127780902 | G | A | A | 1.077284 |
| IBD | ETS1 | imm_11_127781839 | rs73025076 | 197 | 11 | 128276629 | 127781839 | G | A | G | 1.033321 |
| IBD | ETS1 | imm_11_127785739 | rs10893865 | 198 | 11 | 128280529 | 127785739 | A | C | C | 1.035632 |
| IBD | ETS1 | imm_11_127785963 | rs11606595 | 199 | 11 | 128280753 | 127785963 | A | G | A | 1.053418 |
| IBD | ETS1 | imm_11_127786010 | rs7106191 | 200 | 11 | 128280800 | 127786010 | A | G | A | 1.038393 |
| IBD | ETS1 | imm_11_127786836 | rs7123188 | 201 | 11 | 128281626 | 127786836 | G | A | G | 1.037267 |
| IBD | ETS1 | imm_11_127787128 | rs11221287 | 202 | 11 | 128281918 | 127787128 | A | C | A | 1.040202 |
| IBD | ETS1 | imm_11_127788828 | rs10893866 | 203 | 11 | 128283618 | 127788828 | A | C | C | 1.034095 |
| IBD | ETS1 | imm_11_127789306 | rs34431347 | 204 | 11 | 128284096 | 127789306 | G | A | G | 1.037423 |
| IBD | ETS1 | imm_11_127789441 | rs34666372 | 205 | 11 | 128284231 | 127789441 | G | A | G | 1.037304 |
| IBD | ETS1 | imm_11_127791651 | rs11602703 | 206 | 11 | 128286441 | 127791651 | G | A | G | 1.055438 |
| IBD | ETS1 | imm_11_127792287 | rs11221290 | 207 | 11 | 128287077 | 127792287 | A | G | A | 1.036389 |
| IBD | ETS1 | imm_11_127792800 | rs55977286 | 208 | 11 | 128287590 | 127792800 | T | A | T | 1.068345 |
| IBD | ETS1 | imm_11_127793060 | rs12274537 | 209 | 11 | 128287850 | 127793060 | G | A | G | 1.034643 |
| IBD | ETS1 | imm_11_127794685 | rs11604454 | 210 | 11 | 128289475 | 127794685 | G | A | G | 1.05281 |
| IBD | ETS1 | imm_11_127795453 | rs10893867 | 211 | 11 | 128290243 | 127795453 | G | A | G | 1.034646 |
| IBD | ETS1 | imm_11_127796816 | rs117812848 | 212 | 11 | 128291606 | 127796816 | G | A | A | 5.285412 |
| IBD | ETS1 | imm_11_127797523 | rs34747435 | 213 | 11 | 128292313 | 127797523 | A | T | A | 1.034896 |
| IBD | ETS1 | imm_11_127798230 | rs10790952 | 214 | 11 | 128293020 | 127798230 | G | A | A | 1.028462 |
| IBD | ETS1 | imm_11_127799892 | rs2276445 | 215 | 11 | 128294682 | 127799892 | C | G | C | 1.025932 |
| IBD | ETS1 | imm_11_127804916 | rs7108537 | 216 | 11 | 128299706 | 127804916 | C | A | A | 1.033856 |
| IBD | ETS1 | imm_11_127805367 | rs80111275 | 217 | 11 | 128300157 | 127805367 | C | A | A | 1.077566 |
| IBD | ETS1 | imm_11_127806163 | rs10893870 | 218 | 11 | 128300953 | 127806163 | G | A | G | 1.027263 |
| IBD | ETS1 | imm_11_127806304 | rs76647218 | 219 | 11 | 128301094 | 127806304 | A | G | G | 1.082183 |
| IBD | ETS1 | imm_11_127807384 | rs10750399 | 220 | 11 | 128302174 | 127807384 | A | G | A | 1.030051 |
| IBD | ETS1 | imm_11_127808758 | rs11826011 | 221 | 11 | 128303548 | 127808758 | A | G | G | 1.075004 |
| IBD | ETS1 | imm_11_127809308 | rs116927266 | 222 | 11 | 128304098 | 127809308 | A | G | G | 1.1969 |
| IBD | ETS1 | imm_11_127812329 | rs55850544 | 223 | 11 | 128307119 | 127812329 | G | A | G | 1.059518 |
| IBD | ETS1 | imm_11_127812420 | rs7119657 | 224 | 11 | 128307210 | 127812420 | A | C | A | 2.813 |
| IBD | ETS1 | imm_11_127813024 | rs12794572 | 225 | 11 | 128307814 | 127813024 | G | A | G | 1.027018 |
| IBD | ETS1 | imm_11_127819226 | rs9665767 | 226 | 11 | 128314016 | 127819226 | G | A | G | 1.029511 |
| IBD | ETS1 | imm_11_127822686 | rs58847936 | 227 | 11 | 128317476 | 127822686 | A | G | G | 1.079299 |
| IBD | ETS1 | imm_11_127823420 | rs117607284 | 228 | 11 | 128318210 | 127823420 | G | A | A | 1.196872 |
| IBD | ETS1 | imm_11_127824356 | rs4285885 | 229 | 11 | 128319146 | 127824356 | A | G | A | 1.03201 |
| IBD | ETS1 | imm_11_127825016 | rs73581085 | 230 | 11 | 128319806 | 127825016 | G | C | C | 1.076388 |
| IBD | ETS1 | imm_11_127825282 | rs4612820 | 231 | 11 | 128320072 | 127825282 | A | G | A | 1.026511 |
| IBD | ETS1 | imm_11_127825669 | rs11600936 | 232 | 11 | 128320459 | 127825669 | A | G | A | 1.026633 |
| IBD | ETS1 | imm_11_127826087 | rs114534998 | 233 | 11 | 128320877 | 127826087 | T | A | A | 1.037348 |
| IBD | ETS1 | imm_11_127826464 | rs4936050 | 234 | 11 | 128321254 | 127826464 | A | G | A | 1.03236 |
| IBD | ETS1 | imm_11_127827422 | rs6590332 | 235 | 11 | 128322212 | 127827422 | A | G | A | 1.032349 |
| IBD | ETS1 | imm_11_127828334 | rs73581091 | 236 | 11 | 128323124 | 127828334 | G | A | A | 1.074437 |
| IBD | ETS1 | imm_11_127831280 | rs117676130 | 237 | 11 | 128326070 | 127831280 | A | G | G | 1.079965 |

TABLE 1-continued

| | | | | | | | | | | | |
|---|---|---|---|---|---|---|---|---|---|---|---|
| IBD | ETS1 | imm_11_127831611 | rs4328228 | 238 | 11 | 128326401 | 127831611 | A | G | A | 1.031281 |
| IBD | ETS1 | imm_11_127831673 | rs4369416 | 239 | 11 | 128326463 | 127831673 | A | G | G | 1.026652 |
| IBD | ETS1 | imm_11_127834123 | rs8705 | 240 | 11 | 128328913 | 127834123 | A | G | A | 1.031641 |
| IBD | ETS1 | imm_11_127834484 | rs80112582 | 241 | 11 | 128329274 | 127834484 | G | A | A | 1.086814 |
| IBD | ETS1 | imm_11_127837472 | rs34846069 | 242 | 11 | 128332262 | 127837472 | A | G | G | 1.090197 |
| IBD | ETS1 | imm_11_127838265 | rs76404385 | 243 | 11 | 128333055 | 127838265 | A | G | G | 1.047813 |
| IBD | ETS1 | imm_11_127838713 | rs2230004 | 244 | 11 | 128333503 | 127838713 | G | A | G | 1.030912 |
| IBD | ETS1 | imm_11_127839719 | rs78844317 | 245 | 11 | 128334509 | 127839719 | A | G | G | 1.107269 |
| IBD | ETS1 | imm_11_127840459 | rs11606640 | 246 | 11 | 128335249 | 127840459 | A | G | A | 1.069059 |
| IBD | ETS1 | imm_11_127840867 | rs7926975 | 247 | 11 | 128335657 | 127840867 | A | G | G | 1.059212 |
| IBD | ETS1 | imm_11_127841724 | rs10893875 | 248 | 11 | 128336514 | 127841724 | A | G | G | 1.056335 |
| IBD | ETS1 | imm_11_127841864 | rs55661779 | 249 | 11 | 128336654 | 127841864 | A | G | G | 1.029195 |
| IBD | ETS1 | imm_11_127843207 | rs4520612 | 250 | 11 | 128337997 | 127843207 | A | G | G | 1.05811 |
| IBD | ETS1 | imm_11_127843341 | rs4523710 | 251 | 11 | 128338131 | 127843341 | A | C | C | 1.056451 |
| IBD | ETS1 | imm_11_127844385 | rs73029052 | 252 | 11 | 128339175 | 127844385 | A | C | A | 1.066578 |
| IBD | ETS1 | imm_11_127844729 | rs116842927 | 253 | 11 | 128339519 | 127844729 | A | G | A | 1.087129 |
| IBD | ETS1 | imm_11_127845557 | rs6590333 | 254 | 11 | 128340347 | 127845557 | A | G | G | 1.058241 |
| IBD | ETS1 | imm_11_127846698 | rs11600915 | 255 | 11 | 128341488 | 127846698 | G | A | G | 1.065067 |
| IBD | ETS1 | imm_11_127848167 | rs61909068 | 256 | 11 | 128342957 | 127848167 | G | A | G | 1.06541 |
| IBD | ETS1 | imm_11_127848372 | rs12294634 | 257 | 11 | 128343162 | 127848372 | A | G | A | 1.065797 |
| IBD | ETS1 | imm_11_127849992 | rs73029062 | 258 | 11 | 128344782 | 127849992 | G | A | G | 1.065176 |
| IBD | ETS1 | imm_11_127851599 | rs11600746 | 259 | 11 | 128346389 | 127851599 | G | A | G | 1.067929 |
| IBD | ETS1 | imm_11_127852250 | rs4937336 | 260 | 11 | 128347040 | 127852250 | G | A | A | 1.058017 |
| IBD | ETS1 | imm_11_127853705 | rs12276127 | 261 | 11 | 128348495 | 127853705 | A | G | G | 1.057926 |
| IBD | ETS1 | imm_11_127855281 | rs61909072 | 262 | 11 | 128350071 | 127855281 | A | G | A | 1.06503 |
| IBD | ETS1 | imm_11_127855956 | rs4937338 | 263 | 11 | 128350746 | 127855956 | A | G | G | 1.053906 |
| IBD | ETS1 | imm_11_127857027 | rs7130469 | 264 | 11 | 128351817 | 127857027 | G | A | A | 1.060292 |
| IBD | ETS1 | imm_11_127861069 | rs1122832 | 265 | 11 | 128355859 | 127861069 | G | A | G | 1.034187 |
| IBD | ETS1 | imm_11_127863304 | rs35394161 | 266 | 11 | 128358094 | 127863304 | A | G | A | 1.034741 |
| IBD | ETS1 | imm_11_127863391 | rs11221327 | 267 | 11 | 128358181 | 127863391 | G | A | G | 1.03498 |
| IBD | ETS1 | imm_11_127866379 | rs4937339 | 268 | 11 | 128361169 | 127866379 | A | C | A | 1.028356 |
| IBD | ETS1 | imm_11_127868447 | rs7926631 | 269 | 11 | 128363237 | 127868447 | A | G | A | 1.352044 |
| IBD | ETS1 | imm_11_127868927 | rs11604768 | 270 | 11 | 128363717 | 127868927 | G | A | A | 1.031257 |
| IBD | ETS1 | imm_11_127869177 | rs10893881 | 271 | 11 | 128363967 | 127869177 | G | A | G | 1.043651 |
| IBD | ETS1 | imm_11_127870403 | rs3924513 | 272 | 11 | 128365193 | 127870403 | C | A | C | 1.040944 |
| IBD | ETS1 | imm_11_127870895 | rs12805120 | 273 | 11 | 128365685 | 127870895 | A | T | A | 1.040738 |
| IBD | ETS1 | imm_11_127871431 | rs4254089 | 274 | 11 | 128366221 | 127871431 | G | A | G | 1.039764 |
| IBD | ETS1 | imm_11_127872972 | rs3924289 | 275 | 11 | 128367762 | 127872972 | A | G | G | 1.03512 |
| IBD | ETS1 | imm_11_127874486 | rs4937340 | 276 | 11 | 128369276 | 127874486 | G | A | G | 1.039926 |
| IBD | ETS1 | imm_11_127874807 | rs7929911 | 277 | 11 | 128369597 | 127874807 | A | G | A | 1.038031 |
| IBD | ETS1 | imm_11_127877378 | rs7941606 | 278 | 11 | 128372168 | 127877378 | A | G | A | 1.04088 |
| IBD | ETS1 | imm_11_127879923 | rs10893883 | 279 | 11 | 128374713 | 127879923 | A | G | G | 1.032625 |
| IBD | ETS1 | imm_11_127881686 | rs56086356 | 280 | 11 | 128376476 | 127881686 | C | G | C | 1.078091 |
| IBD | ETS1 | imm_11_127882690 | rs7118744 | 281 | 11 | 128377480 | 127882690 | A | G | A | 1.028394 |
| IBD | ETS1 | imm_11_127884689 | rs4937341 | 282 | 11 | 128379479 | 127884689 | A | G | G | 1.055059 |
| IBD | ETS1 | imm_11_127885952 | rs7924522 | 283 | 11 | 128380742 | 127885952 | C | A | C | 1.050035 |
| IBD | ETS1 | imm_11_127886184 | rs11221332 | 284 | 11 | 128380974 | 127886184 | A | G | A | 1.074782 |
| IBD | ETS1 | imm_11_127887077 | rs7108992 | 285 | 11 | 128381867 | 127887077 | A | C | A | 1.050031 |
| IBD | ETS1 | imm_11_127889134 | rs7117768 | 286 | 11 | 128383924 | 127889134 | G | C | G | 1.073028 |
| IBD | ETS1 | imm_11_127891116 | rs11221335 | 287 | 11 | 128385906 | 127891116 | G | A | G | 1.072272 |
| IBD | ETS1 | imm_11_127892632 | rs7946009 | 288 | 11 | 128387422 | 127892632 | A | G | A | 1.050157 |
| IBD | ETS1 | imm_11_127894601 | rs11819995 | 289 | 11 | 128389391 | 127894601 | A | G | G | 1.027193 |
| IBD | ETS1 | imm_11_127894638 | rs78111939 | 290 | 11 | 128389428 | 127894638 | G | A | A | 1.207021 |
| IBD | ETS1 | imm_11_127895279 | rs7120822 | 291 | 11 | 128390069 | 127895279 | A | T | A | 1.075029 |
| IBD | ETS1 | imm_11_127897147 | rs61907765 | 292 | 11 | 128391937 | 127897147 | A | G | A | 1.07393 |
| IBD | ETS1 | imm_11_127898835 | rs118087633 | 293 | 11 | 128393625 | 127898835 | G | A | A | 1.109805 |
| IBD | ETS1 | imm_11_127901157 | rs12805524 | 294 | 11 | 128395947 | 127901157 | G | A | G | 1.049678 |
| IBD | ETS1 | imm_11_127901948 | rs7117118 | 295 | 11 | 128396738 | 127901948 | G | A | G | 1.069811 |
| IBD | ETS1 | imm_11_127905841 | rs35656079 | 296 | 11 | 128400631 | 127905841 | G | A | A | 1.065081 |
| IBD | ETS1 | imm_11_127906568 | rs73030729 | 297 | 11 | 128401358 | 127906568 | A | G | A | 1.037954 |
| IBD | ETS1 | imm_11_127908214 | rs11825217 | 298 | 11 | 128403004 | 127908214 | A | G | A | 1.038876 |
| IBD | ETS1 | imm_11_127911648 | rs3802828 | 299 | 11 | 128406438 | 127911648 | G | A | A | 1.039032 |
| IBD | ETS1 | imm_11_127911985 | rs4520607 | 300 | 11 | 128406775 | 127911985 | A | G | A | 1.033773 |
| IBD | ETS1 | imm_11_127914294 | rs10750400 | 301 | 11 | 128409084 | 127914294 | A | G | A | 1.033742 |
| IBD | ETS1 | imm_11_127915474 | rs10893884 | 302 | 11 | 128410264 | 127915474 | G | A | A | 1.033532 |
| IBD | ETS1 | imm_11_127915554 | rs10893885 | 303 | 11 | 128410344 | 127915554 | G | A | A | 1.036858 |
| IBD | ETS1 | imm_11_127916046 | rs3809006 | 304 | 11 | 128410836 | 127916046 | G | A | G | 1.032452 |
| IBD | ETS1 | imm_11_127929821 | rs78814353 | 305 | 11 | 128424611 | 127929821 | A | G | G | 1.97122 |
| IBD | ETS1 | imm_11_127931099 | rs115308851 | 306 | 11 | 128425889 | 127931099 | A | G | G | 2.369107 |
| IBD | ETS1 | imm_11_127940676 | rs12788788 | 307 | 11 | 128435466 | 127940676 | G | C | C | 1.064003 |
| IBD | ETS1 | imm_11_127943244 | rs12284728 | 308 | 11 | 128438034 | 127943244 | A | G | G | 2.2531 |
| IBD | ETS1 | imm_11_127945727 | rs10893887 | 309 | 11 | 128440517 | 127945727 | A | G | A | 1.093 |
| IBD | ETS1 | imm_11_127945953 | rs10893888 | 310 | 11 | 128440743 | 127945953 | G | A | A | 1.051642 |
| IBD | ETS1 | imm_11_127948912 | rs117334295 | 311 | 11 | 128443702 | 127948912 | A | G | G | 1.14044 |
| IBD | ETS1 | imm_11_127956842 | rs55781052 | 312 | 11 | 128451632 | 127956842 | A | G | A | 1.030903 |
| IBD | ETS1 | imm_11_127957543 | rs78704287 | 313 | 11 | 128452333 | 127957543 | C | A | C | 1.123815 |
| IBD | ETS1 | imm_11_127957904 | rs73030764 | 314 | 11 | 128452694 | 127957904 | C | A | C | 1.122206 |
| IBD | ETS1 | imm_11_127974263 | rs12364915 | 315 | 11 | 128469053 | 127974263 | A | C | C | 1.049778 |
| IBD | ETS1 | imm_11_127979301 | rs11221386 | 316 | 11 | 128474091 | 127979301 | A | G | G | 1.035064 |
| IBD | ETS1 | imm_11_127979905 | rs117333396 | 317 | 11 | 128474695 | 127979905 | A | G | G | 1.120199 |

TABLE 1-continued

| | | | | | | | | | | | |
|---|---|---|---|---|---|---|---|---|---|---|---|
| IBD | ETS1 | imm_11_127981559 | rs56244679 | 318 | 11 | 128476349 | 127981559 | C | G | G | 1.029851 |
| IBD | ETS1 | imm_11_127982379 | rs11221390 | 319 | 11 | 128477169 | 127982379 | A | G | G | 1.029943 |
| IBD | ETS1 | imm_11_127982748 | rs11221391 | 320 | 11 | 128477538 | 127982748 | C | A | A | 1.033682 |
| IBD | ETS1 | imm_11_127983590 | rs73569213 | 321 | 11 | 128478380 | 127983590 | A | G | G | 1.030825 |
| IBD | ETS1 | imm_11_127983743 | rs73569215 | 322 | 11 | 128478533 | 127983743 | A | C | C | 1.029943 |
| IBD | ETS1 | imm_11_127984265 | rs73569219 | 323 | 11 | 128479055 | 127984265 | A | G | G | 1.030692 |
| IBD | ETS1 | imm_11_127984721 | rs10893894 | 324 | 11 | 128479511 | 127984721 | G | A | A | 1.033407 |
| IBD | ETS1 | rs7935286 | rs7935286 | 325 | 11 | 128501572 | 128006782 | G | A | G | 1.048707 |
| IBD | SLC5A1 | rs738203 | rs738203 | 326 | 22 | 32607074 | 30937074 | G | A | G | 1.029285 |
| IBD | SLC5A1 | rs9609429 | rs9609429 | 327 | 22 | 32517431 | 30847431 | G | A | A | 1.041716 |
| IBD | TET2 | rs10010325 | rs10010325 | 328 | 4 | 106106353 | 106325802 | A | C | C | 1.064877 |
| IBD | TET2 | rs17035310 | rs17035310 | 329 | 4 | 106064754 | 106284203 | A | G | A | 1.061851 |
| IBD | TET2 | rs2189234 | rs2189234 | 330 | 4 | 106075498 | 106294947 | A | C | A | 1.03441 |
| IBD | TET2 | rs7661349 | rs7661349 | 331 | 4 | 106066982 | 106286431 | A | G | A | 1.035217 |
| IBD | TET2 | rs974801 | rs974801 | 332 | 4 | 106071064 | 106290513 | G | A | A | 1.056745 |

(Continued, part 2)

| gene.i | SNP | F_A_ce-dars | F_U_ce-dars | OR_ce-dars | SE_ce-dars | L95_ce-dars | U95_ce-dars | STAT_ce-dars | P_ce-dars |
|---|---|---|---|---|---|---|---|---|---|
| SLC26A4 | rs10247487 | 0.2877 | 0.2731 | 0.8841 | 0.04188 | 0.8144 | 0.9597 | −2.942 | 0.003263 |
| SLC26A4 | rs10263826 | 0.3131 | 0.2921 | 0.8917 | 0.0408 | 0.8232 | 0.9659 | −2.81 | 0.004955 |
| SLC26A4 | rs10273733 | 0.3147 | 0.315 | 1.027 | 0.05335 | 0.9252 | 1.14 | 0.5027 | 0.6152 |
| SLC26A4 | rs12539555 | 0.2629 | 0.2472 | 1.074 | 0.04243 | 0.988 | 1.167 | 1.676 | 0.09383 |
| SLC26A4 | rs2248465 | 0.3052 | 0.2718 | 1.085 | 0.04075 | 1.002 | 1.175 | 2.008 | 0.04465 |
| SLC26A4 | rs2808 | 0.3165 | 0.2907 | 1.108 | 0.04051 | 1.023 | 1.2 | 2.532 | 0.01134 |
| DLG4 | rs3785794 | 0.07404 | 0.08212 | 0.7731 | 0.07098 | 0.6727 | 0.8885 | −3.625 | 0.000289 |
| GIPR | chr19:50983512 | 0.2676 | 0.2762 | 0.9193 | 0.05478 | 0.8257 | 1.023 | −1.536 | 0.1244 |
| GIPR | chr19:51014231 | NA | NA | NA | NA | NA | NA | NA | NA |
| GIPR | chr19:51026971 | 0.2793 | 0.3171 | 0.9117 | 0.04067 | 0.8419 | 0.9874 | −2.273 | 0.02303 |
| GIPR | rs10401439 | NA | NA | NA | NA | NA | NA | NA | NA |
| GIPR | rs10402263 | 0.3052 | 0.3394 | 0.9243 | 0.03954 | 0.8554 | 0.9988 | −1.99 | 0.04658 |
| GIPR | rs10421891 | 0.3172 | 0.3509 | 0.9207 | 0.03857 | 0.8537 | 0.993 | −2.141 | 0.03229 |
| GIPR | rs10500292 | 0.3716 | 0.3949 | 0.932 | 0.03805 | 0.865 | 1.004 | −1.852 | 0.06402 |
| GIPR | rs11883351 | 0.3054 | 0.3395 | 0.914 | 0.03949 | 0.8459 | 0.9875 | −2.278 | 0.02273 |
| GIPR | rs12463359 | 0.3664 | 0.3886 | 0.9227 | 0.03818 | 0.8561 | 0.9944 | −2.108 | 0.035 |
| GIPR | rs16980013 | 0.2662 | 0.3005 | 0.9146 | 0.04129 | 0.8435 | 0.9917 | −2.163 | 0.03056 |
| GIPR | rs16980051 | 0.469 | 0.4875 | 0.9272 | 0.03698 | 0.8624 | 0.9969 | −2.043 | 0.04106 |
| GIPR | rs17878252 | 0.2515 | 0.2783 | 0.9247 | 0.04211 | 0.8514 | 1.004 | −1.859 | 0.06298 |
| GIPR | rs2070736 | 0.2674 | 0.3031 | 0.9115 | 0.04125 | 0.8407 | 0.9883 | −2.245 | 0.02474 |
| GIPR | rs2334255 | 0.2628 | 0.2417 | 1.098 | 0.0424 | 1.011 | 1.193 | 2.211 | 0.02703 |
| GIPR | rs4514788 | 0.2802 | 0.2773 | 0.9195 | 0.09025 | 0.7704 | 1.097 | −0.9301 | 0.3523 |
| GIPR | rs4802273 | 0.26 | 0.2896 | 0.9181 | 0.04178 | 0.8459 | 0.9964 | −2.045 | 0.04083 |
| GIPR | rs4802274 | 0.2681 | 0.3032 | 0.915 | 0.04121 | 0.844 | 0.992 | −2.156 | 0.03109 |
| GIPR | rs4803861 | 0.2789 | 0.3162 | 0.9142 | 0.04071 | 0.8441 | 0.9901 | −2.205 | 0.02746 |
| GIPR | rs8111071 | 0.1183 | 0.08879 | 1.139 | 0.05996 | 1.013 | 1.281 | 2.174 | 0.02971 |
| GIPR | rs918490 | 0.2789 | 0.316 | 0.9158 | 0.04067 | 0.8456 | 0.9918 | −2.164 | 0.0305 |
| ZHX3 | rs6072275 | 0.1551 | 0.1448 | 1.143 | 0.05126 | 1.034 | 1.264 | 2.609 | 0.009076 |
| ZHX3 | rs6072343 | 0.1334 | 0.1342 | 1.128 | 0.05394 | 1.015 | 1.254 | 2.239 | 0.02513 |
| ZHX3 | rs6093462 | NA | NA | NA | NA | NA | NA | NA | NA |
| TNRC6B | rs114607 | 0.397 | 0.3784 | 1.083 | 0.2487 | 0.6649 | 1.763 | 0.3192 | 0.7496 |
| TNRC6B | rs137955 | 0.4479 | 0.4323 | 1.11 | 0.03725 | 1.032 | 1.194 | 2.807 | 0.004997 |
| TNRC6B | rs137956 | 0.4584 | 0.4381 | 1.115 | 0.03718 | 1.037 | 1.2 | 2.937 | 0.003312 |
| TNRC6B | rs137977 | 0.3734 | 0.3967 | 0.9134 | 0.03819 | 0.8475 | 0.9843 | −2.373 | 0.01764 |
| TNRC6B | rs137981 | 0.1026 | 0.1205 | 0.8424 | 0.05943 | 0.7497 | 0.9464 | −2.887 | 0.003892 |
| TNRC6B | rs138027 | 0.2471 | 0.264 | 0.8709 | 0.04296 | 0.8005 | 0.9474 | −3.218 | 0.001289 |
| TNRC6B | rs2958647 | 0.4584 | 0.4376 | 1.114 | 0.03715 | 1.036 | 1.198 | 2.903 | 0.003698 |
| TNRC6B | rs713925 | 0.3773 | 0.3875 | 0.9268 | 0.03813 | 0.8601 | 0.9987 | −1.993 | 0.04622 |
| CDK6 | rs2282978 | 0.358 | 0.3463 | 0.9286 | 0.04835 | 0.8447 | 1.021 | −1.532 | 0.1255 |
| CDK6 | rs4272 | 0.2059 | 0.2185 | 0.9167 | 0.05615 | 0.8211 | 1.023 | −1.55 | 0.1212 |
| PRR5L | rs11033597 | 0.1402 | 0.1309 | 1.226 | 0.06517 | 1.079 | 1.393 | 3.128 | 0.001761 |
| PRR5L | rs11600757 | 0.1637 | 0.1433 | 1.213 | 0.06156 | 1.075 | 1.368 | 3.134 | 0.001723 |
| PRR5L | rs11601211 | 0.07153 | 0.07066 | 1.13 | 0.08584 | 0.9549 | 1.337 | 1.423 | 0.1548 |
| PRR5L | rs12281565 | 0.1669 | 0.1468 | 1.214 | 0.06094 | 1.077 | 1.368 | 3.185 | 0.001449 |
| PRR5L | rs1365120 | 0.09551 | 0.09455 | 1.179 | 0.07526 | 1.018 | 1.367 | 2.191 | 0.02843 |
| PRR5L | rs1895840 | 0.1022 | 0.09673 | 1.172 | 0.07468 | 1.012 | 1.357 | 2.125 | 0.03357 |
| PRR5L | rs2303439 | 0.1673 | 0.1518 | 1.072 | 0.0615 | 0.9501 | 1.209 | 1.127 | 0.2596 |
| PRR5L | rs330260 | 0.1842 | 0.1711 | 1.192 | 0.05831 | 1.064 | 1.337 | 3.017 | 0.002556 |
| PRR5L | rs331485 | 0.1142 | 0.1079 | 0.9739 | 0.07277 | 0.8445 | 1.123 | −0.363 | 0.7166 |
| PRR5L | rs4077044 | 0.4605 | 0.4096 | 1.2 | 0.07443 | 1.037 | 1.389 | 2.452 | 0.01422 |
| PRR5L | rs5030437 | 0.1636 | 0.1698 | 1.016 | 0.1083 | 0.8216 | 1.256 | 0.1458 | 0.8841 |
| PRR5L | rs5030445 | 0.1673 | 0.152 | 1.068 | 0.06145 | 0.9469 | 1.205 | 1.072 | 0.2839 |
| PRR5L | rs5030472 | 0.1192 | 0.1064 | 1.163 | 0.07051 | 1.013 | 1.336 | 2.145 | 0.03195 |
| PRR5L | rs7929195 | 0.1381 | 0.1195 | 0.9793 | 0.0679 | 0.8573 | 1.119 | −0.3081 | 0.758 |
| WNT2B | rs10745330 | 0.4958 | 0.471 | 1.076 | 0.03194 | 1.011 | 1.146 | 2.294 | 0.02178 |
| WNT2B | rs2999155 | 0.4903 | 0.4663 | 1.073 | 0.03192 | 1.008 | 1.142 | 2.203 | 0.0276 |
| WNT2B | rs3790609 | 0.2092 | 0.1771 | 1.098 | 0.04041 | 1.014 | 1.188 | 2.313 | 0.02074 |
| WNT2B | rs6682737 | 0.4926 | 0.4667 | 1.079 | 0.03193 | 1.013 | 1.148 | 2.376 | 0.01749 |
| LRRC16A | rs10456320 | 0.1262 | 0.1178 | 1.005 | 0.04921 | 0.9127 | 1.107 | 0.1028 | 0.9181 |

TABLE 1-continued

| | | | | | | | | | |
|---|---|---|---|---|---|---|---|---|---|
| LRRC16A | rs11755567 | 0.205 | 0.189 | 0.9618 | 0.04071 | 0.888 | 1.042 | −0.9579 | 0.3381 |
| LRRC16A | rs13191296 | 0.04082 | 0.08105 | 0.8496 | 0.08258 | 0.7227 | 0.9989 | −1.973 | 0.04846 |
| LRRC16A | rs2690110 | 0.3664 | 0.3425 | 1.08 | 0.03325 | 1.012 | 1.153 | 2.309 | 0.02094 |
| LRRC16A | rs4712908 | 0.3535 | 0.3505 | 0.976 | 0.05691 | 0.873 | 1.091 | −0.4274 | 0.6691 |
| LRRC16A | rs6921589 | 0.1162 | 0.1293 | 1.007 | 0.05161 | 0.9102 | 1.114 | 0.1376 | 0.8906 |
| LRRC16A | rs6937918 | 0.4464 | 0.4014 | 1.067 | 0.0323 | 1.002 | 1.137 | 2.007 | 0.04479 |
| LRRC16A | rs742132 | 0.2809 | 0.2888 | 1.005 | 0.03593 | 0.9367 | 1.078 | 0.1397 | 0.8889 |
| LRRC16A | rs7752195 | 0.0457 | 0.07408 | 0.9385 | 0.07684 | 0.8073 | 1.091 | −0.8261 | 0.4087 |
| LRRC16A | rs7752524 | 0.09413 | 0.09466 | 1.017 | 0.05426 | 0.9148 | 1.132 | 0.3179 | 0.7505 |
| LRRC16A | rs7762757 | 0.4002 | 0.3824 | 1.013 | 0.03876 | 0.939 | 1.093 | 0.3349 | 0.7377 |
| LRRC16A | rs880226 | 0.4469 | 0.4016 | 1.068 | 0.03231 | 1.002 | 1.138 | 2.035 | 0.04185 |
| LRRC16A | rs9295661 | 0.03926 | 0.07291 | 0.8785 | 0.08061 | 0.7501 | 1.029 | −1.607 | 0.1081 |
| LRRC16A | rs9358854 | 0.3764 | 0.3399 | 0.9563 | 0.03384 | 0.895 | 1.022 | −1.319 | 0.1872 |
| LRRC16A | rs9461157 | 0.4459 | 0.4009 | 1.067 | 0.03232 | 1.001 | 1.136 | 1.996 | 0.04589 |
| LRRC16A | rs9461165 | 0.4459 | 0.4011 | 1.066 | 0.03231 | 1.001 | 1.136 | 1.98 | 0.04766 |
| LRRC16A | rs9467445 | 0.2258 | 0.2055 | 0.9524 | 0.03955 | 0.8814 | 1.029 | −1.232 | 0.2179 |
| All Histone cluster1 gene | rs10484399 | 0.05103 | 0.09845 | 0.8471 | 0.08727 | 0.7139 | 1.005 | −1.901 | 0.05726 |
| All Histone cluster1 gene | rs10484439 | 0.05239 | 0.09177 | 0.8574 | 0.07884 | 0.7346 | 1.001 | −1.952 | 0.05098 |
| All Histone cluster1 gene | rs12176317 | 0.06961 | 0.1171 | 0.8307 | 0.06794 | 0.7271 | 0.949 | −2.73 | 0.00634 |
| All Histone cluster1 gene | rs13194053 | 0.1298 | 0.1697 | 1.02 | 0.04971 | 0.9254 | 1.125 | 0.4008 | 0.6885 |
| All Histone cluster1 gene | rs13194491 | 0.0514 | 0.08248 | 0.8723 | 0.06512 | 0.7677 | 0.991 | −2.098 | 0.03588 |
| All Histone cluster1 gene | rs13194781 | 0.05128 | 0.09881 | 0.8476 | 0.08751 | 0.714 | 1.006 | −1.889 | 0.05883 |
| All Histone cluster1 gene | rs13195040 | 0.05301 | 0.09513 | 0.8981 | 0.08556 | 0.7595 | 1.062 | −1.255 | 0.2093 |
| All Histone cluster1 gene | rs13199772 | 0.0514 | 0.09872 | 0.8551 | 0.08745 | 0.7204 | 1.015 | −1.79 | 0.0735 |
| All Histone cluster1 gene | rs13212651 | 0.05115 | 0.09848 | 0.8494 | 0.08765 | 0.7153 | 1.009 | −1.862 | 0.06256 |
| All Histone cluster1 gene | rs1321578 | 0.02515 | 0.02356 | 0.9242 | 0.1494 | 0.6896 | 1.238 | −0.528 | 0.5975 |
| All Histone cluster1 gene | rs13217599 | 0.04509 | 0.05347 | 1.092 | 0.1541 | 0.8077 | 1.478 | 0.5738 | 0.5661 |
| All Histone cluster1 gene | rs13218875 | 0.05028 | 0.09619 | 0.8697 | 0.09246 | 0.7255 | 1.042 | −1.51 | 0.131 |
| All Histone cluster1 gene | rs13219354 | 0.07828 | 0.1193 | 0.9521 | 0.0649 | 0.8384 | 1.081 | −0.7568 | 0.4492 |
| All Histone cluster1 gene | rs16867901 | 0.01178 | 0.009631 | 0.8439 | 0.1903 | 0.5812 | 1.225 | −0.8918 | 0.3725 |
| All Histone cluster1 gene | rs16867911 | 0.01164 | 0.01047 | 0.8883 | 0.1547 | 0.656 | 1.203 | −0.7655 | 0.444 |
| All Histone cluster1 gene | rs16891725 | 0.07382 | 0.1186 | 0.8387 | 0.06792 | 0.7341 | 0.9581 | −2.59 | 0.009589 |

TABLE 1-continued

| | | | | | | | | | |
|---|---|---|---|---|---|---|---|---|---|
| All Histone cluster1 gene | rs175597 | 0.06849 | 0.1182 | 0.8257 | 0.07324 | 0.7153 | 0.9532 | −2.615 | 0.008922 |
| All Histone cluster1 gene | rs17693963 | 0.05933 | 0.1038 | 0.9317 | 0.08051 | 0.7957 | 1.091 | −0.8792 | 0.3793 |
| All Histone cluster1 gene | rs17739310 | 0.1637 | 0.1606 | 1.054 | 0.06205 | 0.9333 | 1.19 | 0.8475 | 0.3967 |
| All Histone cluster1 gene | rs17750424 | NA | NA | NA | NA | NA | NA | NA | NA |
| All Histone cluster1 gene | rs1977 | 0.06961 | 0.1172 | 0.8303 | 0.06792 | 0.7268 | 0.9485 | −2.739 | 0.006165 |
| All Histone cluster1 gene | rs1985732 | 0.2535 | 0.2925 | 0.9425 | 0.0373 | 0.876 | 1.014 | −1.589 | 0.1122 |
| All Histone cluster1 gene | rs200483 | 0.06899 | 0.1182 | 0.8382 | 0.073 | 0.7265 | 0.9672 | −2.417 | 0.01563 |
| All Histone cluster1 gene | rs200484 | 0.06874 | 0.1182 | 0.8328 | 0.07321 | 0.7215 | 0.9613 | −2.499 | 0.01244 |
| All Histone cluster1 gene | rs200490 | 0.06863 | 0.1187 | 0.8227 | 0.07317 | 0.7128 | 0.9496 | −2.667 | 0.007645 |
| All Histone cluster1 gene | rs200501 | 0.06989 | 0.119 | 0.8337 | 0.07267 | 0.723 | 0.9614 | −2.502 | 0.01234 |
| All Histone cluster1 gene | rs200948 | 0.06849 | 0.1183 | 0.8248 | 0.07332 | 0.7144 | 0.9523 | −2.627 | 0.008616 |
| All Histone cluster1 gene | rs200953 | 0.06886 | 0.1188 | 0.8188 | 0.07312 | 0.7095 | 0.945 | −2.734 | 0.006253 |
| All Histone cluster1 gene | rs200989 | 0.06849 | 0.1185 | 0.8206 | 0.07325 | 0.7108 | 0.9473 | −2.7 | 0.006941 |
| All Histone cluster1 gene | rs200990 | 0.06899 | 0.119 | 0.818 | 0.07301 | 0.7089 | 0.9438 | −2.752 | 0.005918 |
| All Histone cluster1 gene | rs200991 | 0.1274 | 0.1585 | 0.9787 | 0.05359 | 0.8811 | 1.087 | −0.4021 | 0.6876 |
| All Histone cluster1 gene | rs200995 | 0.06862 | 0.1186 | 0.8242 | 0.07316 | 0.7141 | 0.9513 | −2.642 | 0.00823 |
| All Histone cluster1 gene | rs201002 | 0.06899 | 0.1188 | 0.823 | 0.073 | 0.7133 | 0.9496 | −2.668 | 0.007631 |
| All Histone cluster1 gene | rs201004 | 0.1514 | 0.1945 | 0.9781 | 0.06811 | 0.8559 | 1.118 | −0.3246 | 0.7455 |
| All Histone cluster1 gene | rs2064092 | 0.09884 | 0.06948 | 1.161 | 0.05845 | 1.035 | 1.301 | 2.547 | 0.01086 |
| All Histone cluster1 gene | rs2072806 | 0.06616 | 0.09787 | 0.7719 | 0.1687 | 0.5546 | 1.074 | −1.534 | 0.125 |

TABLE 1-continued

| | | | | | | | | | |
|---|---|---|---|---|---|---|---|---|---|
| All Histone cluster1 gene | rs2073529 | NA | NA | NA | NA | NA | NA | NA | NA |
| All Histone cluster1 gene | rs2093169 | 0.1479 | 0.1792 | 0.9559 | 0.04838 | 0.8694 | 1.051 | −0.9323 | 0.3512 |
| All Histone cluster1 gene | rs2393997 | 0.08422 | 0.1084 | 0.9463 | 0.05424 | 0.8509 | 1.052 | −1.017 | 0.3092 |
| All Histone cluster1 gene | rs2494711 | 0.3718 | 0.3585 | 1.056 | 0.03353 | 0.9886 | 1.127 | 1.617 | 0.1059 |
| All Histone cluster1 gene | rs2747054 | 0.06874 | 0.1182 | 0.8324 | 0.07315 | 0.7212 | 0.9607 | −2.508 | 0.01213 |
| All Histone cluster1 gene | rs2893910 | 0.1734 | 0.1917 | 0.9412 | 0.04668 | 0.8589 | 1.031 | −1.299 | 0.1938 |
| All Histone cluster1 gene | rs34706883 | 0.05115 | 0.09854 | 0.8501 | 0.0876 | 0.716 | 1.009 | −1.853 | 0.06382 |
| All Histone cluster1 gene | rs370155 | 0.06911 | 0.1188 | 0.8263 | 0.07295 | 0.7162 | 0.9533 | −2.616 | 0.008905 |
| All Histone cluster1 gene | rs3799378 | 0.1841 | 0.2212 | 0.8456 | 0.2738 | 0.4944 | 1.446 | −0.6127 | 0.5401 |
| All Histone cluster1 gene | rs3799380 | 0.175 | 0.1937 | 0.9812 | 0.04545 | 0.8975 | 1.073 | −0.4185 | 0.6756 |
| All Histone cluster1 gene | rs3799383 | 0.08075 | 0.1241 | 0.8228 | 0.06529 | 0.724 | 0.9352 | −2.986 | 0.002822 |
| All Histone cluster1 gene | rs3800307 | 0.1582 | 0.1941 | 1.002 | 0.04583 | 0.9157 | 1.096 | 0.03818 | 0.9695 |
| All Histone cluster1 gene | rs3800316 | 0.2617 | 0.279 | 0.9671 | 0.03862 | 0.8966 | 1.043 | −0.8669 | 0.386 |
| All Histone cluster1 gene | rs4452638 | 0.07766 | 0.1186 | 0.9554 | 0.06539 | 0.8405 | 1.086 | −0.6977 | 0.4854 |
| All Histone cluster1 gene | rs4634439 | 0.06948 | 0.1166 | 0.8152 | 0.06928 | 0.7117 | 0.9338 | −2.948 | 0.003195 |
| All Histone cluster1 gene | rs4712981 | 0.2476 | 0.284 | 0.9437 | 0.03773 | 0.8764 | 1.016 | −1.537 | 0.1244 |
| All Histone cluster1 gene | rs4713119 | 0.08647 | 0.1099 | 0.9468 | 0.05375 | 0.8522 | 1.052 | −1.016 | 0.3095 |
| All Histone cluster1 gene | rs6456728 | 0.175 | 0.1936 | 0.9811 | 0.04546 | 0.8975 | 1.073 | −0.4187 | 0.6754 |
| All Histone cluster1 gene | rs6904071 | 0.1288 | 0.169 | 1.019 | 0.04992 | 0.9241 | 1.124 | 0.3779 | 0.7055 |
| All Histone cluster1 gene | rs6904596 | 0.0623 | 0.1092 | 0.8336 | 0.07738 | 0.7163 | 0.9701 | −2.353 | 0.01864 |

TABLE 1-continued

| | | | | | | | | | |
|---|---|---|---|---|---|---|---|---|---|
| All Histone cluster1 gene | rs6913660 | 0.1292 | 0.1692 | 1.023 | 0.04987 | 0.9275 | 1.128 | 0.451 | 0.652 |
| All Histone cluster1 gene | rs6915101 | 0.01858 | 0.01608 | 0.8718 | 0.1242 | 0.6835 | 1.112 | −1.105 | 0.2694 |
| All Histone cluster1 gene | rs6920256 | 0.0758 | 0.1216 | 0.8308 | 0.0666 | 0.7292 | 0.9467 | −2.783 | 0.00539 |
| All Histone cluster1 gene | rs6923139 | 0.09289 | 0.1142 | 0.8966 | 0.06213 | 0.7938 | 1.013 | −1.756 | 0.07912 |
| All Histone cluster1 gene | rs6932590 | 0.2221 | 0.2553 | 0.9681 | 0.04017 | 0.8948 | 1.047 | −0.8065 | 0.42 |
| All Histone cluster1 gene | rs6933583 | 0.2496 | 0.2851 | 0.9491 | 0.03764 | 0.8816 | 1.022 | −1.389 | 0.1648 |
| All Histone cluster1 gene | rs6934794 | 0.2156 | 0.1878 | 1.092 | 0.03964 | 1.01 | 1.18 | 2.209 | 0.02716 |
| All Histone cluster1 gene | rs6938200 | 0.1611 | 0.1567 | 0.9747 | 0.06571 | 0.8569 | 1.109 | −0.3893 | 0.697 |
| All Histone cluster1 gene | rs721600 | 0.2458 | 0.2271 | 1.057 | 0.03752 | 0.9821 | 1.138 | 1.478 | 0.1395 |
| All Histone cluster1 gene | rs7745603 | 0.1828 | 0.2223 | 0.9949 | 0.04314 | 0.9142 | 1.083 | −0.1189 | 0.9054 |
| All Histone cluster1 gene | rs7746199 | 0.1747 | 0.1929 | 0.9434 | 0.07528 | 0.814 | 1.093 | −0.7735 | 0.4392 |
| All Histone cluster1 gene | rs7749305 | 0.06205 | 0.1089 | 0.812 | 0.07602 | 0.6996 | 0.9424 | −2.74 | 0.006146 |
| All Histone cluster1 gene | rs7749319 | 0.02514 | 0.0407 | 0.8489 | 0.08917 | 0.7128 | 1.011 | −1.837 | 0.06618 |
| All Histone cluster1 gene | rs7756567 | 0.1479 | 0.1794 | 0.955 | 0.04837 | 0.8686 | 1.05 | −0.9523 | 0.3409 |
| All Histone cluster1 gene | rs7773938 | 0.1478 | 0.1795 | 0.9514 | 0.04837 | 0.8653 | 1.046 | −1.03 | 0.3028 |
| All Histone cluster1 gene | rs911186 | NA | NA | NA | NA | NA | NA | NA | NA |
| All Histone cluster1 gene | rs9295739 | 0.01164 | 0.01047 | 0.8903 | 0.1547 | 0.6574 | 1.206 | −0.7513 | 0.4524 |
| All Histone cluster1 gene | rs9295749 | 0.06886 | 0.05046 | 1.147 | 0.06866 | 1.003 | 1.312 | 2 | 0.04548 |
| All Histone cluster1 gene | rs9358944 | 0.148 | 0.1794 | 0.9553 | 0.04834 | 0.8689 | 1.05 | −0.9469 | 0.3437 |
| All Histone cluster1 gene | rs9358945 | 0.148 | 0.1795 | 0.9544 | 0.04834 | 0.8682 | 1.049 | −0.9646 | 0.3347 |

TABLE 1-continued

| | | | | | | | | | |
|---|---|---|---|---|---|---|---|---|---|
| All Histone cluster1 gene | rs9358946 | 0.1483 | 0.1871 | 0.9062 | 0.05661 | 0.8111 | 1.013 | −1.739 | 0.08199 |
| All Histone cluster1 gene | rs9366653 | 0.07035 | 0.1178 | 0.8326 | 0.06753 | 0.7293 | 0.9504 | −2.713 | 0.006659 |
| All Histone cluster1 gene | rs9366658 | 0.148 | 0.1794 | 0.9553 | 0.04834 | 0.8689 | 1.05 | −0.9469 | 0.3437 |
| All Histone cluster1 gene | rs9379844 | 0.421 | 0.3743 | 1.064 | 0.03304 | 0.9976 | 1.136 | 1.887 | 0.05922 |
| All Histone cluster1 gene | rs9379851 | 0.0701 | 0.1178 | 0.8314 | 0.06757 | 0.7283 | 0.9492 | −2.732 | 0.006303 |
| All Histone cluster1 gene | rs9379856 | NA | NA | NA | NA | NA | NA | NA | NA |
| All Histone cluster1 gene | rs9379858 | 0.06998 | 0.1179 | 0.8284 | 0.06762 | 0.7256 | 0.9458 | −2.784 | 0.005364 |
| All Histone cluster1 gene | rs9379859 | 0.06998 | 0.1179 | 0.8284 | 0.06762 | 0.7256 | 0.9458 | −2.784 | 0.005364 |
| All Histone cluster1 gene | rs9379870 | 0.2491 | 0.2842 | 0.9503 | 0.03768 | 0.8827 | 1.023 | −1.353 | 0.1761 |
| All Histone cluster1 gene | rs9379897 | 0.06948 | 0.1166 | 0.8148 | 0.06928 | 0.7114 | 0.9334 | −2.955 | 0.003123 |
| All Histone cluster1 gene | rs9393691 | 0.4209 | 0.3741 | 1.064 | 0.03302 | 0.9976 | 1.135 | 1.888 | 0.05902 |
| All Histone cluster1 gene | rs9393705 | 0.06998 | 0.1178 | 0.8305 | 0.06765 | 0.7273 | 0.9482 | −2.746 | 0.006036 |
| All Histone cluster1 gene | rs9393708 | 0.06998 | 0.1178 | 0.8305 | 0.06765 | 0.7273 | 0.9482 | −2.746 | 0.006036 |
| All Histone cluster1 gene | rs9393713 | 0.06962 | 0.1171 | 0.8318 | 0.06795 | 0.7281 | 0.9503 | −2.711 | 0.006712 |
| All Histone cluster1 gene | rs9393714 | 0.06961 | 0.1171 | 0.831 | 0.06794 | 0.7274 | 0.9493 | −2.725 | 0.006424 |
| All Histone cluster1 gene | rs9393777 | 0.09297 | 0.1022 | 0.8332 | 0.1037 | 0.68 | 1.021 | −1.759 | 0.07859 |
| All Histone cluster1 gene | rs9461362 | 0.1837 | 0.1489 | 1.045 | 0.04316 | 0.9599 | 1.137 | 1.012 | 0.3117 |
| All Histone cluster1 gene | rs9467704 | 0.0893 | 0.1131 | 0.8967 | 0.06277 | 0.7929 | 1.014 | −1.737 | 0.08239 |
| All Histone cluster1 gene | rs9468152 | 0.1702 | 0.1442 | 1.188 | 0.2952 | 0.666 | 2.119 | 0.5832 | 0.5598 |
| All Histone cluster1 gene | rs9468159 | 0.0924 | 0.06363 | 1.194 | 0.06055 | 1.061 | 1.345 | 2.932 | 0.003371 |

TABLE 1-continued

| | | | | | | | | | |
|---|---|---|---|---|---|---|---|---|---|
| All Histone cluster1 gene | rs9468202 | 0.01189 | 0.01056 | 0.8965 | 0.1537 | 0.6634 | 1.212 | −0.7106 | 0.4773 |
| All Histone cluster1 gene | rs9468227 | 0.01808 | 0.01615 | 0.8413 | 0.125 | 0.6585 | 1.075 | −1.382 | 0.1669 |
| GTF2IRD2B | imm_7_74094413 | 0.3916 | 0.4088 | 0.8676 | 0.03268 | 0.8138 | 0.925 | −4.346 | 1.38E−05 |
| GTF2IRD2B | imm_7_74108242 | 0.4014 | 0.4193 | 0.8748 | 0.03242 | 0.8209 | 0.9322 | −4.125 | 3.71E−05 |
| GTF2IRD2B | imm_7_74117236 | 0.4035 | 0.4192 | 0.8776 | 0.03238 | 0.8237 | 0.9351 | −4.031 | 5.56E−05 |
| GTF2IRD2B | imm_7_74118166 | 0.4666 | 0.46 | 0.8855 | 0.03208 | 0.8315 | 0.9429 | −3.793 | 0.000149 |
| GTF2IRD2B | imm_7_74120730 | 0.1026 | 0.1225 | 0.8373 | 0.05057 | 0.7583 | 0.9245 | −3.513 | 0.000443 |
| GTF2IRD2B | imm_7_74133859 | 0.1929 | 0.2297 | 0.7912 | 0.2746 | 0.4619 | 1.355 | −0.8529 | 0.3937 |
| GTF2IRD2B | imm_7_74145400 | NA | NA | NA | NA | NA | NA | NA | NA |
| ETS1 | imm_11_127760024 | 0.09923 | 0.09729 | 1.057 | 0.05358 | 0.9513 | 1.174 | 1.029 | 0.3036 |
| ETS1 | imm_11_127761269 | 0.1045 | 0.08108 | 1.337 | 0.4248 | 0.5816 | 3.075 | 0.6843 | 0.4938 |
| ETS1 | imm_11_127765567 | 0.1225 | 0.1356 | 1.065 | 0.0466 | 0.9719 | 1.167 | 1.349 | 0.1775 |
| ETS1 | imm_11_127767721 | 0.0296 | 0.02617 | 0.8282 | 0.09903 | 0.6821 | 1.006 | −1.904 | 0.0569 |
| ETS1 | imm_11_127770666 | 0.2654 | 0.2634 | 0.9872 | 0.03588 | 0.9202 | 1.059 | −0.3584 | 0.72 |
| ETS1 | imm_11_127770668 | 0.2656 | 0.2638 | 0.9866 | 0.03586 | 0.9196 | 1.058 | −0.3761 | 0.7068 |
| ETS1 | imm_11_127774308 | 0.1281 | 0.1396 | 1.066 | 0.04595 | 0.9746 | 1.167 | 1.4 | 0.1614 |
| ETS1 | imm_11_127775128 | 0.1286 | 0.1396 | 1.069 | 0.04592 | 0.9772 | 1.17 | 1.458 | 0.1449 |
| ETS1 | imm_11_127776527 | 0.03517 | 0.02933 | 0.8327 | 0.09292 | 0.694 | 0.999 | −1.97 | 0.04879 |
| ETS1 | imm_11_127776913 | 0.03344 | 0.02833 | 0.8482 | 0.09417 | 0.7053 | 1.02 | −1.748 | 0.08043 |
| ETS1 | imm_11_127777217 | 0.4176 | 0.4708 | 0.9489 | 0.03186 | 0.8915 | 1.01 | −1.646 | 0.09979 |
| ETS1 | imm_11_127778327 | NA | NA | NA | NA | NA | NA | NA | NA |
| ETS1 | imm_11_127778329 | 0.2401 | 0.247 | 1.034 | 0.03684 | 0.9621 | 1.112 | 0.9124 | 0.3616 |
| ETS1 | imm_11_127779030 | 0.04471 | 0.04792 | 0.888 | 0.07615 | 0.7649 | 1.031 | −1.56 | 0.1188 |
| ETS1 | imm_11_127780425 | 0.03802 | 0.03367 | 1.122 | 0.08549 | 0.9491 | 1.327 | 1.349 | 0.1775 |
| ETS1 | imm_11_127780902 | 0.04581 | 0.0487 | 0.8837 | 0.08254 | 0.7517 | 1.039 | −1.498 | 0.1341 |
| ETS1 | imm_11_127781839 | 0.2692 | 0.2885 | 0.8392 | 0.2397 | 0.5246 | 1.343 | −0.7313 | 0.4646 |
| ETS1 | imm_11_127785739 | 0.1848 | 0.1972 | 0.9376 | 0.04033 | 0.8663 | 1.015 | −1.599 | 0.1098 |
| ETS1 | imm_11_127785963 | 0.1421 | 0.1489 | 1.064 | 0.0447 | 0.9749 | 1.162 | 1.391 | 0.1644 |
| ETS1 | imm_11_127786010 | 0.2006 | 0.1899 | 1.055 | 0.03989 | 0.9759 | 1.141 | 1.349 | 0.1772 |
| ETS1 | imm_11_127786836 | 0.2008 | 0.1903 | 1.053 | 0.03987 | 0.9737 | 1.138 | 1.291 | 0.1965 |
| ETS1 | imm_11_127787128 | 0.2003 | 0.1897 | 1.055 | 0.03992 | 0.9757 | 1.141 | 1.345 | 0.1787 |
| ETS1 | imm_11_127788828 | 0.1906 | 0.2041 | 0.9357 | 0.03986 | 0.8654 | 1.012 | −1.668 | 0.0953 |
| ETS1 | imm_11_127789306 | 0.2006 | 0.1962 | 1.087 | 0.05728 | 0.9719 | 1.217 | 1.463 | 0.1435 |
| ETS1 | imm_11_127789441 | 0.201 | 0.1971 | 1.085 | 0.05721 | 0.9697 | 1.213 | 1.422 | 0.1551 |
| ETS1 | imm_11_127791651 | 0.1622 | 0.1548 | 1.087 | 0.04321 | 0.9988 | 1.183 | 1.931 | 0.05342 |
| ETS1 | imm_11_127792287 | 0.201 | 0.1903 | 1.053 | 0.0399 | 0.9737 | 1.138 | 1.291 | 0.1967 |
| ETS1 | imm_11_127792800 | 0.05115 | 0.04665 | 1.064 | 0.07416 | 0.9201 | 1.231 | 0.8374 | 0.4024 |
| ETS1 | imm_11_127793060 | 0.2016 | 0.1912 | 1.053 | 0.03983 | 0.974 | 1.139 | 1.298 | 0.1943 |
| ETS1 | imm_11_127794685 | 0.1632 | 0.1557 | 1.087 | 0.04309 | 0.9988 | 1.183 | 1.933 | 0.05325 |
| ETS1 | imm_11_127795453 | 0.202 | 0.1916 | 1.053 | 0.03978 | 0.974 | 1.138 | 1.296 | 0.1948 |
| ETS1 | imm_11_127796816 | 0.000277 | 0 | 2.68E+08 | 17210 | 0 | Inf | 0.001128 | 0.9991 |
| ETS1 | imm_11_127797523 | 0.2018 | 0.1911 | 1.055 | 0.0398 | 0.9757 | 1.14 | 1.341 | 0.1798 |
| ETS1 | imm_11_127798230 | 0.306 | 0.2976 | 0.9407 | 0.03477 | 0.8788 | 1.007 | −1.757 | 0.07891 |
| ETS1 | imm_11_127799892 | 0.5051 | 0.4805 | 0.997 | 0.03194 | 0.9365 | 1.061 | −0.09376 | 0.9253 |
| ETS1 | imm_11_127804916 | 0.1434 | 0.1323 | 0.9649 | 0.04645 | 0.881 | 1.057 | −0.7684 | 0.4423 |
| ETS1 | imm_11_127805367 | 0.03579 | 0.0314 | 0.9317 | 0.08952 | 0.7818 | 1.11 | −0.7899 | 0.4296 |
| ETS1 | imm_11_127806163 | 0.3755 | 0.3846 | 1.022 | 0.03283 | 0.9585 | 1.09 | 0.6682 | 0.504 |
| ETS1 | imm_11_127806304 | 0.03443 | 0.03077 | 0.9126 | 0.09083 | 0.7637 | 1.09 | −1.007 | 0.3137 |
| ETS1 | imm_11_127807384 | 0.1611 | 0.1639 | 0.993 | 0.04335 | 0.9121 | 1.081 | −0.1631 | 0.8705 |
| ETS1 | imm_11_127808758 | 0.03592 | 0.03158 | 0.9304 | 0.08931 | 0.781 | 1.108 | −0.8078 | 0.4192 |
| ETS1 | imm_11_127809308 | 0.005202 | 0.008031 | 0.9228 | 0.1958 | 0.6288 | 1.354 | −0.4103 | 0.6816 |
| ETS1 | imm_11_127812329 | 0.05871 | 0.0545 | 1.083 | 0.06867 | 0.9464 | 1.239 | 1.158 | 0.2467 |
| ETS1 | imm_11_127812420 | 0 | 0.000904 | 1.25E−10 | 24380 | 0 | Inf | −0.00094 | 0.9993 |
| ETS1 | imm_11_127813024 | 0.3752 | 0.3846 | 1.02 | 0.03283 | 0.9564 | 1.088 | 0.6007 | 0.548 |
| ETS1 | imm_11_127819226 | 0.1616 | 0.164 | 0.9959 | 0.04328 | 0.9149 | 1.084 | −0.09454 | 0.9247 |
| ETS1 | imm_11_127822686 | 0.03592 | 0.03176 | 0.9255 | 0.08905 | 0.7773 | 1.102 | −0.8694 | 0.3846 |
| ETS1 | imm_11_127823420 | 0.005203 | 0.008031 | 0.9229 | 0.1957 | 0.6288 | 1.354 | −0.4101 | 0.6817 |
| ETS1 | imm_11_127824356 | 0.1587 | 0.1614 | 0.988 | 0.04363 | 0.907 | 1.076 | −0.2778 | 0.7811 |
| ETS1 | imm_11_127825016 | 0.03629 | 0.03158 | 0.9352 | 0.08918 | 0.7852 | 1.114 | −0.7514 | 0.4524 |
| ETS1 | imm_11_127825282 | 0.3776 | 0.3871 | 1.023 | 0.03279 | 0.9592 | 1.091 | 0.69 | 0.4902 |
| ETS1 | imm_11_127825669 | 0.3776 | 0.3869 | 1.024 | 0.0328 | 0.9598 | 1.092 | 0.7097 | 0.4779 |
| ETS1 | imm_11_127826087 | 0.3214 | 0.3391 | 0.9933 | 0.0338 | 0.9296 | 1.061 | −0.2003 | 0.8412 |
| ETS1 | imm_11_127826464 | 0.1491 | 0.1481 | 1.005 | 0.04514 | 0.9203 | 1.098 | 0.119 | 0.9053 |
| ETS1 | imm_11_127827422 | 0.1496 | 0.149 | 1.005 | 0.04498 | 0.9199 | 1.097 | 0.1047 | 0.9166 |
| ETS1 | imm_11_127828334 | 0.03406 | 0.03032 | 0.9041 | 0.09167 | 0.7554 | 1.082 | −1.1 | 0.2713 |
| ETS1 | imm_11_127831280 | 0.01663 | 0.0246 | 1.022 | 0.1232 | 0.8025 | 1.301 | 0.1735 | 0.8622 |
| ETS1 | imm_11_127831611 | 0.1616 | 0.152 | 1.026 | 0.04416 | 0.9407 | 1.118 | 0.5757 | 0.5648 |
| ETS1 | imm_11_127831673 | 0.2755 | 0.2923 | 0.9931 | 0.03555 | 0.9263 | 1.065 | −0.1945 | 0.8458 |
| ETS1 | imm_11_127834123 | 0.267 | 0.3026 | 1.029 | 0.03531 | 0.9599 | 1.102 | 0.7999 | 0.4238 |
| ETS1 | imm_11_127834484 | 0.02106 | 0.02681 | 0.9249 | 0.1037 | 0.7548 | 1.133 | −0.7522 | 0.4519 |
| ETS1 | imm_11_127837472 | 0.01585 | 0.01922 | 1.016 | 0.1212 | 0.8012 | 1.288 | 0.1314 | 0.8955 |
| ETS1 | imm_11_127838265 | 0.07167 | 0.08269 | 1.021 | 0.06775 | 0.8943 | 1.166 | 0.3112 | 0.7556 |
| ETS1 | imm_11_127838713 | 0.4488 | 0.4731 | 1.016 | 0.03193 | 0.9544 | 1.082 | 0.4976 | 0.6187 |
| ETS1 | imm_11_127839719 | 0.008546 | 0.01534 | 0.7867 | 0.1489 | 0.5876 | 1.053 | −1.61 | 0.1073 |

TABLE 1-continued

| | | | | | | | | | |
|---|---|---|---|---|---|---|---|---|---|
| ETS1 | imm_11_127840459 | 0.1553 | 0.1515 | 1.032 | 0.0442 | 0.9466 | 1.126 | 0.7171 | 0.4733 |
| ETS1 | imm_11_127840867 | 0.122 | 0.1295 | 1.012 | 0.06897 | 0.8843 | 1.159 | 0.1765 | 0.8599 |
| ETS1 | imm_11_127841724 | 0.1095 | 0.106 | 0.8683 | 0.05228 | 0.7837 | 0.962 | −2.701 | 0.006915 |
| ETS1 | imm_11_127841864 | 0.43 | 0.4439 | 0.9506 | 0.03218 | 0.8925 | 1.012 | −1.574 | 0.1154 |
| ETS1 | imm_11_127843207 | 0.109 | 0.1057 | 0.8676 | 0.05234 | 0.783 | 0.9614 | −2.713 | 0.006676 |
| ETS1 | imm_11_127843341 | 0.1088 | 0.1053 | 0.8728 | 0.05243 | 0.7876 | 0.9673 | −2.594 | 0.009475 |
| ETS1 | imm_11_127844385 | 0.1558 | 0.1525 | 1.026 | 0.04417 | 0.9407 | 1.119 | 0.5761 | 0.5646 |
| ETS1 | imm_11_127844729 | 0.02551 | 0.01967 | 1.13 | 0.1089 | 0.913 | 1.399 | 1.124 | 0.2609 |
| ETS1 | imm_11_127845557 | 0.1145 | 0.1088 | 0.8748 | 0.05135 | 0.7911 | 0.9674 | −2.605 | 0.009196 |
| ETS1 | imm_11_127846698 | 0.1561 | 0.1529 | 1.028 | 0.04405 | 0.9428 | 1.12 | 0.6218 | 0.534 |
| ETS1 | imm_11_127848167 | 0.1566 | 0.1529 | 1.031 | 0.04402 | 0.9454 | 1.123 | 0.6847 | 0.4935 |
| ETS1 | imm_11_127848372 | 0.156 | 0.1526 | 1.027 | 0.04407 | 0.9425 | 1.12 | 0.6151 | 0.5385 |
| ETS1 | imm_11_127849992 | 0.1561 | 0.1528 | 1.029 | 0.04405 | 0.9434 | 1.121 | 0.6383 | 0.5233 |
| ETS1 | imm_11_127851599 | 0.1577 | 0.1532 | 1.03 | 0.04393 | 0.9446 | 1.122 | 0.662 | 0.508 |
| ETS1 | imm_11_127852250 | 0.1051 | 0.104 | 0.8571 | 0.05302 | 0.7725 | 0.9509 | −2.909 | 0.003627 |
| ETS1 | imm_11_127853705 | 0.1053 | 0.1043 | 0.8574 | 0.05294 | 0.7729 | 0.9512 | −2.906 | 0.003665 |
| ETS1 | imm_11_127855281 | 0.1578 | 0.1537 | 1.028 | 0.04389 | 0.9435 | 1.121 | 0.6351 | 0.5253 |
| ETS1 | imm_11_127855956 | 0.1073 | 0.1055 | 0.8632 | 0.05254 | 0.7787 | 0.9568 | −2.8 | 0.00511 |
| ETS1 | imm_11_127857027 | 0.1036 | 0.1029 | 0.8621 | 0.05334 | 0.7766 | 0.9572 | −2.781 | 0.005423 |
| ETS1 | imm_11_127861069 | 0.2813 | 0.264 | 0.9939 | 0.03613 | 0.926 | 1.067 | −0.1688 | 0.866 |
| ETS1 | imm_11_127863304 | 0.2818 | 0.264 | 0.9915 | 0.03613 | 0.9237 | 1.064 | −0.2355 | 0.8138 |
| ETS1 | imm_11_127863391 | 0.2819 | 0.264 | 0.9934 | 0.03611 | 0.9255 | 1.066 | −0.1826 | 0.8551 |
| ETS1 | imm_11_127866379 | 0.2602 | 0.2434 | 1.01 | 0.03687 | 0.9393 | 1.085 | 0.2617 | 0.7936 |
| ETS1 | imm_11_127868447 | 0.01177 | 0.01215 | 1.459 | 0.2081 | 0.97 | 2.193 | 1.814 | 0.06974 |
| ETS1 | imm_11_127868927 | 0.2025 | 0.1913 | 0.9583 | 0.04052 | 0.8852 | 1.038 | −1.051 | 0.2933 |
| ETS1 | imm_11_127869177 | 0.2994 | 0.3094 | 1.012 | 0.05015 | 0.9171 | 1.116 | 0.2349 | 0.8143 |
| ETS1 | imm_11_127870403 | 0.2722 | 0.2563 | 0.9918 | 0.03655 | 0.9232 | 1.065 | −0.2256 | 0.8215 |
| ETS1 | imm_11_127870895 | 0.2995 | 0.2695 | 0.9909 | 0.03589 | 0.9236 | 1.063 | −0.2535 | 0.7999 |
| ETS1 | imm_11_127871431 | 0.2995 | 0.2697 | 0.9901 | 0.03589 | 0.9229 | 1.062 | −0.2762 | 0.7824 |
| ETS1 | imm_11_127872972 | 0.2003 | 0.1863 | 0.893 | 0.05916 | 0.7952 | 1.003 | −1.914 | 0.05568 |
| ETS1 | imm_11_127874486 | 0.2995 | 0.2696 | 0.9913 | 0.03588 | 0.924 | 1.064 | −0.2438 | 0.8074 |
| ETS1 | imm_11_127874807 | 0.2851 | 0.2647 | 0.983 | 0.03611 | 0.9158 | 1.055 | −0.4745 | 0.6351 |
| ETS1 | imm_11_127877378 | 0.2989 | 0.269 | 0.9921 | 0.0359 | 0.9247 | 1.064 | −0.2201 | 0.8258 |
| ETS1 | imm_11_127879923 | 0.1999 | 0.1907 | 0.9578 | 0.04065 | 0.8844 | 1.037 | −1.062 | 0.2883 |
| ETS1 | imm_11_127881686 | 0.1909 | 0.1676 | 1.043 | 0.04194 | 0.9607 | 1.132 | 1.003 | 0.3159 |
| ETS1 | imm_11_127882690 | 0.4045 | 0.3813 | 1.017 | 0.03273 | 0.9535 | 1.084 | 0.506 | 0.6128 |
| ETS1 | imm_11_127884689 | 0.05927 | 0.06757 | 0.8456 | 0.472 | 0.3353 | 2.133 | −0.3554 | 0.7223 |
| ETS1 | imm_11_127885952 | 0.3706 | 0.3524 | 1.029 | 0.03319 | 0.9646 | 1.099 | 0.8743 | 0.382 |
| ETS1 | imm_11_127886184 | 0.2435 | 0.2214 | 1.066 | 0.03763 | 0.9906 | 1.148 | 1.709 | 0.08748 |
| ETS1 | imm_11_127887077 | 0.3702 | 0.3521 | 1.029 | 0.03319 | 0.9642 | 1.098 | 0.8607 | 0.3894 |
| ETS1 | imm_11_127889134 | 0.2431 | 0.221 | 1.066 | 0.03774 | 0.9904 | 1.148 | 1.705 | 0.08811 |
| ETS1 | imm_11_127891116 | 0.2431 | 0.2211 | 1.067 | 0.03774 | 0.9907 | 1.149 | 1.714 | 0.08661 |
| ETS1 | imm_11_127892632 | 0.3704 | 0.3521 | 1.03 | 0.0332 | 0.9655 | 1.1 | 0.9013 | 0.3674 |
| ETS1 | imm_11_127894601 | 0.2506 | 0.2405 | 0.9395 | 0.03731 | 0.8733 | 1.011 | −1.672 | 0.09462 |
| ETS1 | imm_11_127894638 | 0.003716 | 0.002075 | 1.374 | 0.3097 | 0.7489 | 2.521 | 1.026 | 0.3048 |
| ETS1 | imm_11_127895279 | 0.243 | 0.2207 | 1.068 | 0.03774 | 0.9915 | 1.15 | 1.735 | 0.08275 |
| ETS1 | imm_11_127897147 | 0.2232 | 0.2121 | 1.066 | 0.03857 | 0.9886 | 1.15 | 1.662 | 0.09658 |
| ETS1 | imm_11_127898835 | 0.01239 | 0.01814 | 0.9176 | 0.1286 | 0.7133 | 1.181 | −0.6686 | 0.5037 |
| ETS1 | imm_11_127901157 | 0.3059 | 0.2861 | 1.062 | 0.03509 | 0.9912 | 1.137 | 1.709 | 0.08752 |
| ETS1 | imm_11_127901948 | 0.228 | 0.2155 | 1.061 | 0.03837 | 0.9844 | 1.144 | 1.549 | 0.1213 |
| ETS1 | imm_11_127905841 | 0.03579 | 0.04864 | 0.995 | 0.07786 | 0.8542 | 1.159 | −0.06386 | 0.9491 |
| ETS1 | imm_11_127906568 | 0.388 | 0.3836 | 0.9752 | 0.03276 | 0.9146 | 1.04 | −0.7663 | 0.4435 |
| ETS1 | imm_11_127908214 | 0.3883 | 0.384 | 0.9755 | 0.03276 | 0.9148 | 1.04 | −0.7587 | 0.448 |
| ETS1 | imm_11_127911648 | 0.4828 | 0.4715 | 1.016 | 0.04546 | 0.9295 | 1.111 | 0.3513 | 0.7253 |
| ETS1 | imm_11_127911985 | 0.4903 | 0.49 | 0.9633 | 0.03179 | 0.9051 | 1.025 | −1.177 | 0.2392 |
| ETS1 | imm_11_127914294 | 0.4918 | 0.4912 | 0.9631 | 0.03178 | 0.905 | 1.025 | −1.182 | 0.2372 |
| ETS1 | imm_11_127915474 | 0.4825 | 0.4941 | 1.033 | 0.0318 | 0.9707 | 1.1 | 1.024 | 0.306 |
| ETS1 | imm_11_127915554 | 0.4827 | 0.4941 | 1.034 | 0.0318 | 0.9712 | 1.1 | 1.04 | 0.2983 |
| ETS1 | imm_11_127916046 | 0.4921 | 0.4908 | 0.9665 | 0.03176 | 0.9081 | 1.029 | −1.074 | 0.2827 |
| ETS1 | imm_11_127929821 | 0.000832 | 0 | 2.22E+08 | 9897 | 0 | Inf | 0.001942 | 0.9985 |
| ETS1 | imm_11_127931099 | 0.000124 | 0 | 3.89E+08 | 24380 | 0 | Inf | 0.000811 | 0.9994 |
| ETS1 | imm_11_127940676 | 0.0322 | 0.04675 | 0.8901 | 0.08166 | 0.7584 | 1.045 | −1.426 | 0.1538 |
| ETS1 | imm_11_127943244 | 0.000139 | 0.000904 | 0.1276 | 1.417 | 0.007941 | 2.05 | −1.453 | 0.1461 |
| ETS1 | imm_11_127945727 | 0.3529 | 0.3654 | 1.093 | 0.03356 | 1.023 | 1.167 | 2.647 | 0.008125 |
| ETS1 | imm_11_127945953 | 0.07208 | 0.07679 | 0.9935 | 0.0607 | 0.882 | 1.119 | −0.1079 | 0.9141 |
| ETS1 | imm_11_127948912 | 0.01338 | 0.01886 | 0.8931 | 0.1262 | 0.6974 | 1.144 | −0.8959 | 0.3703 |
| ETS1 | imm_11_127956842 | 0.2394 | 0.2512 | 0.9858 | 0.03721 | 0.9165 | 1.06 | −0.3845 | 0.7006 |
| ETS1 | imm_11_127957543 | 0.01553 | 0.01099 | 1.247 | 0.1637 | 0.9046 | 1.718 | 1.348 | 0.1778 |
| ETS1 | imm_11_127957904 | 0.006936 | 0.01471 | 0.7343 | 0.1582 | 0.5386 | 1.001 | −1.952 | 0.05088 |
| ETS1 | imm_11_127974263 | 0.07146 | 0.07661 | 0.9949 | 0.06078 | 0.8832 | 1.121 | −0.08418 | 0.9329 |
| ETS1 | imm_11_127979301 | 0.1644 | 0.1768 | 0.9816 | 0.04237 | 0.9034 | 1.067 | −0.4374 | 0.6618 |
| ETS1 | imm_11_127979905 | 0.006069 | 0.01065 | 0.8416 | 0.1763 | 0.5957 | 1.189 | −0.9781 | 0.328 |
| ETS1 | imm_11_127981559 | 0.1593 | 0.1708 | 0.9882 | 0.043 | 0.9083 | 1.075 | −0.2764 | 0.7822 |
| ETS1 | imm_11_127982379 | 0.1593 | 0.1708 | 0.9882 | 0.043 | 0.9083 | 1.075 | −0.2764 | 0.7822 |
| ETS1 | imm_11_127982748 | 0.1594 | 0.1709 | 0.9878 | 0.04302 | 0.908 | 1.075 | −0.2848 | 0.7758 |
| ETS1 | imm_11_127983590 | 0.1578 | 0.1698 | 0.9895 | 0.04311 | 0.9093 | 1.077 | −0.2454 | 0.8062 |
| ETS1 | imm_11_127983743 | 0.1593 | 0.1708 | 0.9882 | 0.043 | 0.9083 | 1.075 | −0.2764 | 0.7822 |
| ETS1 | imm_11_127984265 | 0.1593 | 0.1705 | 0.9898 | 0.043 | 0.9098 | 1.077 | −0.2391 | 0.811 |
| ETS1 | imm_11_127984721 | 0.1639 | 0.1818 | 0.9766 | 0.04889 | 0.8874 | 1.075 | −0.4836 | 0.6287 |
| ETS1 | rs7935286 | 0.1731 | 0.1549 | 1.076 | 0.04318 | 0.9887 | 1.171 | 1.697 | 0.08975 |

TABLE 1-continued

| | | | | | | | | | |
|---|---|---|---|---|---|---|---|---|---|
| SLC5A1 | rs738203 | 0.2295 | 0.1081 | 2.421 | 0.3734 | 1.165 | 5.033 | 2.368 | 0.01787 |
| SLC5A1 | rs9609429 | 0.2286 | 0.2801 | 0.8632 | 0.0372 | 0.8025 | 0.9285 | −3.955 | 7.65E−05 |
| TET2 | rs10010325 | 0.4693 | 0.4772 | 0.9764 | 0.03186 | 0.9173 | 1.039 | −0.7485 | 0.4541 |
| TET2 | rs17035310 | 0.1487 | 0.1265 | 1.097 | 0.04675 | 1.001 | 1.202 | 1.972 | 0.0486 |
| TET2 | rs2189234 | 0.3562 | 0.3837 | 0.9611 | 0.03307 | 0.9008 | 1.025 | −1.2 | 0.23 |
| TET2 | rs7661349 | 0.3235 | 0.3641 | 0.9541 | 0.03359 | 0.8933 | 1.019 | −1.399 | 0.1619 |
| TET2 | rs974801 | 0.3636 | 0.355 | 1.028 | 0.03308 | 0.9633 | 1.097 | 0.8306 | 0.4062 |

(Continued, part 3)

| gene.i | SNP | F_A_iibdgc | F_U_iibdgc | OR_iibdgc | SE_iibdgc | L95_iibdgc | U95_iibdgc |
|---|---|---|---|---|---|---|---|
| SLC26A4 | rs10247487 | 0.2562 | 0.2535 | 0.9522 | 0.0161 | 0.9226 | 0.9827 |
| SLC26A4 | rs10263826 | 0.2723 | 0.2697 | 0.9459 | 0.01578 | 0.9171 | 0.9756 |
| SLC26A4 | rs10273733 | 0.2937 | 0.2773 | 1.068 | 0.01553 | 1.036 | 1.101 |
| SLC26A4 | rs12539555 | 0.2607 | 0.2621 | 1.029 | 0.01607 | 0.9967 | 1.061 |
| SLC26A4 | rs2248465 | 0.2781 | 0.2642 | 1.057 | 0.01573 | 1.025 | 1.09 |
| SLC26A4 | rs2808 | 0.2968 | 0.2799 | 1.07 | 0.01547 | 1.038 | 1.103 |
| DLG4 | rs3785794 | 0.07336 | 0.07494 | 0.9162 | 0.02669 | 0.8695 | 0.9654 |
| GIPR | chr19:50983512 | 0.2904 | 0.3095 | 0.9404 | 0.01544 | 0.9124 | 0.9693 |
| GIPR | chr19:51014231 | 0.2991 | 0.3218 | 0.9347 | 0.01531 | 0.907 | 0.9631 |
| GIPR | chr19:51026971 | 0.3022 | 0.3244 | 0.9344 | 0.01522 | 0.907 | 0.9628 |
| GIPR | rs10401439 | 0.2987 | 0.3224 | 0.9284 | 0.01566 | 0.9003 | 0.9573 |
| GIPR | rs10402263 | 0.3321 | 0.3504 | 0.9441 | 0.01489 | 0.917 | 0.9721 |
| GIPR | rs10421891 | 0.3395 | 0.3596 | 0.9391 | 0.01466 | 0.9125 | 0.9665 |
| GIPR | rs10500292 | 0.383 | 0.4041 | 0.9396 | 0.01445 | 0.9134 | 0.9666 |
| GIPR | rs11883351 | 0.3289 | 0.3486 | 0.9389 | 0.01493 | 0.9118 | 0.9668 |
| GIPR | rs12463359 | 0.3775 | 0.3969 | 0.9433 | 0.01449 | 0.9169 | 0.9705 |
| GIPR | rs16980013 | 0.2881 | 0.3073 | 0.9407 | 0.01548 | 0.9126 | 0.9697 |
| GIPR | rs16980051 | 0.4789 | 0.5034 | 0.9424 | 0.01408 | 0.9167 | 0.9687 |
| GIPR | rs17878252 | 0.2689 | 0.2873 | 0.9391 | 0.01577 | 0.9106 | 0.9686 |
| GIPR | rs2070736 | 0.2909 | 0.3101 | 0.9396 | 0.01543 | 0.9116 | 0.9685 |
| GIPR | rs2334255 | 0.2601 | 0.2473 | 1.045 | 0.01603 | 1.013 | 1.079 |
| GIPR | rs4514788 | 0.3041 | 0.3246 | 0.9433 | 0.01517 | 0.9157 | 0.9718 |
| GIPR | rs4802273 | 0.2787 | 0.2977 | 0.9383 | 0.01561 | 0.91 | 0.9675 |
| GIPR | rs4802274 | 0.2915 | 0.311 | 0.938 | 0.01542 | 0.9101 | 0.9668 |
| GIPR | rs4803861 | 0.3016 | 0.3235 | 0.9359 | 0.01523 | 0.9084 | 0.9642 |
| GIPR | rs8111071 | 0.09803 | 0.08834 | 1.066 | 0.02406 | 1.017 | 1.118 |
| GIPR | rs918490 | 0.3002 | 0.3228 | 0.9334 | 0.01524 | 0.9059 | 0.9617 |
| ZHX3 | rs6072275 | 0.1584 | 0.1541 | 1.079 | 0.0193 | 1.039 | 1.121 |
| ZHX3 | rs6072343 | 0.1469 | 0.1415 | 1.097 | 0.01997 | 1.055 | 1.141 |
| ZHX3 | rs6093462 | 0.2969 | 0.3115 | 0.9301 | 0.01516 | 0.9029 | 0.9582 |
| TNRC6B | rs114607 | 0.3738 | 0.3803 | 0.9553 | 0.01445 | 0.9286 | 0.9827 |
| TNRC6B | rs137955 | 0.4466 | 0.4379 | 1.041 | 0.01413 | 1.013 | 1.071 |
| TNRC6B | rs137956 | 0.4545 | 0.4442 | 1.045 | 0.01412 | 1.016 | 1.074 |
| TNRC6B | rs137977 | 0.383 | 0.3852 | 0.9769 | 0.01443 | 0.9497 | 1.005 |
| TNRC6B | rs137981 | 0.1172 | 0.1193 | 0.9627 | 0.0217 | 0.9226 | 1.005 |
| TNRC6B | rs138027 | 0.2464 | 0.2498 | 0.9653 | 0.01625 | 0.935 | 0.9965 |
| TNRC6B | rs2958647 | 0.4529 | 0.4434 | 1.042 | 0.01412 | 1.014 | 1.071 |
| TNRC6B | rs713925 | 0.3734 | 0.3741 | 0.9722 | 0.0148 | 0.9444 | 1.001 |
| CDK6 | rs2282978 | 0.3299 | 0.3463 | 0.9252 | 0.01595 | 0.8967 | 0.9546 |
| CDK6 | rs4272 | 0.203 | 0.2149 | 0.9376 | 0.01859 | 0.9041 | 0.9724 |
| PRR5L | rs11033597 | 0.1408 | 0.1371 | 1.052 | 0.02179 | 1.008 | 1.098 |
| PRR5L | rs11600757 | 0.1609 | 0.156 | 1.069 | 0.02064 | 1.026 | 1.113 |
| PRR5L | rs11601211 | 0.07534 | 0.07393 | 1.056 | 0.02867 | 0.9985 | 1.117 |
| PRR5L | rs12281565 | 0.1636 | 0.1588 | 1.065 | 0.0205 | 1.023 | 1.108 |
| PRR5L | rs1365120 | NA | NA | NA | NA | NA | NA |
| PRR5L | rs1895840 | 0.1078 | 0.106 | 1.05 | 0.02442 | 1.001 | 1.101 |
| PRR5L | rs2303439 | 0.1648 | 0.1563 | 1.071 | 0.02079 | 1.028 | 1.115 |
| PRR5L | rs330260 | 0.1762 | 0.1711 | 1.04 | 0.01987 | 0.9998 | 1.081 |
| PRR5L | rs331485 | 0.1044 | 0.1088 | 0.9352 | 0.02452 | 0.8913 | 0.9812 |
| PRR5L | rs4077044 | 0.4255 | 0.4166 | 1.032 | 0.01527 | 1.001 | 1.063 |
| PRR5L | rs5030437 | 0.1644 | 0.1564 | 1.068 | 0.02047 | 1.026 | 1.112 |
| PRR5L | rs5030445 | 0.1642 | 0.1565 | 1.064 | 0.02048 | 1.022 | 1.108 |
| PRR5L | rs5030472 | 0.1172 | 0.1119 | 1.073 | 0.02363 | 1.025 | 1.124 |
| PRR5L | rs7929195 | 0.1151 | 0.1176 | 0.9472 | 0.02357 | 0.9044 | 0.992 |
| WNT2B | rs10745330 | 0.4918 | 0.4858 | 1.044 | 0.01185 | 1.02 | 1.068 |
| WNT2B | rs2999155 | 0.4886 | 0.4837 | 1.042 | 0.01185 | 1.019 | 1.067 |
| WNT2B | rs3790609 | 0.1816 | 0.1714 | 1.054 | 0.01562 | 1.023 | 1.087 |
| WNT2B | rs6682737 | 0.4882 | 0.4826 | 1.042 | 0.01185 | 1.018 | 1.067 |
| LRRC16A | rs10456320 | 0.1246 | 0.117 | 1.081 | 0.01823 | 1.043 | 1.121 |
| LRRC16A | rs11755567 | 0.1874 | 0.1875 | 0.9515 | 0.0152 | 0.9236 | 0.9803 |
| LRRC16A | rs13191296 | 0.06723 | 0.07411 | 0.9191 | 0.02308 | 0.8784 | 0.9616 |
| LRRC16A | rs2690110 | 0.3606 | 0.3506 | 1.058 | 0.01239 | 1.032 | 1.084 |
| LRRC16A | rs4712908 | 0.3591 | 0.3703 | 0.9622 | 0.01257 | 0.9387 | 0.9862 |
| LRRC16A | rs6921589 | 0.1181 | 0.1271 | 0.9289 | 0.01803 | 0.8966 | 0.9623 |
| LRRC16A | rs6937918 | 0.4176 | 0.406 | 1.031 | 0.01213 | 1.007 | 1.056 |
| LRRC16A | rs742132 | 0.3025 | 0.2961 | 1.035 | 0.0129 | 1.009 | 1.061 |
| LRRC16A | rs7752195 | 0.0614 | 0.06885 | 0.9 | 0.02404 | 0.8585 | 0.9434 |
| LRRC16A | rs7752524 | 0.09931 | 0.09399 | 1.099 | 0.02007 | 1.057 | 1.143 |

TABLE 1-continued

| | | | | | | | |
|---|---|---|---|---|---|---|---|
| LRRC16A | rs7762757 | 0.3822 | 0.3714 | 1.034 | 0.01225 | 1.009 | 1.059 |
| LRRC16A | rs880226 | 0.4177 | 0.4066 | 1.029 | 0.01214 | 1.005 | 1.054 |
| LRRC16A | rs9295661 | 0.06122 | 0.06873 | 0.9067 | 0.02405 | 0.865 | 0.9505 |
| LRRC16A | rs9358854 | 0.3352 | 0.3363 | 0.964 | 0.01258 | 0.9405 | 0.9881 |
| LRRC16A | rs9461157 | 0.4165 | 0.4052 | 1.031 | 0.01214 | 1.007 | 1.056 |
| LRRC16A | rs9461165 | 0.4169 | 0.4055 | 1.032 | 0.01213 | 1.008 | 1.057 |
| LRRC16A | rs9467445 | 0.2048 | 0.2063 | 0.9477 | 0.01469 | 0.9208 | 0.9754 |
| All Histone cluster1 gene | rs10484399 | 0.08249 | 0.08954 | 0.9297 | 0.02116 | 0.8919 | 0.969 |
| All Histone cluster1 gene | rs10484439 | 0.07707 | 0.08335 | 0.9336 | 0.02179 | 0.8945 | 0.9743 |
| All Histone cluster1 gene | rs12176317 | 0.1064 | 0.1129 | 0.9475 | 0.01931 | 0.9123 | 0.984 |
| All Histone cluster1 gene | rs13194053 | 0.1646 | 0.173 | 0.9407 | 0.01584 | 0.9119 | 0.9703 |
| All Histone cluster1 gene | rs13194491 | 0.07371 | 0.06948 | 1.075 | 0.02311 | 1.028 | 1.125 |
| All Histone cluster1 gene | rs13194781 | 0.0828 | 0.08981 | 0.93 | 0.02112 | 0.8923 | 0.9693 |
| All Histone cluster1 gene | rs13195040 | 0.08117 | 0.08842 | 0.9222 | 0.02162 | 0.8839 | 0.9621 |
| All Histone cluster1 gene | rs13199772 | 0.0828 | 0.0898 | 0.9298 | 0.02112 | 0.8921 | 0.9691 |
| All Histone cluster1 gene | rs13212651 | 0.08267 | 0.08977 | 0.9292 | 0.02113 | 0.8915 | 0.9684 |
| All Histone cluster1 gene | rs1321578 | 0.03625 | 0.04163 | 0.9317 | 0.03097 | 0.8768 | 0.99 |
| All Histone cluster1 gene | rs13217599 | 0.07214 | 0.06972 | 1.058 | 0.02321 | 1.011 | 1.107 |
| All Histone cluster1 gene | rs13218875 | 0.08106 | 0.08864 | 0.9279 | 0.02129 | 0.89 | 0.9675 |
| All Histone cluster1 gene | rs13219354 | 0.1074 | 0.1155 | 0.9404 | 0.01886 | 0.9063 | 0.9758 |
| All Histone cluster1 gene | rs16867901 | 0.008384 | 0.008575 | 0.8326 | 0.06461 | 0.7336 | 0.945 |
| All Histone cluster1 gene | rs16867911 | 0.008367 | 0.008525 | 0.8381 | 0.06472 | 0.7382 | 0.9514 |
| All Histone cluster1 gene | rs16891725 | 0.1081 | 0.1149 | 0.9483 | 0.01917 | 0.9133 | 0.9846 |
| All Histone cluster1 gene | rs175597 | 0.1011 | 0.1088 | 0.9258 | 0.01934 | 0.8914 | 0.9616 |
| All Histone cluster1 gene | rs17693963 | 0.08976 | 0.09625 | 0.9418 | 0.02044 | 0.9048 | 0.9802 |

TABLE 1-continued

| | | | | | | | |
|---|---|---|---|---|---|---|---|
| All Histone cluster1 gene | rs17739310 | 0.1507 | 0.1418 | 1.045 | 0.01685 | 1.011 | 1.08 |
| All Histone cluster1 gene | rs17750424 | 0.07922 | 0.08769 | 0.9051 | 0.02218 | 0.8666 | 0.9453 |
| All Histone cluster1 gene | rs1977 | 0.1065 | 0.1131 | 0.9468 | 0.0193 | 0.9116 | 0.9833 |
| All Histone cluster1 gene | rs1985732 | 0.2866 | 0.2918 | 0.9763 | 0.01307 | 0.9516 | 1.002 |
| All Histone cluster1 gene | rs200483 | 0.1014 | 0.1089 | 0.9273 | 0.01932 | 0.8929 | 0.9631 |
| All Histone cluster1 gene | rs200484 | 0.1013 | 0.1087 | 0.9274 | 0.01935 | 0.8929 | 0.9633 |
| All Histone cluster1 gene | rs200490 | 0.1014 | 0.109 | 0.9272 | 0.01931 | 0.8928 | 0.963 |
| All Histone cluster1 gene | rs200501 | 0.1021 | 0.1094 | 0.9303 | 0.01926 | 0.8958 | 0.9661 |
| All Histone cluster1 gene | rs200948 | 0.1011 | 0.1088 | 0.9251 | 0.01934 | 0.8907 | 0.9608 |
| All Histone cluster1 gene | rs200953 | 0.1015 | 0.1091 | 0.9253 | 0.01931 | 0.891 | 0.961 |
| All Histone cluster1 gene | rs200989 | 0.1012 | 0.1089 | 0.9257 | 0.01933 | 0.8913 | 0.9614 |
| All Histone cluster1 gene | rs200990 | 0.1015 | 0.1092 | 0.9246 | 0.0193 | 0.8902 | 0.9602 |
| All Histone cluster1 gene | rs200991 | 0.1474 | 0.1511 | 0.9629 | 0.01661 | 0.9321 | 0.9948 |
| All Histone cluster1 gene | rs200995 | 0.1013 | 0.1089 | 0.926 | 0.01932 | 0.8915 | 0.9617 |
| All Histone cluster1 gene | rs201002 | 0.1015 | 0.109 | 0.9275 | 0.0193 | 0.8931 | 0.9633 |
| All Histone cluster1 gene | rs201004 | 0.1773 | 0.1813 | 0.9683 | 0.01569 | 0.939 | 0.9986 |
| All Histone cluster1 gene | rs2064092 | 0.0821 | 0.07479 | 1.037 | 0.02204 | 0.9932 | 1.083 |
| All Histone cluster1 gene | rs2072806 | 0.1088 | 0.1148 | 0.9534 | 0.01912 | 0.9184 | 0.9898 |
| All Histone cluster1 gene | rs2073529 | 0.1066 | 0.113 | 0.9482 | 0.01928 | 0.913 | 0.9847 |
| All Histone cluster1 gene | rs2093169 | 0.1742 | 0.1786 | 0.9618 | 0.01557 | 0.9329 | 0.9916 |

TABLE 1-continued

| | | | | | | | |
|---|---|---|---|---|---|---|---|
| All Histone cluster1 gene | rs2393997 | 0.1124 | 0.1192 | 0.9672 | 0.01861 | 0.9326 | 1.003 |
| All Histone cluster1 gene | rs2494711 | 0.3864 | 0.383 | 1.028 | 0.01217 | 1.004 | 1.053 |
| All Histone cluster1 gene | rs2747054 | 0.1014 | 0.1091 | 0.9256 | 0.01931 | 0.8913 | 0.9613 |
| All Histone cluster1 gene | rs2893910 | 0.1688 | 0.1672 | 0.9605 | 0.01585 | 0.9311 | 0.9908 |
| All Histone cluster1 gene | rs34706883 | 0.08273 | 0.08976 | 0.9301 | 0.02112 | 0.8924 | 0.9694 |
| All Histone cluster1 gene | rs370155 | 0.1017 | 0.1092 | 0.927 | 0.01929 | 0.8926 | 0.9627 |
| All Histone cluster1 gene | rs3799378 | 0.2164 | 0.225 | 0.9583 | 0.01517 | 0.9302 | 0.9872 |
| All Histone cluster1 gene | rs3799380 | 0.1884 | 0.1907 | 0.961 | 0.01512 | 0.933 | 0.9899 |
| All Histone cluster1 gene | rs3799383 | 0.1152 | 0.1206 | 0.9571 | 0.01841 | 0.9232 | 0.9923 |
| All Histone cluster1 gene | rs3800307 | 0.1926 | 0.1998 | 0.9485 | 0.01492 | 0.9212 | 0.9767 |
| All Histone cluster1 gene | rs3800316 | 0.266 | 0.2635 | 0.9587 | 0.01346 | 0.9337 | 0.9843 |
| All Histone cluster1 gene | rs4452638 | 0.1072 | 0.115 | 0.9426 | 0.01886 | 0.9084 | 0.9781 |
| All Histone cluster1 gene | rs4634439 | 0.1051 | 0.1122 | 0.95 | 0.01907 | 0.9152 | 0.9862 |
| All Histone cluster1 gene | rs4712981 | 0.2765 | 0.2812 | 0.9741 | 0.01319 | 0.9492 | 0.9996 |
| All Histone cluster1 gene | rs4713119 | 0.114 | 0.1209 | 0.9676 | 0.01852 | 0.9331 | 1.003 |
| All Histone cluster1 gene | rs6456728 | 0.1883 | 0.1906 | 0.9611 | 0.01512 | 0.9331 | 0.99 |
| All Histone cluster1 gene | rs6904071 | 0.1645 | 0.1727 | 0.942 | 0.01584 | 0.9132 | 0.9717 |
| All Histone cluster1 gene | rs6904596 | 0.09093 | 0.09787 | 0.9214 | 0.02027 | 0.8855 | 0.9587 |
| All Histone cluster1 gene | rs6913660 | 0.1644 | 0.1727 | 0.9419 | 0.01585 | 0.9131 | 0.9716 |
| All Histone cluster1 gene | rs6915101 | 0.0154 | 0.01453 | 0.9074 | 0.04865 | 0.8249 | 0.9982 |

TABLE 1-continued

| | | | | | | | |
|---|---|---|---|---|---|---|---|
| All Histone cluster1 gene | rs6920256 | 0.1115 | 0.1181 | 0.9493 | 0.01894 | 0.9147 | 0.9852 |
| All Histone cluster1 gene | rs6923139 | 0.09521 | 0.0993 | 0.9267 | 0.01995 | 0.8912 | 0.9637 |
| All Histone cluster1 gene | rs6932590 | 0.2445 | 0.247 | 0.9455 | 0.014 | 0.9199 | 0.9718 |
| All Histone cluster1 gene | rs6933583 | 0.2779 | 0.2825 | 0.9737 | 0.01317 | 0.9489 | 0.9991 |
| All Histone cluster1 gene | rs6934794 | 0.2054 | 0.1997 | 1.032 | 0.01481 | 1.003 | 1.063 |
| All Histone cluster1 gene | rs6938200 | 0.1935 | 0.2009 | 0.9456 | 0.01514 | 0.918 | 0.9741 |
| All Histone cluster1 gene | rs721600 | 0.244 | 0.2357 | 1.052 | 0.01385 | 1.024 | 1.081 |
| All Histone cluster1 gene | rs7745603 | 0.2233 | 0.2288 | 0.9591 | 0.01419 | 0.9328 | 0.9861 |
| All Histone cluster1 gene | rs7746199 | 0.1738 | 0.1696 | 0.9686 | 0.01667 | 0.9374 | 1.001 |
| All Histone cluster1 gene | rs7749305 | 0.09055 | 0.0974 | 0.9244 | 0.02025 | 0.8885 | 0.9619 |
| All Histone cluster1 gene | rs7749319 | 0.03685 | 0.04178 | 0.9446 | 0.0308 | 0.8893 | 1.003 |
| All Histone cluster1 gene | rs7756567 | 0.1742 | 0.1785 | 0.9624 | 0.01557 | 0.9335 | 0.9923 |
| All Histone cluster1 gene | rs7773938 | 0.1742 | 0.1786 | 0.9626 | 0.01556 | 0.9336 | 0.9924 |
| All Histone cluster1 gene | rs911186 | 0.2158 | 0.2223 | 0.9343 | 0.01453 | 0.9081 | 0.9613 |
| All Histone cluster1 gene | rs9295739 | 0.008401 | 0.008577 | 0.8339 | 0.06458 | 0.7348 | 0.9464 |
| All Histone cluster1 gene | rs9295749 | 0.06175 | 0.05791 | 1.04 | 0.02499 | 0.9901 | 1.092 |
| All Histone cluster1 gene | rs9358944 | 0.1741 | 0.1786 | 0.9621 | 0.01557 | 0.9332 | 0.9919 |
| All Histone cluster1 gene | rs9358945 | 0.1742 | 0.1786 | 0.9622 | 0.01556 | 0.9333 | 0.992 |
| All Histone cluster1 gene | rs9358946 | 0.1741 | 0.1785 | 0.9615 | 0.01557 | 0.9326 | 0.9913 |
| All Histone cluster1 gene | rs9366653 | 0.1075 | 0.1136 | 0.951 | 0.01922 | 0.9158 | 0.9875 |

TABLE 1-continued

| | | | | | | | |
|---|---|---|---|---|---|---|---|
| All Histone cluster1 gene | rs9366658 | 0.174 | 0.1784 | 0.9621 | 0.01557 | 0.9332 | 0.9919 |
| All Histone cluster1 gene | rs9379844 | 0.3814 | 0.3795 | 1.018 | 0.01224 | 0.9941 | 1.043 |
| All Histone cluster1 gene | rs9379851 | 0.1076 | 0.1138 | 0.9507 | 0.01919 | 0.9156 | 0.9871 |
| All Histone cluster1 gene | rs9379856 | 0.1062 | 0.1128 | 0.9443 | 0.01944 | 0.909 | 0.981 |
| All Histone cluster1 gene | rs9379858 | 0.1075 | 0.1136 | 0.9507 | 0.01923 | 0.9156 | 0.9872 |
| All Histone cluster1 gene | rs9379859 | 0.1074 | 0.1136 | 0.9504 | 0.01923 | 0.9152 | 0.9869 |
| All Histone cluster1 gene | rs9379870 | 0.2769 | 0.2818 | 0.9731 | 0.01319 | 0.9482 | 0.9986 |
| All Histone cluster1 gene | rs9379897 | 0.1051 | 0.1122 | 0.9498 | 0.01907 | 0.915 | 0.986 |
| All Histone cluster1 gene | rs9393691 | 0.3813 | 0.3793 | 1.019 | 0.01224 | 0.9947 | 1.044 |
| All Histone cluster1 gene | rs9393705 | 0.1075 | 0.1136 | 0.9513 | 0.01922 | 0.9161 | 0.9878 |
| All Histone cluster1 gene | rs9393708 | 0.1075 | 0.1136 | 0.9504 | 0.01923 | 0.9153 | 0.9869 |
| All Histone cluster1 gene | rs9393713 | 0.1065 | 0.1129 | 0.9481 | 0.0193 | 0.9129 | 0.9846 |
| All Histone cluster1 gene | rs9393714 | 0.1059 | 0.1129 | 0.9414 | 0.01932 | 0.9065 | 0.9778 |
| All Histone cluster1 gene | rs9393777 | 0.1291 | 0.1356 | 0.9526 | 0.01746 | 0.9206 | 0.9858 |
| All Histone cluster1 gene | rs9461362 | 0.1656 | 0.1562 | 1.044 | 0.01613 | 1.012 | 1.078 |
| All Histone cluster1 gene | rs9467704 | 0.0935 | 0.09761 | 0.9307 | 0.02007 | 0.8948 | 0.9681 |
| All Histone cluster1 gene | rs9468152 | 0.141 | 0.1351 | 1.054 | 0.01725 | 1.019 | 1.091 |
| All Histone cluster1 gene | rs9468159 | 0.07473 | 0.06852 | 1.036 | 0.02295 | 0.9901 | 1.083 |
| All Histone cluster1 gene | rs9468202 | 0.008533 | 0.008812 | 0.8182 | 0.06399 | 0.7218 | 0.9275 |
| All Histone cluster1 gene | rs9468227 | 0.01521 | 0.01454 | 0.8951 | 0.0488 | 0.8135 | 0.985 |

TABLE 1-continued

| | | | | | | | |
|---|---|---|---|---|---|---|---|
| GTF2IRD2B | imm_7_74094413 | NA | NA | NA | NA | NA | NA |
| GTF2IRD2B | imm_7_74108242 | 0.4115 | 0.4149 | 0.9669 | 0.01207 | 0.9443 | 0.9901 |
| GTF2IRD2B | imm_7_74117236 | NA | NA | NA | NA | NA | NA |
| GTF2IRD2B | imm_7_74118166 | 0.4481 | 0.4464 | 0.9725 | 0.01197 | 0.95 | 0.9956 |
| GTF2IRD2B | imm_7_74120730 | 0.1095 | 0.1148 | 0.9425 | 0.01881 | 0.9084 | 0.9779 |
| GTF2IRD2B | imm_7_74133859 | 0.1855 | 0.1917 | 0.9638 | 0.01538 | 0.9352 | 0.9933 |
| GTF2IRD2B | imm_7_74145400 | 0.2109 | 0.2169 | 0.9643 | 0.01458 | 0.9371 | 0.9922 |
| ETS1 | imm_11_127760024 | 0.09922 | 0.08999 | 1.042 | 0.02024 | 1.001 | 1.084 |
| ETS1 | imm_11_127761269 | 0.09956 | 0.08984 | 1.046 | 0.02016 | 1.006 | 1.088 |
| ETS1 | imm_11_127765567 | 0.1472 | 0.1416 | 1.049 | 0.01691 | 1.014 | 1.084 |
| ETS1 | imm_11_127767721 | 0.02355 | 0.02322 | 0.9396 | 0.03937 | 0.8698 | 1.015 |
| ETS1 | imm_11_127770666 | 0.2646 | 0.254 | 1.034 | 0.01352 | 1.007 | 1.062 |
| ETS1 | imm_11_127770668 | 0.2647 | 0.2543 | 1.033 | 0.01351 | 1.006 | 1.061 |
| ETS1 | imm_11_127774308 | 0.1495 | 0.1444 | 1.046 | 0.01681 | 1.012 | 1.081 |
| ETS1 | imm_11_127775128 | 0.1493 | 0.1446 | 1.044 | 0.01682 | 1.01 | 1.079 |
| ETS1 | imm_11_127776527 | 0.02585 | 0.0254 | 0.9365 | 0.03746 | 0.8702 | 1.008 |
| ETS1 | imm_11_127776913 | 0.02484 | 0.02456 | 0.935 | 0.03816 | 0.8676 | 1.008 |
| ETS1 | imm_11_127777217 | 0.4539 | 0.467 | 0.9649 | 0.01193 | 0.9426 | 0.9877 |
| ETS1 | imm_11_127778327 | 0.2567 | 0.2557 | 1.028 | 0.01368 | 1 | 1.056 |
| ETS1 | imm_11_127778329 | 0.2599 | 0.2578 | 1.032 | 0.01352 | 1.005 | 1.06 |
| ETS1 | imm_11_127779030 | 0.0399 | 0.04089 | 0.9337 | 0.0301 | 0.8802 | 0.9905 |
| ETS1 | imm_11_127780425 | 0.03316 | 0.02847 | 1.065 | 0.03436 | 0.9961 | 1.14 |
| ETS1 | imm_11_127780902 | 0.04105 | 0.0418 | 0.9342 | 0.02972 | 0.8814 | 0.9903 |
| ETS1 | imm_11_127781839 | 0.2721 | 0.2603 | 1.034 | 0.01347 | 1.007 | 1.062 |
| ETS1 | imm_11_127785739 | 0.1949 | 0.1969 | 0.9695 | 0.01494 | 0.9415 | 0.9983 |
| ETS1 | imm_11_127785963 | 0.1598 | 0.1524 | 1.052 | 0.01641 | 1.019 | 1.087 |
| ETS1 | imm_11_127786010 | 0.1928 | 0.1842 | 1.036 | 0.01521 | 1.006 | 1.068 |
| ETS1 | imm_11_127786836 | 0.193 | 0.1845 | 1.035 | 0.0152 | 1.005 | 1.067 |
| ETS1 | imm_11_127787128 | 0.1926 | 0.1839 | 1.038 | 0.01546 | 1.007 | 1.069 |
| ETS1 | imm_11_127788828 | 0.2023 | 0.2042 | 0.9714 | 0.01475 | 0.9438 | 0.9999 |
| ETS1 | imm_11_127789306 | 0.1917 | 0.1836 | 1.034 | 0.01524 | 1.003 | 1.065 |
| ETS1 | imm_11_127789441 | 0.1917 | 0.1835 | 1.034 | 0.01524 | 1.003 | 1.065 |
| ETS1 | imm_11_127791651 | 0.1617 | 0.1537 | 1.051 | 0.01634 | 1.018 | 1.086 |
| ETS1 | imm_11_127792287 | 0.1928 | 0.1845 | 1.034 | 0.0152 | 1.004 | 1.065 |
| ETS1 | imm_11_127792800 | 0.04818 | 0.04146 | 1.069 | 0.02876 | 1.01 | 1.131 |
| ETS1 | imm_11_127793060 | 0.1932 | 0.1851 | 1.032 | 0.01519 | 1.002 | 1.063 |
| ETS1 | imm_11_127794685 | 0.1622 | 0.1544 | 1.048 | 0.01631 | 1.015 | 1.082 |
| ETS1 | imm_11_127795453 | 0.1932 | 0.1851 | 1.032 | 0.01518 | 1.002 | 1.063 |
| ETS1 | imm_11_127796816 | 4.97E−05 | 0.0001685 | 0.1892 | 0.6633 | 0.05156 | 0.6941 |
| ETS1 | imm_11_127797523 | 0.193 | 0.1849 | 1.032 | 0.01519 | 1.002 | 1.063 |
| ETS1 | imm_11_127798230 | 0.29 | 0.2885 | 0.9769 | 0.0131 | 0.9521 | 1.002 |
| ETS1 | imm_11_127799892 | 0.4819 | 0.4679 | 1.03 | 0.01188 | 1.007 | 1.055 |
| ETS1 | imm_11_127804916 | 0.1266 | 0.127 | 0.9676 | 0.01783 | 0.9344 | 1.002 |
| ETS1 | imm_11_127805367 | 0.02671 | 0.02685 | 0.9274 | 0.03669 | 0.863 | 0.9965 |
| ETS1 | imm_11_127806163 | 0.3819 | 0.3803 | 1.028 | 0.01227 | 1.003 | 1.053 |
| ETS1 | imm_11_127806304 | 0.0259 | 0.02615 | 0.926 | 0.03726 | 0.8608 | 0.9961 |
| ETS1 | imm_11_127807384 | 0.1779 | 0.1697 | 1.035 | 0.01568 | 1.003 | 1.067 |
| ETS1 | imm_11_127808758 | 0.02694 | 0.02699 | 0.9302 | 0.03659 | 0.8659 | 0.9994 |
| ETS1 | imm_11_127809308 | 0.00681 | 0.007868 | 0.8251 | 0.06948 | 0.72 | 0.9454 |
| ETS1 | imm_11_127812329 | 0.05509 | 0.0491 | 1.056 | 0.02675 | 1.002 | 1.113 |
| ETS1 | imm_11_127812420 | 0.0003485 | 0.0001181 | 2.813 | 0.4443 | 1.178 | 6.721 |
| ETS1 | imm_11_127813024 | 0.3817 | 0.3801 | 1.028 | 0.01226 | 1.003 | 1.053 |
| ETS1 | imm_11_127819226 | 0.1782 | 0.17 | 1.034 | 0.01567 | 1.003 | 1.066 |
| ETS1 | imm_11_127822686 | 0.02694 | 0.02711 | 0.9267 | 0.0365 | 0.8627 | 0.9954 |
| ETS1 | imm_11_127823420 | 0.00681 | 0.007868 | 0.8251 | 0.06948 | 0.7201 | 0.9455 |
| ETS1 | imm_11_127824356 | 0.1728 | 0.1635 | 1.038 | 0.0159 | 1.006 | 1.07 |
| ETS1 | imm_11_127825016 | 0.02693 | 0.02704 | 0.928 | 0.03657 | 0.8638 | 0.9969 |
| ETS1 | imm_11_127825282 | 0.3867 | 0.3861 | 1.027 | 0.01223 | 1.003 | 1.052 |
| ETS1 | imm_11_127825669 | 0.3867 | 0.3861 | 1.027 | 0.01223 | 1.002 | 1.052 |
| ETS1 | imm_11_127826087 | 0.3308 | 0.3444 | 0.96 | 0.01259 | 0.9366 | 0.984 |
| ETS1 | imm_11_127826464 | 0.1616 | 0.1525 | 1.036 | 0.01634 | 1.004 | 1.07 |
| ETS1 | imm_11_127827422 | 0.1625 | 0.1534 | 1.036 | 0.01631 | 1.003 | 1.069 |
| ETS1 | imm_11_127828334 | 0.02583 | 0.02575 | 0.9352 | 0.03729 | 0.8693 | 1.006 |
| ETS1 | imm_11_127831280 | 0.02528 | 0.02935 | 0.918 | 0.03643 | 0.8548 | 0.986 |
| ETS1 | imm_11_127831611 | 0.1634 | 0.1544 | 1.032 | 0.01627 | 1 | 1.066 |
| ETS1 | imm_11_127831673 | 0.2897 | 0.3008 | 0.9715 | 0.01305 | 0.947 | 0.9967 |
| ETS1 | imm_11_127834123 | 0.3021 | 0.3039 | 1.032 | 0.01301 | 1.006 | 1.059 |
| ETS1 | imm_11_127834484 | 0.02454 | 0.027 | 0.9195 | 0.03741 | 0.8545 | 0.9894 |
| ETS1 | imm_11_127837472 | 0.01796 | 0.01939 | 0.9051 | 0.0438 | 0.8307 | 0.9863 |
| ETS1 | imm_11_127838265 | 0.08005 | 0.08871 | 0.948 | 0.02134 | 0.9092 | 0.9885 |
| ETS1 | imm_11_127838713 | 0.4807 | 0.4766 | 1.033 | 0.0119 | 1.009 | 1.057 |
| ETS1 | imm_11_127839719 | 0.01287 | 0.01496 | 0.9178 | 0.05089 | 0.8307 | 1.014 |
| ETS1 | imm_11_127840459 | 0.171 | 0.1594 | 1.074 | 0.01598 | 1.04 | 1.108 |
| ETS1 | imm_11_127840867 | 0.1083 | 0.1173 | 0.9393 | 0.01868 | 0.9056 | 0.9744 |
| ETS1 | imm_11_127841724 | 0.09519 | 0.09676 | 0.9589 | 0.02015 | 0.9217 | 0.9975 |
| ETS1 | imm_11_127841864 | 0.4192 | 0.4279 | 0.9746 | 0.01201 | 0.9519 | 0.9978 |
| ETS1 | imm_11_127843207 | 0.09459 | 0.09635 | 0.9572 | 0.0202 | 0.92 | 0.9958 |
| ETS1 | imm_11_127843341 | 0.09506 | 0.09672 | 0.958 | 0.02017 | 0.9209 | 0.9966 |
| ETS1 | imm_11_127844385 | 0.1721 | 0.1603 | 1.072 | 0.01597 | 1.039 | 1.106 |
| ETS1 | imm_11_127844729 | 0.026 | 0.02423 | 1.082 | 0.03808 | 1.004 | 1.166 |

TABLE 1-continued

| | | | | | | | |
|---|---|---|---|---|---|---|---|
| ETS1 | imm_11_127845557 | 0.09794 | 0.0995 | 0.956 | 0.01992 | 0.9194 | 0.9941 |
| ETS1 | imm_11_127846698 | 0.172 | 0.1606 | 1.07 | 0.01591 | 1.037 | 1.104 |
| ETS1 | imm_11_127848167 | 0.1719 | 0.1604 | 1.07 | 0.01593 | 1.037 | 1.104 |
| ETS1 | imm_11_127848372 | 0.1708 | 0.1593 | 1.071 | 0.01597 | 1.038 | 1.105 |
| ETS1 | imm_11_127849992 | 0.1718 | 0.1603 | 1.07 | 0.01593 | 1.037 | 1.104 |
| ETS1 | imm_11_127851599 | 0.1724 | 0.1605 | 1.073 | 0.0159 | 1.04 | 1.107 |
| ETS1 | imm_11_127852250 | 0.09357 | 0.09526 | 0.9588 | 0.02029 | 0.9214 | 0.9977 |
| ETS1 | imm_11_127853705 | 0.09349 | 0.0952 | 0.9589 | 0.0203 | 0.9215 | 0.9978 |
| ETS1 | imm_11_127855281 | 0.1721 | 0.1605 | 1.07 | 0.01592 | 1.038 | 1.104 |
| ETS1 | imm_11_127855956 | 0.09482 | 0.09605 | 0.9622 | 0.02019 | 0.9249 | 1.001 |
| ETS1 | imm_11_127857027 | 0.09246 | 0.09451 | 0.9556 | 0.02039 | 0.9181 | 0.9945 |
| ETS1 | imm_11_127861069 | 0.2667 | 0.2531 | 1.04 | 0.01357 | 1.013 | 1.068 |
| ETS1 | imm_11_127863304 | 0.2666 | 0.2528 | 1.041 | 0.01358 | 1.014 | 1.069 |
| ETS1 | imm_11_127863391 | 0.2668 | 0.2531 | 1.041 | 0.01358 | 1.013 | 1.069 |
| ETS1 | imm_11_127866379 | 0.247 | 0.2357 | 1.031 | 0.01392 | 1.003 | 1.06 |
| ETS1 | imm_11_127868447 | 0.001438 | 0.0007947 | 1.274 | 0.1839 | 0.8881 | 1.826 |
| ETS1 | imm_11_127868927 | 0.1886 | 0.1862 | 0.9713 | 0.01518 | 0.9428 | 1.001 |
| ETS1 | imm_11_127869177 | 0.2692 | 0.2553 | 1.046 | 0.01355 | 1.018 | 1.074 |
| ETS1 | imm_11_127870403 | 0.2604 | 0.2475 | 1.048 | 0.01366 | 1.02 | 1.076 |
| ETS1 | imm_11_127870895 | 0.2704 | 0.256 | 1.048 | 0.01351 | 1.02 | 1.076 |
| ETS1 | imm_11_127871431 | 0.2704 | 0.2561 | 1.047 | 0.01351 | 1.02 | 1.075 |
| ETS1 | imm_11_127872972 | 0.1881 | 0.1857 | 0.9711 | 0.0152 | 0.9426 | 1 |
| ETS1 | imm_11_127874486 | 0.2705 | 0.2561 | 1.047 | 0.0135 | 1.02 | 1.075 |
| ETS1 | imm_11_127874807 | 0.2679 | 0.2544 | 1.046 | 0.01353 | 1.019 | 1.075 |
| ETS1 | imm_11_127877378 | 0.2696 | 0.2553 | 1.048 | 0.01353 | 1.021 | 1.076 |
| ETS1 | imm_11_127879923 | 0.187 | 0.1854 | 0.9699 | 0.01521 | 0.9414 | 0.9993 |
| ETS1 | imm_11_127881686 | 0.1838 | 0.1678 | 1.083 | 0.01554 | 1.05 | 1.116 |
| ETS1 | imm_11_127882690 | 0.3868 | 0.3761 | 1.03 | 0.01225 | 1.006 | 1.055 |
| ETS1 | imm_11_127884689 | 0.06242 | 0.06577 | 0.9481 | 0.02426 | 0.9041 | 0.9943 |
| ETS1 | imm_11_127885952 | 0.3619 | 0.3492 | 1.053 | 0.01239 | 1.028 | 1.079 |
| ETS1 | imm_11_127886184 | 0.2407 | 0.2278 | 1.076 | 0.01398 | 1.047 | 1.106 |
| ETS1 | imm_11_127887077 | 0.3616 | 0.3489 | 1.053 | 0.0124 | 1.028 | 1.079 |
| ETS1 | imm_11_127889134 | 0.24 | 0.2272 | 1.074 | 0.01401 | 1.045 | 1.104 |
| ETS1 | imm_11_127891116 | 0.2401 | 0.2276 | 1.073 | 0.01401 | 1.044 | 1.103 |
| ETS1 | imm_11_127892632 | 0.3616 | 0.3489 | 1.053 | 0.0124 | 1.028 | 1.079 |
| ETS1 | imm_11_127894601 | 0.2237 | 0.2193 | 0.9786 | 0.01426 | 0.9516 | 1.006 |
| ETS1 | imm_11_127894638 | 0.003712 | 0.004179 | 0.7901 | 0.09484 | 0.6561 | 0.9515 |
| ETS1 | imm_11_127895279 | 0.2405 | 0.2275 | 1.076 | 0.014 | 1.047 | 1.106 |
| ETS1 | imm_11_127897147 | 0.233 | 0.2215 | 1.075 | 0.01414 | 1.046 | 1.106 |
| ETS1 | imm_11_127898835 | 0.01773 | 0.02054 | 0.8992 | 0.04333 | 0.826 | 0.9789 |
| ETS1 | imm_11_127901157 | 0.3033 | 0.2932 | 1.048 | 0.01299 | 1.022 | 1.075 |
| ETS1 | imm_11_127901948 | 0.2366 | 0.2253 | 1.071 | 0.01406 | 1.041 | 1.1 |
| ETS1 | imm_11_127905841 | 0.04931 | 0.05841 | 0.9326 | 0.02651 | 0.8854 | 0.9823 |
| ETS1 | imm_11_127906568 | 0.3857 | 0.3706 | 1.047 | 0.01222 | 1.022 | 1.073 |
| ETS1 | imm_11_127908214 | 0.3861 | 0.3708 | 1.048 | 0.01221 | 1.023 | 1.074 |
| ETS1 | imm_11_127911648 | 0.504 | 0.488 | 0.958773 | 0.01206 | 1.018 | 1.068 |
| ETS1 | imm_11_127911985 | 0.4904 | 0.4756 | 1.044 | 0.01187 | 1.02 | 1.068 |
| ETS1 | imm_11_127914294 | 0.4917 | 0.4766 | 1.044 | 0.01187 | 1.02 | 1.068 |
| ETS1 | imm_11_127915474 | 0.5043 | 0.4882 | 0.958773 | 0.01187 | 1.019 | 1.068 |
| ETS1 | imm_11_127915554 | 0.5053 | 0.4884 | 0.95511 | 0.01189 | 1.023 | 1.072 |
| ETS1 | imm_11_127916046 | 0.4916 | 0.4769 | 1.042 | 0.01186 | 1.018 | 1.067 |
| ETS1 | imm_11_127929821 | 0.0003317 | 0.0005059 | 0.5073 | 0.2845 | 0.2905 | 0.8861 |
| ETS1 | imm_11_127931099 | 0.0002154 | 0.0003706 | 0.4221 | 0.355 | 0.2105 | 0.8465 |
| ETS1 | imm_11_127940676 | 0.04603 | 0.05305 | 0.9457 | 0.02759 | 0.896 | 0.9983 |
| ETS1 | imm_11_127943244 | 0.0001657 | 0.0002359 | 0.4952 | 0.42 | 0.2174 | 1.128 |
| ETS1 | imm_11_127945727 | NA | NA | NA | NA | NA | NA |
| ETS1 | imm_11_127945953 | 0.07363 | 0.07921 | 0.9453 | 0.02227 | 0.905 | 0.9875 |
| ETS1 | imm_11_127948912 | 0.0179 | 0.0213 | 0.875 | 0.04286 | 0.8045 | 0.9517 |
| ETS1 | imm_11_127956842 | 0.2625 | 0.2581 | 1.037 | 0.01351 | 1.009 | 1.064 |
| ETS1 | imm_11_127957543 | 0.01694 | 0.0148 | 1.114 | 0.04754 | 1.015 | 1.223 |
| ETS1 | imm_11_127957904 | 0.01243 | 0.01016 | 1.184 | 0.05624 | 1.061 | 1.322 |
| ETS1 | imm_11_127974263 | 0.07319 | 0.07868 | 0.947 | 0.02235 | 0.9064 | 0.9894 |
| ETS1 | imm_11_127979301 | 0.1778 | 0.1862 | 0.9641 | 0.01539 | 0.9354 | 0.9936 |
| ETS1 | imm_11_127979905 | 0.01105 | 0.01341 | 0.8977 | 0.05428 | 0.8071 | 0.9985 |
| ETS1 | imm_11_127981559 | 0.1743 | 0.1821 | 0.9688 | 0.01551 | 0.9398 | 0.9987 |
| ETS1 | imm_11_127982379 | 0.1742 | 0.1821 | 0.9687 | 0.01552 | 0.9396 | 0.9986 |
| ETS1 | imm_11_127982748 | 0.1743 | 0.1828 | 0.9648 | 0.0155 | 0.9359 | 0.9946 |
| ETS1 | imm_11_127983590 | 0.173 | 0.1813 | 0.9676 | 0.01555 | 0.9385 | 0.9975 |
| ETS1 | imm_11_127983743 | 0.1742 | 0.1821 | 0.9687 | 0.01552 | 0.9397 | 0.9987 |
| ETS1 | imm_11_127984265 | 0.1741 | 0.1821 | 0.9677 | 0.01552 | 0.9387 | 0.9975 |
| ETS1 | imm_11_127984721 | 0.1797 | 0.1878 | 0.9668 | 0.01533 | 0.9382 | 0.9963 |
| ETS1 | rs7935286 | 0.168 | 0.1606 | 1.045 | 0.01603 | 1.012 | 1.078 |
| SLC5A1 | rs738203 | 0.2253 | 0.2201 | 1.028 | 0.01427 | 0.9996 | 1.057 |
| SLC5A1 | rs9609429 | 0.2575 | 0.2651 | 0.9735 | 0.01351 | 0.948 | 0.9996 |
| TET2 | rs10010325 | 0.4771 | 0.4978 | 0.934 | 0.01188 | 0.9125 | 0.956 |
| TET2 | rs17035310 | 0.1357 | 0.1276 | 1.057 | 0.01753 | 1.021 | 1.093 |
| TET2 | rs2189234 | 0.3781 | 0.3659 | 1.045 | 0.01231 | 1.02 | 1.071 |
| TET2 | rs7661349 | 0.3552 | 0.3446 | 1.047 | 0.01251 | 1.022 | 1.073 |
| TET2 | rs974801 | 0.3639 | 0.3836 | 0.9356 | 0.01226 | 0.9134 | 0.9584 |

TABLE 1-continued (Continued, part 4)

| gene.i | SNP | STAT__iibdgc | P__iibdgc | beta__meta__fixed | se__meta__fixed | P__meta__fixed |
|---|---|---|---|---|---|---|
| SLC26A4 | rs10247487 | −3.044 | 0.002336 | −0.058534716 | 0.015027789 | 9.82E−05 |
| SLC26A4 | rs10263826 | −3.525 | 0.0004233 | −0.063296566 | 0.014717569 | 1.70E−05 |
| SLC26A4 | rs10273733 | 4.232 | 2.32E−05 | 0.062729759 | 0.014911083 | 2.59E−05 |
| SLC26A4 | rs12539555 | 1.753 | 0.07962 | 0.033957032 | 0.015028243 | 0.023849341 |
| SLC26A4 | rs2248465 | 3.499 | 0.0004666 | 0.058825282 | 0.014674647 | 6.11E−05 |
| SLC26A4 | rs2808 | 4.39 | 1.13E−05 | 0.072100199 | 0.014452056 | 6.07E−07 |
| DLG4 | rs3785794 | −3.279 | 0.001041 | −0.108558148 | 0.024982227 | 1.39E−05 |
| GIPR | chr19:50983512 | −3.978 | 6.96E−05 | −0.06312005 | 0.014860986 | 2.16E−05 |
| GIPR | chr19:51014231 | −4.412 | 1.02E−05 | −0.067529657 | 0.01531 | 1.03E−05 |
| GIPR | chr19:51026971 | −4.454 | 8.45E−06 | −0.070871869 | 0.014254528 | 6.63E−07 |
| GIPR | rs10401439 | −4.746 | 2.08E−06 | −0.074292605 | 0.01566 | 2.09E−06 |
| GIPR | rs10402263 | −3.859 | 0.000114 | −0.060155652 | 0.013934687 | 1.58E−05 |
| GIPR | rs10421891 | −4.286 | 1.82E−05 | −0.065331129 | 0.013703526 | 1.87E−06 |
| GIPR | rs10500292 | −4.313 | 1.61E−05 | −0.063324672 | 0.013508683 | 2.76E−06 |
| GIPR | rs11883351 | −4.223 | 2.41E−05 | −0.06640775 | 0.013965247 | 1.98E−06 |
| GIPR | rs12463359 | −4.026 | 5.67E−05 | −0.061150814 | 0.013547181 | 6.36E−06 |
| GIPR | rs16980013 | −3.951 | 7.78E−05 | −0.06459853 | 0.014494808 | 8.32E−06 |
| GIPR | rs16980051 | −4.217 | 2.47E−05 | −0.061384259 | 0.013158489 | 3.09E−06 |
| GIPR | rs17878252 | −3.982 | 6.83E−05 | −0.064733932 | 0.01476836 | 1.17E−05 |
| GIPR | rs2070736 | −4.036 | 5.43E−05 | −0.066027936 | 0.014452018 | 4.91E−06 |
| GIPR | rs2334255 | 2.756 | 0.005854 | 0.050203976 | 0.014994188 | 0.000813298 |
| GIPR | rs4514788 | −3.846 | 0.0001199 | −0.059073081 | 0.014960132 | 7.86E−05 |
| GIPR | rs4802273 | −4.078 | 4.55E−05 | −0.066351462 | 0.014622704 | 5.69E−06 |
| GIPR | rs4802274 | −4.147 | 3.37E−05 | −0.067054341 | 0.014442081 | 3.43E−06 |
| GIPR | rs4803861 | −4.351 | 1.36E−05 | −0.06912685 | 0.014264465 | 1.26E−06 |
| GIPR | rs8111071 | 2.662 | 0.00776 | 0.073099463 | 0.022329376 | 0.001061529 |
| GIPR | rs918490 | −4.521 | 6.14E−06 | −0.071265294 | 0.014270954 | 5.92E−07 |
| ZHX3 | rs6072275 | 3.936 | 8.28E−05 | 0.083189003 | 0.018062159 | 4.11E−06 |
| ZHX3 | rs6072343 | 4.657 | 3.20E−06 | 0.095938396 | 0.018727722 | 3.01E−07 |
| ZHX3 | rs6093462 | −4.779 | 1.76E−06 | −0.072463172 | 0.01516 | 1.75E−06 |
| TNRC6B | rs114607 | −3.167 | 0.001542 | −0.045307725 | 0.014425671 | 0.001685039 |
| TNRC6B | rs137955 | 2.873 | 0.00406 | 0.048254792 | 0.013211434 | 0.000259697 |
| TNRC6B | rs137956 | 3.097 | 0.001955 | 0.052189562 | 0.013200134 | 7.69E−05 |
| TNRC6B | rs137977 | −1.618 | 0.1056 | −0.03176774 | 0.013498551 | 0.018601682 |
| TNRC6B | rs137981 | −1.753 | 0.07963 | −0.0537168 | 0.020383686 | 0.008406691 |
| TNRC6B | rs138027 | −2.173 | 0.02978 | −0.048197853 | 0.015199003 | 0.001518527 |
| TNRC6B | rs2958647 | 2.914 | 0.003573 | 0.049575793 | 0.01319879 | 0.000172591 |
| TNRC6B | rs713925 | −1.906 | 0.05667 | −0.034455366 | 0.013797129 | 0.012514829 |
| CDK6 | rs2282978 | −4.876 | 1.08E−06 | −0.077385341 | 0.01514709 | 3.24E−07 |
| CDK6 | rs4272 | −3.465 | 0.0005296 | −0.06665877 | 0.01764793 | 0.000158637 |
| PRR5L | rs11033597 | 2.333 | 0.01965 | 0.066084117 | 0.020665458 | 0.001384776 |
| PRR5L | rs11600757 | 3.227 | 0.001252 | 0.079494189 | 0.019569349 | 4.86E−05 |
| PRR5L | rs11601211 | 1.906 | 0.05667 | 0.061285288 | 0.02719336 | 0.024215943 |
| PRR5L | rs12281565 | 3.058 | 0.002229 | 0.076286578 | 0.019430079 | 8.63E−05 |
| PRR5L | rs1365120 | NA | NA | 0.164666622 | 0.07526 | 0.028671788 |
| PRR5L | rs1895840 | 1.992 | 0.04641 | 0.059408267 | 0.023210602 | 0.010481334 |
| PRR5L | rs2303439 | 3.289 | 0.001006 | 0.068688505 | 0.019695087 | 0.000487384 |
| PRR5L | rs330260 | 1.95 | 0.05112 | 0.053412942 | 0.018807986 | 0.00451266 |
| PRR5L | rs331485 | −2.732 | 0.006288 | −0.062860555 | 0.023236366 | 0.006824967 |
| PRR5L | rs4077044 | 2.032 | 0.04212 | 0.037590443 | 0.014958442 | 0.011971209 |
| PRR5L | rs5030437 | 3.215 | 0.001304 | 0.064066031 | 0.020113864 | 0.001446701 |
| PRR5L | rs5030445 | 3.046 | 0.002317 | 0.062410516 | 0.01942935 | 0.001317331 |
| PRR5L | rs5030472 | 2.985 | 0.00284 | 0.078591165 | 0.022405282 | 0.000451987 |
| PRR5L | rs7929195 | −2.301 | 0.02139 | −0.050660959 | 0.022266607 | 0.022894005 |
| WNT2B | rs10745330 | 3.629 | 0.0002849 | 0.046712378 | 0.011110013 | 2.62E−05 |
| WNT2B | rs2999155 | 3.507 | 0.0004534 | 0.044692937 | 0.011109171 | 5.74E−05 |
| WNT2B | rs3790609 | 3.389 | 0.0007022 | 0.057908753 | 0.014569453 | 7.05E−05 |
| WNT2B | rs6682737 | 3.484 | 0.0004939 | 0.045366037 | 0.011109592 | 4.44E−05 |
| LRRC16A | rs10456320 | 4.283 | 1.84E−05 | 0.069089475 | 0.017094699 | 5.31E−05 |
| LRRC16A | rs11755567 | −3.27 | 0.001076 | −0.048398263 | 0.014239808 | 0.000676821 |
| LRRC16A | rs13191296 | −3.657 | 0.0002549 | −0.090057293 | 0.02222817 | 5.09E−05 |
| LRRC16A | rs2690110 | 4.521 | 6.15E−06 | 0.058889627 | 0.011610134 | 3.93E−07 |
| LRRC16A | rs4712908 | −3.068 | 0.002157 | −0.037870543 | 0.012274163 | 0.002032874 |
| LRRC16A | rs6921589 | −4.091 | 4.29E−05 | −0.064973129 | 0.017021208 | 0.000134982 |
| LRRC16A | rs6937918 | 2.547 | 0.01085 | 0.034771379 | 0.011355649 | 0.002198387 |
| LRRC16A | rs742132 | 2.65 | 0.008053 | 0.031042809 | 0.012141191 | 0.010563462 |
| LRRC16A | rs7752195 | −4.384 | 1.16E−05 | −0.101626038 | 0.02294336 | 9.45E−06 |
| LRRC16A | rs7752524 | 4.709 | 2.49E−06 | 0.085068327 | 0.018823587 | 6.21E−06 |
| LRRC16A | rs7762757 | 2.712 | 0.006697 | 0.031571387 | 0.011680522 | 0.006873559 |
| LRRC16A | rs880226 | 2.361 | 0.01824 | 0.033189564 | 0.011364287 | 0.003494541 |
| LRRC16A | rs9295661 | −4.072 | 4.67E−05 | −0.100526188 | 0.023046161 | 1.29E−05 |
| LRRC16A | rs9358854 | −2.913 | 0.003579 | −0.037637711 | 0.011791575 | 0.001413326 |
| LRRC16A | rs9461157 | 2.527 | 0.01151 | 0.034772904 | 0.011364722 | 0.002215417 |
| LRRC16A | rs9461165 | 2.596 | 0.009444 | 0.035502949 | 0.011356083 | 0.001769983 |
| LRRC16A | rs9467445 | −3.659 | 0.0002536 | −0.053117524 | 0.013770777 | 0.000114663 |

TABLE 1-continued

| | | | | | | |
|---|---|---|---|---|---|---|
| All Histone cluster1 gene | rs10484399 | −3.446 | 0.0005686 | −0.078059586 | 0.020564152 | 0.000147105 |
| All Histone cluster1 gene | rs10484439 | −3.156 | 0.001602 | −0.074749526 | 0.021002594 | 0.000372182 |
| All Histone cluster1 gene | rs12176317 | −2.796 | 0.005176 | −0.063761509 | 0.018574335 | 0.000597438 |
| All Histone cluster1 gene | rs13194053 | −3.863 | 0.0001122 | −0.053670759 | 0.015092309 | 0.000376306 |
| All Histone cluster1 gene | rs13194491 | 3.139 | 0.001698 | 0.048949414 | 0.021779199 | 0.024606145 |
| All Histone cluster1 gene | rs13194781 | −3.437 | 0.0005871 | −0.077677154 | 0.020530542 | 0.000154643 |
| All Histone cluster1 gene | rs13195040 | −3.747 | 0.0001788 | −0.082582505 | 0.020961156 | 8.16E−05 |
| All Histone cluster1 gene | rs13199772 | −3.447 | 0.0005665 | −0.077401483 | 0.020529767 | 0.000163112 |
| All Histone cluster1 gene | rs13212651 | −3.477 | 0.0005067 | −0.078363109 | 0.020541534 | 0.000136259 |
| All Histone cluster1 gene | rs1321578 | −2.286 | 0.02228 | −0.071077407 | 0.030325291 | 0.019086731 |
| All Histone cluster1 gene | rs13217599 | 2.421 | 0.01546 | 0.057081966 | 0.022951133 | 0.012878599 |
| All Histone cluster1 gene | rs13218875 | −3.514 | 0.0004412 | −0.078092819 | 0.020747093 | 0.000167192 |
| All Histone cluster1 gene | rs13219354 | −3.26 | 0.001115 | −0.060487086 | 0.018110779 | 0.00083827 |
| All Histone cluster1 gene | rs16867901 | −2.835 | 0.004582 | −0.181808618 | 0.061179996 | 0.002961555 |
| All Histone cluster1 gene | rs16867911 | −2.729 | 0.006351 | −0.167952934 | 0.059705622 | 0.004907905 |
| All Histone cluster1 gene | rs16891725 | −2.769 | 0.005622 | −0.062146342 | 0.018449232 | 0.000755768 |
| All Histone cluster1 gene | rs175597 | −3.986 | 6.72E−05 | −0.084555864 | 0.018699048 | 6.13E−06 |
| All Histone cluster1 gene | rs17693963 | −2.936 | 0.003324 | −0.060615226 | 0.019811487 | 0.002216328 |
| All Histone cluster1 gene | rs17739310 | 2.613 | 0.008972 | 0.044605836 | 0.016261099 | 0.006086197 |
| All Histone cluster1 gene | rs17750424 | −4.497 | 6.88E−06 | −0.099709844 | 0.02218 | 6.94E−06 |

TABLE 1-continued

| | | | | | | |
|---|---|---|---|---|---|---|
| All Histone cluster1 gene | rs1977 | −2.835 | 0.004583 | −0.064477268 | 0.018565026 | 0.000514579 |
| All Histone cluster1 gene | rs1985732 | −1.832 | 0.06692 | −0.027838373 | 0.012334681 | 0.024013157 |
| All Histone cluster1 gene | rs200483 | −3.905 | 9.42E−05 | −0.0820908 | 0.018676968 | 1.11E−05 |
| All Histone cluster1 gene | rs200484 | −3.894 | 9.84E−05 | −0.082395729 | 0.018707585 | 1.06E−05 |
| All Histone cluster1 gene | rs200490 | −3.912 | 9.16E−05 | −0.083371878 | 0.018670767 | 7.99E−06 |
| All Histone cluster1 gene | rs200501 | −3.751 | 0.0001759 | −0.0794437 | 0.018617232 | 1.98E−05 |
| All Histone cluster1 gene | rs200948 | −4.027 | 5.65E−05 | −0.085318783 | 0.018700377 | 5.06E−06 |
| All Histone cluster1 gene | rs200953 | −4.019 | 5.86E−05 | −0.085609176 | 0.018669936 | 4.53E−06 |
| All Histone cluster1 gene | rs200989 | −3.995 | 6.47E−05 | −0.085051111 | 0.018690175 | 5.35E−06 |
| All Histone cluster1 gene | rs200990 | −4.065 | 4.81E−05 | −0.08639512 | 0.018659065 | 3.65E−06 |
| All Histone cluster1 gene | rs200991 | −2.275 | 0.02291 | −0.036379215 | 0.015865406 | 0.02184859 |
| All Histone cluster1 gene | rs200995 | −3.981 | 6.85E−05 | −0.084473289 | 0.01867964 | 6.12E−06 |
| All Histone cluster1 gene | rs201002 | −3.897 | 9.74E−05 | −0.083072055 | 0.018658898 | 8.50E−06 |
| All Histone cluster1 gene | rs201004 | −2.05 | 0.04039 | −0.031705869 | 0.015289559 | 0.03810772 |
| All Histone cluster1 gene | rs2064092 | 1.651 | 0.09883 | 0.050392502 | 0.020622596 | 0.014543248 |
| All Histone cluster1 gene | rs2072806 | −2.495 | 0.0126 | −0.050399006 | 0.018998369 | 0.007982551 |
| All Histone cluster1 gene | rs2073529 | −2.76 | 0.005781 | −0.053189829 | 0.01928 | 0.005801251 |
| All Histone cluster1 gene | rs2093169 | −2.503 | 0.0123 | −0.039526244 | 0.014821362 | 0.007656748 |
| All Histone cluster1 gene | rs2393997 | −1.792 | 0.07312 | −0.035650813 | 0.017602717 | 0.042836389 |
| All Histone cluster1 gene | rs2494711 | 2.25 | 0.02442 | 0.030743293 | 0.011439774 | 0.007200984 |

TABLE 1-continued

| | | | | | | |
|---|---|---|---|---|---|---|
| All Histone cluster1 gene | rs2747054 | −4.003 | 6.27E−05 | −0.084226868 | 0.018670435 | 6.44E−06 |
| All Histone cluster1 gene | rs2893910 | −2.542 | 0.01104 | −0.042399602 | 0.015008424 | 0.004727271 |
| All Histone cluster1 gene | rs34706883 | −3.429 | 0.0006061 | −0.077403838 | 0.020531703 | 0.000163269 |
| All Histone cluster1 gene | rs370155 | −3.931 | 8.47E−05 | −0.083316959 | 0.018649027 | 7.91E−06 |
| All Histone cluster1 gene | rs3799378 | −2.808 | 0.004985 | −0.042977293 | 0.015146769 | 0.0045484 |
| All Histone cluster1 gene | rs3799380 | −2.629 | 0.008566 | −0.03770809 | 0.01434693 | 0.008581185 |
| All Histone cluster1 gene | rs3799383 | −2.381 | 0.01728 | −0.054983285 | 0.017719062 | 0.001915318 |
| All Histone cluster1 gene | rs3800307 | −3.542 | 0.0003964 | −0.047615302 | 0.014187129 | 0.000790121 |
| All Histone cluster1 gene | rs3800316 | −3.133 | 0.001733 | −0.041232193 | 0.012710172 | 0.001178508 |
| All Histone cluster1 gene | rs4452638 | −3.137 | 0.001709 | −0.05807739 | 0.018121317 | 0.001350996 |
| All Histone cluster1 gene | rs4634439 | −2.688 | 0.007195 | −0.062071323 | 0.018386175 | 0.000735538 |
| All Histone cluster1 gene | rs4712981 | −1.99 | 0.04664 | −0.029694159 | 0.012451086 | 0.017085387 |
| All Histone cluster1 gene | rs4713119 | −1.777 | 0.07556 | −0.035242617 | 0.017509761 | 0.044141868 |
| All Histone cluster1 gene | rs6456728 | −2.623 | 0.008717 | −0.037625374 | 0.014347244 | 0.008729217 |
| All Histone cluster1 gene | rs6904071 | −3.774 | 0.0001608 | −0.052562718 | 0.015098153 | 0.000498799 |
| All Histone cluster1 gene | rs6904596 | −4.041 | 5.33E−05 | −0.08829141 | 0.019608398 | 6.71E−06 |
| All Histone cluster1 gene | rs6913660 | −3.775 | 0.0001599 | −0.052278347 | 0.015105424 | 0.000538375 |
| All Histone cluster1 gene | rs6915101 | −1.996 | 0.04591 | −0.10249597 | 0.04529877 | 0.023656309 |
| All Histone cluster1 gene | rs6920256 | −2.749 | 0.005984 | −0.062007017 | 0.01821765 | 0.00066485 |
| All Histone cluster1 gene | rs6923139 | −3.814 | 0.0001366 | −0.07921173 | 0.018994782 | 3.04E−05 |

TABLE 1-continued

| | | | | | | |
|---|---|---|---|---|---|---|
| All Histone cluster1 gene | rs6932590 | −4.006 | 6.19E−05 | −0.053482958 | 0.013220111 | 5.22E−05 |
| All Histone cluster1 gene | rs6933583 | −2.025 | 0.04291 | −0.029443093 | 0.012431026 | 0.017859578 |
| All Histone cluster1 gene | rs6934794 | 2.135 | 0.03275 | 0.038420767 | 0.013873353 | 0.005616085 |
| All Histone cluster1 gene | rs6938200 | −3.692 | 0.0002221 | −0.054407673 | 0.014753455 | 0.000226208 |
| All Histone cluster1 gene | rs721600 | 3.681 | 0.0002323 | 0.051261731 | 0.012993034 | 7.97E−05 |
| All Histone cluster1 gene | rs7745603 | −2.944 | 0.003236 | −0.038182055 | 0.01347952 | 0.004617148 |
| All Histone cluster1 gene | rs7746199 | −1.914 | 0.05556 | −0.033135773 | 0.01627573 | 0.041760311 |
| All Histone cluster1 gene | rs7749305 | −3.879 | 0.0001048 | −0.087200073 | 0.019567667 | 8.34E−06 |
| All Histone cluster1 gene | rs7749319 | −1.85 | 0.06438 | −0.068379642 | 0.02911228 | 0.018832771 |
| All Histone cluster1 gene | rs7756567 | −2.459 | 0.01392 | −0.039049815 | 0.014821075 | 0.008419948 |
| All Histone cluster1 gene | rs7773938 | −2.452 | 0.01422 | −0.039214842 | 0.014812449 | 0.008110743 |
| All Histone cluster1 gene | rs911186 | −4.676 | 2.93E−06 | −0.067957693 | 0.01453 | 2.91E−06 |
| All Histone cluster1 gene | rs9295739 | −2.813 | 0.004915 | −0.171929423 | 0.059595654 | 0.003914979 |
| All Histone cluster1 gene | rs9295749 | 1.562 | 0.1183 | 0.050676086 | 0.02348294 | 0.03092816 |
| Histone cluster1 gene | rs9358944 | −2.484 | 0.01298 | −0.039303573 | 0.014820211 | 0.008001058 |
| All Histone cluster1 gene | rs9358945 | −2.478 | 0.0132 | −0.039297112 | 0.014811587 | 0.00797484 |
| All Histone cluster1 gene | rs9358946 | −2.521 | 0.01172 | −0.043426492 | 0.015012525 | 0.003819653 |
| All Histone cluster1 gene | rs9366653 | −2.616 | 0.008893 | −0.060204646 | 0.018485852 | 0.001126775 |
| All Histone cluster1 gene | rs9366658 | −2.484 | 0.01301 | −0.039303573 | 0.014820211 | 0.008001058 |
| All Histone cluster1 gene | rs9379844 | 1.473 | 0.1407 | 0.023173367 | 0.01147771 | 0.04348838 |

TABLE 1-continued

| | | | | | | |
|---|---|---|---|---|---|---|
| All Histone cluster1 gene | rs9379851 | −2.634 | 0.008427 | −0.060564616 | 0.018459972 | 0.001034905 |
| All Histone cluster1 gene | rs9379856 | −2.948 | 0.003203 | −0.057311367 | 0.01944 | 0.003197175 |
| All Histone cluster1 gene | rs9379858 | −2.629 | 0.008567 | −0.060859987 | 0.018496594 | 0.001000683 |
| All Histone cluster1 gene | rs9379859 | −2.648 | 0.008105 | −0.061151979 | 0.018496594 | 0.000945972 |
| All Histone cluster1 gene | rs9379870 | −2.069 | 0.0385 | −0.029856537 | 0.012449286 | 0.016473483 |
| All Histone cluster1 gene | rs9379897 | −2.698 | 0.006973 | −0.06230161 | 0.018386175 | 0.000702752 |
| All Histone cluster1 gene | rs9393691 | 1.526 | 0.1271 | 0.024042273 | 0.01147687 | 0.036184711 |
| All Histone cluster1 gene | rs9393705 | −2.599 | 0.00936 | −0.060068739 | 0.018488308 | 0.001158065 |
| All Histone cluster1 gene | rs9393708 | −2.644 | 0.008194 | −0.060954265 | 0.018497208 | 0.000983088 |
| All Histone cluster1 gene | rs9393713 | −2.762 | 0.00575 | −0.063064838 | 0.018565638 | 0.000681643 |
| All Histone cluster1 gene | rs9393714 | −3.124 | 0.001784 | −0.069719509 | 0.018583234 | 0.00017561 |
| All Histone cluster1 gene | rs9393777 | −2.78 | 0.005444 | −0.052252011 | 0.017217658 | 0.002407016 |
| All Histone cluster1 gene | rs9461362 | 2.679 | 0.007387 | 0.043176822 | 0.01510931 | 0.004268175 |
| All Histone cluster1 gene | rs9467704 | −3.575 | 0.0003501 | −0.075270063 | 0.019116602 | 8.24E−05 |
| All Histone cluster1 gene | rs9468152 | 3.068 | 0.002153 | 0.05299972 | 0.017220624 | 0.002086127 |
| All Histone cluster1 gene | rs9468159 | 1.528 | 0.1265 | 0.05319711 | 0.021460219 | 0.013179903 |
| All Histone cluster1 gene | rs9468202 | −3.135 | 0.001717 | −0.187147607 | 0.05907474 | 0.00153502 |
| All Histone cluster1 gene | rs9468227 | −2.27 | 0.02321 | −0.119017937 | 0.045458584 | 0.008840483 |
| GTF2IRD2B | imm_7_74094413 | NA | NA | −0.1420245 | 0.03268 | 1.39E−05 |
| GTF2IRD2B | imm_7_74108242 | −2.787 | 0.005313 | −0.045845816 | 0.011311498 | 5.06E−05 |
| GTF2IRD2B | imm_7_74117236 | NA | NA | −0.13056437 | 0.03238 | 5.52E−05 |
| GTF2IRD2B | imm_7_74118166 | −2.329 | 0.01984 | −0.039338514 | 0.011214741 | 0.000451913 |
| GTF2IRD2B | imm_7_74120730 | −3.147 | 0.001648 | −0.073603881 | 0.017629911 | 2.98E−05 |
| GTF2IRD2B | imm_7_74133859 | −2.398 | 0.01648 | −0.037488569 | 0.015355933 | 0.014634152 |
| GTF2IRD2B | imm_7_74145400 | −2.495 | 0.01261 | −0.036352829 | 0.01458 | 0.012654926 |
| ETS1 | imm_11_127760024 | 2.032 | 0.04215 | 0.042926789 | 0.018934111 | 0.023380035 |

TABLE 1-continued

| | | | | | | |
|---|---|---|---|---|---|---|
| ETS1 | imm_11_127761269 | 2.237 | 0.02528 | 0.045524943 | 0.020137336 | 0.023776399 |
| ETS1 | imm_11_127765567 | 2.805 | 0.005028 | 0.049598679 | 0.015895787 | 0.001807035 |
| ETS1 | imm_11_127767721 | −1.582 | 0.1136 | −0.079524768 | 0.036584875 | 0.029727209 |
| ETS1 | imm_11_127770666 | 2.497 | 0.01254 | 0.027675982 | 0.012651619 | 0.028702789 |
| ETS1 | imm_11_127770668 | 2.422 | 0.01543 | 0.026754934 | 0.012642548 | 0.034322604 |
| ETS1 | imm_11_127774308 | 2.691 | 0.007129 | 0.047208966 | 0.015786763 | 0.002785991 |
| ETS1 | imm_11_127775128 | 2.544 | 0.01096 | 0.045858868 | 0.015793826 | 0.003689054 |
| ETS1 | imm_11_127776527 | −1.751 | 0.07986 | −0.08202922 | 0.034742961 | 0.018224191 |
| ETS1 | imm_11_127776913 | −1.761 | 0.0783 | −0.080950891 | 0.035366597 | 0.022084689 |
| ETS1 | imm_11_127777217 | −2.993 | 0.00276 | −0.037787017 | 0.011172423 | 0.000719161 |
| ETS1 | imm_11_127778327 | 1.993 | 0.0463 | 0.027615167 | 0.01368 | 0.043523344 |
| ETS1 | imm_11_127778329 | 2.349 | 0.01883 | 0.031728477 | 0.012692271 | 0.012425409 |
| ETS1 | imm_11_127779030 | −2.278 | 0.02271 | −0.075381275 | 0.027992548 | 0.007083243 |
| ETS1 | imm_11_127780425 | 1.845 | 0.06506 | 0.070225777 | 0.031881326 | 0.027614175 |
| ETS1 | imm_11_127780902 | −2.289 | 0.02208 | −0.074442787 | 0.027962569 | 0.007762485 |
| ETS1 | imm_11_127781839 | 2.504 | 0.0123 | 0.032777667 | 0.013448782 | 0.014800589 |
| ETS1 | imm_11_127785739 | −2.072 | 0.0383 | −0.035012045 | 0.014009631 | 0.012449473 |
| ETS1 | imm_11_127785963 | 3.101 | 0.001927 | 0.052040195 | 0.015404731 | 0.000729632 |
| ETS1 | imm_11_127786010 | 2.345 | 0.01902 | 0.037673992 | 0.014211921 | 0.008028412 |
| ETS1 | imm_11_127786836 | 2.275 | 0.0229 | 0.036589399 | 0.014202859 | 0.009989296 |
| ETS1 | imm_11_127787128 | 2.382 | 0.0172 | 0.039414469 | 0.01441664 | 0.006257827 |
| ETS1 | imm_11_127788828 | −1.965 | 0.04944 | −0.033526672 | 0.013833259 | 0.01536634 |
| ETS1 | imm_11_127789306 | 2.183 | 0.029 | 0.036739352 | 0.014727637 | 0.01261043 |
| ETS1 | imm_11_127789441 | 2.164 | 0.03043 | 0.036624882 | 0.014726445 | 0.012882018 |
| ETS1 | imm_11_127791651 | 3.062 | 0.002198 | 0.053955711 | 0.015283716 | 0.000415129 |
| ETS1 | imm_11_127792287 | 2.193 | 0.02832 | 0.035742383 | 0.014204214 | 0.011858661 |
| ETS1 | imm_11_127792800 | 2.306 | 0.02113 | 0.066110717 | 0.026814214 | 0.013681829 |
| ETS1 | imm_11_127793060 | 2.06 | 0.03942 | 0.034056541 | 0.014192892 | 0.01641528 |
| ETS1 | imm_11_127794685 | 2.898 | 0.003755 | 0.051462381 | 0.015253854 | 0.000741571 |
| ETS1 | imm_11_127795453 | 2.084 | 0.03712 | 0.034059211 | 0.014182472 | 0.016327993 |
| ETS1 | imm_11_127796816 | −2.51 | 0.01206 | −1.664950591 | 0.6633 | 0.012069633 |
| ETS1 | imm_11_127797523 | 2.077 | 0.03779 | 0.034301166 | 0.014191533 | 0.01564832 |
| ETS1 | imm_11_127798230 | −1.785 | 0.07422 | −0.028064721 | 0.012258798 | 0.022058826 |
| ETS1 | imm_11_127799892 | 2.523 | 0.01165 | 0.025601331 | 0.011134725 | 0.021491698 |
| ETS1 | imm_11_127804916 | −1.846 | 0.06484 | −0.03329535 | 0.016645797 | 0.045475907 |
| ETS1 | imm_11_127805367 | −2.056 | 0.03982 | −0.074705008 | 0.033949249 | 0.027772097 |
| ETS1 | imm_11_127806163 | 2.233 | 0.02553 | 0.026897717 | 0.0114935 | 0.019270591 |
| ETS1 | imm_11_127806304 | −2.064 | 0.03899 | −0.078980642 | 0.034472261 | 0.021955543 |
| ETS1 | imm_11_127807384 | 2.165 | 0.0304 | 0.029608627 | 0.014745076 | 0.044639585 |
| ETS1 | imm_11_127808758 | −1.977 | 0.04808 | −0.072324763 | 0.033858572 | 0.032672546 |
| ETS1 | imm_11_127809308 | −2.768 | 0.005647 | −0.179735204 | 0.065479608 | 0.006052869 |
| ETS1 | imm_11_127812329 | 2.044 | 0.04094 | 0.0578145 | 0.024925603 | 0.020368891 |
| ETS1 | imm_11_127812420 | 2.328 | 0.01991 | 1.034251522 | 0.4443 | 0.019921533 |
| ETS1 | imm_11_127813024 | 2.23 | 0.02575 | 0.026659 | 0.01148528 | 0.020279014 |
| ETS1 | imm_11_127819226 | 2.124 | 0.0337 | 0.029083683 | 0.014734003 | 0.048391311 |
| ETS1 | imm_11_127822686 | −2.085 | 0.03704 | −0.076311769 | 0.033773092 | 0.0238496 |
| ETS1 | imm_11_127823420 | −2.766 | 0.005668 | −0.179711713 | 0.065475865 | 0.006056594 |
| ETS1 | imm_11_127824356 | 2.321 | 0.02029 | 0.031507947 | 0.014938913 | 0.034934297 |
| ETS1 | imm_11_127825016 | −2.044 | 0.04092 | −0.073610998 | 0.033835636 | 0.029589194 |
| ETS1 | imm_11_127825282 | 2.168 | 0.03012 | 0.026165347 | 0.011458899 | 0.022406326 |
| ETS1 | imm_11_127825669 | 2.152 | 0.03141 | 0.026284858 | 0.011459326 | 0.021804716 |
| ETS1 | imm_11_127826087 | −3.239 | 0.001199 | −0.036667302 | 0.01179811 | 0.001884242 |
| ETS1 | imm_11_127826464 | 2.179 | 0.02933 | 0.031847589 | 0.015364357 | 0.038188781 |
| ETS1 | imm_11_127827422 | 2.146 | 0.03188 | 0.031836913 | 0.0153331 | 0.037861413 |
| ETS1 | imm_11_127828334 | −1.796 | 0.07255 | −0.0717967 | 0.034541489 | 0.03765743 |
| ETS1 | imm_11_127831280 | −2.347 | 0.01891 | −0.076928682 | 0.034934703 | 0.02766032 |
| ETS1 | imm_11_127831611 | 1.965 | 0.04947 | 0.030801761 | 0.015266783 | 0.043636358 |
| ETS1 | imm_11_127831673 | −2.213 | 0.02687 | −0.026302648 | 0.012250664 | 0.03179022 |
| ETS1 | imm_11_127834123 | 2.449 | 0.01434 | 0.031150692 | 0.012207726 | 0.010719278 |
| ETS1 | imm_11_127834484 | −2.245 | 0.02479 | −0.083250933 | 0.035190155 | 0.017993833 |
| ETS1 | imm_11_127837472 | −2.276 | 0.02286 | −0.086358386 | 0.04119264 | 0.036042131 |
| ETS1 | imm_11_127838265 | −2.501 | 0.01238 | −0.0467051 | 0.020354171 | 0.021754875 |
| ETS1 | imm_11_127838713 | 2.706 | 0.0068 | 0.030443434 | 0.011150762 | 0.006330239 |
| ETS1 | imm_11_127839719 | −1.685 | 0.09208 | −0.101896739 | 0.048155183 | 0.034344151 |
| ETS1 | imm_11_127840459 | 4.443 | 8.88E−06 | 0.066778559 | 0.015027999 | 8.85E−06 |
| ETS1 | imm_11_127840867 | −3.349 | 0.0008102 | −0.057525516 | 0.018030387 | 0.001420387 |
| ETS1 | imm_11_127841724 | −2.083 | 0.03722 | −0.05480528 | 0.018801811 | 0.003558098 |
| ETS1 | imm_11_127841864 | −2.143 | 0.03209 | −0.028776523 | 0.01125191 | 0.010543391 |
| ETS1 | imm_11_127843207 | −2.168 | 0.03017 | −0.056484024 | 0.018845217 | 0.002724178 |
| ETS1 | imm_11_127843341 | −2.128 | 0.03337 | −0.054915038 | 0.018825026 | 0.00353269 |
| ETS1 | imm_11_127844385 | 4.361 | 1.29E−05 | 0.064455567 | 0.015018502 | 1.77E−05 |
| ETS1 | imm_11_127844729 | 2.063 | 0.03914 | 0.083540439 | 0.035945727 | 0.020121663 |
| ETS1 | imm_11_127845557 | −2.259 | 0.02389 | −0.056607744 | 0.018571567 | 0.002303036 |
| ETS1 | imm_11_127846698 | 4.256 | 2.08E−05 | 0.063037728 | 0.014963881 | 2.52E−05 |
| ETS1 | imm_11_127848167 | 4.248 | 2.15E−05 | 0.063359292 | 0.014979336 | 2.34E−05 |
| ETS1 | imm_11_127848372 | 4.292 | 1.77E−05 | 0.063723341 | 0.01501456 | 2.19E−05 |
| ETS1 | imm_11_127849992 | 4.259 | 2.05E−05 | 0.063139897 | 0.014980517 | 2.50E−05 |
| ETS1 | imm_11_127851599 | 4.416 | 1.00E−05 | 0.065721185 | 0.014950847 | 1.10E−05 |
| ETS1 | imm_11_127852250 | −2.074 | 0.03811 | −0.056396101 | 0.018949807 | 0.002919607 |
| ETS1 | imm_11_127853705 | −2.069 | 0.03855 | −0.056310436 | 0.018954288 | 0.002969723 |

TABLE 1-continued

| | | | | | | |
|---|---|---|---|---|---|---|
| ETS1 | imm_11_127855281 | 4.274 | 1.92E−05 | 0.063002728 | 0.014965887 | 2.56E−05 |
| ETS1 | imm_11_127855956 | −1.906 | 0.05663 | −0.052503353 | 0.018846373 | 0.005338596 |
| ETS1 | imm_11_127857027 | −2.228 | 0.02586 | −0.058543871 | 0.019045877 | 0.002113268 |
| ETS1 | imm_11_127861069 | 2.908 | 0.003636 | 0.033615546 | 0.012703529 | 0.008141175 |
| ETS1 | imm_11_127863304 | 2.985 | 0.002833 | 0.034151141 | 0.012711732 | 0.007218671 |
| ETS1 | imm_11_127863391 | 2.936 | 0.003319 | 0.0343825 | 0.01271086 | 0.006831048 |
| ETS1 | imm_11_127866379 | 2.209 | 0.02719 | 0.027961868 | 0.013022783 | 0.031781351 |
| ETS1 | imm_11_127868447 | 1.315 | 0.1886 | 0.301617605 | 0.137802383 | 0.028613623 |
| ETS1 | imm_11_127868927 | −1.917 | 0.05524 | −0.030778263 | 0.014215206 | 0.030375071 |
| ETS1 | imm_11_127869177 | 3.291 | 0.0009998 | 0.042725144 | 0.01308094 | 0.00108996 |
| ETS1 | imm_11_127870403 | 3.406 | 0.0006589 | 0.040128462 | 0.012795572 | 0.001711985 |
| ETS1 | imm_11_127870895 | 3.461 | 0.0005381 | 0.039930201 | 0.012643861 | 0.001588174 |
| ETS1 | imm_11_127871431 | 3.409 | 0.000651 | 0.038993789 | 0.012643861 | 0.002042311 |
| ETS1 | imm_11_127872972 | −1.931 | 0.0535 | −0.034517826 | 0.014721847 | 0.019044089 |
| ETS1 | imm_11_127874486 | 3.415 | 0.0006384 | 0.039149608 | 0.012635226 | 0.001945363 |
| ETS1 | imm_11_127874807 | 3.355 | 0.0007941 | 0.037325948 | 0.012669831 | 0.00321861 |
| ETS1 | imm_11_127877378 | 3.476 | 0.0005082 | 0.040066089 | 0.01266069 | 0.001552934 |
| ETS1 | imm_11_127879923 | −2.006 | 0.04482 | −0.032104052 | 0.014245451 | 0.024219122 |
| ETS1 | imm_11_127881686 | 5.101 | 3.38E−07 | 0.07519188 | 0.014571861 | 2.47E−07 |
| ETS1 | imm_11_127882690 | 2.424 | 0.01534 | 0.027998152 | 0.011472767 | 0.014670969 |
| ETS1 | imm_11_127884689 | −2.195 | 0.02818 | −0.053596757 | 0.024228018 | 0.026954177 |
| ETS1 | imm_11_127885952 | 4.173 | 3.01E−05 | 0.04882324 | 0.011607573 | 2.60E−05 |
| ETS1 | imm_11_127886184 | 5.214 | 1.85E−07 | 0.072118037 | 0.013104848 | 3.73E−08 |
| ETS1 | imm_11_127887077 | 4.156 | 3.24E−05 | 0.048819243 | 0.011615795 | 2.64E−05 |
| ETS1 | imm_11_127889134 | 5.127 | 2.94E−07 | 0.070484447 | 0.013134204 | 8.03E−08 |
| ETS1 | imm_11_127891116 | 5.021 | 5.13E−07 | 0.069779303 | 0.013134204 | 1.08E−07 |
| ETS1 | imm_11_127892632 | 4.17 | 3.05E−05 | 0.048939649 | 0.011616223 | 2.52E−05 |
| ETS1 | imm_11_127894601 | −1.516 | 0.1296 | −0.026829502 | 0.013320245 | 0.043989602 |
| ETS1 | imm_11_127894638 | −2.484 | 0.01299 | −0.188155241 | 0.090683227 | 0.037999265 |
| ETS1 | imm_11_127895279 | 5.254 | 1.49E−07 | 0.072347736 | 0.013125964 | 3.55E−08 |
| ETS1 | imm_11_127897147 | 5.135 | 2.82E−07 | 0.071324587 | 0.013275971 | 7.77E−08 |
| ETS1 | imm_11_127898835 | −2.452 | 0.01419 | −0.104184655 | 0.041061849 | 0.011172342 |
| ETS1 | imm_11_127901157 | 3.634 | 0.0002788 | 0.048482987 | 0.012182068 | 6.90E−05 |
| ETS1 | imm_11_127901948 | 4.845 | 1.27E−06 | 0.067482299 | 0.013201602 | 3.19E−07 |
| ETS1 | imm_11_127905841 | −2.633 | 0.008471 | −0.06305062 | 0.02509525 | 0.011989528 |
| ETS1 | imm_11_127906568 | 3.779 | 0.0001574 | 0.037251522 | 0.011449394 | 0.001139605 |
| ETS1 | imm_11_127908214 | 3.85 | 0.0001181 | 0.038139717 | 0.011441168 | 0.000857449 |
| ETS1 | imm_11_127911648 | 3.474 | 0.0005128 | −0.038289326 | 0.011656784 | 0.001020821 |
| ETS1 | imm_11_127911985 | 3.592 | 0.0003287 | 0.033215696 | 0.01112011 | 0.002817358 |
| ETS1 | imm_11_127914294 | 3.612 | 0.0003037 | 0.033184837 | 0.011119682 | 0.00284197 |
| ETS1 | imm_11_127915474 | 3.587 | 0.0003349 | −0.032982076 | 0.011120538 | 0.003018275 |
| ETS1 | imm_11_127915554 | 3.886 | 0.0001018 | −0.036194682 | 0.011136979 | 0.001154232 |
| ETS1 | imm_11_127916046 | 3.497 | 0.00047 | 0.031936936 | 0.011110604 | 0.004047249 |
| ETS1 | imm_11_127929821 | −2.385 | 0.01708 | −0.678652718 | 0.2845 | 0.017059514 |
| ETS1 | imm_11_127931099 | −2.429 | 0.01513 | −0.862513022 | 0.355 | 0.015114905 |
| ETS1 | imm_11_127940676 | −2.022 | 0.04321 | −0.062037894 | 0.026138425 | 0.01762342 |
| ETS1 | imm_11_127943244 | −1.673 | 0.09426 | −0.812307098 | 0.402683738 | 0.043671159 |
| ETS1 | imm_11_127945727 | NA | NA | 0.088926209 | 0.03356 | 0.00805471 |
| ETS1 | imm_11_127945953 | −2.524 | 0.01162 | −0.050352946 | 0.020907291 | 0.016022978 |
| ETS1 | imm_11_127948912 | −3.115 | 0.001838 | −0.131414033 | 0.040583382 | 0.001203184 |
| ETS1 | imm_11_127956842 | 2.659 | 0.007839 | 0.030434638 | 0.012698899 | 0.016546358 |
| ETS1 | imm_11_127957543 | 2.276 | 0.02283 | 0.116729213 | 0.0456538 | 0.010562944 |
| ETS1 | imm_11_127957904 | 3.005 | 0.002655 | 0.115296546 | 0.052991094 | 0.029572303 |
| ETS1 | imm_11_127974263 | −2.438 | 0.01479 | −0.04857884 | 0.020976737 | 0.020566818 |
| ETS1 | imm_11_127979301 | −2.378 | 0.01741 | −0.034463525 | 0.014465314 | 0.017195808 |
| ETS1 | imm_11_127979905 | −1.988 | 0.04682 | −0.113506773 | 0.051876884 | 0.028669391 |
| ETS1 | imm_11_127981559 | −2.045 | 0.04084 | −0.029414518 | 0.014589917 | 0.04379105 |
| ETS1 | imm_11_127982379 | −2.052 | 0.04018 | −0.029503242 | 0.01459824 | 0.043278356 |
| ETS1 | imm_11_127982748 | −2.311 | 0.02081 | −0.033127504 | 0.014582372 | 0.023101611 |
| ETS1 | imm_11_127983590 | −2.119 | 0.03407 | −0.0303598 | 0.014627509 | 0.037937657 |
| ETS1 | imm_11_127983743 | −2.046 | 0.04074 | −0.029503242 | 0.01459824 | 0.043278356 |
| ETS1 | imm_11_127984265 | −2.118 | 0.03414 | −0.030230583 | 0.01459824 | 0.038373979 |
| ETS1 | imm_11_127984721 | −2.201 | 0.02777 | −0.032860786 | 0.014627752 | 0.02467401 |
| ETS1 | rs7935286 | 2.73 | 0.006328 | 0.047557767 | 0.015027868 | 0.001552758 |
| SLC5A1 | rs738203 | 1.932 | 0.05333 | 0.02886435 | 0.014259591 | 0.042948954 |
| SLC5A1 | rs9609429 | −1.99 | 0.04659 | −0.040869749 | 0.012698502 | 0.001288764 |
| TET2 | rs10010325 | −5.75 | 8.95E−09 | −0.062859518 | 0.011131325 | 1.63E−08 |
| TET2 | rs17035310 | 3.138 | 0.001702 | 0.06001359 | 0.016413995 | 0.000255937 |
| TET2 | rs2189234 | 3.607 | 0.0003095 | 0.033831361 | 0.011536644 | 0.003362306 |
| TET2 | rs7661349 | 3.663 | 0.0002491 | 0.034610864 | 0.011723345 | 0.003154135 |
| TET2 | rs974801 | −5.427 | 5.73E−08 | −0.055192987 | 0.011495877 | 1.58E−06 |

Many variations and alternative elements have been disclosed in embodiments of the present invention. Still further variations and alternate elements will be apparent to one of skill in the art. Among these variations, without limitation, are the selection of constituent modules for the inventive methods, compositions, kits, and systems, and the various conditions, diseases, and disorders that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1 GLS-SKAT: A Novel Approach for Gene-Based Analysis in Cohorts with Family Structure Gene-based analysis can be important in identifying novel loci for complex diseases. However most of the available approaches are based on independent assumption, aiming at population based case-control sample. Here we proposed a generalized least square (GLS) based analysis strategy to identify genes using data with complex family structures. Rational of this approach can be described as following.

Given a linear specification of the association of a set of genetic factors X and the outcome y, we have:

$$y=X\beta+e \quad (1)$$

Suppose that the variance of outcome y can be written as:

$$\mathrm{var}(y)=\Sigma_o \quad (2)$$

When the subjects in the sample are uncorrelated, the estimate of β can be written as:

$$\hat{\beta}_T=(X'X)^{-1}X'y \quad (3)$$

$$\widehat{\mathrm{var}}(\hat{\beta}_T)=\hat{\sigma}_T^2(X'X)^{-1}. \quad (4)$$

When the samples are correlated, e.g. in family-based samples, the ordinary least squares (OLS) estimate of β will be problematic and will lead to a biased estimate of $\widehat{\mathrm{var}}(\hat{\beta}_T)$. This will affect any model based on independent assumption, including most gene-based tests.

One of the solutions to the violation of independence assumption in linear model is to perform the generalized least square transformation. Let:

$$G==\Sigma_o^{-1/2} \quad (5)$$

And a GLS transformed model can be written as:

$$Gy=GX\beta+Ge \quad (6)$$

And estimate based on the transformed model can be written as:

$$\hat{\beta}_{GLS}=(X'\Sigma_o^{-1}X)^{-1}X'\Sigma_o^{-1}y \quad (7)$$

$$\mathrm{var}(\hat{\beta}_{GLS})=\mathrm{var}((X'\Sigma_o^{-1}X)^{-1}X'\Sigma_o^{-1}y)=(X'\Sigma_o^{-1}X)^{-1} \quad (8)$$

Clearly this is Best Linear Unbiased Predictor (BLUP) by construction. In other words, after the GLS transformation the data is de-correlated while retaining an unbiased estimator. Thereby any model developed with independence assumption can be applied to the GLS transformed data. Here for gene-based analysis, we choose to apply SKAT-CommonRare in the GLS transformed data as it has better performance in most scenarios while the independence assumption holds. The transformation matrix G was calculated as the inverse of the decomposition of the kinship matrix. We call this approach GLS-SKAT.

Example 2 Multiple Novel Loci Identified Via Gene-Based Analysis

Figure 1A:
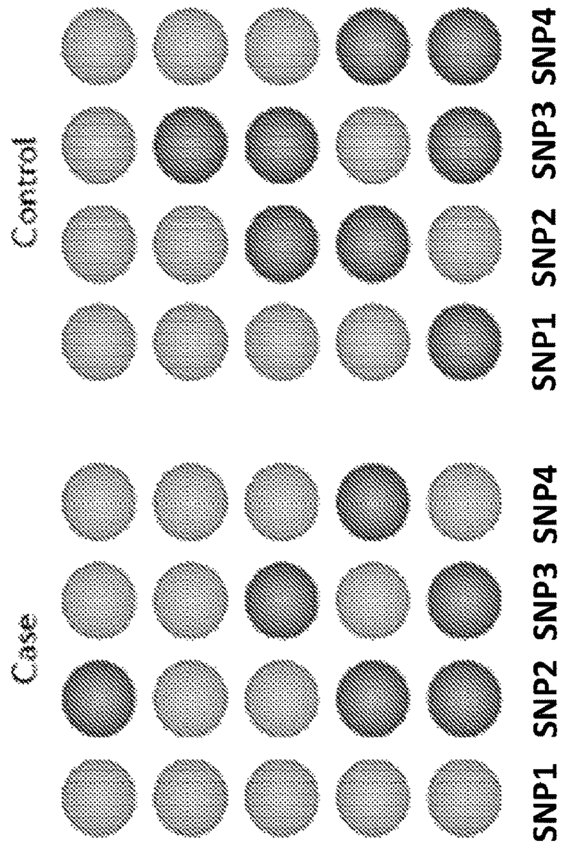
Figure 2A:
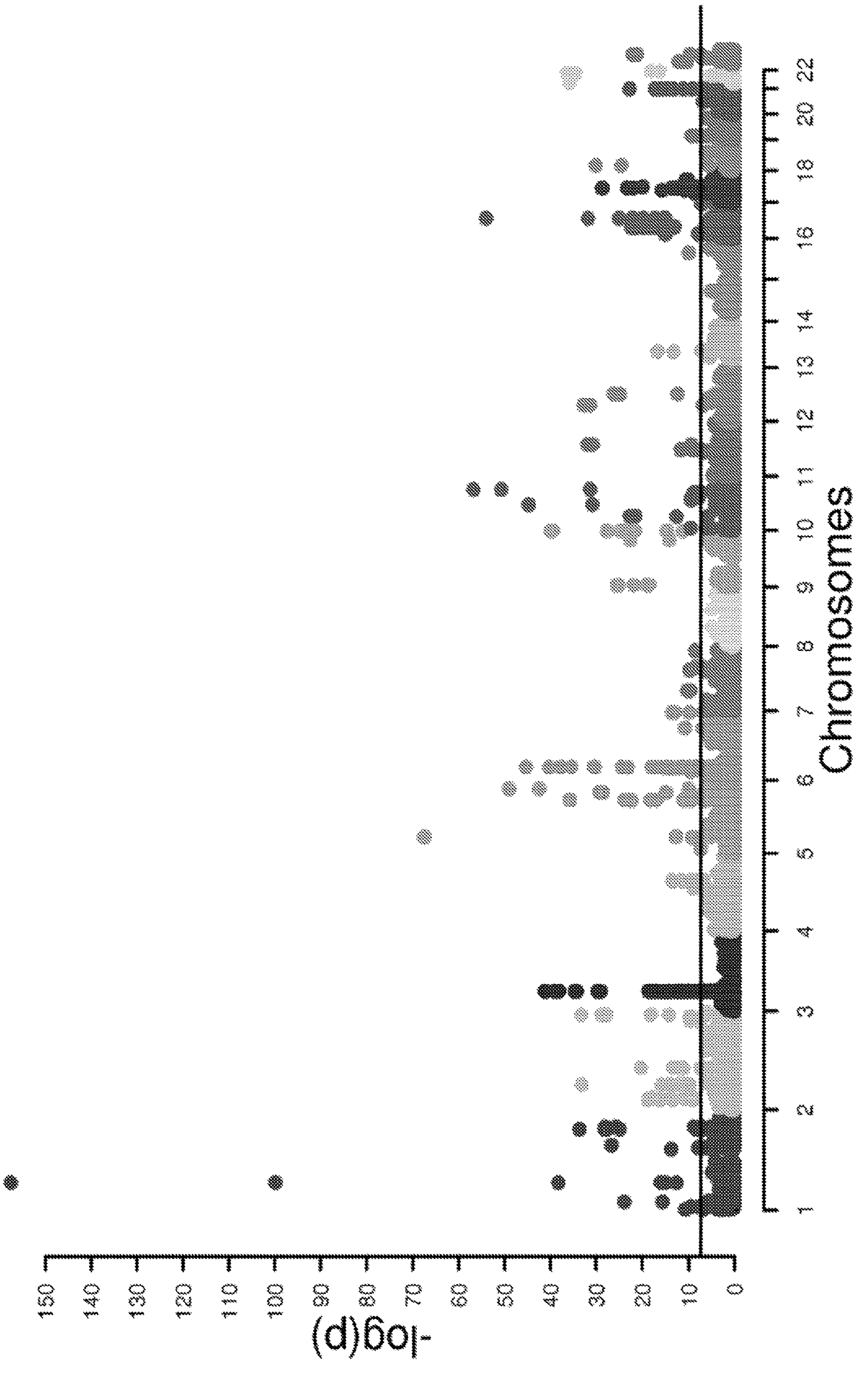
FIGS. 2A-2B depict, in accordance with various embodiments of the invention, Manhattan plots.
Figure 2B:
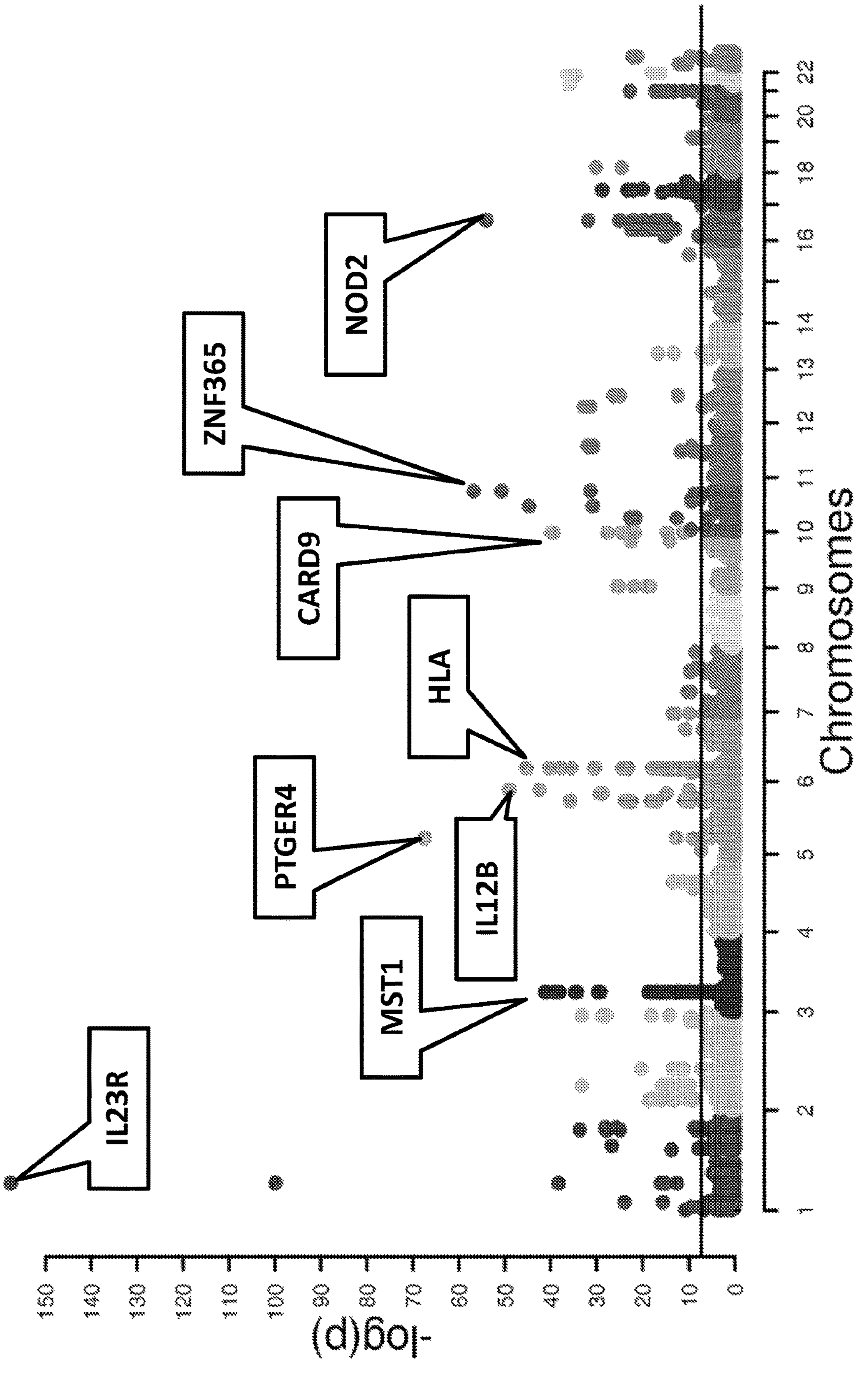
Figure 3:
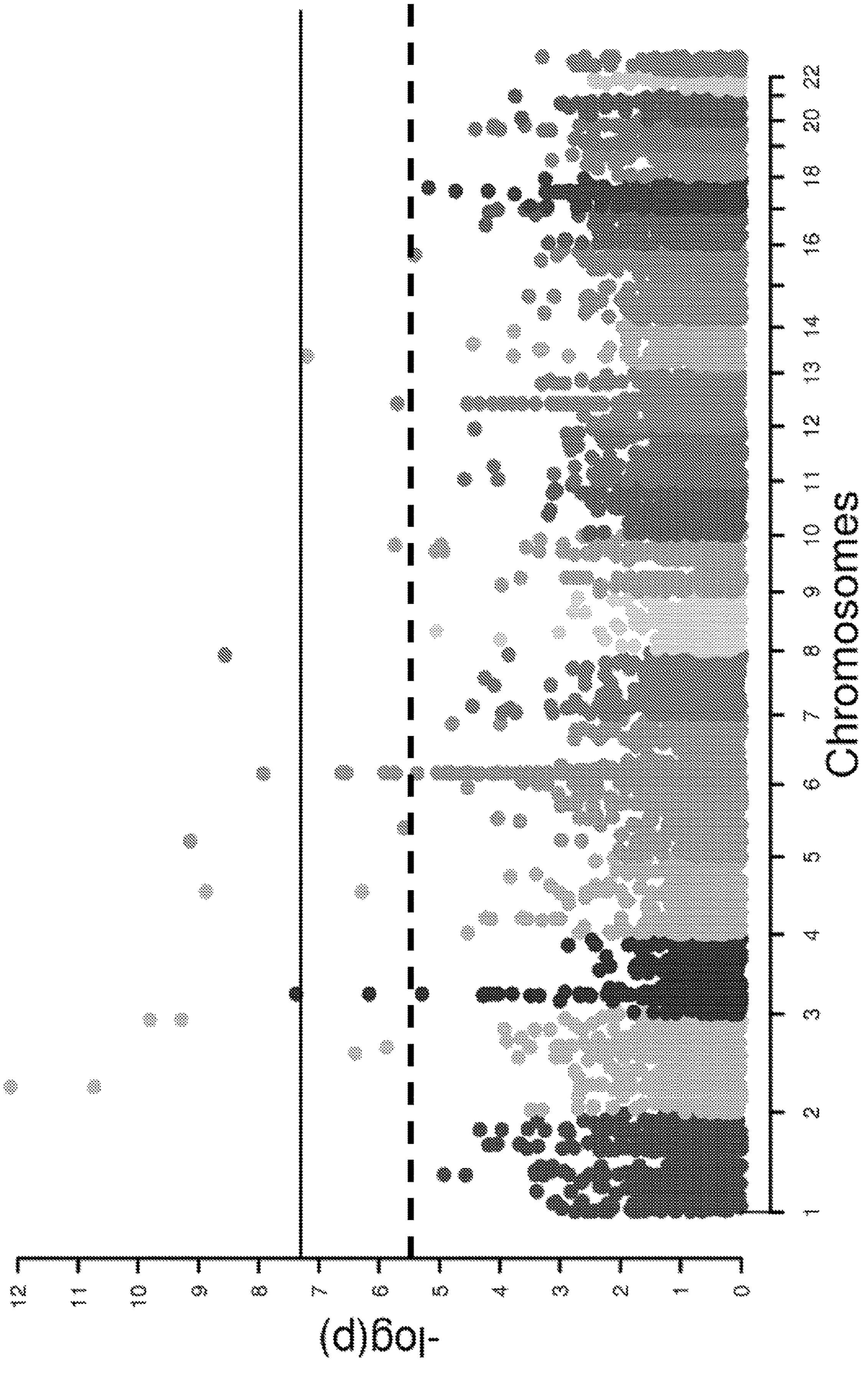
FIG. 3 depicts, in accordance with various embodiments of the invention, Manhattan plot: exclude Jostin regions
Figure 5A:
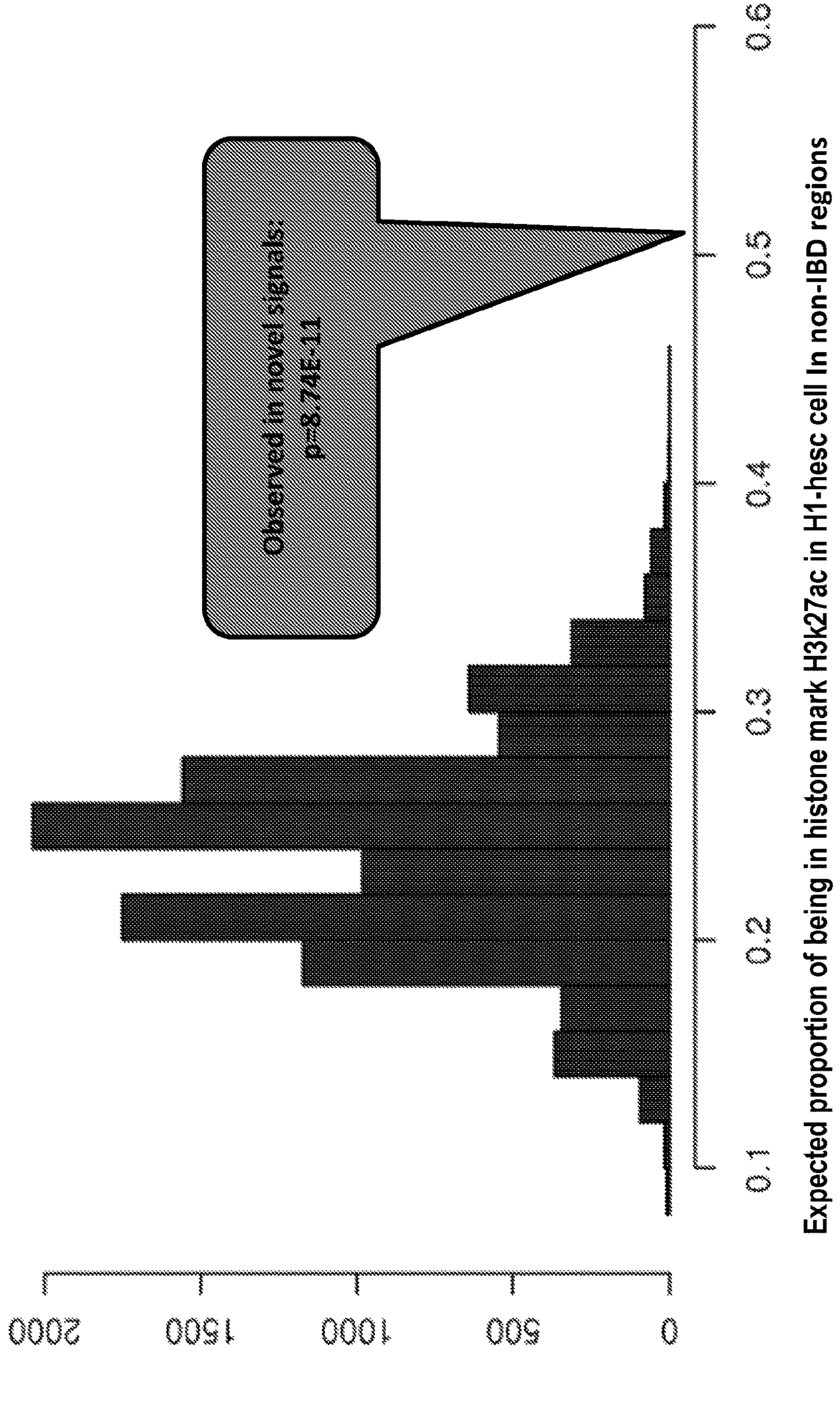
FIG. 5A-5B depicts, in accordance with various embodiments of the invention, (A) increased chance of being in histone marks compared to non-IBD regions and (B) increased chance of being in histone marks compared to known IBD SNPs.
Figure 5B:
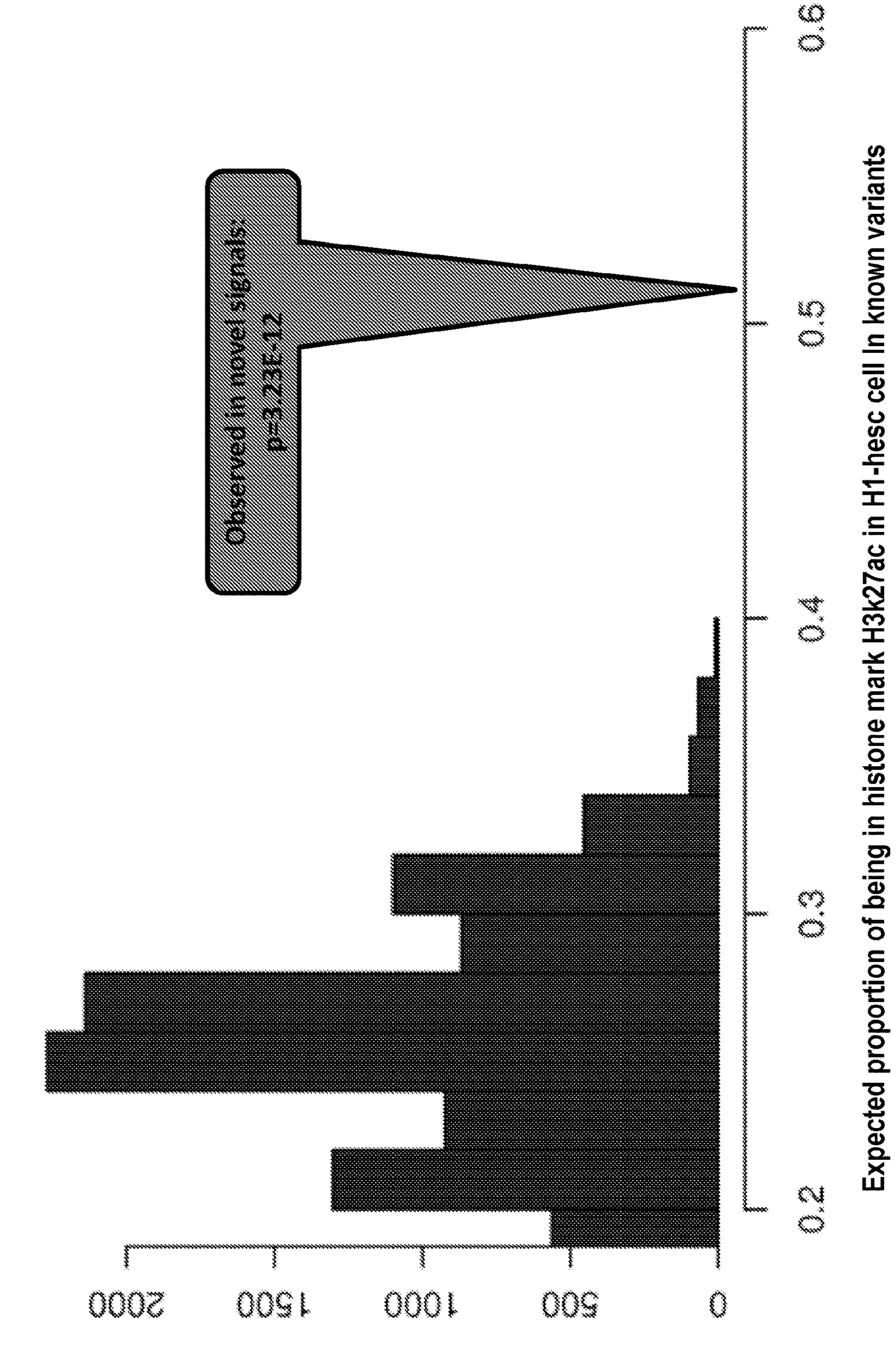
Figure 6A:
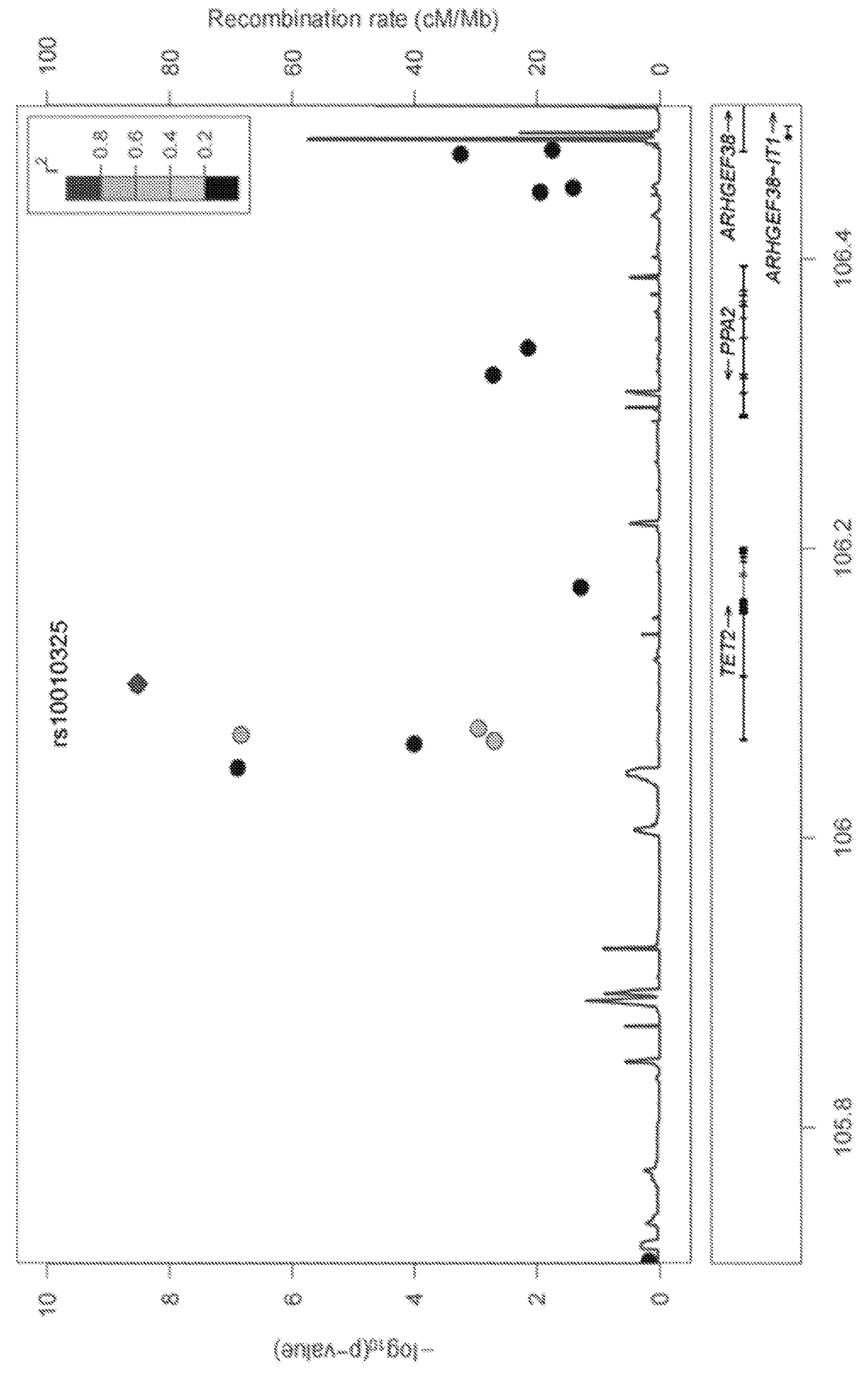
Figure 6D:
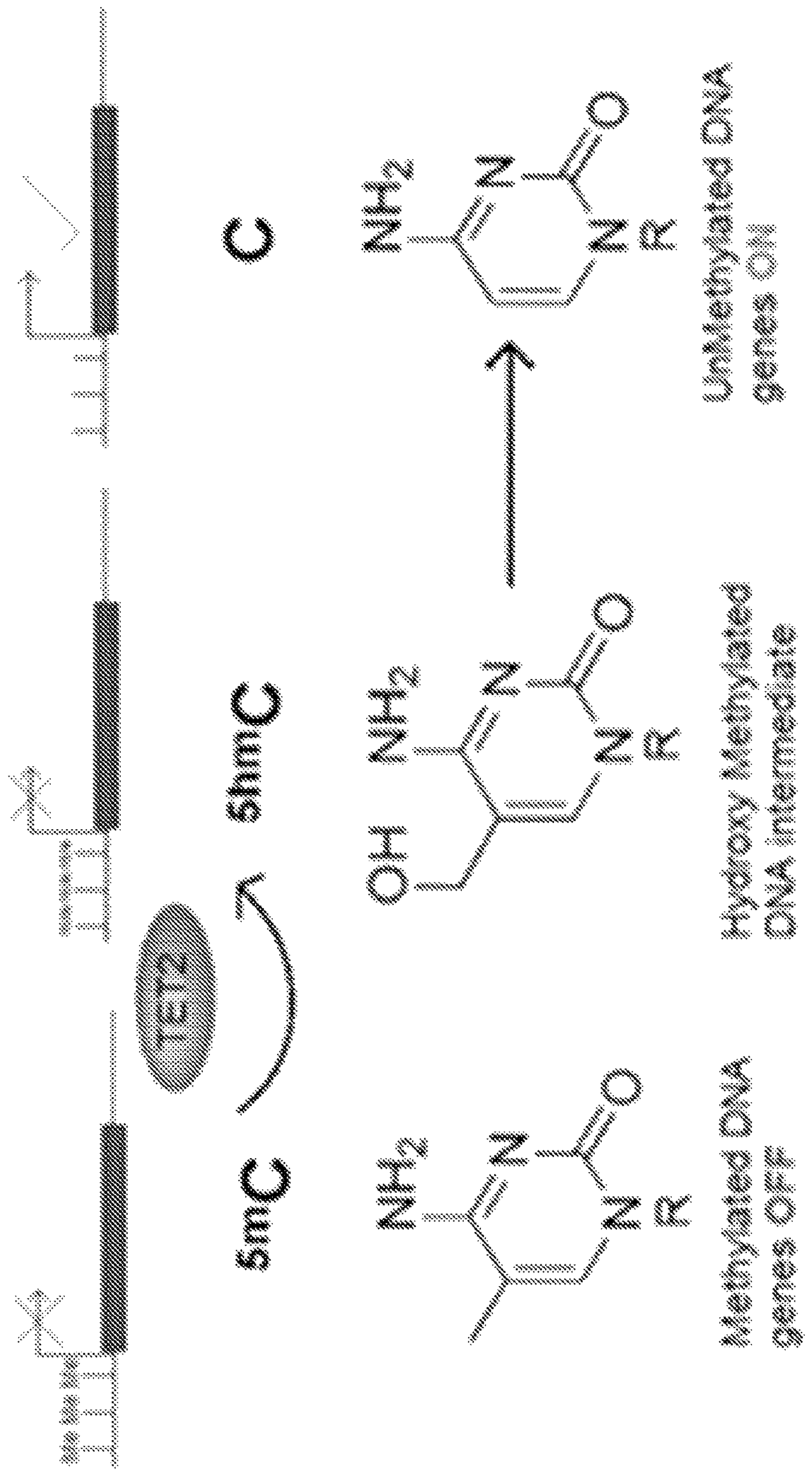
Figure 7A:
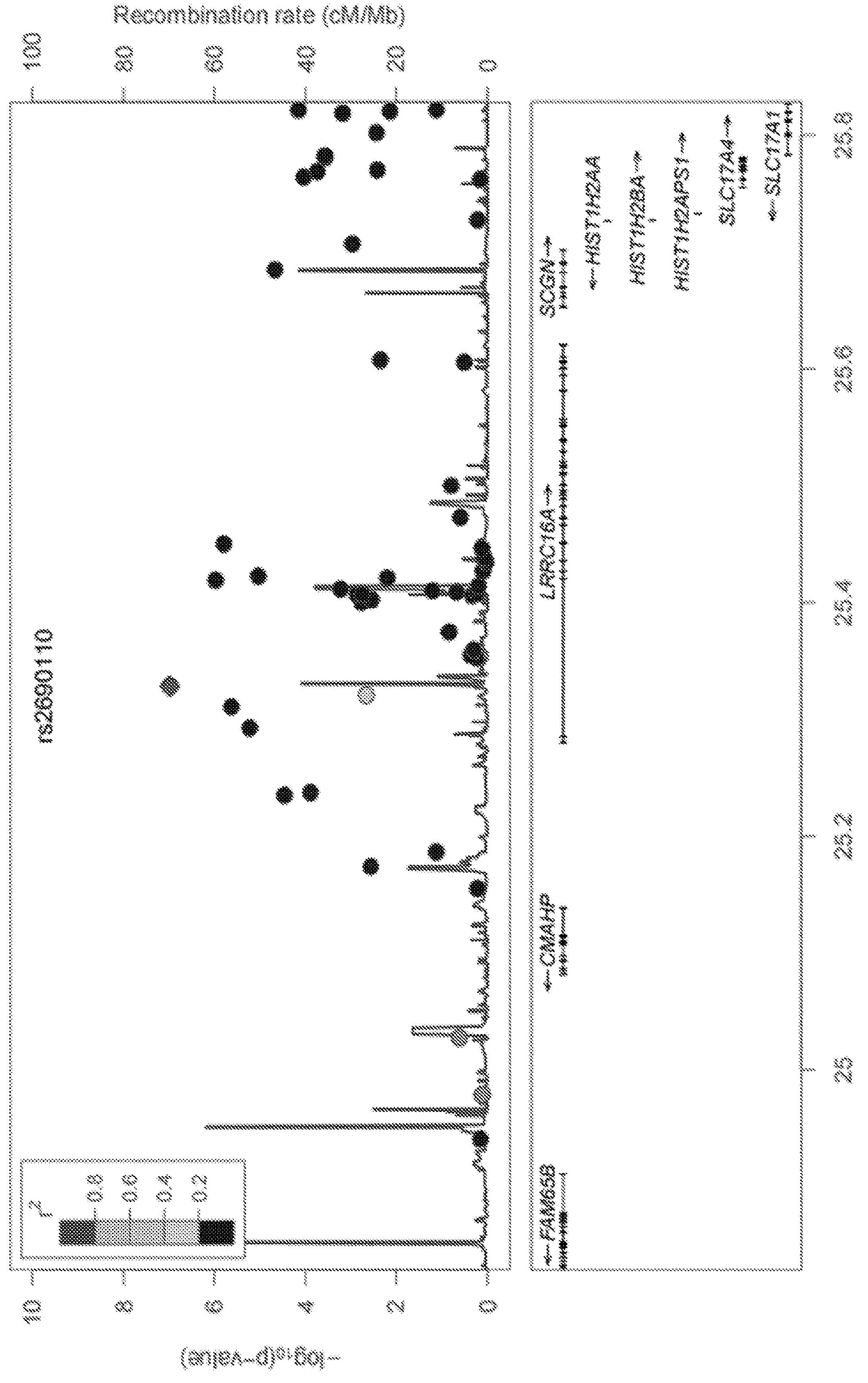
Figure 7B:
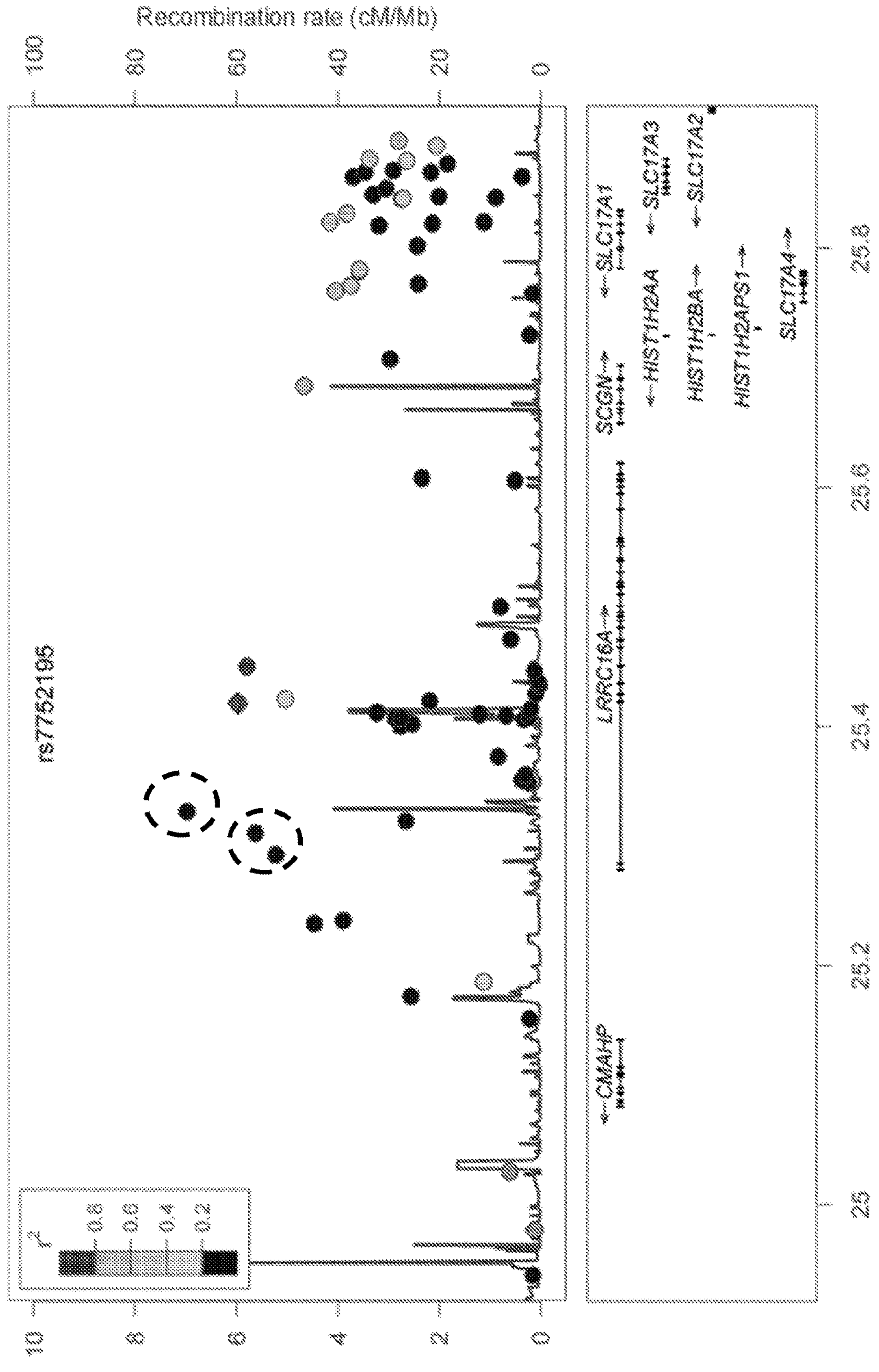
Figure 8A:
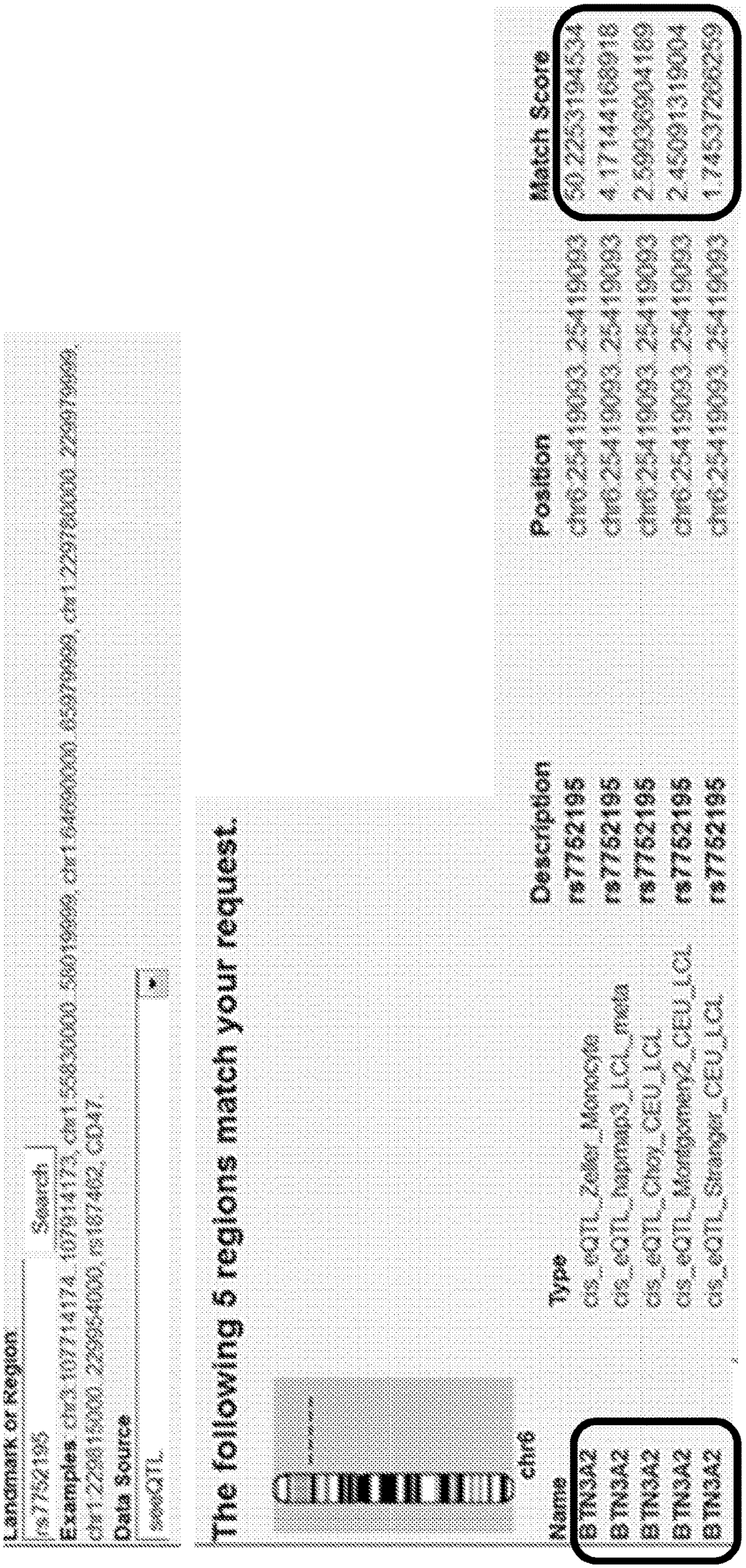
Figure 8C:
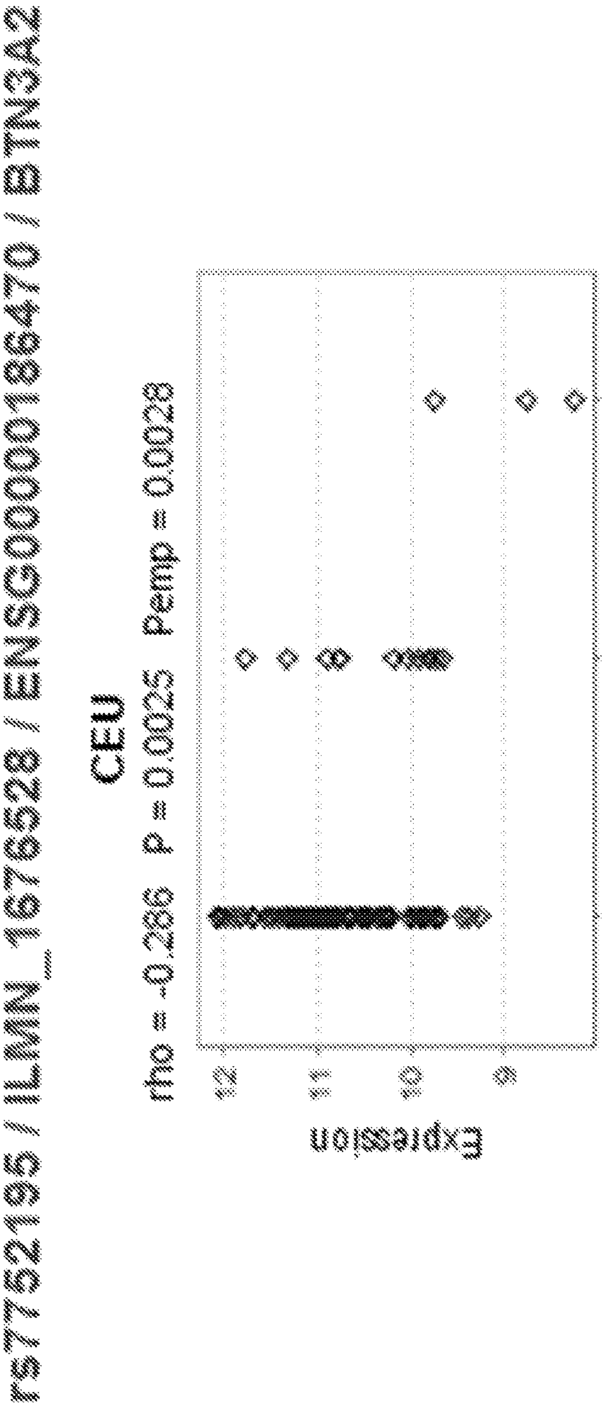
Figure 9B:
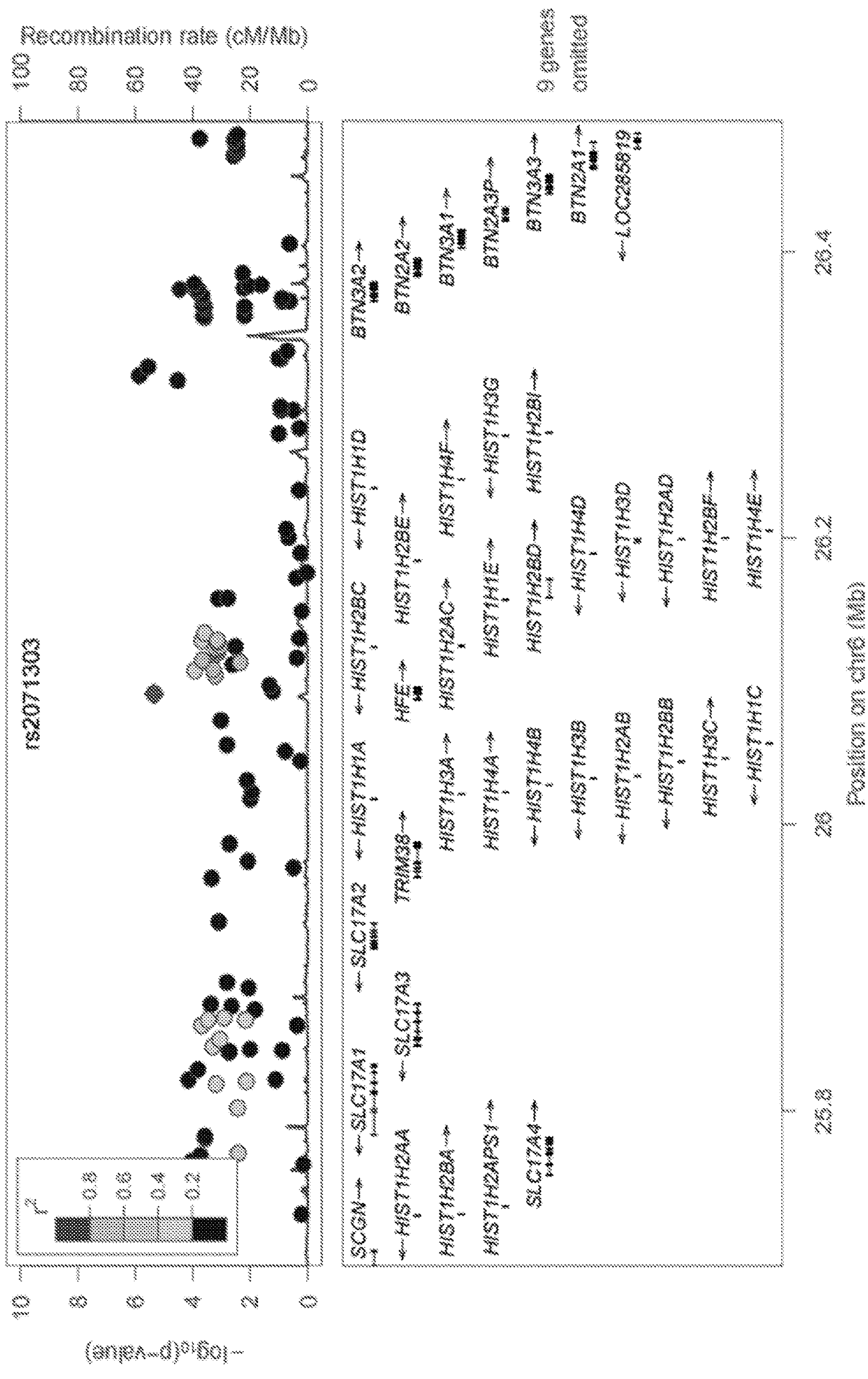
Figure 11B:
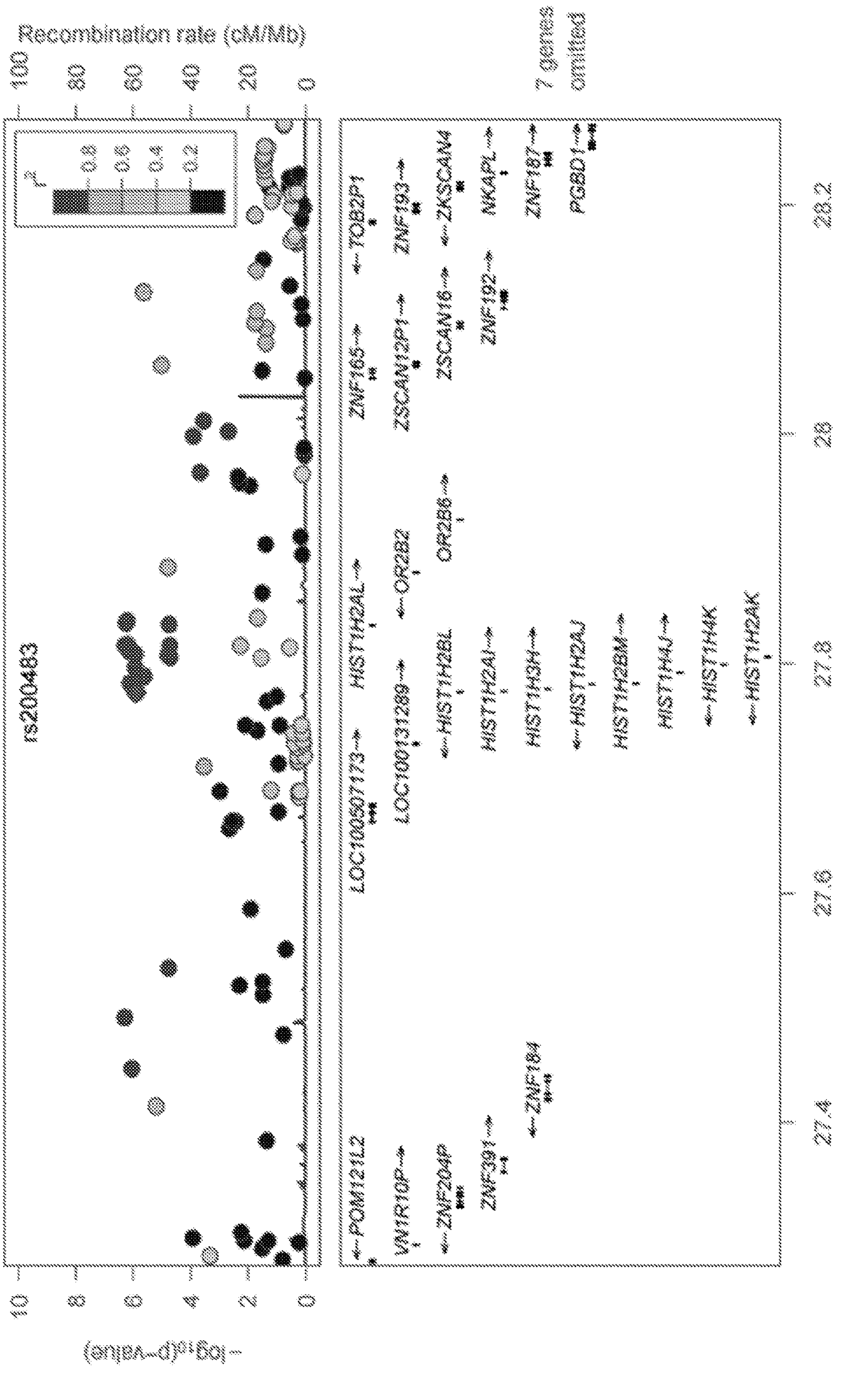

Single-SNP based association drives most GWAS findings mostly because it's simple and straightforward (FIG. 1A). It tests if frequency of a single SNP is the same in case and control. However, it suffers from some drawbacks including: multiple testing correction, forbidding as the number of variants increases, ignoring multiple weak signals; and missing some causal loci.

Gene-based analysis examines a gene as a whole instead of looking at single SNPs (FIG. 1B). It tests if distribution of all the SNPs in a given gene is the same in case and control. It is more powerful, when there are multiple causal SNPs with weak effects. It can reduce multiple-testing penalty for millions of SNPs and about 25000 known genes.

Current approaches for gene-based analysis include data collapsing approaches (e.g., Combining Multivariate and Collapsing approach (CMC), Weighted Sum Statistics (WSS), variable threshold, and comprehensive approach) and distribution based approaches (e.g., C-alpha, SNP Set Kernel Association Test (SKAT), and SKAT-CommonRare. Most of these approaches can only be applied to population-based design, assuming independence of the subjects.

The present invention provides a new approach GLS-SKAT for gene-based analysis in families. Considering the following linear model:

$$\underset{n\times 1}{Y}=\underset{n\times m}{G}\,\underset{m\times 1}{\beta}+\underset{n\times 1}{\varepsilon}$$

For independent subjects:

$$\varepsilon\sim MVN(0,\tau^2 I)$$

For correlated subjects:

$\varepsilon \sim MVN(0, \tau^2 \Sigma)$

To transform the correlated data to independent, we let:

$UU' = \Sigma; T = U^{-1}$

So we can multiply T in the linear model:

$$\underset{n \times n n \times 1}{T \ Y} = \underset{n \times n \ n \times m}{T \ G} \underset{m \times 1}{\beta} + \underset{n \times n \ n \times 1}{T \ \varepsilon}$$

Then, $\mathrm{var}(T\varepsilon) = \tau^2 TUU'T' = \tau^2 I$

That is, the correlated data are now "de-correlated". OLS estimate with the GLS transformed data:

$\beta_{GLS} = (G'T'TG)^{-1}G'T'TY = (G'Y'G)^{-1}G'\Sigma^{-1}Y$ $\mathrm{var}(\beta_{GLS}) = (G'\Sigma^{-1}G)^{-1}$ This is exactly the maximal likelihood estimate of the true model:

$Y \sim N(G\beta, \Sigma)$

GLS-SKAT is applied to iChip data Cedars vs. BBC: 4600 cases and 6800 controls. SKAT-CommonRare is applied to IIBDGC (excluding Cedars and BBC samples): 30200 cases and 29700 controls. PCA is included to control for confounding factors. Gene region is defined as 100 Kb up and downstream of each gene. Analysis is focused on IBD and genes with at least 2 SNPs (about 8000 genes). Thus, the significant threshold is 0.05/8000=6.25E-6. Fisher's combined P value is used for the meta-analysis of the gene-level p-value.

TET2 codes for Tet Methylcytosine Dioxygenase 2, is involved in Foxp3 demethylation to drive regulatory T Cell differentiation and maintain immune homeostasis.

LRRC16A (leucine rich repeat containing 16A) is a protein-coding gene. Diseases associated with LRRC16A include acute urate nephropathy. An important paralog of this gene is LRRC16B. LR16A_HUMAN Q5VZK9 binds CAPZA2 with high affinity and significantly decreases CAPZA2 affinity for actin barbed ends. It increases the rate of elongation from seeds in the presence of CAPZA2; however, it seems unable to nucleate filaments. It rapidly uncaps barbed ends capped by CAPZA2 and enhances barbed-end actin polymerization b similarity. It may control actin dynamics in lamellipodia, and is required for cell migration.

The whole HIST1 region has joint association. HIST1 cluster portion 1 (~26.2M, first portion) and HIST1 cluster portion 2 (~27.8 M, second portion). After combining the ~1.6M (from 26.2 M to 27.8 M) into one big region, the overall region-based association P value is $1.64 \times 10^7$.

BTN3A1/A2/A3 is an interesting gene cluster. Butyrophilin, Subfamily 3; belong to the B7 family members and are expressed in various immune cells such as T and NK cells. BTN3/CD277 comprises three structurally related members, BTN3A1, BTN3A2 and BTN3A3. It plays a role in T-cell responses in the adaptive immune response, and inhibits the release of IFNG from activated T-cells. It plays an important role in human γδ T-cell antigenic activation. It has differential role for CD277 as a co-regulator of the immune signal in T and NK cells (see e.g., Messal N, Mamessier E, et al. Eur J Immunol. 2011 December; 41(12): 3443-54). While T cells express all BTN3/CD277 transcripts, NK cells express mostly BTN3A2, which lacks the B30.2 intracellular domain. Furthermore, NKp30-induced cytokine production is decreased by the specific engagement of BTN3A2, but not by BTN3A1 triggering.

We identified fourteen novel loci via gene-based analysis of iChip data (FIG. 4 and Table 1). All of them have multiple weak signals, while some signals are very strong in joint model. BTN3A2 is also strongly implicated in IBD pathogenesis based on the eQTL analysis of the LRRC16A region.

Example 3 Gene-Based Analysis Identified Multiple Novel IBD Loci

More than 200 genetic loci have been identified in Inflammatory Bowel Disease (IBD), mostly via single SNP analysis. In this study, we aim to utilize gene-based analysis, which combines signals from all the SNPs in a gene, to identify novel IBD loci that have been missed in single SNP analysis.

3312 IBD cases from Cedars-Sinai Medical Center and 7154 family and population-based controls with Immuno-Chip data were included as the discovery cohort. Genes with gene-level p-value <0.05 were then replicated in IIBDGC (30179 cases and 29678 controls, with samples overlapped with the discovery stage excluded). SKAT-CommonRare was performed to evaluate the gene-level association. Fisher's combined p-value was calculated to combine p-value from the discovery and replication cohorts. Bonferroni Corrected significance threshold of 6.25E-6 was used for gene-based p-value to count for 7,924 genes with at least 2 SNPs on iChip.

In addition to the known IBD genes such as L23R and NOD2, we identified multiple novel genes associated with IBD. Those genes include: TET2 (Discovery p-value 0.019, replication p-value 2.82E-9, combined p-value 1.33E-9); LRRC16A (Discovery p-value 1.55E-6, replication p-value 3.43E-5, combined p-value 1.19E-8); and multiple genes in Histone Cluster 1 locus (e.g.: HIST1H4H, discovery p-value 2.89E-5, replication p-value 2.44E-4, combined p-value 4.24E-6; HIST1H1B. discovery p-value 1.45E-4, replication p-value 8.61E-5, combined p-value 2.41E-7). The SNPs of these genes are listed in Table 1.

Our Bioinformatics analysis indicates that top SNP (rs7752195) driving the LRRC16A signal is a strong expression quantitative trait locus (eQTL) (In seeQTL, p=5.96E-51; in SCANdb, p=8E-9; in GeneVar, p=0.0025) of BTN3A2, which plays an important role in regulating adaptive immune response. Moreover, the top gene identified in current study, TET2 which codes for translocation (Tet) methylcytosine dioxygenase 2, was reported to drive T cell differentiation via DNA demethylation of FOXP3. It has also been reported to mediate interleukin-6 (IL-6) transcription by regulation of chromatin structure.

Without being bound to any particular theory, novel loci identified via gene-based analysis in the current study strongly suggest that it is worthwhile to re-examine previous single-SNP based GWAS at gene level.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A method of treating Inflammatory Bowel Disease (IBD) in a subject, the method comprising administering an IBD therapy to the subject, wherein the subject is determined to comprise at least one single nucleotide polymorphism (SNP), the at least one SNP comprising a SNP at rs918490 comprising a "G" allele at nucleoposition 501 within SEQ ID NO: 27.

2. The method of claim 1, wherein the at least one SNP further comprises a SNP at rs911186 comprising an "A" allele at nucleoposition 501 within SEQ ID NO: 147, a SNP at rs138546574 comprising an "A" allele at nucleoposition 501 within SEQ ID NO: 174, a SNP at rs10745330 comprising an "A" allele at nucleoposition 501 within SEQ ID NO: 55, a SNP at rs11600757 comprising an "A" allele at nucleoposition 301 within SEQ ID NO: 42, a SNP at rs137956 comprising a "G" allele at nucleoposition 604 within SEQ ID NO: 33, a SNP at rs10010325 comprising a "C" allele at nucleoposition 501 within SEQ ID NO: 328, a SNP at rs7120822 comprising an "A" allele at nucleoposition 501 within SEQ ID NO: 291, a SNP at rs11221332 comprising an "A" allele at nucleoposition 501 within SEQ ID NO: 284, a SNP at rs6072343 comprising an "A" allele at nucleoposition 401 within SEQ ID NO: 29, a SNP at rs2282978 comprising an "A" allele at nucleoposition 501 within SEQ ID NO: 39, a SNP at rs2690110 comprising a "G" allele at nucleoposition 501 within SEQ ID NO: 62, a SNP at rs2808 comprising an "A" allele at nucleoposition 501 within SEQ ID NO: 6, a SNP at rs3785794 comprising a "G" allele at nucleoposition 501 within SEQ ID NO: 7, and/or a SNP at rs9609429 comprising an "A" allele at nucleoposition 1000 within SEQ ID NO: 327.

3. The method of claim 1, wherein the subject is determined to comprise at least two SNPs, the at least two SNPs comprising the SNP at rs918490 comprising a "G" allele at nucleoposition 501 within SEQ ID NO: 27 and a SNP at rs911186 comprising an "A" allele at nucleoposition 501 within SEQ ID NO: 147.

4. The method of claim 1, wherein the subject is determined to comprise at least three SNPs, the at least three SNPs comprising the SNP at rs918490 comprising a "G" allele at nucleoposition 501 within SEQ ID NO: 27, a SNP at rs911186 comprising an "A" allele at nucleoposition 501 within SEQ ID NO: 147, and a SNP at rs138546574 comprising an "A" allele at nucleoposition 501 within SEQ ID NO: 174.

5. The method of claim 1, wherein the subject is determined to comprise the at least one SNP in a determination method comprising:
  a. contacting a sample from the subject with an oligonucleotide probe capable of hybridizing to the "G" allele at nucleoposition 501 within SEQ ID NO: 27; and
  b. detecting an allele-specific hybridization complex between the oligonucleotide probe and the "G" allele at nucleoposition 501 within SEQ ID NO: 27.

6. The method of claim 1, wherein the IBD therapy is an anti-tumor necrosis factor (TNF)$\alpha$ therapy.

7. The method of claim 1, wherein the IBD is Crohn's disease (CD) or ulcerative colitis (UC).

8. A method of treating Inflammatory Bowel Disease (IBD) in a subject, the method comprising:
  a) genotyping a sample obtained from the subject for a presence of a genotype comprising a single nucleotide polymorphism (SNP) at rs918490 comprising a "G" allele at nucleoposition 501 within SEQ ID NO: 27;
  b) detecting the presence of the genotype; and
  c) treating the IBD in the subject by administering a therapeutically effective amount of a therapeutic agent for the IBD, provided that the presence of genotype is detected in step b).

9. The method of claim 8, wherein steps a) and b) are performed by:
  (i) contacting the sample with an oligonucleotide probe specific to the "G" allele at nucleoposition 501 within SEQ ID NO: 27;
  (ii) generating an allele-specific hybridization complex between the oligonucleotide probe and the "G" allele at nucleoposition 501 within SEQ ID NO: 27; and
  (iii) upon detecting the allele-specific hybridization complex, detecting the presence of the genotype.

10. The method of claim 8, wherein step a) is performed by a genotyping assay, polymerase chain reaction (PCR), reverse transcription PCR, quantitative PCR, a microarray, DNA sequencing, and/or RNA sequencing.

11. The method of claim 8, wherein the genotype further comprises a SNP at rs911186 comprising an "A" allele at nucleoposition 501 within SEQ ID NO: 147, a SNP at rs138546574 comprising an "A" allele at nucleoposition 501 within SEQ ID NO: 174, a SNP at rs10745330 comprising an "A" allele at nucleoposition 501 within SEQ ID NO: 55, a SNP at rs11600757 comprising an "A" allele at nucleoposition 301 within SEQ ID NO: 42, a SNP at rs137956 comprising a "G" allele at nucleoposition 604 within SEQ ID NO: 33, a SNP at rs10010325 comprising a "C" allele at nucleoposition 501 within SEQ ID NO: 328, a SNP at rs7120822 comprising an "A" allele at nucleoposition 501 within SEQ ID NO: 291, a SNP at rs11221332 comprising an "A" allele at nucleoposition 501 within SEQ ID NO: 284, a SNP at rs6072343 comprising an "A" allele at nucleoposition 401 within SEQ ID NO: 29, a SNP at rs2282978 comprising an "A" allele at nucleoposition 501 within SEQ ID NO: 39, a SNP at rs2690110 comprising a "G" allele at nucleoposition 501 within SEQ ID NO: 62, a SNP at rs2808 comprising an "A" allele at nucleoposition 501 within SEQ ID NO: 6, a SNP at rs3785794 comprising a "G" allele at nucleoposition 501 within SEQ ID NO: 7, and/or a SNP at rs9609429 comprising an "A" allele at nucleoposition 1000 within SEQ ID NO: 327.

12. The method of claim 8, wherein the genotype further comprises a SNP at rs911186 comprising an "A" allele at nucleoposition 501 within SEQ ID NO: 147.

13. The method of claim 8, wherein the IBD is Crohn's disease (CD) or ulcerative colitis (UC).

* * * * *

SEQUENCE LISTING

```
<160> NUMBER OF SEQ ID NOS: 341

<210> SEQ ID NO 1
<211> LENGTH: 1001
<212> TYPE: DNA
<213> ORGANISM: Homo sapiens

<400> SEQUENCE: 1

cctaaggaag ttctagacta gtgtttcatg gagcccattc ttttaaatta aaagtagcca      60

tttaaaaaaa ttaaagtccc agaaaatgac cattagaata tgcaatttaa aaatagcaaa     120

taaaacaaac taaggttttt ttgaacagat atatagaaac aaaatttcac ttagtttaca     180

atataaacat gcatttcaca ttagcattaa aatgctattg tgatttatct ctctttcaaa     240

tactattgcc tctacttaca caatcatatt tgtcctttcg ccacaatctg cctatttcag     300
```

```
caaactgcat cagcattccc tttaagtttc ccaatgctaa agctgccagg acggactgtg    360

aaaaacacaa acatcagatg tactttaagt taatgaaata aaccacaggg aagcaaaggt    420

gaaggctata gataagtgtg tgctttaaag ggcctcaaag caaatcaaag cattacaccc    480

ttttccggtg tgcgatgcca ygcaagacac accagaactg ggactctgac ctgttcctat    540

gaatgacttt gtccccacaa cagtgacaag gcctaggctg ctcttgtgat tatgagatag    600

atgatctgat ggcgtttagt agcctgcacc ttgggacaga gaaaggcaga ccttcagacc    660

tatgacagac taacatttgg aataaattcc tcccaagcag agacagtcta atgtgtgttt    720

gtttattgga gtcaaggaga tgggggttgc tctttgttaa aaaaaaaaat agcttgggaa    780

gcttgaggtc ctggaatgag atgacttgag gcgggctttc tgggacagca tgaaacatat    840

ctatctagtt cctgctatat ccccagaacc tactatgtta aatgcataca ggaggggctt    900

taaaattagt cagtgaatga gtggctgagc caatgaatga atatttccca ggccagtact    960

aatccctaca gccaagcttc agacttccaa ttcttccaca g                       1001
```

<210> SEQ ID NO 2
<211> LENGTH: 1001
<212> TYPE: DNA
<213> ORGANISM: Homo sapiens

<400> SEQUENCE: 2

```
ttgtttattg gagtcaagga gatgggggtt gctctttgtt aaaaaaaaaa atagcttggg     60

aagcttgagg tcctggaatg agatgacttg aggcgggctt tctgggacag catgaaacat    120

atctatctag ttcctgctat atccccagaa cctactatgt taaatgcata caggaggggc    180

tttaaaatta gtcagtgaat gagtggctga gccaatgaat gaatatttcc caggccagta    240

ctaatcccta cagccaagct tcagacttcc aattcttcca cagccagaat gtgatctttt    300

atcttgcagg aattgtgata gttaaggtga aaaatgctga atagctaagt atattctctt    360

cattctttgg attttatcgt aattgtagga acatgcccct caccgtcctg ttccccctgc    420

caatttattt tattctgaat ggagtatgga atttgtatac tgctatacca tgaaaacaca    480

gtgtacaaag aaaagccaaa hacagttttt atttttatat cttgaggaca gttgaactga    540

tctgcctatt tctaattttc acaggtaatc cttataatat aatatctaag caattaattt    600

tactaactgt gagaatagag gtcacagttt agaagaaata tggtcttaag tgacttttaa    660

aaaatttggc acacaagtga atgccagtta aaaaatggtg aaaattgaat aaagtctgta    720

atctacttaa catactatac taatgtatag tactgatatt gtactacagc tgtgtaagat    780

gtcaccattg tggtagctag gcaaagaagt cagaggactg tacaacgggc ctctccattt    840

tgcaggactt ttaattctct aagtataaaa tatgtcaaga gacacctgtg cgaagagact    900

tttttttcc attgggcatt atttcccacc tagtcagtat tctacggaaa aacaatttga    960

agtaatttac gatgacatac atatacaaca gattactttt a                       1001
```

<210> SEQ ID NO 3
<211> LENGTH: 1001
<212> TYPE: DNA
<213> ORGANISM: Homo sapiens

<400> SEQUENCE: 3

```
tcttagatat tgaattatat gctaaggttc tttggaacta gcttcctgaa ttttacacag     60

ttgacatatt ttcattggaa caatcataaa acgaaagatc attaaaatat taaggaaaca    120
```

```
aaggttaaag agggaaacgc tgatttcttt actgtaaata gatcccaatt tgcatctttt    180
aaatcctttt ggatttcccc atctggtccc ctccctgtta taggcactaa ataaatatta    240
gaaaacagtc ccttcaaaac atgtagtcct ttccttattt gccctgcctc tcttctaaaa    300
aaaaagaaaa acagaactaa ctagagatta ttggctgcac aaacccatca gcacctgcca    360
gtttttaaat ttcattttgg aaaatcagcc atcacttaag ggacttgtcc ataatagctt    420
cattaaagct ttgtttttta tcaaaagggg gccacatatg taaacttgtg gaagtaattt    480
acctcctcta ctcttgtctt yttatttgat tgcaaaagtt aatgttatta aagttgctat    540
ggaagcatta atgttcagcc tgaacaagag cttgacgaac ttctttatac aagcaataac    600
actctgcaac cccattttat gagatatttt tcatgatgta gacatttact ttcttagcac    660
aagtgatctc ttaagattaa tttcttttcc attttccttc agttttaaat gatgtaatat    720
agtaatcttt ataacatgat cagccaagta taatttgaga agtcagttct gttggcaaat    780
atctgaagga caaaaccaaa gccaccctag ctgaggtttt tgtcccttcc ttctttcatt    840
taccaaaaac cttaattggg ttaacagtag gggaatttta gaaatcatgt tttcctaatg    900
taacctgtga aacaaaagca aaatagatta aggcaagggg aaaaatgaac ttaccaagag    960
tgttcttttt cctaagtaaa aaccacaaat tttatagttt t                       1001
```

<210> SEQ ID NO 4
<211> LENGTH: 1001
<212> TYPE: DNA
<213> ORGANISM: Homo sapiens

<400> SEQUENCE: 4

```
gatttcctgg tggatttttt ggcttgatca gcttaagaaa aatggagttg tcattaactg     60
aggtagaaaa aatgctggta gagcagatta ggggaagatc agcagatcag ccttgacatg    120
ttgaaatcca gaggaagatg ctagaaacat gaattaaata tccctctttt atattcttgt    180
tcatgcagtg tagggtcagc catttaaaaa atttcattta catttctaag tggtaagttc    240
ctgtgtttag acaaaaatat gtatcaagtg cttaaataac ttacaaaata attttaaaga    300
tacactgctc aacatgtatt actttcacac tttatgaatt tctgtaatgt atttgtctct    360
tcacaagttg ttctgtctcc cagttgcctc ctctcccctc caatcttgtt ctggtttata    420
tacgtttatt tttatcttcc aacatggtct cttgacttct tcctaaatta gggatcagat    480
tttggtacta ggaaatttcc ratatgtgct ctgaggcagg caagtagagg ctcagcccca    540
tgtattccca ttactagaag catacccaac cttagtggcc tacaagaaag aaaacattta    600
aggataagga taagtaaacc tctaaggtgt taaggttgaa tgtactgtga tgtgggcaca    660
agaattggag tgcttgtgct tgtttcttga gtttttttgtt tttgtttggt ttggtttggt    720
ttggttggca agaagagtgc agagggcacc tttgcttggg aagatggaga cctcagcgac    780
aatcctatat ataaggcatt tgcctcaact tcaagccaaa tgattgagta aataggctcc    840
tgttttcaat ttcgacttcc tactcttttt agaggagaag ttcttaaccc aagatttgtg    900
aggcatttta tatgtaaatt gtgtgtgtgt gtgtgtgtgt gtgtgtgtgt gtgtgtgtgt    960
gtgtgtgtat tttttccccc aaagtccata gggtgtatga g                       1001
```

<210> SEQ ID NO 5
<211> LENGTH: 1001
<212> TYPE: DNA
<213> ORGANISM: Homo sapiens

<400> SEQUENCE: 5
aattgagtca ttattaaaat gtccaatcgt cccataaatg ccttaattaa aaaacaattt 60
attcaaatca ggagttatac cacctacttt tgatattttt ctttcatctg taggtcactg 120
aatttaaaaa ctaccaagta gcaaggtata aggtatacat tcctcatgct aagatttttg 180
taaaaactag ctccaggctt gtattgccaa aatatactca gtgtgtttat cttctttaaa 240
gaaaataata ataataaggc gcctggatta ggagtctgaa aagtaatctc catttagaga 300
ctccacatcc atcagtctct ggctggacca gaaaataggt ttttgtgtag gaatattttt 360
tcagaggatt aaaaatgtga gcgaggggtg ggacacttaa tcctgtgttc tctagaagag 420
tgcatttaaa aggatagata cagttcttgg caaaagcatg gtaagcactt cagggttatt 480
attttccagg aaatacttat ycttttcca aatagttata aacatcagca gaatccagtt 540
cataactttg tgatttgcaa attggttgtg actgagattg gattgaaaac ccagttttct 600
tgctttttga cagttgttca agaaagagag cctttggtgt gctaaagact cttgtgccca 660
tcttggagtg gctccccaaa taccgagtca aggaatggct gcttagtgac gtcatttcgg 720
gagttagtac tgggctagtg gccacgctgc aaggtaagat gttggcagat tgagagttct 780
ggtctccagc aggagtttaa cacttctccc cagctaccat aggtctgtga cagatggttg 840
cttacccttc aaggcctgta tctttcctgt agagcccctt agtggagaga gtcacctctc 900
ttctcccctt ccttagagtt ctcttcctgg gaaactgctg ccccactagg tgcagaggtc 960
caatttagag gcatatacta ggcagtggct tctcaatttt t 1001

<210> SEQ ID NO 6
<211> LENGTH: 1001
<212> TYPE: DNA
<213> ORGANISM: Homo sapiens

<400> SEQUENCE: 6
tcaggctaat atctcagaga gtagttaaac tttaggctct tgattggggt tccagggcag 60
gactctgtca ctgaaaggga atcctagttc tcagcatact aggaaaaata gccaagagag 120
gaacttatgc cctaaagaac aaggcatgaa tctaattagc agcactgggg tccaagatag 180
agctggacaa acaacaagga taactcatcc caaattctgg agtgcttatc cagaacttgc 240
taagtgctac ttcctaaaga ccagaacctc caggcagatt tgcaagtagg gggaaagtct 300
aataaaactt taggtaattc tgatggaaaa aggcaagaat aacattcctg tgtttgaatt 360
tataatacag cctaagacat aaagaagtca ttattgacaa tgggaaggaa agtaatttaa 420
tatgcaacat aactcaatcc atgaaataaa tatttattta tgtaatacaa tttgctaaac 480
accaccatta ttaaggagag yactaggaaa aactaccaaa cacagcatgt gaaacagttg 540
ggcacggtgg taaagggcac agactctgga gccacagccg gctaatacac tgcaatattt 600
tatgtttagc aaattatagc tggtctgtgt ataaccagaa gagcggtatc tgggggatca 660
ggatatctaa attctagact tacagcctgg ccctgaatct aactatcaat gttgccttgg 720
aaaaactgct caaacttttg atgtctaaag tttcagactt gtaaacttga gagggttgag 780
gtccaaggtc ccttaaatgt aaactttaaa atgctttttt gggaatcttt caaatcttca 840
agctcttcaa agtgcaacca gactttctcc ttactataca gtctgaacaa ctttgagaat 900
cactgtatta tcttagttta tatagtaatc ctgacctaaa ttttattatt ctcattttgg 960
agacaaggaa atagaggcct aggctagcat ggctaaataa g 1001

<210> SEQ ID NO 7
<211> LENGTH: 1001
<212> TYPE: DNA
<213> ORGANISM: Homo sapiens

<400> SEQUENCE: 7

```
actttctcca caaaaccagg tgaccacacc ttcccctcct accctaccga accacgggac      60
ctaggtcccc aggaacagct gtatgtgtaa gagaaagcca cttggagggg ctaccgtgct     120
gggagtgtgg gtgcgcgtgg gtcccgggga gctatctgca ggctcgaagt ccactttcac     180
ccaagcccct ggcaactggc tgtccgggct gcttcctcac accccggtgt cttcctattt     240
tgccccgatt gtcagactcc acgtagctag atcataatgg ggccctgggc agtgggtcca     300
agcttagaag ctcccgggcc tgacagatct caggaaatga cagctacaca tagaagcgag     360
agctaccagg ggccaatgta cttgagaggc cagtgaaact gagatcttca gtgggtctgg     420
ggtctggggg gcagtaagag cagggaccag ggtcgggatc ccaggagttc gaggctgtgg     480
gcagaagaca gggagagaac yggaacttgg gtagagccat aagctgggaa tgaaggggga     540
caccggccca gggctgtgaa caggggacag tggccactaa ctcaggtaca ggattggctc     600
tctggctctg caactccctg caaaatgtgg tcactgcagt gcccatctta gagagcttct     660
gaggattaaa tgagatcatc tttgcacaga cagcacgaag tctagcctag caaatgtgca     720
ctgaacagta gctagagtga cggaagaaaa agctaggaag cagtcttgtc gggagctggt     780
gcttcagcct gagggcagat caggctgggg aaggctgaga ggggccacag ttccatgcct     840
gcatggaggg aggagaaagg cacaagagac tagaaatttc ctgtttgcct gtgtttccag     900
aaattcattg tacaacacac gaaccccttc aatacctgga taggtctcac ggacagtgat     960
ggctcttgga aatgggtgga tggcacagac tataggcaca a                        1001
```

<210> SEQ ID NO 8
<211> LENGTH: 1001
<212> TYPE: DNA
<213> ORGANISM: Homo sapiens

<400> SEQUENCE: 8

```
tactaaaaat acaaaaatta gccaggcatg gtggcgggcg cctatagtcc cagctactca      60
ggaggctgag gcagaattgc ttgaacccgg gaggcggagg ttgcagtgag gggagatcat     120
gccactgtac tccagcctgg gcgacagagc gagactccac ctcaaaataa aaaaaaaaga     180
aaaaatacac ccagaatctg acctcctctc accatcccat tcaaccaccc caagcctgca     240
atgctgtgtg actggcctca ggctccaatg cctgggcctg tctgtcctct gcagccgcca     300
cagcgatgct ctgtgaagta tcagccagca cctggcactg tcctgctctg aacacttcgc     360
agcctctctc aagcagggtt ccagagcctg aggccctaat gctctcaggc agccagtgta     420
tgcaactaag gagctgctct cccaggatga ggtgcctccc atccctggga gaactgaaca     480
aataatcact ctagtcactt mtgccttcca gggctcaggt gagccccaat gagaaaggct     540
cctccacagg cttccaacta agagtaaggc aaaatctctc cgtgaccttc cagactctcc     600
atgagccagc ccctccgtta tttcttggaa ctcatctacc atcttctctc cctcagtaac     660
tgcactggcc acacggcttc tgtgcaatcc tgcatttgtc ctagctggcc ccgatactca     720
gaatgtcctt cttggctggg tgtgatggct cacgcctata atcccagcgc tttgggaggc     780
caaagcagga gaatagcttg agcccaggag ttcgagacca gcttgggcaa cacaaagaga     840
ccccgcctct acaaaaaata caaaagttag ccagttgtgg tggtgcatgc atgtagtccc     900
```

agctactcag gaggctgata tgggaggact gcttgagcct gggaggcgga ggttgcagtg 960
aacgaagatc gtaccactgc actccagcat ggacgacaga g 1001

<210> SEQ ID NO 9
<211> LENGTH: 1001
<212> TYPE: DNA
<213> ORGANISM: Homo sapiens

<400> SEQUENCE: 9
gccaggctaa gggctgtgtt gggcatatgg gcacaatcag agtaatagcg aagggaggga 60
caagagaagg ctggggccgg ggcatacgat gaccccccga ctcaacaccc agtgccagta 120
ccagtaggac ccagagggtt ggcacagcac aagcacccat gaaggcaggc cctggggtct 180
gttccccgag tgggtggcca tgccccaatc cacagtgcta atgggaggcc ccaggagctg 240
cctttgaagc ccttccccaa acaccacttg ccatgtgagt gtcaaccagg aagtctttat 300
tgagccagaa gagcacccca accccccaaa tccttgagag gctaatggag aacaggggtg 360
gggtctctaa gggggggggc gtagacaggt ggggaggagg ctgaatgggc agagcagaca 420
gtggaggtga ggacctgcca gaaaccgagg aagcccctgc tcctcgtcag ggccaggtgg 480
tcactggtcc tgcctgctca rccaccccaa ggctccagaa tcacccctcc cctcttcctt 540
ccctgtcggc tttgccccag ccccccacct gggcctcccc cgagcctccg atccattctc 600
catatagcag cctgaagggt gttttggaaa gctcagacct gacttgcctc ccagagaccc 660
tcaagaaaca aggtcaaatt cccacctcgg cctgcgagac tcctgtgtgg gcaggcccca 720
ggggcacctt tcccaatggc gacagcctga cctcctccct tgaccaggcc ccctccttcg 780
tcccctaggt ccagaaccag ccagcaagca cctccctcgg tccctgcagt ctcctgctgc 840
tgccgcctac tcatccttcc ttggtctcag cctgagtgtc cccttttttcg ggaagtcttc 900 cctgatgtcc cacacccagg ctgggttaca tggcccctct gggctgccca gtcccaggcc 960
acccctctca gttgttactg gccagggact tcttgtctct c 1001

<210> SEQ ID NO 10
<211> LENGTH: 1001
<212> TYPE: DNA
<213> ORGANISM: Homo sapiens

<400> SEQUENCE: 10
agaggactca ccggggctga gtgacaggga taatgggctc tggcctcctc ttggcctgcg 60
gtgcctcttc ctccaggggg gacatggagc tcagggaacc caccaccgag atggcttggc 120
cctgggctga caggcgccgc ttgatcagga cgctctctgt cttcaccacc ttctcctcct 180
tgggctcctc cttgcactgt ttggtctgct ctacacctga gggggaggca gcaaacagac 240
acccagtgcg tcagacccac ctgctccaac ccgaggacct cctgtgtgcc tggctctgtt 300
ctgagccctg tacacacaaa acctcgttta aatccacaca acactgtcct ggagtgggta 360
ctctttttat ccccactttt caatacaact gaggctcaaa ctagaaatgc cattcattgc 420
tggggggagc agcaaatgct acagccactt tggaaacatg atgagcagtt tttgtttttt 480
agactgggtg tcactctgtc rcccaggctg gagtacggtg gtgcaatcag ggctcactgc 540
agtcttgacc tcctgggctc aagcaatcct cctgcctcag cctctcagcc tcccaactag 600
ctgggactac aggcgcatgc caacatacct agctaatttt tgtatttttt tgtagagatg 660
aggtctccat atgttgccca gcttagtctt gaactcctgg gctcaagcga tcctcccgcc 720
ttggacttcc aaagtgctgg gattacaggt atgagccact gtgcccagcc ctcagctgtt 780 tttttggag acggagtctc actccatcac caaggctgga gtgcagtggc ttgatcctga 840
ctcgctgcag cctccacctc ctgggtccaa gccattttcc cacctcagct tctggagtag 900
ctgggattat agacacccac tgccacaccc agctaatttt tttgttttca gtagagacgg 960
ggtttcacca cattggccag gctggtcttg aactgctgac c 1001

<210> SEQ ID NO 11
<211> LENGTH: 1001
<212> TYPE: DNA
<213> ORGANISM: Homo sapiens

<400> SEQUENCE: 11
ccccgagcct tgacactggg agaaagacct tgccaagacc atgcccaaat cccaccatcc 60
aagattcctc tggatgggca acaagcagcc ccgacctccc tccagaggcc tttgtcttcc 120
cgatccaggc ggctggacca cgagggcaac ttgggaaggg ggtggaagaa aactcagccg 180
ccttttacca gagctccccc tgggccaggc ccaggctaag tgctgcggga gcacctctca 240
tgacattctc acggcagcct ccagggggcg aaattacccc tgctaaacag cggaggtccg 300
tgccggtgcc gggacctgtc ctgggtcaca tgtacattct caccgcagcc tccagggggc 360
gacattagtc ctgcggggtt tggttttttt gttctctttt tttttttttt tttttttttt 420
ttttgagaga tggtcttact ctgccgccca ggctagagtg cagtgagtgg cgcgtttctt 480
cctcactgca gccccaaact yctgggctca agcagtcctc ctgtctcggc ctcccaaaga 540
gttggcatta caggtgtgaa ccatcacacc tggccttatc gtggtatttc taaagcccaa 600
atttctagca cctcttaaaa aactgggcca tttttcagct ctgggatgca tcctggccgg 660
gcacacagcg gtggagggtg aggagcagcc atgcctctcc cgggtgcaca ccccttgagg 720
gttaccacag ctcctaccac ccagctgccc tccctcatca cctgggagct ggcccagtca 780
tacaccctgg agcactgcta ttttcttggc aggaggcaga gcagagcctg ctgtcctcca 840
ccgggctccc tccggggtca gacgggggaa ggggagggca agcaggctag aagctgctgt 900
ctgcagcctg gaggcggggt ggccggggat gggttacctg cttcatgatg aggcgggaca 960
ggatgttcat gacgaagccc cccaggcggg ggtacatggt c 1001

<210> SEQ ID NO 12
<211> LENGTH: 1001
<212> TYPE: DNA
<213> ORGANISM: Homo sapiens

<400> SEQUENCE: 12
gaccccacat taagaactcc agctcttggc tgggagtggt ggctcacgcc tgtaatccta 60
atactttggg aggccgaggc aggaggatgg cttgaggcca agagttcaag accaacccgg 120
ccaacatagc aagaccccca tctcaattat ttttatttat ttatttattt ttatttattt 180 attttttttga gacagagtct cgctctgttg cccaggctgg agtgcagtgg tgtgatctcg 240
gctcactgcc aagctccgcc tcctgggttc atgccattct cctgcctcag cctccggagt 300
agctgggact gcatgtgcct gctgccacgc ttggctaatt tcttatattt ttagtagaga 360
cggggtttca tcatgttagc aaagatggtc ttgatctcct gacctcgtga tctgcccacc 420
tcggcctccc aaagtgctga ggttacagat gtaagccacc ccatcctgcc aagactgaag 480
ttgttttgtg actggattgt scaatgctgt ctttcgcctc caggccttgg cacaggctgt 540
gccctaagta tgcttgggcc cccactgacc ctgatgccca cctctcctga ctggctcact 600

```
caccacctcc tcctccatct cctgttcgcc ttcagtgccg cctccactcc gggtgaacag    660

cgccttctgt ttctccgcca tcttgtaggt gggctgcatc tcggggtcgt cccgcagcgt    720

gtccagcttg gggtggaacc actcccactg cgtggtgcgg ttcagagact ccaggacaga    780

caaggggtcc tcaggccgct ggttcaggat cttggtcagc agattcacca ggtgctcgta    840

cctgcctccc gcaggaggag tgggaggaga gggacctcac tcactcagct cactgagctg    900

gctcccatgt gcctggccct gtgcctggtg ctggggacac agtagggaac tgaaaaggtc    960

cctgcccagg tgtagctgac atttatttat ttatttttat t                       1001
```

<210> SEQ ID NO 13
<211> LENGTH: 1001
<212> TYPE: DNA
<213> ORGANISM: Homo sapiens

<400> SEQUENCE: 13

```
gttaacaggt gtgaaccacc gtgcctggcc aacatttgta tttttgtat ttttttttg      60

agacagggtc tcactttgtc actcaggctg gagtgcagtg gctcggtctt ggctcactgc    120

aacctctggt tcccgggttc aagtgattct cccacctcag actccccaga gctgggatta    180

cacgtgtgcc aacatgcctg gctaattttt gtacttttg tagagatggg gttttgccat    240

gttgcccagg ctggtctcaa actcctggac tcaagtgatc tgcctgcctc agcctcccca    300

actgctggga ttacaggcgt gagccaccag gcccggccac agtcagcctt tgaaaccaag    360

ttggtctgat ttccaagcat gtatgtgtca ccttttgctt tgcggaagct gttttgttgg    420

cagtcttggg tgtggtgttg ggccatcatg gaagttggga agggtaagaa gaggtgagac    480

tttggctagg gcttctcagg ragagagcct gaagctctga agagctggca cttggggaat    540

agccagaggt taattctgac tagattctag gatccgagga aggagcaggt agtgactaga    600

aatcaagttt ggtcagcggc caggggctga accacgtaag gccttttgtt tgttggtttg    660

tttgagacag agtctcgctc tgttgctcag gctggagtgc actggcacga tcttggctca    720

ctgcagcctc tgcctcccgg ttcaagtgat tctcctgcct cagcctcccg agtagctgag    780

atcacaggcg tgtgccacca cgcctggcta actttttgta tttttagtag agacagggtt    840

ttgccatgtt ggccaggctg gtcttgaact cctgacttcg agttatctgt ctgcctcagc    900

ctcccaaagt gctgggatca caggcatgag caaggcctta tatgtctcag gccaggagcc    960

ttgaaggttg tggtgaggag tctgagcttc cccctgtggg c                       1001
```

<210> SEQ ID NO 14
<211> LENGTH: 1001
<212> TYPE: DNA
<213> ORGANISM: Homo sapiens

<400> SEQUENCE: 14

```
gttcactggt gaagatgttt ctggctccac ccacctgctt cgtgactcgg tttctcaggc     60

gcagctggct tggctgcgag cccagaccag gctccacctg ctgctgcttc ctgagcctgc    120

tctgcggtga atgccaaaca ggagccaggg ccaggctcca cctctgccca gtaacgttta    180

cgctcctgac taaaaccgac tgtctctgcc ctcgagaagc tcacagccct gccagataac    240

ttttctgcaa agtgagatca cttttccaca gctggaccac cttgagaatg gggctaaaaa    300

tctgtttcct cccaactaca agcctgttat ccccattttc caggtaaggg ccccactgaa    360

cccaaatggc agataggtgg ggattaacat acacttctct ctcccgttta tcacgaaaat    420
```

gttctgtaat ccaaaaatgt caggggcaga aagaaaaaaa gtggtttcaa atcctgctgc 480
aaactggaag agcagacctt ytaatctcag gtgctagtct gtcactgagc tgcttctcat 540
gtgggcagac ctgtgcctct agagagaggg gcaggaagga cttatgttta tgtaatgaca 600
gctaaagagt cccgttagca acactgggaa ggccagctca taaagtgaca gtaacacaga 660
ggtttatgtg cctgagttca tggactcctt gcatcagcgt ggagggactg gaacgtcttc 720
cccattttta ctgacgggcc caaggtcgca gtgagaaagc gagaagtgaa cgcgaaccca 780
ggtctatcag ctccaggctc ctaactgccg ggccacttga cgtttcctca ggagtgacat 840
gcggaccgcc tgcaagctac acagcctggg tcggcccggg gtgaccaccc ttcgggcttg 900
gcacactctg aggtggagca ggttggggaa gagctggagc tggggacaca gccttgcccg 960
tgggtgggca gggcctggtg ggctcagggg cctcaccggc t 1001

<210> SEQ ID NO 15
<211> LENGTH: 1001
<212> TYPE: DNA
<213> ORGANISM: Homo sapiens

<400> SEQUENCE: 15
aggcagcagt gagggaggcc tggaggggca tgaggggaac tatagccacc aacagctcgg 60
gctgcggtgt ttgaaccctc gctgcagacc acacacacac acacacacac acacacacac 120
acacacacac acactctctc tctctctctc gctctctttt tttttttttt ggagacagag 180
tctcgtcgct ttgtcactca ggctgcagtg cagtggtgtg agctcgactc actgcaacct 240
ctgcctccca ggttcaaacg actctccttc ctcaacctcc cgagtagctg ggattacagg 300
catgcaccac cacgcccggc taatttttgt atttttagta gagacagggt ttcaccatgt 360
tggccaagct ggtctcgaac tcctgacctc aggtgatcca cccgcctcag ccccccaaag 420
tgctgggatt acaggcgtga gccacctcgc ctggcctgga ccactctttc tctatgtggc 480
cccaggaagc cagttcacct rtctgagcct cagtggctgc acccaggaaa tggggagact 540
catctggcct ttgttgcagg gtggcagtga agcctggtga caaggtctgc agcacacctg 600
ctgcagtgcc tggcgcccag cagggcctcc agactgggaa gccactgtga ttccactccc 660
gagttggtca tcggtttgga ccagggtgca gagggaaggg cacaggctgg caggatctgg 720
cttcaaatcc aggacctgtc ccctggccca ctcctagcct ctctctccac ttccctccgg 780
gtgcctgagg ccccaacctt aaaaaattcc tgtccattca tccaaaatcc agctccaggt 840
tgggcacagt ggctcctgcc tgtaatccca gcactttggg aggccgagta aggtggatca 900
cttgaggcca ggagttcgag atcagcctgg ccaacatggt gaaaccccat ctccactaaa 960
aatacaaaag ttatctgggc gtggtggcac acgcctgcaa t 1001

<210> SEQ ID NO 16
<211> LENGTH: 1001
<212> TYPE: DNA
<213> ORGANISM: Homo sapiens

<400> SEQUENCE: 16
tcgctttgtc actcaggctg cagtgcagtg gtgtgagctc gactcactgc aacctctgcc 60
tcccaggttc aaacgactct ccttcctcaa cctcccgagt agctgggatt acaggcatgc 120
accaccacgc ccggctaatt tttgtatttt tagtagagac agggtttcac catgttggcc 180
aagctggtct cgaactcctg acctcaggtg atccacccgc ctcagccccc caaagtgctg 240
ggattacagg cgtgagccac ctcgcctggc ctggaccact ctttctctat gtggccccag 300
gaagccagtt cacctgtctg agcctcagtg gctgcaccca ggaaatgggg agactcatct 360
ggcctttgtt gcagggtggc agtgaagcct ggtgacaagg tctgcagcac acctgctgca 420
gtgcctggcg cccagcaggg cctccagact gggaagccac tgtgattcca ctcccgagtt 480
ggtcatcggt ttggaccagg ktgcagaggg aagggcacag gctggcagga tctggcttca 540
aatccaggac ctgtcccctg gcccactcct agcctctctc tccacttccc tccgggtgcc 600
tgaggcccca accttaaaaa attcctgtcc attcatccaa aatccagctc caggttgggc 660
acagtggctc ctgcctgtaa tcccagcact ttgggaggcc gagtaaggtg gatcacttga 720
ggccaggagt tcgagatcag cctggccaac atggtgaaac cccatctcca ctaaaaatac 780
aaaagttatc tgggcgtggt ggcacacgcc tgcaatccag ctactcagga ggctgagacg 840
ggagaattgc aggaacccga gaggttgagg ttgcagtgag ccaagattgc accactacac 900
cctagcctgg gtgacagagc tggactccat ctcaaaacaa caacaatgac aacaacacca 960
ccaccaccac acacacacac acacacatac acacacatgc a 1001

<210> SEQ ID NO 17
<211> LENGTH: 1001
<212> TYPE: DNA
<213> ORGANISM: Homo sapiens

<400> SEQUENCE: 17
tctgattttc ctgtcgcttg gccacctcga ctcccccgaa tcctgtcccc tccaccttca 60
aggagctgcc acctgccctg gctcctgact ttgaacacat cccagagccc ttggccgagt 120
cccatcttac tgactgggac ttggtggacc caaggctcgc ccaatagagg ctaaaacggt 180
ggcccaggcc cctgcgggga cacaggattg ggagtggtac agggatgccc gggaggcgag 240
tgaggaagcc aggccatcct gccaccgtct ccccagcacc aaggctcgca ggttcagccg 300
ccagcacaac cgcatcgtga agcaggacgg ctccagcagc gaggctgagg actgggagac 360
gccaaagccc ttctaccagc tgctggccga gaaggccttg ccgctgcccc cgcacctcca 420
gtgagagggc ggcccctcgc ctcgctcccc tcacccctca tggcaaccgc ggctcttgct 480
ggaagccagg acccatcgat kaacttgtcc ctcctgggcc tccagcccct gagaatgcag 540
gtcccatggg actggggagg ggggcactga ttagccccaa ccgctgggca catttgcctg 600
gagcaccaga gtcacccaca gctgccttga ttctccccca ggcttaggaa ggaaacccaa 660
aatgaaatgc ggggtgtcgg aaggtgaagt ttacccaccc ctctcccctt cccttcccca 720
ccccagagcc actcggttgc aaccctgttc atgctcacct caccctactc ctccctctcc 780
tgttctattt ttagactatt tattgtttta aataaaataa agcaagtgga acctttgtta 840
ccagcaagag agacaagggc aggccctcct gcgtcccccct gctgccccac tggggtgctc 900
cgtccaccct catctggagg cctgtggctt gcaagaggcc tcagtgccac cccctcccca 960
gccactctgt gcatctgaat gcaaacccct cttcccctcg g 1001

<210> SEQ ID NO 18
<211> LENGTH: 1001
<212> TYPE: DNA
<213> ORGANISM: Homo sapiens

<400> SEQUENCE: 18
gcctggccca cataacataa tctataatat aatcttagta aatacaaatt cagcatagtt 60
taaggtaaat aatgaaacat ttcagcatgg tctgcctgcc ccaccccacc agcccctctc 120

```
acccagcttc atcttcttga gtgtggagtc cgagtcatcg cggggccgct tgcgggtgtc    180

cttgctgctc ggcatgttgc gggcgatctc ggcctgaggt gtgcccaggt ccaccagcag    240

ggtggtgatc tgggcctgga actccaagga agccgggtgc ttcagcacac tcaacaggtg    300

cagcttcaga ttcttacgca cactgctcac ctgcgatttg gccagcgtcg gggcaggtt     360

ggctgtgagg aaagtggcag gagctgtgtc ttgtggaaga tctcatggca tgctgccagt    420

cttaattctc aaccccaaac ttgggcagtg gtcttgcagg catctactag aaaagttcct    480

tcaccctcag atctaacgtg hggctttccg ccttacaagc tgatgcttca aaccctgggg    540

gtctccatca gtatcagtca atcttaaaga gaaaaactca ccctctcttt tagtaaatac    600

atacaatttc gtcctcctcc atctctggtc tggaaattca catatgcttc gcttggggag    660

ggttataatc accacttttg cctccagaaa cccccaactg aactgctgca acagctcact    720

gctagtctcc ctgacgccag gatgactttc taatggtcac cctgataagt gagcctcccc    780

tgttccacag tgaaaaagga tgcctgtaat tctgcctgcc tagcatccac tgccccttcc    840

tcagccaaca acacaaccca ctctccgtta agggagaccc cccttctcca gtctccttcc    900

gagtgggcat gagacctggg gccagtgaga ataccacatt cccttggcca ctgtaattgg    960

ctcagagact ggctcataat ctctgctcag ccaatcagaa a                       1001
```

<210> SEQ ID NO 19
<211> LENGTH: 1001
<212> TYPE: DNA
<213> ORGANISM: Homo sapiens

<400> SEQUENCE: 19

```
ttgcagtgag ccgaaattgc gccactgcac tccagcctgg gtgacagagc aagactccgt     60

ctcaaaaaaa aaaaaaaaaa gaaggggatg gatgggaagg agtttggaaa agcacaagga    120

gctgttagct attgtgttga tcggcacaaa tgaatcaata aatttgctct tccccaactc    180

tccacccctc accaacaccc tattgcaata ttctcaattc ccttcccaag ggcctcgggc    240

aaaaatggag ccctcctggc tagactccat ctcccagcgc gcccagcggg gaagcaccct    300

gcgcttgcgc tgccaagtcc tccccggctt tgtctcccgg gagttcgagt cgttcttttc    360

ctccgcccgc ctaatttgct tcctacccca cctccaagct tgaccgtgct gccttctggg    420

ggatgtagtc cgtggctgcc cggacttcaa ttcccagcgg gcttcgggac gagaacccgg    480

aaggggaggc tggagaggag ygagtggggg aaacccgcgt agccgaggga gatgcagcgc    540

gcggcgatgg tgagagccca ggcgcgggcc gggggcgctg gagagtcggg acgggggttc    600

gggaccgggt gacgaggggg aagaggcagg ggcgaaagaa ggggctgggt gaggggagat    660

tgcctgggggg agaggactgg gaggaatggg agccggaggt agtagtagaa gaatggtggc    720

ttggggaggg gtcttggagg tggggtggga gtggagcttt ggaattgatt gtaaaggggc    780

tcagagctgg ggaagtgggc cccgagttgg agactgggct ggacatccag gtagaggccc    840

tgaaggggtc gatttcgatg ggggcttaac ctgcggcgag ggtatgagga tcagggttag    900

gatgagtgag ggggtctgga agctccaagg gacaggcgaa cggtggacgc aatgggttgg    960

ggcctctgga tcggattggg ggcaggaagg caagttgagg a                       1001
```

<210> SEQ ID NO 20
<211> LENGTH: 1001
<212> TYPE: DNA
<213> ORGANISM: Homo sapiens

<400> SEQUENCE: 20
cactcctggg gagagactcc ccgcccctgc cacaagagcc ccaggtctgc agtgtgcccc 60
tcagttgagt gggcagggcc gggggtggtc cagccctcgc ccggccccca ccccagctgc 120
ccttgctatt gtctgtgctt ttgaagagtg ttaaattatg gaagcccctc aggttcctcc 180
ctgtcccgca ggacctctta tttatactaa agttccctgt tttctcagcg ggtctgtccc 240
cttcggagga gatgatgtag aggacctgtg tgtgtactct gtggttctag gcagtccgct 300
ttccccagag gaggagtgca ggcctgctcc cagcccagcg cctcccaccc cttttcatag 360
caggaaaagc cggagcccag ggagggaacg gacctgcgag tcacacaact ggtgacccac 420
accagcggct ggagcaggac cctcttgggg agaagagcat cctgcccgca gccagggccc 480
ctcatcaaag tcctcggtgt kttttaaatt atcagaactg cccaggacca cgtttcccag 540
gccctgccca gctgggactc ctcggtcctt gcctcctagt ttctcaggcc tggccctctc 600
aaggcccagg caccccaggc cggttggagg ccccgacttc cactctggag aaccgtccac 660
cctggaaaga agagctcaga ttcctcttgg ctctcggagc cgcagggagt gtgtcttccc 720
gcgccaccct ccaccccccg aaatgtttct gtttctaatc ccagcctggg caggaatgtg 780
gctccccggc caggggccaa ggagctattt tggggtctcg tttgcccagg gagggcttgg 840
ctccaccact ttcctccccc agcctttggg cagcaggtca cccctgttca ggctctgagg 900
gtgccccctc ctggtcctgt cctcaccacc ccttccccac ctcctgggaa aaaaaaaaaa 960
aaaaaaaaaa aaagctggta taaagcagag agcctgaggg c 1001

<210> SEQ ID NO 21
<211> LENGTH: 1001
<212> TYPE: DNA
<213> ORGANISM: Homo sapiens

<400> SEQUENCE: 21
tcaggtgcat tggagattct taggagtgtc tcttgggggt aatattttat tttttaaaaa 60
atgaggatgt cactcttacc caggttggtc ttgaactcct gggctcaagc aatcctccca 120
ccacgggtct ctcaaagtgc tgggattaca ggcgtgagcc accgcacccg gctttttttt 180
ttttttttaa acggagtctc actctgtcac ccaggctgga gtgcagtggt gcaatttcag 240
ctcactgcac cctccacctc ccgagttcaa gcctcccggg tagctgggat tacaggcacc 300
gccaccatgc ctggctaatt tttgcatttt cagtagagat agggtttctc catgttggcc 360
aggctggtct cgaactcctg acctcaagtg atccacccac ctcagcctcc caaagtgctg 420
ggattacagg cataagccac catgcccggc ccaaatgggc taatgtttta aacagatcct 480
tcttgtctgc cctgtaggag kacaaattat caggggcagg ggtggaagct ggagcccaga 540
aaggagggga ctgcaggtgg gaagtgatgg tggctggacc aggatggagg ccactgaggg 600
gtatgaagca gtcggatttg aagctgttta aaaggtggag gtgagaggat ttcatgaagg 660
agcacatgag gacacagcag cagagaggac tccttggctt tggatggtgg agagactaaa 720
gatagagaga ttgggttcgg gtagggggag aaccacgtgt gctctttgga aaggttaggc 780
tggcagtgtt tgtaggacat gacaggacac tgagtgtaag ggtctggagc tctcaggaga 840
ggggcgagct ggagatagta atgtgagagg cactgggtcc tgagagggtg atttggtgtg 900
gaccggagca caggtgaggc aaggcaggcc tcgcagctga aactttatat ccagagcagc 960
cagggccact gctggctgcg gagtgaggac gcatatcccc a 1001

<210> SEQ ID NO 22
<211> LENGTH: 1001
<212> TYPE: DNA
<213> ORGANISM: Homo sapiens

<400> SEQUENCE: 22
ctcaggcagg gaggtttagt tgcaggataa gagggtctca ggagggctgg gcacggtggt 60
tcatgcctgc aatcctagca ctttgggagg ctgagatggg cggatcactt gaggtcgagt 120
ttgagactag cctgggcaac atggtgaaat cttgcctcta ctaaaaatac aaaaattagc 180
tgggtgaagt ggagcgcgcc tgtaacccca actactcggg aggctgaagc agaagaatca 240
cttgaacttg ggaaggagag gttgccctaa gccaagacca cgccactgtg ctccagcctg 300
ggtgacaggg tgagactatg tctgggggaa aaaaaaagca agagggcttg gggagccaaa 360
tcacgtgttc tggaatcctg actctgccat atcctagctg tgtagttttg ggtaagcgac 420
ccaacttctc tgtgtctcgg tctcctcctc tgtaaagtag gatgagctga tgtgctcatc 480
tccggtgaga attaggtgag dgtgtgcagt gccagcacat gtctgggaag tgaatgctag 540
ctgttgttgg cattgattcc gactcagctg aattagagtc actggttttc catgagggat 600
gatcccttgt ctgactgact gaggcaggca cttcgggtgg ggcccctccc tgcctgggtc 660
ccccacccgc cccactccta gcccctgctc acaggctgag gtcgcaattg atgctggtct 720
gcagcaggta ggccttggcg ttctgcacgg ccagctccag aggctcgggc tcaggcacct 780
gggcactgta gtgtgggaag cccagctcag agggcaagaa ctgaagggca gggtcatccc 840
ttatgtaagg cccgtgctgg gcaccttcag agaactggtc tgtctggtag aggttgaact 900
ggcccaaggg gttgactggg ggctcctgga aggtggggtc cagttgctgg aacaggctgc 960
tttggccctg ctggagccgc tgcagcatta ggctggtggt g 1001

<210> SEQ ID NO 23
<211> LENGTH: 1001
<212> TYPE: DNA
<213> ORGANISM: Homo sapiens

<400> SEQUENCE: 23
gtcacacagc aagcggagga actaggattt gaatcccagt ctttctgctt caaaaactgg 60
agcttatata tcaaccttta tgccacctcc tgggactgtc ccctgctttg tcccactttg 120
gggcagctct tactcttaca tccctacaca ctattaaaac aaatgaaggc cgggcacgga 180
ggctcacgcc tgtaatccca aaactttggg aggccaaggc ggatagatca cgaggtcagg 240
agattgagac catcctggcc aacatggtga aaccccgtct ctactaaaaa tacaaaaaat 300
tagccaggtg tggtggcaca tgcctgtaat ctcagctact caggaggctg aggcaggaga 360
atcgcttgaa cccaggagac ggaggttgca gtgagccgag atcgtgccac tgtactccag 420
cctgggcaac aaggcgagac tccatctcaa taataataat aataataata ataataataa 480
taataataat aataacaatg rtaataaagt aactagggta tgttcaggtt gattagctca 540
gggaaaagga aacttgagaa ttaggttcat atgccacttt agaagtctga gcagctatcc 600
caagaccttt cagtattcat taattcaata attctttatt gagcacccac taagtgttag 660
gcattattcc aggacttaag ggatataacc agcgcagcat tatggcttct gtgggcccta 720
tacaatttta ccttcttgat ccccttcttc catagaaaaa tattaacgct gggtgcggtg 780
gctcacgcct gtaatcccag cactttagga ggccaaggcg ggcagatcac gaggtcagga 840
gttcgagacc agtctggcca acatggtgaa accccgtctc tactaaaaat acaaaaattg 900
ggaggcatgg tggcgggcac ctgcaatccc agctacttgg gttgctgatg cagaagaatc 960
gcttgaatct gggaggcgga gatttcagtg agctgagatc g 1001

<210> SEQ ID NO 24
<211> LENGTH: 1001
<212> TYPE: DNA
<213> ORGANISM: Homo sapiens

<400> SEQUENCE: 24
ggaagtggag gttgcaatga gtcgagatca taccactgca ctccagcctg agcaacagag 60
taagaccctg tctttttttt ttttttgaga cggagtcccg ctctgtaccc caggctggag 120
tgcagtggca ccatctcggc tcactgcaag ctctgcctcc tgggttcacg ccattctcct 180
gcctcagcct cctgagtggc tgggactaca ggtgcccgcc accacgcccg gccaattagt 240
ttttgtattt ttagtaaaga cagggtttca ccgtgttagc caggatgacc tcgatctcct 300
gacttcgtga tccacccgcc tcgggctctg aaagtgctgg gattacaggc gtgagccacc 360
gcgcctggcc atgagacccc atcttaaaag aaatagagtc agatgtatct cactccaaag 420
gctcttgcct tcaaccattc tgtcactcaa ggttcaatag atgtttgttg aatgactgaa 480
tgagctccct ttgttgggac rgttacagga cctgttgatc ttaccttcag aaggtctttg 540
agagtccaga ctctggtgta gcccccaagc taaccttcct gaagtttcaa ttactgaggc 600
atctgtcttg aaatctggga tgatgcccaa ttgctttcta catacaacct ttatactagt 660
aataataagt aacatttata tattacttca tggtttataa ggactttttc ttagcgagtg 720
ccaaccatat gctccaagcc tggtattaga gataataagc ttaaaaagac tgaggctggc 780
tgggtgcagt ggctcacaca tgtaatccca gcactttggg aggccgaggt gggtggatca 840
cttgaggtcg gtagttcgag accaacctgg ccaacatggt gaaaccttgt ctctactaaa 900
aatacaaaaa ttagccaagc gtggtggcac attcctgtag cccctgctac tcaggaggtt 960
gaggtgggag aatcgcttga acctgggagt cagaggctgc a 1001

<210> SEQ ID NO 25
<211> LENGTH: 1001
<212> TYPE: DNA
<213> ORGANISM: Homo sapiens

<400> SEQUENCE: 25
gcaaagtgag atcacttttc cacagctgga ccaccttgag aatggggcta aaaatctgtt 60
tcctcccaac tacaagcctg ttatccccat tttccaggta agggccccac tgaacccaaa 120
tggcagatag gtggggatta acatacactt ctctctcccg tttatcacga aaatgttctg 180
taatccaaaa atgtcagggg cagaaagaaa aaaagtggtt tcaaatcctg ctgcaaactg 240
gaagagcaga ccttctaatc tcaggtgcta gtctgtcact gagctgcttc tcatgtgggc 300
agacctgtgc ctctagagag aggggcagga aggacttatg tttatgtaat gacagctaaa 360
gagtcccgtt agcaacactg ggaaggccag ctcataaagt gacagtaaca cagaggttta 420
tgtgcctgag ttcatggact ccttgcatca gcgtggaggg actggaacgt cttccccatt 480
tttactgacg ggcccaaggt ygcagtgaga aagcgagaag tgaacgcgaa cccaggtcta 540
tcagctccag gctcctaact gccgggccac ttgacgtttc ctcaggagtg acatgcggac 600
cgcctgcaag ctacacagcc tgggtcggcc cggggtgacc acccttcggg cttggcacac 660
tctgaggtgg agcaggttgg ggaagagctg gagctgggga cacagccttg cccgtgggtg 720

```
ggcagggcct ggtgggctca ggggcctcac cggctgctca atgaccctca gcaccgtccg    780

cttgatgtcg gcgatggctt cagtgtacac ggccgccagt tcgtggatca gcttgtggtt    840

ctgaggcagg agggccaggt agaggtacag acactgcttc actgtctcct ccgtccaggg    900

tgctgccacc tctgacaggg caggagcggg catcagattg gcccacactc ttctccaacc    960

ccctcggacc ctcaggaatg tcccttcttg ggcagtggag c                       1001
```

<210> SEQ ID NO 26
<211> LENGTH: 1943
<212> TYPE: DNA
<213> ORGANISM: Homo sapiens

<400> SEQUENCE: 26

```
gctaagggga ggtgggaaac gggctgacag aactgctgtg ttgaggtgag gactcctgac      60

tgtgcgaccc ccattcatgc attcattcac tcattgaatt tttttttttt tttttttttg     120

agatggagtt ttactctgtg gcccaggctg gagtgcagtg gcacaatctt ggctcactgc     180

aacctctgcc tcccggttta agtgattctc ctgcgtcagc ctcctgagta gctgggatta     240

caggtgcctg acaccacgcc tggctaattt ttgtattttt tagtagagac ggggtttcac     300

caagttggcc aggctggtct cgaactcctg acctcaaatg atccacccgc cttggcctcc     360

caaagtgctg ggattacagg tgcgagccat tgcacctggc ccactcattg attcttttct     420

tttttttttt tgagatggag tctggctctg tcgcccaggc tgaagtgcag tggctcactg     480

aaagctccgc ctcctgggtt cacgccattc tcctacctca gcctcccaag cagtggctta     540

cgcctgtaat cccagcactt tgggaggctg aggcgggcgg atcacgaggt caggagatag     600

agaccatcct ggctaacacg gtgaaacccc atctctacta aaactacaaa aaaaatagcc     660

gggcatggtg gcgggcgcct gtagtcccag ctactcagga ggctgaggca ggagaatggc     720

gtgaacctag gaggcagagc ttgcagtgag ccgagatcac gccactgcac tccagcctgg     780

gcaatagagc gagactccgt ctcagaaaaa aaaaaaaaaa aagccaggca tagttgtggt     840

ggtatgtgcc tgtagtccta actactcggg aggctaaggt gggaggattg cttgagccct     900

ggaggtcagg gtagcagtga gttatgatct catcactgca cgccagcctg ggcaacaaag     960

caagttgcta tgtcttaaaa gaaaaaaaaa gctgggcatg gtggctcatg cctgtaatcc    1020

cagcactttg agaggctgag gcgggcagat cacctgaggt caggagtttg agaccagcct    1080

gaccaacatg aagaaaccct gtctctccta aaagtacaaa attagttggg cgtgatggca    1140

catgcctgta atcccagcta cttgggaggc tgaggtggga gaattcgctt gaactaggga    1200

ggcggaggtt gcggtgagcc gagatcacgc cattgtactc cagcctgggc aacaagagcg    1260

aaattctgtc tcaaaaagaa aagaaaagaa aaaaaaaaaa aaccagccag ggcgcagtgg    1320

ctcatgtcta taatcctagc actttgggag gccaaggtag gcagattgtc tgagctcagg    1380

actttgagac cagcttgggc aacacagtga aacctcatct ctactaaaat acaaaaaatt    1440

agccaggtgt ggcagcgtgt gcctgtaatc ccagctactc aggaggctga ggcgggacaa    1500

tcgcttgaac ccaggaggtg gaggttgcag tgagccgaga tcgtaccact gcactccatc    1560

ctgggtgaca agagcgagac tctgtctcaa aaaaaaaaaa agaaaagaaa agaaaagaaa    1620

aagaaaaaaa agaagaaaga aagaaaagaa aaaaaaatgc ctctgtcccc aaaggtttct    1680

gatgggatta tccgctaata tctgttgaac caatgaatgg atggatgaat gaacgaatga    1740

atrttagttg cccagcagag agtaagagct tgatgtcagt attgcagggt catgcgtgag    1800

ccccctgctc ctgccgtttg tgagaggcgg gagtcccggc gctcacctgc ggcaggatgt    1860
```

gctgtgtgtg atgcacccag ttggccatgg agtcgaccag ctccagcacg gggatgccct 1920
cgaagtccgg gttctcctcg tag 1943

<210> SEQ ID NO 27
<211> LENGTH: 1001
<212> TYPE: DNA
<213> ORGANISM: Homo sapiens

<400> SEQUENCE: 27
aacactcttc actgaacctc tttttgcttt ctttctttct ttctttcttt ctttatgaat 60
gagatggagt cttgctctgt cacccaggct ggagtgcagt agcgcgatct cggctcactg 120
caactgctgc cgcctggatt caagcaatta tcctgcctca gcctcccgag tagctgggat 180
tacaggcaca tgctgctgcg ccaggctaat ttttgtattt ttagtagaga cagggtttca 240
ccatgttggc caggctggtc ttgggctcct gacctcaagt gatctacctg ccttagcctc 300
tcaaagtgct gggattgcag gcatgaccca ctgcacctgg cctcttttgt tctctggaca 360
gggtgccagc tctgctgctt cttagccttc tcccatggtg tttctctacg gggaatacac 420
acccctccca cctcaaaacc ttgtcctgta ttatgctgac tcctgccctc ccctcagttc 480
tcagcctagg tgcttcttgc rcagggagcc cttgccttgc ctggctcctg ctgtggctca 540
cagtgccctt catgttaccc tctcaagcac tacactatat aattatttgt tttctctgtg 600
acttccagaa gaggctgggc cccaggagag caggcccaag tcggtcttag gcactgccat 660
ttccccagta ttggcatggg catggaaaga atgcttcttg agttaatgat taaggagagg 720
ctctcttcct gggcatccca caggtcctca tcagcatggt gtacctaccc gaggccatgc 780
cagcctcctt ccaggccatc tacacccccg tggagtcagc aggcacggaa gcccagatca 840
agcacctggc tcggctcatg gccacacaga tgacagctgc cggactggga ccaggtgagt 900
gtgtcctggc cctaacctgg gccagggatt ggcacttgtg gcttctgggt tctccttact 960
ggaagagcaa cttctcgtgg tgcagttgaa aatcatgtgg g 1001

<210> SEQ ID NO 28
<211> LENGTH: 1001
<212> TYPE: DNA
<213> ORGANISM: Homo sapiens

<400> SEQUENCE: 28
cccaacctaa tcttttccat agtattgggc ttgaaccaga gacttacagt gtgcaggatc 60
ctaataatcc agcccaccag cagtcctctt cttataaaga cacctcttct cataaggaca 120
ccataatcag taatcaggtt ttgctggctg tggaagtact ctggacagat tagataacag 180
tatgtatcaa tgtaaatttt tgaagctgat actgtgtaaa tgtaagggaa tatctatttt 240
tagaacatac acactgaaat gtttaggacc atattataag taagtactta taaatgtact 300
ttaggaccat attataagta agtacttata aatgtacttt aggaccatat tataagtaag 360
tgcttataaa tggctcagaa caaacaatta tgtatatata tctgtaaata tacacatgga 420
gagagtgagc atacatgcac actgtgcaaa tgatgaatgg ggtaaaatgt taacagtgaa 480
tctcggtgac ggatgtatgc rtgttccttg tgcctttttc tttgcaagtt tctttaagtt 540
tggggttatt tctaaagtta ggattttttt caagagtaat aattaggatt cacttatatc 600
ttttaggttt ttaagaacct acaactattt atggagaaca agcagcccga ggatgatctt 660
tttgatagac tcaatgtgag tagatgaagc acacaatgtt gaagggagtc ccagccagag 720
cctcacagta cctaaagggg agggttgctg gcagatgact tgggctctcc ctttagcctg 780
gcctgctctg tggcatccca tacactctct cttcctccct ctgagtccac ggtgaatctg 840
tagtcaagag aagacacatc tgctgcagaa caactgctaa agcactcagg gtggggggta 900
gatgagccct accttttatc cttccctgct cctgcagagc tttcccttca ctgaatgccc 960
agccacccct gctggagacc caaaacctgt ccctgatatc t 1001

<210> SEQ ID NO 29
<211> LENGTH: 801
<212> TYPE: DNA
<213> ORGANISM: Homo sapiens

<400> SEQUENCE: 29
acaaccttta tatcaacttt ttttcctcta acaatgaaca atgaaaacaa tttgtgctcc 60
atctttaaaa atgtgtgaca caaaaatttt ttaaataaaa ataaatatgt gataaacatt 120
cctgaatgcc tagtgtgtgc cctggcgctg tgctctgcat ttaatttgga tcagcagttc 180
tcagccttgt ttgtacatta caaccaactg gagaggtttt taaactccca gtatccgggg 240
catcagtatt cgtctagggc acagtgattc taacacacag tcaaggttga gaaccactta 300
tttaattcat cctgtaaatc ctcacaatag aatcctgcaa ggtagctttt atcaccacct 360
ttgccgatga aattgaggct caaagaggta aattgatttc rgcatctgta gccccaacct 420
gtgacctctc cttccttcct tctcgggctc ccttcaggga tttcctgatg ttacagaaaa 480
tggtatgtat gacgctgccc tcctggccac cttgacatag ctctgctccc aacagggctc 540
ttctgagata gcagccagac actacctggg atcaggactg atactaaatg acttctgcca 600
aaatgaggac aactgaggcc agtcacttcc aaacaggttc tgtcaccctg agtcagaata 660
atggcagcta cctctcctcc tcaccgccca gtcgtttcta agcctggctc gtcgccgttg 720
ctgctccgcc aagcctttcc tcggtgccct ctctctttta gaacaaatta cttcatctcc 780
aggcccttct cagggcagct t 801

<210> SEQ ID NO 30
<211> LENGTH: 1001
<212> TYPE: DNA
<213> ORGANISM: Homo sapiens

<400> SEQUENCE: 30
cttcttgttc atcataaata atgattaact tagaatgtac ttctcccctc tcttaaaatg 60
accaatataa aagactactt attaaaagaa tatatattat aaaaatacaa gagtaataag 120
ttcacagcag cacaggataa acaggaaaga caccatcaga atagcatgag gacttctggg 180
ccaaagggag gggaaatgcc atcaggactg actgaatgac agcaatacta agacgtaaag 240
gaaatttcaa tttgaaccaa gcaaaagaag gaaactctaa aactgtgaat ataaccatag 300
aaccctaggg gggaacaaac tcaaattcag agataagtga agctggatgt agaagtagaa 360
gtgagcccag gactgtcagg agaataatta gaggcctatg gaacagctgc atcctccagt 420
gttctcagaa aggctaaggt gtgagaacag ctctctgtaa taaagtggag gatcagctgt 480
gggggaacca cccacacagg ygctgggact acagaatgaa gaaacagcac cacaaatgac 540
aatgcacaca cccacccaga aggcagctga ctgaatccct ggacgtatat ccctggtact 600
tagcaggacc agcactcctg tactctgaat ttacttctgg aagaataatt cccacttgtg 660
ctgagagaac ccactacagt taccactcgg atcacacaaa gagttctcaa tcctggatgc 720
acatcagaat catctgctga gctttttaga aataccaatt gcctgggccc caccgcaatg 780
caactgaatc agtatttata gagggaagag ggatctaggc atttgtattt aaatattctc 840
cagataattt aatgtgccct taagtaataa caaataaaaa cagcaaagga agcagaaaat 900
aattgtagta ttctctgaaa gatctattaa gataccattt caaagatcta tggagatact 960
aagggagagg aacaatacta aaaagttatt agtggggaat a 1001

<210> SEQ ID NO 31
<211> LENGTH: 1093
<212> TYPE: DNA
<213> ORGANISM: Homo sapiens

<400> SEQUENCE: 31
cagtgatgtc tctgagcatc agtggtgtct cttctcagtg gcttacagct ccagacatca 60
catgcagacg tgacaatgtc taatggagaa ggggcacatt ctctcccaat tctactcaat 120
gagaaaccct ttccttcctg gaggtccttc agcggccatt cacacagatc ccactggcaa 180
gactggatcc catgctgttc ttacaccagc catttccaag agaatgaggc caccataact 240
ggcttaggcc aattggtagg acccttcagg aggcagaacc tgggaaccta ggcagggctc 300
tgcccacagg aagaagcagg tgagcgtgtg ggggtggcgg rtggttgtca aaacccaata 360
tacagggaac attacaggaa gagtcactta ctttacaatc atgtcatttc ataaacattt 420
cttgacataa ttagggaaca agaggcagca tgaaggagca cagcttccct gccattcccc 480
ccgccacagt gagacgcctg caaggacaca gacacagcct ttccatcagc cttcctctgt 540
ggatccccca tccacactga gccagcaggt caatggggac aggttccatg ctgttcagag 600
aaaccagcac tgtacacagt ggggccctgc atccactgca ggggtggacg cctcagccag 660
cccaggactg tgccgtcatc cctgagactc actgatcctg atgtgagact ctccccgaca 720
ggggcttcca ggcatggctc tatgcagggt catttgtggc cacactatga cgtgggcgat 780
cccatttcta cacatctaaa ttccccaggg caggcagcat gtggtatctc actccctcgg 840
ctctaacctg gttatgggaa gttgctaggt aactgcttcc cacactggag gaggcttagt 900
taccatggaa agtccagatg ggtggggggg cacagaggaa gggagcactg gctgggggggt 960 ctgcagctgg gattctgtcc ccactctctc ctgagcccct ggacctaagg ggagtctctc 1020
aacccctctg ggcctcagtt tcctcctagt aaaatgaagg aaaggctggg tcacttcttg 1080
ctctaaacca ctg 1093

<210> SEQ ID NO 32
<211> LENGTH: 1001
<212> TYPE: DNA
<213> ORGANISM: Homo sapiens

<400> SEQUENCE: 32
ataataataa tagcccacat tattgatact gacatgtaga taggtgaatc caatataaaa 60
tgataggagg tatgaaagaa gttggtgagt ttggaatatt atttgactgg ctataatata 120
gagtaatggg gtgggagcca gagggaaatc gaaaaggtga cctggaaaac attgttcagg 180
gccttgaatg ctatgttgag gtattttgac tttataaaat agtgggggac aaactacaag 240
tattttatac attgaggtat agtttatgaa gttttttttat atgtatagct tatgtaaatc 300
tcaaaggaat gctgagaagt aggcgttatt atcccattgt acaggtgaga aagctgagtt 360
tgtggaatat gcatacattc tacattattg agcacctgct atttgccaag cactatgctg 420
agctatgaga ctagaaggaa gttgtagttt aatactctaa tagaggaaac aggaataaat 480

```
cagcaattgt aagtagttgc yataataaag gcaaacaatg ttacgggagt gaaaggggga    540

cttgtctata tttgcatagt cagggaaggc ttcctggagg aggtgagctt aaactgagtt    600

tggagaaaca aatagattac agtaattgcc cagagatatt taactaggaa gcagtttacc    660

tgaaacttga acccaaatct cctgtgtcta gctctttccc ctactccaag gaccaatctt    720

tggtccttga ttttaagctc tatcagcaac tcagtcacaa gtggacttgt tatgtttgga    780

gaaggtcaga gattccaatt ttttattttt aaattcattc attttctcct tttaaaatct    840

ctgtgtgtgc tcaaagagta gattggaagc agaggaactg gaagaagaac agaatgttct    900

gatagttcag gcaataagtg atgaaggcca taactaaggc agaggtcatg ggcatagtgt    960

gaatctccac tctgttcact ctcctcacac atatactttt a                       1001


<210> SEQ ID NO 33
<211> LENGTH: 2093
<212> TYPE: DNA
<213> ORGANISM: Homo sapiens

<400> SEQUENCE: 33

tggttttctc ctttaatttt ttgaacttga ggttctataa aagtgaacac agtttgcttc     60

acctgacttc ccggacacca tttctccttc tcatctcctt gactcatccg ttctcaattc    120

tatgacctct caactttgaa ggagcccatt ctctaacctc ttgtcttctc tatctatatt    180

cactccacag gtagtgttat ccacttgcaa agcggtaaat actcttcgat tctgacaact    240

ctcaaggttt tctcttcagc ttctcctgac ctccaaactc gtgtatctaa ctaccttgac    300

ctctactcct ggtcttgcct tccaaacctt ctctcccacg gtctctcctg tctcagtaaa    360

tgacacatcc ttgcttctag gttctcaggc catgaacctg ggagtcacct taactcctgt    420

gtttgtctct tatagctctc atgatatcca tgagcttacc tttgaaatac aaggtggcta    480

cccagtctag ataataaatg atttattgat gctacattct aatacaagat acaataacat    540

tatctatgtt tctagacttt atgatcaccc tgtatattca aaatccaacc acttcccacc    600

actyacatca tcctgtttta agccacaacc atctctggtc tggactatga aagtagcctc    660

ttttttttt tttttttt tgagatggag ttttgctctt attgcccagg ctggagtgca    720

atggcgcaat ctcggctcac tgcaacctcc gcctcccggg ttcaagcgat tcttctgcct    780

cagcctccct agtagctggg attacaggca tgcgccacca tgcctggcta attttgtatt    840

tttagtagaa attgggtttc tccatgttga tcaggatggt ctcaaactcc cgacctcagg    900

tgatccatcc gcctcagtct cccaaagtgc tgggattaca ggcatgagcc aaccatgcct    960

ggccaacagt aggctcctaa ctggtctctc ttcttctgtt cttgctccct tgctatctaa   1020

tttcagcaca acagccagag ctaccctttt aaaacttaaa acccaagtca gatcatacta   1080

ctccccagtt caaaatcttc cattggcttc catctcactc agagtaaaat ccaaaggcct   1140

cgccatggca acaaggccct acatgttctg ctctctctct gatctccatc ccaactcctc   1200

tccacctcac tcacagtgtt aaacatgtct ccacctgaag tctttgcact tgctagtccc   1260

tatacctgca aaagctattt ccccagatgt ccatccagga agtactggct tcttcacttt   1320

gttctagact ttgctcaaat gtcctttgat ttcccaacgt aaaatcgcaa cccccatctc   1380

agccacactc cctgtggctc ttgcatcatt ttatttttct ccctaacagt aggaccatct   1440

gatgtacctt ctgtttctcc ctttaccaga atgtaagatc caggagggca gagattatgt   1500

tttgttcact gatagttttc cagcacctag aacaggacta acacagagta ggtgttcaaa   1560

ctttatttat tgaataaatg aaacgagaat gtctgaatgc acactattaa ataagaagta   1620
```

-continued catattttac cataaagtta aattgagcat aattatggca agaagttcag atattggcca 1680
ggcgcagtgg ctcatgcctg taatcccagc actttggggg gccaaggtgg gcagatcacc 1740
tgaggtcagg agttcgagac cagcctgacc aacatggcga aacctcagct gtcctaaaaa 1800
tatacaaatt agctgggtgt ggtggcaggt gcctgcaatc ccagctactc gggaggctga 1860
ggcaggagaa tcatttgaac ttaggaggtg gaggttgcag tgagccaaga ttgcgtcact 1920
gtactctagc ctgggcaacc gagcgagact cagtctccaa aaaacaaaat aaaacaaaaa 1980
acaaaacaaa acagaagttc agatataaac aaatgacccc tcaaaaggaa ttgattaaaa 2040
aaattttaaa caaagtatgg tttaaaaaag aaacttctcc actgtggcta agt 2093

<210> SEQ ID NO 34
<211> LENGTH: 1001
<212> TYPE: DNA
<213> ORGANISM: Homo sapiens

<400> SEQUENCE: 34
ctgcacagtt gtacatattg gcagggctca gcttccttaa atgccattgg atcagtaggg 60
aaatggtgat tttccttatt gatttaatgc cagttcctct tttatgaaaa atcccacgtg 120
ctgctcactg gcgtatgtac cataaaaact gaacgtaggg ggccagaaat taagtaagtc 180
actcatgttc ttctccagcc atgtgacgtt aaaccatctc tactttcagg ctggagtgtt 240
caatcattct ccctttaaat ttagcagagt gattattcct cctggtggat tgcacatatg 300
ctcctttgat ctatgaaata ctcattctgg atgaacttta agctcccagg aaatgcatgt 360
aaaatactgt ttataaatcg cgggagaaat gtttcacatt cttattactc ccaagtaatc 420
ataccaagcc tctctctcca agattcgctt tttttcctag aagagggaaa aagaacttcg 480
ggcagtagca ctgtgacaat matcaccacg gtcgtacttt ccatgagttt tacgcagtag 540
gctcacggaa gtgacaatgc atggtcgggc gcggtggctc atgcctgtaa tcccaacact 600
tcgggaggcc gaagtgggtg gatcaactga ggtcaggagt tcaagaccac cctggccaac 660
atagtgaaac cctatctcta ctaaaaatac aaaagattag ccggacgtgg tggtgggcgc 720
ctgcaatcct agctactcgg gaggctgagg caggataatc acttcaaccc gggcggcgga 780
ggttgcagtg agccaagatt ataccactac actctagcct gggtgacaaa acgagactcc 840
gtctcaaaaa aaaaaagaag tgacaatgta ggatacccat tcatcagcaa atatttaatg 900
tgagcaggac aatgtgctaa gtccatagac tgcaaagagg agtgaggctg ggttcccatc 960
ctctggggct tacaaggtag ctggagaagt aaaactcaaa c 1001

<210> SEQ ID NO 35
<211> LENGTH: 658
<212> TYPE: DNA
<213> ORGANISM: Homo sapiens

<400> SEQUENCE: 35
tgattaaaca ttcctgaatg caaatgtttt caaatgtcca atgacttccc atcatccttg 60
gtatgaagtc ctaagtccct ggcatgcttt caatgtcctc catgatctgc ccccagtcca 120
atcactgatc ccatctcctg ccagtccatg attgaaccag ttgggtcccc aactcctatt 180
tgcacacacc attctctctg tgtgtcatat atgagctctc tactctgcct agctacttgt 240
ctgcaagact cagttcaatt gtcacctcat ttgggaagct tccactaatc cctcctgcac 300
ctgtctccgt cctaggctag attaggagcc tgccctttgg gttcctgaac cacttgaggt 360

```
gtggttcctt tatcatgctg atctcactgg tttggctgac ttgtttttcc tacaagactg    420

aactgtctga ggtcttaaga tgggctgtct agtccacact ggatcttcat gctctacaca    480

gggcttgaca cagagtgggg cacaggaaat gtttgttgaa cgaatacaca aagcatatgg    540

atactcctga gagagagrag gtgggcaaga cagccttgtg aagttaagca gcagaaaatc    600

tgaaaacgaa cctggataga aatcaccaat tcctggaagt acagagagag gaaggaga      658
```

<210> SEQ ID NO 36
<211> LENGTH: 1001
<212> TYPE: DNA
<213> ORGANISM: Homo sapiens

<400> SEQUENCE: 36

```
tggccaccca gacctccttc ctgcgcttca cactcaaaca aggctgttcc ccatgtcttg     60

ggtctgtctt tcctctacct ggatcgttct tccccatggc ctggtctcag cattgagttc    120

tcaaatgtcc ccccttccct caccttatcc gaaggaccca ttccccgtcc tctctacatt    180

ctgtcctatt accctgtctg gtttattttc ttcctagtat tgattactac tggaatcctc    240

atattcatca gtctgctggt ttaatgcctg ttccctttac tggaatgtaa gcatgatttt    300

ggtctttttc tcctctgtcc tgagtaccca gaacaaagcg tggcctatgg aggacactaa    360

atgaacgcat gggggaaaaa cgggttttat tgcagaggga gaccctttgt ttcatacaga    420

tcgtttgtaa acttagatat tttattagca acaaattatg atagagctta caaactcctt    480

gagaatcgct gcggtagtag rtgggggtgg agcttctcta ggcagcattt cagtgtgtcc    540

tagcttggat gctgtggctt cccgagctct gaatctatac tgcttactct gggcttatgg    600

agtgtgtagc agggaatcct tgttgaagga tccccaaacc cttgatagcc atggacagcc    660

cacagtggtc atggagccgg agccagaatg taattcccag tgtgaccagg agctagagtt    720

taagtcaagg cagcaggtat actcaggtgc attttccatt ccctttgagg gaggggtgga    780

ggtttgagcc ccctccacat cccaccccat tggggtgcct ttgtcactct tgacagcttt    840

agagtgactt agatgggaga ttggtgggga ggagggggggg aggggcactg tttgaatcta    900

ccctgctgga ggcactgaat agttttataa gtatgtgtac actctattgt tcaagtgttt    960

gcttaaatca ctgtatcttc ttagaaattt ttgtaacctt t                       1001
```

<210> SEQ ID NO 37
<211> LENGTH: 1001
<212> TYPE: DNA
<213> ORGANISM: Homo sapiens

<400> SEQUENCE: 37

```
gataataacg cctacttctc agcattcctt tgagatttac ataagctata catataaaaa     60

aacttcataa actatacctc aatgtataaa atacttgtag tttgtccccc actattttat    120

aaagtcaaaa tacctcaaca tagcattcaa ggccctgaac aatgttttcc aggtcacctt    180

ttcgatttcc ctctggctcc caccccatta ctctatatta tagccagtca aataatattc    240

caaactcacc aacttctttc atacctccta tcattttata ttggattcac ctatctacat    300

gtcagtatca ataatgtggg ctattattat tataattatg actgaagtag taggagatag    360

aaacaaatgt tgcttttgtc tactaagtgt tttgttatcc tctgtctttt cccctcatcc    420

tagtcaatat tccattaaaa cacaggttcg attacatttt tcaatgccta ctggataaaa    480

tcaccttgta gtatggataa kgttcttcat gatccaactt ccctctgtta tttaaccttc    540

ctctgctgct ccactaatag cctttgtgac agttgtagta actacagtac atgtagtttt    600
```

tccaagataa taggctggct cagctttcat gcctttacac atgatgtgtc ctttgcctct 660
tacgtcctcc tctactttgt ctatccagtg aactccctgt catcctttaa gattcaattc 720
agatgtaaac tcttctgtga aacctgccct taaatactca gtggcagaat tagatgatct 780
cttctctctt actatgccat acatatcttg ttacaatctt ctctgacggt gcctgtcacc 840
tccactagcc tgtaaacgta tccagcagag ggctgctttt tatctccgag tccttactgt 900
ctggcacaaa gtgggtgctc acggaaaatc agttgaatac atcaacaatt acccgtcagt 960
ggcacctgaa gccatcagtc actggagcta ccccatcatt g 1001

<210> SEQ ID NO 38
<211> LENGTH: 1001
<212> TYPE: DNA
<213> ORGANISM: Homo sapiens

<400> SEQUENCE: 38
gactttactg aagcagagga gaaggagatg atcaatctat tcaatatgaa gaaatatctc 60
tgttgctaat acaatatcct tttgaatatc tcccacatct taggccctgg tgaaaatccc 120
tttcaattgt tctgtctacc tcgtagggat gttgtaagaa taaatgagtt aacatagata 180
tgaagtgcct taggaaaaag gctctataaa aatgcaaggc gatatcatga ttagttgttt 240
ctttgactct tgatcatttt cttcccactt cttatacaaa atgtctctca cttatttcct 300
gaagccatct cttttagaac tattgcttcc tagaagagct gaaaatgatc ctagttccaa 360
catatttatt gattcccaga taataacacc cactggtgtt gatgactgac agggttcatg 420
cctaagcttg agtagaactt gccctttttt cctgggtcaa gaaaagtctg caattgttcg 480
aaaatgtgtc agtaagtgtg mttccatcac gatttcttaa ataagtaaca gttgctgctg 540
gataatcctg ggggcagatg attcattttt gtgcccctat caaacaaact caaaacttgt 600
taaagaatct ttataagttg tttgaatcaa acaatagggt cgctaggtcc ccattttgtc 660
catttgaggt atttgcccag cataccttgg tctgtaaaga aatagcacag ccttggctgg 720
gcgcggtggc tcatgcttat aatcctagca ctttgggagg ccgaggtggg cagatctcca 780
aaaataaata ataataatga taataacaca gcctcatgag tctttttttt tttttttttt 840
ttgagacagg gtctcactct gtcactcagg ctggagtaca gtggcacaat cacagctcac 900
tgcagcctca actaccctgg gtttagtgat cctcccacct cagcctctca agtagctgag 960
actacaggta cacaccacca cacctggcta atattgtatt t 1001

<210> SEQ ID NO 39
<211> LENGTH: 1001
<212> TYPE: DNA
<213> ORGANISM: Homo sapiens

<400> SEQUENCE: 39
gaaacctttt atatccttac aactattcaa tcttcctgtt caggaaaatg gaatatttaa 60
tatctttcta ataatcaaat attctctata tctaggaaag tcatttttat gtatctcaat 120
caagttttat agttttcttg atatgggttc tacacattga cttacatcca tctacatttt 180
tgatttttat actgggaatg agatggagct gctgctaact ctggagaaac ttactgctga 240
tcttttatct ttggacatga tcctgactgt tctcctaagt gatggattat cttagatttg 300
aaaagtatag gaagtaaagg acaagaggga catgtggggg gatgtagtag agtctgtttt 360
atattcatag tgagaagact ctgaacctcc caggagggct ctaaaggtta aaaaacatgc 420
aaccaaaagc accgaggatt agtaaaaaga aataatgtgc agtaagtgct cagagggatg 480
actcattgca ttggatcatc yttgggaaac cacctactaa gcagaattta gcagctaaag 540
cgttattttt ggtgcacagt ttattgctac ttcctcttgg gaaaaaaaga ttaatcctag 600
ctccctaaaa cacttaagaa tggtcaccct ggcaaaccgg cctgtcaggt aacaatgttg 660
tttccagatc agggcagtgt taggttccct gtagggattt cttcagaaca agggagaagc 720
actttaccac atgttatgga aaggagtata gaccaggaga cagaagatcc agctcttagt 780
gctggctctg taactgatta acaaataaat cccagagtgc aggcaggcca cttaatctct 840
gctcatctgc taaaaaacag atatcacagc ttctgtcgta ctccatatca tggaagaaaa 900
taacacaaaa taataaacca tgtgaatgaa gcagttaaaa ctgctgagaa ataaaattaa 960
cctgctcagt aaaagtaagg ctaccaatca agaacaaata g 1001

<210> SEQ ID NO 40
<211> LENGTH: 1001
<212> TYPE: DNA
<213> ORGANISM: Homo sapiens

<400> SEQUENCE: 40
ggcaatcctt gctttttatt accacactgg attgcttctg tacacagcta agttgcctga 60
agcatggaaa cttggacttc tccatctgac acgttctgga agcctcaagg cacaagctga 120
cagttctgct tctacagaaa aactctcaca ctgctctcct ctcaacagta ctgcctgttc 180
ccactactcc acatgacacc tacgagggca ctacatcacg tgagggaagc ttcttcatga 240
gggcagacaa gaggaggcac cacccaggca ctggtctctg cctggcatct attccgaggg 300
ccacctggca cagtttctaa attaaggcat atctaaaatg cttttctacc tttagttttt 360
atttttgcta tatttttgca ctctactata tgcatattta ataaaaacaa ctacaaagtc 420
ctttacttta attcctttac ataatgataa aacacctaga tacccaaaat actacatcta 480
tatattcaaa tctactaatc rtgttacaaa tgcatgcagc ttatttgggg gcttagtcta 540
atttttattt tcttaggtcc atcaatacca tgataatgaa cattagatgc aaaatcctaa 600
cactttctgc cttcagttgt actttcacag gactagtgtg attcagaaat aaataacata 660
catgaataat aatagaaata atttatgcaa atgtagaaca acttgaaaaa aaatccccg 720 cctgtcaggt gctgttcctg ggggtagctg atgctataaa ttccatgtac taactaatat 780
atttactaca ggtaatagga aaacaaatga ataaaaagtg aggaactatg atatacatgt 840
gtatattttt gcaaacacag gatcagaatg aaaagatata tcatgcactg tgaggtttaa 900
gaaatgtatt actgctggga tttgttttat tattcagact ttaagatcaa actgagagtt 960
gttggtgatc acagaaatat tgctagctga tacatattat t 1001

<210> SEQ ID NO 41
<211> LENGTH: 1001
<212> TYPE: DNA
<213> ORGANISM: Homo sapiens

<400> SEQUENCE: 41
cctttccatt taagacatgt ctttgaaaat agactctagt ttaaatgtta gcagatagac 60
tttgaagtaa ttatgaggaa gaacttggga ctgaggatgg tcaaattcta aaacacagta 120
ttggatccaa agacaggttt ctccaccctt taagaataaa tctgtcaggc caggtgcggt 180
ggctcacccc gtagtcccag aactttgaga ggccaaggca ggtggatcac ctgaggtcag 240
gagtttgaga ccagcctggc cagcatggca aaaccctgac tctactaaaa atacaaaaat 300
tagccaggtg tggtggtgtg cgcctgtaat cccagccagc tatttttggg aggctgaggc 360
aggagaatcg cttgaacctg ggagacagag gttgcagtga gccaagatcg tgccacactg 420
cactccagcc tgggggacag agagagaatt tgtctcaaaa aaaaaaaaaa tccatcagaa 480
acgtctcacc tcaatatagc rgccaatgtt gtcccatgta aaagtcaggg cacatggtct 540
attgatatga aaaccataaa tcagaatatt tcccattgaa actgccttag gcacagcttg 600
cacattgtaa tatctctcaa ggcaagaaaa tgacctttca gaatagacgt attctagcta 660
aatccccagg catcccaatc aacaattctg gcttccctaa atttccatct gccagagttc 720
gggctgattc tgggagtctt cttgttttga attctcaatg ggtgttagt gcggttttta 780 acacccctct ccagcctcac ccctgatgtg gctgcatttt ggcagcgagg aaaagtctgg 840
gttagaggtt tgggtttcat gagcccttcc aagaacaaga gcagctaagc tgacacaaga 900
gcacactctc cctaaacagt cttttctgcc acctctccca ctgattttat gtaaccgaga 960
agaattagaa aagtgtgaaa aaagcaagac tgatgtttgc t 1001

<210> SEQ ID NO 42
<211> LENGTH: 601
<212> TYPE: DNA
<213> ORGANISM: Homo sapiens

<400> SEQUENCE: 42
gaaaatctgg agatgaatca gatctgttcc ttctctcagt gacactgcag tctagatggg 60
ttcagtacaa atatctctat aatacaaaat agctctcaga ccagtctttg tagaaatagc 120
tgtatgataa ggcttccaat aattataata ataaaaaacc cagttattgt ctgaaatata 180
aacgctcaaa atgcagaaat gttttattca ttgttctgtc cccaggaatg gtgcctggcg 240
tatagtaggc actcaaaaaa tgttagatga tggcagcaac ggtacttcag ggccagggga 300
rccagcaccc atggagagat gcagaggcag aaatggatta ctcaaattgg gaacctgatg 360
ccccctcttc tcactttaat ggagttgtag tagttgagct tcaaagaaag gagcgtcctc 420
cagtgaggtt cctgcccctt cctgggcctc tctaccacag caagagccag ggccagctgg 480
cagttttcac caccctgctc atgtttttct ggagacacca gcttaaccac agccaccaca 540
gatcggaggg tgctggcccc agcctgctgc ctgctggttc ttctccttcc tccctccctt 600
c 601

<210> SEQ ID NO 43
<211> LENGTH: 1001
<212> TYPE: DNA
<213> ORGANISM: Homo sapiens

<400> SEQUENCE: 43
tacagtcctg caggctgtat atgaaacaca gtaccagcat ctgctcctgg tgaggcttca 60
ggaagcttat aaccgtggca gaaaggtgat ggggagccgg tgtatcacat gatgagagaa 120
ggaagcaaga gatgggggaa gaggcaccag gctcttttaa acaactagct ctcatgtgaa 180
ttaattgaga actcacttat caccaagggg agggcaccta agccattcat gagggatccg 240
ctctcatgac ccaaacacct cctgctaggc cccacctata acactggaga aaacatttca 300
acatgagatt tggaggggac aaatatccaa accatgtcac tgacctgggt tcacattgtc 360
agtctgccac ttatcatctt gatattcttg ggaagataac tttgcttctc tgagccttgg 420
ttttcttcta gaaaataata aaacttgctt cacaggagtg ttaagaagag taagtgagat 480

-continued aatacttgaa aagcacttaa ytttgcatat gacacacagt aagggcttaa gaattgtcgc 540
catcatcatc aatatcatta ttattctctg cacaataaaa tgtgttggaa tcacagcaga 600
taatccagtt atttggatga gtttttccca cgtcatgggc tgagcagatg agttgacaat 660
gggtgactgt tgagtgtcta ccatatactg gcactgttat ggaagtgtgg gcacagctcc 720
tgagagttgc ctaagtgggg ttatgacctg tattttccta gtcatcctac ttaggaaatc 780
atccccccag ttggtgtaag acagtaggct ctcttataca ctgttgctgg gagtacaaat 840
ggatgcaatc tttttggaga gcaacatggc agtatttttt tacgactttt taaaggcata 900
tttggattga gtaattttcc tttgcaggag aataatctgg atatgctgat aaaatatgcc 960
caacgtggca tggataaata tgtttgaaac acacacacac a 1001

<210> SEQ ID NO 44
<211> LENGTH: 1001
<212> TYPE: DNA
<213> ORGANISM: Homo sapiens

<400> SEQUENCE: 44
ggagatattg accactgtga agatctgttt cctcccagct gatgcagaca ggtcctgaga 60
ccaccggaat ggtgcattct caggggcccc agccaggcag ggtgtgcagc ctgtactcag 120
aggaccctga gcttggtttt attttctccc atcagcattt gacactctta atgatttttg 180
aacacgaggc cctgcatttt cattttacgc tggaccacac aaattccata gctgtttggc 240
agccaagcca agggctgagg acagcacctt cctagagggc tgtgcacaag ccaagttctc 300
agcagcaact tttctgagag aaaaccatct agctccaaat cacgtgttca ttatccattt 360
tcttcccacc ttttgccact tctccttttt ctgtggtccc tccctgttta gcaggtatgg 420
aaggtttggg ggagaagcca ctcattttct ctgcatctct tctggccctg tttctacctc 480
caaatctgca ccatagcccc rtcctcagct tccttgtatt tcctgaagct gtgtcctctc 540
tcccccagcc cctggccgca cccatctcag tgtaatggta ccataaaggg gccaaggaag 600
agcctgtttc cttggcagct tacatctccc cctgggattg ccaacatgca ggagtcagcc 660
cttcctgcct cattacctga acagcttccc cttcaatccc tgaaacactg cactggagtg 720
gagtctactt tgaaagtgaa agtgatttag agtctactcc atttcgagaa tttgcatgtt 780
aaccccttgg gctgggcaca gccccatgga gatttgtttc tttcctggcc agtcccctct 840
cctgccaggt ggtctttgct tctttgcagc ccctcaacat gacagcatgt ttgagtcctt 900
tccagcaaga agctgaactc cccaggagtc tgccagtttt ctagaaaaca ttggttactg 960
gctcctttct ggttttgacc attctttact cagggcttag c 1001

<210> SEQ ID NO 45
<211> LENGTH: 1001
<212> TYPE: DNA
<213> ORGANISM: Homo sapiens

<400> SEQUENCE: 45
ttaaggggga cttcaaaata aaaaactatg gacacactcc tggagagcag cacggaggag 60
ggatctatga tggtgtaata attgtgagtt tgggctagat atgactgaac aagtaaaggt 120
tgccccaggc atctcacagc gggatgcaga aaagcatcct gatgctaccc agttgaggaa 180
tccaagacat ctcctcccct cctatcaggg agggcacgaa ggggcttcac tctacaggga 240
gggtggaagc acagcagcct tacattgcag ctagggtgca gcaagccaca gccaaggcca 300
gaattctgca gagtgtccca ggaagagaaa agtctaggta gaaatcagcc aataacagag 360

```
cagaagctaa agagcagaca atgcaacttc caagacaaag acttagcaga aaggactctg    420
aagctagaag cagctgtaac aggggggatg agatggtaat ggttaggaat aaagaagtag    480
aacatgaaga ggggcctttc rccatgctga tagtgataac catttcttta ctgaggagga    540
accagacacg atgtggtaat ctgctttata tactttaaat gtaatgggcc atagccaggt    600
acagtaggag aaccacacac ttgtcctttt ataaaatcca gaatgcaaaa ccttctccac    660
taggtactgt tcatagaatt atctgaacag aaaagacctt tcttaataat ttaagtcaag    720
attctattgc tctacctggg caaatcagta agctacactg cccttatccc ttacaaaatc    780
ctgccttctg tctgggcatg ataacatggt tagacagggt cacatgttat atatatatat    840
gcagagtttt tcattgcagc aaaatataga aatcaacata aatatgcacc aataaagtgc    900
taataaaaag attatgttca tccaggcaat ggaattctat gcaactattt taaaaagggt    960
gtgaagaagt gctctaaata atatgaaaga tctaagtcat a                       1001
```

<210> SEQ ID NO 46
<211> LENGTH: 701
<212> TYPE: DNA
<213> ORGANISM: Homo sapiens

<400> SEQUENCE: 46

```
cacagccact gtcttcacag ggaagcttgg tggccttgag ctaacatgaa ccggtaagtc     60
ctttcctttt taacagcact ttccttggaa gaatttctcg caggccagcc ttacaggctc    120
ctcacatgtc cactcgtgtg aggtgtaccg gcagtagagt tagtcccttg agaggccata    180
tcagggctta ctccacagcc yctgggacga cagcccagtg tttcagcaaa ggagctgctt    240
acaatcttgt ctatattaag gcccctggcc tttcctttaa agaacaggga tccatttaac    300
accaaaacat tttggagccc cctctctcca tccctatcat cagagtcctg ctttctgtgt    360
ccattcattt aaaatatcca taatgggctg ggcacagtgg ctcacgcctg taatcccagc    420
actttgggag gcagaggcag gtggatcact tgaggtcagg agttcgagac cagtctggcc    480
aacatggtga aatcccgtct ctactaaaaa tacaaaatca gtcaggtgtg gtggcacgca    540
cttgtaaacc cagctactta ggaggctgag gcaggagaat cgcttgaacc tgggaggcag    600
agattgcagt tagccaagat tgcaccactg cactccagcc tgggtaacag agcaagattg    660
tctcaagaaa agaaaaaaga gaaaagatcc ataacgatcc a                        701
```

<210> SEQ ID NO 47
<211> LENGTH: 1001
<212> TYPE: DNA
<213> ORGANISM: Homo sapiens

<400> SEQUENCE: 47

```
aactacttgt agttcctcaa atcaccatgc tcactctttc tcactggtct tctctccttt     60
gtcttcttgg aaaactattt cacctgtcaa gattcagccc aaagcatcat gttttgtcaa    120
gtctgtctga atgctttagg cattgctaag tatgcctttg cttctgctca cagcatccat    180
gaataactct attatatcac ttattacact gctttacaac tacatctaca ttcttgttgt    240
tattctccac tacatgatgt aaatattttt ttttacttat attcaagaat taaaagaaaa    300
aaaaacctta ccttttcatg gcaaccaaaa gtactgaatg tgcatggaat tggggctgta    360
gggcagtcta gatcataatg attaggcatc tgaaatccaa aacaaaggct gaaaaatctc    420
ttccttgcat atcattttct agtttgatgc gatcacattt aaactgtatt gtcaatggct    480
```

gctttgtacc acattggcag ytgaataggt gcagcataaa ccatcaccca caaaaattaa 540
aagaacatct actttcaaaa gttatagaga aaggaaatat caacatctca taatatcccc 600
tccaattatc caaaattcat ttcaagaaaa tgaatttgtt cctcttgctg ggaactggca 660
ccctctagtg gcactttaca gaaaaaacac ctaacaatag ctacaagtgc aaactggatt 720
aagactccca ctatggtcta ggccatttaa taggaaccag tcaactgcat gcactgaagc 780
cactgactac acccatactt gcctcatgac cacctctcaa aaatcatctt tgaccacctt 840
tcaacaatct tcttaacttt tgttaagctg ggcatatttt agctacaatg gggagactca 900
gatgttagaa ggtactttaa acacattaat agaagctcta aaaaaagtct cagtcctgga 960
ttttgggact ctaagacaca ttctctaagg taagatcctt t 1001

<210> SEQ ID NO 48
<211> LENGTH: 1001
<212> TYPE: DNA
<213> ORGANISM: Homo sapiens

<400> SEQUENCE: 48
taagtcctgg tgacagttca gcttcacctc taggaccaga aggttccgaa tgccctcgga 60
aagggcttct ccaggggctg ccttcaggcc ctcaggcttt cttaaaacca caaacgtagc 120
caacacctga aaagagaggg aagcttttat tgagaactcc tggcctgaga acacctctta 180
gaggaagttg gctgggactt tccagcctaa ctaccccgaa aacaactgcg ggacccagca 240
atagcatcta ttccctggca ggttcccatt cacaagtttg cacagggctc ttttcggttg 300
taacagtgtg gtcaccctca agtgggaaga cagtgacaat ggggccagcc taaggccagt 360
cctgcagaaa aatgatttct aagctgtgct agactctggt tccaatatgc agccatcagt 420
ttgagcactg cctgggttcc tgtggcccac gatgttgtgc agtaagagat ggatttttaa 480
aaaatgtctc aaggaggaca yaagagctcc tcatcctggc attgatgacc atccatgata 540
tgcccttacc aagccagtct gcatatattg ctcagttttt ctcaaagtat cagtgactct 600
tcactcaagc acatctcacc ttcccttacc tgctgttcct tcactcattt catcaggaca 660
cactcactga gtgtttgcta tttattaacc actgtgagtt gcagaacatc caaagatttc 720
taagaccaaa tccctgctct cagggtactc agcctatgga gaagataaca gtcttttcaa 780
gtattcactc atgcaataaa tatttattga gcagctacta tgcatagcca ctcaggcact 840
gggagatata agatggctcc agaggccctg gtgccctgcc ccgtggagct cgcaaccagc 900
aggcactctt ctatgtcatg cacagtcctt cccccacact tttgctcgta ccaactactc 960
ctcttgccca gaattctctt cctttttccc tctgcttatt t 1001

<210> SEQ ID NO 49
<211> LENGTH: 1001
<212> TYPE: DNA
<213> ORGANISM: Homo sapiens

<400> SEQUENCE: 49
aaatataatt aacactactg aactgtaaag tactgaaatt ataaagaggg tatattttat 60
attgtgtggg gttttgttta accacaattt aaattttttt ttctaaaggt cttgggttat 120
tgggtattta taaggttgaa aaaaaaatgt catcgatgta ttcaagggaa gaatggctac 180
aggttcagcc aactctcaaa tgtgcaaagg ttaatttcta acctctattc ttcccaaggc 240
ttggtaagca ttaactgttt gccagacctt ggaactttcc agcgtcagtt tctcattttc 300
cttcctactt tgtctttcta ggagcccctt tcctggacac actcgtgtct ttcccaggga 360
atgggaagaa acaaaaggat gatgacatga cacctaataa gtctggatct ggaagtaagt 420
ttgatctacg gttcattagg ctggagcaga aaaaaaagaa agggtccggt atgttcgcct 480
gtgtgccagg tatggtgtta ygccactcat gtgccttata ttccctacaa cccctcaccc 540
caatttatca cttcaaaaat gataaaagct gagacttgga gaaactagta actaaccaaa 600
agtcacccaa gaaggaggtg gcaagctaag atcaagcccc actttggtgg gagctaagag 660
tagcccttgg tagagtcatg gggttggcta attcttgcct ttggaacctg tttctatctc 720
cattcagttc ctttctttcc tgtcagttgg actttaaact ctaagatcag gaaatttccc 780
tttatctatc aaatcatacc ctattgagtg agtgcctgct tagcctaatg tcctgcaaat 840
ggacaggact cctctcttct atgactcccc agaaatatta caaaggcctg taggaaatag 900
ctcgggacag accagaggaa atagcatgga ggattcacag tataacttat accttcaaag 960
gtgaccacca gcctgcatcc cattaaaaac aaaaacaaaa a 1001

<210> SEQ ID NO 50
<211> LENGTH: 1001
<212> TYPE: DNA
<213> ORGANISM: Homo sapiens

<400> SEQUENCE: 50
ccatttacat taagaaaaat ccccttcaaa agcaacttaa aagttttggt gctgaaaggg 60
ttaacttcag ttatctggaa agcccaggcc ctgggtccgg gaaattcggt ggcagttaca 120
gggttactgg gaggtatcac aggccttgct aacactcagc ttatatgagt ttcatcaaaa 180
acttccaaga tgtgtttcta ggagaaaaag aatgtgtcat ctcactttct cctcacagct 240
gccacgccag ggcatggaga tggggcacag ccctgcctgc tggggcagtg ggtagaggaa 300
gatgctgcac ttagtggaaa atgcaaatga attccactag ggctccaacc tttgactctg 360
aaaagggaag tagaatcatg gcccaacaac ttaaaataaa gaagtgggtg gcttataata 420
actctgaggc ttccaggaaa aagccattct gagtgtaagt aacaaagaag tcaaagaaaa 480
cagccatgcc atctgatgtg hctgcctgga aaacaaggag aaactagtta ccacggaaac 540
aagagagatg gcctctttta cacacaaccc tcggaagctt ctgcagtcag aaagcccagc 600
gtgcaaatcc ttccctggac catgaacaca ggaatgaccc aatgtccttc cacaccacca 660
ggatttagat aatgatcggt caaactcaac tgatccattc tctaattgca gtcagaatgg 720
tctttctaat gacaaccttg atgatcatga tagcaccatt tactgactgc caactgtgag 780
gcgggcactt gacatgtatt atctcagcat tttaaaaatg aacttagagg gtcttgactt 840
ttagtgaaat ggaatagaaa atatcggagt gcatcacatt tggagaaaat aaatttattc 900
atgattactg ggttaaaatg cctcatttat ttcatacctc atatggcact caaaactaca 960
tgaaagcacc tgtttggaag cacctgtgtc tgatcttaca a 1001

<210> SEQ ID NO 51
<211> LENGTH: 1001
<212> TYPE: DNA
<213> ORGANISM: Homo sapiens

<400> SEQUENCE: 51
tcttgccatt gtttgcttcc tttcaatctg tatgaacctt ccctaggagt ccacatcaga 60
tatagcaagg ccatgggagc tatttttaac ttcgggaata ctgtatcaaa actaaataaa 120
ccacagccgg gctcgggggt tcgtgcctta atctcaacac tttgggaggc cagggcaggt 180

-continued

```
ggatcgtttg aggtgaggag ttccagacca gcctggccaa catggcaaaa ccccgtctct    240

actaaacaca aaaattagtt gggcgtggtg gcgggcgcct gtaatcccag ctattgggga    300

ggctgaggcg ggagaaccca gaggcggggg ttgcagtgag tcgagatcgt gccattgcac    360

tccagcctga gcgacagagt gagactctgt ctcaaaaaaa aaaaaaaaaa cttaagtaaa    420

ccacatgcca agtttctttg cagattcttt ggaattctgt caatgtagtg tagtagtgct    480

ggacagacca tgtttaatag yagctgtggc cagcacttta gtgtaataaa ataaaggcaa    540

ataaatttta aatgcagctt catggacaaa ttggtcaaaa catggataaa agtagtgtat    600

tacaaagtgc aaagctccaa ggtcaggtag acgtgggttc tgatcccaac tctgttactt    660

attagttggg taatcttagg taagttactt aacctttttaa gctccatagt taccactttg    720

ataagtggtg acaacaaaac ttaaatacta cataaagttg ttgtaataat tcattcttac    780

tgcctggcac tgttctaagt gctttgcaca tattaacaca tttaatcttc tcagtaactc    840

aagtggattt tattgttaga accattttac agatgagaaa attgaagcac agaaaggtta    900

tataatttgc ccagctcata aatggaagaa aagagttaaa ttcgtatcat tcaattccag    960

cacctgagct catcaccact tattagcact gcgtttccag c                        1001
```

<210> SEQ ID NO 52
<211> LENGTH: 1001
<212> TYPE: DNA
<213> ORGANISM: Homo sapiens

<400> SEQUENCE: 52

```
cataagaaaa aatggtgtcc tataacagaa ccagatgcag agaacattgt tacatagaac     60

atggaacatc ccaaaagtag tcttacacat aaaaagctac ttaggaaaaa agaacaatgg    120

acagaaaatt gagaaagtta gattcttatc ccagtttcca ctgttgtgtg aaaagtgact    180

tgaatctcct cctctcttga cccttggata aataagtaaa taatttgcta cttttactta    240

aagcaattct aatgcagact ggggagtgac tctatgcttt aaagaaaata gtattttttta    300

aatgtacctt aaattatgat gctactagat aaggataatc tcaaccacac aaagaatact    360

gactctgtaa gtgatcagtt attgtgattt taggcatgtt aaatcttgtt tattacctaa    420

agtgtatggt caactgtaaa attaccagta tttttaaaga aagtattaac tgaaggctct    480

accttcataa tatatccaaa rtccagtccc ttctcacttc ctccctctgc taccaccctg    540

ttgtgactca ccaccagctc tctaacaggc ctcctgcttt ctattcttgt cttccaggct    600

gttctcaata cagcagcggg agtggaccta gtaaaataag taagatgatg tcatctctgc    660

tcagaccatt gtagcagggt atctgggagt aaaagctaaa atccttataa gaccctgtgt    720

gataggccca tgattcattt cctgacctct tttctgctgc actctttgtc cttctaccca    780

ttcattccct ctttgctatc ccttgaacat gtcaggcatg ctcctgcctt ggtgagtggt    840

ggctttagct cttctgtttg taacactctt gccacagcta accccttaac tcttccactt    900

tggctcaaat ctcaccttct cataggtccc ctcaccaccg tatttatacc acagcgtggt    960

tccacctttc ttgccgaaca atcccaatct ctccacctgg c                        1001
```

<210> SEQ ID NO 53
<211> LENGTH: 1001
<212> TYPE: DNA
<213> ORGANISM: Homo sapiens

<400> SEQUENCE: 53
ccaatgtggt acaaagcagc cattgacaat acagtttaaa tgtgatcgca tcaaactaga 60
aaatgatatg caaggaagag atttttcagc ctttgttttg gatttcagat gcctaatcat 120
tatgatctag actgccctac agccccaatt ccatgcacat tcagtacttt tggttgccat 180
gaaaaggtaa ggtttttttt tcttttaatt cttgaatata agtaaaaaaa aatatttaca 240
tcatgtagtg gagaataaca acaagaatgt agatgtagtt gtaaagcagt gtaataagtg 300
atataataga gttattcatg gatgctgtga gcagaagcaa aggcatactt agcaatgcct 360
aaagcattca gacagacttg acaaaacatg atgctttggg ctgaatcttg acaggtgaaa 420
tagttttcca agaagacaaa ggagagaaga ccagtgagaa agagtgagca tggtgatttg 480
aggaactaca agtagtttgt rttgtgctag ttcaacccaa tagcaatgta gatgatttga 540
ggtggaggtg ggggtactag tacctgagct gttggaatac ctaagtgaag acagcttgaa 600
ttatggcgat gaccgtcaag atagacctag gagccagtac atatttagga gagaagatct 660
actgcctgtg tgactaaata aatgtgatga gtgaaggaga gggaggcgtc tagaatgact 720
cttggtttct ggcctttgtc actgggtaga tggaagggcc attcggcaaa aaagagtgaa 780
cacaggaaga actgactgga ggtagagttt aaaaaaaaaa tctgttttaa tgtattgaat 840
tacagataat gacttcaccc agctagggaa caggtgggat gactgacatg cattatgtgc 900
tgtcttaagc cccaaagaga aattaggact cagagtattg atttgggaaa gtgatttgtg 960
gtaataatgg aagttgtgat tgagatcata tggcgtatgt a 1001

<210> SEQ ID NO 54
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: n is a, c, g, or t

<400> SEQUENCE: 54
tggaatcaca gctctgcctt cgagctgtgt gactttgggg cagttagttg gcctctctga 60
gcctgtaaag cgggggtatt agagtctagt catgagatat cttataggta agtaaactag 120
catagtgctg gataatgttg taacaattca tgtaataaca attactatgt gattttaaga 180
tgtcagctcc cttttctgga ttggaggatg gaaaggcata tttgcatatt ttcagttgag 240
ttctcccacc cagtcctaca tttactatag taaaaccttg tagatcaaat gtaagtaatg 300
nctctctttc ctccccacac ctaatgctgc acctcccatt cagagtctta ctagtgaaga 360
ctagtaagtt tagattactt attagtaaga ccagagagtt aggatcaata cgtgcaccct 420
tgtgagatgg aatatatttc tgccctgaga atctctgttg gtcttagcct ggaattaaga 480
tcctgtagca ccacacctct gctctctggg ctttaatagc tcctggctgc aagtttttta 540
gcatgtgcag cttgacattt tatgtggaac tgtcttctgg cctctcctac aagtaatgac 600
g 601

<210> SEQ ID NO 55
<211> LENGTH: 1001
<212> TYPE: DNA
<213> ORGANISM: Homo sapiens

<400> SEQUENCE: 55
atggatggaa ttctctttct aggccatttt tattcgatgc cagattacat agtaaggtca 60
tttcagtttg agatgcactc actcaactat tagcactact gcaaataaca gttatgagta 120
tgatcactaa gtgttcattt tacactgaaa agaaatagaa tagtcagttt ccaaaccaaa 180
tagctatact ccctgaacaa cagtggaaag tcattcttct tgaagtttga cccagaatca 240
agtgcagact cagactccta ggcctacagc cagtggcaac ttaacacatt atatggttga 300
ccttcaggga aaaagggaaa ccactgctct taccactggt gccagaaaaa agccaactaa 360
tctttaaggc acaaaataaa ctattcttaa ggcagaaaaa gaaactgtga ggaaacaagt 420
tagaatggag gcatatagag aaaaatacag aaaatacatt accaagtaag gactagtttt 480
tccatggttc tcagtgtttt yatttttggg aatataatta atcagcattt tctttttggg 540
ttttaactcc tactacctgg tagaaatgca aagatgtaca agaaagatgc atttttaaaa 600
aggcttggag acttaaaggc aattatcttt gctaatttta ctttgagcca gtgacattaa 660
taagttcata tagaaaagta aatagttgct gggcatggcg gctcatgcct gtaatcccag 720
cactttggga ggctgaggcg ggcagatcac ttgagcccag gagttcaaga ccagcctggg 780
caacatggca aaaccctgcc tctacaaaaa atacaaacat tagctgggca tggtggcatg 840
tgcctatagt cccagctact cggggggctg aggcgggagg actgttgaac ccaggaggcg 900
gaggctgcag tgagctgaga tcgtaccact gcactccagc ctgggtcaca gcgagacctt 960
gtctcagaaa aaaaaaaaaa agtaaatagt gatgggatac c 1001

<210> SEQ ID NO 56
<211> LENGTH: 1001
<212> TYPE: DNA
<213> ORGANISM: Homo sapiens

<400> SEQUENCE: 56
atttacaact ccatagtcca caaaattaag tctttaatat ggcaccttcc aagatcctcc 60
atagtaacaa cgataatgca aatacaataa catcaacaga aaacgtttcc tgaatgcatt 120
atctcattca atcctcaaaa caaccctttg aggtagtaat tattatcatc ccattttaga 180
gaaaaagaaa ttgaggtaca catcctcaac cacacttggc ctcttgtcaa tccatcctta 240
tttcagccat tcccaactac ttgtatcact gtgcccctct gcagacttct gtgctgtgga 300
catccttagc ctgcactgcc ctgccttagg ccgcccctgc tgtttgttgg gtgaacaatg 360
gctaatcttt ttagacccag ttcaggaaag gccaaaagct agaggaatgg tatttcagca 420
catatgatca gatttggaag tgatcttaaa gagacatcta gtttcacaat ctatagacta 480
tggattccaa ctcccattag ygggtcaaag ccagggtttt tataaaattg aaataaaata 540
gaataaaaaa tatcagagag cagggagtga aactatgtat tgtttcaagg gcaggcattg 600
ttttgtgaag gttgtgtatg ccaggtccca aagtaaaatg tgttttttac tgtgggtaga 660
ggtccaacca ccaagccact ctccacgcca gaagccagaa tgatctttct aaatctgatt 720
acgtcagact cttactttga aattttctgt gttttcctat ttccattaag attaaagaca 780
aaacaaaaca cctcacaatg cctacccagg gccctgctgg tctcccgttc ttctgaggtc 840
atcccaagcc tttgaaggtg ctgttcctgc ctgtacactc tacccttgcc ctttacacct 900
tctaagtccc attaatcctt caagattcta ctcaaatatc actttcccca agaaacctct 960
gcctaagttt cttgatctag tctaggttgc tagactagga c 1001

<210> SEQ ID NO 57
<211> LENGTH: 1001
<212> TYPE: DNA
<213> ORGANISM: Homo sapiens

<400> SEQUENCE: 57
ctggaggaag tgggtgaatg ggtcagatct catttggtgg cctcttgggg aagaagggtg 60
atatactcct gttttctctc tgaaatattc ttcctgaggc ttgtggtggg atccagggtt 120
aaaactgagt gaagagaaaa tattgccttg agaaacaata atgactctgg caacccacct 180
attctttagt agcccatctc aattgacctt cttttaattg ttcatattgg acagactgga 240
gactgcagtg tggggagagt catcctctta cttatcttgg cctttggctt cccactgcag 300
acagcccttg caggtccatc caggttgggg aagatggttt taaaaggttc attagttaag 360
aaaggccctg gggcctggaa ataaagggtt tgaggaggag agtagagggt ggggtcttcc 420
tccccggacc tcacgattgg gaatgaggat ttttttagc tacacgggtc tgactagagc 480
tgtaaacgtt actcagattg ytcactatgt ctcttcccac gagcccctcc ctgtcaccac 540
ccccctgctg tcaaaccata tcttcgtgga ccagccatgc gggacatccc tcttaatggg 600
agcataagag tgttgtctca gacccttatt ttgttagttt atgtttccat gaagctctta 660
atgtttatta aataaacaga caatgagttt gtgtgacatg cccacagctt ctgtgtatgt 720
gacacatgcc tagcctgtgt tctgggagtg tatgtcactt tggcctttgg ctggggaact 780
ggtgatggtg ggaggccact caattactct ctctgcaact gtataactat taatacttct 840
tcagaactgt gggaaatggt tctactcatc agctttatgg aatgtgggtt agggagaggg 900
gacagaatct cttcaaggtc tggatgctaa acgtacccct tccttattcc ctcccaatgc 960
agaaaaaggt ctgggatgtt ctgacagggc catctctgcc t 1001

<210> SEQ ID NO 58
<211> LENGTH: 1001
<212> TYPE: DNA
<213> ORGANISM: Homo sapiens

<400> SEQUENCE: 58
attttcattt gtgtttttt aaatttctag tgaggtcatc taattcacct ttaaatattt 60
tatcttattc ttttgttttc aaatgctcta cctagccttt caagagtatt cttcacaacc 120
aaagcagtcc taagcctaag cagaaaggag aaataaagtt gatgggggaa aaatgtatat 180
atttttttct aaaataaggc ttaggagtaa tttaaaacaa aatgctgatt tggtattcaa 240
ttgtcctctt taagggctct taatatgctg aatataatta aaacaagcaa ttagcaattc 300
actcaaattt atctattttt caagttaaat aacattctaa taagctaaca agcacaaaac 360
agatcagcag ttatcataag gtcaggggtc ataaatatgt aaatgcctac aaatgccagg 420
cattaaacat aaatgagtga actgaaagca cattcactgt ctcaaaggga gagccacaac 480
tcagttccat cttattactg ycaagtgtaa attcaagttc aattttgccc tatttttcaa 540
acttcaaaag gcataaattc agattttaat gtaaaatctc ctgattttta aatgctgaag 600
aaaaaaatcc aaaaaacaat ggtgggccct tctggataag tttgttctct gccctagata 660
aattaataga ataagaacaa aatctaattt agttattact gatgacagta agtcaagaga 720
aatttgccac atcacaaaaa tacacatttg tatttctgaa aataaaacta ctgatataaa 780
tcatgacctt tatgtgaggg tctgaaaaga tcaatatgga atcaacagtc catttctgaa 840
gatcattcac agatacactc tgtcctcctt gagttcaacc tttagctggg gttagacaca 900
cctctagaga agtacataaa actttgcaag gaccaaaatg gaatacatgg ttttaagaaa 960
atcaacttct aaagcttcaa ctttatcact ctttcctata a 1001

<210> SEQ ID NO 59
<211> LENGTH: 501
<212> TYPE: DNA
<213> ORGANISM: Homo sapiens

<400> SEQUENCE: 59
taggggaagc tttattctga gatctgcaca aaagtgggtt atcctggcag cacagtgtac 60
ctcgtagttg ttctctgatg tgtaaaactt ggtgtaacac atctgagtgt gtgtgttggt 120
gttttattcc agtagttaaa atagacataa gacaaattca tataaaatgt ttgtagactg 180
caatgtcttc tgaagaatgc tgtcagaaaa tcattattct aggtccccag gtttacatcc 240
ctctgtgaga ygctcttgta ccagttgttg ggtaatttga acagttgcct ttgtggtacc 300
attaggagtc tcaactttta aggatcactt acagttctgt gcataggtga ttttcaaagc 360
acctgggtga agttacatgg ctctagaaaa ttgagcttta gaaaacagca ataacactga 420
aacaatcttt gggagtgagt tatcagagaa cgtgcattgt tgccaaggat gctggcataa 480
attctgggaa cctcaaaata a 501

<210> SEQ ID NO 60
<211> LENGTH: 807
<212> TYPE: DNA
<213> ORGANISM: Homo sapiens

<400> SEQUENCE: 60
aagtgtatag actgcacctc cccactgtct cttcctccta ctctggccag gtgaagtatt 60
tgctctccct ttgccctcca ccatgatcat aagtttcctg aggcctcccc aaaagctgat 120
gtcaccatac ctgtacggaa tcatgggcct atggaaccgt gagccagtta gcctcttttc 180
tttataaatt acccagtctc aggtatttcc tcatagcagt gtgagaacaa actagtaaac 240
agtgtaaatg ctttgtaaat agttgttagt taaactgtac tgttttggga ataatgacaa 300
agaaaagagt ctgtatgtat tcagtacaga ggcagccatc catttttaa aaatatcttt 360 aatccacaga tgcagaaccc atgagtgtag agggctggac tgtatacatg aatacatatt 420
gacatcttta tttctatatc tatatatcca aatatatttt gaaaatcatg agtttacact 480
gatacctcta gtttgaatcc rataacacag gttcattcta gtttactccc ttttcatatt 540
tatacctttc ttctctgaca gtgagaaatc aggcttcctt tatcctcagt atattcactt 600
actggctaat ttcccctccc cattgcctat aaactactca tctcccattg gtgctgccac 660
cacaatccct caatctcata tgcatatggg tgacctcctc actccacttg gtctctgaca 720
tcctgtgtga gctccctgtc actgccctcc cccccatatg ggtgctcttc tcacccctct 780
ttggcttaaa aacccaattc tgggttg 807

<210> SEQ ID NO 61
<211> LENGTH: 1001
<212> TYPE: DNA
<213> ORGANISM: Homo sapiens

<400> SEQUENCE: 61
ttatgcaaac cttgagtttt atgcaaataa gaattcagtt ccaagcacaa ataattaaaa 60
gcagggtttt tacagtcacg attgcccccct ggacatttga aattcaagtg agacatgggg 120

```
caattcttca ttctgcagaa atttccatgc aatgccagaa acctaatatc cctagcccta    180

tgtacaaaat gctagttgtg ccccctttat cactgtgata actaataggg ccttctgcat    240

gagtctaaac actctgtaga ggcgggtttg ctatggtcct gctggtaggg cagggactat    300

gctctaatcc cttgaataac ttctcacttg gtggagtgtt gtgtacttgg ggggattcaa    360

tgagtagttg tgaattgatg gagttacagt agcactgaac agagatgaaa ggcagcaaaa    420

tcagttagta tagtacagtc ttccctaagt atcctctggg gattggttcc agaacctccg    480

cggataccag atacccaaat yctcggatgt tcaagtccca caattggccc tgaagaaccc    540

acagataggg ggtgccaagt gtatttcaaa accagtttga tacggaattt gaaaatgtga    600

actgtggtaa gcagaataaa gatgtccacg tcttaggctg ggtgcagtgg ctcacacttg    660

taatcccagc actgtgggag gccgaggcag gtgcatcact tgaggtcaga gtttgaggcc    720

agcctggcca gcatagtgaa accctgtgtc tactaaaaat acaaaaaata aaataaaata    780

aaattagctg ggtgtggtgg tgcatgcctg tagttccagc tcttcaagag gctcaggcag    840

gagaatcgct tgaactcagg aggcagagtt tgcagtgagc caagattgcg tcacagtact    900

ctagttaggt gactgagcaa gattctatct caaaaaaaga aaggaaaaaa aagatatcca    960

catcctaata tccagaactg gtgactattt tatgttacat g                       1001
```

<210> SEQ ID NO 62
<211> LENGTH: 1001
<212> TYPE: DNA
<213> ORGANISM: Homo sapiens

<400> SEQUENCE: 62

```
tctcattgca ttttttttaa atttttaatt attatgacta cataatagtt atatatattc     60

ctcatatctc aatttaatta ccacaatcac tgtttttaca aggtcccagg caagaagagg    120

tgaggcaaat ggaggctctg aggaaagtgg ctccaaagcc tacatgatgg aagataactc    180

tggaagagaa agagatgacg ttcctaagct tgtatagcaa aacttgagag aaggtaacga    240

agatgtgaca tctgaactca gagaaatata acttctatag aaaagaaaca aggccttgca    300

gctctataag gaacagtaaa taaatcaagt atgcacacaa gaagtaaaaa aatatatcca    360

agtagaaagg aagcttttca tgaaatgtcc acagagctca tgctctgtag tgactgtaat    420

gcaagattca aggctctatc tagaaaactc ctagccagtc ttgacggacc aagccctaca    480

ctgagcatgt acagagtctt yctgttccat gcagtacttg ctaacaaaac taatttaaat    540

gccttaccat gactcgatct cctttaaagt acctcattag tccttgatat ccctttgctg    600

tatctctggc ttgccttgcc actgctctgt gagtccccac aactcctcct ccacacatac    660

tcttccccca agagcttggc acagaataaa gatccatttt agatctggat ttaaatagtt    720

ttctttacta gctcatttcc ttatctacta atgagggaaa taccacctac gtcagagtgg    780

gaattaaatg aaataataaa cctaaagacc ccagctcaat ggttcaaaca taaataatgc    840

caaatattca ttcctctccc catgcccata tcctctcacc aagccccaat gttctatagc    900

ttatgaccca aaacgctaaa agtagaacat tctaatattg agcatattaa cagaagcttg    960

aagagatatg caagttataa atctgttttt gttcttcctc a                       1001
```

<210> SEQ ID NO 63
<211> LENGTH: 1001
<212> TYPE: DNA
<213> ORGANISM: Homo sapiens

<400> SEQUENCE: 63
ctacattaga aacaggtttt ggaggagtag tgggaacatt gggtgatttc tagtggggtt 60
agagaaagca gtacctggtt ctttggccac atctaccaaa gcaaagacct agacttgtag 120
aggagagtat tgtttgcttg tttgaggatt gtatttccca ggtttgttca tttgcatgag 180
tggctgaata atgtaacaga gacttcagaa gtaaggaaaa tggttgtcac caaaatatct 240
tgttttacct ttatttggac taaatggaaa acacatgttt aatagctaag gctattgagt 300
gcttatcatt tgccaggaac tgtttctgag cctttcacat ataacacctc attttatcca 360
ccctctaccc ctaacaaatg gtgtggtttg agttggcctt ggtgaggtat gaaaaggaaa 420
caaagcagtg acctcttcct gcaggctggt cagatgtttg ggataacatt ccttagcatt 480
cttggtggaa gtggtgattt ygttgaaagc tgcttcccag ttgctctgga gtgcaggtgg 540
gaggggtgga ctttggcttt tccaaaggat cccaggaatg ggaaggacct taaagatcta 600
gaccaggggt atccaatctt ttggcttccc tgggccacat tgtaagaaga agaattatct 660
tgggctacac gtaaaatacg ctaacactaa tgatagctaa tgatcttaaa aaattgccaa 720
aaaaatctca taatgtttaa gaaagtgtat gaatttttgt tgggctgcat ttaaagccat 780
cctggactgc atgtggccca tggccatga attggacaag ctttatctag actgttctga 840
actactcatc tgcctccccc agccccacc cccaccccac acatccagaa ttctccaccc 900
attggttgtc tggcctctgc ctgaatagct gagtacctgt cttttccaaa actacccctt 960
gaggggagac ttacagcacc ctgtagcata gtatatgata t 1001

<210> SEQ ID NO 64
<211> LENGTH: 1402
<212> TYPE: DNA
<213> ORGANISM: Homo sapiens

<400> SEQUENCE: 64
aacttgatcc ttaacagaat ctcatgagag ctataagtct tattattatc ccctttattg 60
atgagaaaac tgaggcccaa ggaggttcag taacttgacc aaggttaaac ttccactagt 120
atgtggcaca tgtgtgattc taatcaaggg aggctggctg caaagcctct gcttctgtta 180
ttgctagaat ctaataagtt atttactaag tatgtaagga tacagtctca tttaattctc 240
acagtaacat tgtagatgag tgattagaaa atagctaaaa gacagacact tctcaaaaga 300
agacatttat gcagccaaaa aacacatgaa aaaatgctca ccatcactgg ccatcagaga 360
aatgcaaatc aaaaccacaa tgagatacca tctcacacca gttagaatgg caatcattaa 420
aaagtcagga aacaacaggt gctggagagg atgtggagaa ataggagcac ttttacactg 480
ttggtgggac tgtaaactag ttcaaccact gtggaagtca gtgtggtgat tcctcaggga 540
tctagaacta gaaataccat ttgacccagc catcgcatta ctgggtatat acccaaagga 600
ctataaatca tgctgctata aagacaaatg cacacgtatg tttattgcgg cactattcac 660
aatagcaaag acttggaacc aacccaaatg tccaacaatg atagactgga ttaagaaaat 720
gtggcacata tacaccatgg aatactacgc agccataaaa gtgagttcat gtcctttgta 780
gggacatgga tgaaattgga aatcatcatt ctcagtaaac tatcacaagg acaaaaaacc 840
aaacaccgca tgttctcact cataggtggg aattgaacaa tgagaacaga tggacacagg 900
aaggggaaca tcacactctg gggactgttg tggggtgggg ggaggggggg agggatagca 960
ttaggagata tacctaatgt aaatgacgag ttaatgggtg cagcacacca acatggcaca 1020

```
tgtatacata tgtaactaac ctgcacattg tgcacatgta ccctaaaact taaagtataa   1080

taataataaa ataaaataat aaaaaagaaa atagctaaaa gatgtgaagt tggctagtct   1140

aaagattcaa aagtaatgaa tgggagaaag agaaattaga ctcaccatgt cctacttatt   1200

thgacttttt actgagctga actgcttccc ctacctgcat atccaggaaa atgggtaagg   1260

tctggtagat gctttcagcc ttatcgtgct atgatgtttg ggccgcagtg ttatttgctc   1320

attagtcctt tcttgtttct taaaatttaa catttagcca ctgttttgta aattctgact   1380

taggtgccaa gttatggcgc ta                                            1402
```

<210> SEQ ID NO 65
<211> LENGTH: 2022
<212> TYPE: DNA
<213> ORGANISM: Homo sapiens

<400> SEQUENCE: 65

```
gctgggttga agtgaggctg gaggtggagg caggggccag tgtagtggtg cagagccact     60

gaagagctta agcagagaag ggacataata atgtttgggt tcttaaaaga tcacgttcag    120

atcctatatg agcaggtgat ttgagggggc aggagtggat ctgttagaag gctattgcaa    180

gtggtccagg agcaagaggg tggtggcttg gaatagtatc atagtagtag agatggagag    240

aagtgaatgg atgtaagagg tatttaggga ggtagactgc attgaacttg gagaatgact    300

aagataggaa gagaagggga caatgcttgg atttctggct ttggaaacca tatggatgac    360

catccttgtt cctgagccag acctattgtg ggaagggcag attttgaaag aaagatcatg    420

gtttagttgt tgacatgctg aatttaaggg ttggagtaca tacaagtgaa gttagatcaa    480

tagatctgat gatcggaggg gagatctggg ctgtgcataa agttgggagt catctgggat    540

ggactgaagt catgagagag aatgaatggt agcagggaat ggggattgga catgtgacta    600

ggaataacca cagaggccag ttgaaaatgt atggaaacga gaacatcaag catgaagggc    660

catgcccagt gctaaggaga aatctggtta ggaagtgcat ggatttagca gcygtgaggt    720

tggatttagc aatcaagatt ggcacctcaa gcaggagaaa tttaagtgga gttgtgggga    780

cagaagccaa ttttgaacac tagatgagtg aattggaggc aggaatatga agacactgag    840

tatgggtacc ttttttgaga agttgggctc aaagggtaga gacagttaga ggggacctgc    900

aagaggtgtg taggatccag gcatatagct ctaggtctaa acatctctat gtttggatat    960

ttagagatgg aagagaaagg atatttagtt gcttaaggtt cctgcaaaga caggtgggat   1020

gtaacccaga gcccacacga agggacgggc atttatctcc agcacttcag aaggagagga   1080

agaggagggg gtgggtacag ctgcagatgc aggcaggtgt ggaggtttgg agtggaatgg   1140

taagtgatac cattctgata atttctgttt tctctgtgaa gtaggaggga aagtcatctt   1200

cccagatgaa gggaacggaa tcaggttgct gggtaagatc agttctccag ctgtgcttgg   1260

cagctaccac tgcaagcatg gaataggcgg ctaggtaagt tcagccaaga ttgaagtttt   1320

actctgtggg agtaataaaa ggacaaggaa cacgaaggct aaggacatta acacatggag   1380

gaatgatttc agtggaggtt cagttggatg aagataggtt agtgctgatg gagaatgacc   1440

tggcagtgtc agggggcaat aaacagggta gtggtagtac ctgaataagg gaactagcta   1500

tgagtgcttc tccaactgta atgctaatgt gaatcacctg gggattttag taaaaacgca   1560

gattctgatt cagcaggtct gggctgaggc ctcagattct gcatttctaa caagttcctg   1620

tcacgccagc ctctctggcc cgtggatcac actgtgaggg ccaggtgtgg tggtgcatga   1680

ctataatcca aacactttgt gaggcccagg tgggaggatc acttgagctg aggagtttga   1740
```

gaccagcctg ggcaacatag acgtcatctc tacaaaaagt ttaaaaatta cctgggtgtg 1800
gtggcttgtg cctgtagtag ctacttgaaa agctgaggca ggaggatcac ctgagcctgg 1860
gaggtcaagg ctgcagtgag ccgagattgc accactgcac tccagcccgg gtgacagtaa 1920
aagcctgtct cttaaaataa aaaaaaaaaa aaaaaaaaaa gatttcgggc agagagtggg 1980
atgcctgaat tagaaatcgt ttgacatggt ataatctcaa gc 2022

<210> SEQ ID NO 66
<211> LENGTH: 1001
<212> TYPE: DNA
<213> ORGANISM: Homo sapiens

<400> SEQUENCE: 66
gtggcttctc tttggaaaca gttcactggt tttctcaagg gaccaatggg ctatgaagac 60
cagggactgt ccaagctggc cactcgggaa atgaaaaaaa atatgtgacg gaacatggga 120
aagaaccaca agtggaagaa gtttggacac acaggattct acctttttgc tcattctacc 180
caaaccatct gcacattgat aaattattag gatgagctgt gcatcctact ttacaatata 240
catgtccatg ggggagaggt caatagaaac agttaccacg acagttggtg gagtcagaac 300
atctggcggc tacacagaca caccagctgc gtgacttggc aaactcagta tctctgtgcc 360
tcatattcct catccgtaaa atggagcagt gacgaggata ttgagagttc atcaaaaagc 420
acttactata gtgccaagga cacagctaag tgctcaaaga ttagccatga tgatgatctg 480
actatctatt tttatccctg yttgactaat ttttgtggga gaacaagggg aagaggtgaa 540
gaattgatgt aactttcata tattacctat cctacttttg tatatgtttg aaaattctta 600
taatggtaag ttaaattaaa aaaaaaaaac ctaatgtgtg tgtgtgtgtg gtgttttttt 660
gtgtgttttt ttgtttgttt ggttggtttt tttgagatag ggtgacgggg tcttgtcact 720
caggctggag tgcagtggtg tggtcacagt gtgatcacag cctaaattcc taggctcaag 780
ttatcctccc acctcagcct cccaagtagc agggactaca ggtgtgcact accacacctg 840
gccttatttt gtgcaggaga gaataaggtg aagaccaatc catttctaat atttttaagt 900
ttcttctatc attagatttt ctaaactaat agcaaacttt tttgtaaagg gcccaagagt 960
aaatatttta cactttgcag accatatggc cctgttgcaa g 1001

<210> SEQ ID NO 67
<211> LENGTH: 1001
<212> TYPE: DNA
<213> ORGANISM: Homo sapiens

<400> SEQUENCE: 67
tcgtcttgaa attcttaatc atatttgaac aatgtcccta cagattatgt agccagtctt 60
gctactaccg agctgcactt gacctccccg cactcatcct ggccatactt catccctgtc 120
cctctccttt ctactgcctg gtgctttgtc ccatttcctt gcccccaagg ccttaggagg 180
gtgtaaaaaa aaaaaaagat aaattcctca gggaaaagat gtgatttggc tcacagcata 240
tggaatattc aaagatagac atcatctgtt gcccacattt ttatgagact gacatgctgc 300
ctgtagcatt gagaaggcac tggttgccta cacttttaga agtcatttat taatggcttc 360
ctagggcatg ccaactctaa aatcaagcca caaaaatgat accaggtaaa aattgatcct 420
gtgaataact gtgacggtgg catttgggtg aaaggtcttg aaatgggctg tgtcttttcc 480
ctcaactttc ctcacccgct yttatcacac tctcccagcc agtgtcagat tacttctctt 540

-continued

```
ctcatctgtc tcataaatag ttctggcttg agttatcccc taccgtgatg acatatgatt    600
attcaaagaa agattttata gaaaatgcat tgtttctatt tggagttggg agactaggga    660
aaggtataaa gcacgccaca ggggcacagc cttgattgac tttctgtgct cagcttagcc    720
gttcaagccc ggggttgtgt ctgggtaaag ctgtttgact ttgggtaagt cctttaacaa    780
cctgaggtcc cagtgttctt aactttctac agttttgttc taatccagca ttcttgaact    840
agcacataag cataacttgc taaataagca ccacttgcta aatacaggct tagtgacaag    900
gaagttattt ggaaaatgaa aagagggcaa ttctcccatc aggacttgag aagccttgga    960
gttttctttc tttattgaaa agactcatga ggcctgtcca a                      1001
```

<210> SEQ ID NO 68
<211> LENGTH: 1958
<212> TYPE: DNA
<213> ORGANISM: Homo sapiens

<400> SEQUENCE: 68

```
accccaaggt ggaagcttta catgactgag aaagcccatc cactcattgt catagaatca     60
actattaatt caacaaatac ttatggagcc tttgccatgc ctatgagcct tgtgctagaa    120
gccagggata agtaaaataa attctgcacc tgcctcctgc aacttagtcc aatttccagg    180
tctcccttag atttttctct gttttaattt ttattttgaa aatggagaca gggtctcact    240
atgttgccca ggctggtcat gaactcctgg gctcaagtga tcctcccgcc taggcctctt    300
aaagtgctga gattacaggc atgagccatc acacctagcc tctctcttaa aacaacttta    360
ttaaagatgt aattcaggct gggtgtggtg gctcacatct gtaatcccag cacttgaaaa    420
ttacttgaag ttgggaggtg gaggttgcaa tgagctcaga tcatgccact gcactccagc    480
ttgggtaaca gagcaagagt ccctctcaaa aaaaaaaaaa aaaaaaaaag taattcacat    540
accatacatt tcacctgttt aaagtgtaca attcagtggc tattagtata ttcacagagt    600
tgtgcatcta ttaccagaat caattttgag cctttttttt tttttaaccc caaaaagaaa    660
cctcttccct ttaacactta tccccagtcc acctatcctt ctcagccctt ggcaacagct    720
agtctacttt ctgtctctat ggaccggcct agtctagata ttttatataa atggaattat    780
ataatatgtg gccttcatgt ctggcttatg tcatttagca taatattttc aaagttcttc    840
catgttgtag catgggttag aacttcattc ttcttttatt atggttgaat gatattccac    900
tgtatgaata taccacatct tttttttttt tttttttttg gagacagaat cttgctctgt    960
tgcccaggct agaatgcaat ggcacgatct cggctcactg caagctccgt ctcctgggtt   1020
caagggattc tcctgtctca gcttctcgag tagttgggat tacaggtgca cgccaccgca   1080
cccggctaat ttttgtattt ttagtagagg tggggcttca cctccttggc caggctggtc   1140
ttaaactcct gacctcatga tccacccgcc tctgcctccc aaagtgctgg gattacagga   1200
gtgagccacc ccgccgggcc acatcttttt ttaatctatt ccttcactaa tagattgtgg   1260
gttgtttcca ccttctcact atgtgagtaa tgctcttatg agcgtgcata caagtttttg   1320
tgtgggcata tgtgctcaag tctctgatcc cctagatgtc ttgcctatcc tacagatcca   1380
ggcctaccac aaaaaagtgt agaaggatca tataccatga gaacataaag gagggacatg   1440
tagacttaat tagggagtca gggaaggctg cccctgaggc caccatatcc aagctgcggc   1500
ttgagagatv ggttgaatag aaaagttttt caaactgcag ctgatcaccc attagtaggt   1560
tgtgaattca gtttagtgaa tcatggccag catttttttag gaggtgaact aaaatagaat   1620
agtagatgtt agaggacatt ccatgtggta agggtaagta ttgttgcatg aaatttattt   1680
```

```
tcagtagcta tatgagcgca tctagcaaat tgtgacgtaa gaagtattct atattccggg   1740
ttgcaatcag aaaaatatga aagccactgc tctagggatt ttttaaaagg agattattta   1800
ttaatctgga gctttaaata tggttccact agaagattgg agagatacag gagagagaag   1860
aacctagaaa gctgaagatc ctttgaaagc ttaaagttct gtgatttcta cacttttaaa   1920
atgattcatt tattcaacaa atattaaaat atttacca                            1958
```

<210> SEQ ID NO 69
<211> LENGTH: 1001
<212> TYPE: DNA
<213> ORGANISM: Homo sapiens

<400> SEQUENCE: 69

```
tcatatactg caacacaaca cacacacacc tcacttacat agacttttga tttaagctgt     60
gttcagattt ctcttagcac attcaagttt tccttccttc ttcccagaag cacctaaagg    120
ctgtaatgag aaacatattt tttactcctt tgttccctct ctttgtgtaa aggcatccca    180
agaaaatcag tgaaggattt tgtgctctat gtccctaagg ctccatgtcc cagttatttt    240
tctctctcaa ctggggcttg atttccactt tattcaagtc tacttcttat ttccttcggt    300
gatccgaagt actggcagat tttctaaga cttcagacat gtggggagta actttcataa    360
ctccaaagaa tacactacca gaaatgtaac catctcagct gttctccgtc tactctgatg    420
ttgcctgtaa gaaataacaa gatgccactc tgttctttaa aagagatata taacattttt    480
cataagatgt ccttcattac wtggtgcaga attcgaactg atcgtttgtg gattaatcat    540
aataatgact tattttgttt atgttaacta aaaggagttt atcattttta tatgatattg    600
actgaatggt cataggaaat tgagatcttt ttcctaaaaa ggtgataaca tttactggag    660
tgttgtttta gtagataact tgatccttaa cagaatctca tgagagctat aagtcttatt    720
attatcccct ttattgatga gaaaactgag gcccaaggag gttcagtaac ttgaccaagg    780
ttaaacttcc actagtatgt ggcacatgtg tgattctaat caagggaggc tggctgcaaa    840
gcctctgctt ctgttattgc tagaatctaa taagttattt actaagtatg taaggataca    900
gtctcattta attctcacag taacattgta gatgagtgat tagaaaatag ctaaaagaca    960
gacacttctc aaaagaagac atttatgcag ccaaaaaaca c                       1001
```

<210> SEQ ID NO 70
<211> LENGTH: 1001
<212> TYPE: DNA
<213> ORGANISM: Homo sapiens

<400> SEQUENCE: 70

```
cattgaattg ccttattaat ctcttgggtc atgcaattca gtgatataac tagggttagc     60
ctgagtgttt caaagcaaga ttaatggaag ctcattcgcc agctgtcggg ttaggagatt    120
attcacaaat gttgccctgt catttgaatc tggtagggtt tgctgatgaa taaatgaacc    180
ccattatact gacagccacc tcactaatcg atcctaacta aaccacctta tcctcttcac    240
cttccaattg tgtagccagc aacttgccag atctcaggga cgttgttggg acatgtggaa    300
ggtctgagac agagggccgg aaggacagac aatgccacca actctattaa tcagtccgca    360
tttctcagac ctggctctca gcctactgaa tttgacaacc aaggatttgc gtgtagtttt    420
ttttttttt cattttcaat taatttccct ttttatgcct tcctaatttc tcttcttttc    480
tgactaagct atatatttac rctgtgaaat tgactgtcat taatcttttt ctgccttgat    540
```

-continued ttcctcaact aaaaaatggt taaactaata ccagcccttt cattcatggt gatcttggga 600
ggaaaaaaaa aagagataac tgatgtcaga gagtgctttg aacttaaagc aggaagattg 660
ttcaattata ataagactct tctatcttta tttttatgtg acatttagaa tgttagcgtt 720
gaatacgcgt caaggaagaa aatcccattt tgaatgacag tgttagaatg acggcctgta 780
agatattgga attgcatgca aaaaccaaga aaatgtgttt aaaaactgct aagaccaagc 840
cagctactgt ttcttttcaa agaatatatg tagggaatag gagaattagg taactctagg 900
gcataataaa aaagaagaac atgtgctttc tgattttgcc aatctatttt gtacttactt 960
tataattcaa ttttaagagt aaagtgtaat gtctgattca t 1001

<210> SEQ ID NO 71
<211> LENGTH: 1001
<212> TYPE: DNA
<213> ORGANISM: Homo sapiens

<400> SEQUENCE: 71
ctttgggatg gttggctgta cttttaacca ctactctgtc ttgtctctgc atgtgtgggc 60
atgaactttg ttaggttctg aggaggagga tggggggttg ggaggagctg catatgttct 120
ctgccccaga agaatcatgg cccaggggaa gaggtagcaa aaggaacaac tattccagta 180
tgacttgatc agtttcttga tggacatgtg tgcaaggcac tatagaagga cagaagagat 240
ttttacttta attaattgaa aattagtaat ttatatttgg tatatacgta atctaataat 300
tcattaagtg gagcaacttt tcaaactatt ctaacaaaat ctaacattat aaaactataa 360
catggagact gcattgctaa ataccttca tctacaaagg aaagttatag ggatttatta 420
tgttttctag atttctagct ctctagtgct caaaaaaatt gaaaattgaa aaattgaaga 480
aaaactgaaa ttgaagtgac mctcatcttt gttgaagaaa aaggaatgtg acaaaattta 540
tttctatgtg cagtcaaaaa gtgtggtttg tgaaatgtgt tgttgttgtt gatcttacag 600
gagaatcatg aaaaaagtct ccatggagcc atctgagcgc ctggctagtc tccaggcgct 660
gtgggacagc cagaccgtgg ctgagcaggg cccctgtggt gagcatgcat tttaaaactg 720
aaatgtgaat agctggatgg atatcccccct gccaggaagt taagtctatt cctagtgtgc 780
tactgtaaag gtgcaattag tttcaaggtg taattagcag cgcacagact ttagattggt 840
ggacaaaagt cctatattta agctgtattg catcctgcta tgtacttact atagaacagg 900
gaggagaatc tttgctgttt tcccccctaa aaaggaaaag gataatcagc attgtcaaca 960
tcggccatat ttaagcttta aaattttaat ttaaacatca t 1001

<210> SEQ ID NO 72
<211> LENGTH: 1001
<212> TYPE: DNA
<213> ORGANISM: Homo sapiens

<400> SEQUENCE: 72
gatttggttt ctgtctctac tgagttctgg ttgttctttt gattacaaga actactcaat 60
ttcctttaag taaatttatt tattcttaaa attctgttgc ttgaaactaa gaataagccc 120
taataggcac agaggaataa tttaactctt cctgatctgt ttcctcatct gtaaaataaa 180
ggaaaagggc acacatatcc cctgacccct cttaactctc tcatctttag ctagaattgg 240
gttctagtga ttctcaaatg gatgtgttct aaaagaggct ggctggccct gtgttggga 300 agcagaagtt ttagtaatta attaggttaa tatgaacttt atagttatat tttttctgta 360
ttccctgaat aactgtgact ctattacttg tgaatttatt taaaacataa atatgacagt 420
gatgactaga tgaggtctct tagcacacat gccctatgca gacctgtgag tcccctgctg 480
tctgctcacc caatagttga rggcctgggt aggagttctg ccacatgtga gttcttaaca 540
caaaatcctc atggaccctg tgggcctgga gctggatact tcactcatct tcacccttgg 600
cctcatgcta agaattacca tcctgccacc acttaaagat gcccattcat gttagtgtgt 660
cactgctaaa gtactgtcat taaagaagac ctatcattac tctgacttta aaatacattg 720
ttctaacaga atcactatgg gagattccag acttctgtat cagcgggtgc tttgaaaaga 780
ggatctgata tgtactggcc cctgtgttca cctgtgggcg aacattagac atgtttgttt 840
cttttatgct ttgataacac cttacaactt gcaatagtgt gactttggaa agaatgaagt 900
gattgtgtct ggcatgctgt atgtaaacat tccatttcta cataatgtga aaaggaatga 960
attaggtgaa aataaatgga tttgcacagg tgttagagta c 1001

<210> SEQ ID NO 73
<211> LENGTH: 1001
<212> TYPE: DNA
<213> ORGANISM: Homo sapiens

<400> SEQUENCE: 73
taagttttgt ttaacttatt taactaaaaa atgatgctaa tgaatgtgga ggggtgattt 60
ggatagaacc tgttctgtgt ggggccttca tgtaatccct agagaacgtg taaatcaaat 120
tatgcctgga ggaaatttta tttccaattt cagttgcttt actgatatgt taagggaatt 180
aaaaaatatt tagctcggcc tttcagagag ctgttattac tggttgaact atgactgtta 240
ttttaattct cattagataa ctagtatctt ttgagctgtt gttagctagg ctgtgtgcta 300
aaaagtttta tatacatcct cttatttaat cttcacgaca cttataggag gtagatacta 360
cattatgtgt ttttacagcc aagggtgagg tgtaggggat ctgataattc gctccaaatc 420
acacagctag taaatggtgg agctggtcca ggcgtgtctg tcttgagaag cgctgtacca 480
ttcaccttac aattatatct rtaggtattg tctgactcat agaatccatg cagtacatct 540
gtgcagcttc catttctgtc cttagcctca attcctttct gtctttagtt ctctatcttt 600
accttaaaat ctccatgtaa atcatgctaa cctagcacga tccatggtgc acccacttgg 660
cattttcagg gaaaagggat aaggcctata aagaaagtcc acacccagcg cctggttctg 720
cctgtgccca ttctgactgc tttatcttca gtgctttaga tgaatgtgca tcttcctgga 780
tgcttttcct tcctgcatga tttggaagaa ttagaatcag tcttccttcc atgagtttcc 840
cagggaatca gagggacttt ttaagcataa tgatggaatt tttattgtca ccttttgttg 900
taaaatgctc tatagatgag aaatagatta tatccatccc cccaccagct gtgcttcatg 960
gtaatggcca aaaaaatgtt cagaattaag actgggaatt t 1001

<210> SEQ ID NO 74
<211> LENGTH: 1001
<212> TYPE: DNA
<213> ORGANISM: Homo sapiens

<400> SEQUENCE: 74
tgtagtctgg actttcttag ggaagtcctt tacctgaaga atgagtaggc atgagccagg 60
tgaaggtaaa gcaagagggg gaagggatag ctcctaaagc agaggtgggg caggagccct 120
cctcttggga gagcaacaga aggccagtgt ggctgggttg aagtgaggct ggaggtggag 180
gcaggggcca gtgtagtggt gcagagccac tgaagagctt aagcagagaa gggacataat 240

```
aatgtttggg ttcttaaaag atcacgttca gatcctatat gagcaggtga tttgaggggg    300

caggagtgga tctgttagaa ggctattgca agtggtccag gagcaagagg gtggtggctt    360

ggaatagtat catagtagta gagatggaga gaagtgaatg gatgtaagag gtatttaggg    420

aggtagactg cattgaactt ggagaatgac taagatagga agagaagggg acaatgcttg    480

gatttctggc tttggaaacc rtatggatga ccatccttgt tcctgagcca gacctattgt    540

gggaagggca gattttgaaa gaaagatcat ggtttagttg ttgacatgct gaatttaagg    600

gttggagtac atacaagtga agttagatca atagatctga tgatcggagg ggagatctgg    660

gctgtgcata aagttgggag tcatctggga tggactgaag tcatgagaga gaatgaatgg    720

tagcagggaa tggggattgg acatgtgact aggaataacc acagaggcca gttgaaaatg    780

tatggaaacg agaacatcaa gcatgaaggg ccatgcccag tgctaaggag aaatctggtt    840

aggaagtgca tggatttagc agccgtgagg ttggatttag caatcaagat tggcacctca    900

agcaggagaa atttaagtgg agttgtgggg acagaagcca attttgaaca ctagatgagt    960

gaattggagg caggaatatg aagacactga gtatgggtac c                       1001
```

<210> SEQ ID NO 75
<211> LENGTH: 1001
<212> TYPE: DNA
<213> ORGANISM: Homo sapiens

<400> SEQUENCE: 75

```
gaactcctag gctcaagtga tcctcccacc tacagcctcc caaagtgctg ggattataag     60

cataagctac cacacctggc tgagaattct catttttaac tttctacctg gtggccctat    120

gtatggcaga tgcacctgac agcaataatt taacttaagc atactctgta tggcagatgc    180

acctgacagc ataatttcac ttatgatatg agggttgcca tgtggaggtt gtgtggaagg    240

aggtggggtt gggggaagga gtgttaagga aaaatgctat ataaacagca cgcttttttta    300

aagtgatggt tgttcttctg accagcccac tgccactgga ctgccctgta agttcccaaa    360

taaattctat gtttcacctg ctggctccat gtctcttctt cagtcttgtg aacctggtgc    420

catccctatt gaagttaata agggtcatat aatccataag gcaggattct cagtcatttg    480

tgggtaatgc tctcctttga raatctatca ccccctaaca tgcatgtaac acaacatttt    540

gcttatagtt tcaggagatc tataggcccc tgaagcccat ttctggccct tctaagagaa    600

cgtgaactcc agattcaaca tttctgttcc aaatgttcct gagcaacaaa attttctagg    660

tctacctcat cccttggaac ctgatccaac tgtgttccca aaactaccag actctctctt    720

ccatgccaca ttcatctgtt tcttgttttt ctatcatgaa attttgtatt ttgctactgc    780

ttttttacca aaattccttt agataatctc acggctttgc cgaaatccaa ttcacaatgc    840

tctgtctaac ccacgaggat ggactataac tacttcctcc caatcctaga caatgtttct    900

gatgtgttcc tttaagctcc gggagctgcc agtgaatgtg tacctaaggc cctagggaaa    960

gaatccctgc tttaaagagc ttaagaaaga ccatgaggga a                       1001
```

<210> SEQ ID NO 76
<211> LENGTH: 1001
<212> TYPE: DNA
<213> ORGANISM: Homo sapiens

<400> SEQUENCE: 76

```
cctccaggtg acaacacggg tggtgagagc cgccgcatga atccacactg cggctgaagg     60

tcaagaattg gcggtagccc atcggtagcc cagagaccca aactgtgtcc gatgtgagtg    120
```

-continued

```
aaggtcaccc cagatcagtg cgtcagttcc gttttggcgg ccaaatttct gacgatccca    180
tgtaagaaat gccacacctg tcaataggag cgactcacgc gctgggtctc tttctcggat    240
cgggtcgcca ccccagtgcc gggactatgc taaagactag agtctcagac ttggaatttc    300
gaggaaggtg ttccaaaacg ctgcgctccc tccggcgagg gacaagagca ggagcctggc    360
ttgcctgggt ccaaggacag tagctgggag gggtgtggca gccgcttagc ttgaaatctt    420
tcagataccc caccgaaata tcataaagag cacaaagaac ttttacgtag gaacaaaata    480
gtgaatctac aacaccttaa rcgcctgata acttcacaat gcatgcctag gaaaccaaat    540
agcagtcaaa tggagttagt ccccagagaa gaggaaacgc agaggaatct gatagggagc    600
aggcttcaga aatattgagc tgcctctctc ttctagaagg agagaaccaa ccctgagctg    660
aaatttctgc aaatagaact gagattatac cagacaatgt catggctgaa ggagggtagg    720
aaagtttata aagtgcttgt gttgctgggc acagtggctc acacctgtaa ccccagcact    780
ttgggaggct gaggcggatg gatcacctga ggtcaggagt tcgagaccac tctggctaac    840
atagtgaaac cccgtttcta ctaaaaacac aaaaattagc cggccgtggt ggtacgcgcc    900
tgtagtccca ggtattggga gcccgaggca ggggaattgc ttgaacccag gaggtggaga    960
ttgcagtaaa ctgagatcat gccactgcac tccagcttgg g                       1001
```

<210> SEQ ID NO 77
<211> LENGTH: 1001
<212> TYPE: DNA
<213> ORGANISM: Homo sapiens

<400> SEQUENCE: 77

```
aagcctggcc aacatagtga aaccccgtcc ctactaaaag tacaaaaaat tagccgggct     60
ttgtggcggg tgcctgtaat cccagctact caggaggctg aggcaggaga atgtcttgaa    120
cccgggaggt ggaggttgca gtgagatgag attgtgccat tgcactccag cctgggcgac    180
agagcaagac tctgtctcaa aaacaaataa ataaataaca aaaaataaat tcatattgtc    240
ttaaaccacc aaatttgtgg taagcaatag gaagctaata aaaagccact aagatagtac    300
catgaatagg gctaaacagg cagaaagaag tctacagggc ttttttctgg aacaattttt    360
agaggccaga ggagttcatg gagctcactt ttgttgtcat tgagagccct ggaggatatg    420
ttttgaactg tagagagagt caacagaagg aatttagagt cccaccaaca gttgggattt    480
ctgtatttgg agtccagagt rttaaccgtt ataccatggt atctttgtat aacaaaggtt    540
ctagggaaga cttgtatact attgcatctg gtcagttaac ctttaaaatg ggcatagatt    600
caatgtaagg aacactaata gcttctcata gggagaaaaa tgcaggttct cagatgactc    660
aatttgtggt ttgcacatat tcatgcccga gtccagagat agcatagaga gcattcggag    720
tgagctctga agaagaaaaa agtcataggt ggggcctctg acacatgaac ctttactcat    780
cccagcagat gattaactta cagtggtcta actgacttca ggctccagca aagcaaagca    840
aagctttcaa aagaagagct tctaggatac atgagggtga tgggcagtgg acaactttca    900
gtagccagag aaaagagcaa gaagcgggat gttgctccag aaaagaagtg caaatatgtg    960
agactatcta tacatgccca agtgtgcttc tccatttggg t                       1001
```

<210> SEQ ID NO 78
<211> LENGTH: 1001
<212> TYPE: DNA
<213> ORGANISM: Homo sapiens

<400> SEQUENCE: 78
atacaaggga atactgcaca gtttgtaaaa ggaaaaagaa gcaattctct ctatactaat 60
atggaaagat ctccaagata cactttacac agaaaaagca agatgcagag ggacgtgtat 120
agaatgctat ttttagttta aacaagagga aaaataagaa tatattttaa tttacttttt 180
tttagttctc aattgggtta gtttacattt ttaaacttca acaagcaatt ttgtaacact 240
tactgtacat caggcacttt ataagtatta attcaattct tctaacctca ggaaataggt 300
attatcatta ccctcatttt acattagtag attaggccac tacaaacaga gaggttatgt 360
aagtagtcca acatcacact gctagtcaca tgggggagcc agcattgaaa cccataccct 420
ctgactccac aggttatgtt cctaagcatc atattaagtg gactaagaag ttaatacatg 480
gagggaggga ggacagggtg ratgagagag ttgcgtgact ttatgtgtat gtagttttga 540
acgatgtaaa tgtgttacct attgaaaaaa tatttagaaa aaatgtgtat gactttgctc 600
aagttacttt ccatgtgaga ggcagacatc tcaagataag taatagtagt agcttgtagt 660
gagggtttac caaagtctta tctatagtcc tctgagactt tagggagaga atccttattt 720
aacctcatga gatagattcc ccacccccga cctgagctga gcagctaaag cttggggtgc 780
tgcaggctgg ggaggctgag cgcaccagcg cccatgacct acagctctcc ccttcgcaga 840
ccccttcttc aggagcgccc agccctggat cgcagccctg gcagggaccc tgcctatctt 900
gctgctgctt ctcgccggag ccagttactt cttgtggaga caacagaagg aaataactgc 960
tctgtccagt gagatagaaa gtgagcaaga gatgaaagaa a 1001

<210> SEQ ID NO 79
<211> LENGTH: 1001
<212> TYPE: DNA
<213> ORGANISM: Homo sapiens

<400> SEQUENCE: 79
atgaagagtg aaggaagaaa tgtaaatgag acacgtgcca ggcacacggg gacccagtga 60
ccagactcca agaaagcgca ggacagggct gggcgcggtg gctcacgcct gtaatcccag 120
cactttggga ggccgaggcg ggcggatcac gaggtcagga gatcgagacc atcccggcta 180
aaacggtgaa accccgtctc tactaaaaat acaaaaaatt agccgggcgt agtggcgggc 240
gcctgtagtc ccagctactt gggaggctga ggcaggagaa tggcgtgaac ccgggaggcg 300
gagcttgcag tgagccgaga ttgcgccact gcactccagc ctgggcgaca gagcgagact 360
ccgtctcaaa aaaaaaaaaa aaaaagaaaa agaaaaaaag aaaaaaaaaa agaaagcgca 420
ggacagaaag agcgaggtgc taagacttag agtggaccca gaggctctgg ccctcctgtc 480
tcccaccacg cactccattt ytgtcacatt tcaaacctat cgcttttacg atatatgttc 540
aaaaattgtt taatgaactg taaatggctt ggtaagggcc gcatcgtaaa tggcttggta 600
tgggccacat cgagaacagc tgtcaaatat aagcctaagg ctaaccacgg atctatttta 660
acactgagca gttgtggctg agtgtctgga gcttggcaga aagcaacgtc acaagtctgg 720
ctttttccca cgtagactga accctcgccc tcaaagctac aaacacaaca atttaaccaa 780
ctgagtgatc aactaggaga agaatcaata tgatctcttt caaaagctta aaatatgtca 840
aaatagtatt atctcagaaa gtttttttttt cccaaaataa tacaagacat tatcgaattc 900
ttatttaacc cttttctaaa atcacccacc cacctcattg aatttccttt aaaaaatctt 960
catcctggcc gggcgcgatg gctcatgcct gtaatctcag c 1001

<210> SEQ ID NO 80
<211> LENGTH: 601
<212> TYPE: DNA
<213> ORGANISM: Homo sapiens

<400> SEQUENCE: 80
actagagata atatgcatag cttaactaaa aattccaact gctaggaaag aaagtgcaca 60
aatgctaagg gaagaatgca gagaaaaagt gctcccacac atccaggctg acatgtcact 120
gatgtctgat gtcacctata cctctcttcc ttgtataaga aggggcagct ccaggcacag 180
tgcatcaaac actgctgtac aatggctctg gctcccttgt ggaccagaaa gaagcagatg 240
tttctggatg ggagttggga aatgatcagc caccttctcc ctgggccctg gaatcttcct 300
yttccacaag tgacagaaga cctcagaatc ttctctttca ctgcctaccc ctgaccagct 360
ctgccctgga cagtcccctt ccaaagccaa aggcagcccc aatccacagt tgtcaggtac 420
actcacctgg ggagtctgtg cagcatgcct ctgggtggct gttctggcag agcagcacca 480
accagggcct gtttatattt ccccaagtcc cagtgctcat gggcaactcc cactggtgtc 540
acaatgtcaa tgtcataatt tctgactttg ccaaaggaaa aggggtcctt ctgtacaatg 600
t 601

<210> SEQ ID NO 81
<211> LENGTH: 1001
<212> TYPE: DNA
<213> ORGANISM: Homo sapiens

<400> SEQUENCE: 81
agcattgtgt ccctgtgagc ccctctacgt tattttacct ctgactggaa cacacctcca 60
tcatttttcc ctcacttcct gcaagttgct gtctaaaggt gactgttcca catttttgtt 120
atgatagagg gtccttattg gtaccatgtg agaaattacc ttgatgccct ggtaggctcc 180
aagtatagtc ccatgcaagc tctcccagag gacacagcac aaataggttt gcagactatg 240
cagtgaaatg ctcaaatcac agcttcatta aaaaacatag caagcagcaa ggggaaaaag 300
aagagcaagt taatggttta gtgtgtaagt gaattggaag aaccacacta tctgactcaa 360
gtgtgagcag tttccgtata tctgatctct tttacatcgc tcaatcagcc tgtaggatag 420
acacagagat atatatgcct ggacccaacc aattagttgg ttgaatagcc atggatttta 480
tttttgttcc taaagtagag racttatggt gtctccaatt tgtggctgac tcaaggcctc 540
atgaataatg agtcagtgct tcgatgtctc atatatctgt gaattctgaa tgtgtggctc 600
cttttgtata ttttgtgcat caggaacatt aggtatcttt tgacccttcc atcccttata 660
tctatattta acaacatatg ctctttttac taactactta tgtctactta aaacatctta 720
agcatttttg cctacatttt actaactaaa agcatattta tcttttataa tagaattgct 780
catttacaaa agtaaatatg tgttacaatc catatcattt attggtgtat ccctgacata 840
tagtaggcac tcaatacata tatggaatga gagaattgtg ctttctctct cccttttcgc 900
cttcccctcc tcctgctttt tctcctactc tcacactgtc tctctctctc aaacacacac 960
acacacacac acacacacac acacacacac acattggaca g 1001

<210> SEQ ID NO 82
<211> LENGTH: 1001
<212> TYPE: DNA
<213> ORGANISM: Homo sapiens

<400> SEQUENCE: 82

```
tctcagcctc caggaccatg agccaaataa acttctattc tttataaatt atgtagtctg     60
tggtattctg ttatagcaaa aaaaaaaaga ctaaaacaga aaattggtaa aggctatttt    120
aatgaggtcc tagatggaaa tgaggagcaa ggtattggaa actagagtaa aggccatcct    180
tgtatacagt tgcaaagaac ttggggggatt gtgtctgcgt tctagggcct tataaagtgc    240
agaacttaac agtgacgaac tgggatatct ggtggaagaa atatctatgc agcaaagcat    300
tcagactgct gtgtggctgt ttttaactgc atacaatgag atgtgagagg aaagaaataa    360
agatggaatt tataattaaa agagaatcag ggtagaaata tttggaaaat gtatagcctg    420
gccatataaa taatagaaaa gtatgttcag gagagaaaac taagtgtgtg gctaagtgac    480
tttttactaa ggagataaac rtggacaaaa ggaaggtgct attcattaag acaatgggag    540
acagaccata aagcatttca aagatcttca agtctgcccc tacaatcaca ggcccagaac    600
tctaaaaggg taaaatgatt taggggaaag gcccaaggca ccctccatgg actcagctca    660
gagctgcctc aggtctgctc ctggggttcc agagcagcac tctgtggcca ccctagccat    720
ggctcattag gcccaggtat ggcttgatcc agaaaatgca agctgtagag cttggcagtg    780
tccatgtggt gctgatgcag caggcatgca caatgcaata gctgtgaaga cctggcttcc    840
tccacctaga tttcaaagga tgttgctgac agtctggggg cccaggcaga gaattgtgca    900
gggacacagc cactgcagag agcccctacg acaatgacaa gtggaaatgc ggggtcagag    960
ctgacacaga gtctccacta gggctgccta gtagagcatg g                       1001
```

<210> SEQ ID NO 83
<211> LENGTH: 1001
<212> TYPE: DNA
<213> ORGANISM: Homo sapiens

<400> SEQUENCE: 83

```
gcgggagagc tgggccactg gttaaacatt tggaacgttt gttatgaaaa gataaagcat     60
ttttcatcta gagcttagga atgactttta ggaaaaacct tacaggattc aggtgacatg    120
tttaagtcag aatgtgaact agttatttaa tgtagggctt acaagaatgt tcgctgtgtt    180
tattcatctc gtgttatatg aactagaacc aataaaaaaa aatccagagc caggctcagt    240
ggctcacgcc tgtaatccca gcacttttgg aagctgaggc gggaagatcg ctggagctca    300
tgaattcgag atctgcctgg gcatcatagc ggatacaaaa attagccgac cggggtggtg    360
cacgccttta gtcctagcac ttcacagagg ctgaagtggg acgatccctt gagccgggga    420
ggctgaggct gtagtgagcc gagaccacgc cactgcacgc cagcctgggt gacagcgaga    480
acctgacttg aggaaaaaaa rataatccag tacagaatga cacggtcata tcaaattggc    540
atgtaataga gaccccatct tgaaacttgc tactatattg tcttgtgcgt tgatagcata    600
ttatattaat gccgaacaca ttagtgacgc cgaagtagct ggtgcctaaa tggcttaaac    660
gcggaaaaac cacatacaga tgatggaaca aaaactggcc aatcagatta tagagcgggc    720
tttttaaaat ataagaagct tctttgtagc taggcgtctg acaaaaagct tgacaccaac    780
ttaacaaaaa ccaacggctg gaattcatac tctaataaca gactgcatgg gtaaactacg    840
tggggagtcc aaccaacacc ctggactctt gcttgccttg cgttactcga ttagggttga    900
gggagaactg cccgagattt ttcgaatgca aggaatcttg ctgcctgatc taacatgttg    960
tgcacagcca ttttttagag gtctctgggt ggctctgaaa a                       1001
```

<210> SEQ ID NO 84
<211> LENGTH: 1001
<212> TYPE: DNA
<213> ORGANISM: Homo sapiens

<400> SEQUENCE: 84
aagaaggcag tgacaaaggc ccagaagaag gacggcaaga agcgcaagcg cagccgcaag 60
gagagctact ccgtgtacgt gtacaaggtg ctgaagcagg tccaccccga caccggtatc 120
tcgtccaagg ccatgggcat catgaactcc ttcgtcaatg acatcttcga gcgcatcgcc 180
ggcgaggctt cccgcctggc gcattacaac aagcgctcga ccatcacctc cagggagatc 240
cagacggccg tgcgcctgct gctgccaggg gagctggcca agcacgcggt gtcggagggc 300
accaaggccg tcaccaagta caccagttcc aagtgagccc gcccaccgcg gaacgttcgg 360
tcagtctcgg cccacacccc aaaggctctt ttcagagcca ctcagtcttc ccaaagagaa 420
ctggcactca ctgttcttac agcaggtatt tcttacttgc tacaaagacg atttccaaga 480
ttcctttagc cttgttagaa rctaattttg gctcaagcct ctaatcccgg ttcgggaaac 540
cgaagcgggt ggctcacctg aggttagaag ttcgagacga gcctagccaa catggtgaaa 600
cccgtctcta ctaaaagtac aaaaaaatag ctgggcgtgg tggcggacgc ctgtaatccc 660
agctacccgg gaagctgagg caggagaatc gcttgaaccc ggcagatgga ggttgcagtg 720
agccgagatc gggccattgc accccagcct gggcagtaag agcgaaactc tgtctcaaaa 780
aagaaagaaa aagaaaagaa attaattagc actgcagtgt actgcatgtt gcagcaacgc 840
ttgagacaat tttatatctg aagaaggatg aggtttatca tcagacaaac ctagtaaagg 900
gaaaattcag ttcctgttga ccccaaagaa aatataatac ttaagtgtca ctggtaaaat 960
atccacagtg cttccggcgc tctgtcccta aacttcatgt g 1001

<210> SEQ ID NO 85
<211> LENGTH: 2052
<212> TYPE: DNA
<213> ORGANISM: Homo sapiens

<400> SEQUENCE: 85
tgaattcagt atatgttgta aagagggtaa ggtagcatag gttaattgaa tacgttaatc 60
taagggtaaa tacaaattaa aaatgagagg cttaattatc tgttgaaaac aaaagacttc 120
cctttccttt cccatcactt tcaaaatgtc tttctctgtc cttttaaaat gtatgtaaat 180
ccttttaatg gctaaatagg ccttataact cagaatattt tctcaatgcc tggagagcca 240
tccctttgaa atgttaatca ttaaaaaaga tagtggtctg tctcccagtt tccagcgaga 300
aaatgggctg aactttagct gtcacctgac ttcgaattgc aaaacctatc caatgtagcc 360
atacataata agcaagattt ctttctgctt ttgcaacctc ttcataaggt ttcctgtgat 420
aagcaactct ccctggttta atgcttattc aataataaaa ttatttcctt tgtcttcttt 480
gggagaagat tttaaaattg tatttcccca acattagtta acaagtatat ttctctactt 540
gagcttctca ctaatcagaa gccttttttct gtatctgatt tcatgagttt tcgcatagca 600
attagtgaca aggatagcaa tgaatggtaa aaggtggcag agcatgccat cccaaaatat 660
gccattttgg aataagaatt attctgagat acaggcaatt ttaaaaagag taggtacaag 720
aaaggcactt tgaccgttcc cttttacccc cttaaaagca ggaattaaaa ttcccmtgtg 780
gaagatgtcc tccctgtacc aaaaggaaaa gaacattttc atcaaggaca ggaagttgaa 840
accaagagaa ttctgtccaa gcagatctta aaataattct tgttttcctt tagccttcct 900

```
acatagttac atttccacaa tttactccat tcaacctact ataaaagcat ttaggttttg      960

ctacttcttt ggggtctatt attagagctc ccatgtccca tgccacataa aatttatatt    1020

aaatttatat ggttttctcc tcttaatctt atgtcagttt aattatcagg ccagccataa    1080

aaactcttaa gaggacagag gtaaaatttt gcctccccta caaggatatt tgagtttgtc    1140

agactcttta gtttctgaaa ttgacggtaa atttagttct gaaatagtaa acatacacgc    1200

agtataacat tttaaaaaaa tgttatgcta atcagtctgt tttctaacag gataactgac    1260

tatcaagata aacttagttc aaatagagta actctgagtt ctcacattct ttcacattac    1320

aaaacaaatc tggcagcaaa cttTgtcaga ggcgtttaaa ccagagaaac tccatcttga    1380

atagggGctg ggtaaaataa ggctgaggcc tactgggctg cattcccaga ggcttaaggc    1440

atttgtagtc acagaatagg tcagcacaaa gtacaggtca caaagacctt gctaataaaa    1500

gcatgcggta aagaagccag ccaaaaccta ccaaaatcaa gatggtgagg aaattgacct    1560

ctggttatcc tcactgctca ttatacacta cttataatgc attagcatgc taaaagacac    1620

tcctaccagt gccatgacca tttacagatg ccatggcaac gtcggaaagt taccctatag    1680

ggtctaaaag ggggaggaac tctcagttgg ggaattgccc accccgttcc cagaaaactc    1740

atgaagaatc cacccCttgt ttagcatgta gtcaagaaat aactataaat atccttagaa    1800

tagaacaaaa gaacaatttt ctttacttct ctaataaact tgctttcact gtactctatg    1860

gatttgcctt gaattctttc ttgagaaaga cccaagaact ctctcttggg gtctggattg    1920

ggaccccttt ccagtaacag ttacacttgc aaagtacatc ctgtgtccaa ccactgtata    1980

tttaattgtg aaatttatta aatattaatt taaataagtt gaaagacctt taaagacagg    2040

gcaattcaaa aa                                                        2052

<210> SEQ ID NO 86
<211> LENGTH: 701
<212> TYPE: DNA
<213> ORGANISM: Homo sapiens

<400> SEQUENCE: 86

ataagccaga aaatcggaag agggagaaaa atgaaaaatc agcaacaaaa ctgggtcgag       60

agtgaaaata gctttagtaa gaggaattaa gttcaattct atcgtggccc tgtagctcag      120

cggttggagc gctggtctcg taaacctagg ggtcgtgagt tcaaatctca ccagggccta      180

acagactgcc ctttgggttc yggtgtttac ctacacttct tgtgtcttat ttttatgttt      240

ttttgagaca agtctcgct cacgtcaccc aggctggagt gcagtggcgc catctcggct      300

ctatacaacc tccgccttcc gggttcaagc gattttttcc cgcctcagcc tcccgagtag      360

atgggactac aggcctgcac caccaagccc ggctaatttt tgtgttttag ggtagagaca      420

aggtttcgcc atgttggcca gactggtttg gaactcctga tctcaagtga tctgcccgcc      480

tcgcCctccc aaagtgctgg gactacaggc gtcaaccacc gcgccctgcc gaagggtgcg      540

tttattagat gccaaaacct aaaactggaa attattcaaa tcgataagca cccatttTag      600

cccaccttct cagaatacag gaatgtactg gtagcaaaag taggaaatgc tagaaataca      660

ctctggttcc aaaatggcag aagcaagctg gcttcactgc t                         701

<210> SEQ ID NO 87
<211> LENGTH: 1001
<212> TYPE: DNA
<213> ORGANISM: Homo sapiens
```

<400> SEQUENCE: 87

```
atttatccac tcttaaaagg gtatctttaa atagctgtgg tatccttttg tatttcagac     60
attttatgta atttaaattc tgattcatat ccctaatttt aggattaaag tgtttgttaa    120
caactaaaaa gcaaaacaaa acaaaactag gaagtcctta tctgcatctt taagattata    180
tcaaataggc tactgagtgc ttacctgtta acacctgctc caattgcttg caattgtggc    240
taatgtctta aaggtggtag atttctctgc tttccaataa aatcacattg ccagcatctc    300
cagatacaat tattctcatt ttgaatagcg aacattccat tgactagcaa aacaaaacat    360
ttgaattata tgagatatct agcagatcag aaagagacca tagcaattgg attaaaacag    420
aagttaatgg aagagaattt tagaaagctg ctgaggggat ctttatagtt tttatctgtg    480
atcactttag aatgttttaa ygcctagttt agaatactta cctagatgaa tacacatcct    540
tacctccttt cttacctgtg tattggttga ccttatgttt gtcatcttcc tcttgagttt    600
tctgattata tatatatttt taaatttttt agttattttt aattttatta ttattatact    660
ttaagtttta gggtacatgt gcacaacgtg caggtttgtt acatatgtat acatgtacca    720
tgttggtgtg ctgcacccac accaacatgg cacatgtata catatgtaac aaacctgcgc    780
gttgtgcaca tattttttaa tattaaaaaa ggtgaggttc aacagagtct tcaaagcatc    840
tttttaaatt gcactgtgga acaaaaatcg agacaagaga ggcaacaaga gttttagtcc    900
caaatctgcc atccaaagtc actgtataat tgggcgagtt agttaatagc tttggccgtc    960
agttttattt tctgtaacat tataaggttg ctgttttcct c                       1001
```

<210> SEQ ID NO 88
<211> LENGTH: 1001
<212> TYPE: DNA
<213> ORGANISM: Homo sapiens

<400> SEQUENCE: 88

```
attctcctgc ctcagcctcc cgggtagctg ggattacagc agtatgccac cgcgctcggc     60
taatttctta tttatttatt tatttatttt tggtatattt agtagagatg gggtttcgcc    120
attttggcca ttatggtctc gaactcctga cctcaggtga tccgtccgcc tcggcctccc    180
aaagagctgg gattacaggc gtgagccgcc gcccaaccac tttttttagt attttaaatc    240
aagtatcttt ttgtttgttt gtttcttctg tgcctatgct tacccagaca gtttcttcat    300
ttattttccc ccgccttggg caggcttcca ctcttcagac cctttcctgc acaactttgt    360
ccctgagcat aggtcctgga cgtaaaagaa gggacatcgt ctggagaaat attgaattaa    420
gaaaggcgcg gctgtgaaga atagaaatca gtgtctccct tagtctctca gttcggcgat    480
cttggtaatg ccctgtccca ygcctgctaa cgcgattcag cctcgatatc cccgtccagt    540
cccacgatcg caccaagaag agcttgcgag ccttcctgct acatactgac attaagaaac    600
cggacttgaa agggatccca gacaaacgtt aaacatgcaa caagagggat agggtgtaag    660
gaagagaatc cttggggcgg tgtctgataa aacagatggc tctcctttcc aggtgtttct    720
gaatttgatc cccgacgcct ggggcatcgt ggaggaactt gcataggaaa tcaaggtgtc    780
gcaggaaaga gaacacgcac aagcaaaaga taccttaatt tgtagtatac tcaatattta    840
tcgtacagaa gtgtatcgac gatagacaat gtgcgatgtg atgggtgctg ggaacttaac    900
gaactctcca cgcgcctaga cctcattgga tccactttct cttgggctgt gagccggtaa    960
aaaaaaaagg ggtggatgtg gaggacggtc caaaggattc g                       1001
```

<210> SEQ ID NO 89
<211> LENGTH: 501
<212> TYPE: DNA
<213> ORGANISM: Homo sapiens

<400> SEQUENCE: 89
tgtggagctc cgccactccc agcccgggtg aaggaaaact gggaaacaga atgaatgtga 60
ttatctattc gaagataaat ttccacaaag catgccgttt gatagtagct tataatgtgg 120
aagtaaggca tcctgtcatc cggccggtta gctcagttgg ttagagcgtg gtgctaataa 180
cgccaaggtc gcgggttcga tccccgtact ggccaagtat tctctgtggc ttttatcacc 240
agaatggata rtaacccaga catcgatcta aacgtgtacc tgtgtgtttc tccaggctta 300
actttgcccc gagaaaacgg atctgtgaat ttggtgcgcc ctcgcttact cgacagcggt 360
taatttgaac ggggacgttt ctttccgctg cctccaaggc atacccacat cctacccgta 420
aaacaaaggg gctataggca ccttacagtg acagaggtac gttacggttg gaggcttttg 480
tgatttttgt cctcctctgc c 501

<210> SEQ ID NO 90
<211> LENGTH: 501
<212> TYPE: DNA
<213> ORGANISM: Homo sapiens

<400> SEQUENCE: 90
tttttgatgc ggatcgaaag ggactggccc cggagcctac aacctgacgc aggtgggact 60
tggggaaatg tcgagaaacc taggtctggg acttgagttg gcttccaggg cacacattct 120
tgttcagaag aaacacattg caaaaatcgg gaggtgacgg gcagatgaag tgtcggcgct 180
tcgcctcggg actccagtgc aacctatggg gcttttggaa atgaggaagt cgatgactct 240
gcagggactc mtctgaccca ggagcagatg gcgctcgtct gggcactccc caggagaaaa 300
ggtgcatcgg gaagcagcct ggcttgtgga tggtaataag tcactgttga tgggttgggt 360
gcagggaggg atttaagttc ttgagcgaca gatgctaggg agtttacctg ctctggataa 420
cagtatcttg tggaggatag tcacctggaa aacagaaatg gcgtgactgt gttgaataca 480
ctgtttgatg attctgggca t 501

<210> SEQ ID NO 91
<211> LENGTH: 1001
<212> TYPE: DNA
<213> ORGANISM: Homo sapiens

<400> SEQUENCE: 91
tggggcctaa ggagattctg ttgtccagaa ttcagaaaat tctgcctcca gaaatacaaa 60
tatgctcttt tctaaacaag tgacaacaca atgtagccat aggctccctt aagcagccac 120
ctcatgtcaa ctaatagtct ttgctctcta gcctctctcc tccaaagtcc atttcgtctc 180
ctgaggcttc agctattact gtcagaccct cagttacttc tgatgaacag ggattaggct 240
tgagaaaatg gagatgcatt tagattggca gatatggggg acttcttaat gtgcttttat 300
tgctgcctta tctctgaaaa caggttctgg gagtttggga ataagtctga gggcatataa 360
aggattgaga ctgagtgact taggagtgtg agaggaaata tcttgatgtt gagaacaggg 420
ttgatgtgga ggggtattct ctgtgttatg catgtaaaaa gaaaaaaagg aaaaaaaaat 480
cattactggg aaagaaaaca ycccaagctg aagtccaaga aaggtacaca gaggaaacac 540
agaaacagtt gtgttagcag aagatgacat gaaacccagc tgacagtgaa attaggaagt 600

```
tgccttggaa tttcaagaac ttgcattctc aagtttatgg ttctgtgtcc aacagagcag    660

caaaatccag cacttcttct tttgagtctc catatcgtgc taacagaaag acaaggggtc    720

gggagatgca gagatgagga ggagctcaag agtgacagtg ttgaagagat tctgagcaga    780

actccacagt gatctgtgta actgatatcc aaccctgatc cctccatcgt ctgcctgtcc    840

aacccttgct tagatctcaa tgtaacttca cttcattgtg tccaagaagt tctctgatct    900

cttcccctgt ggatttagca accctccatt ttagaggcat tttcaggaat ctttttgcaa    960

tgcatcatct ctatgaaagc tcagcttcct gctccccagg c                       1001


<210> SEQ ID NO 92
<211> LENGTH: 1001
<212> TYPE: DNA
<213> ORGANISM: Homo sapiens

<400> SEQUENCE: 92

ttgctgtaat gaaataaaca aaaaaaaaat aaaaataaaa ataaataaaa aaggagcatg     60

tccagtacta cgtcataact gaagaatggt agactgcatg aaatctagaa atgagtgaaa    120

aagaattagg ctttgtcagt atgtttcttg caatctccat ggaagggagt gctctgtttc    180

caatgaggaa aatataaatt tttctagtct ggccaaagac catttattca ggtaaatagt    240

tgtttttca agacatagct gtaaaaaaaa aaaaaaaaaa aagtccttta ggaccagatt    300

ctctcatata attctatgtt ccaatctgtt cctttttgcc ctacaaattg ttcttcagaa    360

aaaaaaatat atatatatat atagacatat atatatagac atatatatag acatatatat    420

atatacatac acaaaaagtt atttggggca aaacatgaat catgtgcttt cttgaagcta    480

ccatataaaa gttccagtgt raagcactaa catgacaacc tggtttggat tagctctaat    540

caattcccca aggctcatta gcaatgtcat aaattaatca agattgtttc agcaacagag    600

ggtaccatgc ttggctatca ggtgcaaata acttaaaaga tctatctttg agtccttatt    660

tctctttatc tctctgtttt agaaatttta acttcttaat aactgagagt aatgggcctg    720

atatgtgaac tttgtaaaga agtgttcaat ttttttctga atgcttctct ccattctcca    780

cacagatttt agccaccgca cacacaatat tcttctagac atcttcttcc ctgctgacaa    840

ttccaggtta ttcaagtagt ccctgatggc ccaaacttca tatagacata tagatgcaga    900

aatatagaca tctatctata ttctctgtat gtttaataag gagtcacttc actattcttt    960

attctggcct ggagaatgtg tttaggtatc ttaatccttc c                       1001


<210> SEQ ID NO 93
<211> LENGTH: 1001
<212> TYPE: DNA
<213> ORGANISM: Homo sapiens

<400> SEQUENCE: 93

cgcttgtaat cccagcactt tgggaggccg aggccggtgg atcacctgag tcaggagttc     60

gagaccagtc tggccaacat ggtgaaaccg tgcctctact aaaaacacaa aaattagctg    120

ggcgtggtgg caggcacctg taatcccagg tatttgggag gctgaggcag gagaaacgct    180

tgaacccttg aggcggaggt tgcagtgagc caagaccaca ccaatgaact tccagcctgg    240

ctatcaagag cgaaactcca tctcaaaaaa taaataaata aaattaaaaa ataaaaaaag    300

aaaaagtaag gtattctacc catgaagctt gaaagatcat gctatacaaa taaaaaactc    360

tcatcttgga ttgacctaga tgagtttgta ggccaaggca aaaattacac ttctactgca    420

gagactgaac cctgcttcat acaaaacaaa agatacttga aactgtacta atgctaggaa    480
```

```
gaaagacatg atgacaagct vagagtgtca attggcagga caggcatagt tggggttctg    540
gggtttttct ggggacagaa ttactgggaa attcactgat cttccccaca tgcagaataa    600
tctgccatca gattctataa aacaagtttt tctactttac tttgaaactt tgaagaagat    660
agccccacaa aatattatca tattgcagaa aattttccta gatcattaaa gtaaaagaaa    720
tgttaattaa cagtaaataa cttgttaaac ttaaattttc cctctgctca aaataacttc    780
ccttcttctt caccacaagt ttactcaaat tttagatata cctcaagaat aatcttccct    840
tgggaggttt cctcagacca acgtgagtta catgtccttc ctctgtttcg atttgtcacg    900
acaaaaatat tatatgtatg aatttctaca tggaataaaa gtaggatttt attcttaaaa    960
aatatagttc ttagattttg ctctgcaggc attgagtttt t                       1001
```

<210> SEQ ID NO 94
<211> LENGTH: 1001
<212> TYPE: DNA
<213> ORGANISM: Homo sapiens

<400> SEQUENCE: 94

```
ttataaaaac tgatacagga agtaatagaa aatttaaata gtgctattaa acaaatgaat     60
cagtaattta aaaaccttct tacagagaac actcccagct tatactgctt caaaggtgaa    120
ttcttccaaa tatttatgaa acaaataaca tgaatcttgc acaaactctc aagcaataga    180
gagaaaggaa cacttcctaa aatattttgt aagacaagca tactcttggg tatcagacat    240
atcttatgtg ccacctctga ttctcttgcc atcttacctt gcaacttgtt ttaccccaat    300
agtcatggca atcaatttcc tctgagtgca gaaaacaaca ggacttcact gttcacctct    360
gttgaacttc tcgtcttctg ctataaggct tctctgctgc tgttgaaaca tgagctgctg    420
agcgatcttt gatatctgca catgcccaac ttctatatgt agggctatta atgctctatg    480
gagcaaaact ttgatcagtt rgatatagta gctgaccaat aatttttttt ttttttttgag   540
atgtgtcttg ctctgtcacc caggctggaa tgcagtggca tgatcttggc tcactgtaag    600
ctctgcctac ccagttcaag caattctcct gcctcagcct cccaagtagc taggattaca    660
ggtgtgcacc accatatcca gctaatcttt gtatttttag tagagatggg tatcactgtg    720
ttagccaggc tagtcctgaa ctcctgagct caactgatcc tcccgctttg gcctcctaaa    780
gtgctgggat tacaggtatg agccaccatg tccagccgtg accaataaat ttttcccact    840
ttcttcccct aaatagcctt ccctgagatt acactcctta atacattaat aatacattat    900
aatttgattc agtggatgct gtttacatga gtgtgttcag tttgtgaaac ttcatcaagg    960
tttacactta caggtggagt tttatgtgtg tatgttatgc c                       1001
```

<210> SEQ ID NO 95
<211> LENGTH: 1001
<212> TYPE: DNA
<213> ORGANISM: Homo sapiens

<400> SEQUENCE: 95

```
aaaccacatc tctactaaac atacaagaat tagctggaca tggtggctca tgcctgtagc     60
cccagcttct cgggagggta aagcatgaga actgcttgaa cccaggaggc ggaggttgca    120
gtgagtggag atggcgccac tgccctccag cctgggtgac agagcaagat tctgtgttaa    180
aaaaaaaaaa aaaggatggc ctttttcaca gcctaatgcc cttgagatcc atccaatttg    240
ttgtatcaac agttcctgcc ttttaattgt tgagtagttg tttatagtat ggatgtacca    300
```

cagtttcttt aaccatctac ctattgaggt acattttagt agttttctag tgttttgcta 360
ttataaataa aggattacaa ataattgtga tagacttttg tgttgacata gttttcatgt 420
catttttatt atcgttatat attattgaat atatacaata tatattgaat gctacacatg 480
tagcattcac gtttctgttt yataaaatgt ctctgtttca tcactgtgaa atgcctcctt 540 ttcttttta ttatgtcacg tctctatggt aatactcctt gtcttaaaat ctacacttta 600
tgttaataca tacgttttat gttaattttt ttatggttcg cctttgtggg gttttttttt 660
tttttggttg ttgttgtttt taactttatt ttattttatt tattttattt atttttgag 720 actcactctg tcacccaggc tggagtgcaa tggcgtgatt ttgtctcact acaacctctg 780
cctcttgggt tcaaacgatt gtcatgcctc agcctcctga gtagctggga ctataggggt 840
gggccaccac acctggctaa tttttgtatt tttagtaaga gacagggttt caccattttg 900
gccaagccag tcttgaactc ctggcctcaa gtgatctacc tgcctcagcc ttgcaatgtt 960
ctggaattac aggtatgagc taccacaccc agcctaacct t 1001

<210> SEQ ID NO 96
<211> LENGTH: 1001
<212> TYPE: DNA
<213> ORGANISM: Homo sapiens

<400> SEQUENCE: 96
tgggtcaaaa tgacaccgga gaacggatac tggactatgg gcctgactga tgggaataag 60
tatcgggctc tcactgagcc cagaaccaac ctgaaacttc ctgagcctcc taggaaagtg 120
ggggtcatcc tggactatga gactggacat atctcgttct acaatgccac ggatggatct 180
catatctaca catttctgca cgcctcttcc tctgagcctc tgtatcctgt attcagaatt 240
ttgaccttgg agcccactgc cctgaccgtt tgcccaatac caaaagtaga gagttccccc 300
gatcccgacc tagtgcctga tcattccctg gagataccac tgaccccagg cttagctaat 360
gaaagtgggg agcctcaggc tgaagtaaca tctctgcttc tccctgccca gcctggagct 420
aagggtctca ccctccacaa cagccagtca gaaccataaa gctacaggca cacactgaag 480
cactttactg atattcattc rattattcca taggacagtt gtttgagttt ggtgccacct 540
tattggcccc tttatacaga taaggaaact ggggtgtaga aaagtgtatt gactttacaa 600
agcagacagg aatagtgaac aacagagctg ggatctgaac aacaatgact aacattaatg 660
gagaatttaa aacgttctga gtgctgtgtt atgagctttg gtgggtgtca ctcctttaat 720
cctcacaaca ccctgtcagg tagtctcatt tggcaagtat ggaagcagag gcagggcaac 780
attaagtagc ttacataact cacacggtaa tttgtgcagt tgggagatgt tcagcttcag 840
tccctggcca attgcccgtt cttttccagc ctgatttttc ctgcatggga agagcccaca 900
tgtagccctg aggttccctt cccaggacag ctccaggatc gagatcactg tgagtggttg 960
tggagttaag accccctatgg actccttccc agctgattat c 1001

<210> SEQ ID NO 97
<211> LENGTH: 2802
<212> TYPE: DNA
<213> ORGANISM: Homo sapiens

<400> SEQUENCE: 97
tctttctaca tttttgttgt ttccctcccc acattgattc tgcccactga tgctttatac 60
tcagaggtta atttctttt cttttctttt tttttttttt tttttttttc ttgagacaga 120
gtctcgctct gtctcccagg ctggagtgca gtggcgtgat ctcggctcac tgcaagctct 180

-continued

```
gccttccggg ttcatgccat tctcctgcct cagcctcccg agtagctggg actacaggtg    240
cccgtcacca tgcccggcta atttttttatt ttttgtattt ttagtagaga cggggtttca    300
ccgtgttagc caggatggtc ttgatctcct gaccttgtga tccgccctcc tcagccttcc    360
aaagtgctag gattacaggc atgagctgct ghgctggccc tcagaggtta attttcaatc    420
ttcactcgac cactcgtgag ctaaatgagt tccccttttc tgcagtctat ttttccatac    480
atccaattta tttaacaagg tggagcctca tctgaagcat ttcctcacct gaaaaatggg    540
gataaacata tgaatctcta gcgctgtaga aggcaatcat attatttact cagcccacag    600
caggccatga aggaagctcc tcatcttcct gatagctgca aggccgtctc tgtgctgggc    660
tctgtgtggg gccttatatg ccctagattc actctccagc cttcagcttt ctccaccctc    720
ttctggaccc caggaatctg tcctctatgg acagtgccac tgggctccct tgtcctctgg    780
tttgctgctg tgtttggcca atgggaggcc ctgatagaag attagaagga gaaagaaagg    840
agatacacac cgtttaattt cctgcttcct ccctgccagc agcagctggt ggtgctctaa    900
caaggcccga ggactcttct caggaagctc cctcgttaag ctacctcttt ctctgggttc    960
cagtaattgc ctcccctttt tagccctccc aggctagggg tggagacagc tccccactgt   1020
tgggaaccat gggggcactg cacttttcct tgttgctttc ccttaaccct tctttctgga   1080
aaccttgtcc aactacccag tttgagctca ccatctattt cttgctaggt ttctgccaag   1140
catgttcatt attccttcag tcttcacctc aacccccatg aaaaacagat tgcaatcatc   1200
atctaaaaat gtggaggcca aagcttggaa gcattaaatc ctttgaggag atacaggcag   1260
taggtggcat gagaagcctg ggaaggacaa agttctttgg gcaggcatca cctcctctcc   1320
ttggcatttc catcctcact ctccctgcag tattactcag tgtgtgtctc cttcccttca   1380
cctccaccct ttatgcgtct tcctacccac gaaggaagtc aagggaactt ttctgctcca   1440
aatcacaaga gttggagaag aaaaaaggaa aaaggaatat agtccctcag gttgttggtc   1500
cagggaacat gcagtgattt actcaccagg cttgaagagg gccatttttc cattctgaaa   1560
ggaaggagac acagataaga aaaaggtcag tatttttgta cttttcccac tccattctcc   1620
tctcactaca tgttttctct ccttttcttt agagtctctt ccagggtcca gcttccctcc   1680
tctacagctc tgatggatca gaggtggcac cttctcaaaa atgtcaggct tggctccctg   1740
tgtcatgggg ggtgcaggat gcatggccag gctttacaag ggggtgtgca ggatcaggag   1800
tttctcagag gctccagaaa agcggaggtg aacccccacc acacagaaat tgagtcttta   1860
gattagatct aattaatcca gctgagaaca tccacgggtc acagtggaga aaaagttgaa   1920
atattcaggg catgtgaccc agcaaactta cagagcatca ggctgactta ttggtatcgg   1980
acgaagactc ctctccacct acaatgaaag aaaggtagag gtgtcaccag aactctgcct   2040
tttctgtgtt ggccccttcc ccttcttttt gcatccatct agtctttttt tttttttttt   2100
tttttttttt tttttttttt tttaccatcc cacccttccc catggtctcc atcttcaggt   2160
acaattcttt cttcacctct tcttaatatc aagtctggga acatcggttg aacgctagtg   2220
gcagggcagg cactgtgaga gttccttccc aatggggtcc agctcatctg ttttgaatgt   2280
gtacctgggc ataggtgtca ccatgtctat atgtgtatgc ctaggagtac aagattcatc   2340
cttctcaatc tgtatcattt cgtaccttgc tctaaaaaga atttgggaaa tttaatgagc   2400
aatttcaggg actagttttt gaaagcagtt atgatctatc tgtaccaact gagccactgt   2460
agctactcct ctttattaga cacacttttc tccctccctc tctcttttct gatttcttta   2520
```

-continued

```
tttcttaaat cttccattct tgttttcctt tcaacagcct ctagattatg ggaaacaaca   2580

agtaagtttc ctgccataga aaatgcacct catccttctc ttccctcttc cttttgaagt   2640

gtacccctgg atattcctca gtgcttttta gagcttaagg gtctgtagcc cctagtacaa   2700

agagattgaa gacctctttt tttttttttt ttttttctag agagaaaaag cactgggtgg   2760

tttctccaaa gagccacact tgttttcttt ttctgggtaa ag                      2802
```

<210> SEQ ID NO 98
<211> LENGTH: 1001
<212> TYPE: DNA
<213> ORGANISM: Homo sapiens

<400> SEQUENCE: 98

```
tgggtgaaaa caagaaaaac ttttaaaaat ctactctggc atcttttgct agcaggcatt     60

gacaattagg agaaggcaag gtgttaactt ttactgatct cccacttttt tttttgagac    120

aaggcctggc tttatcaccc aggctggagt gcagtggtgc gatctcagct cactgtaaac    180

tccgcctacc aggctcaagc catcctccta catcagcccc ctaagtagct gggacaacag    240

gggcgcgcca ccactcctgg ctaatttttg tgctttttgc agagacgggg ttttgctatg    300

ttgcccaggc tggttgcgaa ctcctgggct caagggatcc gcccgcctcc acctcccaaa    360

gtgctgggat tacaggcatg agccaccgcg cccacccctc tagtttccag tttagtcgga    420

aagattaaaa acgccagcct tgttttccta gtgctgtttt tggtttttac ctcgggtctt    480

ttgtcgtgcc ttaaaatcat rtctggttgc gcaagtgagg gaaaggattg ggtaaagggg    540

gcgccaccgc aagttgctgt gcaacatcca gacatcacca gacccaccac ctggagcctg    600

gcctggcggt gtcaaacgca ttctggtctc atctttttag aaacccgtgg atgctcaagg    660

aatttccgga taacgtgatc ccggatgcgc ttgactgact tacacggaac gagcaaagcg    720

caaagcagtc cctgctaagg acttagttta tgccctcaag cgcaaaggtc ggaccctcta    780

tggtgttggt agctatatgc acgtacctca tgtacatttc accttaaatg gctttcaaag    840

agctagatta atttagtgga tagatcaaaa tgatttatga cccctcgccc cccagtgata    900

ggaagagcga accagctctt ctttagataa tagtgagtgg ctctgaaaag agcctttggg    960

ttggacaaga gcttgagaat ttacttggag ctggtgtact t                       1001
```

<210> SEQ ID NO 99
<211> LENGTH: 1001
<212> TYPE: DNA
<213> ORGANISM: Homo sapiens

<400> SEQUENCE: 99

```
atttagtgga tagatcaaaa tgatttatga cccctcgccc cccagtgata ggaagagcga     60

accagctctt ctttagataa tagtgagtgg ctctgaaaag agcctttggg ttggacaaga    120

gcttgagaat ttacttggag ctggtgtact tggtgacggc cttggtgccc tccgacaccg    180

cgtgcttggc cagctccccc ggaagcagca ggcgcacggc ggtctggatc tccctggagg    240

tgatggtcga gcgcttgttg tagtgcgcca ggcgggaagc ctcgcttgcg atgcgctcga    300

agatgtcgtt gacgaaggag ttcatgattc ccatggcctt agaagagatg ccggtgtcgg    360

ggtggacctg cttcagcacc ttgtacacgt acacggagta gctctccttg cggctgcgct    420

tgcgcttctt gccatccttc ttctgggcct tggtcaccgc cttcttggag cccttcttcg    480

gggcgggagc agacttggcc rgctcgggca taatgaaaca atagtggcaa aaccaaaaca    540

agaagtcggt ctcctctttt tatataatag tttatgcggc cgaggtagtg ggaaggtctc    600
```

tgctgattgg taattatccg tggatgacga cagatgccag ttttgcccaa tcaaaatagg 660
tatcctgcat aatcgagtcc tattggtcta aataaaaata aaacgtaagc caatcgcaca 720
gcttcctttt cgcgcccagt agaggctata aaatgtacgt tttctagtt tcacttcagt 780 ctttcttgac cgtatagata ataggccttt tgccatgtct gggcgtggca agcagggagg 840
caaagctcgc gccaaggcca agacccgctc ttctcgggcc gggcttcagt ttcccgtagg 900
ccgagtgcat cgcctgctcc gcaaaggcaa ctatgcggag cgggtcggtg ctggagcgcc 960
ggtgtacctg gcggcggtgc tggagtacct gaccgccgag a 1001

<210> SEQ ID NO 100
<211> LENGTH: 1366
<212> TYPE: DNA
<213> ORGANISM: Homo sapiens

<400> SEQUENCE: 100
ggtatttcct atgatttcat aatagacaaa ggtttaatta cacaactcct ggctgaatct 60
agagtactaa aatgtggctg ttagaaaagg ttgctctctg ggcccgatgc agtagctcat 120
gcctgtaatc ccagcacttt gggaggccaa ggctggcaga cagctttagg ccaggagttg 180
gagaccattc tggcctatgt gttgaaaccc cgtctctact aggaatacaa aaaattagcc 240
gggcgtggtg gcacacacct gtaatcccag ttacttgaga ggctgaggct gagaatcgct 300
taaacctggg acacagaggt tccagtaagc cgagatcaca cctctgccct ccagcctggg 360
tgacagagtg tcgccaaaca aaacaaaaca aaacaaaaaa acaaaaaaaa agattgctct 420
tacccaggga tgatggtcag atgcaattac aggttatgaa tttggcataa aagtaatgct 480
aagtgtttca cactgcactt actgttgtca gtgttctaag tgttttttat ttaccaattc 540
atttacactt gtttgtcttt tttttcaggt ctccaactcc tgggctcaag ctgtcctccc 600
acttctgcct ccccaaaagc tgagattaca ggcgtgagcc acccggccct actcatttaa 660
tccttacaac aacccttaga gctgggaact atttttatca tcatcacata attgtttaca 720
aaaataaath gaggcttaga gagcatatgc acctcaaccc aagatcccac aagtagaata 780
ttattgttac agatttggtt gcaaataatc tgcttcttat gattgtgctt taaatttttc 840
accgtgtcac atcactttgg tggtgtaaaa ttataaaaca acatttaagt cttaacttta 900
aaaatgtgtt tttggcctgg tgcgatggct catgcccata atcctagcac ttggggagga 960
tgaggcagtc agattgctta aggccaggac tttgagacca gcctggacaa catggtgagg 1020
caatttctct actaaaaata ctcaaaaatt agctgggcct ggtggcctgc gtatataatc 1080
tcagctactt gggaggctga ggcacgaaaa cccaggaggc agaggttgca gtgagccgag 1140
atcctgccac tgctctccag cctgggtgac agactaaggc tctgtctcaa aaaaaaaata 1200
tatatatata tatacatata tatatatatt tatatgtata gacatacata gttaaaatat 1260
atatattatt ttttacatct taaagagaaa cattatttat atgcaaaaaa ttttatttag 1320
gcccacttag caattccaga tctgacaact tttgaggatt taaaat 1366

<210> SEQ ID NO 101
<211> LENGTH: 528
<212> TYPE: DNA
<213> ORGANISM: Homo sapiens

<400> SEQUENCE: 101

```
aacataaaac tctaagcatt tattcaaata tattagaaat ttaaatgaca taaaaattgt     60
taagtacttt atttggacta gtgcaaatag cataaatgtg aatttaaata tatacaaaaa    120
gttaagtaat tgaatatcaa taaaatatta ataaacagta aatataaatt ttctatatgt    180
gactagtgag atctactaag ctagtctagc catttttctc aattatctcc attatttcct    240
aaagtatcct gtggagtaac tctgattgcc tttactctca ttaaaaagat gaggaaatta    300
agacaaaaac agcaaaagta tctgcaayga agccacaatt tcagtctagg tttgtttgat    360
tgcagaggct gaactcacta ttctccaaag taaatattta catggaaaca ctaaaaaaca    420
aagaaattac attttaaatt gtgtcaagat tacactttct ttagagttaa aagaattcca    480
cagtgtatcc atgcatgtaa aaaatattaa atatatgaaa agacgact                 528
```

<210> SEQ ID NO 102
<211> LENGTH: 801
<212> TYPE: DNA
<213> ORGANISM: Homo sapiens

<400> SEQUENCE: 102

```
cagccttctt ggccttctta ggcgtggccc ccgcgggctt cttagcttta gcggcgcctg     60
ccttcttggc tttgggcttg gcttccccgg aggccgcctt cttgttgagt ttaaaggagc    120
cagaagcacc agtgcccttg gtctgcacca gggtgccctt gctcaccaag ctcttgaggc    180
ccagcttaat gcggctgtta ttcttctcca cgtcgtagcc accggccgct aaggccttct    240
taagggctgc caaagaaagg ccattgcgct ccttagaagc agccacagcc ttggtgatca    300
gctctgagac tgggggcccc gtcgctttgc gcttagcagc gccggcgccg gcagccttct    360
tagttgcctt cttcttagcc ggggatttct ccaccggcgc yggggtggct gtctcggcag    420
gagcggtttc cgacatggtg gcaagaaact gctagaagag aataagctcg aaatctaaag    480
agcaggtttt gcgttgctgc tatgctcggg ccccgggctt atataagccg gcgctgccct    540
gtgattggtg gagcgtccaa tccaccgccc tctggccgcc gccgctcgcg gttggactcc    600
caaattgtgt ttgttagtcc tcaaaatttg attaaatgct taaaacaatg gtacagaatt    660
tggcactttg aagctccaaa ggaggaaaac agcctccagg ttcacatact tgtttgtgtt    720
ttcaagaatc ttgtgcaatt gatgaaagat attttaaaaa atcccttcag cttttcataa    780
gaatccattg ggctgagggc a                                              801
```

<210> SEQ ID NO 103
<211> LENGTH: 1092
<212> TYPE: DNA
<213> ORGANISM: Homo sapiens

<400> SEQUENCE: 103

```
gatttggatt cctaatgaaa tcaacagtca cttatttctc attcttgaaa tgctgtgcaa     60
gaaaatttaa agtagccaat gcacttcatc ttctaagaac tcctggagaa gttggcagac    120
tatggccaaa tctggacaat ggcttttttc tgtatggccc tcaagctaag aagtgtcttt    180
atgttttaaa agtattgtta aaaaaaaaaa aaacaaaaac aaaggctggg cacggtggtt    240
catgtctgta atctcagcac ttggggacac tgggataggt gggttgcttg agctcaggag    300
ttggagacca gcttgggcaa cttggtaaaa ccccatcttt aataaaaata caaaacattt    360
tgctggatgt ggtggcacat gcctgtagtc tcagctactc gggaggctga ggtgggagga    420
```

```
tcacttgaat tcagggtgtc aaggctgcag tgagcaatga tagcagcact gcactccagc    480

cagggcaatg gagcaagatc ctgtctcgaa aaagcaaact aactaaaaac taaagagtgt    540

gtgacagaga ctatatatgg cctttaaacc ctaagctatt tattacctag cccttttgct    600

gtgttataaa tttctccaca gagacacaga tattgtatag gcctcttacc gaacaatgca    660

aattgagaac taaagaaaag gagatcttca ygagcaaatg atctaaccaa gcactttcca    720

ctgttccaaa cacaaaactt agaaggtcca ggagaaaaaa accccaaaac tccatgtgta    780

atggagccag ggtataacaa taagagctga cactcattca gcatttacta cctgacagga    840

agtaatctta aatatgttct acaggtttct attaatttgc tacatttaca gctatacaag    900

atgaggccca gatagagaat taataacttg tcaaaggtta tacagctatg aagtggcagc    960

tctaaatttt aaacctagaa acatggcctc agctctatta tggagggaaa atccttgaag   1020

aggtgagaag agaactatct tcaaagcttg gaagaggcag tgtcaagttg ttcctacacc   1080

tagcaaacag cc                                                       1092
```

<210> SEQ ID NO 104
<211> LENGTH: 1001
<212> TYPE: DNA
<213> ORGANISM: Homo sapiens

<400> SEQUENCE: 104

```
gatctcaggt gatccgcccg ccttggcctc ccaaagtgct gcgattacag gtgtgagcca     60

ctgtgtctag cctatattgc cttttaattc ttgtttttta caatgatggc aatccataat    120

gttattcaat tgttgtttaa tcctttcata agaatgttat tctagttttt ctggtaatta    180

aaaagacagc tctggaaact tccgtagact tacctataaa tctgttattg ttttgatttc    240

atatcacttt taaagattgt gtacattttg ttttgttttt ttaagtaatg tggtccagct    300

agtcacccag gctgaaatgc agtggggcca tcctagctta ctgcagcctt gaacttctgg    360

gctcaagcta tcttcctact ccagcctccc aagtagctgg gactatagac atgaggcacc    420

tctcctagct tcacttttaa aggttttaaa atctaatctt tctctggttt tagcttgctt    480

aatacaaaat tcaattatgt yctataggaa aaatttcctc tactttggga tcttggcagt    540

gatcctccta gaaatggtga tgggcaaaac aaaaggcttt tgattttgtt gaaatgtgtt    600

tgataggcta cattaaagcc acagcacaaa gaaaccttgt agagcaaagg aataaagaaa    660

ttattgatga aactctgaat cctggaagga aactcaaaga tcatcttact aaaccctacc    720

tttatttaca tttgaaggaa tggaaaccaa gaagtatttg tgaaaaacat gctgtcacgc    780

cagaacccag atctctggga ttcctgtcca atgtgtgtgt gtgtgtgtgt gtgtgtgtgt    840

gtgtgtgtgt gtttgagaga gagagacagt gtgagagtag gagaaaaagc aggaggaggg    900

gaaggcgaaa agggagagag aaagcacaat tctctcattc catatatgta ttgagtgcct    960

actatatgtc agggatacac caataaatga tatggattgt a                       1001
```

<210> SEQ ID NO 105
<211> LENGTH: 1001
<212> TYPE: DNA
<213> ORGANISM: Homo sapiens

<400> SEQUENCE: 105

```
cacagcacaa agaaaccttg tagagcaaag gaataaagaa attattgatg aaactctgaa     60

tcctggaagg aaactcaaag atcatcttac taaaccctac ctttatttac atttgaagga    120

atggaaacca agaagtattt gtgaaaaaca tgctgtcacg ccagaaccca gatctctggg    180
```

```
attcctgtcc aatgtgtgtg tgtgtgtgtg tgtgtgtgtg tgtgtgtgtg tgtttgagag    240
agagagacag tgtgagagta ggagaaaaag caggaggagg ggaaggcgaa aagggagaga    300
gaaagcacaa ttctctcatt ccatatatgt attgagtgcc tactatatgt cagggataca    360
ccaataaatg atatggattg taacacatat ttacttttgt aaatgagcaa ttctattata    420
aaagataaat atgcttttag ttagtaaaat gtaggcaaaa atgcttaaga tgttttaagt    480
agacataagt agttagtaaa magagcatat gttgttaaat atagatataa gggatggaag    540
ggtcaaaaga tacctaatgt tcctgatgca caaaatatac aaaaggagcc acacattcag    600
aattcacaga tatatgagac atcgaagcac tgactcatta ttcatgaggc cttgagtcag    660
ccacaaattg gagacaccat aagttctcta ctttaggaac aaaaataaaa tccatggcta    720
ttcaaccaac taattggttg ggtccaggca tatatatctc tgtgtctatc ctacaggctg    780
attgagcgat gtaaaagaga tcagatatac ggaaactgct cacacttgag tcagatagtg    840
tggttcttcc aattcactta cacactaaac cattaacttg ctcttctttt tccccttgct    900
gcttgctatg ttttttaatg aagctgtgat ttgagcattt cactgcatag tctgcaaacc    960
tatttgtgct gtgtcctctg ggagagcttg catgggacta t                        1001
```

<210> SEQ ID NO 106
<211> LENGTH: 1001
<212> TYPE: DNA
<213> ORGANISM: Homo sapiens

<400> SEQUENCE: 106

```
tattgagtgc ctactatatg tcagggatac accaataaat gatatggatt gtaacacata     60
tttacttttg taaatgagca attctattat aaaagataaa tatgctttta gttagtaaaa    120
tgtaggcaaa aatgcttaag atgttttaag tagacataag tagttagtaa aaagagcata    180
tgttgttaaa tatagatata agggatggaa gggtcaaaag atacctaatg ttcctgatgc    240
acaaaatata caaaaggagc cacacattca gaattcacag atatatgaga catcgaagca    300
ctgactcatt attcatgagg ccttgagtca gccacaaatt ggagacacca taagttctct    360
actttaggaa caaaaataaa atccatggct attcaaccaa ctaattggtt gggtccaggc    420
atatatatct ctgtgtctat cctacaggct gattgagcga tgtaaaagag atcagatata    480
cggaaactgc tcacacttga ktcagatagt gtggttcttc caattcactt acacactaaa    540
ccattaactt gctcttcttt ttccccttgc tgcttgctat gttttttaat gaagctgtga    600
tttgagcatt tcactgcata gtctgcaaac ctatttgtgc tgtgtcctct gggagagctt    660
gcatgggact atacttggag cctaccaggg catcaaggta atttctcaca tggtaccaat    720
aaggaccctc tatcataaca aaaatgtgga acagtcacct ttagacagca acttgcagga    780
agtgagggaa aaatgatgga ggtgtgttcc agtcagaggt aaaataacgt agaggggctc    840
acagggacac aatgctcagc agtttgagga acatcaacgg ggccagggta gctagagtag    900
aggaaacaag taagacagcc ctaggagatg aggccaaata catcactggg gccagagtat    960
gcaaaacttc atagggcaag gtaagggctt tggaagtttc t                        1001
```

<210> SEQ ID NO 107
<211> LENGTH: 1001
<212> TYPE: DNA
<213> ORGANISM: Homo sapiens

<400> SEQUENCE: 107
agacttcttt agttgtcctt taggatgtat gtcctttagg acagtgacca tgttcttttg 60
tattgactgt ttctccaagg acacattcaa tgataatcaa tgtggaggac ttccgagata 120
atgacccttt gccatcacag gctgtctacc tcttctcagc attaagaccc tctgcttatt 180
cacatgccca cagctctcga gggaagaaaa gaagtctaga aatacccaac caggcgcatg 240
gacaaattgg cctacgtagg ccttcctcca tgcctcccct tcccccaaac ccacatttat 300
tttcattcct ttccttctag tctggcacaa catgtcagta aaaaggacac aagactagaa 360
agcaaattct gagatttgga gcatctgtct cagaataagc agttgcaata tgccttatct 420
ttcccagaat atgttcttgc tccacatcta acaataaagt tccaagaagg ggaattcgtc 480
aacatctctc tgactgattt racaaggtga agacatatct gtttaagagg tattgctggt 540
agccagacga gagaagctat tgagacatct gcagtgaggt acctgttgca aagccccacc 600
gagaaggtgg ctgcggggaa ctcattcctt ctttgggatc agcatggttc tgtattacat 660
ttttagaaga gctgagtttc catgtgttct taaggtctag gatgtataca ggagctccag 720
tatcacagtg gaccccacag aagtggccaa ctacttacat ttcaatatcc ttctctgctt 780
ttttgtttat cagaccaaag ctgaatgtga atctgatggc tgctgcttta gttcaaagcc 840
aatggagtgc tatacctaca gaagcagaac tttaataaac tggcctgagc aatagcaaat 900
ggggaggact tctgaattaa cgaccctttg ccatcacagg ctgtccactt cttctcggta 960
ataagaccct ctgcttattc acatgtccac aggtaacctc t 1001

<210> SEQ ID NO 108
<211> LENGTH: 1001
<212> TYPE: DNA
<213> ORGANISM: Homo sapiens

<400> SEQUENCE: 108
cagtgccagg tattttaaaa actctcttaa aagttttcat tatcacgcac ttgtgtatac 60
ttattctgta taagcgcttc tatatacact tcaacaatgt ataatttggt tttattttca 120
ttttatttat ttatttattt atttatttat ttatttattt atttatttat tttaagaggt 180
agggtctcac catactgccc aggctggtct tgaactcctg agcttaagca aacctcccat 240
ctcagcctcc caaagtgcta ggattacagg catgagccac catgcccagc catggtttta 300
cttctgagtt taaaaaaaat gttattatat atgaaccttc tgagacttac atttctaaaa 360
ttcaaccagg tactgtgtgt acctcaataa atgcattatt ttgaccatga acatgtagtt 420
gcctctagta tttttatcta ttaaaaatgg catttttttcc attctcatat gtctcctgtt 480
gcatgtgtgc aaaatattct ytcatgtaaa cagctaggaa tcgaatggtt gggtcactgg 540
agtacactta ctggataaaa aatattatca aaaaccttca gcaaatacaa tttgatgtgg 600
aagagttccc acactgattc ttggcaaaga ccaaaatact tttaaatatg ccactcctaa 660
gtgtttaaaa tgaagacact cattttgatt tcctgagttg ggggtggggg aaaacaatgg 720
agaacagccc ttctcctcct ctattttttt ttcttttaac atttcttcca attactagag 780
atacagtaaa cgcaagtgac acagacaaga aaacatggag cagaccctaa cagaaaaagt 840
agggaataga aactatgttc ataaatagga attccacaca agagaattat gggaatgagt 900
aagacagcaa gattcctcca aaaaacctgc actgccaaga attttcccaa ctagaacact 960
caccagagaa aacggtggcc aagtttcaaa ctgccctcgc a 1001

<210> SEQ ID NO 109
<211> LENGTH: 1204
<212> TYPE: DNA
<213> ORGANISM: Homo sapiens

<400> SEQUENCE: 109
tagagctgtg ttcagtttta tctgatagtc gagtcatttt gcaatggcac tggaatgctg 60
tatggagatg aagcaaaact aaacggcttt tacaccacat tgttttgaga tagaaagtag 120
acattgaaat gtttacggta catcaagaaa tttaggcgcg gcagctcgcg cctgcaatac 180
agctgaaaca ataagaaaag tgaggcaaga gaataacaaa gggagctgaa agttagaggg 240
cagaataagt aaaagcaaag ggcagaagta aggtagatgg gcgggtgaac aagaagcgag 300
ataacaagca gtgaaccttt tgcagccgaa acaaaagaga taatgtgagc aaggacctcg 360
tggccggcaa gatctggaac aaaccagttt aagaggcagc tcttcagaga tgggcatgcg 420
tattagagag gaaaagtatc cttaacaaaa gcccgtatga taatcagcta cttaaggttc 480
atgcatatgg gctacatatc atgcatatat ttaagattat aagatagagg cacaagccac 540
agaggacaaa gtaagcaaca aacctatcaa taaaagggca gatgctggct atagattagg 600
cagcactggg aacagaaaac atacacacac gcacgcacac acataaaatg actcaaacta 660
cagcaagctg acgctgatct cacctcgcag aggtcagtcc gctctctccc rcccccgaga 720
gtgtaatact ctgtttacta aacttttgct gctttgcttt gctatctgtg tgtgtgtcgt 780
ccaatttcta ccgggcacca agagcctgga actgtttggc accatccggt aaacagaacc 840
gctttgggaa gccgaggcgg aaggaccgct agagccttgg agttcgaagc cagcctgatc 900
tttacaaaag taaaataact aaccgtgcct ggcgtctcat agcctgtagt cctagctact 960
cgggaggctg agaccagaag gatcacttga gcccaggagt tcgaggctgc aatgagctat 1020
gattgcacca ctgcagtcca gcttgtgtga cagagcaaga gtgtttcaaa tgaacctagt 1080
gtcagatatt tactttctgt attacagagg actgaaagct agctaaataa tacttttcag 1140
tgtacctggg ttccagagat aaaattggta aactaacctt tgctccttac ttgggctttt 1200
agtt 1204

<210> SEQ ID NO 110
<211> LENGTH: 1538
<212> TYPE: DNA
<213> ORGANISM: Homo sapiens

<400> SEQUENCE: 110
agattttaaa catgtttctc aggtatccat ttatgaaact aaaccggtaa gcagtgtatg 60
ccaacagtaa gccttaaaag ggcgaggcaa ttgtcatcat ccaatatttg tcagtaagcc 120
aaactgtcat ttctctatgt accaggatgt taccttttaa ggaggagtac tccacaaata 180
tgaaatatgc aactggggga aaattagctg atcctaacca ttttgtagta tctgaagcaa 240
gaatcaacct tattaattta cctagattta tcctgacatt tatgtgtttt catctttttg 300
catttttctg tgctggactc tccttaagat ttttggaaac ctgtgttctg aattcctccc 360
tttccctggg ctagagtggc tggaggcttt ggctcttggg aatggtctcg cgtccttcac 420
cagaacttac gggaatcatg tttggctgaa gagtcggaga cctctccaga gtcatctttt 480
ccagttagga tagaaacgag cccccctcct cacctcgcaa gcccgcgcca gtccagtttt 540
agccgttctt ttggaagagc aagtcagttg aacgccatcg aagaggctcc tgatttagat 600
attaattgtg cttaaatgca gatgactccc cactctcatg cgttccctta tttcccgttg 660
cttctcccat tggcatttac agacttgagg ttgcttggac tctcaattca atactccttt 720
tctgcgggtt cgtgagaatt aggtgtgaac gtgatgtccg cggatatcag tggctagtgg 780
gcaagctcca gcgcccagga actttgagtc gcttgtctag gagtcctgta ttgaattgca 840
acactaagtg caatattctg gttcttgttg tgttctgaaa gagctctttc actcatgagg 900
agagacctgc acgagactgt gaagaccaac tgcttctcag cgctccacgc atccattatg 960
agttcaccgc aggattttac ctgmaaaaat tttgcgtaga ttaagtcacg cttattgcct 1020
cctacttttg tcagtgaaca ttatgtcaca agcattttcc cagaactatt acagtcttcc 1080
agcatgtcgt ttctagtggc ttggtaatga cctattaggc agatggagca ataataataa 1140
taaacaactc tcattttaat atctattttt cactatcaca attagaaata aaaataaaga 1200
ttcctgcata gtatatgtct tcctttggtt aagcttattt cctggctggg tgcagtggct 1260
cacacctgta atcccagaac tttgggaggc ggagatggaa gaatggcttg agaccagggg 1320
tttgaacaag gagtttaaga ccaggctggt caacacagtg aggcgccgca tttctattta 1380
taaaatataa aacaaacaaa caaataaaaa gattatttct ctaggagagc ggttctgaaa 1440
cttcagtggg catcagtacc agcaggatga cttgtttttt gtttgtttgt ttgtttttg 1500 agatggagtc tcactctgtc tcccaggcta gagtgcag 1538

<210> SEQ ID NO 111
<211> LENGTH: 1001
<212> TYPE: DNA
<213> ORGANISM: Homo sapiens

<400> SEQUENCE: 111
cacctgccac cacgaggcgt aggatggcct catcgtagga cctgccttct tggaagtaac 60
agcggtagat cccattctcc tgggctgtga cgttatgtat gaccagggcc acgctgcccc 120
tgttgatgtc tttgctcaca aaggtgattc ttccccggta ctcctccatc tgctcctctg 180
ttctctctct cccaccctta tacacaaaca ctgcggggga gaactgagac cggaaccacc 240
gcacctccat gtcctcagca tttttctcgg gtgacagatg gcagcgtaat gtagtgtttt 300
ctcccaccat ggccaggatg ggattagctg gccccacgac agtaaactgg gctgttcaac 360
aagggcagaa tcagacaagg atgccagtta tcacaactct aaggcaaaac aaaaaacaaa 420
aaacaaaaac aaacaaacaa aaaaaactcc agggatgaaa ggaagcagat attccaaggc 480
tacaggggtt cttgggctga saacccttct ggggaccagt agctgtggct ggtcggcagc 540
accaacccct gggagcagta actattgagg ctgctcctgc ttcacgaagg aaacattggg 600
gagcccgccc tgggcaccct gtgcccctga gattttcctc cattttgcaa tctagcactg 660
tgcctgagtg tagtgtaaac ttgaactgtc cattagggta tctatccact agctatttaa 720
cagttccaat aaaaatgaac tctaagtgta aaacacacac agattataaa gatttaaaat 780
ttcaaaatgt caaatatctc attggtaata gttctattaa ctaagcattt aaatattgat 840
atgtgattat ttatatgaaa caaaatacat tattaaaatt tatttcaagt atgtttttac 900
cttttaaaat aaaaagtaga ataggcacag ggtcttgcgc ctgtaattgc agatatttgg 960
gaggccaaag tgggaggatc cttaacagct aggagtttga g 1001

<210> SEQ ID NO 112
<211> LENGTH: 1001
<212> TYPE: DNA
<213> ORGANISM: Homo sapiens

<400> SEQUENCE: 112

```
tggatgttct cagctggatt aattagatct aatctaaaga ctcaatttct gtgtggtggg     60
ggttcacctc cgcttttctg gagcctctga gaaactcctg atcctgcaca ccccccttgta    120
aagcctggcc atgcatcctg caccccccat gacacaggga gccaagcctg acatttttga    180
gaaggtgcca cctctgatcc atcagagctg tagaggaggg aagctggacc ctggaagaga    240
ctctaaagaa aaggagagaa aacatgtagt gagaggagaa tggagtggga aaagtacaaa    300
aatactgacc tttttcttat ctgtgtctcc ttcctttcag aatggaaaaa tggccctctt    360
caagcctggt gagtaaatca ctgcatgttc cctggaccaa caacctgagg gactatattc    420
ctttttcctt ttttcttctc caactcttgt gatttggagc agaaaagttc ccttgacttc    480
cttcgtgggt aggaagacgc rtaaagggtg gaggtgaagg gaaggagaca cacactgagt    540
aatactgcag ggagagtgag gatggaaatg ccaaggagag gaggtgatgc ctgcccaaag    600
aactttgtcc ttcccaggct tctcatgcca cctactgcct gtatctcctc aaaggattta    660
atgcttccaa gctttggcct ccacattttt agatgatgat tgcaatctgt ttttcatggg    720
ggttgaggtg aagactgaag gaataatgaa catgcttggc agaaacctag caagaaatag    780
atggtgagct caaactgggt agttggacaa ggtttccaga aagaagggtt aagggaaagc    840
aacaaggaaa agtgcagtgc ccccatggtt cccaacagtg gggagctgtc tccaccccta    900
gcctgggagg gctaaaaagg ggaggcaatt actggaaccc agagaaagag gtagcttaac    960
gagggagctt cctgagaaga gtcctcgggc cttgttagag c                        1001
```

<210> SEQ ID NO 113
<211> LENGTH: 1001
<212> TYPE: DNA
<213> ORGANISM: Homo sapiens

<400> SEQUENCE: 113

```
ctttaactca aatgataatt tttttttca ttttctaaat acactcatca aagggcttga     60
aaaattctga gtttttaccc ctattgttcc acagacaaca aaccttttat aaacccctcc    120
gttactgcaa aatggaaaag agcacaattg tgtccaggtc agagagtctt cacttctcca    180
ggattctgag ctccttcctc ccaagggctc aaggcctcac gatatatgaa aatgaagaat    240
atttgagacc ctgtctctac caaaaaaagg aaagtagggt gaagtcagga caataatgaa    300
ttcataggct gctcctaaga tgtctaagtc ttgcattttc acatttatca tagcctgtcc    360
tcgcgcggga gaatgtacac ctgttttgga aggatctacc ccaccaggta acagtaagaa    420
agactaagat gaacagatat ggaagatagc tcagaggctg caatgggata aattctgggc    480
agaactcaaa cagtggtcca ygcaaccttg atcccttccc tgaactcttt ctctcttact    540
caatccaacc tcaatttatt ggctcccata agttccctgt ctacccctct tgttctagga    600
actctccatt tcaaaagtac ttccaagaat ataattcagg gacgtccaca ctctaccaga    660
tctcagcctt ttgcttcccc agggcaaacc cctgctaacc cctcttccac acagaagtcc    720
accatcttca tctccacacc atcttcactt cacttcccct ccaccttcac atatgcaagc    780
tgttgtgcat aaattacaca aattataatt ataacattat acaaactctg tatgtataat    840
tttaacacgg gcttggtaaa tagcggaatt atgtcactgt aataatgttg aagcaccatt    900
aggtcatatc tgattattac taccatatca atagtgtgtg cccccaagaa agagcagctg    960
accacaaagc tcactagtaa gccacagaag aatacagtat t                        1001
```

<210> SEQ ID NO 114
<211> LENGTH: 1093
<212> TYPE: DNA
<213> ORGANISM: Homo sapiens

<400> SEQUENCE: 114

```
tggccttgac taagtttatg gcgacagcag gtaagtctgg agagaaagct ttacaggaca     60
tgtgggtggc ttggacatgc ttctcctagc ccaatgctgt ccaatagaac tttatcctgt    120
atctgtgttg tccaacacag taatcgctat gtacatgtgg ctattaaact cttgaggctg    180
ggcatggtgg ctcacgcctg taatcccagc acttttggag gccgaggcag gcatatccct    240
tgacctcagg agtttgagac tagcctggac aaaatgatga aaccctgtct tcacaaaaaa    300
tacaaaaaaa attatcaggc atggtggcat gcccctgtag tcccagctac ttgggaggct    360
gaggtgggag gatcgcttga gcctgggagg tcgaggcatc agtaagctgt atttgcgcca    420
ctgcactcca gtctgggaga cagaaataga ccctgcctca aaaaaaaaaa aaaaaaccac    480
ttgaaatgtg gctagtacta atgaattttt actgaatttt agtggctact ktattagaca    540
atacaactca actctaggca gtggtttctt aataggcagg tagtataacc agattatgtc    600
ttagattata gttataatat ggagaatgca ttgaacaggg acaagaccaa aaacagtaaa    660
atcagtcaaa agactctcgg aataatctag gtaggtgtgt gtaaactttg gcccccccttt    720
agttatcagt ccttaattct actctgattt ttttcagtta ggatgtttat ttgattagta    780
ccataaagac caagtaacaa tgattaagca agatagaaaa ttttctttgt catataaatg    840
tgctgttgaa gggcaaacca gagacttcta gaagcccttc tccacaaagt tctccagggg    900
tctatgttct tctagctgct tttggacctc ctgaggattg ccttgttcac atgggtgaaa    960
cagaatcaca gcctgcagga aggggaaaga aaatattgtg acttagaagc ttccttttaa   1020
gcaatgacag aatgaaagtt gcatataaca ctttggctca cattctatgt taagctaaaa   1080
cttgggagat tct                                                      1093
```

<210> SEQ ID NO 115
<211> LENGTH: 1001
<212> TYPE: DNA
<213> ORGANISM: Homo sapiens

<400> SEQUENCE: 115

```
acagcagcaa tataaaacta cttagaaata aataaaacat agccatgcca aataaagcat     60
aggaaaactt ctccctcctg agacccaaaa atagactcga ataaatggaa ggacagcctt    120
tgttcttgca tagaacaatt caacattatg aagatgttcc ctcctaagat ttataaacaa    180
tgcaatctca ataaaaataa caagcttctt tatgaaacta gactaagggg tggcaaacta    240
tggcccacag gccaattctg gcctgccacc tgttttttttc aaataaaatt ttactgaaat    300
agggtcatac ttattcatta atgtattgaa aggcagaatt gagtagtcac aatagagacc    360
agatagccac caaagcctaa atacaatact ttctggccct ttaaagaaaa atctccaatg    420
cctaagctgt acagttgcta ctcaagttca ctttgaaaag accaacaagg acagccatga    480
agcaatgaaa agacagacta ygaagggtaa ctaaacccat gagacattaa aataaacttt    540
aaagcttcta atattaaaac aacagagttc caaaacacaa ttagataaag ggacaaatag    600
aaaaggaaat ccagaaataa acacatatag aaatttagta tacaataaag atgacatctc    660
aaatcaccag ggcaaaaatg gactttttaa taaatgatgg taaaacatca aggtagccac    720
atgaaaatag gtacaatttg gtctacactt cataccacac accaatataa actcccaatt    780
```

-continued

```
ggttagggtt ctaaatgtat acatggaaat gataagatac tacaagaaaa ctaaagtaaa     840

ttctacatta atcttagggt accaaaaatt ttctatctgt aagactgatc atttgactaa     900

aaataaaaac tttttttaaa gttttctttt atatatacat acatatgtgt gtgtgtgtgt     960

gtgtgtgtgt gtgtgtgtgt gtgtatatat atatatatat a                        1001
```

<210> SEQ ID NO 116
<211> LENGTH: 1072
<212> TYPE: DNA
<213> ORGANISM: Homo sapiens

<400> SEQUENCE: 116

```
ccgagggcac caaggccgtc accaagtata ccagctccaa gtgagcctct cgctgcagta      60

acagttccgc cgtgacccac accccaaagg ctcttttcag agccgtccac gtttctcaag     120

aaagagccag ttcactgtta agtttgtctc ccattaggta ccctttggga ctcgcttcgt     180

acatataaat gtacttgtat rtgtgggttt tttttgttt tttgttgttg tttttgaggt     240

gtagtctcac tttgttgccc accctggagt gcaatggcac gatctcggtt cactgcaatc     300

tccaccttcc gggttcaagc gattcttctg cctcagcctc tcgagtaggt gggaccacag     360

gcatgtggca ccaggccctg ctactttttg tatttttagt agatacgggg tttcaccacg     420

ttggccagac tggtatcgaa ctcctgacct taggtggtcc acttgcctcg gcctcccagt     480

gttgggatca caggtgtgag ccactgcgcc cggcccaaaa tattttaaag aggattatta     540

gcaactatga gtgaccgtgg cttagggaag acacaatccc ccgagaccat gagaaagtgg     600

ttctgaggca gtcagaatgc aactgttttg tacattttag ggaagcagaa gttataggta     660

aagtcataaa taaatatgtg gagggttagt ccaggcgtgg tggctcacgc ctgtaatccc     720

agcactctgg gagtcagagg cgggcggatc acttgagatc aggagtttga gactagcctg     780

gccaacgtgg tgaaaccccg tctgtactaa aaatacaaaa aattaaacgg gtgcagtggc     840

acgtgcctgt aacaccagct tctcgggagg ctgaggcagg agaatcgctt gaacccggga     900

ggcagaggtt gcagtgaacc gagtcgtgat cgcgccactg cactaacctg ggcaacagag     960

caagactctg tctcaaaaaa aatcaggtaa atcaaagaaa atgaactgga aaaaataatt    1020

gctcttaata tcactgtgaa tacctagtga gtgttctgta gatgtgttac ag            1072
```

<210> SEQ ID NO 117
<211> LENGTH: 2784
<212> TYPE: DNA
<213> ORGANISM: Homo sapiens

<400> SEQUENCE: 117

```
tgataaggta tatgacaaat aagtcctagg aattattgaa ttatttcctc tgaagaaata      60

attcaaaatt tatagtggaa aaatcatcaa agaaattaaa tgctacagta taaaatattt     120

gcttaatgca aaaatggaat ataggaggaa tggaagaacc aaaaaggcat gagacataca     180

gaaaataaaa agttaaatac cagacaaatc caaatatatc agtaataata atgttatatg     240

taaatatatt aagcaattga atcaaaaggc agagactgtc agggtggata aagaaacagt     300

attcagctat cttttgtcta gagaagacac catttacatt taaagataca agtaaattga     360

aagtaaaagg atggaaaaca tatgtcatgc aaacttcatc caaaaaaagc tgtaatgact     420

atacgagtag wcaaagtaga ctttaaaaca aataatgtta ctagggacaa ataaggacag     480

aaagggctaa tccatcagga agatatcaca attataaaca tctatgcaat taataagagc     540

accaaaatac ataacgacaa aagtgacaga aatgaagaga aaaatagaca atgcaaaaat     600
```

-continued

```
aatagttgga gtcctcagtg ccccactttc agtaatgaat agaacaacta agaaatagat    660
cagtagggaa atacaagact tgaagaatgc tataaaccaa ctagacctaa caaatattta    720
tagaatctcc attaaacagc agcagaatgt acattcttct caagagcata tggaacattc    780
tctgagatag atcctatgct aggtcataaa acaaatccaa ataaattgaa aaggatagaa    840
ataatgcaaa gtatgtttgt ctgatcacaa tggaatgaaa tcagaaatca aacacagaga    900
gaaatttaaa aatccacaaa taagtggaaa ttaaatttct aaatagccag tgggttaaag    960
aagaaatatt aagataaatt agaaaatatt tgagataaat gaaaataaag aaacgacata   1020
ccaaaactta tgggattcag gtaaattagt gtttagagga aaatttatag ctataaatgc   1080
ccatattaaa aaagaagaaa aatatcaaat gagtaaacta agtttttacc ttaagacact   1140
ggaaaaagac caaactaaac agaagcaaaa ttcaggataa cagtgaaatt aatgaagtta   1200
ataatagaaa aatgtcaaga aaatcaatga aatgaaaaac tagctcttca aaaagatcaa   1260
taaaattaac aaacctttag atagagtgac caagaaaaaa agagaactga aattattgga   1320
atccaaaatg aaagagtgaa cattactact aaccatatag aaataaaaag actgtaaagg   1380
acagctgcga aaaactgtat gccaaaacat tagataactt agatggaata gacaaatccc   1440
tgtaatgatg ctaactactg aaactgactc aagaagaaat agacaatctg actagacctg   1500
taataagtaa agagataaat tagtaataaa aaaactatat acaaataaat gtccagactt   1560
agatggcttc agtgttgaat tctaccaaac acttaaaaga attaatacca actcttcaca   1620
aactcttcca aaaaacagaa gaggaggaaa cacttctcaa ctcattctac aaggccagta   1680
ccagtatcct tataccaaaa ccaggcaaag ccatcacaag aaaagaaaac tacagaccaa   1740
tatttcttat gaatacagac ataaaaatac tcaacaaaac accagcaaga tgaatccaac   1800
aacatataaa aagaactaga tatcattacc aagtgggatt tatcccagaa gtgcaagatt   1860
gttttaaatt ctgaaaatca gttaatatga tacaccatgt caacagaata aaaaacaaaa   1920
accacatgac catctcaaaa gatctctttc atgttaaaaa gtctcaacaa actagaaata   1980
gaagggaatt tcttcaaccc taaaaatgca cctacaattg catggaaccc ttgaaaaact   2040
agaacaaagt tgaaagactc acacttcctg atttcaaaat ttactataga gcaacagtaa   2100
ttaaaacaat gttgtactgc cataagcata aacatataga tgaatggaat ctacagttga   2160
gaggccagaa ataaacccat atgtctatgg ccaactgact ttttccaaga gtctgagact   2220
attcagtagg aaaagaatag tctttccaac aaatggtgcc gggacaaatt gacagacatg   2280
tgcaaatgaa taaagtttga cacttacctc acaccatata caaaaattga ctcaatggat   2340
taaagagcta aatataagag ctaaaactat aaaacccaat atttgggaaa ccactgcctt   2400
atagaaagct tatacatttg tactacaagg caaatacatg aatgtttata gcagtattat   2460
ttagaatata aaaaatctgg aaggtatctg aatgtgtatt cacaaaaacg aacaccagag   2520
aatttaattg tgatatacct gcgcagggga atacaatacc acaacgtaaa ctgaatggtc   2580
tccaggtaca ttcaataaca tggatgaata tcacaaacca aaagttgtgc aaaagaaggc   2640
aggcaaagaa taaaaagaca gtatatatat aaagttcaaa gactggaaaa tacattttgt   2700
cttttgattc atacacatga ggtgtattag tatcaagtaa ggaaaacaga gatcacactg   2760
attattttaa caggattact agat                                          2784
```

<210> SEQ ID NO 118
<211> LENGTH: 1001
<212> TYPE: DNA

<213> ORGANISM: Homo sapiens

<400> SEQUENCE: 118

```
gcttcgaact ccaaggctct agcggtcctt ccgcctcggc ttcccaaagc ggttctgttt      60
accggatggt gccaaacagt tccaggctct tggtgcccgg tagaaattgg acgacacaca     120
cacagatagc aaagcaaagc agcaaaagtt tagtaaacag agtattacac tctcgggggt     180
gggagagagc ggactgacct ctgcgaggtg agatcagcgt cagcttgctg tagtttgagt     240
cattttatgt gtgtgcgtgc gtgtgtgtat gttttctgtt cccagtgctg cctaatctat     300
agccagcatc tgccctttta ttgataggtt tgttgcttac tttgtcctct gtggcttgtg     360
cctctatctt ataatcttaa atatatgcat gatatgtagc ccatatgcat gaaccttaag     420
tagctgatta tcatacgggc ttttgttaag gatacttttc ctctctaata cgcatgccca     480
tctctgaaga gctgcctctt maactggttt gttccagatc ttgccggcca cgaggtcctt     540
gctcacatta tctcttttgt ttcggctgca aaaggttcac tgcttgttat ctcgcttctt     600
gttcacccgc ccatctacct tacttctgcc ctttgctttt acttattctg ccctctaact     660
ttcagctccc tttgttattc tcttgcctca cttttcttat tgtttcagct gtattgcagg     720
cgcgagctgc cgcgcctaaa tttcttgatg taccgtaaac atttcaatgt ctactttcta     780
tctcaaaaca atgtggtgta aaagccgttt agttttgctt catctccata cagcattcca     840
gtgccattgc aaaatgactc gactatcaga taaaactgaa cacagctcta cttggtgaaa     900
aagtaggtgg ctctgaaaag aaccttttg gtttggaccg aggtatgagt aatgaactgc     960
tccagccccg ctacttgccc ttggccttgt ggtggctctc a                        1001
```

<210> SEQ ID NO 119
<211> LENGTH: 1001
<212> TYPE: DNA
<213> ORGANISM: Homo sapiens

<400> SEQUENCE: 119

```
aatagggctg aggactctac cctcagtttt caatctagag actgtgaaac tgtagagaaa      60
cacactgtct agtagcaatc catatacttt ttctagtaag catattaaaa accgaatact     120
atactatatt ccttacagcc cagtgagttt cccagaatca taaataaaac ccaccagtac     180
ctactatgta actcccagta agaggctttg acttttgtca aagttgtgtc ccagtaaaat     240
gccttcaaga taccacaaac tggcctggcg cagtggctca cgcctgtaat cccagcactt     300
tgggaggcct aggcgggtgg attacctgag gtcgagtcag agaccagcct ggccaccaag     360
gtaaaacccc tgaaaacacg tgttagcaaa cgtaccttgt tagtatctac attaagaaaa     420
aaaaaaaaa aaaaaacctt gaaattcagg caatgtaaac aggttaaaga ttaacaccga     480
aacatcatga gtgtactgtg kagtggtgaa gcagctgaaa acggactcgt gtcatctttt     540
tatgattgtt gaagtggctc tgaaaagagc ctttgttttt atgcgctttt caactcggtc     600
tttacttagt cttgtggtgg ctctcagttt tctttggcag cagcacggcc tggatgttgg     660
gcaggacgcc accctgtgcg atggtgactt tgcccagaag cttgttgagc tcctcatcgt     720
tgcggatggc cagctggagg tgacgcggga tgatgcgagt cttcttgttg tcgcgggccg     780
cgttgccagc cagctccagg atctcggcgg tcaggtactc cagcaccgcc gccaggtaca     840
ccggcgctcc agcaccgacc cgctccgcat agttgccttt gcggagcagg cgatgcactc     900
ggcctacggg aaactgaagc ccggcccgag aagagcgggt cttggccttg gcgcgagctt     960
tgcctccctg cttaccacgc ccagacatgg caaaaggtct a                        1001
```

<210> SEQ ID NO 120
<211> LENGTH: 1001
<212> TYPE: DNA
<213> ORGANISM: Homo sapiens

<400> SEQUENCE: 120
tcactaccaa agtatatgac tactactata gatattttat tttatttatt gattgatttg 60
tagagatggg gtttcattat gttgaccagg ctggtcttga attcctgggc tccagggatc 120
ctcccatctc aacttcccaa attgcaagga ttacaggcat gaaccactac ttaaacttgt 180
attcctttat gctttttttc atttgcaata ttgactataa tcaggaaaaa aaatatatcc 240
tttatgaaga agaaaaactt atgtctcatt ctaaggacag cagagaaatt gttaactcag 300
ggaaaatgat aataaaaatg ataccccctc tatagcaaca taaagagcag tttcgaggag 360
caaaagatgt ggtgaaatgc attgtttact ctgggtgggt gcaagatcca ggcaggggtg 420
aagcatggcc ggctgcacag atctctgttc tcttgtttcc tttacatccc tccccacctc 480
cctctgcaga tcttgttctc rgaggccatt cccagaccca cagcaagagg gattatggct 540
gcaggcctca tgctcctttg ttttggaaga aactgttgag gagttagtat ttactgagca 600
gctaatatgt tcccgtcact attgtaactc ataataatta ttgttaagta atacacgaaa 660
agttttaaat ttaaagcatt ccaatatttt aaaagtaaag ggaacaaaag gccaagtgtc 720
ccttcactca ctaacctctg atcttcagat tagcatgcgt ctttttgag tttttcaggc 780 atttacataa atagttatgc agaaatggat agctttgctt ctgttcttca attgaatctt 840
tagtatagtt gtgcaaggtg ttttttgatc acttagtgtg tctccgttat ctaggttcat 900
gacaacaaat caactctttt tacctgctgc attgaattcc ctccgaggga tgagccgtca 960
ttcctctaag cagtctcctg atgggtggct ggttcagttg g 1001

<210> SEQ ID NO 121
<211> LENGTH: 1001
<212> TYPE: DNA
<213> ORGANISM: Homo sapiens

<400> SEQUENCE: 121
ggggatggtg tagactgtgc caagttgaag acccatgtag ggaagaggcc aggagggtcc 60
ctagtaagcc tgacataagg gtgtaccaat aggtggccag aaatgccttt ctgctcttaa 120
gagaacacta atactttgtg tatagcctgc cgtgggaggg atttcaggtg ggtgggagag 180
cacagaaccc aattgcccac tcccagtgag cacttttcat cttatgattc agcccctctg 240
cccataagca ccacagaatc caagctttac cagataccat ggcacatgga cctttcctct 300
ttaggtgaat ttcaaaattg ccactgtcaa cttgggacaa aatagcaaat tgtcacagcc 360
agacatatta acttggggaa tggaggaaat cattttaaca caatagaaaa gtagactgaa 420
taagtaagaa taaatacaga tgggagaggt ctgcagaatg cccggagtct ggagcatttc 480
ttgtacctac agaagtgata ygtgaagaca tcagacccat gttgttgaag caaaactgga 540
tgggaatagt tactccctac atttgcccac agacccctca ggcaacaggt tttcttttgg 600
ggacatttat tctccttctt catttttga agggtgccct tgttagtcat ttaagtcagt 660
tgtgatctgg taaaaggaac acataggacc aatgaagaga ccctttatcc tccaggacag 720
tgtgaaggga aagactcacc ttagttgatc caccggggag aggaggagca ggacataaag 780
cctttgtgct ggtttaagcc aagttggaaa gtttctaagt aaagaaaatc ccagagatca 840

-continued taggtcttca tttggggttt tgttttgttt tgttttgaga tgatgtcttg ctctgtcacc 900
caggctggag tgccatggca caatctgggc tcactgcaac ctctgcctcc cgggttcaag 960
caattctcgt gcctcagcct cctgagtagc tgggattaca g 1001

<210> SEQ ID NO 122
<211> LENGTH: 1001
<212> TYPE: DNA
<213> ORGANISM: Homo sapiens

<400> SEQUENCE: 122
aaagacattc ctagaagtca tccttcagtg atatcaccac ttgctcagtc accatctcaa 60
ccttatgtca cctcagccct catctcaatg cccaaacccc ttacacacac cttcagttag 120
cttcaactgc ctccgtttcc acactgtgca cctttcactt tccctaccca gctttcctac 180
atgctgcctc tcctcagggt cccctgaatg ctgcatcatt gtgttcagtg cagctggact 240
gattgcacct gtgtatttgc ccctgagcac tttcctttac acatgtggct tgtcttgcca 300
atagactcca ggcttatacc ttccatttcc atcgtattct ccagtttcca ggatagacgt 360
tgctcatcgt ctttacctaa taaataagtt tgtctgattg ctgaaagcaa cctcttaacc 420
tttctttttt aatatcaact gaaacaaaat aaaacatagg gcaagaaacc tgcatgggaa 480
tgcagctgtc taaagctttg hcattgtatg tggtctaaga cccatcccta ggcctgatgg 540
cagtgggctc accagggcag gtgcacatgg gggctgatgc ctcatgaggg aacaactgct 600
taccagggtc ttcaagcagg aatacagaat ctcaactcag gaacaatttt ttattagtcc 660
atcctcatat ttctgtaaag aaatacctga gactgggtaa tttataaaga taagaagttt 720
aggccgggca cggtggctca tgcctgtaat cccagcactt tggaaggccg aggcgggtgg 780
atcacgaggt caggagtttg aaaccagcct gacaaacatg gtgaaacccc gtctctacta 840
aaaacacaaa aattagccgg gtgtggtggc aggcacccgt aatcccagct gctcagaagg 900
ctgaggcagg agaatcactt gaacccggga ggcagaggtt gcagtgagct gagatcgcgc 960
cactgcactc cagcctgggt gacagagcaa gactccattt a 1001

<210> SEQ ID NO 123
<211> LENGTH: 1001
<212> TYPE: DNA
<213> ORGANISM: Homo sapiens

<400> SEQUENCE: 123
cattatggtc tcgaactcct gacctcaggt gatccgtccg cctcggcctc ccaaagagct 60
gggattacag gcgtgagccg ccgcccaacc acttttttta gtattttaaa tcaagtatct 120
ttttgtttgt ttgtttcttc tgtgcctatg cttacccaga cagtttcttc atttattttc 180
ccccgccttg ggcaggcttc cactcttcag accctttcct gcacaacttt gtccctgagc 240
ataggtcctg gacgtaaaag aagggacatc gtctggagaa atattgaatt aagaaaggcg 300
cggctgtgaa gaatagaaat cagtgtctcc cttagtctct cagttcggcg atcttggtaa 360
tgccctgtcc catgcctgct aacgcgattc agcctcgata tccccgtcca gtcccacgat 420
cgcaccaaga agagcttgcg agccttcctg ctacatactg acattaagaa accggacttg 480
aaagggatcc cagacaaacg wtaaacatgc aacaagaggg atagggtgta aggaagagaa 540
tccttggggc ggtgtctgat aaaacagatg gctctccttt ccaggtgttt ctgaatttga 600
tccccgacgc ctggggcatc gtggaggaac ttgcatagga aatcaaggtg tcgcaggaaa 660
gagaacacgc acaagcaaaa gataccttaa tttgtagtat actcaatatt tatcgtacag 720

```
aagtgtatcg acgatagaca atgtgcgatg tgatgggtgc tgggaactta acgaactctc    780
cacgcgccta gacctcattg gatccacttt ctcttgggct gtgagccggt aaaaaaaaaa    840
ggggtggatg tggaggacgg tccaaaggat tcggagctcc ttaaaatgct actcaaactt    900
tatttagcgc gctggagaat ccctgagaag gagtattata cccagttttc cgggacttac    960
ctccagtgat tctacgtcga ttctttgatg aggcccatta a                       1001
```

<210> SEQ ID NO 124
<211> LENGTH: 1001
<212> TYPE: DNA
<213> ORGANISM: Homo sapiens

<400> SEQUENCE: 124

```
gaaaaatttg aacaggcgct tcacaaagac ggccaaatgg caactgaaca atttgcaatc     60
agaaaaaaaa aaagaaagaa agaaagaggg aagagggtct aaacaagcaa ataaacgaaa    120
aacgagaggc gaggctacca ggtttcttcc atttctggca aacatttatt gttgttgttt    180
tttccttcac agaattattt tcagaaacct tccacaggag attcgtgcgt ggagggggtg    240
gggtggaaag aagtagggaa tggagaagat tactaagaaa agtttcctgt ctggaactgc    300
ggcagatctc tttggataga gatgactact taacctcact ctgctttcct tcgccgcggt    360
tgcggccgcg accctgttct taccaccagc aattcctcca gggacttggt cagcagccca    420
acttgatctg cgtctctctg ctaaggtgtt tccgcaacag ggtcaactcc aagtctcacc    480
tttctaggaa tcccgggcgc mgcgcggggg tcgggactcc gacctgtatt tccaggcgga    540
ggtttccctg ggtcaggcgg ccactctctg ccagagattg tcagttatcc aactgtcaat    600
agagccgccg ctccagcgag tttaatttag gcacagaaaa gtcctgcctg ggttgaggtg    660
ggcttaggat gagtttactt gagtgtgtga tttagaaata gatctatggg acagacagac    720
acgaaatcgg gcattggggc cctcgcaggc agggtatcta gactggcagc tgccggtgca    780
ggatattgcc aaggactcgg catccggctc agctcaaggt ggggacgaag acgtcctggt    840
tgcaaggagg agccctactc cccccggaat cagaactgtg catagcgggc tctggatttg    900
ccgggatgtt tgaggaattt gaaatgagaa aggagaggag gaaatggttt aatggtatat    960
tgagttactg gagtgtattt tagtcaccga ttttggtttt a                       1001
```

<210> SEQ ID NO 125
<211> LENGTH: 1001
<212> TYPE: DNA
<213> ORGANISM: Homo sapiens

<400> SEQUENCE: 125

```
tttgatcctc ttaccggcca catgaggaga attagttctt taccactttt gttgatcaca     60
tctcctgtga attctgcttc cagtttctcc gaaagtaagc tctatatcgc cactactgaa    120
ctggaaacac agtctttcaa aagaagaaat gtgggcgagg gcggtggctc acgcccgtaa    180
tcccagccct ttgggagacc gaggtgggcg gatcacttca gttcaggagt tcgagaccag    240
cctagctaac atggtaaaat ctccgtctct actagaaata caaaaattag ccgggcgtgg    300
ttgcgagcgc ctgtaatccc agctactcgg gaggctgaga caggagaatc gcttgaaccc    360
gcgggggga gtgggggggg ggcggcgcgc agaggttgca gaaagccaac atcgtgccac    420
tgcactccag cctagctgat aagagcgaaa aaaaaaaaaa aaaaaaaaaa gaagaggtaa    480
catgtgagag ctaagacgga rgccttcatt tttgttttta agtaaaattg agtaaggtaa    540
```

ggcgtgtgtg ctaagggaag gggaactagc gttaaacaat ttccagtttt gttttagaca 600
aaactttctg aaacatcgtt tcacattaaa cttgtgaaag acaaaaaaag attctatttg 660
ctgtggctgg ttagctcaac tggttagaat tcggtcatag attcccgttt gtccctgcct 720
aagaacactt tgtggtctcg caagtcctct ccaagattta acaacgtccc caataaatct 780
gtagaatccg atggctgttc cctcacagtt taggtctttg cttttatttc catcttcata 840
catagaaaat tggcctatgt gaattgtctc catctgagaa gaaattgtaa agccatctgc 900
acttccaatc acttccacac ttgggttttc accggatcac atgaaatagg atttttaaat 960
gacatatgtg aacaattttc attaacatca acacactagg a 1001

<210> SEQ ID NO 126
<211> LENGTH: 1001
<212> TYPE: DNA
<213> ORGANISM: Homo sapiens

<400> SEQUENCE: 126
ggtgcaagca tgcatgtcct gttgcttcgc tgcgcgaggc tgaggcacga gttgctggat 60
tttgggggtg gggagtgcgg tgcttggctc ctggctggtg aatcagtctg tgaggatgct 120
ggggtgggcg ggcggagggg atatggggag agtgggtagc gcagtgtgtc tggtggttct 180
ttagttctcg gattgttact atttgtgttc ttatcccggc tctgttcacc tctctttccg 240
gacctgttta ctggtttgtt acatgaatac aacctgagta aaagtctcgt cagcttttct 300
acaaaactga acataactct ttagcattgc tgcctaggtc aagaaactat ttgatcaacc 360
gcccctcttc tttccaccct caattttaca ttgaggctga ggacttgtgc cggttttaag 420
cagcgttcag ggctggccag attaaggagt ggacaattaa ggaaagaatt gagttagcta 480
gaggaaaggg tgcgatttac rgttcccttc ctcctgggca aaaactcttc aggtgggact 540
cccactggca gatgtgaaga acgttgcggg cagtgggagg tgcttttgag tgagtgctgc 600
ataggcgtcc tggacgggtc tttgtctttg gcgcgcagac cggttcgtga gacgcaagaa 660
gaaggcagca gcagctgccg gaggaaaaaa gcggtcctac accaaggact acaccgaggg 720
atgggtggag ttccgtgaca agcgcatagc caagcgcgtg gcggccagtc tacacaacac 780
gcctatgggt gcccgcaggc gcagcccctt ccgttatgat ctttggaacc tcaaggtgag 840
aagatagatc tttctgccac acctctcacc ctcccttctc cccaactctg gcccaagtat 900
ccccatggcc tctcattggc cttgtcccct tgtctcatct ttctccctaa tctgcactat 960
cctgatcttt tcttcttttc tgcccacagt acttgcaccg t 1001

<210> SEQ ID NO 127
<211> LENGTH: 1399
<212> TYPE: DNA
<213> ORGANISM: Homo sapiens

<400> SEQUENCE: 127
tccctcatga tctgtttcct ctgatttcaa caagcaggtg ttctttctcc tgtctcaggc 60
taattctgca cccacatcgg ggagccccca ccccagcttc cctcaggctt ctctatttgg 120
tcaattcatt aattcattca tttgacaagg atccatgaac gctaactatg tgccagtcac 180
tattctaggt ggtggagtca yagaagtgaa caaaaacagaa agttctcatt caaaaacaac 240
ataacttgtg gtaggaggca gacaggaaat gaaataatta gtaatatata tggtgtgctg 300
gatgatgata agtgctcagg agagaaataa acctggaata gcagaacttg catttctttt 360
tgaaggggtc ttgctctgtt gttcaggcta gagtacattg gagtgatcat agctcactgc 420
agcctaattt tttttttttt tgaaagacag agatcttgct atgcatactg cccaggttct 480
tgaactcctg gcctcatgca attctcctcc ctcgatcttt caaggtcctg tgattacacc 540
tgtaagccct cgttcccggt tggaagttac agtttaaaat agggtggtta tgagcaaggg 600
gagcgaggca cagaatactt gggagaaaag cattccgagt tgagagaaca gcagtgccag 660
agcacagagg cagaagcact gtggtttgtg tgaagaaaag caatgaggct ggggtgcgca 720
gagcacacag ggtgatcagg agaagaggag gtgacaaggc cagagggggt tgagggccag 780
atcatgtatg gccttgaaag tcatcatgct gacctgggct ttacctctga gaggggagcc 840
actggaaggt tagagcagaa aaaggactgg actgacttat gttttaagaa gttacttcac 900
atgctagacc aagatgggct gtgggtaggg gtggtggatg gaggcctgaa gacccagctg 960
ggagctactg cagtgatcca ggggaaagat gcagatgact tgtaccaggg aggagccatg 1020
aaaatgttat gatgctggat ttattttcaa gatagaataa aaaggctttg ctgataaact 1080
tacaggtggg gtgtgaaaaa ggagggcatc aagggtgacc acaaggtttt ggtcctaaga 1140
aacggtacag atggagttgc cacttactga gatggggaaa atgagggaga aaccgcttgt 1200
ggaggccaga ggaggagcca gcacagaatc caaaggtcag ttttgaatat gttgggtttg 1260
aggagcttac tagagattcc cgtggagatg tagagtaggc aggtcaataa taagcttgca 1320
gtccaggcaa cgggtcaggg ctggaaacac aagttattct ctttgtcttc tttatattca 1380
tgtttgttgc cactgtgtg 1399

<210> SEQ ID NO 128
<211> LENGTH: 1001
<212> TYPE: DNA
<213> ORGANISM: Homo sapiens

<400> SEQUENCE: 128
tgagaaacag cttaatggtg tcttgtgata aaattgttaa attttcacga agtcaaattt 60
atttcaattt tgtttactta tttttgtatc tccctatgaa atctttgttt ccccaaggtc 120
atggaaatag cctatgctcc acgacccccc cccccactta cataatcatt taccttttat 180
ttatttattt ttattttatt tattttttttg agccatcttg gctcaccaca acctccatct 240
cccaggttca aacaattctc ctacctcagc ctcccgagta gctgggatta caggctcccg 300
ccacaacacc ccgctaattt tgtattttta ttagagaccg ggttactcca tgttggtcag 360
gctggtctcg aactcccgac ctcaggtgat ccccctgcct cggcctccca aaaccctggg 420
attacaggcg tgagccactg tgcctggcca catcatttac cttttatttt taggaatatg 480
atcaaaagac ctgaacaggc rcttccaaaa tagaatatgt caatggccag taagcacata 540
agcagatgtt gtgatatcaa taaaaagttt gcttatttat tttaaccagt ggtgaccaga 600
caaaagacct caactgtctc tggaaacttt attttatttc cagaaatctt ttcaaaactc 660
ttctgtgaag gttgtgtttg tctgggggag gggtgaagtt gtggtttggg atgagttgca 720
gatgaaggag ataagacaag gtttctgcct tcaggatctt caggaatatg tgtcctttaa 780
tcagactgct taacttgatt tggctgatcc ccctttcttt ttcagttccc tccatccctc 840
taatccccat cacctaaaaa gacctccaga gacttagttc atagctgggc ttgatctata 900
tctctttgct ccagacattt ctgctctgtg tcaatgccag cctgcatcta tctgggatgt 960
tgggtggggt agtagagtgg gatcggtctc tctagccata a 1001

<210> SEQ ID NO 129
<211> LENGTH: 1001
<212> TYPE: DNA
<213> ORGANISM: Homo sapiens

<400> SEQUENCE: 129
aagaagctcc tgaaattttt atgttagttt tgtcttttta ttttcctcct tcttcttctt 60
cctctttttc ttcttcctct tcttcttctt cacaccacta tacaaaggag gaagtttagt 120
tttgtctttt actttaaatt acacaagatt ttttttcttt tctctctctg tctctttatt 180
attttaaatt gtttgtagag atggagtctc gctcgaactc cttagttggc tcaagtgatc 240
ttcctgcatt ggcctcccaa agtgctggga ttacaggtgt gagccaccgt acccagctga 300
ttttctcttt aacctggcaa tgactcttgt ttctgtttta ttatagaatg gaaactggct 360
cgatcttgtg caggttagtg gctgggcact gctctgggtg ctgagattta acctctgagg 420
tatccaaaga cctaaaataa gtggaaatga aaaatgctga taccctttta gtgatgaaca 480
cagagatttt aagttgtggg raaaaaaaaa agaaagaaag cctaatactt ccttggaaca 540
cagagagggg ctttggaaga tggccaagag tccagcttcc tgtgagatta tctcacgagg 600
cattacaagc ctgggcacag tcaactctta acatcaccct ctggctgctg gtgacagagg 660
gagcctgggg gaatggagac cccttagcag gccaaacagc cctccccctg aggagaccta 720
tcaactccta cagcagtgct ctgtttctta gaagcaaaaa tagtcctgta accataacac 780
tcaccaatgg tcagactttt tgtttctgtc tttctctcca gttgaagtga ctctggaccc 840
aaacatagcc ctccctcacc tctttcttta ttaggattca aatctgtttg actggaagat 900
tcatgtcaga aactgcctga aaaaccagag agatgtgact cctggccctg tgtgctaggc 960
ctggaagcct tcacctcgga gagacattac caggaagtgg a 1001

<210> SEQ ID NO 130
<211> LENGTH: 1001
<212> TYPE: DNA
<213> ORGANISM: Homo sapiens

<400> SEQUENCE: 130 caccettcta tgcatcctca agcctaatct ttcctggtta tgtgacaaga acccggtttt 60
tagctgaact aaggagaaag tcctacaaca ctgccaccat gtggcaatta ctccaaatag 120
aaggagaggc tgaaggacac acaaccagga tgcagagaaa aagatggaga cagagtctgt 180
gcaagatggg attgatactg agactgggtt agccacctct cctagacagt gaaacagatc 240
gcaagagagg ctgacccaga aagacacatg caaaacaatg ggcaatagaa cacatgacct 300
gaattagatt atctgggttc aaatcctgat tttgctattc attatctgtg tatcactggg 360
caatttactc aatctctctg tgcctgaata tcctcattca aaatcaggga tgaaaagagt 420
acttatctca aagggctatt tgctcactta ttgcacaagt aatttggcat ctgatatgaa 480
ccaggtgcac ctctagatga rgatactgtc acattgaatg aagaccagtg accagaagcc 540
tgcctcacag cccagctcag tgagaaaaat aattccattc tcacctctaa tctcaaccct 600
gtgtcaccat ttatgtatag tcctttgcat tagtgtctgg aaaggtcatt ttttgagggc 660
agaatgaata acctatagaa ggatcattct tgggtataat gaattaaaga agtattatga 720
agctttataa ggcaggatta gctcataaaa atggagggtt cttttgcttt tccagtccca 780
tttgttgttt cacagacaaa gaataaaaca atcactgatg gcaaagactg caaactgcca 840
acgttcatcg gtagagcaag gtgacgctcg tcctgtccag gcctgtggtt gggataagct 900
cagaaagcag agtctccagg gctggtcatc atctatcata accctgcgta taaagaaagc 960
cttgagaaag aaaagaagtg acttattatg tgtcttctga c 1001

<210> SEQ ID NO 131
<211> LENGTH: 1001
<212> TYPE: DNA
<213> ORGANISM: Homo sapiens

<400> SEQUENCE: 131
ctgtggacac tgctgaggaa gcactgttaa acgcccttct tcccactgcc atcatatcta 60
agtcagcgtc tcctaaagag cccgaacagc tgctgaagct tttcattgtc attggagggt 120
tgaattttgt ttttttcggt tttgtttttg ttttttttga gacgagtctc tttctgtcgc 180
caagctggag gagtgcagtg gcgcaatctg ggatcgctgc aacctccgcc tcctgagttc 240
aagtgattct cctgcctcag cctcccaagt agctgggact acaggcgggc accaccacgc 300
ctggctaagt gtgtgtgtgt gtgtgtgtgt gtctgtgtgt gtgtagtaca gacgtggttt 360
cactatgttg tccaggttgg cctcccagag tgctaggatt acaggcatga gccactgcac 420
ctggccagga gggttgagct ttgaaacaac tgatgagagc ctgaggagcc attttgagca 480
atagggaacg ctcacggact rtgtagtaaa gaaagatcca aacaccaagc actccagggg 540
ctttgggttt gtcacatatg ccggtatgga aaaggtggat acagccatga atgcaaggcc 600
gcacaaggtg gatggaagat ttgtggaacc aaagacagct gtttcaagag aagattctca 660
aagaccaggt gcccacttaa ctgtgataaa gatgttaaag aagaactgaa gaacataaac 720
taagagatta tattgaacag tatggaaaaa ttgaagtgat tgagatcatg actgaccgag 780
gcagtggcaa gaacaggggc tttgccttgt aacttttgat gaccatgact ccatggaaag 840
gattgtcatt cagaaatacc acactgtgaa tggccacaac tgtgacttta ggagtgctct 900
gtcaaagcaa aagatgttta gtgcttcatc cagccaaaga gatcgaagtg gttctggaaa 960
ctttggtggt ggcgttggag gtggttttgg tgagaatgac a 1001

<210> SEQ ID NO 132
<211> LENGTH: 1001
<212> TYPE: DNA
<213> ORGANISM: Homo sapiens

<400> SEQUENCE: 132
ctaccttgac agctataaaa agtcgctcta aagaaaaaga accagctctg gccaggcgca 60
gtggctcaca cctgtaattc cagcactttg ggacaccaag gcaggtggat cacttgaggt 120
caggagtttg agaccaagcc tggccaacat ggtgaaaccc tgtctctact aaaaatacaa 180
aaattagtgg agtgtggtgg tgctcgccta tagtcccagc tctcaggagg ctgaggcaga 240
attgcttgaa tcagggaggc ggaggttgtg gtgagtcaag attgcaccac tgcactccag 300
cctgggtgac agagtgagaa agaaaagaaa agaaggaaag aaaagacagg aaaaccagtt 360
atttccactg ttttcacaga acaaatcaac agactgaagt ttactcgtgt caacagtgtg 420
tgaggttaca atgtgatact tactattctt gagatggaaa tgttcagaaa agaagccaca 480
taaagcacat ggtggaagag maaaaatgca aaacaggctt aaagaactgt gagagtttag 540
aaaaaagcaa tagatcaaag ggatcaagaa tgggcattag aagatgaaac tgaagacaga 600
atagggagta gggggttcca ggcatggaaa taggatattc tgtatgagga aaagagaaga 660
acctctttag ttgggcatga aacatacatt ctaagtagaa ataatttttt ttttcttgag 720
atgacatcta gctctgtcac ccaggctgga gtgcaatggc acaatcttgg ttcactgcaa 780
cctccgcctc ccaggttcaa gcgattctcc tgcctcagcc tccaagtagc tgggattaca 840
ggtgcccgcc accacgccct gctaattttt gtatttttag tagagacggg gtttcactgt 900
gttggccagg ctggtctcta actcctgacc tcgtgatccg cctgccttgg cctcccaaag 960
tgctgggatt accggcatga gccaccgtgc ctggcccggt a 1001

<210> SEQ ID NO 133
<211> LENGTH: 2091
<212> TYPE: DNA
<213> ORGANISM: Homo sapiens

<400> SEQUENCE: 133
gtaagtacca ttaacagctt ctcttgaact ggtttctcta aaaattcctc ctttaccttt 60
cttctaaagt gtcggatcct ttacctttca aaaacgagga ataggtctcg tggctcatgc 120
ctagcgagac ctcatctcca caaaaaataa taataaaaaa attagccagg tgtggtggtg 180
tgggcctgta gtcctagtta ctggggaggc tgaggtagga ggatcactta agcccaggag 240
gtcaaggtta tagtgagtta tgatcgtgcc actgcactgc agcctaggtg acagagcaag 300
accctgttcc ccaccctctg caaaaacaaa caaacaaaaa agcatcctga taaacataga 360
catgaaattg aaacatacag gtgaagggtc acagatttat gcctcagtct tctcatctgt 420
aagacaaaga cagcctcatc acttttaatg aggtgagyga atgagggagg agaccacccc 480
tcatattgtc ttatgcccga tttctgcctc caaagaaaga agaagtaaaa actaaaaagc 540
agaaatgaaa tccacaggca gacagcccgg cgccacgccc tgggcctggt agttaaagat 600
taacccctga cctaacactg gttatgttat ctatagtttc cagacattgt atggaaaagc 660
attgtaaaaa tccctgtcct gttctgttcc gttctgatta ctggtgcatg cagcccccaa 720
acatgcaccc cctgcttgct cagttgatca cgaccctctc atgtggaccc ccttagagtt 780
gtgagccctt aaaagggaca ggaattgctc actcagggag ctcggttctt gagacagaag 840
tcttgccgat gctccaggcc aaataaaccc cttccttctt taactcggtg tctgaggggt 900
tttgtctgcg gctcttcctg ctgcacatta agtgaggtac accactgcat attacatggc 960
aggtgctcag tctcctcctt ccacttcctc actggttttc tagtgaagag agaatgaagg 1020
ggtgggttgc ccctccacac ctgtgggtgt ttctcgtaag gtggaacgag agacttggaa 1080
aagaaaaaga cacagagaca aagtatagag aaagaaataa ggggacccgg gggaccagcg 1140
ttcagcatat ggaggatccc accagcctct gagttccctt agtatttatt gatcattcgt 1200
gggtgtttct ccgagagggg gatgtgtcag ggtcacaaga caattgtggg gagagggtca 1260
gcagacaaac acgtgaacaa aggtctttgc atcatagaca aggtaaagga ttaagtgctg 1320
tgcttttaga tatgcataca cataaacatc tcaatgcttt acaaagcagt attgctgccc 1380
gcatgtccca cctccagccc taacgcggtt tttccctatc tcagtagatg gaacgtacaa 1440
tcgggtttta taccgagaca ttccattgcc cagggacgga caggagacag atgccttgct 1500
cttgtctcaa ctgcaagagg catgccttcc tcttatacta atcctcctca gcacagaccc 1560
tttacaggtg tcgggctggg ggacggtcag gtctttccct tcccaagagg ccatatttca 1620
gactatcaca tggggagaaa ccttggacaa tacctggctt tcctaggcag aggtccctgc 1680
ggccttctgc agtgtttgtg tccctgggta cttgagatta gggagtggtg atgacgctta 1740
acgagcatgc tgccttcaag catctgttta acaaagcaca tcttgcaccg cccttaatcc 1800
atttaaccct gagtttgaca cagcacatgt ttcagagagc acggggttgg gagtaagttc 1860
atagattaac agaatctcaa ggcagaagaa tttgtcttag tacagaacaa aatggagtct 1920
cctatgtcta cttctttcta cacagacaca gtaacaatct gatctctctt gcttttcccc 1980
acagagaagg cccatgcaac acagacctaa accccttga gaggaaaata gggcatttgg 2040
tggaggggag gggaggagtc ctggcttgcg gctataaaaa tgtttttcca c 2091

<210> SEQ ID NO 134
<211> LENGTH: 1001
<212> TYPE: DNA
<213> ORGANISM: Homo sapiens

<400> SEQUENCE: 134
cctctttccc tgttttatta ttatttttct ccaatcgctt atcactatta ttttgtttat 60
ttaatgcttt attatccgct tccgccactg ccatgtaatc ttgagggcaa gggtctctca 120
tgttttcttc accgttatct gcagtgcctt gaacactaat actggttgaa tgaacgaacg 180
cattaatgga gcggtgatat tggggcagag aggatgcagg gcttgctttt caccgccatt 240
tttcagccgg cagagacaga ccgagaaagg aatgaaggcc acggggcgtg tgcagaagta 300
gctaccagag agtccatgcg ctgcgagcct ggaccagcgg gcaaacgcgg cttacaggcg 360
ttcacccaga tattacgggt acaacctagt ttcttatgaa atacctcgcc cctaaggtac 420
gcgcagggcc agtggcgcaa tggataacgc gtctgactac ggatcagaag attccaggtt 480
cgactcctgg ctggctcggt rtaagcaggg tcgttttaca actttctgac tccgcaggag 540
taaggaaatt cctgcaagat aaatttgcct ggaagactca gaagcaagag gggcagctcc 600
cgacaacata tggggttatc atttctttgc ggagcattct gccactgacc acgtggtaac 660
gccaactacg ccagagaaac gctcgcccta cccaagttgt gcccagcctt gcctggccat 720
tttggccgaa gaacgaagga ccgttcagag attaaattaa agtctctatt gtgttcttcc 780
ctattcagtc atttgtagaa taaattctat ggcttcagtt tgaacactgg aggggctggg 840
tctgagcttt tcattggttt ttctggtttg agaggtcggt acagagacgc acgcgcacat 900
cagcaaaaca cgcacttgga acgaagaaac acggaactag gcaggaagaa ctatttactc 960
tgaaaaataa gcccttagtg ggtttccgta gtgtagtggt t 1001

<210> SEQ ID NO 135
<211> LENGTH: 1001
<212> TYPE: DNA
<213> ORGANISM: Homo sapiens

<400> SEQUENCE: 135
cgcggggaga ccccaatgga tttcaagtcc atcgccttaa ccactcggcc acgactacgt 60
acctccttca acaacctgga tatattccca tgaggaatat atgtttcttt tcacagacat 120
ctttaaattt gtttattttg acaaggtaac aactctggaa tgtctctcat cctggttaaa 180
aaacaaaatc aaaattttaa agatttagat attggctaaa agagatattg caaattgcaa 240
gacttgtctg atgtaggaag tacgaaagac tttacgaggg ggccacacgc caacccctaa 300
atggtctcca aacctacgaa actggctgaa agctctccac acctaattag taggattaca 360
gatattgaag cctacaaatg cgcatttcca ccaggatacc ttgtggattc ttacacgggt 420
caggtccgct gacgtttagc acgcctactt taaaacctct tttctgtagg gtcctagtct 480
tcaagtaaaa tatatgcggc yatatagcag aggatggttt cgatccatcg acctctgggt 540
tatgggccca gcacgcttcc gctgcgccac tctgctgtct cgacagtccg ctccgccact 600
ctgctgtttc aacattactc ttgtcaagta tgtattagag gctacaattt tcggcatctt 660
cctaatttta aatgatttgt tgtcgtttgc caaattatcc tggagaatga gaagtgcaca 720
ctggccatcc atatggggct gcacgccact tccaaacacc agcggtttag aattcttcct 780
cgataaattc gaatcagctg aggttgaagt tctctaaaac ggaagcatgt ttcgagttat 840
gggaaaacaa agtgcaggct aattggcata atttataaag gtgaaattat aaatgcttgg 900
gcaaatttca gccattcctg gataccggag ggagtcgtta ttacttccaa acattttta 960 cttgagattt tcatcgaaaa tgttcacagg aaaaaaaaaa t 1001

<210> SEQ ID NO 136
<211> LENGTH: 1256
<212> TYPE: DNA
<213> ORGANISM: Homo sapiens

<400> SEQUENCE: 136
ctgttaggct ttctccaaca gcagaaggct ctgtgatctc catctcttgg gaggcagaaa 60
attaccacaa gaaaatagcc gggaggcagc ggattgaacc ctggaaacgg cccgctcttt 120
gtgctgggcg gtgctcgaag ggaagaaact gagggcccgg gagtcgagtg tgtccagttg 180
tctgccaggc aggataagga ctgggaaaaa tgaaaaaaaa attcctagac atacacaacc 240
taccaagcct gaatcatgaa gacacagaaa atatgaacat accaatagta gataaggaaa 300
ttgaatcagc aataaaaaca tctcccatca aagaaaagcc caggacctgt agcgtctcta 360
gtgaattcta ccaactattt aaagaactaa taacatttat tatggaaaac agtattgtgg 420
ttcctcaaaa aattaaaaat agagatacca tatgatccag caaactctct agtgggtata 480
tagctaaagg aagtgaaatc agtatgtcca agagattatc tgcataccac caagatatgg 540
aattcttctt yttttttttt tttggtggca cagaatctct ctctgtcgcc cagggtgcga 600
ttttgactca ctgcaacctc tgtctcccgg gctcaaacga ttcttgtgcc tcagtctccc 660
gagtagctgg gattacaagc ctatgccaat ataccccgct gatttttttt ttttttgta 720 tttttagtag ggcgcgtttt tcaccatgtt gcccaggctg gtcttgaact tctgggctct 780
cctcggcctc ccaaagtgct gggattgcag gcgtgagcaa cggcgcccag ccaagatatg 840
gaattcttgt gttcaccaat ggatgaatgg atagagaaat gcgtttagct tccctgtgcc 900
ttggaagtat catttccaat ttatcatggg tgtgtacatt tttattggtg tacttgtgag 960
ctcatcacta atttttgcag tctgttaatc taccatagtt tcagtttcat tgtattttct 1020
tatatattta tattgtgtac tgatgtgtgc atggattagt aatgagtact ctattatttt 1080
taatgtcata attattcatt atttatttat tatttattaa aaataatatt taatattaaa 1140
tattatttat tacttatatt atttattatt ataataattt ataatatgtc acattataaa 1200
atattattta attaaaattt aatgtcactc tattatttta atatcataaa atacat 1256

<210> SEQ ID NO 137
<211> LENGTH: 7021
<212> TYPE: DNA
<213> ORGANISM: Homo sapiens

<400> SEQUENCE: 137
ctaatagagt cctccctctg atcagtggca aagagtagcc attatcattt tttaatggta 60
ataatattta ttacttttta aacttatttt ttaatggtaa taacatttat attatactgg 120
gtgtctgtat attgagttgc cattccaaag gactatataa aaaatatata tctaaatgct 180

```
tgacaaaaaa aaaatgcaat ttttttggaa aggaatatat ttggtggctg cctcatgcag    240
cttaagtgtc caaaatctga tagattggtg tatcccagtg gtagttttct gttgccacaa    300
actccaatca gcaggaatgg gggttgtaac tcctgtacaa tagttctacc ttatccacag    360
ttctgttttc tgcagtttga gttgctcctg gtcaaccttg gtctgaaaat attaaatgaa    420
aaacttcaga aataaacatt tcatatgttt taagttgcaa ctgactctgg gtaggataat    480
gaaataccac cctgtccagg atatgaatca tccctttgtc ctgcttatcc aagctgtgta    540
tgctaactgc ccattagtca ttgacatcat ctgcccctga catccaacca cagacgttat    600
catggctcag tgatccagga tcacccaggc agatgatcct ccttctgatg tatcatgagg    660
tcaacagtag cctaacgttc catcacagtg cctacttcac tcatctcgct tcatctcacc    720
acttaggcat tttatcacct catcatcata agaagaaggg ggagtacagc acaagacgat    780
attttgagag agagacccca ttcacataac ttttattaca gtgtattgtt ataattgttc    840
tattttaagc tagtgttgtt aatctcttac tatgcttaat ttataaattc aactttacca    900
taggtatgtc tgtgataaac attgtatata tagtgtttga cacatccata gtttcaggca    960
tccactgagg gtcttggaac atgtccccca aggataagtg gggactactc tagtgccatc   1020
aggctagcag gctgtaaagg ttttaatggc agtccctgga ccatggctta tttaattgct   1080
tccaaggccc actgctacaa agggcctcat tcaaagctgg tggctttgtt ggtcaccctg   1140
acttagggga ccaaaagaac actcaggtgg ggtacatgtt gcctccaatg cccaagtacc   1200
caaagaggcc ttccagctgt tgggcctcct ttttattagt ggatgtctcc aaaattaaat   1260
tttttgctt ggttgtatct agaatacttt tctggcttac tgcccatgtg gccttcgcat    1320
ttagcccagg gacagtccac tgttagtctc cacatccgaa agccttttg actagccaaa    1380
ctgagctgtt acattatgac agggtagttt gtagcatttc catttgtaac aataattaac   1440
acaataatgt cctgttcttc agttagtatg cagtactgtt tttttgaata acccactggg   1500
acttgggtgg cttaggtggc agacaggcat ggatatgccc cgccgtaacg gctggaattc   1560
ttagctgtga gcgggcgcac ccctcaggca gtgatgatgt gctgagcccc aagcagccaa   1620
aatgtcaatg actataagac attcagccac aggaaccaaa gtcaccggca cctcaaatgg   1680
ccagaggcac cccacagcag ataagcacca taggtcactg cttttgtccc caagcctctt   1740
aatgtcacca gtttaatttt tcccttaagg agacctggaa atattgtcac atgggttcca   1800
atatctaaga acaccagaaa aatatgaatt cctttttccc cctttttatc ttttaaagga   1860
atattattaa ttttaaaagc agggaccatg ctaatcatct ctatatcatt ccaatttcag   1920
tatatgtgct gctgaagcaa gcatgtcttt ttttttttaa tttttaaatt ttaaatttta   1980
tgagcacata gtaagtggat atatttaata ggtacgtgag acattttggt acaggacgca   2040
atctgtaata atcacatcat ggaaaatggg gtatccatcc tttcaagcat ttatcctttg   2100
tgttaaaaac aatccaatta tactcttagt tattttaaaa tgtacaatta agatattatt   2160
gactatagtc ttcctgttgt gctgtcaaac attaggtctt tttcattctt ctgttttttt   2220
ttgttttttt ttttgttttt ttcttttttc agatggagtt ttgctcttgt tgccctggct   2280
ggagtgcaat ggcatggtct cggctcactg caacctgcgc ctcccgggtt caagtgattc   2340
tcctgtctca gcctcctgag tagctgggat tataggcaca caccaccatg cctggctaac   2400
ttttgtattt ttagaagaga cagggtttca ccatgttggc caggctgatc ttcaactact   2460
gacctcaggt gatccacccg cctcagcctc tcaaagtatt gggattacag gcacgagcca   2520
ccacatccgg ccctttttca ttaaccatcc ccacctcctc tcccgcttcc tcccacttcc   2580
```

actacccttc caagcctctg gtaaccatcc ttatattctc ttatctccat gagttcaatt 2640
gttttgattt ttagatcctg caaataactg agaacatcca aagtttgtct ttctgttcct 2700
ggcttattat aagaactcct gttttatctt gacaggaata tagagtgact gacctccagt 2760
ggggaggaaa ccagagaccg tggccccatt cccaactggg ccattcagcc tgagacattt 2820
ggatttgata gaacctcttt gatagaacca tggcttattg atgaagtgga aggagtgata 2880
cccgaagtac ccagcccacg gtgtagacat caacctacag gggtgcggaa gctggacaca 2940
ccacccagcc tgcacaagat ttagctggct attctccatt tttattcttt ggataatgag 3000
tttctgctct gtaaatgccc ttatgaactg tgtttggttc cctctcagat gcctcaggga 3060
ccaccagagg acctcttcct cttccctctc agggttctca gggatcaact gagtatccat 3120
ttcctgagtt ctctagctct cgggaatgaa caaccataca agtgtccaac aatcagaggg 3180
tggcttgcca ctgtcctatt ctatatttct ttctctctgc cccagtcagt gcagccagct 3240
cactcatatc cgcagggttg gggtgacct atgtcctgtt tacaaaaaga gtcaaactgt 3300
aaaacatttg aagagattta ttctcagcca aatatgagtg accaatggcc tgtgacacag 3360
ccctcaggag atcctgaaaa catgtgccca aggtgatcgg ggcacagcca ggttttatag 3420
agtttaggga ggcatgagac atcaatcaaa cacatgtaaa aaattcattg gttgggtctg 3480
gaaaggcagg acaactcgaa gctgagaaag ggtggtgggg tgagggtgtg gcttcctggt 3540
tataggtaga tttaaaattt tgtgattggc aactggttga aagagttatt atcaatagga 3600
aggaatgtct gggttataat gataaggggt tgtggagaac aaagctttat tatgcagatg 3660
aagccttcag gtagcaggct tcagagagaa tagattgtaa atatttcttg tcagacttga 3720
ggtatgtgtt gatgttaatg ctggtcagct tttcctgaaa gccaaacttg agtggggtat 3780
aattggccct tctttcctgt catgacctga accagataat caggtaaact ttggaatgcc 3840
ctggccaaga ggaaaggtcc attcagatgg tgagaaggcc ttcaaatttt attgttggct 3900
tataatctca cctctcattc ttccttttat aaatcatctg gctgcttgtc cagctcctgc 3960
acmcctctag gttgatgtct acaccctggg ctgggtactt cggggtatca ttccttccac 4020
ttcatcaata agccatggtt ctatcaaaga gggccctgct cacttcacca attttgtgaa 4080
ccagattcac catgcactgg tgaattttgt gaacctgcct gagcctggtg agacagaaga 4140
cactcacatg caacaagtta catgaagcaa atgtattact tacagatagg aagcaagaga 4200
caacagaaga ctagaattca ttatgtgcca gtttcccaag gcttatgaaa gctgccttgg 4260
gtggatggag cttcaattgc acatggccta ctgttgttgc agctgagggg ccccaaaagc 4320
agcttacccc aggctcagta cctcaggggc cacaggaatc actgggtaaa tctcatccta 4380
ctttcaggga gagaggaaca aggctctggt tgtcctagca gttcctcctt aattcaatat 4440
gttacattct ttaggagagc caggagccag gcccaggctg tttcaggcag ttcctccctg 4500
cctcaggata tgggcattcc cacacactct acagttgttc ttcagactac aagcaagaaa 4560
tggaggagaa ctgggtcagt gcctggccac ttggagaaca gttctgcaga aagaagtcac 4620
acctgtgaaa actgcctgcc aagaggaaac aactacattg acatgtatgt gagcaagaaa 4680
tcaattgcta tttggttaag ccattgaaac tttctatttt tctttctttt ttttttttctt 4740
tttttgaga aagggtatca ctgtagctca ggttgtagta cagtggcatg ttaatggctt 4800
actgcagcct tgacctccca gatccaagca atccttttga gtatctagaa ccacaggtgc 4860
acactaccat gcccagctaa attttaaact ctctaaagag acagggtctc cctatgtggc 4920

-continued

```
ccaggcttgt ctcaaacttt taggctcagg tgatccttcc acctctcgac atcccatagt    4980
gctgggatta caggagtgag ccgtcttccc tggcctgaaa cttttacata tatttgttac    5040
agcagttgac actactctaa gcaggatata taccttgcat gttcaataaa gaatatatag    5100
aaatagcaac agttttcagg ggaacattgt ctttgaggat gaaactctga cttttttttct   5160
tatcttggcc aaactcctcc ctaagggacc ttgggagtca cccctacaaa ccataaagtt    5220
tcatcagagg ggttttattt aaccctatgt gacgtggttt gctttccaac ctggctctgg    5280
catgacctca cataataaat aaggaaagaa atgaaaatat tttagcccca aatatatttc    5340
cttgtcttga aatgaccctg caaagttgtc tctctcttgt gggaataaaa tctacatctt    5400
tttttttttt tttttttttt tttttgaggc gaagtttcgc tgttgttgcc cgggctggag    5460
tgcaatggcg tgatctcggc tcactgcaac ctctgcctcc caggttcaag cgattctcct    5520
atctcagcct cccgagtagc tgggattaca ggcacatgcc accacacctg gctaattttt    5580
ttggtatttt tagtagagac ggagtttcat catattgttc aggcaggtct tgaactcctg    5640
acctcaggtg atccacccac ctcagcctct taaagtgatg ggattacagg cgtgagccaa    5700
cgtgcccagc ccgttctttt cctttttttt tttttttttt tttttttgag atagagtctt    5760
gctttttttc ccaggctgca ctgcagtagc gtgatcttgg ctcactacaa cttctgtctc    5820
caggttcaag tgatcctcct gcctcagctt ccagagtagc tggcgtgcac ctccacacgc    5880
agctaatttt tctatcttta tttatttatt tattctgaga cgaagtttgg ttcttgttgc    5940
ccaggctgca gtgcagtagt gtggtctcag ctcactgcaa actctacctc ctgagttcat    6000
gtgattctcc tgccttagcc tcctgagtag ttggggttac aggcatgagc caccatacct    6060
agctaatttt tgtgtatttt tagtagagat ggggtttcac catgttggcc aggctggtct    6120
cgaactcctg acctcaggtt atccactcgc cttgacctcc caaagcactt ggattacagg    6180
aatgagcaac cgcagctggc caacttttgt atttttagta gaaatggggt ttcaccatgt    6240
tggccaggct ggtcttgaac tcctgacctc aaataatcag tctgtcttgg cctcccaaag    6300
tgctgggatt acagacatga gccatctcgc ccggccaaaa cttttttttt tttttttttt    6360
gagacaaagt ctcactctgt cacccaggct agagtgtaat ggtatgatta tggctcactg    6420
cagccttgaa ctcccaggct ccgcttccca gtagctggg actacaggtg catgccacca    6480
cgcctggcta ttttttgtat ttttgtagag attgggtttt gccatgttgc ctaggctggt    6540
gttgaaatcc tgggctcaag tgatccactg tgcttggctt ttttttttctt tttttttttt    6600
gagaccgagt ctcgctctgt cacccagatt ggagtgcagt gactcgatct tggctcactg    6660
caacctccgc tcggctgggt gcggtggctc acgcctgtaa tctcagcact tcaggaggcc    6720
gaggcgggcg gatcaccaga ggtcaggagc tcaagaccag cctgggcaac atggtgaaac    6780
cccgtctcta caggaaatac aaaaattagc caagagtggt ggcgggcgcc tgtaatccca    6840
gctactcagg aggctgaggc aggagaatca ttggaacttg ggaggcggag gttgcagtga    6900
actgagattg cacccatgca ctccatcctg ggcgacagag atagactccc tttcaaagaa    6960
aataataata ataataataa tgttttcatg atgctttgtt gatatctcct tcatcttaac    7020
a                                                                    7021
```

<210> SEQ ID NO 138
<211> LENGTH: 2457
<212> TYPE: DNA
<213> ORGANISM: Homo sapiens

<400> SEQUENCE: 138
ttcacattat cctctaagcc atttccagat tgactgtaga tctgaatata aaagtaagca 60
aacaaagctt gtagaataca acatcgggga atatctttat gactttgacc caaggaaata 120
ttttctagac ttgatgctaa aagcgttagt cataaagggc aatccttccc gtctagatct 180
tcaagtcctt cagttctgag aatttttctt atatttcttg gtaaaattat cctccatttt 240
tcctttgtct tgctggaact cccagtaatg agatgatatt gaatctctgg aatgggttgt 300
tcaattttct ttccactact attttccatc tttgatgttt tcctactgtt tttgaagtag 360
ttctaaactg taacttccaa atttttcatt aaatgttttt cttttcccct gctactttat 420
tctttatttc taggagatct tgtttcatta tcataaaaag atagtacccc aagttactat 480
ttccaggtga gatgaagtgt gttttacatt ttttctccta tcaaacacaa ctataagtta 540
tgggcagaat gcatgaaata actatttgaa gactctgata ataaaagagt aaacaaaaga 600
gtgtaaggat ggaaaaagaa caccagaatt atcctatatg ttctccccaa attgagtata 660
gatgtaatgc aattgctatc aaaattccag tagaattttt tggagataga gaaaagctga 720
ttctaaactt tatatggata gatgaaagaa ttagaatagc taaatcaatt ttgaaaaaat 780
gcagtgaata atcacattac ctgattttca gatttaatac caacttcagt aatcaagata 840
gtaargtatt ggcagaaata taaacatgta gatcaattga tcagaacaga gattccagaa 900
ataaatttac acaaatatgg cgaattgatt tttgacaaag gtgcaaataa aataaatgaa 960
gaaattaaaa ttgttcaaca aataatattg ggacaatggg ctatccatat gcaaaggaaa 1020
gaaagaaagg agagaaaagg agagaaagaa aggaaggaaa aaaagtaagg aaggcgtgga 1080
agaaagaagt gaaggaaaag tggaaggaag aaagaaaaga tatcctaaca taaatctaac 1140
aatttataca aaaattaact aaaaaattga tcatatatgc aaatgtaaac ataaaactat 1200
aaaactgtta aaagaaaaca taacagaata tccacatgac cttgagttgg gtgatgagtt 1260
cttagatatg gcactttcca aaaaagaaaa aaaaatacat tggacttaat caacttttaa 1320
cacatttgct ctgcaaaaga aactgttaag acattgaaaa aaataaagac tggcagaaaa 1380
tatttgtaag tcatgtatct gatagagaaa ttttatctag aatatataaa gaatccttaa 1440
aactcagcaa taagaaaaca acccaataaa aattgggtaa aggcataaac actttaccaa 1500
acagagtata aggatggcaa ataagcacac aaaaaatgtt tgacatcatt agccattatg 1560
aaatgcaact tttttttca caattgcccc aaactggaaa caaatgtcac acaacacaaa 1620
tgtccttcaa tgagtggata aactgtggta catccgtgca atggaattct attcaagagc 1680
aaaaaggaat gaaattttga tatttgtaac aacttgggaa aatcttcatt tatttctttt 1740
ttttgagacg gtgtcttgct ctgtagccca ggttggagtg cagcagcgcg atttaggctc 1800
actgcaagct ccgcctcccg ggttcgcgcc attttcctgg ctcagccttc cgagtagctg 1860
ggactacagg cgcccgccac cacgcccggc taattttttg tatttttagt agagacaggg 1920
tttcatcgtg ttagccagga tggtctcgat ctcctgacct cgtgatccgt cctcctcggc 1980
ctcccaaggt gctgggatta caggcgtgag ccaccgctcc cagccaactt gggtaaatct 2040
taaggcatta tgctaagcaa aagaagctga tctcaaaaag ttacatactg tatgattcca 2100
tttctacatt ttccaaaagg ccaaaatata caaatggaaa gagtatttat gattgtcagc 2160
tgctatgtgt gggattagga tgagactata aaggaacagt gctagggagg cttatggact 2220
gatagaactg gtgtgtatcc tgatatggta atgggtatgt gtatatacat gtaagtgctt 2280
tttaaaagtc aattttactt aatacttttt aaaaatacag atagctccca tttgtggcat 2340
agactgtacc ttctccatgg tttctgtgag aaacactttc accgagctct tgaaagagtt 2400
tattttgagc agggtttgga ggagagaaaa cccggtgaga ccctggagca ctgcacg 2457

<210> SEQ ID NO 139
<211> LENGTH: 3772
<212> TYPE: DNA
<213> ORGANISM: Homo sapiens

<400> SEQUENCE: 139
aatcgtacat gaatatgtat taatttagca aatatttact gatttctcca ctctttagaa 60
tgcaataatt agttgttatt ctatgtctgg tagttgctga tgagatattg ttatgtggaa 120
aaaacagaat ccaaaacagt tttgcaagat tatgattttt agtttaaaaa aaactgtatt 180
atgggatgat ttatatatga tarcgtgtac aatttgatgt tttggcatat tttatacatac 240 atgtaacaac taccacaatc aaagtagaga acatttccat gatcctaaaa agttcccttg 300
tggcctgtga tagtgaaacc tgtgaatatg ttatctttca cagcaaaagg aactttgcag 360
ctgtgattaa attaaggatt atgaaatgag gtgattatcc acaattacct ggattgggcg 420
ttgtaatcac aaggatcctt ttaagaggga tcattgtcag agaaggagat gtgacagtgg 480
aagcaaaagt tggaatgatg aggccgggcg cggtggctca tgcctataat cccagcactt 540
tgggaggctg aggtgggcag attgcctgag ctcaggagtt tgagaccagc accaccaaca 600
tggtgaaacc tcatctctac taaaaataca aaaattagcc agtaatcctg actaaatgct 660
cctgtaatcc tcgctactca ggaggctgag tcaggagaat tgcttgaacc cgggaggcgg 720
aggtcgcaat gagcagagat tgtgccactg cactccagct tgggcgacag agtgagacgc 780
cgtcttaaaa aaagaaaaaa agttggagtg ctgcagggcg atgagccaag taatgccagc 840
agcctcttct agctggcgaa ggcaaggaaa cagattctcc tctagagctt acagaaggaa 900
gatagccctg ctgactcact ctagacccct gacatccaga gctgtgagat aataaatttg 960
tgttgtttta agctattaag tttgtggtaa tttttcacag cagtaatagg aaactaatgc 1020
atgccctttc ccagtcagtc acactccgac cacacaattt ccagtcaact ataggccctt 1080
tccatcatga tggttttgcc ttttctggaa tttaatctaa atggattaaa ttatatgcta 1140
tgtactctag ttcctggttt ttgctcagaa catttttgag attcattcat gttgttgcac 1200
atatcagtaa tttattccat ttattagcac tttattggta aaatgtattc tatttgtaca 1260
gacatgccac aatttgtttt tccattcatg tgtgggtgaa cattttttatt attttcacat 1320 tctagctatt ataaataggg ctgctgtgca aatttgtgta acaagtcttt gtgtagacat 1380
atataagcca gagttcttca gaaacagaaa accaatagtg tgtgtgtgtg tgtgtgtgtg 1440
tgtgtgcgtg tgtgtgtgta gacagtgatt ttaaggaatg gacttacatg attgtagagt 1500
ctggccagtt cagattctgc acggtatgcc agcaggctgg aaacccagga aaaagttaat 1560
gtggcagcta aaactcaaag gctgtctgct ggcaaaagtc cctcttccta gggagagaag 1620
ttagtctttt ttctcttaag tatttttcaa ctgataggaa gcaatctgct ttactcaaag 1680
tgtactgaat taaatgttaa tctcatccag aagtaccttc acatcaacgt ctaaactagt 1740
gttcgatcaa atatctgaat actatgagct agccatgttg acacgaaaaa ttaaccattg 1800
catatgtttt cacttctttt ccaggaaata cctaggaatg gaattgctgg tcatttagta 1860
agtgggtgtt taactttata agaagctacc agtgttttcc aaagtggtgg ttcactttac 1920
attccaaaaa gcattatatg agagttccag ttgtacaacc tcctcagcat ttgttattgt 1980
cagacttaat gtttatgcaa agatatccta tgacatcttt gcctatttca taatcatgat 2040
tttctcctat atttccttct cagagattta taaattagca cttttgttta ggcctatgat 2100
ctattttcag ttaatttttt tatgtattct aaaataagga tcaaagttaa tttttttcca 2160
tatggctatc tccttgtttc tgcaccattt ttgaaaagac tatcctttcc tcataaagta 2220
cataggcact tttgttgaaa gtaaatttat tatacatgta catctatttt tggagtccct 2280
attttattcc attaatctat atgactttcc taattatact ttaatttgca ggccagttag 2340
gatggctatt atcaaaaacc agaaaataaa ttggtaagga tttattggta aggaacttta 2400
tgtattgctg gtggaaatga aaagcagagc agccactgtg gaaaacagta agattcctca 2460
aaattttctt ttcttttttt ttttttgaca gagtcttgct ctgtccccca ggctggagtg 2520
caaggcgcga tctcagctca ctgcaacctc cgcctcctga gttgaagcaa ttctcctgcc 2580
tcagcctcct gagtagctgg gactacaggc gcacgccgcc atacctggct aatttttttc 2640
gtattttagt agagaccagg tttcattgtg ttgcccaggc tggtcgcaaa ctcctgagct 2700
caggcaatct gcccaccttg gcctcccaaa gtgctgggat tacaggcatg agccactgca 2760
ccctgccaat cctcaaacta ttaaatgtag aattaccata tgatccagca attccatttt 2820
tgcatatata tccaaaataa attaaaacac gggctcagat tcatagcagt gttattcaca 2880
atagccaaat atccatcaac agattaatgg ataaacaaaa tgtggtatac acacaatgga 2940
atattattca gccttgaaag gaaattctgg ctgggcacag tggctcatgc ctataatccc 3000
agcattgtgg gaggcccagg tgggtggatc acctgaggtc aggagttcaa gaccagcctc 3060
accaacatgg cgaaaccccg tctctactaa aaatacaaaa ttagcggggt gtggtggctc 3120
atgcctgtaa tcccagccgg aggctgaagc aggagaatcg cttggaccca ggaggcggag 3180
gttgcagtga gccaagataa caccattgca ttgcactcca gcctgggcaa caagagcaaa 3240
actcagtctc aagaaaaaaa aaaaaaggaa attctgacac atgctaaaac atgaatgaac 3300
cttgaagaca ttatgctaag tgaaataaac caatcacaaa aagatgaata ttttatattc 3360
catttatata acgtaccaaa gtagtacaat ttatagagag ataaagtgga atggtggttt 3420
ccaggggact agaaagaggc aaggatgtgg agttagtgtt taataagtac agtttcactt 3480
ggaaaagatg gaaaagttct ggagacaaat ggtgataatg gttgtacaac aatgtaaatg 3540
tacttaatgc cacagaactg agcacttaaa aatggctaag atggtaaatt ttatattatg 3600
gttgcttaca taataaaata attacacacc agagacctat gacatatgta ttagccacat 3660
ttttaaaaat gataaaagtg taacacctta ttagagactg actcaggtac ctacagcaag 3720
taataggtgg agttgtcagt agcctctcaa actcaggtgt ttgatggtcc ct 3772

<210> SEQ ID NO 140
<211> LENGTH: 1001
<212> TYPE: DNA
<213> ORGANISM: Homo sapiens

<400> SEQUENCE: 140
ttttggaagg tgacgagtgt attttgtgag agagactggg gtcataggtg gacagaggtc 60
ctatctggta ggcagcctct aagatgaccc ccaataatct ctacctcctg gtattcttgc 120
cctggtgtag ttccctatgt accaggggtg gtctttgtgt ctaatgtaag tgatagataa 180
gctctagagg gaagccagtt actatgtcac cagcagtcct gtttagtagc ctatttgggg 240
agggagtgag ccttcctgcc aacacccact agggagattg gaagaagatc ctccagacac 300
agtcaagcct tacgatgact agagccctag cctggcatct tgattgcaac cccaggagga 360
accctaagct ggaactaccc aaatacaaca ctttgatttt caagttacag acacagtaag 420
ataataaatg tgttgtttta aaccactaca tttggagtta tttgttacag caattgataa 480
gcaatacaaa tctcaaataa rttaagttta taacttaagg ctccctggac tattcaggaa 540
atgcacttcc aggatgccga tctactgtag gtcacctttg tggctttgat ttatcaagat 600
gaagatattt tctacttctt ttctttactt ggtgcattcc taagtgacaa gactactttt 660
cgggcagttc actagggatg atagttgagt tttctctcta gattattatt aatctgcatg 720
tatgacactg aggacgtgta gagtggttct ccattttcag caggtcctag tgacttcggt 780
tttcctcaat ttagaagctg ccaaagcata agcccaaatt tgcctccatg agcaagagct 840
ctaaaagcat aagcaactgg ttgttgtggt gctctgctta tctgtgttct catttccttt 900
tacatttgtt ttacatgtct cttaggtttc tttaatgttt tatcacttca ttgtctaaaa 960
caaaccttta aagaattgat ttagaacata ttttaataaa a 1001

<210> SEQ ID NO 141
<211> LENGTH: 1001
<212> TYPE: DNA
<213> ORGANISM: Homo sapiens

<400> SEQUENCE: 141
caggtacttg ggaggctgag gtgggaggat cacttgagcc tgggaggcag agatttcagt 60
gagccaagaa tgcatcattg cactccagcc tgagcaacag agccagaccc tgcctcaaaa 120
agaaaatata tatgtatatt agtttgataa actccaatat aacttttttta cataaaattg 180 attttttaag tttataaata taaatattta aatatgatat ttaaatccaa ttttgctgga 240
aagcctaaac acaatgtgga agctattgac ttgtcccatt atcaatctta catactatta 300
taaaataaat gatataccat tatagcttct cccaactatc caaatgctta tgggttaggt 360
gtgaaaccta caagatgaag caaatgaggc tttatctagg ggtgacagtt ttatggaaag 420
aaatgagtat cagggaaggc tacacaatgc aaaaacaaaa ttctgtgagg acttgaaccc 480
aaggcatttt gcttaccaga yaagtaagtt gaatgacaaa gcaacaattc cctgtcataa 540
aagttaattt atttgctatt acagtataga cattttaaaa cacaccagaa gaattttaga 600
gtttgaaaat gacaagttgc attttgtttt gagcaggaaa catatcaaga caaacttcct 660
tcatactaga cagtattgta atcccagcga ctcaggaggc ccaagcagga ggaccacttc 720
aggccaggaa tttgagatta gcctaggaaa catagcgaga cctcgtctct aagaaaataa 780
attagtcatt gtagtagcac acacctgtag ttctagctac ttggaaggct gaggtaggag 840
gatgacttga gcccaggagt ttgaggctgc agtgaaccat gatcacgcca ctgcactcca 900
gcctgggtga tagatcgaga ccccatttct gggagggtgg gaaaaccaga cattgacaag 960
gcctgagcag aggaggctgc caactgtaga aattgcaagt t 1001

<210> SEQ ID NO 142
<211> LENGTH: 1001
<212> TYPE: DNA
<213> ORGANISM: Homo sapiens

<400> SEQUENCE: 142
tatgtaatac tatacatatt tttaaaagaa tgaagaaaac ttgtctattc tgatatggaa 60
agtttgcaaa agtacattgt aagtaaaaat ttaaaaaggc aagggactta aaaagtgtat 120
aaaatgccac tattcatgaa gagaaaaaag aaaacacttg tgtaactttg tctatgtatt 180
caaaatctct ggaacgataa acaagacatt aaaaacaatg gtaaagcttt tgggaaacaa 240
tggctgagta gacaacgatt gggtttaacg gcccctggaa tggtgactag aaccacattt 300
ctagcatttt tcaataccaa ggtcttcgaa gcgacctttg atttgaggtc actttaggaa 360
tctgaaggaa cacataggaa gactcccaaa ttgaggatct agacataaga aacctgggac 420
gatctcgatc atgggaccat cgagaatcag actcgttggg aatatccttc aagtaccaat 480
ttgtatgttg tattagtgag yggcttttac gaagcaaaga ctcattaata tttcaccgaa 540
tctgattcat tgtctgcatg tattgactag acattcagaa ggcagcaaat atttccataa 600
attgctgggc cattagccac agtttgaaat gtttaagcgt cctctttcaa gtctacgaat 660
acagccattt tgctttgttt ttgcgttaag aggaaatttc tcgttatttc tattaagact 720
ctaaagcaac taagaaattg ttcctccctg taagacaaac aggaattacg ttgaagaatt 780
taatactttc acggagaagg ggcgaggatg cgggtgagat gaataacaaa agcacagatt 840
tgcggtcggc cggttagctc agttggttag agcgtgctgc tactaatgcc agggtcgagg 900
tttcgatccc cgtacgggcc tttggctttt tccccccctcg agaaatttgg ttttcatgct 960
ctaagatgat tcaaattaac cgtccccatt tcttaacgaa c 1001

<210> SEQ ID NO 143
<211> LENGTH: 1001
<212> TYPE: DNA
<213> ORGANISM: Homo sapiens

<400> SEQUENCE: 143
cgagaccggg tagatatact cccttgggtt ggtgtgagcc tagagactta gggacctcat 60
cagagcaaga aagtgcaagt aggcttttct gcatcatttt ctggccctcc agttcagaca 120
caaatcaaaa gttagtccct tcttgaaagc cattagcatt catcaaggag cctcaatgag 180
aggaagtttc aaacaaaaac taaatgtgtc aggcccagat ttacggtgag ggtctgattc 240
cacttccttg cggggtcagt ttgggtccag gtgagagagg tacagtggtc tctagttttc 300
tggaaacggt actgctgata gggcaaggac tccttgcggc tgccccagag aggttggctt 360
gtcttatcca acttgcactt cacgttagag tttctaatga actcgcagac tccagtttct 420
tgcccaggaa accattttta ccgtattttg ttcttttgac cgtttcttgt cagttagctg 480
gtgtaaattc tgtttaaaga hgtgaaggga gccttctcca ttcgtgtagt cgtggccgag 540
tggttaaggc gatggactag aaatccattg gggtctcccc gcgcaggttc gaatcctgcc 600
gactacggga tgttttactg agaacagttc agcgaggaaa taggatctca catttgcttt 660
cagtttggga gtaaagaaac tcgtgataga gcctctgcgt gtcacctaac atagcctgaa 720
cttttgccga cttcgggatg ttttactgag aacagttcag agaggaaata cgatgtcata 780
tttgctttca gtttgggagt aaaggaactc gtaatagagc ttctgcgtgc cacttaacgc 840
agcctgaact tttgccgact tcgggatgtt ttactgagaa cagagaggaa tcgtatttac 900
ttcagagagg aaatacgatg tcatatttgc tttcagtttg ggggcgaggg aactcgtgat 960
aaagcttctg cgtgccactt gacgcatcct gaactttaaa a 1001

<210> SEQ ID NO 144
<211> LENGTH: 1001
<212> TYPE: DNA
<213> ORGANISM: Homo sapiens

<400> SEQUENCE: 144

```
cgaatccgag tcacggcagt accttgatgt cgcctcaatt tctcaacgta ctgagcagta      60
ccttgacgtc gcctcaattt ttcaacatac tggagtggag acagtctcgg aaaaacccct    120
gcaaaattga attgacttac gatctaatct gtacacaaaa aacactagta ttcatcatgg    180
tgccccaacc agtcagccaa gcagagagtg tctacgcttg ttgccttgtc ttttttttcc    240
cctctccaaa gattctcttc ccaaccctac ccaagcccta cagtcttgtt ggcattggct    300
gtatgtgaag aaactgaggt aattttttt taatggaaaa cttttacttt caaacactgg     360
taggcatgag gaaaggactg ttcaaaaggg gatccaggtt tgttgtggag atctttctta    420
aaacacaaaa gacaaattat taatcacgcg tttctaagta tcctagctgg accaatgctg    480
aaaaactgta acctttgatc rtctggagaa aattaaagaa atttgagtaa ttgaaggaat    540
ttgggtgggg gggaataatg gcccagaaga acagccccca tttctagccc gttcagtttc    600
tagaatgagt tctaaagagc caagtagact gggtgaggcg ggagtggagg agagctgatc    660
tgagatacgg aggtggctgg aaagaagtag ttggtgctac ctaggaccag taggaggtgg    720
ctggagacag gcagatcccc agaggcgctt ccatgagccc agttctagtt agtagcacag    780
cactctgaga acacattaat ggcacttcgt ccctcctggc cctggtggaa ggttagtatt    840
caaacaggtg tggtggctca tgcctataat cccagcactt tgggaggccg aggcgggcag    900
atcacctgag gtcgggagtt cgagaccagc atggccaaca tggtgaaacc ccgtctctac    960
taaaaataca aaaattagct tggcatagtg gcataggcct g                       1001
```

<210> SEQ ID NO 145
<211> LENGTH: 2290
<212> TYPE: DNA
<213> ORGANISM: Homo sapiens

<400> SEQUENCE: 145

```
gagggagaga aataacgtga tttctctcac atgaactcag gggccaactt tggatagaac      60
tgaaagctgt acctgagaaa caaagagaaa tattccttcc tccttcattt tatactattt    120
ccagcaccaa aaccttttct tctctctgcc tgccccttc cacacaaact gtccaactcc     180
attctcattt ccccactgag gtggatgctg tggtgccctg ccctggtcac tccgtgttgg    240
actgagacac acaatcaacc agctgcagag agtgttggtg gctcagggcc ctcagctgac    300
tccataccat gaattgttaa agagccaaag agagccctgt kgcccaaggt tattccacct    360
ctcagtgagt ggaccacatc caatgactgg aaaacatagg tgtaaaggtc ctggacccct    420
tgcacaaggt acacaactct gaagggtcac cccagttcca gagttcattg tgagactgca    480
ttatatttca acttttcctt ctgtctatcc tctttcctta acttcctcaa ggtattgatg    540
ctgcggggct ctccagtgga tgtcctatag tctatttctc tggaaccacc aaagacaggg    600
attcttaaaa gtgtggtctg accctaagat tctttcaggg gatccatgag gtgaagactt    660
tttttttttt ttttttttga gatggagtct cactctgtca cccaggctgg agtgcagtgg    720
tacgatctca gctcactgca acctctgcct cctgggttca agctattctc ctgtctcagc    780
ttcccgagta gccaccactc ctgcctaatt tttatatttt tagtagagat ggagtttcac    840
catattggtc aagctggtct caaactcctg acctcaggtg atccacccat ctctgcctcc    900
caaagtgctg agattacagg tgtgagccac cgcacctggc caagacaatg tttataatga    960
tactaaaatg ttatttgtgg ctgggcatgg tggctcatgc ctgtaatccc aacgctttgg   1020
```

gagaccaagg caggcagatc acttgatgcc agaagtttga gacctgcctg ggcaacatgg 1080
tgaaaccctg atctctacaa aaaatacata aaattatctg ggcatggtgg tgagttcctg 1140
tagtcccagc tactcaggag gctgatgtgg gaggatcacc tgagcctcgg aagtcgagga 1200
tgcagtgagc catgatcacg cctctacact ccagcttggg tgacagagtg agaactctgt 1260
ttcaaaaaaa aaagaagcga gaggatcact tgagcccagg aattcaagac cagcctggac 1320
aacatagtga gacccccatc tctatttta aaaataaata aataaatttt ttttaagtta 1380
tttgcctctt ttactcacat actctcacat gtgtgcattg gagttttcca gatgttgaag 1440
acatgatgac atcatccctc tgacacctat tggaatgtat gtcacaatgt gtattattgt 1500
gtttaaaatg ctgtgtttta agggccgggc atggtggctc acacctgtaa tcccagcact 1560
cagggaggcc gaggcaagcc gatcacttga gcccaggagt cagacctggc caacatggtg 1620
aaaccttgtc tctatgaaaa ataaaaaaat tagccagaca tggtggtgca tgcctgtaat 1680
cccagctact aggaaactga ggcaggagaa tcacttgaat ttgggaggcg gaggttgcag 1740
tgagccgaga ttgtaccact acactccagc cagggcaaca gagcgagact ctcatttaaa 1800
aaaaaaaaaa aaacctgttt tatttattta tttgagacag ggtctcaatc attcgcctag 1860
gctggagagt agtggtgcca tctagactca ctgcaacctt cacctcccag gctcaagtga 1920
tgttcctgcc tcagcctccc acgtagctga aattacaggt gcatgccacc acacatagct 1980
aatttttgta tttttttgta gagacaaggt ctcactatgt tgcccaggct tgtctcgaac 2040
tcctgagctc aagcgatcca cccaccttgg cctcccaacg tgctggagtt acagatgtgc 2100
accaccacac ccagcccagt tttaattttt aaatgctaag tgttgataga tataactcac 2160
ataaataaaa actctctggg attctcaatt attttcaaga gtataagaag gtcatgagac 2220
caaaacatct gagaattgct gctctaagat aaccaaatct accctgggag gaaaaggctg 2280
aggttttaaa 2290

<210> SEQ ID NO 146
<211> LENGTH: 1001
<212> TYPE: DNA
<213> ORGANISM: Homo sapiens

<400> SEQUENCE: 146
gaaacaaata cacatgaaaa tacagtatgg cacaaataag gagcaagagg tgaagaaagc 60
ttcagtcaca cccaaaataa ttttgtgaaa aatataaaat atgcagttat agacagcact 120
aactctggat accagaaaat tctataattc ggtaatggat ctgagacctg aattttggag 180
gtactaaaat agatgcaata gatctagttt tcattatgtt catactttca tttggctctg 240
tggtaaaaga tgataatatc caaaacaaaa gatgataata tcctccatgt aacaattaca 300
tgcaagggga tgtctgcaaa ctgccacagt atcattttaa ttaataccta tcttctcttc 360
ttaaaatctt ttcatttttc cactcagttc tcctgatatt tctgttatga tataaaagac 420
agctgaatgt gaagaaacac tgattgtaca cgtaacacac acattaatga ttcaaatatg 480
taaacacaga gagctgcaaa yactttgaga ggtagggctg aaacttttcg tcaatgtgta 540
caattcaata tcgtttcagt tttcattcta accgtcccca gtggcttctg cccagcaact 600
gatgagaaat ggtacctctg agccaatcaa aacacgaatt cctacaaaga ggattctctt 660
agtgtttctc ggaccgagtg tacagcacat gctttctttt cctttattct ggatcagaga 720
atcttaacta aagcagaaat aattgtgtta aattaaacta aatttggtat gagatatgta 780
tacatttagc ctgaggg atg gctcttgagc ccttaaataa tgaactgcaa cctaacttag 840

```
tatgtaaact aactgaaagc ttaaggcatg ggagtatact tttgtaacaa atagctgagt    900
ctcagccaat cccagtagcc gaacttcagt cggcggcagt caaccctgca gccaagtgat    960
cagactatgt tcaaataagg ccaactctga gctgtaacca a                        1001
```

<210> SEQ ID NO 147
<211> LENGTH: 1001
<212> TYPE: DNA
<213> ORGANISM: Homo sapiens

<400> SEQUENCE: 147

```
gagtttctct tggtctgtgt gggagaagat ggagatcaca gctggagggg gaagacaagg     60
ggttagatgg aaaatgggtg cctcttggga ataggcagct tgctagcttg cttagctact    120
taatctgtga ggttatttcc cggctttcaa aagatgggtt attttggtgt cctgggacat    180
ggacaactgc aatctcttcc ggcagctgaa gattttctag cacttgcata attaattcct    240
tgtgggccaa atcttggccc ttactattga tgaggcctcg ttcagtccag atcttttccg    300
aaggcatact tggagtaagt gtaaatagtt ccttcctgat tctgcaggga ttttaaggct    360
tggtttaatg caaagagttc acatatttgg gcagaccact tatttggcag tctttctgac    420
tctaccactg tgagggtttc cctatcaact atggagtacc cgttgtgcct ttttccttca    480
atgacctggg aggagccgtc yataaagagg tgatgccctg tttggaaggg ggtttcatgc    540
ctggatgcgg tctgactcta gtttgaaaac tgattagatc taagcagtta tgctcacatt    600
cctcctggtt tggatttcct gttaggaaag cagcggggtt gagtgaattg tcagtggtta    660
gtgttaggtt atctccctct aataagatag cttcatattt taaaatcctt gagtcagtga    720
gccatctccc tgccttctga ttaagaatgg ttctgacttg atgaggggca cttacgaaga    780
ggtttccccc aaaggttatt ttcctgcttt cttctgttag caaggcagtt gctgctatgg    840
attgaacaca ttcgggccat ccacgggtta ctgggtcaag gatttttgac agaaagacta    900
caggctgccg gtggcctcca tgtttttggg tgagtacccc taaggccact cctttgctta    960
cattaatgaa aagatggaat ggctgttcta aggagggcaa a                        1001
```

<210> SEQ ID NO 148
<211> LENGTH: 501
<212> TYPE: DNA
<213> ORGANISM: Homo sapiens

<400> SEQUENCE: 148

```
ctccagtgca acctatgggg cttttggaaa tgaggaagtc gatgactctg cagggactcc     60
tctgacccag gagcagatgg cgctcgtctg ggcactcccc aggagaaaag gtgcatcggg    120
aagcagcctg gcttgtggat ggtaataagt cactgttgat gggttgggtg cagggaggga    180
tttaagttct tgagcgacag atgctaggga gtttacctgc tctggataac agtatcttgt    240
ggaggatagt yacctggaaa acagaaatgg cgtgactgtg ttgaatacac tgtttgatga    300
ttctgggcat caggtgaata ggaaatgtgt aacgttatgg atgagtgtgt gctcatcgga    360
cagtagcagt gcatcttaac agtcggcctc tcagtcctcc tcttccttag aatcacctat    420
agagctttaa aatttcctgg ataatgttaa tgtgcagcca gcgatgatga ccattgggct    480
acagtcaaat ccaagaggcg c                                              501
```

<210> SEQ ID NO 149
<211> LENGTH: 1001
<212> TYPE: DNA

<213> ORGANISM: Homo sapiens

<400> SEQUENCE: 149

```
cccacctcgg cctcccaaag tactgggatt acgggcatga gccaccatgc ctgtcctaca     60
tatatcttat tcattgtctt attcaatcat acaacttcct gataaaatga ggctgatttt    120
cacccctatt ttgctgttaa ggaaactggt ataatgagtg tcactgactt gtttgtgatc    180
acacagtgga caaaatggca tttgtttctt tgtggtgatc tcacaaaggt caagatgacc    240
ttagatcctc agttttggct gttttttttt tgttgttttt ttgtttgttt gtttgtttta    300
caccaaggaa ccaggttcta gctcctatgt ttgttcattg catggaaagg aacaggaaga    360
tctgggggcc actgaatgga aggttagatc cattttcttg gttaagcttg taggttttct    420
cgtctctttt ccttcctgca gcacaattct tatgaatggc aatatcttct attaaaattc    480
tcagtctgta gtcttcttgt ycatacagaa aatagatttc aggtcaacac atttgatagt    540
ctggactgtg ctaactgctc caatatttga gtacatcttt tggggatgtg ggaatttagt    600
gttgtaggcc tcaagtgggg ttcgttccca gaatttggag aggctataga aatataacct    660
ggttggccag gcacggtgac tcatgcctgt aaccccatca atgtgggagg ccgaggcagg    720
tggatcacct gaggtcagga gttcgggacc agcctggcca acatggagaa accctgtctc    780
tactaaaaac ttttaaaaaa ttaggcgggc gtggtggtac gtgcctgtaa tcccagctac    840
ttgggaggct gaagtaggag aatcccttga acccgggagg tggaggttgc agtgagctga    900
gatcacacca ttgcactcca gggcaacaga gtgagactcc atctcaaaaa aaaaaaaaaa    960
agaaaaagaa atataacctg gccataatat aagcataaat a                       1001
```

<210> SEQ ID NO 150
<211> LENGTH: 1181
<212> TYPE: DNA
<213> ORGANISM: Homo sapiens

<400> SEQUENCE: 150

```
gaggtcctgg ctgagccaag gagtaatgga ccagatctac ctcagtattc aagttcagtg     60
gggacaccag tggcttcaaa cttcctggtt tcatgatatc ttgagacgcc ttacaaatga    120
tggaggattc caaagagttt ttgtttattt gggttaatat ttgttggtat ttatggcatt    180
tgagattgaa actaagaaat gttttaattt attaccttta caacatttat ttacattaca    240
tacatacatt tacaacattt attaatttat attaaaatag catgaataag ccaattatag    300
gttaatataa gtagaatgtt tgtgaaaaat aagtatggta tccaaagcaa aataaatttt    360
attgtgaagt gtggcattga ttvacttttt ccagatctaa tgtgtggctt gaaagaatat    420
gactggattc tcatatctgc ctttatactc actctgttga gatatcatag actatatagg    480
ctcaagaaaa ctttatccta gtgacagaat gagattaaaa acaacaaact gtgttttatt    540
attaatatga aaatacgatt attaaccttg caggcccctt aaaacagttc tggttaactg    600
agaccttgtc tctaccaaaa acaaacaaaa aaaattaggt gtggtagcgc acgcctgtag    660
tccctgcttc aggagactaa aaagactaac tccaactcct tgcttgagcc aggagttgga    720
gtttgcaatg agctgtgatc ctgccattgc actccagcct aggcaacaga gtgagactct    780
gcctcaaaaa accaaaacac aggtcgggca cggtggctca cgcctgtaat cccagcactt    840
taggaagccg aggtgggtgg atcacctgag gtcaggagtt caagaccagc ctggtcaaca    900
tggcaaaacc ccatctcact aaaaatacaa aaattagcca ggcatggtgg cgggcaccta    960
taatcccagc tactcaggag gctgagacag ggaatccttg aaccccagtg ggtggaggt    1020
```

```
tgcagtgagc caagatcgtg ctgcttcact ccagcctggg tgaaagagtg aaactcccgt   1080

ctcaaacaaa gagggggagg gaacttatgt cagagacccc ccccaccccca ccccaggaat   1140

cctgaaacca tatttgagag ttgggataga ggattcggga a                        1181


<210> SEQ ID NO 151
<211> LENGTH: 1205
<212> TYPE: DNA
<213> ORGANISM: Homo sapiens

<400> SEQUENCE: 151

ttatgggaag aatcaggaac atatatttaa atacctgatt tgttaaggca gaaaacaggg     60

ttgtttatgt gcatgtttta gtctgcccag acagctatga caaatatacc aagactgagt    120

cgtttataaa caaccaaaat ttttttttctt gcactctggg ggctgggaaa tgtaagacca    180

aggcaccagc agtttggtaa ctggtaagag cctgcatcct tgttcacagc cttttaaatg    240

tgtcctcata tggcaaagga gaaaagtaga tctttggttt ttgtcccaag aaactggaaa    300

gatgggccgg gcacggtggc tcacgcccgt catcccagca ctttgggagg ccaaggcagg    360

tggatcactt aaggtgagga gttcgtgaac agcctggcca acatggtaaa accctgtctg    420

tactaaaacc cagaaggtgg aggttgcagt gcaccactgc actctagcct gagtggcaga    480

gtgagactct caaaaaagaa aagagagaga aggaaggaag gaaaggaagg aaggaaggaa    540

ggaaggaaaa gtaactggaa agatgaagtt gttaatttct gagatgggga aacggagaga    600

caaggagcaa gacgggagtg gtacagaacc aaaggttcag ttgtggatac attaaggttg    660

aggagtctat attagagatg cacatggaga tgcagagtag tccattgaat aaccaagagt    720

ccaggtgaga cctcaaggct ggagrtagag attccatact caactttcct atatgtttga    780

agagtttcat gatacactgt agtgggtaga gggaagaatt gtattttgtt attaataaca    840

gtcctgaata tcattggctt tgacaaaatg aggacttctt ttcatgtcaa taaatatgga    900

tggtggccat caagggctga tctgagagct tgaaatgtca tacatgcccc agcttagttc    960

tgtctttatt ttcttctgtc ttagcatgtg gcttgcatct tcaatgttgc ctcatggtca   1020

caaaagggct gcccagctcc aaagtccata ttctagataa gaggaagtag aaagtaaggg   1080

gagtgtaagg gtctaccagc tgttttagcc tcccccttaaa taatctgtct gataaacttc   1140

caccctcaag caattggctc aaacttagtc ccttggcttc ccctgtctac aaatgagatg   1200

gacac                                                                1205


<210> SEQ ID NO 152
<211> LENGTH: 1001
<212> TYPE: DNA
<213> ORGANISM: Homo sapiens

<400> SEQUENCE: 152

cttgtcagat cccagccccc tggttgagat tttcctggac tatgaagcag gaggcatctc     60

cttctacaac atgagtgaca gaacccctta tctatgcttt ccccaaaggc tctttctctg    120

gctcccttca gcctttattc ttcttgtggt catgcgataa aaagcccctg accacctgcc    180

caattgttga tggactttca ggaggtcaca gtcttgtgaa gcctggggcc taaggagatt    240

ctgttgtcca gaattcagaa aattctgcct ccagaaatac aaatatgctc ttttctaaac    300

aagtgacaac acaatgtagc cataggctcc cttaagcagc cacctcatgt caactaatag    360

tctttgctct ctagcctctc tcctccaaag tccatttcgt ctcctgaggc ttcagctatt    420
```

-continued

```
actgtcagac cctcagttac ttctgatgaa cagggattag gcttgagaaa atggagatgc    480
atttagattg gcagatatgg rggacttctt aatgtgcttt tattgctgcc ttatctctga    540
aaacaggttc tgggagtttg ggaataagtc tgagggcata taaaggattg agactgagtg    600
acttaggagt gtgagaggaa atatcttgat gttgagaaca gggttgatgt ggaggggtat    660
tctctgtgtt atgcatgtaa aaagaaaaaa aggaaaaaaa aatcattact gggaaagaaa    720
acaccccaag ctgaagtcca agaaaggtac acagaggaaa cacagaaaca gttgtgttag    780
cagaagatga catgaaaccc agctgacagt gaaattagga agttgccttg gaatttcaag    840
aacttgcatt ctcaagttta tggttctgtg tccaacagag cagcaaaatc cagcacttct    900
tcttttgagt ctccatatcg tgctaacaga aagacaaggg gtcgggagat gcagagatga    960
ggaggagctc aagagtgaca gtgttgaaga gattctgagc a                       1001
```

<210> SEQ ID NO 153
<211> LENGTH: 4000
<212> TYPE: DNA
<213> ORGANISM: Homo sapiens

<400> SEQUENCE: 153

```
atatagtgtt tgacacatcc atagtttcag gcatccactg agggtcttgg aacatgtccc     60
ccaaggataa gtggggacta ctctagtgcc atcaggctag caggctgtaa aggttttaat    120
ggcagtccct ggaccatggc ttatttaatt gcttccaagg cccactgcta caaagggcct    180
cattcaaagc tggtggcttt gttggtcacc ctgacttagg ggaccaaaag aacactcagg    240
tggggtacat gttgcctcca atgcccaagt acccaaagag gccttccagc tgttgggcct    300
cctttttatt agtggatgtc tccaaaatta aattttttttg cttggttgta tctagaatac    360
ttttctggct tactgcccat gtggccttcg catttagccc agggacagtc cactgttagt    420
ctccacatcc gaaagccttt ttgactagcc aaactgagct gttacattat gacagggtag    480
tttgtagcat ttccatttgt aacaataatt aacacaataa tgtcctgttc ttcagttagt    540
atgcagtact gttttttttga ataacccact gggacttggg tggcttaggt ggcagacagg    600
catggatatg ccccgccgta acggctggaa ttcttagctg tgagcgggcg cacccctcag    660
gcagtgatga tgtgctgagc cccaagcagc caaaatgtca atgactataa gacattcagc    720
cacaggaacc aaagtcaccg gcacctcaaa tggccagagg caccccacag cagataagca    780
ccataggtca ctgcttttgt ccccaagcct cttaatgtca ccagtttaat ttttccctta    840
aggagacctg gaaatattgt cacatgggtt ccaatatcta agaacaccag aaaaatatga    900
attccttttt ccccctttttt atcttttaaa ggaatattat taattttaaa agcagggacc    960
atgctaatca tctctatatc attccaattt cagtatatgt gctgctgaag caagcatgtc   1020
ttttttttt taatttttaa attttaaatt ttatgagcac atagtaagtg gatatattta   1080
ataggtacgt gagacatttt ggtacaggac gcaatctgta ataatcacat catggaaaat   1140
ggggtatcca tcctttcaag catttatcct ttgtgttaaa aacaatccaa ttatactctt   1200
agttatttta aaatgtacaa ttaagatatt attgactata gtcttcctgt tgtgctgtca   1260
aacattaggt ctttttcatt cttctgtttt tttttgtttt ttttttgtt tttttctttt   1320
ttcagatgga gttttgctct tgttgccctg gctggagtgc aatggcatgg tctcggctca   1380
ctgcaacctg cgcctcccgg gttcaagtga ttctcctgtc tcagcctcct gagtagctgg   1440
gattataggc acacaccacc atgcctggct aacttttgta tttttagaag agacagggtt   1500
tcaccatgtt ggccaggctg atcttcaact actgacctca ggtgatccac ccgcctcagc   1560
```

```
ctctcaaagt attgggatta caggcacgag ccaccacatc cggccctttt tcattaacca   1620
tccccacctc ctctcccgct tcctcccact tccactaccc ttccaagcct ctggtaacca   1680
tccttatatt ctcttatctc catgagttca attgttttga tttttagatc ctgcaaataa   1740
ctgagaacat ccaaagtttg tctttctgtt cctggcttat tataagaact cctgttttat   1800
cttgacagga atatagagtg actgacctcc agtggggagg aaaccagaga ccgtggcccc   1860
attcccaact gggccattca gcctgagaca tttggatttg atagaacctc tttgatagaa   1920
ccatggctta ttgatgaagt ggaaggagtg atacccgaag tacccagccc acggtgtaga   1980
catcaaccta caggggtgcr gaagctggac acaccaccca gcctgcacaa gatttagctg   2040
gctattctcc atttttattc tttggataat gagtttctgc tctgtaaatg cccttatgaa   2100
ctgtgtttgg ttccctctca gatgcctcag ggaccaccag aggacctctt cctcttccct   2160
ctcagggttc tcagggatca actgagtatc catttcctga gttctctagc tctcgggaat   2220
gaacaaccat acaagtgtcc aacaatcaga gggtggcttg ccactgtcct attctatatt   2280
tctttctctc tgccccagtc agtgcagcca gctcactcat atccgcaggg ttgggggtga   2340
cctatgtcct gtttacaaaa agagtcaaac tgtaaaacat ttgaagagat ttattctcag   2400
ccaaatatga gtgaccaatg gcctgtgaca cagccctcag gagatcctga aaacatgtgc   2460
ccaaggtgat cggggcacag ccaggtttta tagagtttag ggaggcatga gacatcaatc   2520
aaacacatgt aaaaaattca ttggttgggt ctggaaaggc aggacaactc gaagctgaga   2580
aagggtggtg gggtgagggt gtggcttcct ggttataggt agatttaaaa ttttgtgatt   2640
ggcaactggt tgaaagagtt attatcaata ggaaggaatg tctgggttat aatgataagg   2700
ggttgtggag aacaaagctt tattatgcag atgaagcctt caggtagcag gcttcagaga   2760
gaatagattg taaatatttc ttgtcagact tgaggtatgt gttgatgtta atgctggtca   2820
gcttttcctg aaagccaaac ttgagtgggg tataattggc ccttctttcc tgtcatgacc   2880
tgaaccagat aatcaggtaa actttggaat gccctggcca agaggaaagg tccattcaga   2940
tggtgagaag gccttcaaat tttattgttg gcttataatc tcacctctca ttcttccttt   3000
tataaatcat ctggctgctt gtccagctcc tgcacacctc taggttgatg tctacaccct   3060
gggctgggta cttcggggta tcattccttc cacttcatca ataagccatg gttctatcaa   3120
agagggccct gctcacttca ccaattttgt gaaccagatt caccatgcac tggtgaattt   3180
tgtgaacctg cctgagcctg gtgagacaga agacactcac atgcaacaag ttacatgaag   3240
caaatgtatt acttacagat aggaagcaag agacaacaga agactagaat tcattatgtg   3300
ccagtttccc aaggcttatg aaagctgcct tgggtggatg gagcttcaat tgcacatggc   3360
ctactgttgt tgcagctgag ggccccaaa agcagcttac cccaggctca gtacctcagg   3420
ggccacagga atcactgggt aaatctcatc ctactttcag ggagagagga acaaggctct   3480
ggttgtccta gcagttcctc cttaattcaa tatgttacat tctttaggag agccaggagc   3540
caggcccagg ctgtttcagg cagttcctcc ctgcctcagg atatgggcat tcccacacac   3600
tctacagttg ttcttcagac tacaagcaag aaatggagga gaactgggtc agtgcctggc   3660
cacttggaga acagttctgc agaaagaagt cacacctgtg aaaactgcct gccaagagga   3720
aacaactaca ttgacatgta tgtgagcaag aaatcaattg ctatttggtt aagccattga   3780
aactttctat ttttctttct tttttttttt cttttttttg agaaagggta tcactgtagc   3840
tcaggttgta gtacagtggc atgttaatgg cttactgcag ccttgacctc ccagatccaa   3900
```

gcaatccttt tgagtatcta gaaccacagg tgcacactac catgcccagc taaattttaa 3960
actctctaaa gagacagggt ctccctatgt ggcccaggct 4000

<210> SEQ ID NO 154
<211> LENGTH: 1181
<212> TYPE: DNA
<213> ORGANISM: Homo sapiens

<400> SEQUENCE: 154
gaggtcctgg ctgagccaag gagtaatgga ccagatctac ctcagtattc aagttcagtg 60
gggacaccag tggcttcaaa cttcctggtt tcatgatatc ttgagacgcc ttacaaatga 120
tggaggattc caaagagttt ttgtttattt gggttaatat ttgttggtat ttatggcatt 180
tgagattgaa actaagaaat gttttaattt attaccttta caacatttat ttacattaca 240
tacatacatt tacaacattt attaatttat attaaaatag catgaataag ccaattatag 300
gttaatataa gtagaatgtt tgtgaaaaat aagtatggta tccaaagcaa aataaatttt 360
attgtgaagt gtgrcattga ttaacttttt ccagatctaa tgtgtggctt gaaagaatat 420
gactggattc tcatatctgc ctttatactc actctgttga gatatcatag actatatagg 480
ctcaagaaaa ctttatccta gtgacagaat gagattaaaa acaacaaact gtgttttatt 540
attaatatga aaatacgatt attaaccttg caggcccctt aaaacagttc tggttaactg 600
agaccttgtc tctaccaaaa acaaacaaaa aaaattaggt gtggtagcgc acgcctgtag 660
tccctgcttc aggagactaa aaagactaac tccaactcct tgcttgagcc aggagttgga 720
gtttgcaatg agctgtgatc ctgccattgc actccagcct aggcaacaga gtgagactct 780
gcctcaaaaa accaaaacac aggtcgggca cggtggctca cgcctgtaat cccagcactt 840
taggaagccg aggtgggtgg atcacctgag gtcaggagtt caagaccagc ctggtcaaca 900
tggcaaaacc ccatctcact aaaaatacaa aaattagcca ggcatggtgg cgggcaccta 960
taatcccagc tactcaggag gctgagacag ggaatccttg aaccccagtg gggtggaggt 1020
tgcagtgagc caagatcgtg ctgcttcact ccagcctggg tgaaagagtg aaactcccgt 1080
ctcaaacaaa gagggggagg gaacttatgt cagagacccc ccccacccca ccccaggaat 1140
cctgaaacca tatttgagag ttgggataga ggattcggga a 1181

<210> SEQ ID NO 155
<211> LENGTH: 4000
<212> TYPE: DNA
<213> ORGANISM: Homo sapiens

<400> SEQUENCE: 155
agacgtttac ctggagttgg tcctttttag ccgccagaaa gatacaggga ttaaaaacac 60
aaattgtaaa ttgagtgata atatttctta caaaggtaac attaaaactg tgttgagtcc 120
tattactatt attggatagt gtcctgaccc agatgctgcc attcataaat gggagtgcta 180
acttccatat cgactgctga attgggcccc tctttccttg atgacgccgc tgaggcaaag 240
gcggactaaa gcctgttccg tgccaagcca gttgcgtggc agattaggat tgaatcccaa 300
tgcgatatag cgaagaaatg ttaaatgttc accaccagtg gcagcgaagt ttgttccatg 360
aggtctgatt ctcatctctc ccaaatgacc acagggaccc cagtcaataa tgtctcccat 420
taacatagac ttgtctagct aaggggtcaa gacactggat ccaaggaggg gggtgagaat 480
tattgaaggg agcccattct gtataatcaa tacaatttgg acgatggggc tgggagagat 540
tagtaaatcc accagtaata ttattagagc taaggcctaa taggtacata atgtttccat 600

```
ggtgactcaa ccatgcctgg gattggactg caaggcaact gccattgagc gatgtatcct    660
tggtgatgca taaagggagt ccctccaatg gggcagtgta attgatacta ttgttctgac    720
agtctaatag ttctgtgtca gggggagtta ggggtcctgg ggtccatgct ccctgatcac    780
gatatacctc aggaggagtg tcactccaga gtacaggtcg cactactcag gggttaggaa    840
catatgcccg acatgttttt gcttctacac aggggaaaca taccacacag gacactacag    900
ctagtatggc caagaacatt gattcagggg tttttgcctg accctggcac tccagcattt    960
tctcagcttc ctgcatggtt ttcttgatct gtccccatgt tatgagggtg gatgtcaatg   1020
tgactccagt cggcccttgt tccatctttg cattcagatt caactggcct atggcttgta   1080
ctgggggaac cgggcccatg gttgcgatcc acggatccct ccagtctccc gttccatggt   1140
tgcacgtacc tggagggcac ctacacagtt tgtccatctc ctgtaaaaac acaagcatac   1200
cctcatcccc acatcagcaa atccactggg cctttccttt gtccttcttc tggggatttc   1260
cataacacct ttggataaac ttgcctcttt ccctctaaca cttgccaatg ttgttctgct   1320
agagtcttac catccatacc aggcatcaaa aaatttaaag taaacaagac taaatgtaat   1380
tttgtttaag gtggtagctg gtctcctatt ccccctttt ttctcaacat acgctgtagt   1440
gtttgatgtg cccgctctat aatgccttgt ccttggggat tgtaaggaat tcctgtttta   1500
tgaatgattg cccataactg taaaaaattt tgaaaagcat gactaacata agcaggtcca   1560
ttgtcagttt ttaattgttt agagaccccc atatgggcaa atgacgacaa acaatgccat   1620
tggacatggc cagcagtttc ccctgtttga catgtggcat gtaacatatt ggagtaggtg   1680
tctatagtca catgaacata gctaagtttg ccaaaggctg ctgtatgtgc aacatccatc   1740
tgccagattt catttggagc caagcctcgt gggtcgcatc cttccacggg tgcaacacca   1800
gggacatgct gacaagtgga gcaggcttgc acaatagctt gagcttgact gcaaggcaga   1860
tgaaacatat gagtaagggc agaggtgttt tgatgcagta atgcatggga agcttgggct   1920
tgttggaata cagaaccaat taatttatct gctttatcat taccttgaga tagtggtcca   1980
ggaagttgcg tatgagagcr aataggagca gcacaagaga gaatagcttg ctgaagtctt   2040
agaaacaaat taagcagctc tggttctagg gtgcccttaa tagtggcagt ctcaatgcaa   2100
ctagctgcat ttacaacata ggctgaatca caaacaatat taataggaga taaagccgtg   2160
agctctaaaa cctgaataac tgcgattaac tctgagcatt gagctgaaac tccagagatc   2220
tttattgttt gagtatgttt agttgcataa atagctgtgc ggcctttgta agagccattg   2280
gtaaaatatg tctttccacc tggaatgggc ttgtgatggg taattacagg gaggataaaa   2340
gggtgaactt tataaaattg caaaatcttg tctgatggat aatggttatc tattattccc   2400
acaaaatctg caaaagcaat ttgccatgca gtcgacattt cccatgctgc ggcctgttgt   2460
tgggaatcca agggaacaat aattttatca ggatcatatc ccgtaagcat tttttacctg   2520
tgcctaccta ttgttataag ttgagtaatt aaagaaagat aaacttgcaa agatttcact   2580
gtcagattga ataaaaaaaa aaaaagcctt tatattacca ttacagattt gtctatgaat   2640
tggcctaaaa atcctgatgg agaatggggg gtaggaagaa taaacaaaag caaaggcttt   2700
tgtggctgta gccgggaggc atgttgttgc tgaaggatct gttctacacg ctgtcactca   2760
gcttctgcct cgttagtaag ttgccgagga gaatctaatg aagaatctct ttggagggtt   2820
tgataaaggt gtgtgagttg gtagatggca atacctagca tcaggcacag ccaattgata   2880
tcccctaata attgttggaa gtcattcaga gtttgtaccc tctccctaca gagagttact   2940
```

-continued

```
ttctgaggcc gaacacttct tccagtaaca atagtaccta agtactggta tggggaggtt   3000
gtttgcacct tttcaggagc tattttgaga ttccatgcag tcaagactca ttttatttcc   3060
ctgaataact gatgtaacat ttgatctgta ggagcggcca aaagaatatc atccatataa   3120
tgaatgatgt aggcattggg aaatatattg cgaggctcct ttaaagcttt tcctacaaaa   3180
tgctgacata acataggact gttgagcatg ccttgggcta aaactttcca ctgagagcga   3240
gagacaggct ctctttgatt aatagaaggc acagagaagg caaattgagg cttatccttt   3300
ttgtgtaatg gtatattaaa aaaaaaactc tttaagacct attactacaa gagtccaatc   3360
tcttggaatg gctgctgagg atgacagacc ttgctgtaat gcacccactg gtttaatctg   3420
tgcatttaat agctctcaaa tcatgtagca gttgccattt tcctgacatt tttggatcac   3480
aaatacaggt gaattccagg ggctgactat tctgtatgtt ctgcttccag ttgctctctc   3540
actagctgat ggagttgcat cagtttctcc tgtgataggg gccattgatc cacccacaca   3600
ggtttgtcag tcagccactc tagcggcaaa gcagtgggtg gaggagaaat accaatgacc   3660
cccaccaaaa atcctgatga cctagccctt ttctgttttg tccagttatt gatattggat   3720
cagggtttcc ctgcaggggc tttcctaagc cttttccact ctgaatccca ttttctttaa   3780
cattttaaat cctggattat caatagtttc ctttttaagt ctcatgtccc atgctgtcag   3840
taaatctcgg ccccatagat taacagctat atttgcaaca taaggttgaa aagtacatga   3900
ctgtccatgt ggtctgagac aggataaaat ctcagcactc cactgaacac tttgagcttt   3960
cctagtccca ctaaggatgt agaagttaat tgcaggggtc                         4000
```

<210> SEQ ID NO 156
<211> LENGTH: 3639
<212> TYPE: DNA
<213> ORGANISM: Homo sapiens

<400> SEQUENCE: 156

```
agttagtatg cagtactgtt tttttgaata acccactggg acttgggtgg cttaggtggc     60
agacaggcat ggatatgccc cgccgtaacg gctggaattc ttagctgtga gcgggcgcac    120
ccctcaggca gtgatgatgt gctgagcccc aagcagccaa aatgtcaatg actataagac    180
attcagccac aggaaccaaa gtcaccggca cctcaaatgg ccagaggcac cccacagcag    240
ataagcacca taggtcactg cttttgtccc caagcctctt aatgtcacca gtttaatttt    300
tcccttaagg agacctggaa atattgtcac atgggttcca atatctaaga acaccagaaa    360
aatatgaatt cctttttccc ccttttttatc ttttaaagga atattattaa ttttaaaagc    420
agggaccatg ctaatcatct ctatatcatt ccaatttcag tatatgtgct gctgaagcaa    480
gcatgtcttt ttttttttaa tttttaaatt ttaaatttta tgagcacata gtaagtggat    540
atatttaata ggtacgtgag acattttggt acaggacgca atctgtaata atcacatcat    600
ggaaaatggg gtatccatcc tttcaagcat ttatcctttg tgttaaaaac aatccaatta    660
tactcttagt tattttaaaa tgtacaatta agatattatt gactatagtc ttcctgttgt    720
gctgtcaaac attaggtctt tttcattctt ctgttttttt ttgttttttt ttttgttttt    780
ttcttttttc agatggagtt ttgctcttgt tgccctggct ggagtgcaat ggcatggtct    840
cggctcactg caacctgcgc ctcccgggtt caagtgattc tcctgtctca gcctcctgag    900
tagctgggat tataggcaca caccaccatg cctggctaac ttttgtattt ttagaagaga    960
cagggtttca ccatgttggc caggctgatc ttcaactact gacctcaggt gatccacccg   1020
cctcagcctc tcaaagtatt gggattacag gcacgagcca ccacatccgg cccttttca   1080
```

ttaaccatcc ccacctcctc tcccgcttcc tcccacttcc actacccttc caagcctctg 1140
gtaaccatcc ttatattctc ttatctccat gagttcaatt gttttgattt ttagatcctg 1200
caaataactg agaacatcca aagtttgtct ttctgttcct ggcttattat aagaactcct 1260
gttttatctt gacaggaata tagagtgact gacctccagt ggggaggaaa ccagagaccg 1320
tggccccatt cccaactggg ccattcagcc tgagacattt ggatttgata gaacctcttt 1380
gatagaacca tggcttattg atgaagtgga aggagtgata cccgaagtac ccagcccacg 1440
gtgtagacat caacctacag gggtgcggaa gctggacaca ccacccagcc tgcacaagat 1500
ttagctggct attctccatt tttattcttt ggataatgag tttctgctct gtaaatgccc 1560
ttatgaactg tgtttggttc cctctcagat gcctcaggga ccaccagagg acctcttcct 1620
cttccctctc agggttctca gggatcaact gagtatccat ttcctgagtt ctctagctct 1680
cgggaatgaa caaccataca agtgtccaac aatcagaggg tggcttgcca ctgtcctatt 1740
ctatatttct ttctctctgc cccagtcagt gcagccagct cactcatatc cgcagggttg 1800
ggggtgacct atgtcctgtt tacaaaaaga gtcaaactgt aaaacatttg aagagattta 1860
ttctcagcca aatatgagtg accaatggcc tgtgacacag ccctcaggag atcctgaaaa 1920
catgtgccca aggtgatcgg ggcacagcca ggttttatag agtttaggga ggcatgagac 1980
atcaatcaaa cacatgtaam aaattcattg gttgggtctg gaaaggcagg acaactcgaa 2040
gctgagaaag ggtggtgggg tgagggtgtg gcttcctggt tataggtaga tttaaaattt 2100
tgtgattggc aactggttga aagagttatt atcaatagga aggaatgtct gggttataat 2160
gataaggggt tgtggagaac aaagctttat tatgcagatg aagccttcag gtagcaggct 2220
tcagagagaa tagattgtaa atatttcttg tcagacttga ggtatgtgtt gatgttaatg 2280
ctggtcagct tttcctgaaa gccaaacttg agtggggtat aattggccct tctttcctgt 2340
catgacctga accagataat caggtaaact ttggaatgcc ctggccaaga ggaaaggtcc 2400
attcagatgg tgagaaggcc ttcaaatttt attgttggct tataatctca cctctcattc 2460
ttccttttat aaatcatctg gctgcttgtc cagctcctgc acacctctag gttgatgtct 2520
acaccctggg ctgggtactt cggggtatca ttccttccac ttcatcaata agccatggtt 2580
ctatcaaaga gggccctgct cacttcacca attttgtgaa ccagattcac catgcactgg 2640
tgaattttgt gaacctgcct gagcctggtg agacagaaga cactcacatg caacaagtta 2700
catgaagcaa atgtattact tacagatagg aagcaagaga caacagaaga ctagaattca 2760
ttatgtgcca gtttcccaag gcttatgaaa gctgccttgg gtggatggag cttcaattgc 2820
acatggccta ctgttgttgc agctgagggg ccccaaaagc agcttacccc aggctcagta 2880
cctcaggggc cacaggaatc actgggtaaa tctcatccta ctttcaggga gagaggaaca 2940
aggctctggt tgtcctagca gttcctcctt aattcaatat gttacattct ttaggagagc 3000
caggagccag gcccaggctg tttcaggcag ttcctccctg cctcaggata tgggcattcc 3060
cacacactct acagttgttc ttcagactac aagcaagaaa tggaggagaa ctgggtcagt 3120
gcctggccac ttggagaaca gttctgcaga aagaagtcac acctgtgaaa actgcctgcc 3180
aagaggaaac aactacattg acatgtatgt gagcaagaaa tcaattgcta tttggttaag 3240
ccattgaaac tttctatttt tctttctttt tttttttctt ttttttgaga aagggtatca 3300
ctgtagctca ggttgtagta cagtggcatg ttaatggctt actgcagcct tgacctccca 3360
gatccaagca atccttttga gtatctagaa ccacaggtgc acactaccat gcccagctaa 3420

```
attttaaact ctctaaagag acagggtctc cctatgtggc ccaggcttgt ctcaaacttt   3480

taggctcagg tgatccttcc acctctcgac atcccatagt gctgggatta caggagtgag   3540

ccgtcttccc tggcctgaaa cttttacata tatttgttac agcagttgac actactctaa   3600

gcaggatata taccttgcat gttcaataaa gaatatata                          3639
```

<210> SEQ ID NO 157
<211> LENGTH: 1001
<212> TYPE: DNA
<213> ORGANISM: Homo sapiens

<400> SEQUENCE: 157

```
tatataatta ttgggagtct ctgtgagcct actctgactc agaaagccgc tcctaaagaa     60

gaaaaaagaa caaacaaaca aataaaaaac ccgaattatt tttaaaactc tttattttgg    120

atttttcagt ttctacattt tgttactgta gattttacta gattgaacag ccttatccat    180

aaatatttgc atcaatctct aaattttttt cttcaacact aacttttata gttggaattt    240

tgggggcaaa taatacaaca ttttaaaggc acttgccatg tgtacatggc caaatgcttc    300

cagaaacatt tccacttcca ttagcaaagt atataactac agagtattta aggttttatt    360

cctttatatt tttttctttg gcaaaattgt ctatagtaga aagaatgaat aataaataac    420

ctaaaaaata aaagttctcc ctctgaggac agcagagaaa tttttagctt agcttaataa    480

tacctccttc tccttaggag mataaagagc agtttcgagg agcagaagat gtggtgaaat    540

ataatgttta gtctgatggt ggatgcaaga tccaggcagg ggtggagcat gaccagctgc    600

acagacctct gttcccttgc ttcctctaca tctctcccca cctccatctg cagaccttgt    660

tctcagaggc cattcccaga cccacagcag ctggtatgat ggctgcaggc ctcatgctcc    720

tttgttttgg gagaaactgt tgaggagtta gtatttactg agcagctaat atgttccagt    780

cactattatt cctcataata attagttatt aactaataca tgaaaatttt aaacttaaag    840

cattccaata attttaaaag taaaggaagc aaaaggccaa agcgtccttt cactcactta    900

acctccaatt ttcagtttag catccatcat tttagacttt ttcaggcatt tacatatata    960

gttatgcaga aatgtatagc tttgcttttg tttttcaatt g                       1001
```

<210> SEQ ID NO 158
<211> LENGTH: 1001
<212> TYPE: DNA
<213> ORGANISM: Homo sapiens

<400> SEQUENCE: 158

```
ttaaaagtaa aggaagcaaa aggccaaagc gtcctttcac tcacttaacc tccaattttc     60

agtttagcat ccatcatttt agactttttc aggcatttac atatatagtt atgcagaaat    120

gtatagcttt gcttttgttt ttcaattgaa tcattagtat agttctgcaa ggtgcttttt    180

aatcacttag tatatctcca ttatccaggc tagtgacatt aaatcactct ttttaactgc    240

tgcattgaat ttcctcctag ggatgagcca tcattcctct aaccagtctc ttgtgagtgg    300

ctggttcagt tggtaaccac ttttatactt taaaaatagt gctgcagtgt cattcccaca    360

gaggcttctc tctgcaccca tgcgagtact tcgctgaagt aaccatcagg aagtggaatt    420

gctgggccaa ttgtgaacat tctaagtctc atactcgata tttttgagta actaaagttg    480

aaatggtttt gtcccatgac ygagatcatc aagcttgtga cttgtagagc ctttacctat    540

tgtctaccct ctttgtgttc ctaactctac catagtgggt ccagcccatt gtgggtgctc    600

agtaaatatt tgttgaataa ctttatgaag ggaagaaaga aaagatgagt aaagcctggt    660
```

cttattcaaa gctctcctaa tcaatatctt tgtgattaaa cgtggtgggt tcagcccctg 720
actgacttca gagcctctgc caggcagtct gcctggatcc caccaggagc caccaggcca 780
taagttgact gtagtaatgg ccaagagttt gacgcttgag gagtccatag tgttggacac 840
ccacagagct gaacaagggt gggaccaggg aatccagtga agagggtcct tcatgaatca 900
gagggggatg atggaagctt ggacctggca agggaagtgt ggggaagtga taggattatg 960
aatattttaa tattttaatg cagtagagtc agagatgtcc t 1001

<210> SEQ ID NO 159
<211> LENGTH: 1263
<212> TYPE: DNA
<213> ORGANISM: Homo sapiens

<400> SEQUENCE: 159
agaactcctt tcctctggcc accagagata taagcgaagt gaaggacgag ggataggaag 60
cataagaaac catctcttca gtgactggta cacagtcatt ttggtttagt tgtgtaacag 120
atggcttctg ttgtgtctcc aagtgcacac taccatgggt cctgggaggt ggaatagtga 180
ctgtatctgc tgccagtgtt ytccaactag ccatccccag gaatactcct gtagtagaac 240
tagctgtatt tcttacgtgt tgcagtgagg aagaacacac atcatgggga gctgtggcgg 300
ggtctcagta agaaggtgtt agagcagact tggtatacaa tttgggcttg tgttagggga 360
ttggggccgg gggagttcat agacttagcc ctctgctctg gatgagattc catcaggaag 420
gtgtgggcag gttaattctg agtgagagcc ttaatcaatc ttatgtagga agaaggagac 480
cagggtgaga caaaagctgt aattgatgaa ggggcagcaa tccctcattg ctgagggggg 540
atgtttggtc actgctgtgg tttggacaat gttcatgttt ttctctatgc tcacatatga 600
tgtggggtgg tattgttttt cccatgatcc atcatagtca caaagtgcca ttgtctgtgt 660
tctgtgaaat tgcttatgtt caacaggatg acacagagac ccggtgtcag tttccatatg 720
ttgggacagc ttttctcttt ctcagtgcaa tcccttgccc tgtggctgct ggttaggttt 780
ggtttaaggg gatctctagc agacaatcat aggaggaaga gaaaaggaag aagtctgggt 840
gcttattcac tggcttcctt actgcaagtt accctcaggc tggctgcatt gccttgctga 900
aggtaacagc tcctctaaag gaagtcctca atgcatgaat ctcttctttt ttgtgttcaa 960
aacagcttcc tctcctcctc cctctggtaa ttggggtggg tgggaatagc cccactgttt 1020
ctgaccctgg gatactgcac tagcaaattt agttttcccc tcatcatgac cacacttttg 1080
taaacagctc ctgaatgaaa tatctcttga attatcaaat ctgagcctga cattgattcc 1140
cattgagacc ctccctaata caggagctat ccagaattta ggccaaatta tccttccaca 1200
gcactgggtt ctaatcttca cgtcgaagtg aagggttatg aggatggagg gatccatctg 1260
gag 1263

<210> SEQ ID NO 160
<211> LENGTH: 1001
<212> TYPE: DNA
<213> ORGANISM: Homo sapiens

<400> SEQUENCE: 160
tacacttcaa aaggaagagg gaagagaagg atgaggtgca ttttctatgg caggaaactt 60
acttgttgtt tcccataatc tagaggctgt tgaaaggaaa acaagaatgg aagatttaag 120
aaataagaaa atcagaaaag agagagggag ggagaaaagt gtgtctaata aagaggagta 180
gctacagtgg ctcagttggt acagatagat cataactgct ttcaaaaact agtccctgaa 240
attgctcatt aaatttccca aattcttttt agagcaaggt acgaaatgat acagattgag 300
aaggatgaat cttgtactcc taggcataca catatagaca tggtgacacc tatgcccagg 360
tacacattca aaacagatga gctggacccc attgggaagg aactctcaca gtgcctgccc 420
tgccactagc gttcaaccga tgttcccaga cttgatatta agaagaggtg aagaaagaat 480
tgtacctgaa gatggagacc rtggggaagg gtgggatggt aaaaaaaaaa aaaaaaaaaa 540
aaaaaaaaaa aaaaaaaaag actagatgga tgcaaaaaga aggggaaggg gccaacacag 600
aaaaggcaga gttctggtga cacctctacc tttctttcat tgtaggtgga gaggagtctt 660
cgtccgatac caataagtca gcctgatgct ctgtaagttt gctgggtcac atgccctgaa 720
tatttcaact ttttctccac tgtgacccgt ggatgttctc agctggatta attagatcta 780
atctaaagac tcaatttctg tgtggtgggg gttcacctcc gcttttctgg agcctctgag 840
aaactcctga tcctgcacac ccccttgtaa agcctggcca tgcatcctgc accccccatg 900
acacagggag ccaagcctga catttttgag aaggtgccac ctctgatcca tcagagctgt 960
agaggaggga agctggaccc tggaagagac tctaaagaaa a 1001

<210> SEQ ID NO 161
<211> LENGTH: 1001
<212> TYPE: DNA
<213> ORGANISM: Homo sapiens

<400> SEQUENCE: 161
agtgtgcata tggtgaatgc ttattacagg aaattcatga gaaatgcaca tgttatagac 60
tagagaatga agtgtacctg ccaatatgag tggatttatt ttatctagca ccaagagtag 120
caaactgagt aataattctc agtcatgatc ctgtggttgt agtgtatact ctgattcaac 180
ttagtttcac tcctgactga gaagctggga ctctgcattt gatggcaatg gagtgggctg 240
atttctttcc aaataagttg aggtgggact cctggtagag taagagggct ttaatagggt 300
atgtctgggt gcctaaaagc tttctctctc tttttttttt tcagagacag ggtctctcta 360
tgttgctcag gctggccttg agctcctggg ctcaagcgat cctcccgcct cagcctccca 420
aagtactggg attacaggca tgagccacca cgccctgccc taaaaatgtt caaaagtcgt 480
atttacagct actctcaaat ycctttttttt ttgtgattcc ttataaaacc tttctccctg 540
catttatctt gttatattac agtagaatta tgaggggaaa atcctttggt ggaagtctag 600
ggacatgctc agttcccagg aggcttaatg tgaattttag tgaattgctt aagatccagt 660
attagatctg ctggtccctg cccacccccc ttttattttt tgagacaggg tctcactttg 720
tcacccaggc tggagtgtag tggcatgatc ctgtctcact gtagcctcca tcttctgggc 780
tcaagcaatc ctcccacctc agtttcctga gtagctggga ccgcaggcat gcaccatcac 840
gcccagctaa tttttaaaat attttttgta gagatgaggt ctcactgtgt tgcccaggct 900
gctctcgaac tcccgttctc aagcgatcca cccaccttgg cctcccaaag tgctgagatt 960
acagccacgg tgctcggctc ccatcttgaa atcaatacct g 1001

<210> SEQ ID NO 162
<211> LENGTH: 1001
<212> TYPE: DNA
<213> ORGANISM: Homo sapiens

<400> SEQUENCE: 162
taaacgttac tgaacttgct tcttcccgac tacattaaag cacttacttg agatattaaa 60
cattttctca ttagtcctgt ttgcctagtc agtcacttgt atagacaggg caacagcacg 120
gcctgaatat tgggcaggac accgccctgc gcgatagtaa ctttgcccaa cagcttgttg 180
agcttctcgt cgtggatggc gagctgcagg cgtcgggggg tgacgcgggt cttcttgtct 240
cgggccgcgt tgcccgccaa ctccaggatc ttggcggtca ggtactccag caccgcctcc 300
aggtacaccg gcgcaccggc ccggacccgc ttggcgtagt tgcccttgcg gaggaggcgg 360
tgcactcggc ccacagaaaa ctggagacca gccctggaag agtgcgtttt agccttggcg 420
cgagctttgc tgccctgcat tccacatcca gacgcagtga agtatttaaa tacttgttta 480
gaagaaggaa agtgattgat yctagtaaaa cgcaagagct aaactcttat aatctatatt 540
cggcaaagta gactgtgcta tctcctgaac acagatttca gccaatcgaa aagcaggtgt 600
ttaaaaaaat ttaaaaaaaa aaaaaaaaaa aaaaccactt ctgacttaca tacttatagt 660
tgaaaggtca aattatgcaa ggttgagctt ctgggagagc cgatgagatt taggagttca 720
gaaatggcct atcatatatt cagacactaa aagaaccaat gagaaaccga aactcagcca 780
gcctcatttg catatacacg aggtaaataa tgagggcgtt tgggctcacc agcattttcc 840
tgtggtcatt tgacggtatc acttcggctg cgaacatgcc tgaaccagct aagtcagctc 900
ccgccccgaa gaagggctcc aagaaggcgg tgaccaaggc acagaagaag gatggcaaga 960
agcgcaagcg cagccgcaag gagagctatt ccgtgtacgt g 1001

<210> SEQ ID NO 163
<211> LENGTH: 1001
<212> TYPE: DNA
<213> ORGANISM: Homo sapiens

<400> SEQUENCE: 163
gacctcagct cactgcaacc tctccctcct gggttcaagc aattctcctg cctcagcctc 60
ccgagtagct ggagctacag gcacccacca ccacacctgg ctaatttttg tatttttagt 120
agagacgggg tttcaccata ttggccaggc tggtctcgaa ctcctgacct tgtgatccgc 180
ccaccttggc ctcccaaagt gctcggattg caggcgtggg ccaccgcgcc cggcctcctt 240
ggacttttta tctgcattgc aggcactcag tggtccaggc cacctacttc tgctctacct 300
ttggacatcc tggcaatgtg ctgctcctca gcctgaccac aacacctgca gtgtcccaaa 360
catatcatgc agtttcatgc ctctgcaccc atttcctctc cctggtcaac acacctgggt 420
gacccctatt ctactcactc agacaaacca ggacaggatc cttgaccttt ctgcaactct 480
atttttctca cctagaaata raattaatga catctacttc tttagcagat gtttaggaat 540
gagatacggt gtggagagca cctggtgcga acacagcgcg tatctgtgat agtgaccgtt 600
agccgttatc ctcatcacca catcctttcc ccacatctca gatggtgcca cagtctacca 660
cctcagagag aaaatagaaa agggaggtcc caaacttcct gctccaccac ctatacctgt 720
ccctcatgat ctgtttcctc tgatttcaac aagcaggtgt tctttctcct gtctcaggct 780
aattctgcac ccacatcggg gagcccccac cccagcttcc ctcaggcttc tctatttggt 840
caattcatta attcattcat ttgacaagga tccatgaacg ctaactatgt gccagtcact 900
attctaggtg gtggagtcac agaagtgaac aaaacagaaa gttctcattc aaaaacaaca 960
taacttgtgg taggaggcag acaggaaatg aaataattag t 1001

<210> SEQ ID NO 164
<211> LENGTH: 1637
<212> TYPE: DNA
<213> ORGANISM: Homo sapiens

<400> SEQUENCE: 164
catttctttt tgaaggggtc ttgctctgtt gttcaggcta gagtacattg gagtgatcat 60
agctcactgc agcctaattt tttttttttt tgaaagacag agatcttgct atgcatactg 120
cccaggttct tgaactcctg gcctcatgca attctcctcc ctcgatcttt caaggtcctg 180
tgattacacc tgtaagccct cgttcccggt tggaagttac agtttaaaat agggtggtta 240
tgagcaaggg gagcgaggca cagaatactt gggagaaaag cattccgagt tgagagaaca 300
gcagtgccag agcacagagg cagaagcact gtggtttgtg tgaagaaaag caatgaggct 360
ggggtgcgca gagcacacag ggtgatcagg agaagaggag gtgacaaggc cagagggggt 420
tgagggccag atcatgtatg gccttgaaag tcatcatgct gacctgggct ttacctctga 480
gaggggagcc actggaaggt tagagcagaa aaaggactgg actgacttat gttttaagaa 540
gttacttcac atgctagacc aagatgggct gtgggtaggg gtggtggatg gaggcctgaa 600
gacccagctg ggagctactg cagtgatcca ggggaaagat gcagatgact tgtaccaggg 660
aggagccatg aaaatgttat gatgctggat ttattttcaa gatagaataa aaaggctttg 720
ctgataaact tacaggtggg gtgtgaaaaa ggagggcatc aagggtgacc acaaggtttt 780
ggtcctaaga aacggtacag atggagttgc cacttactga gatggggaaa atgagggaga 840
aaccgcttgt ggaggccaga ggaggagcca gcacagaatc caaaggtcag ttttgaatat 900
gttgggtttg aggagcttac tagagattcc cgtggagatg tagagtaggc aggtcaataa 960
taagcttgca gtccaggcaa cgggtcaggg ctggaaacac aagttattct ctttgtcttc 1020
tttatattca tgtttgttgc cactgtgtgt ttcacttacc taaygcattc gtgatttatt 1080
gctgcataac aaattaccac aaacttagtg gtttaaaaca gtacactttt ccagcctggg 1140
caacatgatg aaaccccatc tctactgaaa acgcaaaaaa taaaagataa aaaattagcc 1200
cagcgtggtg gcacacacct ataatccccg ctacttggta ggctgaggca caagaattgc 1260
tagaacccag gaagtggagg ttgcagtgag ccaagattgt gccactgcac tccagcctgg 1320
gcaacacagc gagactctgc ctcaaaaata aataaataaa taacagtaca cttttatcac 1380
ttcagtttct gtgggtcaga agtccaggca gagcttagtg ggcttctctg ctcagaactt 1440
cacaaagcaa aagtattatt catgcatgta aacctctaag cacaatacca acatcacggt 1500
aggttctatg tgagtataag ctattattaa gaataataat caatcctctt ccctctcctc 1560
catccctaag gcctcatcat ttcttgcctg gagtgtcaca gtagctttct tcctggtctc 1620
cttgtcttct accatct 1637

<210> SEQ ID NO 165
<211> LENGTH: 1001
<212> TYPE: DNA
<213> ORGANISM: Homo sapiens

<400> SEQUENCE: 165
cctatcttgc tgctgcttct cgccggagcc agttacttct tgtggagaca acagaaggaa 60
ataactgctc tgtccagtga gatagaaagt gagcaagaga tgaaagaaat gggatatgct 120
gcaacagagc gggaaataag cctaagaggt atccaacgca agcagagaat ctaagctctt 180
ggcttgcatg ccccagcctg aaaacctcac ctctctcccc taccctggca ctgcatcatg 240
tttaaggttt atttcccgaa acaccaacct cacccataac agttcatctt tttttttttt 300
tttttttttt tttggttatt ttccagagag cctccaggag gaactcagta agttaccatt 360
cccccagaga tccagacatg tcttcctatc ctcgctttga gcaccttgat gactcttccc 420
tgttcattcc attgcagaga ggaaaaaaat ccagtacttg actcgtgagt ggctttgaca 480
ttttctctga attcaaatct rttactctct ctctgcttca ttattttcca gcccataagt 540
catagcccag ggttgaaaag tggtcttgga tccctttacc cagaaaaaga aaacaagtgt 600
ggctctttgg agaaaccacc cagtgctttt tctctctaga aaaaaaaaaa aaaaaaaaag 660
aggtcttcaa tctctttgta ctaggggcta cagaccctta agctctaaaa agcactgagg 720
aatatccagg ggtacacttc aaaaggaaga gggaagagaa ggatgaggtg cattttctat 780
ggcaggaaac ttacttgttg tttcccataa tctagaggct gttgaaagga aaacaagaat 840
ggaagattta agaaataaga aaatcagaaa agagagaggg agggagaaaa gtgtgtctaa 900
taaagaggag tagctacagt ggctcagttg gtacagatag atcataactg ctttcaaaaa 960
ctagtccctg aaattgctca ttaaatttcc caaattcttt t 1001

<210> SEQ ID NO 166
<211> LENGTH: 1001
<212> TYPE: DNA
<213> ORGANISM: Homo sapiens

<400> SEQUENCE: 166
aactgctctg tccagtgaga tagaaagtga gcaagagatg aaagaaatgg gatatgctgc 60
aacagagcgg gaaataagcc taagaggtat ccaacgcaag cagagaatct aagctcttgg 120
cttgcatgcc ccagcctgaa aacctcacct ctctccccta ccctggcact gcatcatgtt 180
taaggtttat ttcccgaaac accaacctca cccataacag ttcatctttt tttttttttt 240
tttttttttt tggttatttt ccagagagcc tccaggagga actcagtaag ttaccattcc 300
cccagagatc cagacatgtc ttcctatcct cgctttgagc accttgatga ctcttccctg 360
ttcattccat tgcagagagg aaaaaaatcc agtacttgac tcgtgagtgg ctttgacatt 420
ttctctgaat tcaaatctgt tactctctct ctgcttcatt attttccagc ccataagtca 480
tagcccaggg ttgaaaagtg ktcttggatc cctttaccca gaaaaagaaa acaagtgtgg 540
ctctttggag aaaccaccca gtgctttttc tctctagaaa aaaaaaaaaa aaaaaaagag 600
gtcttcaatc tctttgtact aggggctaca gacccttaag ctctaaaaag cactgaggaa 660
tatccagggg tacacttcaa aaggaagagg gaagagaagg atgaggtgca ttttctatgg 720
caggaaactt acttgttgtt tcccataatc tagaggctgt tgaaaggaaa acaagaatgg 780
aagatttaag aaataagaaa atcagaaaag agagagggag ggagaaaagt gtgtctaata 840
aagaggagta gctacagtgg ctcagttggt acagatagat cataactgct ttcaaaaact 900
agtccctgaa attgctcatt aaatttccca aattcttttt agagcaaggt acgaaatgat 960
acagattgag aaggatgaat cttgtactcc taggcataca c 1001

<210> SEQ ID NO 167
<211> LENGTH: 1001
<212> TYPE: DNA
<213> ORGANISM: Homo sapiens

<400> SEQUENCE: 167
gaaccaccta gtcttcaggt ttgcctggtg ctcaccagct gaagaaatcc tttaacgacc 60
tttattcagt caagtaaatt gttttctttt ggcaacttgc atgttatttt ttaggttttc 120
atttatttat ttttttatat ttaaagtcat attttcttcc ttttattcac tttgctggtc 180
tttctcactt tgattttttt ttgccttgtt ttgcatttgt ttactttaac atttttttgta 240 acttatctct tttattttgg aaattattca cattatcagt tttcttttgc taggcaattt 300
tgatattcta ataaacatta ttaacataaa atataaagtt tactaacacc aagcccaaac 360
aatacaaagt cttagggctc tttaattgca attatttaaa aatatttgct acaaattgtt 420
cattatttta tatttacgtt gtttttctta ttcccacaaa tcacatattg ttggtgtgtt 480
tgttaaataa aaatctttaa ytgcaattgt ttaaaaatat ttgctacaaa ttgtttgtta 540
ttttatattt acgttgtttt tcttattccc acaaatcaca tattgttggt gtgcttgtta 600
aataaaattg tgattgctta tatatatttt ttcacatcct ttcttcttgt aatattttgg 660
aatttacatc cagttaatta tcctttattc tatagtatat actgtaaaag ttactagtct 720
tgctagtaaa ccctcagttt ttggattgtc tgaagatgtc tctattttga tctgctcttg 780
aattctaaat ctaattgaca taaaattcta gatttgccat tatcatttat tagcctttca 840
aagatattcc acaattttct gactttcaat atttttgttg gtaaaaatgg ggattgttaa 900
tcggcttgca tattctgttt tggatattcc attgtttcct tataatttgt ttatttataa 960
ggaaacttat aaacaaatta taaggaaaca atagaatatc c 1001

<210> SEQ ID NO 168
<211> LENGTH: 1001
<212> TYPE: DNA
<213> ORGANISM: Homo sapiens

<400> SEQUENCE: 168
agccgggggg tgcggagatt gcagtgagcc aagatcgcgc cactgtactg cagcctgggt 60
gatagagcga gaatccgtct caaaaaaaaa aaaaaaaaaa aaaaaaaaag tgggaagcaa 120
ccagtggaaa gcaatggtaa gagcctgaca aatctcataa aatctcccat tatttttttc 180
ttggtgcaag aaaaaagcaa gtcattaaaa aggaagagaa tgtcgtggtg actgtgatgg 240
gcctactttg tacttttcac tgctctgggg tgttcttgcc tgtctaaaag aattttgaca 300
aacgtgatac ctaccacaat tttttcagtg gacatctaac gtttttcatt aagtttaaat 360
ttttctgaag gatatagtga cttgtatcat aggaatctaa aaaccacagt aatttaatac 420
ttaccagcaa ccttttaaaa gagagaggtg aacattgcta cctctttaat tgtggaagat 480
tttacattga tcctttattt ytctgcattc atagtgccat tgcctgtctc ttatagaatt 540
tttatcccag tacaatgtca ttttgtagtt ttttcttgat ctttctatga tacttctttg 600
gaccaaatat aggtataaat attgaagtcc attgttattt cctgttaccc aaaatgtgtg 660
ttaaaaatag tttttctgga ttgtgttata tttgcatcta ctgctagtac ataatcaaaa 720
cataataggt aaataacaat tttaaagccc ctttactgaa aggtgtaatg gaagtcaatg 780
tggaatttgt catccccttt cctccaagaa attgtacaca atatgcaagt ccacctcgat 840
ggatggaggc tctaacttag tattcccaat tgtttccatg ttgggagctc gagaggagag 900
aatttttagg cctggagcaa tgtgtcatag gcaaacaact accagaaatt tatcaagtga 960
tatctttcca tggagtgcca tcactgattt gattatcaga c 1001

<210> SEQ ID NO 169
<211> LENGTH: 1001
<212> TYPE: DNA
<213> ORGANISM: Homo sapiens

<400> SEQUENCE: 169
agataagcaa aggaagagtc aggaagcaaa gagggcaggg catgagcatg gaaaaagcgc 60
caatgtttag gggtttatgt gtaggaaaag ttatctaatg ccaaaagaga gcgtttaatc 120
tccctttaaa gaggtggcca aagatagact gtccacgagg ggaattcttc attttagagt 180
cataacagca agccaagggc aaaagagaca gatctcactt atctgtgaat gcagaaaaca 240
aaacacgtcc tttaatgtca acgtcttgag ttctttttcc caggttgact gactaaatat 300
ctcagtacag atacttttgc ccccttccaa aacgcaacca cccatgaccc cgacgtgatt 360
tgaacacgca accttctgat ctggagtcag acgcgctacc gttgcgccac gaggtcacgg 420
agaccctcca ttttcctttt aagataagta tctaatctta tcctcctccc aaacaatttc 480
tttattattt gatttgatct yttttcacag ttttgctaag gctttttga gaaaaataag 540 ggagtggctg gattaaatat taaccccaaa cccaaataaa tgctccatat atgaaaaaca 600
gtggtttctc aagttcaatc tttctatttc tcgaatttct ctgtttcgag aaaaagtgtc 660
tatgtgttgg gtttagatta gcagtgaaac agtaataaga acggttatga agtttgtact 720
actactttct gtaaatgcgc tagactactc cctcttcagg aagagaattc cagcattgca 780
ctgccccgca agacctggcc tagctagcac ttacttcact caaacccatc cgcacacccg 840
ccccatcctc aacctaatgg gattcgaaag cctaacataa ataatatctc tagcctaaac 900
gttcacttct cagtccaaat tcgcgggccc tctggtctct attgtgtaca caagccattc 960
agttcacaac aataacccca aagaatccgt taacatttac t 1001

<210> SEQ ID NO 170
<211> LENGTH: 1001
<212> TYPE: DNA
<213> ORGANISM: Homo sapiens

<400> SEQUENCE: 170
gctgttggat gccaaatgta atagtctaat catgactctg aataaatgtg tctctttgaa 60
aaatgtgcta tgtaaagtta gtctactctg aagccatctt ggtaaatttc cccaacattg 120
tgaagggaat tccttcaggg tgatgccaca ttctatttgg aatttgtata tgacctgctt 180
gggtggagaa gccattatct tcagtaacct tggtgtagtt gaactgatag ttactgttgt 240
gacttgaagt tcaccattaa aagagttcac cgggccaggc gcggcggctc acatttgtaa 300
ttccagcact ttagaaggct gaggcaggag aattgcttga acccagaagg cagaggttac 360
agtgaggaga gatcttgtca ttgcgctcca gcctgggcga cagagtgaga ctccaactca 420
aaaaaaaaaa aaaaattagg ctcaaggatt ccagaaataa catggaagta gatatctggc 480
tatttgactt tcattctggg mtgggggtag ggggttcttt acagcctggg gcaatgaaag 540
tctcagctcc ctgttctgct ttcttcgaga agtgtgtgtg tgtgtgtgtg tgtgtgtgtg 600
tgtgtgtgtg tgtgtgtgtg ttggaggtag agggaatgca ccttgttaca gcttgatgga 660
agtctagatt ccccactttg cctttgctgt tgtgtgtgaa ggtttggacg acagttgttt 720 ttttttttt tttcctcttc cagcttccca agagcagaag tccgtagaaa tggagtttgt 780
aactccactg aacacacaaa attagctaaa aaaaaataac aagtcacaaa acaaaaattt 840
taaaaatgta aaacttttag aagtagagtc aggcttcggc cgggcgcggt ggctcacgcc 900
tgtaatccca gcactttggg aggccgaggt gggcggatca cgaggtcagg aaatagagac 960
catcctggct aactcggcta actcggtgaa accccgtctc t 1001

<210> SEQ ID NO 171
<211> LENGTH: 1001
<212> TYPE: DNA
<213> ORGANISM: Homo sapiens

<400> SEQUENCE: 171
cacttggttt aattttctga acaatgcaat ggttgatcaa accaatttaa ccaataaagc 60
acatgtccag ttctcctttt tacgtttgta actcgccagt tcctttagca gaatgtccag 120
atgctctata gaaatgaaat gaaatgaaaa aaacaaaaac aaaaaaccaa aaaacaaaga 180
actctaaatg tggatgccag atcccaagat gcatagatgt acagatccca ctttatggtc 240
agaaaaatgt taatcgacaa aatgaatttg atgcatcttg agaaagctaa ttgtttggtt 300
ttaatatatt atatttaacc ggaagtaaca aagtgccttt tacatagcat tctatttaat 360
tcatatatca cggagaaagt ttttttccag aaaactgaat ctttttcaaa atcaaataat 420
ttccttttat ctgtacctag agaaagttaa ttatgtcatg actgataaac agaataaatg 480
tggtcatgga aagtaagaat rcatcacact tactttctat atatagatgt ttatatcgaa 540
caagagcatt actaatgtgt tttttattgg ccatctttgg aaaacgtgca gtcatttgct 600
ttaaaagatt gtataatgta ttttaaatct ttattttcag ctgggcgcgg tggctcacac 660
ctgtaatccc agcactttgg gaggccgagg cggatagatc acctgaggtt aggagttcca 720
gaccagcctg accaatatga tgaaaccctg tctctactaa aaatacaaaa attagctggg 780
cgtggtggca tatgcctgta atcccagcta ctccggaggc tgagacagga ggattacttg 840
aactcgggag gcggagattg cagtgagccg agactgagcc attgcactcc agccacttca 900
gcctgggcaa ctagagtaaa attccttctc aaaaataaat acataaataa atatttattt 960
attttctgcc tgtcccttta ggactatttt tggagcaggc c 1001

<210> SEQ ID NO 172
<211> LENGTH: 626
<212> TYPE: DNA
<213> ORGANISM: Homo sapiens

<400> SEQUENCE: 172
agactacttg tgattcatgt caaaacaaag tttaatcaag ccatatttaa agagacccta 60
caaatcataa gagaaagacc taacaactaa gtagaaaaat tagcacagaa tactatgcat 120
gtaacagaaa aggaaataca aatggctttt aaacatataa aaaggtgctc aaggacaata 180
taaccagtta aatgcaaaat aaaactccct gagggatcat tttcacattt caaactggaa 240
aaaacaagat aaactctgtt gagaaggact caaccatgct cttcagagtg tgtgagagac 300
agccctagct aagggttggg cttttcttgt acaatcattt ggaaactatg aaaatcctgg 360
ggagtggctc ttatttcctg ggaggtacct agaactagag tttcttacct gtggccttcc 420
ggtcaratag cctcagaggt tcagttcctg gtggaattga aaatcctgga gtaggccatg 480
gatgtgagcg gtggatatga gggatttttc cttctattgg caatctgata ggttgtggta 540
gagaatcatt cacacactac tgcctgttga ggcgatttct ttagatttga agacaaaaaa 600
acgtcagtgt taacgcaaag gggtag 626

<210> SEQ ID NO 173

<211> LENGTH: 656
<212> TYPE: DNA
<213> ORGANISM: Homo sapiens

<400> SEQUENCE: 173
ggctgtatct cacttttaga tatgtcttca gcatgttcct tctcctttct ccaaatgttt 60
gcgtaactcc tttcttactc atatcttatt tggaaaggca tatcttactt gggaagagga 120
ggtgacaatt ctcatgttta cttccaacaa attacctatc ttccagtgaa tagaaaatac 180
actgaggttg aatataattt tatattttct tgcactcgaa ggcaaaacac tgttactgac 240
ttttgcctga gaccattggt tattgtaaat cgttattgtc tttttgcttc tacgggagcc 300
tcctgcttct tttgctcttt tgttcatctc tatgcatgat ttattaaatt catttcgtgt 360
actgtgaatt cttctctaaa gctatctgtt acgatggcca aaagacatca tttataccct 420
cctccttcca tacttacaga aactagacac atggartgtt atgagaaaga gaagcaacaa 480
tgaagttaag tgtaaaatgg ttgattctac ttggatagat ttttttaaaa aatgtaaatg 540
gtagaaaaca taggggtaca tttaaagcat tttgtgaatc agaattccat gggcaaactc 600
agaagaccaa taatctttat tttgtctgct taccttctag aagcatttta actaac 656

<210> SEQ ID NO 174
<211> LENGTH: 101
<212> TYPE: DNA
<213> ORGANISM: Homo sapiens

<400> SEQUENCE: 174
actgcctggc ttggaaaagt taagaagccc ctcaggaaga gaatcgaggc yaagttcctc 60
tgcgccgagg gccccgagca tatccgccaa ggctcagctg c 101

<210> SEQ ID NO 175
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 175
ggtttttttt tgtttttttt ttgttntgtt tttttcctcc ttgcttggca a 51

<210> SEQ ID NO 176
<211> LENGTH: 1168
<212> TYPE: DNA
<213> ORGANISM: Homo sapiens

<400> SEQUENCE: 176
cactttccag aaggaaggtc cctctggtgc aggctcacta ctaggtggca ctgtgcacta 60
ctgggctagt tctggtaaaa taccccctgcc ccagctaaag tctctccttc cctccctccc 120
tccttccctc cttctctcgc tccctccctc cttccttccc tccttctctc cctccctccc 180
tccttccttc ccctcctctt cttccttcct tcctcccttc ctttctctct ctctctttct 240
ctctcccttt cttcccttct ttcttttttt ttgagacgga gtttccctct tgttccccag 300
gctggagtgc aatagcgcaa tcttggctca ctgtaacctt cacctcccgc gttcaagcaa 360
ttctccttcc tcagcctcct gagtagctgg aattacaggt gcccaccacc atgcccagct 420
aatttttgta tttttagtag agacggagtt tcaccatgtt ggccaggctg gtctcgaact 480
cctgacctca ggtgatctgc ctgcttctgc ctcccaaagt gctgggatta caggcatgag 540
ccaccacgcc tggcctcttt cttttccttt catttccttt cctttctctt tctctctctt 600
tccttccttc cttccttctt tcttttctct tttccwcttt attttctttt aaattttaat 660
ttaatttaat ttaatttaca gagatggaga ctctctatgt tgcccaggct ggtttcaaac 720
tcctgggctc aagtgatcct cccacctcag cctcccaaag tgctaggata acagccatga 780
gccacggtgc ctggccagag cttcagtttc tatggacagg tgttttcggg cttgctaaat 840
caaaattctc cagaattcct aagatcagcc aattttaaga gcagtaattt ttttttaac 900 agtcttgctc tgtcacccag cttggagtgc agtgatgtga tctcagctca ctgcaacctc 960
tgcctcccgg gttcaagcaa ttctcgtgcc tcagcttccc aagtagctgg gattacagcc 1020
acgcaccacc acgcccagct aatttttgta tttttggtag agatgggtct caccatattg 1080
gccaggctgg tctcaaattc aagctgtctg cccatcttgg cccccagagt gctgggatta 1140
caggcgtgag ccaccatgcc cggcctga 1168

<210> SEQ ID NO 177
<211> LENGTH: 701
<212> TYPE: DNA
<213> ORGANISM: Homo sapiens

<400> SEQUENCE: 177
atgtggaaga aaggtggtcg aaaatgaaat ttacaggtga gttcctaaaa ggcctaccct 60
tccccatgtt gagttaagtg tcaaaacatt tctagggaga tgactgtggt aaacccgcgg 120
ggcggtcaga ggcatgcctg agaggggccc gtgagaactc agcagaaagc tgggggagtg 180
ctgtctgttt caggttgagc rccatgtgtt agcttggtgg gagaagaggg ggcatgagca 240
ttggttttaa tgtgtaaaac ctccggataa attttttttt ttttttgag atggactctt 300 gctctgtcgc caggccagag tgcagaggcg caatctcggc tcactgcaac ctctgcctcc 360
caggttcaag tgattctcct gcctcagcct cctgagtagc tgggactata ggcacgtgcc 420
agcacgcccg gctaattttt gtagttttag tagagagggg gtttcaccat attggccaga 480
atggtttcca tctcttgacc tcatgatctg cctgccttgg cctcccaaag tgctgggatt 540
acaggcatga gccaccacgt cctgccctct taggatgaat ttttacaaat taagttttta 600
ttttaccaaa ttgattttta aacattcccc tttattcatt ttatttttat ttcatttttt 660
tcattttatt tttatttatt ttttgtttgt ttgtttgagg t 701

<210> SEQ ID NO 178
<211> LENGTH: 1001
<212> TYPE: DNA
<213> ORGANISM: Homo sapiens

<400> SEQUENCE: 178
ataaagaatc aacaaggttt gtccagctgt cttgagcaat cccactgatc tgctcaggaa 60
ataccacatt tcactcatta gatgtggctc aatcgatcaa gccactcagg cctgatttga 120
ggctccagtt cacagtgaaa tggtccctgc actcttccat cacccttcaa taggtcaact 180
cacctccttc cctgtcagtc aacacaagag agtgagctcg gccgcaggag acctgcagca 240
cccgtgtctc ctgaggtctg tccagaggca gggagacggg tgagggctcc aacacatact 300
cgtagcccct cgctggaaaa gacacaggac actgattgag gcatgcattt ctaccactgg 360
aaatcatact gtccaactcc acgctactac actggaaaaa agagagtcgg aggtaggaaa 420
gactcatcaa gacaggtaag ttaggcgcag agcaaggacc agaagcccaa ctcccagccc 480

-continued atggcatggg ctgtctctat yacataatgc gggttccaga aaagcatact tggtcttctg 540
gctgggcgca gtggctcatg cctgtaatcc cagcactttg ggaggccgaa gcgggcagat 600
cacctgaggt caggagttcg agactagcct ggccaaaatg gtgaacccca tctctattta 660
aaatacaaaa attagccggg catggtggcg ggcgcctcta atcccagcta ctcgggaggc 720
tgaggcagaa gaactgcttg aacccggaag gcggaggttg cagtgagctg agattgcgcc 780
attgcacttc agcctggggg acaagagcga gacttcatct ggaaaaaaaa aaaaaatgca 840
tacttcgtct tcttattaaa gaaatcttgg ccgggcagtg gctcatgcct gtaatcccag 900
cgctttggga ggccaaggca ggcggatcac ttgaggtcag gagtttgata cccacctggc 960
caacaaggtg aaaccccgt ctctactaaa aatacaaaat t 1001

<210> SEQ ID NO 179
<211> LENGTH: 1449
<212> TYPE: DNA
<213> ORGANISM: Homo sapiens

<400> SEQUENCE: 179
aaccccatct ctactaaaaa taccaaaaaa attagccagg tgtggtggca ggcgcctgtg 60
aacccagcta cttggaaggc tgaagcagga gaatcacttg aacctggaag gcggaggttg 120
cagtgagccg aggttgagcc actgcactct agtccgggca acagagtgag actccatctc 180
aaaaaaaaaa aaaaattaag aaaaaagaca agaggccagg tgcagtggct catgcctgtg 240
gtcccagcac tttgggaggt caaggtgggc ggatcacctg ggatcaggag ttcaagacca 300
gcctcaacat ggagaaaccc cgtctctact gaaaatacaa aaaaaaaaaa aattagctag 360
gcgtggtggt gcatacctgt ggtcccagct actcgggagg ctgaggcagg agaattgctt 420
caatctggga ggtggaggtt gcagtgggcc aagatcgtgc cattgcactc cagcctggac 480
aacaagagca aaactcagtc tcaaaaaaaa aaaaaaaaga caagagaaaa tatttagaca 540
ggtaacgaag ggttttatgc aaatatatca agtactccta caaagtaata agagacaaac 600
aatccagtat gggtgcggtg gtggctcacg cctgtaatcc cagcactttg ggaggctgag 660
acgggcggat cacctgaggt caggagttcg agaccagcct ggccaacatg gtgaaacccc 720
gtctctgcta aaaatactaa aattagccag gcatggtggt gcacgcctgc agtctcaggt 780
acttgggaga ctgggacatg agaatcactt gaacccatca ggcagaggtt gtggtgagcc 840
gagatcggac cactgcactt cagcctgggc gctgggccac agagtgagac tctgtctcaa 900
aaaaaaaaaa aaagagacaa cccaatagaa acgtcaccaa ggatatgagt agatttgcaa 960
ttctcagtag aggagacgtg aaactgtaag atgttcaact yttccagaga ttacagaaat 1020
ataaagtaaa taaaaaatga gatatgtttc aagtagcaga ttggcaaaca tttaaaaaac 1080
gtgggcgggg cacagtggct tatgcctata atcccagcac ttggggaagc tgaggcagga 1140
ggattgcttg agcccaggag ctggagtcca gcctgagcaa catagagaga cccccgtctc 1200
tgcaaaaaat tttagaaatg tccaggtgtg gtgaggtgtg cctgtagtcc tagctacttg 1260
ggaggctgag gtaggagtat cacgagagct ggcaagattg aatctgcaga ggctgcagtg 1320
agctacgatg gcaccactgt actccagcct ggttgataga gtgagacctt gtctgggaaa 1380
aaaaaaacca agtcgtgtag cagggggata tgtaaaagca aatcccactc ataatattga 1440
agcacaact 1449

<210> SEQ ID NO 180
<211> LENGTH: 501

<212> TYPE: DNA
<213> ORGANISM: Homo sapiens

<400> SEQUENCE: 180
ggcctctcaa agtgctggga ttacaagcgt gagccactgc gcctggccaa ataattttta 60
aaatttgccg ggtgaggtga tgtgcgcctg tgatcccacc tactcgggag gctgacgtgg 120
gaggcttgct tgagtgcagg aggttgaggc tgcagtgagc tatgactgta ccactgcact 180
ccaacctggg tgacagagca agtccatctc ccctcaacac acatagcaaa aaaaaaaaaa 240
agagagagag wgaaagtggt agaatctggg caaagttaga gctgccggag gaatctgaag 300
gaatggtgtg gagcgtggga ggaataagat gcttccaagg cttctggctt gagtaagtgg 360
aggaatggag tttcattcat tgagctggag aagactgcag gagaagtgtg gggagcgtga 420
gacatgttct tcttgggatg cctattcatt ctccaagata aaaatttttt ttcttaagtc 480
gctgtacaag tggagatttc a 501

<210> SEQ ID NO 181
<211> LENGTH: 601
<212> TYPE: DNA
<213> ORGANISM: Homo sapiens

<400> SEQUENCE: 181
ttattattca ctgaacccct tctgtaatcc actctgatgt ctattttaga ctgagcttgg 60
gtgtatgatt gtcatttgta ttagggcctt tactaaattc ctataactgt atcaatcatt 120
cttctcaact actccccccct caaaaaaaat ataggctagg gtatttttat ttaatgattt 180
tattctacta ttgtttgacc tacactatgg agacacagac acactgaaac acatgcatcc 240
atgcatacac acatttgttt taaattctct tccagtttat gtatcagtga ccttgaacaa 300
wgtcacctag attctgtgtt tcagttttct cttctccaaa taaaagaagt tactttacat 360
aaatttgttg ggattcaatg aaatattatt tagaaatgtg ctgtgtgtgg catatatgtc 420
taaaggacag aattaatgga tatatatata tatatatata tatatatata tatatatagg 480
aatgtattaa atactcacat gatcacaagg tcccacaata ggccatctgc aggctgagga 540
gcaaggagaa ccagtccgaa aaactgaagg atttggaatc caatgttcaa gggcaggaag 600
c 601

<210> SEQ ID NO 182
<211> LENGTH: 549
<212> TYPE: DNA
<213> ORGANISM: Homo sapiens

<400> SEQUENCE: 182
ggatcaagaa gttgcagtct gtgtcctaat ttccactccc tgccatgggt gcggaacctt 60
gagcagtaga ttgggcccta ttggggacat ctggatggta acacagactc caaaatgcaa 120
gggctaatga cccatcccct agtccgtggg agactgcaag tctctggggc attttgggct 180
ccccgaattg tctctatgtg cccagaccac ttacagcatg atgtctggac acaggattca 240
ggcatcacta tttggaaaaa aagccatctc agtggattcc aatatggcgc caaagtcaag 300
aaccactgct cagcggattc caatatggcr ccaaagtcaa gaaccactgc tctttgagaa 360
gtcagctcaa ggtcacatcc aaggtggcac aggagagaga gggacagagc acagcattgg 420
aggaggcagg tggctagaaa ggtgggctct gaggcagtac tctggccctt tccagaacgt 480
gtgtgtagaa tgcagaaatc ttgaggacca catgttccag gaggagagtg gtgaggaagt 540
ggaagaata 549

<210> SEQ ID NO 183
<211> LENGTH: 601
<212> TYPE: DNA
<213> ORGANISM: Homo sapiens

<400> SEQUENCE: 183
gtgccaaaag aagaactcaa aatccctgtc tctcacctga aaatgataca gaagactgga 60
cctaggggtg aggcctctgc aagcggggat tggagaagcc tgacctcaaa tctagaagat 120
cctataattt atattgcata atcacaggtc atagactcag ccacactgtt gggctgtagg 180
aaagcattgg tttacttcca agcaaagagg gatgcctgtg aagagccagc agtccttcca 240
ttcctgattt tcctccttct accaacccac aggaacattc ctaggctgcc ccactctgaa 300
yccagtgttc cttctgtaag aaaggccaga tatgactgtt tattttcagg atgcatgcta 360
acagggccgc caggaaggta tctcagcttt catgccagaa ccaatagagt attccccagc 420
tggaatttag agtgatccag gcctgaaatc tcactttcag caataattaa aattttatta 480
gtgcttcaga atttaagata tgtgtttctc attcaccatt tcatttaatt atcatgacat 540
tatattgtta tcccacttac acagaagata aaactggggt taagagaagt tatgtatcca 600
a 601

<210> SEQ ID NO 184
<211> LENGTH: 401
<212> TYPE: DNA
<213> ORGANISM: Homo sapiens

<400> SEQUENCE: 184
cccctatcca caacccacag ggataaacag ggtaaagaaa ggaggaccag agcagaggtg 60
ggtgtggctt cagtagaact cagcttatcc agaaaccaag ctgaaatttc agccacactc 120
tgtgggtttc cccagaattt gtcttctgaa cactctataa atcccagaag actgaagggc 180
ttcctattga atttcagttg ycccattgga ctcaatattt ttattgagaa tttaatattt 240
ttattgggtc caatgggaca actgaaaatc agtatttttg ggatattttg ggaaactcat 300
cagccaaggt cctaaggcct ggccaggtca tgagtccctt ctgattagat gatcgttact 360
cacatcttag agaccattcc cactttagag aggagtaact a 401

<210> SEQ ID NO 185
<211> LENGTH: 1001
<212> TYPE: DNA
<213> ORGANISM: Homo sapiens

<400> SEQUENCE: 185
agtcacccaa atgctttgtg aagatccatg tttcttcctc gtgggctgtt cacagttaat 60
ttgtgatccc atcttcatct cactcatccg cccattcact cattcaatgt gtgtgaatgc 120
cctccataaa tttgtactgt gctagtcact gaagtacaga gctgaataaa acaagactgc 180
ttctctcaag gagaggagag gataaaggat ataaacaaat aattattttg gaaaggatct 240
tagtctacct ctccagcttt tactaacacc atgatgaact ctgcccccca ctacagtttc 300
acgctgcgtt tcacactatg ttctgcaagc acctgatgac ttgaagcctc acaaaggcat 360

```
catcctttgc cttcaagatg tggcctctgt ttctcctttc actactggtg tgctaccctg    420
ccctctcttc ccagttaatt cttactcatc cttctaggct cagctcaggt gtcagtttat    480
ccaaaaggta acaatgatgt mtcctcccca taggttatgt gtccctccca tcagctccca    540
aagaatgtct cagattttcc caacacaccc ttcacacact taacattgta attatctgga    600
tatttttctt tctcgtttac tatattgaga aggctaagag ggaatggagt cacgttacaa    660
ttgttttgga gcctagctca atgcacaacg tacaagtgct caagaaatgt ggaaagaaga    720
aattaactgt ttttgtataa aggagggaga ggtcaattct ggagtaggga atcagagagg    780
gcttcacaga aactattgaa ttgaatcttg aagaattaac gtaaattcac cagatggaca    840
agtttcagaa aaaaactttc caggaaaaac aaacagtaca tacaaaacca aaaagaaaga    900
aaacaaacat tcaaagaaat gtaagtattt aacatgtctg ggtataaat tgcgatgatt    960
aaaatttggc tatgattaag aagttcaccc tcaccaatgt g                        1001
```

<210> SEQ ID NO 186
<211> LENGTH: 1001
<212> TYPE: DNA
<213> ORGANISM: Homo sapiens

<400> SEQUENCE: 186

```
tcacccaaat gctttgtgaa gatccatgtt tcttcctcgt gggctgttca cagttaattt     60
gtgatcccat cttcatctca ctcatccgcc cattcactca ttcaatgtgt gtgaatgccc    120
tccataaatt tgtactgtgc tagtcactga agtacagagc tgaataaaac aagactgctt    180
ctctcaagga gaggagagga taaaggatat aaacaaataa ttattttgga aaggatctta    240
gtctacctct ccagctttta ctaacaccat gatgaactct gccccccact acagtttcac    300
gctgcgtttc acactatgtt ctgcaagcac ctgatgactt gaagcctcac aaaggcatca    360
tcctttgcct tcaagatgtg gcctctgttt ctcctttcac tactggtgtg ctaccctgcc    420
ctctcttccc agttaattct tactcatcct tctaggctca gctcaggtgt cagtttatcc    480
aaaaggtaac aatgatgtct yctccccata ggttatgtgt ccctcccatc agctcccaaa    540
gaatgtctca gattttccca acacaccctt cacacactta acattgtaat tatctggata    600
tttttctttc tcgtttacta tattgagaag gctaagaggg aatggagtca cgttacaatt    660
gttttggagc ctagctcaat gcacaacgta caagtgctca agaaatgtgg aaagaagaaa    720
ttaactgttt ttgtataaag gagggagagg tcaattctgg agtagggaat cagagagggc    780
ttcacagaaa ctattgaatt gaatcttgaa gaattaacgt aaattcacca gatggacaag    840
tttcagaaaa aaactttcca ggaaaaacaa acagtacata caaaaccaaa aagaaagaaa    900
acaaacattc aaagaaatgt aagtatttaa catgtctggg gtataaattg cgatgattaa    960
aatttggcta tgattaagaa gttcaccctc accaatgtga a                        1001
```

<210> SEQ ID NO 187
<211> LENGTH: 1001
<212> TYPE: DNA
<213> ORGANISM: Homo sapiens

<400> SEQUENCE: 187

```
gtatatgtgg aggtggggag acagaaacag agacagagag agagagagag agagaaatac     60
tgagacctag aaagcttgaa taactcattt caagtcaaga gcaacttaat ggtaaacttg    120
gatcaaaaca caaaacacta ttctttttag tcctgtattg tttccactat atcacaatac    180
agtgttcaat agttctcttt aaatcacata ccaggagcta aatttactga agtattacaa    240
```

```
aaccaccaaa tgagctttca caggagacct aaaagaggaa attaaagatg caaatagttt    300

aagaaaaatc tgtgtttgat tcagaaactt aaaaccagtt tcttcaaaaa cttgttaaaa    360

gagaaagaaa caggcatttt tacccaaaga aagaaatacc atattctaga gattcactaa    420

ataattttta tgattctcta tgctactttc aagaaactct gacttcagtt atgtagacta    480

aggtgacaag aaccatttat rtaatcaact gtaattacat gaaattctct ctttagcaca    540

tggtacccac tgaatgtggc acaaaagagg atatgatcag ttgattcagg atgatgtcat    600

ttccatgatt ctaaaccaag aatcttcaag aaagcctggg ctgcaagttc cagggtcaaa    660

ttgcagactg cttgcagaga gtggctctgc tattccaaga acctcagatg gctcactgga    720

gtgatctgct ttagatagtg tgatcatatg tcttgaaatt tccatgacag tcttgtttat    780

acatgttgct ccagaatatt tattatagtg ctctctttca caatcagagg tgttccgctt    840

tgaatggtga gttataaaat agttacccta gccatgtgga gtgtgctcgc tcacttaaca    900

ttcaacatgc agtaagccac tttcacacat ggccctgtgc tcacgactta atagaggtta    960

ttaggcaaac ccagcttcac tctgctaaag gtattttatt t                       1001
```

<210> SEQ ID NO 188
<211> LENGTH: 1001
<212> TYPE: DNA
<213> ORGANISM: Homo sapiens

<400> SEQUENCE: 188

```
caatcagagg tgttccgctt tgaatggtga gttataaaat agttacccta gccatgtgga     60

gtgtgctcgc tcacttaaca ttcaacatgc agtaagccac tttcacacat ggccctgtgc    120

tcacgactta atagaggtta ttaggcaaac ccagcttcac tctgctaaag gtattttatt    180

ttaaaattac tcaaagcctg tctgaattcc accctaactc cataacagac attgggtgcc    240

ttcaggaaat tacttagctt ccctctggtt tattcatgtt tactatgaaa tgggaataat    300

tgcatcagtc ttaccacacc aggtaataaa taatggtcga ggaagtaatt aggcttagaa    360

gctggataga aactaagatg cctaagtact aattaggaat acagctgagt agattgtggt    420

tgatggccgt ccaaatgaat atgtcacctc taatttctgc cttgtttctt gtcttatttt    480

aattgtatct atcttctaag ygtcttatct ttacaaagta ccaatcctga accaacgagg    540

ttagatgctt aatttttctc gtgttttgct gggcatttgc tggctctaac agcaaagggg    600

cattaaccta accaaaaata aaatggtttc atatcattat aaaaattatt ctgtcagtgt    660

gaaatgccat aacaaaaaag cttgtatatg ttgatgtcat atatatatat ttatatttat    720

gtattcattt attcttattt tacatatata gttatttgtg gataagcagt tttggtgaag    780

aatagctagt atgtttttga gtagtgtcaa ggcctatact tttgagctat tttctaactc    840

caaacagatc tagaatcaat taacctttac caagggcctg ctatatttca gggtctggac    900

tgaacagacg attatgtcat tgaatcttca ttgaattcct gcataatgga tattctgatt    960

ctcattttgc aggtgagtta cctaaaattt agaaagaaaa a                       1001
```

<210> SEQ ID NO 189
<211> LENGTH: 401
<212> TYPE: DNA
<213> ORGANISM: Homo sapiens

<400> SEQUENCE: 189
agtcctggat tctgagtgca aagtatagcc ttctctgttc ttgatgctac cagactgtat 60
tcaggaacac ttaagagaaa tgatggaagt cagagctgaa agctgtgtcc tcgccagatc 120
agtggaaggg cacgacaatc attcagctaa cgaaggaaac tccttggcta gccatgagtt 180
cattataacc aaaagtggga rtgggcagga tggggtgttg agggatacat gaattgttga 240
gcaactgctt tggaagggca ccaaacttca tgtttgttcc cttgcacact tgtcctttcc 300
ataattcata gaataattct atctaaaggt taatatagac cttgaagttc tcctagccca 360
gcccccactt cacgtttgaa tgttttctat cacatctcac c 401

<210> SEQ ID NO 190
<211> LENGTH: 401
<212> TYPE: DNA
<213> ORGANISM: Homo sapiens

<400> SEQUENCE: 190
ctatcacatc tcaccaaaca tcatgcctgg gtaagtccag gaataaataa ctcattgctt 60
cctgagccat cccagctcat tttgaggcaa ctctaactat ttgaaaaacc atcattcatt 120
tattcaataa atatttatta aatgccaact aagtgcccaa gcctggtttt agatgataga 180
aaaaaaaagt aaacaaacaa rcaccccgca cgcccccacc aaaaaaatcc ctactttcat 240
gaagtttgct tttcttacac taagccaagc taaaagttga tcttacctaa ccttcttcct 300
cactgagcta cttacaaccc tctaggtcct ctcattaggc atgggaaaag tgcttagttc 360
ttctcccatg taaatattta aagacactgg tagtaccccg t 401

<210> SEQ ID NO 191
<211> LENGTH: 1001
<212> TYPE: DNA
<213> ORGANISM: Homo sapiens

<400> SEQUENCE: 191
cacatctcac caaacatcat gcctgggtaa gtccaggaat aaataactca ttgcttcctg 60
agccatccca gctcattttg aggcaactct aactatttga aaaaccatca ttcatttatt 120
caataaatat ttattaaatg ccaactaagt gcccaagcct ggttttagat gatagaaaaa 180
aaaagtaaac aaacaagcac cccgcacgcc cccaccaaaa aaatccctac tttcatgaag 240
tttgcttttc ttacactaag ccaagctaaa agttgatctt acctaacctt cttcctcact 300
gagctactta caaccctcta ggtcctctca ttaggcatgg gaaaagtgct tagttcttct 360
cccatgtaaa tatttaaaga cactggtagt accccgtttg gccttgtctt tttagttcct 420
acatttatcc atagttacat gttttcaagg ctcttcacta caccggctcc aaatttctgg 480
gcttgttctg cttcgttgtt sttccttttc aagtgcaatc ctcagaagtt aatcagctac 540
tccagatgag ttctgaccag cacagaatat agcagcggca tcattacctt gttctagttc 600
tcggatgtcc attaatacaa tctgagttta agttgccatt tttgatttca caaatcactg 660
ctgatgcaca tgaaactcag ctaatttttt caaccctgtt attatgtaag atacttactt 720
agattggaaa taggtccaca gcaaccagca acaaccacac tgctcatgag attctcctga 780
aaaacaagct cagcctccct caaagagagc tacgggacat tttcagccag cctgaagacc 840

```
acaagtgtgc ctggtgccag ccagaattgt cttccattga gagaatttgc agattctagt    900

aaatctcaag tctaaacctc agctaaatta tttagaaaca atgagcaagg gcagctctaa    960

cttggcccaa tatctgcaat aataaaagtt aatacatttt g                       1001
```

<210> SEQ ID NO 192
<211> LENGTH: 1001
<212> TYPE: DNA
<213> ORGANISM: Homo sapiens

<400> SEQUENCE: 192

```
aatcccttgc ccaaacttag acagatttta agggcaagta ggactcaaat atagatgagt     60

ggactccaaa gcccatgtac ctaaccactc taatcaccag acttctcatt ttcattgcta    120

acctgtcaag caatgttgct tgagagggaa ggagatgcat tccccaaca cattattctt    180

tctaaatttt ttaagaaatg ttaataatca agcttagaaa caagcaaaaa aaaatgactc    240

cacagacata ttagcttggg agggatcaag ttggtttctc ccacaggttc tgagaagcag    300

ggaggctatc tgggatcctc tcataaaaaa tccttctgat tctgattctg atgtccacct    360

cacaagtcaa atggggaact gagcttgaca acaaatagcc gctttcttat ttctactcct    420

ttcccataat tttcaacagg agatgactat gttttatcta atgatctgac tctgtggagt    480

ggtctctagg ttgcaccccc vccccccccg agtgtgagct aatggaaatg ttttggagac    540

cactgatcca acttgctcta gagttagggc tggccccctc catccaaaac actcaagggc    600

cctgatatct tagtctgctc agtacaaagc cacacaatct gactctaccc tgcccaggca    660

atagtgcagt cctaaacact gtcctctgac ttcaggtagc tcatgtacca gggagagacc    720

tttcaaagac cggtgagaat acccaactga ccagtgatta agaaagggaa atttcagatt    780

cttgcacagt gaatacacag ttgagccaag tacagaattt tgattttctc ctctctgctt    840

atggataatt cattcttta tttcttcatc tatatgtgaa aatttgtttt ccttatattt    900

tctgtgttgc ttctattcct atcaggcttt cctgtacaca ctgtgtaact ccaacagaaa    960

caacctgaac tcctaaggat acaattgaaa ctattagttt g                       1001
```

<210> SEQ ID NO 193
<211> LENGTH: 1001
<212> TYPE: DNA
<213> ORGANISM: Homo sapiens

<400> SEQUENCE: 193

```
tcccttgccc aaacttagac agattttaag ggcaagtagg actcaaatat agatgagtgg     60

actccaaagc ccatgtacct aaccactcta atcaccagac ttctcatttt cattgctaac    120

ctgtcaagca atgttgcttg agagggaagg agatgcattc cccaacaca ttattctttc    180

taaattttt aagaaatgtt aataatcaag cttagaaaca agcaaaaaaa aatgactcca    240

cagacatatt agcttgggag ggatcaagtt ggtttctccc acaggttctg agaagcaggg    300

aggctatctg ggatcctctc ataaaaaatc cttctgattc tgattctgat gtccacctca    360

caagtcaaat ggggaactga gcttgacaac aaatagccgc tttcttattt ctactccttt    420

cccataattt tcaacaggag atgactatgt tttatctaat gatctgactc tgtggagtgg    480

tctctaggtt gcaccccccc bccccccgag tgtgagctaa tggaaatgtt ttggagacca    540

ctgatccaac ttgctctaga gttagggctg gccccctcca tccaaaacac tcaagggccc    600

tgatatctta gtctgctcag tacaaagcca cacaatctga ctctaccctg cccaggcaat    660
```

agtgcagtcc taaacactgt cctctgactt caggtagctc atgtaccagg gagagacctt 720
tcaaagaccg gtgagaatac ccaactgacc agtgattaag aaagggaaat ttcagattct 780
tgcacagtga atacacagtt gagccaagta cagaattttg attttctcct ctctgcttat 840
ggataattca ttcttttatt tcttcatcta tatgtgaaaa tttgttttcc ttatattttc 900
tgtgttgctt ctattcctat caggctttcc tgtacacact gtgtaactcc aacagaaaca 960
acctgaactc ctaaggatac aattgaaact attagtttgc t 1001

<210> SEQ ID NO 194
<211> LENGTH: 501
<212> TYPE: DNA
<213> ORGANISM: Homo sapiens

<400> SEQUENCE: 194
acagaaacaa cctgaactcc taaggataca attgaaacta ttagtttgct ataacttttc 60
tatttgattt accaagatac tctccctata gccaaaataa ttatatagca atctatgttg 120
tagcaaaagg aaataaacaa cggtgtttct taaacactta catagagagt ttagatgtat 180
tttttaacct tcttttctct ttttcatcta atttaaggtg agattccagg atctttctca 240
tgaaagatcc ycagagaatg tgcctgctaa acttgataga gtcacaaagc taggttacaa 300
aagagagcaa attaaattta gacccaaaag tgttgatacc acatatactg acgcatttct 360
tcaacagttt tcctttgttt atttattcag ggcactagag aaggtgctct aatcttttaa 420
taacagactc aatctgccat tgtcaaaatt atcaacaaaa ataataaaat gggttaaata 480
caaccacaaa aattcactgt g 501

<210> SEQ ID NO 195
<211> LENGTH: 401
<212> TYPE: DNA
<213> ORGANISM: Homo sapiens

<400> SEQUENCE: 195
agtcagtaaa atccagcaag cacaggtacc aacattataa agatgattca tacatggttc 60
caggcttccc aactagtgga agaggcagag ctagaaacag atgagttcaa tgtcatcttt 120
taaaatgatg gttattcata ggatgcttgg aaatgcagag gggcactaaa tatttatgct 180
caataaatag ttgtggcctc vctgtgtggg agtgtttgga gatctaaagg tagcatgaga 240
tgtacaaatg tggagtttag ttttaaagag accaccaaga attgcttcat ttatgagtgg 300
ccctggccct gccactgatt agctccatga acttgagcaa gtaatccttc tcagaatgtt 360
tcttttgttg ataaagttag gagttgcatg ataatgatgt c 401

<210> SEQ ID NO 196
<211> LENGTH: 501
<212> TYPE: DNA
<213> ORGANISM: Homo sapiens

<400> SEQUENCE: 196
ttttatgcca gatggcttta ttatttccct ggttccagat ccctttccct cttgcctttc 60
acgccctgtg ccctagggct gtatggtgtg taccccctata attctcccag cctgcagggc 120
aaaatgtaaa aacttcaagc ctctttttca gcagacagaa gggagggtca gggcaggatc 180
tcggtaggtt ttgtccaagc agtcggctca ctcttaagct ggcctgaggc agcagcacct 240
ccttacgctc vtgtgcagag atccagccct cccagtgccc cgctttgagt cccagggctt 300
ttctcagccc ttgcagccag ctgagccact tctaccactc ccaccagctt ataagagaaa 360
gagacttctt ctgtgctatg tctaatatta tcaggtccat tttgaaaatg agactaacat 420
agccacagct cctccctcca agggagactc tcatagcact attcaaattg catgatgaat 480
caagccctgc tgaactgcat t 501

<210> SEQ ID NO 197
<211> LENGTH: 1001
<212> TYPE: DNA
<213> ORGANISM: Homo sapiens

<400> SEQUENCE: 197
aggtgttcct cagggcccag tccatgacac atgcttttcc atattaatgt atggaaaata 60
ctcctgtaga tttgagcagc taccattgct ttccctagcc ctttgctcag aagtaggcac 120
cagtccactg gctgttgggc aaaagcctgc tgagaaatcc aatgccttgg ccaaagatgc 180
tttgaagaaa tagtaagtga ggcagctctg acctcttctt atagaactcc ctgattcata 240
aaatcaaaca gcaaagactc ctagagacca ctgagtccaa gcctcttcat tttatagaag 300
agaaactgag gtccatagaa gcccattttt ttatagaatg agaaggaaag tgacttgccc 360
agggctcctg cttacagtag agttgggact ggcatttaca tctccttatc ctttacttag 420
tcctcttcgt aataaacagc gaaacactca ggggtccttc cttcctcttt ccaaaccctg 480
gaggagctga gggggagaca ygggggcttt actcctcgtg ttgtttcaga ctcagacttc 540
tcagcttcca cattgagaga ctatttgcaa ttgcttctcc ttgttgccca aattcctggc 600
tggcattcca gactgacacc agagacttcc ttcccaggga catccatcct gggcaggtca 660
gcagtttgca tcttccctgg ggcagaagtg gcagagtctc agaactcttg cttcttaaga 720
ctcagctcaa tctccacctg actcagcaga ggtttctgga atctcagatg ggtcctaacc 780
agaagcagct aggttgcttc tctgtttcta taatgagaaa acaaaaaaaa aagctgacta 840
tgaccattga gaaagaaaat gcacccatgt aaacacagca atctttaccc tataaataac 900
cctaattaaa atgaaaacac ccgagtgctc ccatcttttt tgattttttc tttctgctgg 960
acaccatggg aggtccttgc agcagagctc tggtgcttgc c 1001

<210> SEQ ID NO 198
<211> LENGTH: 1001
<212> TYPE: DNA
<213> ORGANISM: Homo sapiens

<400> SEQUENCE: 198
ctatatctcc aatctcctct tctatccgtc tccctctctt aatcagtttt tgataatggt 60
ggcctgatgt tctttcctac cacagtcccc agcaatcttc acacacacac tgtttcttca 120
gcctgggatt ctcttcacca tctctaaaat gtaagcagct cctacacatc cttcacttac 180
agagacaccg tatcttccac acagacactc ctcggtcatc tccagactaa ctcgctgcta 240
gtgagcaact gcaacttatg ttcccatgta tccattcaat cttctcttaa taagcatatt 300
ccctcatttc tgggggactc tctgtccctc gctcttgaac cacatctcat tttggtgagg 360
ctccacatgg cacaggctta tgccaaatgg tggttggtat gaagatgggt tcattacaca 420
atcatacttt ttctgaggat gttggaatca acatctcact ttttcctact gtcttggagc 480
tgggatgtga gctgtaatgc hgctgtagct ggaaccctct caaaatggca ttaacacagt 540
agacgcagag ctttgaaatg gagaaagaga aaccagatat aaatggctat ggaattactg 600
ttgccaggga agcctgaagg cttcaactta taaaattcct cttcttcttc ttcttctttg 660
tttttatttt cgattaaagc agcttgactt gagttttctc tcatttttaa aagaaaaatt 720
ctccgttgca cactttgagc accctgagtc ttctcacatt ttggcattca cgacaagggt 780
aagcatttgt tcaatttcta tctctttcat actagattgg aaattccatg gaagttggaa 840
tcctatgagt cttatatatc actatttctc tcgtttctag tacaatgtgg agcacataat 900
gaaatatcaa taaaatattt ctgaatttaa tgaatgaatg aatgggagat tctgagatcc 960
caacccctat caggcctttt gttccatgat cctgatctga a 1001

<210> SEQ ID NO 199
<211> LENGTH: 601
<212> TYPE: DNA
<213> ORGANISM: Homo sapiens

<400> SEQUENCE: 199
tactttttct gaggatgttg gaatcaacat ctcacttttt cctactgtct tggagctggg 60
atgtgagctg taatgccgct gtagctggaa ccctctcaaa atggcattaa cacagtagac 120
gcagagcttt gaaatggaga aagagaaacc agatataaat ggctatggaa ttactgttgc 180
cagggaagcc tgaaggcttc aacttataaa attcctcttc ttcttcttct tctttgtttt 240
tattttcgat taaagcagct tgacttgagt tttctctcat ttttaaaaga aaaattctcc 300
rttgcacact ttgagcaccc tgagtcttct cacattttgg cattcacgac aagggtaagc 360
atttgttcaa tttctatctc tttcatacta gattggaaat tccatggaag ttggaatcct 420
atgagtctta tatatcacta tttctctcgt ttctagtaca atgtggagca cataatgaaa 480
tatcaataaa atatttctga atttaatgaa tgaatgaatg ggagattctg agatcccaac 540
ccctatcagg ccttttgttc catgatcctg atctgaaaaa agtgaatcta gttcccagtg 600
c 601

<210> SEQ ID NO 200
<211> LENGTH: 601
<212> TYPE: DNA
<213> ORGANISM: Homo sapiens

<400> SEQUENCE: 200
tcttggagct gggatgtgag ctgtaatgcc gctgtagctg gaaccctctc aaaatggcat 60
taacacagta gacgcagagc tttgaaatgg agaaagagaa accagatata aatggctatg 120
gaattactgt tgccagggaa gcctgaaggc ttcaacttat aaaattcctc ttcttcttct 180
tcttctttgt tttttatttc gattaaagca gcttgacttg agttttctct catttttaaa 240
agaaaaattc tccgttgcac actttgagca ccctgagtct tctcacattt tggcattcac 300
racaagggta agcatttgtt caatttctat ctctttcata ctagattgga aattccatgg 360
aagttggaat cctatgagtc ttatatatca ctatttctct cgtttctagt acaatgtgga 420
gcacataatg aaatatcaat aaaatatttc tgaatttaat gaatgaatga atgggagatt 480
ctgagatccc aacccctatc aggccttttg ttccatgatc ctgatctgaa aaaagtgaat 540
ctagttccca gtgcctagac ttgctgttct gttatggaaa gatctctatt agggagcatt 600
c 601

<210> SEQ ID NO 201
<211> LENGTH: 601
<212> TYPE: DNA
<213> ORGANISM: Homo sapiens

<400> SEQUENCE: 201
ggcaataaag gcaatagttt aatcttcaac ctgtggaatc cattggctat cccttagctg 60
gttataaaca aaggtaggaa aaaaatggga tactacttat tttccttgtg aagcccaaca 120
tatggttgga aacatttaga aatagaaaag gattggaatt tggtaaatta aatggcattt 180
ttacctcaag gcttcctgtg gggccttgat tataggcatg aggctataga ttttagcaac 240
taggtattgt gggattttga ccctatgtca cggggttggt tcctatatct gtgtggctgg 300
yttttaacta gtgcacttgt aaaggcctta gcctttagaa gtaaatcata tggcattttg 360
acttttataa gtcactagag ttaacggcaa ctttgtttgc aaatgataac tttttgtaac 420
attcagaaat ctaagcaaat gccaactaaa tggggtgagg ggcttagtaa acctgtgcaa 480
gccatgttat ttctggcaag gatctgatca aaggaaaaga gtcttcctgt tacacacatt 540
taggcactgt ggcagaacag ggaggagccg agggatatcc aggaaggggt gccgcagaag 600
a 601

<210> SEQ ID NO 202
<211> LENGTH: 601
<212> TYPE: DNA
<213> ORGANISM: Homo sapiens

<400> SEQUENCE: 202
gtggctggtt tttaactagt gcacttgtaa aggccttagc ctttagaagt aaatcatatg 60
gcattttgac ttttataagt cactagagtt aacggcaact ttgtttgcaa atgataactt 120
tttgtaacat tcagaaatct aagcaaatgc caactaaatg gggtgagggg cttagtaaac 180
ctgtgcaagc catgttattt ctggcaagga tctgatcaaa ggaaaagagt cttcctgtta 240
cacacattta ggcactgtgg cagaacaggg aggagccgag ggatatccag gaaggggtgc 300
mgcagaagag tcgtttgctg tttgaactgt gtttctcagt caagaaagga gttctctatt 360
ttaaacttca aaggtagcta ctttgcgttt gtgctacaga gcactgttat atgtgagatg 420
ctagctttac acttttaaac caagaatagt tagtccttga ttaagtaccc ataattttgt 480
tcattgttga tattattttg aacctctttt agagcctgga gaggaggtag ggaagaaata 540
actttgaatt caagtggttt atccacagat ccaagagtca ccacagagta aattgcttta 600
g 601

<210> SEQ ID NO 203
<211> LENGTH: 1001
<212> TYPE: DNA
<213> ORGANISM: Homo sapiens

<400> SEQUENCE: 203
ctggagtgat tcccaagtgg cacctacaac ttcacctgtc ttgacttttt ctggtctttt 60
tctcctgatt ttgtattttc acttttgttt ctttacttga ccaagtttgg ctctgggtat 120
gatttatctg tggctgatgt ggtattcccc atagacggca acaatgattg agaatctggt 180
tttgtcatct gtccatttgg tgatctcttg gataacaaga atctagtctc tctaaggtga 240
gaaacagtag ataatgtggt taattaattt ttgtttgtct ttttgtctac ccatgagctc 300
aaataaatat tgtatgtctt ccaaaaagga taacaaatct ttgagatcca gcccggtgag 360
tgtgtttttg tgtttacttt gactcatgtc tgaagttata gaactgaagc catgggctct 420
ctgtatatct gtaagtgaag aaagccttta cctctcagta cataaatgtg aaatattctt 480
ctacctctgg agtgtattaa kaaattatgt cacaaagtat tttaaattat gttctatgtt 540
gtaattagct tagagagaat acgtgcttaa atgaatctat tattttccca gaattcagaa 600
tattttccta gaaaataaac taaaatttta atattttaaa tatattttaa agactatact 660
ttaagtattt tttaaaagta taaaaagccc tttttataaa aataattagc ccaaaagcat 720
ttttatgtaa aaatccaagt ttactgaatc aaggtgaaat ttttgttagg tcaaactggt 780
ttgtttggcc attttgtttc aaaatagcca tatatatagt tcccctgatc ttattagtgt 840
attaagcgta agtatatatt ttagttttat aagatttgag gtgtttcctg ataaagtgac 900
tagttattct gaacttccta aatttcttat attgacttac tgatcaaatt agctaatatg 960
acttctacat aatcatgatt gtgaaaattg taaaattatg t 1001

<210> SEQ ID NO 204
<211> LENGTH: 601
<212> TYPE: DNA
<213> ORGANISM: Homo sapiens

<400> SEQUENCE: 204
tataaaaagc ccttttttata aaaataatta gcccaaaagc atttttatgt aaaaatccaa 60
gtttactgaa tcaaggtgaa atttttgtta ggtcaaactg gtttgtttgg ccattttgtt 120
tcaaaatagc catatatata gttcccctga tcttattagt gtattaagcg taagtatata 180
ttttagtttt ataagatttg aggtgtttcc tgataaagtg actagttatt ctgaacttcc 240
taaatttctt atattgactt actgatcaaa ttagctaata tgacttctac ataatcatga 300
ytgtgaaaat tgtaaaatta tgttttcaac caaattgaaa tacaatttta acaaagtttt 360
aacacattct ataatgtttc tgcttaaaaa taacttccaa gatccttagt taattttaag 420
atggactaac attacaccta gttaattaat ggctaattgt tggatgccta gataatttcc 480
aagtaagata gaatactcca aaattgatca ccatatacat agtatatata tatatatata 540
tagagagaga gagagagaga gagagagaga gagaaagaga gagagagaga aagagagaga 600
g 601

<210> SEQ ID NO 205
<211> LENGTH: 601
<212> TYPE: DNA
<213> ORGANISM: Homo sapiens

<400> SEQUENCE: 205
atatagttcc cctgatctta ttagtgtatt aagcgtaagt atatatttta gttttataag 60
atttgaggtg tttcctgata aagtgactag ttattctgaa cttcctaaat ttcttatatt 120
gacttactga tcaaattagc taatatgact tctacataat catgattgtg aaaattgtaa 180
aattatgttt tcaaccaaat tgaaatacaa ttttaacaaa gttttaacac attctataat 240
gtttctgctt aaaaataact tccaagatcc ttagttaatt ttaagatgga ctaacattac 300
rcctagttaa ttaatggcta attgttggat gcctagataa tttccaagta agatagaata 360
ctccaaaatt gatcaccata tacatagtat atatatatat atatatagag agagagagag 420
agagagagag agagagagaa agagagagag agagaaagag agagagagag agagagagat 480
tgagagagag taagaaacta tatgtacata gtttttttact tttatatgtc atggagtggc 540
tacacctttc agtcatgtta atgaatatgc tcttttttgc cactttagaa aggatttgtg 600
t 601

<210> SEQ ID NO 206
<211> LENGTH: 601
<212> TYPE: DNA
<213> ORGANISM: Homo sapiens

<400> SEQUENCE: 206
tgatgggcct gatttgaccc agtgggccac agtttgtcaa catgtgatct aaagcatcct 60
aaaatttttc tatttgctac cctgggacct tgattatttc agggccaacc taatttccaa 120
gtccaaggta tatgaagcat aagctttctt tggaggactt tttaatgggc ctttggattg 180
gtgaaaccat tttcttttac ctctgtctaa ttggatattt tatcttctat gtggtagagg 240
ctaacaggca ccagtcatct tctacccaag ttggaattaa gagagaaaca cctaagttag 300
rcaagtaggg attaaaatgt cagttttatt atagataaaa tccatttcag agaatccagc 360
tgaggtttac agctagtgac tatgcaagta atttattctg aattaaacag acctgctcac 420
ccaatcacaa gcacatctgg acacaggcct ctccacatgg acctatgtcg gtaaaagcta 480
gagtgcaaag caacaaggat gtgttcgctc tgcagcaata tctcaggaga tgaggaagga 540
aggtgctgaa ttatgcatcc ccaagtttat ctcccaaatt ctcaattgga aaatattatt 600
c 601

<210> SEQ ID NO 207
<211> LENGTH: 714
<212> TYPE: DNA
<213> ORGANISM: Homo sapiens

<400> SEQUENCE: 207
ataacttctt actcttttac tcccttgatt aaaatgttaa atgacccctc tttcctcaaa 60
agaaaaaaaa aatcagttct gatatcttat cctggtatta aacatgcttc actctctggc 120
actagactac tactacctag tatgactctc ctctctggcc aggtaagtct gtttataacc 180
tctgtaagat gacacttaaa ttttgcctcc ttgyctttgc caaggccatt gcttccacct 240
ggaatgcact ctttaattgt tttacttgat tcatatctat ctttcagcgc ccagctctag 300
cctctgtgaa gccttcctgg atcactctag ttctcaaagc cctctctgcc cttgaactac 360
taaagtcctt actgtctgta tcttaggcat ttgcagttgg tgttgttaat tttgcataat 420
tatatcctat ctccaaattg agatgttcag ttctttgagg atcagaaaca tttgttaggc 480
atctttatac cctcaaagca actagcacag tgatttcaca taatgtaagg gttcatatgt 540
ttgctcatgt gttatatacc ctttaaaata atttattaaa taattattta attacttatg 600
ttatgttata aatatataac aacaacgact tctcactaat ccagactagc tccattagta 660
aaagttaatg aggatgtgct ctattcagaa tacgtttcat gtgtttttgt gctg 714

<210> SEQ ID NO 208
<211> LENGTH: 701
<212> TYPE: DNA
<213> ORGANISM: Homo sapiens

<400> SEQUENCE: 208
cattgcttcc acctggaatg cactctttaa ttgttttact tgattcatat ctatctttca 60
gcgcccagct ctagcctctg tgaagccttc ctggatcact ctagttctca aagccctctc 120
tgcccttgaa ctactaaagt ccttactgtc tgtatcttag gcatttgcag ttggtgttgt 180
taattttgca taattatatc ctatctccaa attgagatgt tcagttcttt gaggatcaga 240
aacatttgtt aggcatcttt ataccctcaa agcaactagc acagtgattt cacataatgt 300

```
aagggttcat atgtttgctc atgtgttata taccctttaa aataatttat taaataatta    360

tttaattact tatgttatgt tataaatata taacaacaac gacttctcac taatccagac    420

tagctccatt agtaaaagtt aatgaggatg tgctctattc agaatacgtt tcatgtgttt    480

ttgtgctgct gttgcctaga wccatgaaac agatttgtag ttggttgttt ccagtcctga    540

ggaaatgtgg gcttgctgag cttctgaact acatccttct tgtgagcagc ttagatttca    600

aggttacgtg cttccagaaa tagaaaggga gtatttagat tctttccttc cctgtcaaga    660

aactctgttg aatcatcttt tggcaataat gccaaagtaa t                        701
```

<210> SEQ ID NO 209
<211> LENGTH: 701
<212> TYPE: DNA
<213> ORGANISM: Homo sapiens

<400> SEQUENCE: 209

```
cttctgaact acatccttct tgtgagcagc ttagatttca aggttacgtg cttccagaaa     60

tagaaaggga gtatttagat tctttccttc cctgtcaaga aactctgttg aatcatcttt    120

tggcaataat gccaaagtaa tttgtaagcg ttagaacatt tgtgcagaca gcataagttc    180

cttcaaataa tgcagttgca yaaagcagta atgttaatta gtcaaagcaa ctttttttaaa    240

atcagtagtt ctatgcacat gtgacaccac cttggtaaaa agagctttag aaatttgaag    300

aaaattttga gttgtcccaa tatcgagagg ggatgccact gtcacttatt gtgaaatagc    360

tagggatgct agatgtcctg caacgtgtaa ggcattctca tgcagtgaaa aattgcccca    420

cattctaact ggtcttcaaa tgtccctcca tacatttatg tggatgaaaa ctatttaaac    480

ttatctgagc ctaacactta atgccattta catataaaca cctaggatct agtttttgta    540

cagtttaaat acatgatttt gtacagtttg aatttttgca actgttatgt aaatcaaaga    600

aagattacgt tttgtctcat atggaaattt aacaagcttc atttatcatt gtgaaaaatc    660

atgttaccag tggaagtacc acttttggta tttgaatacc c                        701
```

<210> SEQ ID NO 210
<211> LENGTH: 1001
<212> TYPE: DNA
<213> ORGANISM: Homo sapiens

<400> SEQUENCE: 210

```
cctcaaagtg gcttaaaata acaacgattt aattatcatt tacaagtctg tggatcaatt     60

aagaggttct gctgatccaa ccccagctct aatctcagct gtgcttcctt atgagtttat    120

ggtcagctgg gagttggctg gtctgggaca gcctcagtca ggatcctcca gcagactagc    180

ctgggctttc tgggtaatgg tggggttcaa agagagtaag cccaggcctg caaagccttc    240

tgagactcag aattggcaca gtcaccactc tgcagcattt cattgaccaa ggcaagtcac    300

aaggccagcc cagattcaca gggtaggaaa agagacttca cccctcggcc atggaaggag    360

ctgcaaagtc acattttaaa gagggtaaga gtgtagacac aggaaggggt ggccattgtt    420

gtaatcagca gcaccaagtt aaggcgtaaa gaagggatag gagtcaacca aacagttagc    480

tgaagagaac tgtggtcagc rtgtcaaggc cctgaggcaa gaaatagcat gcagtcgtcc    540

agaaggctaa gaaagccaga gcggcagcat gctgagagtg aggggtgagt tgtacaaaat    600

gaggctggta agaaggaaag ggtcagatgt tgcagagcca tgtagtgtgg gccttgttgc    660

gattttcatc ctttatctga agaaatgttt taagcaggag agggagatga ttagttattt    720

aaattttctc cagtgatacc aatgtgcaac caaggttgaa actctctgtg taaaagaaag    780
```

gcacaactta ggaagttgtt attacttgtt atccaggtga aagacgacag tagcttgaat 840
gagtgtagtt acttagtgaa tgaatgaata aataaaatta aactccaagg gagagattta 900
ggatccacag gaagactgcc ttgtttcaaa tcacagctcc agcacccact agctgtactt 960
gctggggaaa cctcagtaca ttctttcatc cctttgtgcc a 1001

<210> SEQ ID NO 211
<211> LENGTH: 701
<212> TYPE: DNA
<213> ORGANISM: Homo sapiens

<400> SEQUENCE: 211
tgtaaaagaa aggcacaact taggaagttg ttattacttg ttatccaggt gaaagacgac 60
agtagcttga atgagtgtag ttacttagtg aatgaatgaa taaataaaat taaactccaa 120
gggagagatt taggatccac aggaagactg ccttgtttca aatcacagct ccagcaccca 180
ctagctgtac ttgctgggga aacctcagta cattctttca tccctttgtg ccacagagcc 240
ttctttccca aaacggagat agcaataata cctaccttag cagtgcatta taaaaactaa 300
tgcattaatg ctcatagagc agttatcatc atgccaggca aatgataggc actccataaa 360
cgttaactac tgtgattgtt gttaaaagga tgatgtctga ggcagtacag tatctcatgc 420
agaaaagctc tcatcccaaa atgaatctct attctaatcc caactatacc ctgtagctct 480
gactgtgctc atgtggttgc rattaagcca aagcccaagg tgggaccaga tactgtccat 540
ttcatctcgg cttgtcatcc atcctcctca ggtctgcctg gtgctctgac atctggcttc 600
cactcatctg gggaggaca gggagaagcc agacagccat gaatcctgct gtctgctcac 660
aaattcgcag tctagggagg gctaggggga gttgctgtca g 701

<210> SEQ ID NO 212
<211> LENGTH: 401
<212> TYPE: DNA
<213> ORGANISM: Homo sapiens

<400> SEQUENCE: 212
gtcacctagg tgctattggt agatacaaag tgttttatga gcgatgctgg taagagctct 60
tttccaagtt atctccccag gcacctctgc ctgaaattgg tggtggttac aagcagagtt 120
ttgaagaaag acctgggtct ggaccctctc tcccctgctt acagttgtgg gattccaaaa 180
aagctactgt ctctgtttct yatctggcgc tggggcaatg actcctgcct tacacagcca 240
ttgtgtgaat actaatccat gatgtcatac cgcacatgcc caagagcagg caggaggccc 300
tctccctcac ttcttccagg ctctgatgga atggcagctt agtaacagcc ttgctgtagt 360
caccccgtat tcagcagagg ctctcctcca gcccaacaca t 401

<210> SEQ ID NO 213
<211> LENGTH: 701
<212> TYPE: DNA
<213> ORGANISM: Homo sapiens

<400> SEQUENCE: 213
aaaggctctc cccagcctcc tgccctgctt caccattccc cagtgtcttt atctccacct 60
gaagtttcac atgtacttgt ctgtctctcc gaagaattta agtgccacga gggcacggtg 120
gtttattcac ctctttaata gtagctggca tgcagtaggc actctgtagg catttggaat 180
taatgaataa gtaaatacct ggattaatta actagtattt caagggagag tgggatcctt 240

-continued gggaaagaag gatagattac accacagttt gctatagaag gatgcctaag attggtcttt 300
gtcagttaat tactcactga tataacattg gctagtcagt tgctcttgag cctcagtttt 360
ccatatctaa aaaagagaca atgtcactta ccatacttac ctcaaacagc tagatggagg 420
ataaatctca aacatgggaa taagtctgct ttgaacactg taactcacca tgtaaaaatg 480
agaatttgga ttttttaag waacttagca gttaatttcc tgggtaatat cctaatagag 540
aaatgtccca cgtggtatgg gacaaaggag aatgcctcat ttggatccac atctgatttt 600
aaaccttgct gcatcaacct gacccaccca acacaacttc actcccttgg tcccagattg 660
gcaggcacac aagccctgag gacagtatgg cttcaggtct c 701

<210> SEQ ID NO 214
<211> LENGTH: 1001
<212> TYPE: DNA
<213> ORGANISM: Homo sapiens

<400> SEQUENCE: 214
gccctgtcaa gcaagacgcg cagcttggca cagccagccc tgtagccagc ccaggcctcg 60
taatgggata cagagctcgt cgctaggtgc agcagagttt gcatcaggcg ttgtcactgt 120
ctggtggttg cctggtgacc ctaatggaaa atgagtggag gcagccccta ccacagaaac 180
cactccctca gctggcaggc ttgtcggaaa gcccagtgcc atgggagggg gaggggctgc 240
cacagaggag ctgtcaccca ggcgccctgt gtaggtggtg gcagggacgg ggagagaagg 300
gcgcagagcc acaggagggc tcagcagtgg tgtctgctct cccttctgca tgaattgttg 360
ctcataaaag atgggtgagc ccagcacagt aactaatgct tatccccagg cccaaattta 420
ggtaaaagca cacaaaaagt ctcatcagtg gtcaatgctc cacagctcca aacacaggaa 480
ggtgcattct caagctgtta ygagaagctc actcaagctg atggtattga cagccacagc 540
ccccatgcag ggaaggctgg acccgacacc tgcccacgag aagcagcata cctgggactg 600
gagggacttc ctggcctata agaagaacac taagagggga ggaggactcg ggctgattgg 660
gaaaacagat ggtgagctcc atccgtggga aaataaatga cagcgtgcat ttaagaggtt 720
gagccccaga gccaagcctg ctgaaatgcc agcttatcaa aagcacagga gcactgtgtg 780
ctagacgctc tatcatactc tcttccatcc tggtttctct taatcccaag ataatgtctg 840
taggcattgg aaagtcttgc ttgagagacg aagaaatgta ggctcagaga ggttgaacag 900
tttgtctgag gtcacacagc tactcaatca caggatttaa cacaggcttt tctgctttca 960
agtctaacat tccttctcct aacatcgtgg gagaaagtga t 1001

<210> SEQ ID NO 215
<211> LENGTH: 1001
<212> TYPE: DNA
<213> ORGANISM: Homo sapiens

<400> SEQUENCE: 215
gttaattgtg gctcaccaag gcttggagag agctggatga gaggggagca gagtccagcg 60
tgggtggggc tggactggca gtggcagagg agaggcagct gctgttcaca tcagggtctg 120
gatggccttg tcgccgcagg aggctgcgct gctccaccct cccaagcgtt tcccagctcc 180
gtcacagggt ctccgttccc accacagtgt gtcccagcag ttccatttgt atttgtaccc 240
agagagctcc actgaggcct gtggtcacag agtgactccc ttccatgttc tgccacaggt 300
tgcaagccat agggtgaagg tcacacagtt ttgtttggcc ataacagctg cctccatggc 360
aacagcgtgt gatatcactg gaaaagccat ttgtgggact ccaagctgga aggaaaaggc 420
agagttggag agagctgtag cgggagacag agaaagggca gggtctctcc ggatgctcca 480
aggtgctgga cgcacaggtc sctttctgta gtccttgtca tgtaagatct tttcatttag 540
gctaagcaaa tccagatgtt cttcaaataa ttcaggcata tttggcccaa gcataaactt 600
gtcttcattt ttcatccaat ctgacaaacg tttgcaatcg cctcactctg tgagttccag 660
gacaccttcg ggctggaagg ggttaatgag aacaagccct ccctggtggc ttcccttccc 720
cctggtgctg cccctcggcc cctcccaggc cagcaggatt tgctgtccaa aggccctcaa 780
aagacatcca agcagtcttt tcttagaaac aggaaactgt cttcggccaa gtacaaatga 840
agtgaagcac ccagaaacct gaggaccgct ccaaactgag gcctggaggc agacagggag 900
ggcccaactc ctggcagggc ctccaggact caggctctca tgaatgagac tgagctcagc 960
tgcagcctca gccattcttc gttgcactca acccattatg t 1001

<210> SEQ ID NO 216
<211> LENGTH: 1001
<212> TYPE: DNA
<213> ORGANISM: Homo sapiens

<400> SEQUENCE: 216
agggatagct gactatgagc ggccccactg ggctctcaag gtaccatgaa ggatccagtt 60
cccctctggc tgagctgttt gatcctaaga catccctgtt ggttggcagg gaccattttg 120
tcactgtttt ctgtcatgcc ttgttttctc attctttctg tcacatattt ctaagtgaga 180
gggaaagtta aagccacgga atcgcttatc atctcctccc tctgcctttg ggtttactca 240
gagaaagtca tatcttgaca ttcccaggag tattactatg cctttaccca ttttcagtag 300
taataataac caagttccct ttcccatttc cacctacatc cagccactga aatggaatta 360
acaagagtac cagaactaca tatattgcca gcagttattc ctgggaagat ggaagaagaa 420
aagtcctaaa catccaactc ctgggtacct gcttgcttga aactctaaac atcagtctta 480
ttcgctagtt atggaagtaa hgatatgtta ggtgatactc tgagaaagct gtgagctaaa 540
agttgcctta cattgcagaa ctctcagttt ccagagaagc agcagacaac acagattata 600
gactctgcag tcaaccaacc agtcctgtta agaacaaact cagccactta gttacgtgaa 660
tttggacacg ttgtttaatc actccccata cttgcctcag ttttctcata agcaaaatag 720
gcatattgag agtacattgc tcttaacatt gttgtgacaa tgaaatgata taatttatgc 780
agagtgaaca acactatgcc tgacacatag caagggctct acaaatgtta gatgttgttg 840
ttgttactat tattcggtat actggataat actgccagat tcaacatgtt tgtgcatttc 900
tctcaaattc gcggttgaaa gtatacaaaa aacaaaatca aaaaaatgtc tatttctctt 960
agccctgtgg tgtctctggc acaactcgtt ctaagaaaag t 1001

<210> SEQ ID NO 217
<211> LENGTH: 501
<212> TYPE: DNA
<213> ORGANISM: Homo sapiens

<400> SEQUENCE: 217
tttctcataa gcaaaatagg catattgaga gtacattgct cttaacattg ttgtgacaat 60
gaaatgatat aatttatgca gagtgaacaa cactatgcct gacacatagc aagggctcta 120
caaatgttag atgttgttgt tgttactatt attcggtata ctggataata ctgccagatt 180
caacatgttt gtgcatttct ctcaaattcg cggttgaaag tatacaaaaa acaaaatcaa 240

```
aaaaatgtct mtttctctta gccctgtggt gtctctggca caactcgttc taagaaaagt    300
tagagctagg tatggtgaat tgtcccaaca acaaagcttt catcaaacaa agcagcaggg    360
agattctcaa gtctcctttt attattatta ttgtacttta agttttaggg tacatgtgca    420
caacgtgcag gttggttaca tatgtataca tgtgccatgt tggtgtgctg cacccattaa    480
ctcatcattt acattaggta t                                              501
```

<210> SEQ ID NO 218
<211> LENGTH: 1001
<212> TYPE: DNA
<213> ORGANISM: Homo sapiens

<400> SEQUENCE: 218

```
ccccggtgtg tgatgttccc cactctgtac ccaagcattc tcattgttca attctcatgt     60
gagtgagaac atgcggtgtt ttttaatggg ctttccacct ttgtctgtag cgggggcaat    120
gttatctatt cagttcagtt cagacacaca agtgggctcc caacttccct caggctccaa    180
tattagccat tttcctctta gtgtgaattc caccagaata ttatcattcc cccactgtag    240
tagtgtggaa acacttatac tcagtgtcaa atggaaattt gggagcagat gtgcaagcac    300
gaagttcttc cagggaattc taaaagacaa acagggaagg cacttgtata tgggaacctc    360
aagtgctcgg ttgtcaagta gagcctcaat tcaaatcatc tcatttgtta ttttcataaa    420
ccctcaatgt tttctggaaa ctatattttc caggatgttt ctcacacttg gatgtagcaa    480
ggaaatcatt ttttatatca ygtgagtctc aaatttagtc catgaaattg agcaaattca    540
ttaatggaaa gacccttgga ctgagaattt attctactgt cactagagga ctttaatggg    600
ctaagaaaga gaagaaatta cagataatat ccaaagccca gcacgatacc ataaaggccc    660
ctcccagatg agtccaagac ctccagaaag aactaccaat gcctgaagtt ccagtaaaaa    720
cctccctcaa gaatgatcac attcataaca gaaagttatt actaccatca tccctggaga    780
atctcaaagc aaaatctatt atcctaatac agcatcactt gaattataaa gtctgatgaa    840
accagacttg gaggctaaat gatgtacaca gagttgcggc atctatcagg gagctcatcc    900
tagaacttga ttgtcataac aggttcattg caattttcgc tgcctgtgga actttgtgcc    960
ataacctgac tctccaacca aatgtgaatg tagcttaatt a                       1001
```

<210> SEQ ID NO 219
<211> LENGTH: 401
<212> TYPE: DNA
<213> ORGANISM: Homo sapiens

<400> SEQUENCE: 219

```
tatattttcc aggatgtttc tcacacttgg atgtagcaag gaaatcattt tttatatcat     60
gtgagtctca aatttagtcc atgaaattga gcaaattcat taatggaaag acccttggac    120
tgagaattta ttctactgtc actagaggac tttaatgggc taagaaagag aagaaattac    180
agataatatc caaagcccag yacgatacca taaaggcccc tcccagatga gtccaagacc    240
tccagaaaga actaccaatg cctgaagttc cagtaaaaac ctccctcaag aatgatcaca    300
ttcataacag aaagttatta ctaccatcat ccctggagaa tctcaaagca aaatctatta    360
tcctaataca gcatcacttg aattataaag tctgatgaaa c                        401
```

<210> SEQ ID NO 220
<211> LENGTH: 1001
<212> TYPE: DNA
<213> ORGANISM: Homo sapiens

<400> SEQUENCE: 220
gcagagcccc gaggcagata tggcatttac ggagacttta tcatggaagc acaacagctt 60
gtcctcagtg gaatacagca ggagatccct cgaagatctg tcaggcttgg ccatttagag 120
gcttggaccc ctgactcctg ccaagagcag taaggaagcg tgggggccaa cacctgtgca 180
catactctca tgccctcact ctccactcat tgtgcagagc agaaaccaga ctcagaagtg 240
ctccaggcca ggctttcttc accaaccttc accagcctct gctggatttg gccgtttgca 300
gtgaaaaatg agcctgaaag ccctggaggc ttcctggtga tttaccgaga attttacttc 360
cacatgggct ttccagctgc agccaacccc aagaggcaga ggtaggaaga ggaagaaaat 420
cataaatgga tagtaagatg agaaacagat gtttggaggc ttcactggaa gggaattctc 480
cacctctact ccctttcttc rtgagatgag aaggctcggg ccctaatgag cagtttctca 540
ctatacctgc aattcatctc cttcccccac caccagctct ctcaagtgtc acttttcaag 600
ggtcttcctg gtcctgccac atgggcatca actttgttgg gtgatttgtt tctggtttta 660
gccaaaataa atgaatgcta ggtgctctga ccatagacac atgttagaca atctcctgcc 720
ctcagggtgc tcaccagccg gaatgaataa gcaggtgcaa gcgtctgccc cctgacagag 780
gcaaggactg gaccctgaaa acccacagga ggggcagcaa acccagcctt ggctcaagga 840
ggcactggag ggtcaaagga aagctcagct gagttgtaaa gatgttaatc aattgaaaat 900
ggatagaagt cactttggag gtattaacct agcaggcttc aagagagttg tatatttatt 960
cagtgtaaca caagggttga gagcaacatc cccaaagcta g 1001

<210> SEQ ID NO 221
<211> LENGTH: 601
<212> TYPE: DNA
<213> ORGANISM: Homo sapiens

<400> SEQUENCE: 221
ccacatggac tggtgcacaa cccatctcta gcccccagct ctctctcacc cccgctgagt 60
caggttctca ctgctgttca catcatattt ttgacgccca aattttctca tagcattcct 120
caatttaaga ttcttttgtg gtcccccatt ggctattgaa aagtaacgga attccttaat 180
gtgacagatc cctttgtgaa tcgattctta ttttcctatc cagtcccagc tctggacacc 240
ctcagtgcct ccacccagtg gatgtattct tccgtgaaac cactgtgctc ctgctgtgga 300
yacgttgtct cccataacag gaacagtgtc tctgtcctgt ccaccaaaca ctccgacttt 360
ttccctaaga attttcacat tgcttcgtct gtgacaacgt ctgtgattcc tttgggtccc 420
cctttctcaa gttccttgtg ctctgcacct gtctacatga atgatgggga gggttggaag 480
gagcagaaca tattaatagc actctccttt tctacccaag ctctgcaaaa attaagaaat 540
aaaaataaaa acaaaaaaca gcatatgaga caggatacca aaatatgacc cttattactg 600
a 601

<210> SEQ ID NO 222
<211> LENGTH: 401
<212> TYPE: DNA
<213> ORGANISM: Homo sapiens

<400> SEQUENCE: 222
gggagcttcc taatgatatt tccagattag gctaacttac actcccaaat gcaggctcag 60
atgaacaggt cacctttccc cactcggggg cctataccag tatgagaatt atggcatggc 120

```
ctaacaaaaa caaatataaa tccctcacgg gcaggactaa tttcttcttt caaaacccac    180

ccattaaaca tagtattcct rggaggggag caagcaagga gcagagaaaa gctgggagtg    240

tcacactaat ggagctcctt ccacattaaa ggaaacacca ggagtaaaga agaaaagtgc    300

caacatgtta tatagtattt tcatttttgt gtctcttgat gaaactaaaa gctatttgta    360

ggcgagaata atgctttttc atctaatatt ttcatcctat a                        401
```

<210> SEQ ID NO 223
<211> LENGTH: 701
<212> TYPE: DNA
<213> ORGANISM: Homo sapiens

<400> SEQUENCE: 223

```
aaccccgtct ctactaaaaa tacaaaaaaa aaaattaact ggatgtggtg gtgggcgcct     60

gtaatcccag ctactccaga ggctgaagca ggagaatcac ttgaacccag gaggtggagg    120

ttgcagtgag ccgagatcat gccactgcac tccagcctgg gcaacagagg gagagtctgt    180

ctcaaaaaaa aaaaaaagaa gaaagaaaga agaaagaaag aaagaaagaa agaaagaaag    240

aaagaaagaa agaaagaaag aaagaaagaa agagaaagaa agaagaaaga aagaaagaaa    300

gaaagaaaga aagaaagaaa gaaagaaaga aaagaaaaaa gaaaagaaaa gaaaagaaaa    360

aaaaagtatt atgtgcatgg actttgaccc agtagagtgg aaacagagtt gcttgccagg    420

cactctgttc tggaccctgt ctgcccaccc tcaagagaag cccccagtga tgggtgtctt    480

tccccacagc cacagctaca yaggcaggag taagcactga gccccgtcct ctggattttt    540

aaattgtaac agagaaagag agagatttgg cctcttgtta tgtagctgga ccgatgatgc    600

ataaattctg gaattgctgc aaggtcatgc ttcctatcat gtggaacaag aaaaacagtg    660

gaaacttgcc taccaagaga gagaagaatg ccacagatgc a                        701
```

<210> SEQ ID NO 224
<211> LENGTH: 1202
<212> TYPE: DNA
<213> ORGANISM: Homo sapiens

<400> SEQUENCE: 224

```
tttagaaaca gctgctcaca tataccatta gtagaaatat aaagataaat cattttggag     60

agaaatctgg gaatatacat taaaagtgtg gctcatgcct gtaatcccag tactttggga    120

ggccgaggtg agtggatcat aaagtcagga gttcaagacc agcttggcca agatggtgaa    180

accccgtctc tactaaaaat acaaaaaaaa aaattaactg gatgtggtgg tgggcgcctg    240

taatcccagc tactccagag gctgaagcag gagaatcact tgaacccagg aggtggaggt    300

tgcagtgagc cgagatcatg ccactgcact ccagcctggg caacagaggg agagtctgtc    360

tcaaaaaaaa aaaaaagaag aaagaaagaa gaaagaaaga aagaaagaaa gaaagaaaga    420

aagaaagaaa gaaagaaaga aagaaagaaa gagaaagaaa gaagaaagaa agaaagaaag    480

aaagaaagaa agaaagaaag aaagaaagaa aagaaaaaag aaaagaaaag aaaagaaaaa    540

aaaagtatta tgtgcatgga ctttgaccca gtagagtgga aacagagttg cttgccaggc    600

actctgttct ggaccctgtc tgcccaccct caagagaagc ccccagtgat gggtgtcttt    660

ccccacagcc acagctacat aggcaggagt aagcactgag ccccgtcctc tggattttta    720

aattgtaaca gagaaagaga gagatttggc ctcttgttat gtagctggac hgatgatgca    780

taaattctgg aattgctgca aggtcatgct tcctatcatg tggaacaaga aaaacagtgg    840

aaacttgcct accaagagag agaagaatgc cacagatgca cagacaggag aaacaagaga    900
```

tggagaggaa gttctgacag tttttcagtt cctggctctg gaacctgcac agttccagct 960
gccttcctga caatcacaga ggcccatcac tcacctctga atctagaaat ttttttttt 1020 tcccaaggag agctcaagat gcttcctatt acttgcaact aaatgagtct caacagtaat 1080
tccattccta agagttttag ccttaagaaa cagtttcaga cacacagttg catatgtaaa 1140
gataaatacc atagtattgc atgtaatttt gataaaatga tcgatttgga tattaatgtg 1200
ac 1202

<210> SEQ ID NO 225
<211> LENGTH: 1001
<212> TYPE: DNA
<213> ORGANISM: Homo sapiens

<400> SEQUENCE: 225
gatgcacaga caggagaaac aagagatgga gaggaagttc tgacagtttt tcagttcctg 60
gctctggaac ctgcacagtt ccagctgcct tcctgacaat cacagaggcc catcactcac 120
ctctgaatct agaaattttt tttttttccc aaggagagct caagatgctt cctattactt 180
gcaactaaat gagtctcaac agtaattcca ttcctaagag ttttagcctt aagaaacagt 240
ttcagacaca cagttgcata tgtaaagata aataccatag tattgcatgt aattttgata 300
aaatgatcga tttggatatt aatgtgactc ttgtcaaaca aaccatctta atagtagaaa 360
catattaata tcattaatta atgcttaagc cttacttcat attcattttg tctcaggggt 420
tggattttgt gcttcacata catctatttt aatcctcaca gcagccctag aagatgggta 480
ctattacctt aagataaaca ygtaaagtgt ttagcatatt gttttgcata tagcaggact 540
tgcaaaatag ctaactacta ttattccaat ttctacagat gagaaaatta gaactttttt 600
agctttatag ccagaaattc caaaggtgct cagataaatg tagtgggaaa atgtaatgat 660
gtgtgggaaa gtgagacagg cagagcacct aaaaggtacc ccctcctacc tattgatctt 720
gacagcaagt atcagatggc tgtacttaga ttgagtgtta gaggctaata cagtaattca 780
agatgtgtaa aagtcaacaa aaagaattag ttatcaaaca agttacattc aaggtatgga 840
atgaactata cacaaacggt caacagacat gcaaacacac atgcactttt ctaccaataa 900
cagcagatat agccacacgt tgggcagtta ataccaagtt ttgcttgttg gctaagggaa 960
ctttcagtat cctaattctg attccatttt ttttttcact g 1001

<210> SEQ ID NO 226
<211> LENGTH: 3766
<212> TYPE: DNA
<213> ORGANISM: Homo sapiens

<400> SEQUENCE: 226
ctaactgggc tatgaatgac ttgagcttgt ggtcttggcc tcattaacac tggacaacaa 60
ccaactgagc taatcagcca ctgctgacat tacagagaaa ctttattgag gtataattaa 120
agtacattaa accatacatg tataaaatgt acaatttgat cagcttttga atacgtatat 180
actcatgaaa ccatcaccac aatcaaaata acaaacattt aatcaactcc agaagtttct 240
ttgtgtccct ttataatcca ttattcctgc acctccatcc tcagcaactg ctgatctgtt 300
ttctctcagg acagaataat ttgctttttt ctagaatttt atataactgc aataatacag 360
tttgtactat ttggcttgtt atattttaat atctttagaa actagatatg ccccctctct 420
catttttgat attggtagtt tgtcttttct ctttttgtgc taataagtct agctagaaga 480

-continued

```
ttattgatct ttatgagttt tgcaaggaac catctcctga tttcattgat ttttttcaa    540
ttgtttttct gttttccagt gcatttattt tggctctgat catttcatgt cttttccttt   600
ctttgggttt tatttgcttt tattcttcta gtttcttaag gcagaagctg agttcattga   660
tttgaagatg tttttctttt ttaatatgaa accttttgt tctataaatg ttcccctaag    720
tgctgcctga gctacatctc acatattttt tgtattttgt tttcattttc atcgagttcc   780
aaatactttc cagtttctct tttgattttg tcaatgatcc atgagttatt ttaaatatta   840
tcttgagact acttgggata tcccagatat ctttctgata cactcatttc tgatttaatt   900
caattgtggt tactgtagga cagattttct attacttgac tccttttaaa tttactggga   960
tttgttttct cattcaacat atggtctctc ttgggaaatg tttcattaat acttaaataa  1020
aaagtatatt cggtggttgt tgttgttggg tgcaatgttc cgtaattgtc agttaggtca  1080
atttagttaa tagtgttatt caaatcttct aaatacttat ggactttctg tctatatgtt  1140
ctatcaatta ctgaaatctc tgactataac tgtgaatatg tttgtttttc cttaagtttt  1200
gctccatgta ttttgatgct cagttattat atgtgtaaat atttaggatt gttatatcat  1260
cttgatgagg cgactacttt atcattatta aatggccctc tttatccctg gtaatctttg  1320
ctttaaaacc tactttttaa tatgaatata gcctcattag ctttattttg atgagtatta  1380
acattgtata taacttttca tctttttatt ttaatatgtt tgtatattta aagtgcattc  1440
cttataggta acatatagtt gagtctttct ttttatccaa tatgacacct ctgacttgac  1500
tttgaagtgt ttaaactttt tgtatttaat gtgaatatgt atatgatcgg ttttaaattt  1560
accagctggc tagtttttc tgtttattcc atctattatt ctttgttccc tttttcctct   1620
atgctttctt ttgggttaat tatactttta aaaatatttc gtatatcctt tgttgtatta  1680
ttttagtggt tgatatagtg tcattgatta cgtctttaac ttatcacagt tatctttcaa  1740
gtaacattat accactttgt acatgygtat tagaaaacct tgcaacaatg tacttccatt  1800
ctctgtctcc tgaattttat actactgttg tcgtcataca tattattttt atttctacat  1860
atgtaataag acctatatta cattgtttct gtgtttgctt taaaaaacca agttttcaat  1920
gaaatgttta aaatgagaaa atatatttgt ctacataatt ttttttcaag gctcttaatt  1980
ctatccagta tatcagactt ctatctggta tcatttttct tctgcttgaa agatgtcttt  2040
tatcagggat gccctctctt accactccta ttcaacatag tgttggaagt tctggccagg  2100
gcaatcaggc aagagaaaga aataatgggt attcaattaa gaaaagagga agtcagattg  2160
gccctgtttg cagatggcat gattgtatat ttagaaaacc ccatcatctc agcccaaaat  2220
ctccataagc taatcagtaa cttcagcaaa gtctcaggat acaaaatcaa tgtgcaaaaa  2280
tcacaagcat tcctatacac caataacaga aaaacagaga tccaaatcat gagtgaactc  2340
ccatttacaa ttgctacaaa gagattaaaa tacctaggaa tccaacttac aagggatgtg  2400
aaggacatct tcaaggagaa ctacaaacca ctgcgcaacg aaataaaaaa ggacataaac  2460
aaatggaaga acaatccatg ctcatggata ggaagaatca atatcgtgaa aatggccata  2520
ctgcccaagg taaatttata gattcaatgc caccccacca agctaccaat gactttcttc  2580
acagaattgg aaaaaactac tttaaatttc atatggaaca aagaaaaacc tgcattgcca  2640
agtcaatcct aagcaaaaaa aaaaaaaaag ctggaggcat cacgctacct gacttcaaac  2700
tatactacaa ggctacagta accagaacag catggtactg gtacaaaaac agagatatag  2760
accaatggaa cagaacatag gtctcaggta taacaccaca catctacaac catctgatct  2820
ttgacaaacc tgacaaaaac aagaaatggg gaaaggattc ccttttttaat aaatagttct  2880
```

```
gggaaaactg gctagccata tgtagaaaga tgaaactgga tcccttcctt acaccttata   2940

caaaaattaa ttcaagatgg attaaaggct taaatgttag acctaaaacc ataaaaaccc   3000

tagaagaaaa cctaggcaat accattcagg acataggcac gggcaaggac ttcatgacta   3060

aaacaccaaa agcaatggca acaaaagcca aaatagacaa atgggatcta attaaactaa   3120

agcacttctg cacagcaaaa gaaactacca tcagagtgaa caggcaacct accgaatggg   3180

aggaaaatgt ggcaatctac ccacctgaca aagggctaat atccagaatc tacaaagaac   3240

ttaaacaaat ttacaagaaa aaacaacccc atcaaaaagt gggcaaagga aatgaacaaa   3300

cacttctcaa aagaagacat ttatgcagcc aacagacaca tgaaaaaatg ctcatcatca   3360

ccggtcatca gagaaatgca aatcaaaacc acaatgagat accatctcac gccagttaga   3420

atggtgatca ttaaaaagtc aggaaacaac agatgctgga gaggatgtag agaaatagaa   3480

acacttttac actgttggtg ggagtttaaa ctagttcaac cattgtggaa gacagtgtgg   3540

caattcctca aggatctaga actagaaata ccatttgacc cagtgatccc attactgggt   3600

atatacccaa agatcataaa tcatgctact ataaagacac atgcacacgt atgtttattg   3660

caacactgtt cacaatagca aagacttgca tccaacccaa atgtccatca atgatagact   3720

gaattaagaa aatgtggcac atacacacca tggaatacta tgcagc                   3766
```

<210> SEQ ID NO 227
<211> LENGTH: 938
<212> TYPE: DNA
<213> ORGANISM: Homo sapiens

<400> SEQUENCE: 227

```
ctggcactct gctcattttt ctttgcaccc tttattttat atgtgcttta ttatgggtcg     60

tttctatgct gggacttcac agtgttgaat ctgccattaa tcccacccaa tgtatctttc    120

atgtcatatg ttatatagct ctcaactgca gaattttgac ttaggtcttt tgtatcgcat    180

ttggcatgtt tggtcttttc tctagcttct tcaacatgtg aaattgttac tctcttttaa    240

tgtccttggg tactaattct atcgtctgtg tcatttcttg gaaattttca actggctgat    300

tttttcttc attatgggtc atattttcct gcttcttagt atgcctggta attctttatt    360

ggatgccaga cattgtggac tgggtggata tttttgtatt cctaaaaata ctcttgagtt    420

aagttacttg gaaatagttt gaccctttcg agtcttgcct ttaagcttta tttggcagga    480

acagaacagc atttactctc rggctaattt tgctttacta ttgaggcaaa acctttcagt    540

actataccca atgcccataa attataaagt tcaagaacag gcaaaactat gccaatagaa    600

atcagaatag tgattgacgg tagggtgtgg atattggaat tttctggggt attgcttaca    660

caaatgtacc tattaaaatt catcaaactg ctcaaaatct gtgcatatca ctgtatatca    720

attttacctc tataaaaatc atgtttggta tcaaatatat gtgtacataa ttaaatgctg    780

aaaagattta tactaaaatt tcaatagtga agaatatcag gtagttttct aattggcttc    840

tgaatatttt catgttatct aaattttcaa tatatataac cttttaaaaa tacataaaac    900

taatatttaa tgaaacaatt taagggggac tctctacc                            938
```

<210> SEQ ID NO 228
<211> LENGTH: 401
<212> TYPE: DNA
<213> ORGANISM: Homo sapiens

<400> SEQUENCE: 228
acaatataac aactctatca agtaggtatt atcccatttg caaaagagaa aacagtgatt 60
cagacttatg gttatgtgtc caaggaccct caacttgatc ttaggtctgc ctgcttctga 120
agtcggtatt ttgattctaa gagaattaag ccctcaagac ggatttctga aattcagaga 180
gtaaagaatg cttggtagga yagaagaatc ccagaaatac attactgtct acgagcatag 240
gaattggcac attggactct gggagttaac tattaaaatg ggaaagtgaa ttatccaaat 300
gtcagagtca caaatcaagc acagttaatc tgaaacccaa gaaagtctga cctgagacaa 360
ggaaagaggt gggtggctca gaggaaaaaa aaaaaaaaaa a 401

<210> SEQ ID NO 229
<211> LENGTH: 1001
<212> TYPE: DNA
<213> ORGANISM: Homo sapiens

<400> SEQUENCE: 229
gggctgtggg agagcacacc catgaggttg ctcagggagc aatgggccac agcagttttc 60
cctgtgaatt gtgttcaggt aagaccctgc agtcagacca gctcactcct cctttgctat 120
ttctttatat atagtctctt tccattccga aaatgtactc tgagccctgg cctttaacag 180
cttcatttgt tttccttcat ctcccagttt acaactgtga aggaaacatt cattgatcaa 240
gttctttcag cttggaatgg agtctctgac tcccaaaaat ctctcccagg accaactgca 300
agggggtagt ggatctagga ttaaggctgg agcctgaagc actgctgaga atggggagtc 360
tgacacgtaa tgacctccat atatacaagc tggtcagtgc tctctcagag cctgcatgtg 420
gctttgtcca gagaatatga atcccagttt gagcagcaat atggatcaga gttggtagag 480
aggaagattg aggctctcac vctaggatgt cttcagcatc cttcttgtat ccttgtgtgc 540
aaaatgggag cctgggaaag gaactagaag aactgaaccc catccctctg atacatacac 600
attgcttttt tccttcttta tagcatagct tggctgtcca aatgttctgg cagagaccaa 660
gctccaggct cagtgggggg ttctaatttt ccatggctca ttcacttctg agaactttgg 720
ctcagttgca taatgggggg ctacttcctg ccagttgtgg ccctgttgtg tgataccttc 780
tgacacatac gttttttttga aaaaagattg tctgctggga actggactga aaccaacata 840
taaccgtttg tttcatactg gttaggaagc caccaggaag gcctacccaa agtggtttta 900
aatacataca cacacagtcc tctcctctta gagccaagaa caggccatta gtgatgtgtt 960
agaaaatcca ggctgacctt ctcagtcatg agggaagctc c 1001

<210> SEQ ID NO 230
<211> LENGTH: 501
<212> TYPE: DNA
<213> ORGANISM: Homo sapiens

<400> SEQUENCE: 230
cacacagtcc tctcctctta gagccaagaa caggccatta gtgatgtgtt agaaaatcca 60
ggctgacctt ctcagtcatg agggaagctc cctgggccca ccagcaggct tttgccaaga 120
atgggctcca tcttgagccc acagctcttc cctagcttcc cagcagaagc aaggggagag 180
tggagaagtc aaacacttct tgagcattgc ttactatatg tcaagttcta ccctggaccc 240
tcaatagaaa statttcact gatcctcaca atagatctgt ggggtaagtg tcactattgt 300
tattttgagg aaactgaggc tcagaaaagt tacatgtatt cccaaagtca catagtaaac 360

```
tgagtgtgta aacttgagtg gtagagtcag aatttaaaca ctgattttta tctgttgcaa    420

atgttgggct tttcccacca ccagcagaaa tcttgctggc cctcagcaaa tattccttta    480

cagcagtcat ttcaaaactt t                                               501
```

<210> SEQ ID NO 231
<211> LENGTH: 1001
<212> TYPE: DNA
<213> ORGANISM: Homo sapiens

<400> SEQUENCE: 231

```
cttagagcca agaacaggcc attagtgatg tgttagaaaa tccaggctga ccttctcagt     60

catgagggaa gctccctggg cccaccagca ggcttttgcc aagaatgggc tccatcttga    120

gcccacagct cttccctagc ttcccagcag aagcaagggg agagtggaga agtcaaacac    180

ttcttgagca ttgcttacta tatgtcaagt tctaccctgg accctcaata gaaagtattt    240

cactgatcct cacaatagat ctgtggggta agtgtcacta ttgttatttt gaggaaactg    300

aggctcagaa aagttacatg tattcccaaa gtcacatagt aaactgagtg tgtaaacttg    360

agtggtagag tcagaattta aacactgatt tttatctgtt gcaaatgttg ggcttttccc    420

accaccagca gaaatcttgc tggccctcag caaatattcc tttacagcag tcatttcaaa    480

acttttctga ccctatactc ycatcagtaa acatttttaa gaaccacctt caatacagac    540

atatttattt atttataaac tccacgcact agctaatatc tgttagcatt gcctggtaat    600

ataatacccc agagcactaa tcatcattaa tgacaataaa tatatatcca tgtttaatgt    660

agtcttcatg acttggaaaa ctttttggcc agatcttgtg aaatctaatt aaattgcttt    720

tgttttagct tcaatacatg gctggcaaat aatttgttcc aggagtagaa gaaatgatat    780

ggcattcttc ttaccttctt gggcatgagt tgctcctgct gtcaacaatc tccagtttcc    840

ttacagaaga atttttaaga cacttttcca ttttttaaaa gtgattcggt taaaatggga    900

taatatggtt tgtaaatcga ctcactgtgt ttatgcaaga ccatggaata ctatgcaccc    960

atataaaggg atgagttcat gtcctttgca gggacatgga t                        1001
```

<210> SEQ ID NO 232
<211> LENGTH: 1001
<212> TYPE: DNA
<213> ORGANISM: Homo sapiens

<400> SEQUENCE: 232

```
atttttatct gttgcaaatg ttgggctttt cccaccacca gcagaaatct tgctggccct     60

cagcaaatat tcctttacag cagtcatttc aaaacttttc tgaccctata ctcccatcag    120

taaacatttt taagaaccac cttcaataca gacatattta tttatttata aactccacgc    180

actagctaat atctgttagc attgcctggt aatataatac cccagagcac taatcatcat    240

taatgacaat aaatatatat ccatgtttaa tgtagtcttc atgacttgga aaactttttg    300

gccagatctt gtgaaatcta attaaattgc ttttgtttta gcttcaatac atggctggca    360

aataatttgt tccaggagta gaagaaatga tatggcattc ttcttacctt cttgggcatg    420

agttgctcct gctgtcaaca atctccagtt tccttacaga agaattttta agacactttt    480

ccatttttta aaagtgattc rgttaaaatg ggataatatg gtttgtaaat cgactcactg    540

tgtttatgca agaccatgga atactatgca cccatataaa gggatgagtt catgtccttt    600

gcagggacat ggatgaagct ggaaaccatc attctcagca aactaacaca agaacagaaa    660

accaaacacc acatgttctc actcataggt gggagttgaa caatgagaac acatggacac    720
```

aggaggggaa cgttacacac cggggcctac caggggggtgg tgggctaggg gagggctagc 780
attaggagaa acatctaatg tagatgatgg gctgatgggt gcagcaaacc accatggcac 840
ctgtatacct atgtaacaaa cctgcacgtt ctgcacatgt atcacagaac ttgaagtata 900
tatatatata tatatataaa acaccataat atgctaaaag agaaatcagg gcaccagtag 960
gacctccccc acccaccttg cagaatttca ctttcctcac a 1001

<210> SEQ ID NO 233
<211> LENGTH: 1001
<212> TYPE: DNA
<213> ORGANISM: Homo sapiens

<400> SEQUENCE: 233
tgagttgctc ctgctgtcaa caatctccag tttccttaca gaagaatttt taagacactt 60
ttccattttt taaaagtgat tcggttaaaa tgggataata tggtttgtaa atcgactcac 120
tgtgtttatg caagaccatg gaatactatg cacccatata aagggatgag ttcatgtcct 180
ttgcagggac atggatgaag ctggaaacca tcattctcag caaactaaca caagaacaga 240
aaaccaaaca ccacatgttc tcactcatag gtgggagttg aacaatgaga acacatggac 300
acaggagggg aacgttacac accggggcct accagggggt ggtgggctag gggagggcta 360
gcattaggag aaacatctaa tgtagatgat gggctgatgg gtgcagcaaa ccaccatggc 420
acctgtatac ctatgtaaca aacctgcacg ttctgcacat gtatcacaga acttgaagta 480
tatatatata tatatatata waacaccata atatgctaaa agagaaatca gggcaccagt 540
aggacctccc ccacccacct tgcagaattt cactttcctc acagtgcttc gcacggatgc 600
aaatgactcg tgggagtctg agggtaccgg ggtccatata tacattcaat attagtacat 660
agaaaagtag ttcccatttt tagattgaaa gtacctatga atagaagctc taatggtttc 720
ttcccttatc tcgtgttcta ttctgcgcaa ttcctggagc gggcagtccc cgccttggag 780
actcctgcct tacaggaagg ggtcacatat tcctgaattg gaccccactc agatgcagaa 840
ggctaagagt ttggatgaga aaagcgggcc agtgaacagg agagccggtg ggtggggtgg 900
atggaaggag gtgcccactc tggagggcaa gagaaaggca cgaaagcatg gggccacatg 960
agcgcggcgt tctgggccat ccccggtgga ctcctgccta g 1001

<210> SEQ ID NO 234
<211> LENGTH: 1274
<212> TYPE: DNA
<213> ORGANISM: Homo sapiens

<400> SEQUENCE: 234
cagagcacta atcatcatta atgacaataa atatatatcc atgtttaatg tagtcttcat 60
gacttggaaa actttttggc cagatcttgt gaaatctaat taaattgctt ttgttttagc 120
ttcaatacat ggctggcaaa taatttgttc caggagtaga agaaatgata tggcattctt 180
cttaccttct tgggcatgag ttgctcctgc tgtcaacaat ctccagtttc cttacagaag 240
aatttttaag acacttttcc atttttttaaa agtgattcgg ttaaaatggg ataatatggt 300
ttgtaaatcg actcactgtg tttatgcaag accatggaat actatgcacc catataaagg 360
gatgagttca tgtcctttgc agggacatgg atgaagctgg aaaccatcat tctcagcaaa 420
ctaacacaag aacagaaaac caaacaccac atgttctcac tcataggtgg gagttgaaca 480
atgagaacac atggacacag gaggggaacg ttacacaccg gggcctacca gggggtggtg 540

-continued

```
ggctagggga gggctagcat taggagaaac atctaatgta gatgatgggc tgatgggtgc    600

agcaaaccac catggcacct gtatacctat gtaacaaacc tgcacgttct gcacatgtat    660

cacagaactt gaagtatata tatatatata tatataaaac accataatat gctaaaagag    720

aaatcagggc accagtagga cctcccccac ccaccttgca gaatttcact ttcctcacag    780

tgcttcgcac ggatgcaaat gactcgtggg agtctgaggg taccggggtc catatataca    840

ttcaatatta gtacatagaa aagtagttcc catttttaga ttgaaagtac ctatgaatag    900

aagctctaat ggtttcttcc cttatctcgt gttctattct gcgcaattcc tggagcgggc    960

agtccccgcc ttggagactc ctgccttaca ggaaggggtc acatattcct gaattggacc   1020

ccactcagat gcagaaggct aagagtttgg atgagaaaag cgggccagtg aacrggagag   1080

ccggtgggtg gggtggatgg aaggaggtgc ccactctgga gggcaagaga aaggcacgaa   1140

agcatggggc cacatgagcg cggcgttctg ggccatcccc ggtggactcc tgcctagggg   1200

aggggtgcgt cggcggcggc agcccagttt tctggatttc tttatttctg agtccaggtc   1260

tttcagaagc ctct                                                     1274
```

<210> SEQ ID NO 235
<211> LENGTH: 1001
<212> TYPE: DNA
<213> ORGANISM: Homo sapiens

<400> SEQUENCE: 235

```
tgggagctcc agagtgggcg aggacttcgg gcagacccgg cgttgctgtt ggacatcatt     60

cagaagtccc cgctcagcgg gggcagcccg aagagcaaaa caaacagagc gaggagtagt    120

ggaaaatgct gagtcctgga gctggccgga acggccttcg cctttccacg cccaaagcca    180

gccgctctgc ccacctgcag ctgcaatagc aagcagggcc gcagcaggca gggaggcctt    240

ggcaccagag cccgtccagg gctgggaagg cggggaacag acactcctct ctcttcagac    300

aggccctcca gagtcctcac cctgaaggct gaggtctttt tcttgttcca ggagtccagt    360

gaaaaaatag ttctcaaaaa cggagaaaaa gactttcttg aactgcagtt tcagatttac    420

taatagagtc catttacata gcacttacta aatgtcaagc accaacacag atgaattggc    480

aatcaccatg tcagtcctgc raggttggta cttttatccc catttcacag atgaaaaaag    540

ccaggcacag agaagtcaaa taacttaacc caagttcaca atgctcaaca atggcagggc    600

caggatttac cacctggttt aaaatttaaa acgtaggatt taaaacctac tttacagtct    660

taaaggtgac tgccttttct cttcagctta ttagatttcc tctctaggaa tacaagatgt    720

gcaacacaaa gagaggaaac tcaagatgga gagtaaaggg aatgaatgag agacaggaga    780

atcaccaagg actagaataa tacaaaagat ttatttaaaa agcaggtggc catcggccca    840

ggagaaggag tgtgagacca aggtacagaa gtggcaagaa atgctgagct ggggctggaa    900

ggtatgacag tactagtcag acaggcacct gttctgtcca aaacaggatt ccagaagtaa    960

tgtgaagagg tcacttggca aagggggctc acacagctct a                       1001
```

<210> SEQ ID NO 236
<211> LENGTH: 501
<212> TYPE: DNA
<213> ORGANISM: Homo sapiens

<400> SEQUENCE: 236

```
ccattcctct aagccaagag ctcttgtccc cagaggaaag aggagaagga agaaaggaac     60

aaacaaatga acagaggaag gaatgaagag agagagagag aaggagggag gaagggctgg    120
```

```
aaggaagaaa ggaaggggct gttttttttc ttgtgtttgg aagaacaagc tgccaaccct    180

cattaaatgc ataggattgg ctttagagtt actacaccta aattctaatt ctgtctctgt    240

caccggttag yaatgtgatc tcatggaaat cactgaaact cccttaacct gaaaccccat    300

gtctatacaa tgaggacact ggaattcacc tctaaggttc tctctggatc taaaatctac    360

actctgatga tactgagacc aaggacaggg actttgattg ttgccttttc atgccaccca    420

aggtctacat cctagcacag tgcccaccac ccatccacac cgaccagaca cccagggcta    480

gtgattctgt gttctcaaca c                                              501
```

```
<210> SEQ ID NO 237
<211> LENGTH: 401
<212> TYPE: DNA
<213> ORGANISM: Homo sapiens

<400> SEQUENCE: 237

ctggcctttg ttgattccct aggttgctgt gggcagatga tcatcgccat cattactttg     60

gatgtcagga cattgagata caccaggcaa tctgatgcaa ctggctttcc cagggcagaa    120

gcatttgcca ggaaagtgga aacagggaaa gggactggaa cattgagtaa atcaggaaat    180

agcactgacc aagggacaga raggccagag ccactttacc ccctcatttg gggttctaaa    240

ttcttatcaa attttttttc ctcaagttca aaccttgtgg cattttcacc aattgatcaa    300

caactgcctt tatcagactc cttgaatctc tgcctcactg caaaaagtgc caggggaatg    360

cttttctctt ctattattta ggtgaggatt ctcacggcat g                        401
```

```
<210> SEQ ID NO 238
<211> LENGTH: 1001
<212> TYPE: DNA
<213> ORGANISM: Homo sapiens

<400> SEQUENCE: 238

ggcagatgat catcgccatc attactttgg atgtcaggac attgagatac accaggcaat     60

ctgatgcaac tggctttccc agggcagaag catttgccag gaaagtggaa acagggaaag    120

ggactggaac attgagtaaa tcaggaaata gcactgacca agggacagag aggccagagc    180

cactttaccc cctcatttgg ggttctaaat tcttatcaaa ttttttttcc tcaagttcaa    240

accttgtggc attttcacca attgatcaac aactgccttt atcagactcc ttgaatctct    300

gcctcactgc aaaaagtgcc aggggaatgc ttttctcttc tattatttag gtgaggattc    360

tcacggcatg gagggatctc acagagtagt gagatgccag cagcatgccg agccaatatg    420

cccataaatg caagggccag gtccttaatc cagccatgag gatggtcaag gatccctgta    480

tacaagccag agaagggact ytgtacaact agaactgagt cgcaaaccat cttccagagc    540

agcccctggg gaaaagcaga ggccaaacag cagtatggaa gtgaaaaggc tcacgtactg    600

aaagaagact ttgtccttgt cccatatttg atgtgtgaaa cgtacccctt agtaaccagg    660

cctgtggctc ccagagctgg tgagccatca gccagcatca tcaaaagaga cttttcagcg    720

ttctatgcca gcaatacggc atcatggaaa gaacagggct tagaagtcag atggttctct    780

gatgaacctg atgacctctt gtactctctt ccaccgtagg ctctagaata aaatgagctt    840

catgccaagt aaacatggaa tgtggataga tatctacaca ggggtcacaa aattaaattc    900

tacagggaca aggcaggaat gtcaatgtgt gggcctgacc tatgagagtt aaaataaggggg    960

actgatatgc acctaaagga ggcagcttca gttcagtgcc c                       1001
```

<210> SEQ ID NO 239
<211> LENGTH: 1001
<212> TYPE: DNA
<213> ORGANISM: Homo sapiens

<400> SEQUENCE: 239
gatgcaactg gctttcccag ggcagaagca tttgccagga aagtggaaac agggaaaggg 60
actggaacat tgagtaaatc aggaaatagc actgaccaag ggacagagag gccagagcca 120
ctttaccccc tcatttgggg ttctaaattc ttatcaaatt ttttttcctc aagttcaaac 180
cttgtggcat tttcaccaat tgatcaacaa ctgcctttat cagactcctt gaatctctgc 240
ctcactgcaa aaagtgccag gggaatgctt ttctcttcta ttatttaggt gaggattctc 300
acggcatgga gggatctcac agagtagtga gatgccagca gcatgccgag ccaatatgcc 360
cataaatgca agggccaggt ccttaatcca gccatgagga tggtcaagga tccctgtata 420
caagccagag aagggacttt gtacaactag aactgagtcg caaaccatct tccagagcag 480
cccctgggga aaagcagagg ycaaacagca gtatggaagt gaaaaggctc acgtactgaa 540
agaagacttt gtccttgtcc catatttgat gtgtgaaacg taccccttag taaccaggcc 600
tgtggctccc agagctggtg agccatcagc cagcatcatc aaaagagact tttcagcgtt 660
ctatgccagc aatacggcat catggaaaga acagggctta gaagtcagat ggttctctga 720
tgaacctgat gacctcttgt actctcttcc accgtaggct ctagaataaa atgagcttca 780
tgccaagtaa acatggaatg tggatagata tctacacagg ggtcacaaaa ttaaattcta 840
cagggacaag gcaggaatgt caatgtgtgg gcctgaccta tgagagttaa aataggggac 900
tgatatgcac ctaaaggagg cagcttcagt tcagtgccca tggtggttgc tatgaaggaa 960
tatgctagaa tccaaagaca tcccattaac ctactacggt a 1001

<210> SEQ ID NO 240
<211> LENGTH: 1001
<212> TYPE: DNA
<213> ORGANISM: Homo sapiens

<400> SEQUENCE: 240
ggtctgacaa ggccagggac attccacaaa ggatgacaca atatattcaa agattgggat 60
gttcgatgac ttccctatat tcctgttata tttctcacct tattaggaaa tctttatctc 120
caatggtcct gagctagtga gatcagaaag actaaactgc atccctctgt gcttgcctct 180
ggttggttga tttgtcctgc tttaatacat gatccagaca agaaagaatc aagccaaagc 240
cacagcatta tgaatgaaat tctttgtttt taatttcaca cagtttaaaa tacaatatga 300
aatcaggcta cagtatataa aaaactctcc agcaaaatga tgtgccagca tcagctacta 360
aaataaacaa acaaaaaact ccgccataag aatttttttg catttttttt taaaaaaaca 420
tcgacactta catcgctaca tctctaagct acctcagttc tgatttttaa aaagcacctg 480
cttttccttt ttttcatctt rcttctaaat tttcagcttt taaaaaatat aaattatatg 540
aaaatacaag ttggaaaata gtcaaacaca atataacatc tttttcatcc ctatacttct 600
cagcttaaaa aaaaagtatt cttaaaaaaa aaagttcaat aactgaggca gtattcctga 660
taattttatt ttaatatata tattttatat atgtatatgt atacatatat ttatggttcc 720
ttgaaacttc tttggaatgt aggtaagagt tcaacaaatt tatatagacc ccaacagagt 780
aagcggcatg cacagcatga ctagaagaga gatggtgtat ttctcaccat gaaggttagg 840
caggttaatg ctgtaaaacc cagagtgttc atctccaaag tgaggaaaag cacatctgat 900
ctttgaatgc tacctccaat ccccacagcc acaaaaatca gggctctatg taggggaagt 960
ccctctccag aatggagaag ggaacaaaag tgactctgaa c 1001

<210> SEQ ID NO 241
<211> LENGTH: 401
<212> TYPE: DNA
<213> ORGANISM: Homo sapiens

<400> SEQUENCE: 241
aattttattt taatatatat attttatata tgtatatgta tacatatatt tatggttcct 60
tgaaacttct ttggaatgta ggtaagagtt caacaaattt atatagaccc caacagagta 120
agcggcatgc acagcatgac tagaagagag atggtgtatt tctcaccatg aaggttaggc 180
aggttaatgc tgtaaaaccc rgagtgttca tctccaaagt gaggaaaagc acatctgatc 240
tttgaatgct acctccaatc cccacagcca caaaaatcag ggctctatgt aggggaagtc 300
cctctccaga atggagaagg gaacaaaagt gactctgaac cctaaagcca aaaccaacaa 360
aggttaaggc atctctggga aaataagggt ttcacccagc t 401

<210> SEQ ID NO 242
<211> LENGTH: 601
<212> TYPE: DNA
<213> ORGANISM: Homo sapiens

<400> SEQUENCE: 242
acattagtct ctttctctgt taagccagag ccttcaagct tctgagaagg cccttctccc 60
tctcctgaaa atttgctcaa gaatttctgg tcccacccac cccacaagtc ctggctttcc 120
tttcccaact gcgcacaatt gattacagct gcaactgact tagctcccac ccctgaaggt 180
aaaaaatgag ttctggaaaa taaaaaatag aataacaatt caaaattcag agtccaacca 240
acacggctgt ccttggaagg tctcagcagg gtttccccag ccccttcagt gccatcactc 300
rtcggcatct ggcttgacgt ccagcatggc gtgcagctcc tcaggggtgt accccagcag 360
gctctgcagg tcacacacaa agcggtacac gtagcgtttc cccgctgtct tgtggatgat 420
gtttttgtcg taatagtagc gtaggccacg gctcagtttc tcataattca tcttaggttt 480
gtttttcctc tttccccatc tcctggccac ctgaaattta aaaagaaaaa taaaggagga 540
gtaggcaaaa atctacaaga caggccaaat atatatgttt ctatgcctat gctataccca 600
t 601

<210> SEQ ID NO 243
<211> LENGTH: 1001
<212> TYPE: DNA
<213> ORGANISM: Homo sapiens

<400> SEQUENCE: 243
atacccattc atggtgaccc atgatgctca agtaagatga tttgagattc atgtagatat 60
agaaaatatt tttcgggcct atctcctgaa ttccattttt catgggttgg gcaaggatgg 120
gagtcacaat gattctttaa gttgatgaaa acacagtgac cctgaactag gattaaatat 180
gtgactttaa aaaacaaaca aaaagccaca ctatacattc tcctctttcc gcatattatt 240
agtaaaatct ccttgctttg caagcatgaa atctaacagg gaagtgtgaa gcggaggagc 300
tgagctgcaa tcatacctgc ctttcatcaa caggaagtgt ttttttccca taccagggca 360
caaatatttt ctcatgtctg ccagaacaaa gatgttgtct ctcctgttca ttgtttttta 420

```
tcctcagaat tgggcatggc acggaaccac tactccataa acatgtgtgt aatgaaataa    480

gaaactaatg agccaatctc ycaaggcctc ttgaactgtc tggccccttt cacactcaca    540

gagccaccgg gctaggaaga ggctaagtca caggaggcag ctctatgggt gataactgac    600

ctactgccag gcacgttaat gccttctatc agctaatcct gtaagacaaa tggggtaaca    660

tagatctttt ctctattttc caaataatga acctggagct cagacaggct acctagcttg    720

ctccgggtgg caagtggcag agctgggaat cccaatcctg gaacacgtca ttcaggccca    780

cgccacccct tccaggagtt ttctctcatc cttcctcaac acagtactcg caagcccctc    840

cttccttacc tcatctgggt cagaaagttt gaattcccag ccatctcctg tccagctgat    900

aaaagactga caggatttat cagtgagtaa ttccagaaga aactgccata gctggattgg    960

tccactgcct agaaacacaa gccattgtga atcattacac c                       1001
```

<210> SEQ ID NO 244
<211> LENGTH: 1001
<212> TYPE: DNA
<213> ORGANISM: Homo sapiens

<400> SEQUENCE: 244

```
cacaaatcag gggccacagg ctccctacta cagagcagtg cttatgagcc ataacttgtg     60

tttggaactg gcaaagacat tcattccttc gttaatatgt ttcttacttc tgaaggcaaa    120

aataatgact tagtttttgc aggtgtaaaa gattatgctg ccttagaata tcccagagga    180

taggcacagt gttctctttc tagaatttgt ttagcaataa aaatgaaccg atccttaagt    240

taatcaaaat aaagcacttg acacattttc ttccatgctt ttgttttata gggaggcctt    300

tgtcttttct atctgttcga gctcataaca cttcctccga catgtgcact gtctgttgcc    360

ttcattttct cctggctgga tgggctgaga gaagagggat gtgggagtgc cgtgtgtggg    420

gattagctgc gtagagtgct gaatatctgg tgtaatgatt cacaatggct tgtgtttcta    480

ggcagtggac caatccagct rtggcagttt cttctggaat tactcactga taaatcctgt    540

cagtctttta tcagctggac aggagatggc tgggaattca aactttctga cccagatgag    600

gtaaggaagg aggggcttgc gagtactgtg ttgaggaagg atgagagaaa actcctggaa    660

ggggtggcgt gggcctgaat gacgtgttcc aggattggga ttcccagctc tgccacttgc    720

cacccggagc aagctaggta gcctgtctga gctccaggtt cattatttgg aaaatagaga    780

aaagatctat gttaccccat ttgtcttaca ggattagctg atagaaggca ttaacgtgcc    840

tggcagtagg tcagttatca cccatagagc tgcctcctgt gacttagcct cttcctagcc    900

cggtggctct gtgagtgtga aaggggccag acagttcaag aggccttggg agattggctc    960

attagtttct tatttcatta cacacatgtt tatggagtag t                       1001
```

<210> SEQ ID NO 245
<211> LENGTH: 401
<212> TYPE: DNA
<213> ORGANISM: Homo sapiens

<400> SEQUENCE: 245

```
tcaacactct gacagtcaat ttattctatg ctaaaaggtt tatatcacac cgatttcctt     60

tgaggatact tttctcatct gaaatgacaa tgccaccagt gattcttaat ttataggtgt    120

cggtggagag acaaataggg gttcaaaagt ccatgcttct tgttacactg ccccttataa    180

cataaacaaa ctgggcagag ygggactggg aaagacccag tccatgtctc tggatacagc    240

ccaggaagca ccagctccta caggaaagct ttgctcacta aggctctaat ttttcaccgg    300
```

agttgcaaat ttgtctgatc caaagtaaac tgagatttaa caggaaacaa actttaagtt 360
ccctctcaat ctaaaaaaga aattgccttc ataatccata a 401

<210> SEQ ID NO 246
<211> LENGTH: 601
<212> TYPE: DNA
<213> ORGANISM: Homo sapiens

<400> SEQUENCE: 246
ggcaacctcc aatgaagtaa agaaacagct actgacacga gctatcatcc cacagccaaa 60
ggaagtcctc ctccagtaac aacttcctaa tggtggtttc caaggctcct ctcagcactt 120
gccacgctaa atatgaaaac atgaaatagc tctacctcct ctttctgaga atggaccatt 180
agctctttaa aactatcttg caagaaatac cttacatgta ttccacaata aaatggctca 240
gtgaatgcct ataaaataaa gtaacattcg aacaacagcc cagagggccg cactggtaaa 300
dccgtagctt cctctgtttc tactttcatt caataaaaac cgtttcgtat tcaactcagg 360
gacatttgca ggtttcttgg gagttgccta aagtcatgag ctacttgttt tctgcctggg 420
ctcacaaaac taaccgtgac attctcagag gaatccactg agaagccatc ctaacaggca 480
caaagaagta aaacagcaaa tcgctctcaa gaaatgcagc tgccagagcc ctggtcacag 540
aataggtttc ttggagaaac tcacgataac tatagagact gaagagagac atgaagaaaa 600
c 601

<210> SEQ ID NO 247
<211> LENGTH: 1001
<212> TYPE: DNA
<213> ORGANISM: Homo sapiens

<400> SEQUENCE: 247
accttacatg tattccacaa taaaatggct cagtgaatgc ctataaaata aagtaacatt 60
cgaacaacag cccagagggc cgcactggta aagccgtagc ttcctctgtt tctactttca 120
ttcaataaaa accgtttcgt attcaactca gggacatttg caggtttctt gggagttgcc 180
taaagtcatg agctacttgt tttctgcctg ggctcacaaa actaaccgtg acattctcag 240
aggaatccac tgagaagcca tcctaacagg cacaaagaag taaaacagca aatcgctctc 300
aagaaatgca gctgccagag ccctggtcac agaataggtt tcttggagaa actcacgata 360
actatagaga ctgaagagag acatgaagaa aaccattcta tcccaaagct atgtaaaaga 420
agcctcggag gagagggggt tgccttagac cctgacagag aaaaactaat gagtgctatg 480
cttgacggtg cacctactac rccgcagaca ctgtgagtga cgctctacac tcgtttcctt 540
cattcctccc aataattctg tggggtggat gcaactgttg tgctatttgt ttctaccact 600
tcacagcaga gaaaactgac acactgcaag gccatttaga tcagcagtgg agtagccggg 660
actggaaccc atgcagccca tccccaggtt cttcatctca atgctacgtt gcccctggac 720
aggaccaggc caaaggcctg gcatctaaac tgcctgactg agtgcaatgt tccaagggat 780
aaggggacct gacttgaaaa actctctccc ctacttctca cagcagttgc aggacacggg 840
atagccagtg gttctcccag tcatccgacc accagtggcc gtgccaggcc ccgccatggc 900
atccacctcc acaggagata tttccagcat cctcttgtgg tagccattat gttacattac 960
ttcattgttt ctccttccca atgttcacct ttgaacctct c 1001

<210> SEQ ID NO 248

<211> LENGTH: 1001
<212> TYPE: DNA
<213> ORGANISM: Homo sapiens

<400> SEQUENCE: 248
cagtcatccg accaccagtg gccgtgccag gccccgccat ggcatccacc tccacaggag 60
atatttccag catcctcttg tggtagccat tatgttacat tacttcattg tttctccttc 120
ccaatgttca cctttgaacc tctctcccac tatctgaaaa tctctttggg gcacggggtc 180
tcatgacacc aagccgagga aagggatggg aagatcgaga tccttccccc ggatgagtct 240
ttggcaggga gctgtcagca catctgctgg tgctggagaa cagggcccag gagcacactg 300
cagtctcctg cccttgggac ttggcagcca caatgcagag aagggacctt caattcccgt 360
ggtttgcacc agctcccaga ggacgaaccc tctgacggaa tggttagttt tccttttcta 420
ccagtgcatt ttccaaactg aaatgtcaag cagtcatagg ctgtagatgc cctgccctgc 480
cctttctctg tgatgtcagc rtacgggacc cggtgagtct gggacagggt gagtactcgt 540
cagaggactt ttgtcctcat tgtgactttt cctttgttca aaaggaatga aagaaaaaaa 600
aattaaattc aggccctaga agcccaagtc ctaggtgcag agctctctaa ctcttttttt 660
tttctgttta cacccaagga aagagggagg atagatagga aaagcagata cctaaagaaa 720
taatgggaat atgaatggga agaaatctct cccgttggct tcataatagg acagtcaaca 780
taacagagat gtcagttcct ggctccctcc cccgattcct gtagagaaac cccacaggcg 840
cactccagcc taactggtgc acacagggct cacccttcag aaagcccaca tttttgtacc 900
aagtgagagg agttcatgat ggccgctgaa gcgtcccctc tagcaccttt ttgctgactc 960
ctaaactgcc tttttgttgt ggggagcaag agaactagga a 1001

<210> SEQ ID NO 249
<211> LENGTH: 1001
<212> TYPE: DNA
<213> ORGANISM: Homo sapiens

<400> SEQUENCE: 249
tctctcccac tatctgaaaa tctctttggg gcacggggtc tcatgacacc aagccgagga 60
aagggatggg aagatcgaga tccttccccc ggatgagtct ttggcaggga gctgtcagca 120
catctgctgg tgctggagaa cagggcccag gagcacactg cagtctcctg cccttgggac 180
ttggcagcca caatgcagag aagggacctt caattcccgt ggtttgcacc agctcccaga 240
ggacgaaccc tctgacggaa tggttagttt tccttttcta ccagtgcatt ttccaaactg 300
aaatgtcaag cagtcatagg ctgtagatgc cctgccctgc cctttctctg tgatgtcagc 360
atacgggacc cggtgagtct gggacagggt gagtactcgt cagaggactt ttgtcctcat 420
tgtgactttt cctttgttca aaaggaatga aagaaaaaaa aattaaattc aggccctaga 480
agcccaagtc ctaggtgcag rgctctctaa ctcttttttt tttctgttta cacccaagga 540
aagagggagg atagatagga aaagcagata cctaaagaaa taatgggaat atgaatggga 600
agaaatctct cccgttggct tcataatagg acagtcaaca taacagagat gtcagttcct 660
ggctccctcc cccgattcct gtagagaaac cccacaggcg cactccagcc taactggtgc 720
acacagggct cacccttcag aaagcccaca tttttgtacc aagtgagagg agttcatgat 780
ggccgctgaa gcgtcccctc tagcaccttt ttgctgactc ctaaactgcc tttttgttgt 840

```
gggggagcaag agaactagga aagacatgga aatgttcttc cagccagaaa cactgggcca    900

gggtgggcgc agttcctggc tgggcccgtg gatggtctaa tacaggagcc tgtctccaca    960

gcaatgcatc accctcactt caggtctggg aggggacttc a                        1001


<210> SEQ ID NO 250
<211> LENGTH: 1001
<212> TYPE: DNA
<213> ORGANISM: Homo sapiens

<400> SEQUENCE: 250

tcagtgacct ttgtccccta gagcagaaaa cggtactaat aatagcgcca gtcatgggaa     60

ggggagctca catgttcaat gtgactcata atggtgtccc tgtctgggat ctccaaggca    120

gtcaacagca cccttcacga tgctgcccgg gagtgtcaca catcaggaat ccagtggcat    180

cactgggaaa gtatgcttct caagtcgaag ctctgagcca caacaacaga ggggtccctg    240

ttagaaggag gtctctttcc agagccatgc gggcgggaga gcaccacaca cacactccac    300

acacccatct cccatggcac ggagcctcca cacccctgc tgtctgctcc ctctccaccc     360

tccctctcag gcggctgcag gggaatttcc ttctactgct ttgttcttct cagcctctgg    420

agaagaggac agttcttact acacactgac aggtctgatt tgaagaacgt gctacaagct    480

ctgaagaaga aataccaggt rggaacttgg agagctccca agcctacaaa gcaaatcaca    540

ccaaggatgt tcacccccta aggggacccc caaggctcct caaatctaag gcaacaatct    600

cactttttaa aaaaagtaaa gcttcaagta aattactgct catttgggtc atatttcctt    660

gtctgggagc tgcaaggccc actatctgtc tcaatgagga gctggttatt aaaaatcccc    720

tgctattctg gtcccttgcc ctgaggctga gaactgagca gcataaatac atatatagca    780

atgggctagg acaaggtgtt agtaacatgc tcttgatgga aatcccttcc atttcccgat    840

ttgtcagtat cattcttctc attttccaga tctgggagtt gcctgcctgt gacaaggaca    900

tcctcacagc aagtgaacag ggtcaggttg aacttcactt tttccttcta ctccttcctc    960

atttccattt caaccacaag ttctcactct tgtcacctgt g                        1001


<210> SEQ ID NO 251
<211> LENGTH: 1001
<212> TYPE: DNA
<213> ORGANISM: Homo sapiens

<400> SEQUENCE: 251

tcacgatgct gcccgggagt gtcacacatc aggaatccag tggcatcact gggaaagtat     60

gcttctcaag tcgaagctct gagccacaac aacagagggg tccctgttag aaggaggtct    120

ctttccagag ccatgcgggc gggagagcac cacacacaca ctccacacac ccatctccca    180

tggcacggag cctccacacc ccctgctgtc tgctccctct ccaccctccc tctcaggcgg    240

ctgcagggga atttccttct actgctttgt tcttctcagc ctctggagaa gaggacagtt    300

cttactacac actgacaggt ctgatttgaa gaacgtgcta caagctctga agaagaaata    360

ccaggtagga acttggagag ctcccaagcc tacaaagcaa atcacaccaa ggatgttcac    420

cccctaaggg gacccccaag gctcctcaaa tctaaggcaa caatctcact tttaaaaaa     480

agtaaagctt caagtaaatt mctgctcatt tgggtcatat ttccttgtct gggagctgca    540

aggcccacta tctgtctcaa tgaggagctg gttattaaaa atcccctgct attctggtcc    600

cttgccctga ggctgagaac tgagcagcat aaatacatat atagcaatgg gctaggacaa    660
```

ggtgttagta acatgctctt gatggaaatc ccttccattt cccgatttgt cagtatcatt 720
cttctcattt tccagatctg ggagttgcct gcctgtgaca aggacatcct cacagcaagt 780
gaacagggtc aggttgaact tcactttttc cttctactcc ttcctcattt ccatttcaac 840
cacaagttct cactcttgtc acctgtgctc tgctgagagg agaacacagg agttttcttc 900
caaacagaag gaggtcaacg ctgggcaggc accttcccag gcagtctcct catatttcca 960
tagtacatgg cttacaccaa gaccacccca ttggtttggt c 1001

<210> SEQ ID NO 252
<211> LENGTH: 501
<212> TYPE: DNA
<213> ORGANISM: Homo sapiens

<400> SEQUENCE: 252
ggattagaaa gtccgctcaa atggcttctc tctattaaac aatatttggg gccaaacaat 60
atgggtgacc ctcaggctgc atttcatcaa cgtgttccca aaaatgaaaa tgactacctg 120
tcctttggga gttaatttgc tactttaaga agctaatccc tttagctcta ttctaaaagt 180
caaatcaaat acctcggtgt gggcaggaca ccacatttat tttaacctat gaaactctca 240
tggttggtca mccttgcaat agggctgact ctgccctgat agcacacatc tggcaggtgg 300
ccctaaaaca gaggaacagg cctgctggcc cctcccttcc agccaggtgt ctctacccac 360
agccaaacga tgatggcaaa aacagaacat tcgaatccag aaatgaccca tctgttcaca 420
agtgtatcaa tctgcctttc atgctaccac aggaggacgc acctctgagg gtggggtggg 480
tgactcccca gtccaagcat c 501

<210> SEQ ID NO 253
<211> LENGTH: 401
<212> TYPE: DNA
<213> ORGANISM: Homo sapiens

<400> SEQUENCE: 253
atccagaaat gacccatctg ttcacaagtg tatcaatctg cctttcatgc taccacagga 60
ggacgcacct ctgagggtgg ggtgggtgac tccccagtcc aagcatcacc cctttctgtc 120
aaccctcttc taaatcacca ttcacaaagg cccctaaatc tcctgatttc cattaagttt 180
aaggacaaaa cagaaaacat yctgacagtt tcttggcctc tggaccaagc tcaacctgaa 240
gctgcacaaa gtcttgttgc ctgaggatga ataactcaag aaactgtatt gctggactga 300
ctggcaatca agaccctgag aaaattattt taagaagatt aagggccagg agtgcttgat 360
attttggctg agttctatgt ctctcatttc ttctgagttg t 401

<210> SEQ ID NO 254
<211> LENGTH: 1001
<212> TYPE: DNA
<213> ORGANISM: Homo sapiens

<400> SEQUENCE: 254
gtgttcctgt atcagtggct aataactcaa gggcagtgat tgggaatata acttccaata 60
attcaactca aacaacaaag aacattctga caggtgtttg gaaagcatac ttgctgaaca 120
cgatgatgaa caaacaacaa ctttataaac ttgtatttgt tgctgagata gccagtatct 180
aaccatgaaa aagagtgaga aaacagctct caaatcagtt aaaaccagtc tttgactgcc 240
gagttcatgt ctcttgcatg ttagatcaaa aacgaaagga ggaggagtgt caaaaaattt 300
aaaaataaaa gccattttac atgtcaggca gtggagtact gagtgatgac ggcatcctat 360
aaaattaaaa tatatgatgc ctgtgggaaa gccccgggta gggagttgag ggtacgaggc 420
tttgatatca gttcttacct gaatcaccat atgcaatctt atgcaactca tttaatctct 480
ctgggcttta ctttttcctt ycctaaaatg gaaatagtaa tctctgcttc tctttagttt 540
ataaaaatgt aaattaagtc cttattacaa aaatctgcat atatacatat atatagacag 600
agagagagaa agacacttaa agaggtgaac aatttaggag caactgaata tacaataatg 660
gaattacaaa gaagaatgaa acaacagaaa atatattttt aaaaacaatt ttcagtaaaa 720
aacaagaaaa aagatgcatt taaaaaaaat tgtaaaagca ctagaaaaaa tctaattaga 780
cttccaagga ttaaattggc cttcgtatgg caactttgaa aaagtagaaa gttggaggtt 840
aaggaaaaaa aagttacagt atacgaatgt aaaaattttt aatattttca atgagaataa 900
gcatttagga ctttttaag ttagggaaga ctctgaaatc cttgttccca tgttaaaagt 960
gcacacgcac caaaagagac agcagatgca aactgctttg c 1001

<210> SEQ ID NO 255
<211> LENGTH: 601
<212> TYPE: DNA
<213> ORGANISM: Homo sapiens

<400> SEQUENCE: 255
ttatttggcc agtctgactt gggtctgaga acaagacagt tacacatttt tagggtatga 60
gggaaagacc tttgtttttg ctctggctct gcacacctgc aagtgctcaa gtacacatgt 120
gtgggggcgg cagcaggaga aaggggactg ttcctctctt aaaggggcag tctctattca 180
aatgcaacca cctctttctt ctaaacccat cagtaactct gtctaacaca ttcaagctaa 240
cactcagaca caaacttgga cagtgagcca gtgaagctca agtcaggaag tgggtttctt 300
yatagctctt tcctcctgat gtcttctagg taaccggttc ttttaagaag tcaccagaga 360
tgggttaggt ttggatttgg gggaagggga taagaatttt gttataaacc aaagaaaagg 420
tttttccagc cactataaat gtacaaagaa aaatcttcct aagtgtgtag gtaatgagaa 480
gaaagaaaga tatgttcact gatcagggtt agaaaacagg actttagaag tctgaagatt 540
atagtctttt ctcagtagga ttctcaactt gctctctgga atttatttta tcctaggggt 600
t 601

<210> SEQ ID NO 256
<211> LENGTH: 501
<212> TYPE: DNA
<213> ORGANISM: Homo sapiens

<400> SEQUENCE: 256
atggtctgaa ggttccgctg ccttctcttc gctgcctttt tttccttcat agatgctcct 60
tccgtaaaca tcttgcacat ctaatcatgt cttggcacct gctttccggc acactcaaac 120
taacacagta ttttgaatat tttctgacat gtgaaaaccc tgaaagtcat cttatttgtt 180
gtttgctgtg taacattggg ctagacctcc tcctctaaaa agaaaaaaaa aagtctcgat 240
tccctcattt rtacaatggg cataacagaa acttcctcat gtgatatttg gtgaaggatt 300
taaaaagtca gtgtatatga aggagtctaa gcacacagta ggaacttaat acatctggga 360
ttgagctaaa taattgaaaa gacctaatta ttattaaatg cctgctacgc cccatgacac 420
tgccagcaat tactgcaatt ctataagtaa aatgcgttgt tccctggcct caaggaactt 480
agaattatac tggaaaaata a 501

<210> SEQ ID NO 257
<211> LENGTH: 714
<212> TYPE: DNA
<213> ORGANISM: Homo sapiens

<400> SEQUENCE: 257
tgaatatttt ctgacatgtg aaaaccctga aagtcatctt atttgttgtt tgctgtgtaa 60
cattgggcta gacctcctcc tctaaaaaga aaaaaaaaag tctcgattcc ctcatttata 120
caatgggcat aacagaaact tcctcatgtg atatttggtg aaggatttaa aaagtcagtg 180
tatatgaagg agtctaagca cacagtagga acttaataca tctgggattg agctaaataa 240
ttgaaaagac ctaattatta ttaaatgcct gctacgcccc atgacactgc cagcaattac 300
tgcaattcta taagtaaaat gcdttgttcc ctggcctcaa ggaacttaga attatactgg 360
aaaaataaaa ggtttggaga atactatgga atgtaggtga cagctagcac ttagagccta 420
gcttcctgta tacccagcac tgctccaagt gctctccata aactaattca ttagttctca 480
caacaagcct atggtataga aactattatt actgccattt gcagatgaga aaacagatac 540
agagatgtta gcttgccaaa ggttacacag ctgctcactg gcagggcctg actccatgct 600
ctcaattcta cagggatggc ccctgaatgt tgcccttggt aaaactgcat gggatgacca 660
ctctttcttg tgtttaactt ggacttctct acctgcaggc atccccaagt gact 714

<210> SEQ ID NO 258
<211> LENGTH: 501
<212> TYPE: DNA
<213> ORGANISM: Homo sapiens

<400> SEQUENCE: 258
ctccactgag atccccaggt ccacgccagg cacccctta ggatccactg ctaaacccag 60
caccgtgaat ggaatccctg ccagcatctc agctgctggc tgacaggaag gctctattta 120
agctgagggg gctgccagct tcctgcaact agttaatcac aacagcctct gagcaagaaa 180
gggaagacac tctgtttctg cccttctcat tcccaagctc ttttcctctt atccaatcag 240
gtactgccca rggatggtct acattgagac tgtgatggct tcagcaagcc tggaagccag 300
ccccagcttt gcctggcctg cagacctcag tgaaatgccc taacttctct gggcctgact 360
ttagccaatt cacactgtct tacacaacag catttacatg gagagacttt agattccaga 420
gcttcgctcc tgttatctcc ccaaattaaa aggctctacg ctgttcctaa tcacatgccc 480
acagcacaaa ttcacactgc a 501

<210> SEQ ID NO 259
<211> LENGTH: 601
<212> TYPE: DNA
<213> ORGANISM: Homo sapiens

<400> SEQUENCE: 259
tctgtggcta tgtctgacaa tctggaatga agttcaataa aggtgattta taggtcaata 60
attctggacg gaagccaagg ccagctctct tccctcccac atacccctaa cccacatgca 120
tatagtgttc attagtgaca agagggagat aaggtcctaa tcagtctagg caggcaactg 180
caataaccaa ggagtactct cattatctaa tatgaagaaa agattttcta ttcaggtgag 240
acatttggtg cttaagattc aattcagaag ctacctctgt gcagaatgca attacataca 300
yggccttgaa taagtcattt ttttgtgcct cagtttcatc atctatgaaa tgggactaga 360
ggggttgaga ggaagagaga ctactatgtg acaacccatt atattattct atacctactg 420

```
aaatggagaa gcaagaggaa gaagagatgc ctatgttttt caaggacttg gaaagcgttt    480

tgcttaggtc tataaaatgt atatagaaag cattgggcta cttctctagg actgtgttgt    540

aattagaagg ggttcataat gtatcttcga acaaaagaaa atggagcttt ctgatggtat    600

c                                                                    601


<210> SEQ ID NO 260
<211> LENGTH: 1001
<212> TYPE: DNA
<213> ORGANISM: Homo sapiens

<400> SEQUENCE: 260

tatgtttttc aaggacttgg aaagcgtttt gcttaggtct ataaaatgta tatagaaagc     60

attgggctac ttctctagga ctgtgttgta attagaaggg gttcataatg tatcttcgaa    120

caaaagaaaa tggagctttc tgatggtatc agtttgataa ccgtaaacag ttcacagtaa    180

ggtaagaagg tacattttgg cggaagccaa cattgcattt gatgtattct taactcagct    240

aacaggcagg ctttcaagcc acgttatctg cccccgcatc ttgacctcat ttaacaagtt    300

gctatgggag cccagtgaag gttgatgcaa ttttcttatc tttggaggaa gaatgtaact    360

gtgcaggaga atgtgaaaat tcagtttcta actggcttcc gcacttacag tgcagtaaga    420

aagacatcct atcaagaagt aaaatgtatt cctttggacg tgatagggac aaagacccag    480

actcctggtg aaatggcagg dagatggatt ctcttcccag cttggagaat ctaagcatgc    540

accctttagt tcaggccaag taatagtgac atagagctat gtgtacccct actgtgtggc    600

caaacatact ctggagcaat caaattttaa gggaacagac agaaaagttg agcagaacct    660

gagaaggtga gtgtgacttt tacaagcaat aaaatgtatt gccaacaagt ctatacaatg    720

atttctgctt tccaaagtac ttttgcaaat ttcagctcat cttaacatgt ctgcataaag    780

ctagacagcc atttataggc actctagtga ctgcctcagg tggtgggtga ggctgtatgg    840

gcacatttca tccgcttccc tattccctag gacgcatctt aaatgaggtt ggcgggggca    900

ccatgagggt gtgagatcac cctcagaggg tgagtctgca gtacaggcag gaggtgttca    960

ccaggtatca attacaggga aaaaataaat actaaaatgt g                       1001


<210> SEQ ID NO 261
<211> LENGTH: 1001
<212> TYPE: DNA
<213> ORGANISM: Homo sapiens

<400> SEQUENCE: 261

ggagaaagaa ttaaatggta agaggcttca aaaatgtttt ttcattaaaa tgattacttc     60

agactttgag acttttaaga gataatcacc accccttctc ttctactcac taaatgtttt    120

actcccttat cccatttctg aagaaagaga gagagaaaag aaggaaagga gggaggaagg    180

gaggaaggag ggagggagag agggagggaa ggagggaagg aaagaaggaa ggaaggaagg    240

aggaaggaag gaggaaggaa ggaggaagga agggagggag ggaggaaggg agggagggag    300

gaagggaggg aggggaagga aagaaggaaa ggaggtaggg agggagagag ggagggagga    360

aggaaggaag gaaggaagga aggaagggca gaagagaggg tgggcaggca actatcaatc    420

tatccaaaca taactcagac ctagagcata gttttctctg caccacaaaa acagaagcaa    480

gcactgccaa ttagagataa ygtctacctc ccaaggccac aaagtcattt tagagctacc    540

tctgcctttc ctttctcttc ccaattaagc agcacatctc ccttccttta tcactatatt    600
```

```
caactgcagt ctagttcttt aacccctaac aggtataact gcatgagctg gcactcttgt    660

acttcctgag agtgacttaa tacacttttc ctcatcccag acgtttttaa tggaaatgga    720

tatacttcct aataatctcc tttcaaagat gggaaaggac tcccttgaaa agtactaagt    780

tcctacatgc tagccatgtt caagcaaaga ccaccagggt attgtagaaa gaataaagta    840

aggaccttta agttccattc ctggccttga ccttgttgct actccaacat gtagacataa    900

ttcctgagca ctactcatgc aatgaactgc actaggagct acatggaatg caatataaga    960

gagatactcc tgatctttga aggaggagta agttttcaag c                       1001
```

<210> SEQ ID NO 262
<211> LENGTH: 501
<212> TYPE: DNA
<213> ORGANISM: Homo sapiens

<400> SEQUENCE: 262

```
gaaaaacacc caaaatgtaa gtttcctacc attcttggaa atgatccctt tgaagagaat     60

gatactattt gcttccaaaa atcaatggct attcacaagc agagtggctg gagagagact    120

aaagaattct tagagagact tctcccccgt gccctgcaaa agggagtctc tcgtcgtctc    180

tggtcagagg tgcagagtgc cttccaggac cccacccaca gaaacgtgca gatggagttg    240

gcctaagcag ygggagggcg cctacctgtg tagccagcta gggcagcagc aggaatgaca    300

ggcttgtcct tattgaggtc agcacggtcc cgcacatagt ccttgaaggt gcccttgggc    360

ttgtggttgg gcagggcagc cggatagtcc tctgagtcga agctgtcata ggagggaaca    420

cgctgcaggc tgttgaaaga tgactggctg ctccaggact gggtgaggcg atcacaacta    480

tcgtagctct ctatgctttc a                                              501
```

<210> SEQ ID NO 263
<211> LENGTH: 1001
<212> TYPE: DNA
<213> ORGANISM: Homo sapiens

<400> SEQUENCE: 263

```
caggctgttg aaagatgact ggctgctcca ggactgggtg aggcgatcac aactatcgta     60

gctctctatg ctttcaaaag agtcctggcc cccgagttta cctggaggta aaggaggagg    120

taggaagagg acagggggag gagggagtgg gaaaaaaaaa aaactgtaaa aaccctctta    180

tggaggacag attgctaatc agatctgcag gaaggacgga agaagggaga ggcgagtggg    240

aacagaagct tcaggggtca tgggtttact ctgaggaaag ggctgcact aggccaccat    300

ccgagggtcc acggccactc tgctgcctgg tttgagaact ccaagtacag agattcagag    360

tcaaacgttg ctcacatctg tcggagtagc gtttgggtcc tcaagagttc taaagccaga    420

aatctagaag ctgaggatca cacatgttat gatatgattt ctggctgatg tcgtaggccc    480

aatgaataaa tgaagaaatc rgagcaatgt caggctgaat tccccactcc agctcaagcc    540

aatgagatga cttcaaaagg cccagtttgg aaaacatttt ggtcataaga aaaaagaatc    600

ccattagact aagagcagat tagcctgttt tgaccttgga actaagtgct atttttagc    660

atttttccca aatactattt taatatgaaa tacatgtact gaccctatgc cttttcaaat    720

agagtaagat ggtgtaagat gcttttccca agagattttt taaaatcaca cacactatca    780

ctcttctaaa cagaaaacca tattctttat cctctccaag taaaattatg tacttgaaat    840
```

-continued

```
ttaaacttca ttggaaaagt gtaggcaata tttaaaaggt ttattaaaga gttaaggtcc    900

acagcagtgt cagaaatcct ttactgtgtg agttgcttaa ggcattctta actgaccaca    960

agatcatgca agttcattaa tttcccaaac caggttataa a                       1001
```

<210> SEQ ID NO 264
<211> LENGTH: 1001
<212> TYPE: DNA
<213> ORGANISM: Homo sapiens

<400> SEQUENCE: 264

```
agcaaaaaaa aaaaaaaaat agttttggag gaaaacaaat gaatctaaga gcgaaaaagg     60

ctcgcaggaa tggtttttat atgcaacttt cagatacttt tcaagtaacc taagttaaat    120

cataggagac tagatggtca cctcaattca gcacaggcca aaaggcaaag ggatgtgaca    180

aatgtttacg gagaaatatc cgtaagtcaa ctcttaattg ttcaggggtg gttgatctat    240

aaatttcaaa tcccagaata aggctgactt atacaacttc atattagtgt gcctccagtg    300

tatttttccc tccatgacag cggagattgg ttaaaacaat aaacatcaaa catgaacaga    360

tgcccaaacc taaattaaat atataggaaa atatgttgct cccaacattg tttaaagatc    420

cggataaaat gtattcggtt gagtgtgtac tttttgtaaa atccactgct gtgggttttc    480

tctacatcct gaccccctct rgaactgctt taaacagaaa ggtggtgtca tccgtttcat    540

ctcattcctt cctccactca tccattcaga ggagggtaat ctctggaaag caaactgaag    600

agcttcatgg agttatcagc cctgcccacc cagtccacta gcaaaagggc acctcttcat    660

tcttactaaa aatgaatata tatttcttta taattcttaa aaattctttc ccatttaccc    720

accagaaaag tcatcttttt caccttttta gagatcattt aattttcttt caagaaattc    780

acactaaatg atttaagaaa acagcctaca accagaatgt caaagccttg ttttagcaga    840

acaggaaatt ctgtggcgtc tcataaaaag gtatttgttc ataccagcta ctgatcttca    900

tggtcactta ttttctcttt gagacaaaca taccaaaagc ctaagaagga gaatttatat    960

tttcatcaac accgcaccaa gtcgatagta tttatgctaa a                       1001
```

<210> SEQ ID NO 265
<211> LENGTH: 1002
<212> TYPE: DNA
<213> ORGANISM: Homo sapiens

<400> SEQUENCE: 265

```
caggcttact gcagggtcgt tcagagcttt ctgtccgcag gtgcacttcg tctcccttcc     60

tctccttttc ctaggggagt tggcatctgg gcaggagctt gactgggttg ctcttctctc    120

ccttgacaca agcgcagtcg catttcacca aatggagtca ccttaccagt gtcctgcttc    180

ttgtctgggc ctgaacttga aacctgaggg caatgggaaa aatacaaaac aaaaaccaga    240

catctgttag aggaaatgga gaacgtaaaa tctatggcct aaagactgca atatattttt    300

gagaaatttt gaaattgatt agtttggggg ttggggattg atcctgctaa cctgggatgt    360

actcaagcct ttggctatag tgtggtcgac atacacgcag cacgaatgca ttgagaatga    420

atgctgaatg ccttctgagc ccttagagat tactcatgga ttctctttcc aagatactaa    480

atcccatttt gcagctactg aaataataac cttagtcata ttttttgat ctcatcttta    540

gacaaggcca cagtcaggac agactcagat accaacccag ttaatgagta tgcagatttc    600

ttagaaaagg ggttgagatc attgtggtct ttgcatccaa gatcctttta ggccaagcat    660
```

```
gacttgaata ttgacctctt tgttccttcc ctatctgttc attacagagg atgtgaaacc    720
atatcaagtt aatggagtca acccagccta tccagaatcc cgctatacct cggattactt    780
cattagtaag ttcatttcta cccctcttct ctcatgataa tagcaaacta ggaaaagacc    840
cctatctcag tgaatctcag gctccttcat ggtaattcta tcaaaaatar tatcttctta    900
gatgtagact cttctttgtt actttatttt attattttcc acaaagcaca aagtttcaac    960
ctatatatat gtttcattaa cctaccaagt tcctacacac ta                       1002
```

```
<210> SEQ ID NO 266
<211> LENGTH: 1001
<212> TYPE: DNA
<213> ORGANISM: Homo sapiens

<400> SEQUENCE: 266

actgcactcc agcctgggtg acagagcaag actctgtctc aaaaaataaa taaaataaaa     60
taaaataaaa atatactgaa agttgaaata aaatgaagaa aaggagatga gtgatactga    120
agaaatcgcc taccctgagc ttcattttac agacaaggac aataatagga cttgtcctta    180
ctatctcaca gttattttga taatccaaag agaaaatgta tttgaaagca ctttggaaac    240
agggagacat gatagagata ttaattgtaa ctacaatcag agatgggctt agatagccca    300
aaacacctag cagctccatt ttgataaatg gaggaaaaca gcctcttagt agaatatact    360
gggttacaca gtctgattga atctgctatt gtgtttagaa gtcaacagtc aaatcagatc    420
tgttaggagc ctgccgtatc gtttccctct ataaacaggt cgctcatgtc aacacctatg    480
agtgggtgtc tgtgcatgga daacatgccg gtgctttgca actgcctgcc atcctcggta    540
aaagcagcca cagaaagact cacctagttc tttcctgtat tcctttatgt cttatttttc    600
aacagaaagt gaaaagaagg aataaagata acatttttga gcacagagaa atctagtttg    660
ggtctctctt gagcactgca gaatggaata tattcttaac caaaggaagg tataatgcgg    720
ggtaaaagtg ctaatcctga gttttgctcc cctcccccag cgtctgtgcc aagggttaga    780
gctgatgacc acagggaaag gatgggcctg ggttagagag ggcaatgggc ttctaggctt    840
acagtcagct gaagggcact gctgactgct ggtaactgca atttatttta agaaaaaatt    900
caaaaaaata agcacaaaaa cacccaagtt tgccgcctgc tgctgtttct atactcagcc    960
aggactgtgg tacatgagtc acttggtcca aaaaggttgg a                        1001

<210> SEQ ID NO 267
<211> LENGTH: 1001
<212> TYPE: DNA
<213> ORGANISM: Homo sapiens

<400> SEQUENCE: 267

ataaaatgaa gaaaaggaga tgagtgatac tgaagaaatc gcctaccctg agcttcattt     60
tacagacaag gacaataata ggacttgtcc ttactatctc acagttattt tgataatcca    120
aagagaaaat gtatttgaaa gcactttgga aacagggaga catgatagag atattaattg    180
taactacaat cagagatggg cttagatagc ccaaaacacc tagcagctcc attttgataa    240
atggaggaaa acagcctctt agtagaatat actgggttac acagtctgat tgaatctgct    300
attgtgttta gaagtcaaca gtcaaatcag atctgttagg agcctgccgt atcgtttccc    360
tctataaaca ggtcgctcat gtcaacacct atgagtgggt gtctgtgcat ggagaacatg    420
ccggtgcttt gcaactgcct gccatcctcg gtaaaagcag ccacagaaag actcacctag    480
ttctttcctg tattccttta ygtcttattt ttcaacagaa agtgaaaaga aggaataaag    540
```

-continued ataacatttt tgagcacaga gaaatctagt ttgggtctct cttgagcact gcagaatgga 600
atatattctt aaccaaagga aggtataatg cggggtaaaa gtgctaatcc tgagttttgc 660
tcccctcccc cagcgtctgt gccaagggtt agagctgatg accacaggga aaggatgggc 720
ctgggttaga gagggcaatg ggcttctagg cttacagtca gctgaagggc actgctgact 780
gctggtaact gcaatttatt ttaagaaaaa attcaaaaaa ataagcacaa aaacacccaa 840
gtttgccgcc tgctgctgtt tctatactca gccaggactg tggtacatga gtcacttggt 900
ccaaaaaggt tggaagaggc tgttagggga ggccatgtca ttataaggtt gcaacatagc 960
gtcctgatat aaccccagtt cctgctccag atgtaaaagg t 1001

<210> SEQ ID NO 268
<211> LENGTH: 1001
<212> TYPE: DNA
<213> ORGANISM: Homo sapiens

<400> SEQUENCE: 268
agtggcgtga tctcagctca ctacaacctc tgcctcctgg gttcaagcga ttctcctgcc 60
tcagcctcct gagtagctag gattataggc atgtgccacc atgcccagct agtttttttt 120
atttttagga gagacagggt ttcaccatgt tggccaggct ggtctcgagc tcctgacctc 180
aagtgatcca cctgcctcgg cctcccaaag tgctgggatc ataggcatga gccactgtgc 240
cagcatgagc aggcaacatt taaggggctt tccacattgt gctaggtcta aaatgtcctg 300
catccctgac aaacaaatat gtttactctt cctgaacacc tctactagtt tatacacagt 360
ccctgcttat ctttcacatt taccgagaat attaatgtta ctacatactt tcagttacct 420
atgaaaatga aataacaata ttcattcatt caacaaatga ttatctagca cttgctttgt 480
gcaaggaatt aaagaaacaa magtgagcaa cacagaaata gtctccacag gagctagcta 540
tctgattctt gcagtagatt cagccactaa aaatctatct acacagttaa atgttcaaat 600
gcaatgtcaa taagggcttc aaaggagaag tacatgatgc aacgttaatg tgcaacagga 660
attcctggaa gtctgaagga aacaggaaag gcctccctta gaagatgaga gatgtttgac 720
ctgaattgtg aaggatgcat gagaatttag gaagaaaaga atactccaga tcagtggttc 780
tcaaagtgta gtcctcagag cagggacatc agcatcaact acaaaaagat cattttgttt 840
taagatcacc ttatccgttc tgtaaagagt gatttagggg tgagtatgaa tggatgagca 900
agacatttta gaaagttatt gcatcagtcc tggtgagaga ggatggtggc tttgactaca 960
aaagtggcaa ggcagataac ataagtgaac atgacttcaa g 1001

<210> SEQ ID NO 269
<211> LENGTH: 401
<212> TYPE: DNA
<213> ORGANISM: Homo sapiens

<400> SEQUENCE: 269
ggaactgaag aatgagactg actaggaggc ccccagaatc ttctcaacat gaaagctggg 60
acagtgggat gccagtgtga ggtgacagcc aaggacgaca gcagaaagcc tgaaaaagaa 120
gttccttgag tctgcctccc ataactacac aagccctggc agtgtggtct ggacaggact 180
gctgagctga caattctcca ygtaggtttc tgcttcctgt cagggggcag gcacttctgg 240
gttctcactt gttctctccc aggaaagcag ctagaattac ttttgccttt ccacctcaat 300
gccatctcca caagcccagt ccacgtgctg ttggggcccc atcagaggtg cctggctctg 360
cccctctggc tgtgagactc aagtgctaga tctctttaaa a 401

<210> SEQ ID NO 270
<211> LENGTH: 1001
<212> TYPE: DNA
<213> ORGANISM: Homo sapiens

<400> SEQUENCE: 270
gctgagctga caattctcca cgtaggtttc tgcttcctgt caggggggcag gcacttctgg 60 gttctcactt gttctctccc aggaaagcag ctagaattac ttttgccttt ccacctcaat 120
gccatctcca caagcccagt ccacgtgctg ttggggcccc atcagaggtg cctggctctg 180
cccctctggc tgtgagactc aagtgctaga tctctttaaa aaaagggttc acatcccagc 240
tgggggaaac catccctgtc cacttaggac acttgcattt ggacttgatc agctccagag 300
aaggcacagc attgtctttg gagccaaagg attcagatgt aaaagtcaga actttatcct 360
ataaagtgtg gaattgtagt ttaaaaagaa aaaaaaagtc aaactccctt ctataactaa 420
gtgaacagtt ggcaaagatt gtctttttcg gttgtgtgag cattgctctt aagtgatgac 480
taatcatgct caaaaatgta yattaaatag aaaataaact caccatataa aatactaatt 540
caaaaattct cttcatgttg tttgcagatt gtagcagttc tgttcaatat actcatcaaa 600
aacaatgaca aaatcattac acgggtgaaa aatctgacat gacttagcct aagcagatat 660
cgctttactc ttaaaatact ttacttcatc acctattata atatttttac attaggtaca 720
aaatatttct aattttagaa tcagtgtctg aaagttaatc actacctcca tagacattaa 780
ctaattatat tttatggaaa aatactgaaa tctcctttgt gctaataatt acaatatctt 840
aaattcaaat aacgtatttg tttcaaaatg ctgagaatcc ggcctggaga aacactacgc 900
caacacagtg gagattctaa acacaacgca ctggaaaatg aggacataaa tatattgcaa 960
ttatattaga tttcctgccc actgattatt ccttgggacc c 1001

<210> SEQ ID NO 271
<211> LENGTH: 1001
<212> TYPE: DNA
<213> ORGANISM: Homo sapiens

<400> SEQUENCE: 271
catccctgtc cacttaggac acttgcattt ggacttgatc agctccagag aaggcacagc 60
attgtctttg gagccaaagg attcagatgt aaaagtcaga actttatcct ataaagtgtg 120
gaattgtagt ttaaaaagaa aaaaaaagtc aaactccctt ctataactaa gtgaacagtt 180
ggcaaagatt gtctttttcg gttgtgtgag cattgctctt aagtgatgac taatcatgct 240
caaaaatgta tattaaatag aaaataaact caccatataa aatactaatt caaaaattct 300
cttcatgttg tttgcagatt gtagcagttc tgttcaatat actcatcaaa aacaatgaca 360
aaatcattac acgggtgaaa aatctgacat gacttagcct aagcagatat cgctttactc 420
ttaaaatact ttacttcatc acctattata atatttttac attaggtaca aaatatttct 480
aattttagaa tcagtgtctg raagttaatc actacctcca tagacattaa ctaattatat 540
tttatggaaa aatactgaaa tctcctttgt gctaataatt acaatatctt aaattcaaat 600
aacgtatttg tttcaaaatg ctgagaatcc ggcctggaga aacactacgc caacacagtg 660
gagattctaa acacaacgca ctggaaaatg aggacataaa tatattgcaa ttatattaga 720
tttcctgccc actgattatt ccttgggacc ccaaatttca gttaatattt ataggaattc 780
ccctagacct ctgaaaggac agttgtgcag aagctggtga ttaaataacc attgcaggag 840
attgcacagt atttagacag aagtgagcag gtagctttct ctgaatctac agaagaataa 900
gctagtggca ttttgaatgc agggaaacat ctgctcattt ttcattgtgg cctaaccctg 960
aaccacctca tagatgtttc aagtgaaatg taaaacaagg g 1001

<210> SEQ ID NO 272
<211> LENGTH: 1001
<212> TYPE: DNA
<213> ORGANISM: Homo sapiens

<400> SEQUENCE: 272
caatcaatga tcatgtgaag actggagcgt ctgggatcct agggttagga gatgagggat 60
acagccaagg acaagaaatc caaggtgcat gtcccagttt tgcatgacca ttgaactggg 120
cccaacccca tcagattatg ataccagtca tgtgtgttgg gtatggtcac actcaatagc 180
agcatgaaag aaatactaag agtgagtaat atgccttata cctgagaaat gctttacagt 240
ttgccaagac tcttcacata cactattcca aaatatcctc taaacataaa actggagggg 300
cctggaaagg tatcacaagg tccccatttc acagatgagg aaatcaaggc cctgggagat 360
caagagcttg acctaaagtc acaaggccaa gagggaccag ctggggctag aagccagtct 420
tctaactctt aaagttcagg gtctttctct ctattccact gcaaacagaa atggatcaga 480
tatccaggaa aactaacatt kttcagagct gagaaaaaaa aaatgggact tttcctttct 540
tattttgaaa gattttagga gtgattaaaa acttaaaact attccaagaa acccagggtt 600
tcatacagct agccccgtaa gaacataatt aagagccatt tacagaatca actataatct 660
tttcttttcc tggcactcag gcaactgagg cttccttcca tatgaagcaa atgagttaag 720
tgaaaacctg gcttccttct ctgtccaacc ctgactcaac ctaatgggta actttgcata 780
taacagaagt ttaatttgtt acataaaggc ttactgaaat atattttta aagtaaaagt 840 aaaccaagaa taaaccttct ggtccacatg gagaggataa aagaacagtt ctccaaactg 900
aaagatagga ttctaaagac aaagaaaaaa gagagagagg ggcgtgcatt gttgataact 960
tgttgatcaa aatccatagg ttctgatttc acatacgcca t 1001

<210> SEQ ID NO 273
<211> LENGTH: 1001
<212> TYPE: DNA
<213> ORGANISM: Homo sapiens

<400> SEQUENCE: 273
ctaacatttt tcagagctga gaaaaaaaaa atgggacttt tcctttctta ttttgaaaga 60
ttttaggagt gattaaaaac ttaaaactat tccaagaaac ccagggtttc atacagctag 120
ccccgtaaga acataattaa gagccattta cagaatcaac tataatcttt tcttttcctg 180
gcactcaggc aactgaggct tccttccata tgaagcaaat gagttaagtg aaaacctggc 240
ttccttctct gtccaaccct gactcaacct aatgggtaac tttgcatata acagaagttt 300
aatttgttac ataaaggctt actgaaatat atttttaaa gtaaaagtaa accaagaata 360
aaccttctgg tccacatgga gaggataaaa gaacagttct ccaaactgaa agataggatt 420
ctaaagacaa agaaaaaaga gagagagggg cgtgcattgt tgataacttg ttgatcaaaa 480
tccataggtt ctgatttcac wtacgccatt agtgtagaca cactggataa gtcacttact 540

-continued

```
caattcactt tgaaaagagg tctgttcata ggtggtgtct atatccctca tagagtttta    600

catttttat ttggcaattt tcaaacatac ataaaagtag agagaaactc tactcaaaat    660

ttatcaatac tacccgtttt tatttcatct tccacacaca tgcacaccca tacacacacg    720

cagaagaatt atacacctaa tcccagaaaa caagtcattt cacccacaaa tatttcattg    780

tcacaaggat attttttaga taaagggaga tcatagagtt aaagttcaat aagaggcaaa    840

taaactcaag gaaaaagaaa aaaagccttc aagttacttt ctctcatgct taaatctagg    900

tctatatttc atgcattggc ccacttgaac cacagaactt ctttcaaagc aacactgtca    960

tgatctggaa agtgccaatg ttggatcaca gagatgattt c                        1001
```

```
<210> SEQ ID NO 274
<211> LENGTH: 1001
<212> TYPE: DNA
<213> ORGANISM: Homo sapiens

<400> SEQUENCE: 274

tactcaattc actttgaaaa gaggtctgtt cataggtggt gtctatatcc ctcatagagt     60

tttacatttt ttatttggca attttcaaac atacataaaa gtagagagaa actctactca    120

aaatttatca atactacccg tttttatttc atcttccaca cacatgcaca cccatacaca    180

cacgcagaag aattatacac ctaatcccag aaaacaagtc atttcaccca caaatatttc    240

attgtcacaa ggatattttt tagataaagg gagatcatag agttaaagtt caataagagg    300

caaataaact caaggaaaaa gaaaaaaagc cttcaagtta ctttctctca tgcttaaatc    360

taggtctata tttcatgcat tggcccactt gaaccacaga acttctttca aagcaacact    420

gtcatgatct ggaaagtgcc aatgttggat cacagagatg atttcaaatc aagatggtaa    480

gccagttcca gggacttcca yttcctacaa gcagaaggct gcagtgatat ttcctcttaa    540

tggtcaacat cctcatgaac ttacaactgt aactaaagtg tacaaaacaa ataaaaaggc    600

tcggagttct ggccagcaca gaagggcagt gtgaaaggta atatcattgc caaactgccg    660

acaacaagtc ccagtttagg agataaggtg cctttacccc ttcagaccaa cacaaataga    720

gaaatggctg cagccacact gacggctctg cttctgaagt tgatgacccc tggagggtgg    780

tcactggtct acaagaggat tctcctgata aaaaagctaa tgatctcaga agaatgtgca    840

aaggaatctc aaagaaagac agtctctatt gccctctctc attcatataa aggcagggtt    900

gaagtagagt agaagggagt ggtaagtgat tcctgtgata ggcactagaa accgggcagg    960

caggacttcc agcttaggga ggtactataa tccacaaagc t                        1001
```

```
<210> SEQ ID NO 275
<211> LENGTH: 1001
<212> TYPE: DNA
<213> ORGANISM: Homo sapiens

<400> SEQUENCE: 275

ctgatttttg cgtttgtttt tcttattttc tcagtcgctt atttgtacct ggagaaattg     60

ccagattcct tcttgatgtt tctgtaagca ttgggaaata aaatcttttt ttttaagtct    120

ttatatttta taagatgctt ttcagtataa tcaagtagcc aatgatttgt tgagcaccta    180

ctatgtctta agctttggca ttgtcacaca tagtccactt aatcctcaca gcatggtggg    240

tagagcatcc tagagaatga aagcgagctt catctgaggg gctttgagac ctggtttatg    300

taccttcact tgccaggctg ctagagaaaa acacatattt aaaagccttt ccagcaggac    360
```

acattcattc atgtatttcc tattttaggc catttgccca atgtttaggg tgggagattt 420
gaactagtct aaggaatgag cgagaaaatt tagctacagg accaaggggg cagttctgct 480
ttctggctgg gatcctggaa yggaagagcc tctctgggtt tccctgaaca cctggaattg 540
atttgggttt tgctctgact tcgaaacatt tgctgaggtg gaggatggtg gaggaggtag 600
gaaagaaata aatccagtga ttaaaaatag cttgtgcatg tcaggtgcct gaacgaattt 660
gggaacatgc ctgcaatccc ttttgtctgg caggtctgaa ctccggcgct gccgaattac 720
aactgctttc atttgttttt cctgcttccc taccatgtaa tggtcaaggg ctcattggaa 780
ccatgtgtga gcctggtgag tcaccaaatc ctcaggactt cagtggtaat aatgtgttaa 840
aactcctttt gggggatggg gcaggaggtg gatgaaggga agagggagaa gtctgaggtc 900
acttcctaca gatgttcagt gtgctgagcc ctctctacag gcttctttct caggcctggc 960
tgcaggacct gaaaccagct tctccatgca atttggagct g 1001

<210> SEQ ID NO 276
<211> LENGTH: 1001
<212> TYPE: DNA
<213> ORGANISM: Homo sapiens

<400> SEQUENCE: 276
tacacctgac tcccaccaca tgacatactt tatagttcct aaatgtccca gaacagtgtg 60
acttctttat ctgaaaaaca cagagccatg gtctctacat tactcaggag gaaagaatga 120
gttgggctct ttcgtctcca tggctttgca gagaaccaca ttgcatccta ttggttcttc 180
ccacatctta cacttctgaa tgaggaaaac tcctgccctg ccttcactaa aattctcatg 240
acaggatcat acggcttttg gtaccaacat gacataggat aaccccatcc aggaagacaa 300
tggagaatat ctgacaacta catcttgcta taatcccagc ttccactaat tctggtttac 360
ataatagcct ttgaggcctc atcctctgag atcttgcaga tgctgatgaa ttgggctaac 420
caatttattt taatttcact taactcccac ctataattat cattcctgct atttgactag 480
aactgtatct tttagaaagc rttttcttga atattctcat atgatttttc aaaacaagca 540
cttgtagtta ttatctttat catgtaggtg aggaaactga ggctcacaaa tgtttcttaa 600
gtgacttaac taagattatc aaaccagtaa agtgatataa caaggattca atcccacatc 660
ttcagacacg caagccacgt gttttctccc tgcacctatt cacagaatta aaagcaaatg 720
aggcaaaaat gatggggcat gataacattt ctttttttcat tttctccaac attttcattc 780
tagaaaaagc tctttctgta gcagggaaga acctcaatcc ccgagactct ctaccgacag 840
caggctccat tgcacgtcct acccagaact ggcctggtca aacctcggct cggggcccac 900
ttggcacttg gtcgggggt aaaacaggca tcgggagagt ggtgctgaga atcaccaaga 960
aggccaggct gggcaaggtg tacgatgagg agttttctcc a 1001

<210> SEQ ID NO 277
<211> LENGTH: 1001
<212> TYPE: DNA
<213> ORGANISM: Homo sapiens

<400> SEQUENCE: 277
atcttgctat aatcccagct tccactaatt ctggtttaca taatagcctt tgaggcctca 60
tcctctgaga tcttgcagat gctgatgaat tgggctaacc aatttatttt aatttcactt 120
aactcccacc tataattatc attcctgcta tttgactaga actgtatctt ttagaaagca 180
ttttcttgaa tattctcata tgatttttca aaacaagcac ttgtagttat tatctttatc 240

```
atgtaggtga ggaaactgag gctcacaaat gtttcttaag tgacttaact aagattatca    300

aaccagtaaa gtgatataac aaggattcaa tcccacatct tcagacacgc aagccacgtg    360

ttttctccct gcacctattc acagaattaa aagcaaatga ggcaaaaatg atggggcatg    420

ataacatttc tttttcatt ttctccaaca ttttcattct agaaaaagct ctttctgtag    480

cagggaagaa cctcaatccc ygagactctc taccgacagc aggctccatt gcacgtccta    540

cccagaactg gcctggtcaa acctcggctc ggggcccact tggcacttgg tcggggggta    600

aaacaggcat cgggagagtg gtgctgagaa tcaccaagaa ggccaggctg ggcaaggtgt    660

acgatgagga gttttctcca tgggcaaatg aaaaatctgg gcaaacaaat ggagtagagc    720

ccgtttattt aggctggaag aggtaaagtt tttctgcact tttgaactgt tttctcaagg    780

cctgcctctc cctcccacgc aggaaacaaa cacagagaca ggcctcttcc agtgagggct    840

tcagttgttc aaagttagcc cgggaagggc agaaggaaga aaggcttaga gaaaggaagg    900

aggaacgggg gctaggaagg tggtgcagtg gccatggggg tagccgccaa gggagaaggc    960

tggagctggg atcagacaga ggaggagagc tggccaagaa g                       1001
```

<210> SEQ ID NO 278
<211> LENGTH: 1001
<212> TYPE: DNA
<213> ORGANISM: Homo sapiens

<400> SEQUENCE: 278

```
cacatatctt tgtcttgacc acaaatatat catggaaaga ctcagacaaa agcattactg     60

gaatcaaaat atgaggttac aatattcagt tggtctccca cttgtggagc cagttctccc    120

ctcgagtttc taagcatctg gcaagtgaaa ggtggctgat agtacaaatg gttgagctgg    180

aattcagacc cctgtacagt gaaataaaga aagacagaga aagggggtgg ggtggagaga    240

gagagagaga gagaaagaga gctgcagcca cagcattgct ttgcttctag aaacaatggg    300

cagttagaga acaatggcta cagacaaagt cttggtctat ttatatctgc cactgttagt    360

cccagacagg aggaactgga agtctgccct gtatgcacag ctccaactgg acccaagttg    420

ggaggaagat gaggtcacca agaaggctgc ctgcttagaa atgggcttct tttttcttcg    480

tatagttgct tcttagccta raggttctct taagcttgct tgccttctgc taaaatacag    540

ccactgctga gaagggagag atgagaaaag taactgctgc tctgcccagc ccaaagcaat    600

taaggcctct ctgtacagag gttgcaggaa ggtgggaacg ccaaggaaaa aataaccaat    660

cgatggaggt caactctatg gtttctgaaa caacagtctt attaggtctg ttaattatac    720

atgtttagga gcactataaa ggagcttttc cctgggaaag ttccctcctc atttctttgg    780

agacaaataa agaggccaag agctgaaatt cacagatatg tatgcattac atctcaggga    840

caatctcttc ttccctttat ttcagcccct ttttgatggt atctctattt tctggaattt    900

catcttttgc tctaacatgg ctttggagag atactcaatt ttaatccttc ccaaactgtg    960

ttacttgtat ccttaatcct cctacagcct tactaaaaag a                       1001
```

<210> SEQ ID NO 279
<211> LENGTH: 1001
<212> TYPE: DNA
<213> ORGANISM: Homo sapiens

<400> SEQUENCE: 279
atttccctgc ctctgtccct ctatcccgcc ctcactatag ctataggatg cataaagcct 60
tatccaggac caaaaagcag aaaagaggaa tttacagaat ttgctataaa actttaacaa 120
ctccttggag ggatgttctc tttccttgca accagacata gttataaaat ggatgaaaag 180
tggagagaag gaggagccaa gctctgccac tggtcagggg tcttacacta ttcctggaat 240
acagaattag aagacgcttt cgatgtcatc tagttcaaac cttttctttt actggtgggt 300
aaaatgaagc tcaaggtgac atcaacttgc cttaagtcac tggttactaa ttctagaact 360
ctggctccct ctcaggattt ttttttcctc tacatcattg ctgtttactt acaacagtgg 420
actgggaggg agaggctttc tcctatatct tcactactat caagtcctgg ttcatcattc 480
tggataaaca ctactcctcc ycaagttatt aagaatcaca gaggaatgag ccatccaaag 540
atctaataaa tatgatggga ttttacagat tcatgatgct atccactcct atttcaggtt 600
ataagtctgg aataccaatg gtcagactct aaggtggaaa agcttcctcc tagcaaagat 660
ccttgttgca taccagggat attaagcaac tttcaacagt caactccgat agcatgatac 720
catggtgtct gatggctctg aaatttgagg gtgctattcc tgtcaatcca gaaagagtga 780
agactgcagt taacttcagt gatctatgaa cctttatcta aaaagcactg aaaggcagag 840
tgcctcatat catttaaagg ttttacacca ctacccttct agtcctgctg gtattccaaa 900
tagggtcact gagccatggt gatagggttg agggaataca acaaacccca ctgacaaagc 960
cagaacttaa tatcaggggc actggccagt aagttgaatc t 1001

<210> SEQ ID NO 280
<211> LENGTH: 1001
<212> TYPE: DNA
<213> ORGANISM: Homo sapiens

<400> SEQUENCE: 280
tacgagccct tctcctcaca tcccagctgg acagcattct ttttttcaga aagagctact 60
gactgctcat gagcatgggg cttcttttgg gagtgatgaa aacattctgg aattagacgt 120
tgatgatgat ggcacaactc tgtgaatgta ctggaatgca ctgacatgta cactttaaga 180
tggtaaattt tatgttatat caattatatc tcaatttaaa aaaaagtaaa tgttagagag 240
agaaagagct actggcccac tgctatgagc ccaacaatga ataccttggt gatagatccc 300
tcaggcagag tttccctcta gtgggagaag caaacaccgc ctaagtacag aagcaatagc 360
tatatgctca caacagacga tgagtgctgg gatcacggct gaagcggaag gttttgcaat 420
gcagagtgag tgaactagcg gggtccagaa gcactagggg agggggtagg aaggagtgca 480
cgtaagatgt cctgggtgta sggcgtgagg gacagaaggc gggcaaggtg tccaggatgg 540
cgcccctggc agttggtggc attactgaaa gggaagacga gaggatgaga tctcccacag 600
ccacctccgc cacctggaaa tccttgtgag atggaagccc cgcgatgctc actgggagac 660
cgaccgtggg agaggctggg cacgggccat ttccagaggc agacacctgg taactgcaat 720
ttctgggacc acttatgtga ggactaaaga ggaagggcca caggttctag gagacgaaca 780
aaatccctca agttccctac cctaaagatg ctcccagaaa aggctgccga gtgctctttt 840
aaagtgatat gtgcatcttt atacttacat acaaaagatt ctcaagggga agaagtctcc 900
atcagacagg gctctttcgc cctccagtcc ctggtggggg agacagagga aaagctgata 960
gggcggtggg gtgtgggggc ggtgaaggct cactgcacag g 1001

<210> SEQ ID NO 281
<211> LENGTH: 1001
<212> TYPE: DNA
<213> ORGANISM: Homo sapiens

<400> SEQUENCE: 281
tgaggaaggt gcagtcacaa cactgtgatg ccagggatct ttttgggaaa ttcttttcca 60
aaagggatca tgaattttgg cccctggaat gccccagagc acctctgatt ggttccctgg 120
ccctgactca gatcgagccg ggctccaccc tccatgagta aataaaggca gggacggagg 180
gagggagagg gaaggagagg gagcggagtg ggcagacagg aaccagaagg ccagcgctgg 240
ttcagggaac acaccagatg agatttcagc gacgggtggt gtggcagaat tcaagacata 300
attctctgag ccttacacac cactccagtt gggattcagc cctgccttgg cagccggctc 360
agtgctgctt tataatatac tgaattagtc actggattag caagcacatt tacacacagt 420
ggcgcacagc tgtttaaaga cgcaggatcc ccttttctag gtgccagatt ctggctataa 480
atcaaccatt gcaatcagca rccagcaaac cccagaggtg catggttcct gcagacatct 540
tccttagggg aagcctgcta gaactgcgat ggccattttc tggggacagg agggacatct 600
gtggcaaaga aggaaaggtc ggtgggcttt ttctgtcttg aatcttatta tcttcagggg 660
gctgccaggt cttcactgac ctggaccttc ccggcagcag cctagctcag gaaatgacgc 720
ctgggagaac aggagttcta atcctgcctg gctgtattat caagtacaga gtttttctcc 780
taaaccttga atggctgggt cacctcccag aaaagaaaag actccagggc aaagaggaca 840
gtacttcagc aattaaaata attttaaatc ctgataacat caattccaaa aaactgcctt 900
gttgaagtgg caagggcaat gtctaaaaat aatgctttag agttggaatc ataactcaag 960
ccctaactca cgttcggtaa gaatgcgtga gaggcatttg a 1001

<210> SEQ ID NO 282
<211> LENGTH: 654
<212> TYPE: DNA
<213> ORGANISM: Homo sapiens

<400> SEQUENCE: 282
cttgtgcctc tgaacatccc ctccctggag aactctcaag ctggggtgga gctctcactt 60
cattcctcaa ttgtctaatc tggagagtgg gggccaaagc accaattctg tacacaagtt 120
tagtaaattt ggctagccac ctttcatgtg tctactttgg atttgaaaat gcaccatgga 180
aatcaggtga aaattttttt tttttttttt ttttttttta ctttccyact actaacacat 240
cccaatggta gatatgtata agtgaaatga gtgcgttctt cctgccccta taatgacaag 300
cctgacagag aacacatcac acagaagaat gtgccaagaa tcaagacctc ttagaagaat 360
gttagaaagt tttctctcca aatggattct gtctaagtag gaaggccttg gcaactagaa 420
aggtctaaga tcaaatttat gacttgaaaa ctctatggct ttgggcaaat tatctgaact 480
taattctgga ctcaatttct tatctacaaa atgggaatta aggcatcaac ctcaaagggt 540
tgtttaaaga atgtgattat gtatttctgt aaagcacatt gcaaagtatc tgacacatag 600
taggtactct ctgtaaatat tagcttcact tctctcactc ctccaactga actg 654

<210> SEQ ID NO 283
<211> LENGTH: 1001
<212> TYPE: DNA
<213> ORGANISM: Homo sapiens

<400> SEQUENCE: 283
agacatgtgt ccatatctgg tggcttaagg taaagccaga cttgggtatc ctgattctca 60
catcaggcaa cagaaggtaa taagatgacc acctatgcca ccctgcccag ttaacagcag 120
agaaaatatt caaaccgggc aaagctaaga ccaaggaccc cttaggcctg acccaaaact 180
attggtacat ggagggcacc aagccatagt gctgaacccc aattggagga ggagacacac 240
ttcgtgacct cactaggatt tgctttacaa gataagattt tcctggcaag cattgaagtt 300
agtgcccaga ttcaaaacag caaacttaaa actattatct tcatgcttgc tataatcagg 360
tgtaccgccc aacttcccat ccctacctcc ccttccctag taatccagag gtactcaagg 420
tcactactgg ctacttaagg tttacatcca ctcccaagga aacaccagca accaaaagaa 480
tacttcccag atggaaaacc mgtcatttga ccttggaatg ctctgcctcc cataatgacc 540
aaaataaggt ccggccagag gggcttacgt tttttggtaa ggaacaacac attgttttag 600
agagataatc tgacataact ctgctaagct ctgagtgtct atgcatggta ccacagcaaa 660
caccctatgt cccaaatgga aactagcagg gtgaaaaaat tgttcatcta agatgacatt 720
aatctctgta tgcctccttg gtacagttct tttccacaac atgcagctta agattcaaca 780
attttttcat tgtgttttgt gtttcctgaa gcattcctcc agctacctga agctctcact 840
gattaaaata gacctccttt actaaaaggg gtaaactgag gcacagaaga acaaagcaat 900
gtgccttata gttcagaata ggtaaacaaa aattggacat ctattatttt caaatctctt 960
tagattaaaa gaaaaaaaaa tgtatttctc aaagtccaaa g 1001

<210> SEQ ID NO 284
<211> LENGTH: 1001
<212> TYPE: DNA
<213> ORGANISM: Homo sapiens

<400> SEQUENCE: 284
agacacactt cgtgacctca ctaggatttg ctttacaaga taagattttc ctggcaagca 60
ttgaagttag tgcccagatt caaaacagca aacttaaaac tattatcttc atgcttgcta 120
taatcaggtg taccgcccaa cttcccatcc ctacctcccc ttccctagta atccagaggt 180
actcaaggtc actactggct acttaaggtt tacatccact cccaaggaaa caccagcaac 240
caaaagaata cttcccagat ggaaaacccg tcatttgacc ttggaatgct ctgcctccca 300
taatgaccaa aataaggtcc ggccagaggg gcttacgttt tttggtaagg aacaacacat 360
tgttttagag agataatctg acataactct gctaagctct gagtgtctat gcatggtacc 420
acagcaaaca ccctatgtcc caaatggaaa ctagcagggt gaaaaaattg ttcatctaag 480
atgacattaa tctctgtatg yctccttggt acagttcttt tccacaacat gcagcttaag 540
attcaacaat tttttcattg tgttttgtgt ttcctgaagc attcctccag ctacctgaag 600
ctctcactga ttaaaataga cctcctttac taaaaggggt aaactgaggc acagaagaac 660
aaagcaatgt gccttatagt tcagaatagg taaacaaaaa ttggacatct attattttca 720
aatctcttta gattaaaaga aaaaaaaatg tatttctcaa agtccaaagt caaccttctc 780
caaagggaaa ctgcatgtct gtctagtaac ctataggatc attcacactt ttttttcctt 840
gagaaggaac taacttgcca gcctaccaac aattttgcca gtgccttggc atcaggcata 900
tctgcacaac ctttccagag cctatatcat agtgatctgt tcaagctgct caaagctcag 960
taatcatact aatctgtgca tagtgaccag tgctacctgc t 1001

<210> SEQ ID NO 285
<211> LENGTH: 1001
<212> TYPE: DNA
<213> ORGANISM: Homo sapiens

<400> SEQUENCE: 285
aggcatatct gcacaacctt tccagagcct atatcatagt gatctgttca agctgctcaa 60
agctcagtaa tcatactaat ctgtgcatag tgaccagtgc tacctgctca aagctcagta 120
atcagccagc tatgtgggac ttgttataga tgcataaaat atgtgggtga aatctacctc 180
caccaaaaga gaaaagaatg ccttgttgac actttgatct caagctaacg tttattaata 240
acatcattat tatatttaag tgaatgtact agatactcat cgaatcaaag aaatgtttaa 300
aatccatgtg gctgaactca aatgtcaggg gatttggaga aactgactgg agcttcatgt 360
tctaactctc cgcttatttg ccctggaacc ttgggagggt aacttggcat cggtgcactg 420
cactttcctt atttgtaaaa tattggtaac tctaaggatt accatgagct caaatgtggt 480
gaagtcacat ggcaaactgt maaatgctac cagatatagc caagtattaa gatgaactag 540
caaacaatat gcacaaacgg accttagtat ttcccccaaa ttccacaaac acccaaatat 600
ttctgagaat tctgaaaaca acagacatgg aattttcaag ttagctacag ctgggtttga 660
atctgaactc ctccactcag cagctttgca accttgggca agtcgtttaa tctcagtttc 720
ttcatctatg aaatggcaat aataatgctt cactattggg gcgaaataat gaggatactg 780
gcacaaagtt tgcgcccaat aactatcaga aaataaacag aacatgagga aaaaagaaaa 840
gatggatgga gatgagaagt gcttacacaa gcaccagtag ataaactcta cactgtcatc 900
aatgatcgtt ttccttgttt ttcccccaaa aactggcatg ctgaacttag gtccctgctt 960
tggaaagaga agggtaactg cgacagacct ttctcaaaat g 1001

<210> SEQ ID NO 286
<211> LENGTH: 1001
<212> TYPE: DNA
<213> ORGANISM: Homo sapiens

<400> SEQUENCE: 286
aatacggtaa ggtcttcctt atcatctgtg attcttcatt gcattctgtg catttatttc 60
gtgtcttaat gatgtgagac aactgatgca taaggtatgg aattaactta aatttttggc 120
aaaagatatc aaataggaga aatgtgtagg tactagaagt acaaaagtcg gttacatgga 180
aactctttca ctgaaaattt cctgtgataa atttcttaaa gggtatttca aaatcagact 240
tgggcagggg cagtggctca tgcccgtaat cccaacattt taggaggcca aggtggaaag 300
attgtttgaa gccaagagtt taagaccagc ctgggcaaca tagcgagacc tcatttctac 360
aaaaaagaaa aagaaaatca gactcaacaa cacattttta ttctgaacat gaatgatact 420
aatgcatcac acaactctaa acgcatcaca caactctaat tgcacacaaa aaaagtaatt 480
aattgagaac aggtataaca sctggcacat agtgggagac cctagatact tcaaaaaacc 540
cgtatctaca aacactcacc aggcttagca gattcctgtg cctgaccgag gttattttcc 600
atttgtacct tgaaaatatg tacctgattg attttgtcat cttctctgag gtttaacgct 660
tattctgata aactgataca gaggttttaa caacagtatg agtaggagga aaagtaacca 720
aaaaaaaaaa gttacctatc tcataagctt actcaataac tctgctctac ccttaaatat 780
tcctactttc aaaggcaaaa ttcatcctga ggttcaaaac gctctttggg tcctggcctc 840
ctacttcctt ccttcatccc tttctacaag taagtttttt ttccttcatg tttatctaag 900
catctctttc attccaaact tgcagcattc ttcccacgct gctctctata tggaaaataa 960
tcctttccct gttcttacac ctccttcaaa tgcttcagaa g 1001

<210> SEQ ID NO 287
<211> LENGTH: 1001
<212> TYPE: DNA
<213> ORGANISM: Homo sapiens

<400> SEQUENCE: 287
tagcttactt agatggtcta aaccctgaaa ttggcaattg agagaagata ttctagaaag 60
tacgattgac caaatttagt gtctaactcg ggtggccctc atctgtgggg agagccccag 120
ttaatgtctg tcattctgat gcaattatta atagtgcccc tttacactct caaaggtatc 180
ccagtttggg tggtaaatta tacgattttc tatctctaca ccattatgat ctgaagtcca 240
acagccttaa aatttctaat attactttgg gtctaaaagc actatctggg tcaatattcc 300
acaactctta gagacagtac taaatgctac aagaaagaac aattgagaaa agtggaaggg 360
gcagtaataa gccacatttg aagtgtcaag tgacaggctt gcacccaagc agtagacact 420
ggaaagcacc tgggaaatat gacagcgttg gccaagtgat caataaaata tttacggctt 480
gaatagcaat attttgagcg ygtctgttaa gcatggctct ctgccaatga aaccagacct 540
accacaatcc accctgcaga cctatgtctt tctgtatctg catggagatt atacattata 600
caatcagaag gaaaaggggg tgcagatagg cgaaggcttc agaaaagcag ccaagtagaa 660
atagcctgtt tatgcaattt ggaaaacatc cactgaagtt ttgaaaaaga tatcatcaac 720
ccgacagaaa aaataaagca gaaagtagct agagacacat gacaagtaaa aatgatagat 780
ttgggaatag ccttgacatt cctaaccctg agttaagaac agcttaacag ctgtgagcga 840
agggtagacc tagaatactg caaacataga ggcaaatgct atcagaggtt ccttgtgagc 900
aggaaaatgg agccaaggtt ttcattaagg agcagctaaa taaaaacacg gagatgatgt 960
tgttcatata caaattcctc tctgcggtga cagtgtgggc c 1001

<210> SEQ ID NO 288
<211> LENGTH: 1001
<212> TYPE: DNA
<213> ORGANISM: Homo sapiens

<400> SEQUENCE: 288
acaagaatcc tggttctctg cctttcattc tgaggtaagc attgctggaa ctttcaaaca 60
tctttctaaa gcaacacatc tggactgcca ggcctgggga caacccacag gatggaccct 120
ttccccaagc cgtatgaagc actgagctaa caatgaggcc acctgattca gctcaggggg 180
ctcttgcaga gatagcaggg agccactgta cctcctgaac ccccaaagca ccgaccagca 240
ttgccttctc acctgcctgt gttctaattt ccagagtttt tgagaataac tcaaaatttt 300
aggtataaaa tgcctacaac atctcatcag tttctaaatt tctagagtgt ggccttaggc 360
caagtatgca tctctcagaa actcattttc ctcatctgaa aaatggagaa aataatactt 420
ccaccacacc tcagagtaag tgtgaagcat aaaagtgctc ttttatctgg ctgtgcccag 480
cacacaatgc aggctcgatg ygtgcttcag aaatatccca acaacttttg aatgacaaga 540
acctaccacc ttcaatgcaa gctcatggaa ttccaccaca gccatggatt attcattaca 600
caaaccagag agacatctgt aattacactg tcactgtaac cattgcagag ttatctgctg 660
tattctgaaa cagggagact ctcctgaaaa atcctgacct acactaacca gctctcagtt 720
tgcagagatt tgatggagcc cagagagacc tgggctccgg gaggttgacc acgagctggt 780
ttgtctcctg gagggaggcg atgctcctac agggtggtct ggcctcttta agagaaaaaa 840
aaagttacac agacaaaaaa acagcaacac aaaccaacca aaaatgccag gaatgcaagc 900
tctgccaacc aaataaataa ataaaatagg agatgcttta taataactgg acatgatgca 960
tttctcagcc ctgcataatt gaaaacttga cttttccatc a 1001

<210> SEQ ID NO 289
<211> LENGTH: 1001
<212> TYPE: DNA
<213> ORGANISM: Homo sapiens

<400> SEQUENCE: 289
tggctttggc acctggcccc ttcacagcag gctccaccag gagagaacca ggagtgaacc 60
caatggctat atttgttttt aagctattta agatccttgc aatcacactg ttgcaatcaa 120
atagcatatc ccaccttact cttacacttg caaggaaaag tcaattctac tgttatttca 180
gagtatatgt taatttagca cttaacgctg tcaaactcct gtgaagtctc aaaatagaat 240
aaaagtgcat aaaggttctt ggtcaggtcc tagccaggaa aacaaataat ccaggtcttg 300
cggctcctgt ttggacaccc cactttctta ctgcctctct ttggcactca tgaatttggg 360
agggggtggg gagaaaattc tggtttaatc atttaagcca gataagatcc cacactagct 420
gtctccacac ataagaaact aagcaaccca aagaaatcat tctgacaaat atttaagtca 480
cagctgtgga taaaaagcta ygctgtgaga agttaaactt taaacacatg tcctatatgg 540
tctgatgggc aaggcaaatc cgcacttagc caatgtcttg tccttccact aacaaaagca 600
gacagccctg gccagaaaca ccgtttctcc catccttgct ttgcacctgc aagttaagtc 660
tcagctgagg tttctttgct gagcttttgg aaggtatctt gcaacattac tcaaagcaat 720
atacattgcg aagttagaaa caggaattga ttgtacttca gccactggct cactacatat 780
ttttatgtca attatttacc tttcctgtga ctctattttc ctctctgagg tatgggcata 840
atgttcgcat ataagcaact aaaggtccag aaaaaaaaaa gttgattata gtctatatat 900
tttttcaagt ttttgtcttt attttttcca agataataaa taatggtgct agaaatcaaa 960
cctctttaca atgaatggca gaagactgcc caatttcttt g 1001

<210> SEQ ID NO 290
<211> LENGTH: 401
<212> TYPE: DNA
<213> ORGANISM: Homo sapiens

<400> SEQUENCE: 290
tctttggcac tcatgaattt gggagggggt ggggagaaaa ttctggttta atcatttaag 60
ccagataaga tcccacacta gctgtctcca cacataagaa actaagcaac ccaaagaaat 120
cattctgaca aatatttaag tcacagctgt ggataaaaag ctacgctgtg agaagttaaa 180
ctttaaacac atgtcctata yggtctgatg ggcaaggcaa atccgcactt agccaatgtc 240
ttgtccttcc actaacaaaa gcagacagcc ctggccagaa acaccgtttc tcccatcctt 300
gctttgcacc tgcaagttaa gtctcagctg aggtttcttt gctgagcttt tggaaggtat 360
cttgcaacat tactcaaagc aatatacatt gcgaagttag a 401

<210> SEQ ID NO 291
<211> LENGTH: 1001
<212> TYPE: DNA
<213> ORGANISM: Homo sapiens

<400> SEQUENCE: 291
ctgagctttt ggaaggtatc ttgcaacatt actcaaagca atatacattg cgaagttaga 60
aacaggaatt gattgtactt cagccactgg ctcactacat atttttatgt caattattta 120
cctttcctgt gactctattt tcctctctga ggtatgggca taatgttcgc atataagcaa 180
ctaaaggtcc agaaaaaaaa aagttgatta tagtctatat attttttcaa gtttttgtct 240 ttatttttc caagataata aataatggtg ctagaaatca aacctcttta caatgaatgg 300
cagaagactg cccaatttct ttggccagtt gaaattttgt tgtatcgaag ttcacataca 360
aaagatgacc aatggcttgg aaatcttttt tgaaaaagaa agccattgca aatatgctta 420
ttataatgga cgctgactgt agcgttaggc cttattgttc ccattttaca gaatagaaag 480
ctaaagaaag ttacttgccc wgagcttatt tttaatcagt aactgaaatg acggcaccat 540
atacattgtc tctaatattt aatattaaat taccaaaaaa attgcctcag ctgttcactg 600
tgatctgaaa catgtgttgc cagggctctt tttcattccc aggatgaaag atcccttgta 660
ggtatgtgga ctgacatatc gacacgatat ttcccagatg accaaatctg tctcttcccc 720
cataaacacc cataacaaca catataaaca agctgttctt aaggaaagga cctattagtt 780
gagtttatat ctttgatgtg aactatcttt tcacttctat atatggtttc aatcaactga 840
caaacagaac tcattctagc ttcctcgaac ccccaaacac aaccatcata gaaacagcat 900
ttctgaattg taggcctaag tgccttaaat gtctccatgg ttccagctgc gctctcagca 960
ttgctcccac caccatcatc cttgcgagga gacaaaatct c 1001

<210> SEQ ID NO 292
<211> LENGTH: 1001
<212> TYPE: DNA
<213> ORGANISM: Homo sapiens

<400> SEQUENCE: 292
tcctctgagg cagcgtccat ctccccttaa cattaaggaa taaggccaga gggttctcgc 60
tcatttggga aaataaaaaa agcaggaatg gggcgctgga aattctataa gcttttcccc 120
accactcaca aaaacacagc tgtgaaaata aataccaccc cccaaaccaa gggtctaggg 180
ccaccaacag tcctcctcct cctcctcctc ctccttctcc tcctcgtcct ccagatccag 240
ctgccaacag catcccccgc tcctgaagaa atgcaccgcc cagaagggaa cggcgaaagg 300
gggaagaagt ccaggggacc cccggcctct ggccgagagc ttgggtgggg gcctcggccg 360
tcgccactca cccggggagg ggaaaagctc cagatcgact ttttccgtct tgatgatggt 420
gagagtcggc ttgagatcga cggccgcctt catggtgcca ggagtggggg acgtacggga 480
tggtagcaag tttgcagtta btgttgtttt tctttttaat gaggattagt aacaggggga 540
aggggacggg ggaaatccga ctttcttccc aaaaatctca aattcccgct gcctttcttt 600
cccccgcgcc cggacggtgc gcgcccggca ctccagggga agttggcact ttgcggcgaa 660
gtgagcgcgc tcgggtccca gcctcgcccg cgccgcgccc gctcctcctg cccggccctc 720
gcccgctccc tcctctccgc cggcggctgc ctcgttcgct ctcgatctcc cggccgctct 780
ccctccctct cgccctcccg cgctctcccc tcctctttag ggcgtttctc gcggcgccgc 840
gtctcggccg ctgggtccgc gcgccctggg ccgggcgatg tccgcttggg ggagcgaggg 900
gcggggcgtc ggggcagggc ggggagccgg gggcggggcc gagcaccgcg gccaatctcc 960
gcccgcggcc caaagcgaaa ggaagggctg gcgagcgcgg g 1001

<210> SEQ ID NO 293
<211> LENGTH: 401
<212> TYPE: DNA
<213> ORGANISM: Homo sapiens

<400> SEQUENCE: 293
agcatttgac tgtaactgta acctctgcct ctggtaagtt ttgacacaca ggcttacctt 60
catctaatcc cagttttgtg cccttgaagc cttagtaatt tgcagatttc ccacagcaaa 120
tcggggagga agccaggaac agaaaaatct gtggctcctg gtctaaactc cagattaaat 180
ccctccttag tgaccagagg raaatatttg tatgtgatag tcctaatttt tgaaagaaca 240
aagactgttg caatccagct gtgtttccac aaggtatgag aaaacaatgc tggcctccag 300
atgacaagaa cagacccttc tggtcctggg aaaagcctag agaaacagct gatgaatgaa 360
ttgtacattt acacgtccaa atgaaccaca aaaaaaaaaa g 401

<210> SEQ ID NO 294
<211> LENGTH: 1001
<212> TYPE: DNA
<213> ORGANISM: Homo sapiens

<400> SEQUENCE: 294
taacggctga tccagaacca gtttatgact cacagatgtt gatttactgg tataaatgta 60
agatttagaa aaaaaaaaaa aaaaaaaaaa gccctcaatt aacaacaacc tgtctgagct 120
gcatttgtgg tctcattttt ctctgagaaa aggcaacagt ctctgtcata cacagaaaca 180
agctttgaaa gcttacttct aaggcaagtg gtttctatgt gagaagttta gtcattaaaa 240
gtcacactag ggaagaaaaa tgcctggcac ttcaatatct acattatcaa gcagcaataa 300
aatggaaaat tagagatagg aaggaaaatt aaaataactc tcttaattaa acttggatgc 360
caaaaagcct tagggtcagt taagggaccc aagccagggg actcagatgg tactgttgct 420
gactgcaggc tggctctgtg acctcaccaa agccacttaa cctttttgtg tcacaacctc 480
atctctgttt cagggaataa ratcagccct agctctccct agaatggaac acagactcat 540
tggctattgt ttagaaggca caataaacaa tgagggtagg aggagctgca gtcaggaggg 600
aagaagggag ggtggggtgg ggttggggga gaggggagga cttgggagcc tgtttgccct 660
ggaaagctca atataagaaa acaaagagga tagtagtgtg ggctttggaa taagactcag 720
gttcaaattc ttactctacc aactagccag ctgaattgcc acaggtaagt catttaaaca 780
atcccgaacc tcagttcctc catgtttcaa ctagggataa tagcagcaca cacctttttaa 840 ggctatttga atgattaaat gagataatgt atgcaaagaa tttagcacag tgtctaggtg 900
agaattagta tttgattatt gttattaaga tctagtatac ggtagaatat gtgggaaatc 960
acattaaatg tctgtctaca gccatctctt tgcagaatag c 1001

<210> SEQ ID NO 295
<211> LENGTH: 1001
<212> TYPE: DNA
<213> ORGANISM: Homo sapiens

<400> SEQUENCE: 295
cagttcctcc atgtttcaac tagggataat agcagcacac acctttttaag gctatttgaa 60 tgattaaatg agataatgta tgcaaagaat ttagcacagt gtctaggtga gaattagtat 120
ttgattattg ttattaagat ctagtatacg gtagaatatg tgggaaatca cattaaatgt 180
ctgtctacag ccatctcttt gcagaatagc ttggatgctc aattttcctg aacgatctcc 240

```
agcgagagat agaacaacta tcaccacatt tcatttaaaa atctcttcaa gacccttcct    300

cagttcttaa actggcaacc tgcccagcat cagcctcact tgagaaattc gagaactacc    360

tgattggaga agagaactag atttatattt gttttgagtc acagaaaagt gacagtttaa    420

attctgaaag aagatcacat ttgtagtgcc tctttggaga caaaacctta ggtcttggat    480

ttgtcacatg ttagagctca rtgggagttt atcagtgctc tccaagtcca gcactcctat    540

ttaccagagg tgaaaaatga gtgtgagtga ggaaattatt atttccaggg ccacacaatc    600

taaaaaagtc agtgtcagta ctagaaccag atgccctgat agcagttctc tccctggcat    660

ctccttgcat ttactttgca tttcactttg gcaggagaag taccagacac ccttgagaca    720

caagacagga tacaatggac atgggagtag atagatgagc agactcaatt tctagaaatc    780

caacttctct acactggatg tattgtcttt gggcaaatac attgcaggat aaccacacta    840

tggttccctg tgggagacag cttggcatgg gctgtcagga gagaaagggc ctgggttggc    900

tctattgctg tctgcagttt ctttagacta taattatgaa ccattcaact gcatctgcag    960

ccccaacaat gtggggtgga ttggcctaat ccacagacca a                       1001


<210> SEQ ID NO 296
<211> LENGTH: 601
<212> TYPE: DNA
<213> ORGANISM: Homo sapiens

<400> SEQUENCE: 296

tgtgaaacac tttcaagagt ccagggctgg cagtgagagg taatgacagg taacgtgcag     60

aatgaagaaa gcagaaagca tatagaagtt gcttcttaat ggaaacgtgt ttcatcagaa    120

tgatcagaaa catgtgttct ccccagattg ggaaaccatc ttgaaagact tcatcacaaa    180

aaggccttgg gtgggaagta ccacaaggga cccatccagg aggggtggga ggaggtgcag    240

ctgggtggga agctggcaat ggactgtgag aggaaaaaac aaagggcagt cagcgctctc    300

rtggcagatt cccaagagag aaccctttcc aggaatttaa aattctgaat aattgttgag    360

aatttctaaa aatcaagaag attataaact tttctttcag gggattccac agcattgaga    420

gagaccagat ggctggcaac aaaattccag atccaggaaa ggtccagcat ctacatatcc    480

atccactttt agtgagctaa tgctttctcc tacagagtgt atttgtctaa ttgaattgaa    540

ttgaattgaa ctgaggtgtg gaggtaaaaa ggctattgca aataagtgtt cctgtttcca    600

a                                                                    601


<210> SEQ ID NO 297
<211> LENGTH: 1001
<212> TYPE: DNA
<213> ORGANISM: Homo sapiens

<400> SEQUENCE: 297

taattgaatt gaattgaatt gaactgaggt gtggaggtaa aaaggctatt gcaaataagt     60

gttcctgttt ccaaatagtc catacaaaaa cctgcagttt cttgccaagc agaaactacc    120

aggctttggt ttcctcacta tagaataaat ttaaactcta aaataaccag ggaggcaaca    180

tagtagagtg ggttaagagc acaagcttgg cagtaaatag acgagagttt gaattttagc    240

ttggctgctc tccagatgtc agtctttgac ctcagaaagc ctcagtttct tcatctacag    300

aatggagatg cggaaagtgc ctagttcaca gagttgaact gagatgagat gagatgaatg    360

ggtgccaagt gctttgcact gtgcatgatg cagaatgaag actcagtaac ccttcactgc    420
```

```
tattattgat tttaaaaatc agaattgtga cttcggattt agtgagcata aaattttcat    480

gaatgttaat ccaaactgta rtatatagta ttcttatgaa gaaatgagga cacagtgtcc    540

tatcttcatg tgcgctgtta aaatcatgac atagtgacaa agataagttt tggtctaggt    600

atgcaaatca tgcaaatcct tgacaccatc cctcttggat gaaaggggat taattcccac    660

tatatagatg tgagatacaa ttatgaaagt tctaatcata tactcacagc tacattacaa    720

attagcagca aagagaatat gtaccctctt gaatttcttc cagtattggg ttctccactc    780

tctggattgc acgtttgata gccaatgatt tttgcaacct aaacaaaata agaccttctt    840

aagcaactgg cctcagcatt tgactttcaa tctgggaaga atcccacatg ctattcaata    900

tgccccccata gcactctgcc taggtacttc ccaaactagc acccattagg cagcacctta    960

ctgcactcac ttcacagaag tctttttcta tgttattgca t                       1001
```

<210> SEQ ID NO 298
<211> LENGTH: 1001
<212> TYPE: DNA
<213> ORGANISM: Homo sapiens

<400> SEQUENCE: 298

```
tgatggggac atactccaaa atgtacatgg ctgagtcctc ttgctctcct tttttttttt     60

ccccagtgac tttggggagg tttgggcagt gatcctgcat acacaatact gttcttgttc    120

ttcttttctc ttacagagca gccttgaata gctctgtcta aaattattag caggggcagc    180

cctaggctcc aagagatcac agccctcatg ctgggcctga acaaagaccc tgctttttcc    240

caacaattag ccctgcaaaa aaggacatct atctccctct attaaaacca ccacgtgcct    300

tcaagtcagc ccattgtaaa gctaattaaa taacacgcct ctctccccat gcaggtctcc    360

tgattagctt tcctctgtca gaaacctctg caaagagcct agtgatagac aagccaatgt    420

tccacttctc cttagccccg ctcccatcgc caattagccg tcgcctttga aaagccatcc    480

ttatcaatgt tggtgagttt rttcacgctc catatccatc caaagcccag acgctagtca    540

cctccacctt aaaggaatgg ataaggttca tactgctttt aaaataaatt atttggaaag    600

gcaaaagttt tcatcacagt gtaaaatctt tggccagcat tccccacatc gcaatacaca    660

agggctgccg ccgccattgc aggagagtgt cagagaagga cttttctgaa agtcagagag    720

cctgggcaag atgcagccaa ggtggccatt tctaccagat ttctaaaaac aggatgcaga    780

agaccaccct ttaggttaaa ctcccttaga tactcctcac cgccaaacag ataaaatcca    840

agcacagtcc aaaaggccaa aattggtcct ctttaccttt tgaccacacc tcaccttctc    900

ccccacatag ggaccctgct ctctgacaat cctggacttg tggcaatccc ttgaacacac    960

tctagttctt cactctttta tgcattttta caggcttttt t                       1001
```

<210> SEQ ID NO 299
<211> LENGTH: 1001
<212> TYPE: DNA
<213> ORGANISM: Homo sapiens

<400> SEQUENCE: 299

```
ggcagtaagt tctttattac tctcccttac cacagtgtgc ctccattctc agatgtttcc     60

ttaaagaaga gtaatctaag acctctaaat acataaaaaa taggataata agtaaagaca    120

aagagaccct catttttata tagatttgtc tcctccagat gcagcttggc atgtatacat    180

gtatacaaag cagccattga gaattaagca tgtgaaaatc acacctgtta atttgtcaag    240

gacagaccaa gtaaactata aggcagaaat aaaactgttt caacaaagat aaatggaaaa    300
```

catggttgaa aaagaagaat gatttggaat gaatgtcata gtattaatca aataaaaata 360
taagatgcat atagtcaata taatttattc aaatagtaag aagagaagaa atatgtatca 420
taaatgaaca ttatcatgag atattgggta caagaattca atacattggg taaacagact 480
gtagagatct taagagctta rgatttcaga gaatagcata cattctgtgg tctagaaaaa 540
gctgttttct gatccaattg agactgtgag caatgttaag aggcataaca gccaaatcaa 600
gacacacaag aagcctctca ttaggaggag aaagagcttg gaattggttg aagggagcag 660
ccgtgttgac agttcatgtc aatacattcc agttagcagg ttatttaagc aatgacttca 720
ggctaagctg gccttgtaat tctgcaaatc agatcccata gaagagcaat tagcagacat 780
tcatttcata ctctcttcat aaagtttggg tcattttaaa ttttttatgt gtcaaacttc 840
agaagtaaat atgaatacac atcacctctt tcctttgatt aaaacaatag ggatgcttta 900
ccttatttag catgaaagat cacaaaataa ttccaacatc acctcacagc acctctgaga 960
aatgcctaag aggtgggaaa ggatcccagc ctcactgtat g 1001

<210> SEQ ID NO 300
<211> LENGTH: 1001
<212> TYPE: DNA
<213> ORGANISM: Homo sapiens

<400> SEQUENCE: 300
atagtattaa tcaaataaaa atataagatg catatagtca atataattta ttcaaatagt 60
aagaagagaa gaaatatgta tcataaatga acattatcat gagatattgg gtacaagaat 120
tcaatacatt gggtaaacag actgtagaga tcttaagagc ttaagatttc agagaatagc 180
atacattctg tggtctagaa aaagctgttt tctgatccaa ttgagactgt gagcaatgtt 240
aagaggcata acagccaaat caagacacac aagaagcctc tcattaggag gagaaagagc 300
ttggaattgg ttgaagggag cagccgtgtt gacagttcat gtcaatacat tccagttagc 360
aggttattta agcaatgact tcaggctaag ctggccttgt aattctgcaa atcagatccc 420
atagaagagc aattagcaga cattcatttc atactctctt cataaagttt gggtcatttt 480
aaatttttta tgtgtcaaac ytcagaagta aatatgaata cacatcacct ctttcctttg 540
attaaaacaa tagggatgct ttaccttatt tagcatgaaa gatcacaaaa taattccaac 600
atcacctcac agcacctctg agaaatgcct aagaggtggg aaaggatccc agcctcactg 660
tatgcagtat ctgtccaggg tacagagact ctctccaatg ttttgcacaa ctttgatcca 720
agtcagctgt gcaaaatact gaagatgcat attagctcaa ctctttcaaa tcattcatgt 780
gtccaaaatc actttcacct accaaagtcc ttaaaatgtg attttctcct gccaagtctt 840
tagtcgtcat ttgttggttt ttttaattag accttttatc actatgtacc ataatttacc 900
tgagacatta ttttcccact aacacagagt gtgtaggggg agagggaggg aaagcatggc 960
atggtgaata aagagactat taatccacta attcctactt g 1001

<210> SEQ ID NO 301
<211> LENGTH: 1718
<212> TYPE: DNA
<213> ORGANISM: Homo sapiens

<400> SEQUENCE: 301
gaggaaccac ttaatacaaa taattatttt gccatagatt aaggaggtag ttcgtaggtg 60
acatatgtat ttaaaaatct ctatccacga cagtggacag acaatggaga aagaatactc 120

```
ttttaacaaa taatagggga gaaccagata cacatacgaa aaagaaagaa actagacctt    180
tgtgcataaa agttaactct aagtggatca gagacataaa tgtaagagct aaagctataa    240
agctcatata agaaaaaaca ggattaaatc ttcataacct tgtgttgggc aataatttct    300
taggtacaat gctaaaagca ctagaaaaac aaagaaaava tagataaatt gggctatatc    360
aaatctaaaa cctatggtgc tgcaaattct aaacatccag aaagtaaaaa gacaactcac    420
tttatgggag aaatatttgt aaattatatg cccgataagg gcttgtattc agaatatgta    480
aagaactctt acaactcaac aataaaaaga caacccaatt taaaaacggg ccaaggattt    540
taatagacat ttctccaaag aaggtataag aatgactggt aaacacgtga gaaaagctca    600
atatcattaa ttattaaaga aatgcaaatc aaaacgacaa tgaaatacta ctgctcattc    660
accatgagga taaattggaa ccctcttaca ttgctagtag gaatgtaaaa tgaagcagcc    720
actttcaaaa acagttgggc agttccacaa atagagttac catacgaccc agaaattcta    780
cccctggaga aatgaaaaca tattcacaca aaaaacttgt acattaatgt taatagcagc    840
cttatttata ataaccacaa agtgaaaagc acctaaatgg ccatcaaatt atggataaat    900
aaaatgtgcc atggccatat aatggaatat tattttgatg ataaaaggat atactgatgc    960
ctgctacaac atgggtgaaa cttgaaaaca ttatgcttag tggccagtca caaaggtcac   1020
atattatata actctactta tgagaattcc agaataggca aatttataaa gatagaaatt   1080
agaccagtag ctgttgaggt gtggagacag gaagaatgag aaagaatgaa gatcgactgc   1140
taatggatat aagatttctg ttaagaagaa taaaaatgtt gctgggcgca gtggatcatg   1200
cctgtaatcc cagcactttg ggaggccaag gcgggcggat cacctgaggt caggagttgg   1260
agaccagtct gaccaacatg gtgaaacctt gtctctatta aaaacacaaa acattagcca   1320
ggtgtggtgg caggcgcctg ttatcccagc tactcaggag tctgagactg gagaatcact   1380
tcaacccagg aggcggacgg aggatgcagt gagcggagat tgtgccattg tactactcca   1440
gcctgggcaa caagagagaa attccatctc aaaaaaaaaa aaaaaaaaga agaagaagaa   1500
aaatgttcta aaattaaatt gcaatgatag ctgcacaata ctgtaaatac actaaacaga   1560
actgtacact ttaaataggt gaattgtata gtatgtgaat tatatctcaa taaagctcac   1620
ctcaataaac cgtttaaaaa aaaaagttgg ttttctggag gtgaaggcaa gacaaaaaaa   1680
gagggagaat ttcctatcat ccaggaaagc ctgcccag                           1718
```

<210> SEQ ID NO 302
<211> LENGTH: 1719
<212> TYPE: DNA
<213> ORGANISM: Homo sapiens

<400> SEQUENCE: 302

```
gaggaaccac ttaatacaaa taattatttt gccatagatt aaggaggtag ttcgtaggtg     60
acatatgtat ttaaaaatct ctatccacga cagtggacag acaatggaga aagaatactc    120
ttttaacaaa taatagggga gaaccagata cacatacgaa aaagaaagaa actagacctt    180
tgtgcataaa agttaactct aagtggatca gagacataaa tgtaagagct aaagctataa    240
agctcatata agaaaaaaca ggattaaatc ttcataacct tgtgttgggc aataatttct    300
taggtacaat gctaaaagca ctagaaaaac aaagaaaaaa tagataaatt gggctatatc    360
aaatctaaaa cctatggtgc tgcaaattct aaacatccag aaagtaaaaa gacaactcac    420
tttatgggag aaatatttgt aaattatatg cccgataagg gcttgtattc agaatatgta    480
aagaactctt acaactcaac aataaaaaga caacccaatt taaaaacggg ccaaggattt    540
```

taatagacat ttctccaaag aaggtataag aatgactggt aaacacgtga gaaaagctca 600
atatcattaa ttattaaaga aatgcaaatc aaaacgacaa tgaaatacta ctgctcattc 660
accatgagga taaattggaa ccctcttaca ttgctagtag gaatgtaaaa tgaagcagcc 720
actttcaaaa acagttgggc agttccacaa atagagttac catacgaccc agaaattcta 780
cccctggaga aatgaaaaca tattcacaca aaaaacttgt acattaatgt taatagcagc 840
cttatttata ataaccacaa agtgaaaagc acctaaatgg ccatcaaatt atggataaat 900
aaaatgtgcc atggccatat aatggaatat tattttgatg ataaaaggat atactgatgc 960
ctgctacaac atgggtgaaa cttgaaaaca ttatgcttag tggccagtca caaaggtcac 1020
atattatata actctactta tgagaattcc agaataggca aatttataaa gatagaaatt 1080
agaccagtag ctgttgaggt gtggagacag gaagaatgag aaagaatgaa gatcgactgc 1140
taatggatat aagatttctg ttaagaagaa taaaaatgtt gctgggcgca gtggatcatg 1200
cctgtaatcc cagcactttg ggaggccaag gcgggcggat cacctgaggt caggagttgg 1260
agaccagtct gaccaacatg gtgaaacctt gtctctatta aaaacacaaa acattagcca 1320
ggtgtggtgg caggcgcctg ttatcccagc tactcaggag tctgagactg gagaatcact 1380
tcaacccagg aggcggacgg aggatgcagt gagcggagat tgtgccattg tactactcca 1440
gcctgggcaa caagagagaa attccatctc aaaaaaaaaa aaaaaaaaga agaagaagaa 1500
aaatgttcta aaattaaayt gcaatgatag ctgcacaata ctgtaaatac actaaacaga 1560
actgtacact ttaaataggt gaattgtata gtatgtgaat tatatctcaa taaagctcac 1620
ctcaataaac cgtttaaaaa aaaaagttgg ttttctggag gtgaaggcaa gacaaaaaaa 1680
gagggagaat ttcctatcat ccaggaaagc ctgcccagt 1719

<210> SEQ ID NO 303
<211> LENGTH: 1799
<212> TYPE: DNA
<213> ORGANISM: Homo sapiens

<400> SEQUENCE: 303
gaggaaccac ttaatacaaa taattatttt gccatagatt aaggaggtag ttcgtaggtg 60
acatatgtat ttaaaaatct ctatccacga cagtggacag acaatggaga aagaatactc 120
ttttaacaaa taataggggga gaaccagata cacatacgaa aaagaaagaa actagacctt 180
tgtgcataaa agttaactct aagtggatca gagacataaa tgtaagagct aaagctataa 240
agctcatata agaaaaaaca ggattaaatc ttcataacct tgtgttgggc aataatttct 300
taggtacaat gctaaaagca ctagaaaaac aaagaaaaaa tagataaatt gggctatatc 360
aaatctaaaa cctatggtgc tgcaaattct aaacatccag aaagtaaaaa gacaactcac 420
tttatgggag aaatatttgt aaattatatg cccgataagg gcttgtattc agaatatgta 480
aagaactctt acaactcaac aataaaaaga caacccaatt taaaaacggg ccaaggattt 540
taatagacat ttctccaaag aaggtataag aatgactggt aaacacgtga gaaaagctca 600
atatcattaa ttattaaaga aatgcaaatc aaaacgacaa tgaaatacta ctgctcattc 660
accatgagga taaattggaa ccctcttaca ttgctagtag gaatgtaaaa tgaagcagcc 720
actttcaaaa acagttgggc agttccacaa atagagttac catacgaccc agaaattcta 780
cccctggaga aatgaaaaca tattcacaca aaaaacttgt acattaatgt taatagcagc 840
cttatttata ataaccacaa agtgaaaagc acctaaatgg ccatcaaatt atggataaat 900
aaaatgtgcc atggccatat aatggaatat tattttgatg ataaaaggat atactgatgc 960
ctgctacaac atgggtgaaa cttgaaaaca ttatgcttag tggccagtca caaaggtcac 1020
atattatata actctactta tgagaattcc agaataggca aatttataaa gatagaaatt 1080
agaccagtag ctgttgaggt gtggagacag gaagaatgag aaagaatgaa gatcgactgc 1140
taatggatat aagatttctg ttaagaagaa taaaaatgtt gctgggcgca gtggatcatg 1200
cctgtaatcc cagcactttg ggaggccaag gcgggcggat cacctgaggt caggagttgg 1260
agaccagtct gaccaacatg gtgaaacctt gtctctatta aaaacacaaa acattagcca 1320
ggtgtggtgg caggcgcctg ttatcccagc tactcaggag tctgagactg gagaatcact 1380
tcaacccagg aggcggacgg aggatgcagt gagcggagat tgtgccattg tactactcca 1440
gcctgggcaa caagagagaa attccatctc aaaaaaaaaa aaaaaaaaga agaagaagaa 1500
aaatgttcta aaattaaatt gcaatgatag ctgcacaata ctgtaaatac actaaacaga 1560
actgtacact ttaaataggt gaattgtata gtatgtgart tatatctcaa taaagctcac 1620
ctcaataaac cgtttaaaaa aaaaagttgg ttttctggag gtgaaggcaa gacaaaaaaa 1680
gagggagaat ttcctatcat ccaggaaagc ctgcccagtg gggtctatga acatcatctt 1740
aagaccatat gcttcaccaa agttcagtgg aaaaatgtct aacatttcca tgaccttct 1799

<210> SEQ ID NO 304
<211> LENGTH: 1001
<212> TYPE: DNA
<213> ORGANISM: Homo sapiens

<400> SEQUENCE: 304
taaatatttg tatcctggtt gtccaaactt gtcctagcta gtggagggat ggttggtgtc 60
ttggtcctca gttagatcat gggtaattcc aagttactga ctggtttagg gtgtcagtga 120
cattagagca tctttacttt gtcccctatt aatcaacaca tatttattaa gcccttgttc 180
ttcatgaggc gttggggcta tgaagtgtgg ttcagtctca tcctcaagga acatcacgca 240
acctggctgc cgtgctgaga cggacacagc caagctgcag agctggtgag caccagggga 300
ctgggaatga tgagagggat ggtcctgttg agactagaat tatggagaga ccctcctgag 360
gcctcccagt cacgtgaaac tgagggtgag gggtttgcc ttgaggagca ctcattcatc 420
caaacttagt tggcagaatg aggacagagc tcgatttgga aaggggtgt tttactggtg 480 tttggaagag tggccactcc rgctctgctt tatgtatcct tgagcgttgt tattctttct 540
tctctctcct gtgttgattt tcacctccct caccctggtc tggcctctcc gtggccttcc 600
tgccgctttc agagatgagc ttagactcca cacggggctc ccaatctgaa tgaaatatcc 660
cattcctggg accgctgctc cctcacttca ttagtgctcc ttgctgttta taaagccagg 720
agataatatt tttaaattcc atttggagtt tcccgggcag cctctctcta agccacttag 780
gaagtttaga aaagaaggtc atggaaatgt tagacatttt tccactgaac tttggtgaag 840
catatggtct taagatgatg ttcatagacc ccactgggca ggctttcctg gatgatagga 900
aattctccct cttttttgt cttgccttca cctccagaaa accaactttt ttttttaaac 960
ggtttattga ggtgagcttt attgagatat aattcacata c 1001

<210> SEQ ID NO 305
<211> LENGTH: 401
<212> TYPE: DNA
<213> ORGANISM: Homo sapiens

<400> SEQUENCE: 305
aacatcttta cctttgagaa acttgacaaa gagcagcatg aaaaatcatc tccacttggg 60
agtttatgta cttcagttta aggaaaagga aggccatgtc tctttgctat gaagaagaga 120
cattctgatc ttcaggctat gagcaaatgg agaaggcctc agatgttaat aagatgtaac 180
ttgtagcaag cagagaccat ygagagctgc aagtgttaaa gcaaggcagc tttaatctca 240
gttgcattgg gagatataag acttaagcct tgtggcatta ataggattca agaattatac 300
aaatataaat acagccattt tgaccttttg cttatacaaa caaaacctat tttgtttaga 360
attttaaagg atcacttttc tcatgtcctc aaatttttag t 401

<210> SEQ ID NO 306
<211> LENGTH: 401
<212> TYPE: DNA
<213> ORGANISM: Homo sapiens

<400> SEQUENCE: 306
ggcagcactg ccaccagcaa gtggaaggag agaagggaga gagagacaga ggaaaaagaa 60
ttgggatcca ggtgggcatg gacagagagg ccaggaacaa tggaaacaga tgatcatcga 120
aagaaagcat gttctctaag aaggccgagc aattcacaca cctctgttta tccagctcag 180
actctgtgac tgcaaaactt ytaggctctc tgacaacagc caaaacgggt gtcaggaaat 240
gcaggatagg caaaactatt tgcaaggtga agacctaaag caacctttct tgggcccatt 300
cctagagttt agacttcctg tcggggaata aagtaaccca aaatttatgg agaaggcccg 360
ggactttcca ttcaagaaca atagcatctg tacccgcata a 401

<210> SEQ ID NO 307
<211> LENGTH: 701
<212> TYPE: DNA
<213> ORGANISM: Homo sapiens

<400> SEQUENCE: 307
ttgtaaggag ttgttatgga tgtgttcccc caaatttaga agttgaaatg taaaacacca 60
atgtgataat attaacaggc ggaggcatta tgaggtgagt aagttgtcag ggcaaagccc 120
tcaaggatgg gactaggacc ctttaaaagg acctgaagga atgggtttgg cctcttccct 180
cccttccgcc actgaggaca cagcgttcat cccctctaga gaatgcagca ggaagggtcc 240
atcttggaag ctgagacggg actctcacca gacacagaga ctgccaatgc cttgatcttg 300
aacattccag catccagaac ggtgagcaat aaatttctat tctttttgaa ttacccagtc 360
tcaggtattt tgttatagca gcactaatgg accaagacag gagtgctata acaaaatacc 420
tgaggaaact ccagtaattc atttaacctc ttaggatctg aatttcctga tattgcaaga 480
tggtctttac attgtggtct sactctgaaa ttctctagct tgtgatgatt gaacctagta 540
gcttacagaa gccccacagt ccaagatgct ggaaaaatat aggttatttt cttctttcct 600
tcaatttctg tgacaaccac taagagttat gagcataaat aatttcccta aacattatgt 660
ttcagcagtc tcattcccac tttggtttta aatttctttt t 701

<210> SEQ ID NO 308
<211> LENGTH: 401
<212> TYPE: DNA
<213> ORGANISM: Homo sapiens

<400> SEQUENCE: 308
tgaggagttt ttaatacagt tacttcaccc tcaaattacc aggaatgtcc cttaagccca 60
gagtcttatc ataggaaatt ctggcacttg gggatatgta gttagcctct tgggcatagg 120
tgccttccct gaggtggagc acagtgggcc actcctgccc gagcatgttg ttctatctcc 180
caaagtctgt ggctctggga rgaggtgagt gggcagttcc tttcctctgt acagcccaag 240
gtgtttccta aagcccgcat ggccaaaggg gtcactagtc ccccaggaac tcctccgcac 300
atcctccttg ccggtgagac atcccaggct gggccatgtt tagtcaaaac tgagagcagc 360
ccagcccgct cattcccgcc actctcagct gggccagcac a 401

<210> SEQ ID NO 309
<211> LENGTH: 1001
<212> TYPE: DNA
<213> ORGANISM: Homo sapiens

<400> SEQUENCE: 309
taggatgaca ttatattata tctgcaactt ttatacttat aataggcttt ttatctcagt 60
gtctaaacta agtacatatt tgtgtgacat ttctttcttt ctttcttttt cttttccttt 120
tttttttttt tttagatgga gtcttgctct gtcacccagg ctggagtgtg caatggcaca 180
atttcagctc actgcaacct ccacctcctg ggttcaagcg attctcatgc cacagcctcc 240
tgagtagctg ggattacaag gcatgtgcca ccacacctgg ctaatttttt ttgtattttt 300
agcagagact gggtttcatc atgttggcca ggctggtctc aaactcctga cctcaactga 360
tccgcccgcc tcagcctccc aaagtgccag gattacaggt gtgagccact gagcccagcc 420
atggcatttc attcttagcc aaaatattaa tctgttttaa tttgattata gtacctgtaa 480
atagaattaa catggactgg yttttaaatc ttatttttca agtcaatgac acattttgct 540
ctgaaatcac aatatcatta tttattttaa caaatttcta caatatcgtc tttaaggaaa 600
ttttaatgtc atttgtgtta actttaaata atgacctcta tgtgaggaaa aggaggagga 660
gcccttttct ggcaacttct tcagccctcg atatgatctt aaactgcaag tcctttggca 720
atcgctacta agcaaactcg agtgactcct tgcctggact tgtcgtgtag tggagtgttg 780
gggagtgggc agtttaaaca tatttctgat atatattatc gtctaaacct ttttctgatt 840
ctaatttttt gtaaaagtaa acggtgctta catgaacaca gaagccattt taaaaagaag 900
aaaaatgtgg taaaaacagc tactgaagag agatgtctca atcatcctta aaatgtgtct 960
tttcccttga acagaatagc tactgagagt ttttggtttt t 1001

<210> SEQ ID NO 310
<211> LENGTH: 401
<212> TYPE: DNA
<213> ORGANISM: Homo sapiens

<400> SEQUENCE: 310
tgacacattt tgctctgaaa tcacaatatc attatttatt ttaacaaatt tctacaatat 60
cgtctttaag gaaattttaa tgtcatttgt gttaacttta aataatgacc tctatgtgag 120
gaaaaggagg aggagccctt ttctggcaac ttcttcagcc ctcgatatga tcttaaactg 180
caagtccttt ggcaatcgct rctaagcaaa ctcgagtgac tccttgcctg gacttgtcgt 240
gtagtggagt gttggggagt gggcagttta aacatatttc tgatatatat tatcgtctaa 300 accttttttct gattctaatt ttttgtaaaa gtaaacggtg cttacatgaa cacagaagcc 360
attttaaaaa gaagaaaaat gtggtaaaaa cagctactga a 401

<210> SEQ ID NO 311
<211> LENGTH: 401
<212> TYPE: DNA
<213> ORGANISM: Homo sapiens

<400> SEQUENCE: 311
aggtatgtca cccagtaacc caagaaacag ataaacagag agaaaccctg caaaagggat 60
tgagcattat tgatcttgaa aaaaggagaa gggctattaa ataacttgtt gagagctatt 120
ttctacattg gaagtctgag tgtctagaat gcttgagcaa ttttctggct gaagggattt 180
tccagttagc tactggtcat yattacatat cgaacatctc tgttgaccta aatactttcg 240
aaagttcatt acacactttc ataaacttaa tactatgcat ttaaaaagtc gttcttgaat 300
aatctcgaag attaaattcc taggcatacc aatcagaggc caaattctta ttgttaggaa 360
gtgacgcttt aacttcactg ctttccagtt tgtatttgtc t 401

<210> SEQ ID NO 312
<211> LENGTH: 1001
<212> TYPE: DNA
<213> ORGANISM: Homo sapiens

<400> SEQUENCE: 312
tcttaggtct aggaatctaa ctaagaaaat gccaattcta gtctctgaaa cctttgaaat 60
actaacaatc tacactttct agtcaatcat acttctgtca gaacatcttc ctgaagatca 120
aaggtaatat tcaatacact gccttaccat aaaagtggcc atagcctgtg tacaaatgct 180
atgcctcaaa tcctgtattt taccatgaaa ttcaacaaat gatcacactt ggccttagga 240
tgtactcctg agccagaagc atggtaagta ctcataaata actgaataaa taaataagga 300
ttgtgtttta cttcgaacct caaaacaaaa aaagaataag ctggaggaat aatgtagagt 360
actctttgct ttccaagaat ggtcgtaata gaggccatgg aataagagat tgttttccaa 420
gtcaaatgca aagaagggcc acgagattaa aaacgtcaac tctaatccaa tgaatgctgc 480
caatgaaacc tctgaagaga ytagcatttt aaagaattac attacagact cttagcctgt 540
gaagcatgtc agacataatc tagagtttag acttggctct ggctctaaag gaattctcaa 600
caaaactgag aggcaccata aatagaaaga gatattacaa gaacaatgag aggggactgg 660
atagttgcaa taatgcccct ttaaaattga actaaaagat accagctgcc ttagatctct 720
caaatccagc aagcaacttc ttggactatg tctgattgtg attttcatgg tggagtttca 780
tttgttttat tacccgaaat gtaaggttcc aatttctcag tataatgcta aacagcttgc 840
tagcattctt atataaagag ggattgtgca attccagtga attttggagt tggaaaaaat 900
tcatcaatct tctcatttat ttcaatgaac tgagtcctaa gaggttacgt gtttagcagt 960
gatcaagaac cctggagtta catactatgg gtgaacgtag a 1001

<210> SEQ ID NO 313
<211> LENGTH: 401
<212> TYPE: DNA
<213> ORGANISM: Homo sapiens

<400> SEQUENCE: 313
actgcttgct gcgtgtatgg ccatgagcaa atttcttaac ctcacaatca gtttcctcaa 60
ctataaaatg caggtaataa tatcaacact ttcaggatta tagaggagga tcatacaaaa 120
cacaaatact tagcagcatg ctgtataaat agtaaaaatg gtcaataaat aataattgtt 180
attattgcta ttttatcagt mgtgcctggc aattagtaag cattagtaaa tgcttactaa 240
tgtcactaat tagtaacact actgttttat attaattact tttttctact gcccaacatg 300
gcagaggtta tttaagtgtt agagctagaa catggatagc taaatctctc atctcttttt 360
ctaaagactt gtattcaagt catgaaaaca ggattccctt t 401

<210> SEQ ID NO 314
<211> LENGTH: 401
<212> TYPE: DNA
<213> ORGANISM: Homo sapiens

<400> SEQUENCE: 314
taaagacttg tattcaagtc atgaaaacag gattcccttt cataatcata ggttgagtag 60
cattagtcaa gaattttgca ggagaaaaga gccacaattt ctgtttaatg gtagtctgtt 120
tgtaccattg ttatgcataa aaccaagaag taagcatttt tcttacagtg gagaactaac 180
tcattgaaag attgcatagc mcaaatggtg aaatattgca gcttcctgag ttaaaccaac 240
atctttttga tataatgtcg atcttttgtg gacttacgct ttagcaacta gatacaaata 300
taaggaagta gtaaagcact gcggaaaata gtgcaagatt tcttgtttgt tcattttttt 360
catttttgct ttttcatttg tttttgcttt ttctttagag c 401

<210> SEQ ID NO 315
<211> LENGTH: 713
<212> TYPE: DNA
<213> ORGANISM: Homo sapiens

<400> SEQUENCE: 315
ctcttctcat tgagatggtg aaaaataaaa tgagaaaata gagagagaaa atgctttgaa 60
agaagaacac tttgcatatg aaagaaattg gagattttgt ttatgatagc tcagatgaat 120
cctgccttgt ctcattgcaa cagcctgtta taatatttca ttgttggaac tgaaattgcc 180
tcataataga caagtgtcat aggacttgga tcagtagata aacactacag ggaagcctat 240
ttcagatcaa aatggtgaag tgcttttgaa catttagaga gcttttgaat atttggagcc 300
attcaaaaac aaaatgagtg cctggaaagc actgaataag ttgaaacaga gctataagac 360
cagctagcag agatgctgta gaaaagtttc ttgcactgga mcagacaaca gctaacattc 420
tatcccagta agaatctggg aattcactac aatgattttt aatgctgctt ttaaataggt 480
gaagggctgt aatgtagaag aggaagtgtt ttctttcaga ttatcagact aagcccagtt 540
gatggaaagt ataagaagac gaactttggc acaatgcagc caatgcaaca atattcacaa 600
tattcatggc atttagaaat gccatataat taattttttc aaagtcgggt agatgtgaga 660
ataatctgac caaagctaat ccaccagtgt tagacctcaa actttagatt ctg 713

<210> SEQ ID NO 316
<211> LENGTH: 610
<212> TYPE: DNA
<213> ORGANISM: Homo sapiens

<400> SEQUENCE: 316
ctggctctgt tctatgccac ccacagcaat gggctagata cactctctga atgccaaact 60
tgtgcttccc aggcaccctg ctgccaaaat atagctggag aaagcagcca gagaacccca 120
tagtcaaggc aagcacaaga gcttaactgg agacaagact gtggggttga aagggaggga 180
gatgaatcct cttagatgtg tgttgactcc ttcctaagtt caaagcattt atgcttttaa 240
atcatctctc ctccaagtaa atttgtggga caagctgtat tttctccact taatagacga 300
tgaaattgag gctcagattt gatttggatc atagccagtt tgcatagata gcaccagatt 360
ctattccttg gccttctcac ttcagggact ttttcctara ccacattacc agtagatgtc 420
attctttgac cagcagacaa atgccagaga gtagaaattc tagccacttg gctgaaagtt 480
caggttcagg gagtatcttc aagagaggga gggactcgag accagtgtgc ccagctcctt 540
cgcctctgcc ccacccagag ctgagggcct ggacctcatg tgccctcccc acacggtgcc 600
tactttctct 610

<210> SEQ ID NO 317
<211> LENGTH: 401
<212> TYPE: DNA
<213> ORGANISM: Homo sapiens

<400> SEQUENCE: 317
tagaccaggt gggttcaaat ttcccctatt ctaattttaa tttccacatg atcagaataa 60
acatggctgc cttgagatct cattttccag tgctgccaga aatgaaaatt ccacatagcc 120
tagtggacct tcccacctcc tttcactgga cagcttgctg tttagaggct cctgccattc 180
ttaacacggc agctgtcaca rcagttagcc atggaaagac ccattctctc atttgatccc 240
atctccctgc caggacagga tataggcctt aaaagtgctt cctggtgtaa ggactgagtc 300
ggggtttatt tatcctaggt tacagcaaac attacttcaa aaaacaggaa agagagtctc 360
atcttgttga ttatgatacc agttatagca atgaggtgga g 401

<210> SEQ ID NO 318
<211> LENGTH: 501
<212> TYPE: DNA
<213> ORGANISM: Homo sapiens

<400> SEQUENCE: 318
agaagcatca tgaccaatga ccttggataa ctccactttc ttacagcccc tgcctcaaac 60
agggattaag gaagaaaata atctctggga tgctaccttc catgaatcag ggtctagcac 120
caacaaatat ttgggtatga ttcatccagc atcttcactc tcattgtcat atttgatgtg 180
tgggacaact atatgaatta ggccagtcag ataatactac tttacagata atacaactga 240
agctcagaaa scaggtgcag ttgagagttg agccagatcc ggtttcaaat cctatctgtt 300
ttctataaaa taatggcagc ctcttctgag aatgagaatc tgccccattc atgccaccct 360
aaagagatgg tttgctttac ctgggacttc gagctccacc cttgtggcac agatgtcatt 420
cgtggaggtt aagtgttctt ggcgggcaga ggtttccatg agagctcatt tatgttggct 480
acaagactgt tcttctccta g 501

<210> SEQ ID NO 319
<211> LENGTH: 501
<212> TYPE: DNA
<213> ORGANISM: Homo sapiens

<400> SEQUENCE: 319
cccatggttt ttaggatcct tagccctgcc aatggttatc tgagcagggg aagcatattt 60
gttttaagca actgggagtg tagaagacat gggtgcttcc ttcctgggat ggccaggcaa 120
caagaggcat gtaagaagat ttccaaggaa gagaaggcaa gccatggggc tgagtgggag 180
caagttggtc tgctgggaag gagcagaaat actgaccacc tcaagtcctg aacacccagt 240
ggaggtcatg yctttccatg ggtggtctcc aaattctggg catgcttttt cttcctgttt 300
ccaaatagct tagcaagctt aatccatcca cacaacatgt aataagctct tctgtgttcc 360
agatatttga taagaactga aaataaatga taaagcaaga ttctgttctt aaagagctta 420
tcagaggagt aagtaacaag aaatggtgtg aatttttagc agaagcttgt aaaacatcag 480
acgagaaaaa cacgatatgt g 501

<210> SEQ ID NO 320
<211> LENGTH: 720
<212> TYPE: DNA
<213> ORGANISM: Homo sapiens

<400> SEQUENCE: 320
ttctgttctt aaagagctta tcagaggagt aagtaacaag aaatggtgtg aatttttagc 60
agaagcttgt aaaacatcag acgagaaaaa cacgatatgt gtgttctata tggattggca 120
gggtacatta ttttatacca actcatgacg ttccttaccc atttgatgtg tgttaaatcc 180
tagttcccca agtccataag gagctccttg agggcaggak caagactcat gtttatttgt 240
tcaacgatac ctcacccagc attaagcaca tcaaaagttg ttcactaatc tggacaagtt 300
cttcccctat ctggacatgt ggtagaatcc cactccctgc cctgttgaaa ttgggagtgg 360
tcctaggatg tgctttcact gatgaaattc gaacagggtc acttggcaga aaattagagg 420
accactgaag agtttcggcc tttctgtttg tctctctggc acgtgtcagg tgacagctgc 480
ttatcagcta gggcccggag taactctgat accatggaac aaaacccccct gccagcccag 540 tgttcatgca gcatgagtaa gatgtgttgc ttcaagccac tgaggtttgg ctcttgttac 600
cacagtgtaa cctagtccag tctgcctggt acagaagtgt tccacaaata tttgctgatc 660
tctgtactga tgcctcgatt atagcagata ggtaaggaag taaataaagt aagttggtag 720

<210> SEQ ID NO 321
<211> LENGTH: 501
<212> TYPE: DNA
<213> ORGANISM: Homo sapiens

<400> SEQUENCE: 321
aggccattga cattccatct ctttcagcat ttcttccact ttgaggctgc tttgtggctg 60
ctcaaactca gatttaagtt tgctgtgaac cttagcagtg aatgcctcta tctttgcctc 120 aagactttg tagtcagaat aggcaatgca ataagtagtc ctagatagag aatggtagac 180
aatttaggga agagttaaat gagagattgt ctgaaaaagt gtgcgaagat tggaaaggaa 240
aagttccacc ragacagagc ttcccaggga ttgcagtcaa aaaccactag gaaattgaga 300
tagatggtga tgcctttagg agcttggcct ctggcatcag gcaaacccga ccttgaatcc 360
cagctattca ctcacctact gagtgactga gcaatttact gaacctttct aaccaattca 420
gtttcctcat ctgtcaaaca agagtaagga ttgagctcag ctcttagggc cattgaccac 480
ataggaaagt aattttcctt a 501

<210> SEQ ID NO 322
<211> LENGTH: 501
<212> TYPE: DNA
<213> ORGANISM: Homo sapiens

<400> SEQUENCE: 322
agtagtccta gatagagaat ggtagacaat ttagggaaga gttaaatgag agattgtctg 60
aaaaagtgtg cgaagattgg aaaggaaaag ttccaccgag acagagcttc ccagggattg 120
cagtcaaaaa ccactaggaa attgagatag atggtgatgc ctttaggagc ttggcctctg 180
gcatcaggca aacccgacct tgaatcccag ctattcactc acctactgag tgactgagca 240
atttactgaa mctttctaac caattcagtt tcctcatctg tcaaacaaga gtaaggattg 300
agctcagctc ttagggccat tgaccacata ggaaagtaat tttccttaat aataaggaca 360
catttttata ttatgtgctt ttaaaaggag ccttaaataa agagaagtga gatcattttc 420
cagtgcactt agcatagtaa cgacaacata gaaagcgtta aaaaaaatga cagcttaaga 480
aagcaaagga tgtggaaaca c 501

<210> SEQ ID NO 323
<211> LENGTH: 501
<212> TYPE: DNA
<213> ORGANISM: Homo sapiens

<400> SEQUENCE: 323
tgaaagaggg ctctgcctgg gctcagcttc caggaaactc tcaaactctt gcccagagca 60
tcgtgatgta gccattggaa cctcacgcag gcgatgatga tccttttacc agatatcaga 120
acttacctaa ccttcagcca cttaaaaatg ctctctggaa agtattcaac aagggcttga 180
gaaaccaagg agaccctgat ggaggagatg tcaaataacg tgagagcctt gttctgtcta 240
agctaatttc yggcactttc cagagagtta gaagtgattg gtcttcggtc tgctcagctg 300
actttgaagc attggccaaa gggctcggga caagcaggga gaagctggaa gtcgtctatt 360
gcctccacct gggactgcct caatgtcctt ttgttccagc tggatgtagc cccagaaata 420
gcagtaaagg aaaaacatgt gatttgagtt tccccatctc ccttttctgt gccctctccc 480
ttaccagggg atttttcctg t 501

<210> SEQ ID NO 324
<211> LENGTH: 601
<212> TYPE: DNA
<213> ORGANISM: Homo sapiens

<400> SEQUENCE: 324
tagccccaga aatagcagta aaggaaaaac atgtgatttg agtttcccca tctccctttt 60
ctgtgccctc tcccttacca ggggattttt cctgtgccca ggcaccccat gtttcttgaa 120
gttctgcccc agagacaatt attccctcca gtggagtgga gaaaacaaga gacttggaat 180
taaaagacac atatccaaat ctggatgctt tcacatgcca gttcttatct gattgcccct 240
gagcctcagt ttcctggaaa tagcagtaac caccccacag taggtaatta ttttattata 300
ytatagtact ttaacagatt tgggtttgat ttgaacagca gagataagaa gaattaattt 360
ctgctcttgt agatgaagcg aaatttttca accaggtaaa attccctaac ttgctcactc 420
cattaattcc tccaaccatc cattcactca ataaacatgt attctgagcc tactattgtg 480
ttaagtagca ctaattgacg agagctgaaa gagaattcag accttgggaa tgaggctgac 540
agagaaacag atggtaaagc aggagagtgg ctgcggtgtt taaagcagcc cagcagataa 600
g 601

<210> SEQ ID NO 325
<211> LENGTH: 1001
<212> TYPE: DNA
<213> ORGANISM: Homo sapiens

<400> SEQUENCE: 325
cacagaataa atgcccaaca aataatagcc ataattattc ccattcttgg tcgaccacct 60
taataaaagc taccatagag gcagggaatc agtaagaaga gatgactaag aggatgctta 120
ctgcatgtag gaaaatcagt taatgctcgt gtgactggct tatttccctt tgcatactgt 180
ccttcaggtc catccatgtt gtcacatatg gcacgatttt catttttttt taaggccgag 240
taatattcca ctgtctgtat ctacccattt tctttattcg cccattgatg aacatttagg 300
ttgtttccac atcttagctc atcttgacag tgctacaatg aacatgagca tgttaatatt 360
tctccaagat catgatttca attcttttgg ataaatacct aaaagtggaa tggctggatc 420
ctatattagt tctgttttcc tctttttgag gaacctccct actgttttcc atagcggcta 480
taccatttta cattcccacc rtctgcgcca gagttcgaat ttctccacat cctcaccaac 540
actttttatc ttttgttctt ttgataacag ccatcctcac tattgtaagg tgatatctca 600
ttatggggaa aaattatatg aaaaggaagc atcaaattaa taggcaagaa aaccagtaca 660
tagtatttgg acagttggca tattacttaa aaattatgta tgaatccaaa aaattaatta 720
actcttacta tattagtatt ctgattgttg acattaacct gtaacaatag gagaaaaagt 780
tagttcagga atcacttccc aattacatct gttacaaatg caaggagaaa caaatacaag 840
gagaaactcc tttgcataca atattttaaa gaaaaggaca ggtgagtttt gggatgcgag 900
gagaggggca agaaactgtc ttctgtgtgg agagggatct tgaaacatat cttccaatgg 960
gaggccaaat gcagggggc attgctttca agaaactaaa g 1001

<210> SEQ ID NO 326
<211> LENGTH: 1701
<212> TYPE: DNA
<213> ORGANISM: Homo sapiens

<400> SEQUENCE: 326
ggtcaaatga gcaaaggcac catcccaggc acagaatgtg catcctgtgg ttgttggggg 60
gagtctgtca gagtcttatt ctggactaga gtcaggactg ggtcccataa ggtcagggca 120
gggtgagtgt gaccttgggg ctacaggcaa ggccaggcat ccaaggggtc tcaactgccc 180
caaacaaccc catcctgcca ggccccactc cccctgtccc tccctcccat tgttcagtcc 240
cctcaccccc tcaccatggg cacctgcagt ctcattcaga gacaccctca tcttagagtc 300
cctgatagtg gggagtttgg cccctcagag gccttggttg ctttggtcaa tccataatgc 360
ctgggcctgg gacccccacc atttcttgtt catcagggac acagcagctg tgaaggcagc 420
tgccttcacc agagcagcga tgtagcccag caagggcagg gacagagacg caaggtctgg 480
gggatttttc cacaatgctg cagaaagaaa gtccctgtgg agctcagtct cagccatccc 540
tgccccagct gtgagctgaa ctgaatttca ggcatctcag agtcccttca cctttgcatg 600
acccatttcc aggacatgac aggtcaagcc catgggagag gggatcaccc aggtctccct 660

-continued

```
catctccatg gacctcctgg gaacattgcc agggtccact ccacccctgg acgctgtccc    720

caagcttcac cctcttttta taagttgtac atttttatta tgaagatctt tgaacacaaa    780

aatagggaga tgaaagaata ataatgtccc caaggttccc atcaccgagt ccccataatt    840

tttgattttc aaataatgtt gactcaccca caacagagta aacgattccc tcagacaata    900

gtctgaagca gatgcgaaag ccatcacaaa cttaaatgga gagaatcaat gatttcttga    960

cacgaaaaaa cagttaacga gggtctcacc aaatgtcttg tgaatttcat tgtgtatatt   1020

tttagttgac ttcgtggtgc attacgtatt tgtggattta actttagttt ctatgtggag   1080

taaatacttg atgttatcag tggtgaatgt gtttttagac ccattctatc tacagctgtc   1140

tcccaaatgg ctgtcaggct tttcctggca aggcaggagt ggcaggagca gagagctggt   1200

cctgagaccc tcccacagtc aggatgcagc cactgcctcc ctgagcagga acccagtgct   1260

tcctttagct tctcttttcc tgaaaaattg ttctagcatc aagaggctca gtggggttca   1320

ggctggacat tggcataact gcttcctagg acatgtggtt acttctagca aagccaccca   1380

tgttcatcat tcttttagtg acrttagctg tgtttgatga tcgataactt tgtgcttcag   1440

ataaaaagga agacagaggg ttgaggcttc cattcacctc ctcgtgagag ctgcagtgtg   1500

tcgctgaagg gagggcccag cagctgtgct atgaacctag gagtgtgctt cctgctttgg   1560

aaaaaaggaa gaaaagtagt ttcttccctt ttattcacca ctttgataat ggacgatctg   1620

gtgctcggcc atactcgagg gtgaacagaa caacatagag ccagagtgag ctccagcatg   1680

tgaggacatc tgacatgtgg g                                              1701
```

<210> SEQ ID NO 327
<211> LENGTH: 2000
<212> TYPE: DNA
<213> ORGANISM: Homo sapiens

<400> SEQUENCE: 327

```
ccgccacact tcagcacaaa caggaggagg tggccgtcta gagtctggag tccggggaga     60

ggaggaccgc tcctctcttg gagaccaccg ctgtcactga cgtgtccacc acccaccact    120

ggcagtgcag cccctgataa tgccccataa ctcatcccca tctaggatac tgcagcaccc    180

gatggtgccc acaacctgcc ccctgccatt ggcagtgcag cccaggttaa tgcccccaaa    240

ctgctccctg atgttggcag tgcagccacg gaaagtgccc ccaaccagcc tcccgccatg    300

ggaagtgact cccgggatag cgcccccaag cagaccctag ccttgggcag tgacgcccgg    360

gtaggtcgcc caaccgccac ccaccccgtt gccgagagtg cagcaccaga tagcgacccct   420

aacatgcccc ccatcactgg cggtgtagcc caggatagcg ccgccaaccc ctcacttgac    480

gcgacagtgt agcccctgat agtgcaccca atctgccacc cactgccggc actgcaaccc    540

cggatagtgc acccgacaca ctccctgctg ggcagtgcag ccccccaata gcacccaacc    600

cgtccctcca cccctgccac tggcagtcca ctcccgataa tgcccccaac acgttcctgg    660

ctgtgggcag tgtagtccat agatagcgcc ccaaaccagc ccccagccat gggcagtgac    720

acctcagata tcacacccaa ggagttcccc accatgggca ctgatgtccc agacagcacc    780

ccaactcgag cctcgtgtga ccaatgcagc cacagatagg cccccaacaa gcccccaccc    840

caccactgct gcaggaaatg atgcctggga taacacccaa ccattcccca ccgtgggcag    900

tgcaacaccc agtactgccc ctaacacacc ccccacacaa gatggcgccc ccaatccccc    960

cctcaccttg ggcagtgtag ttcacgatag tgcatccaay ccttggcccc tgagctcact   1020

gcccctctcc ccccgccaca agtccctgga tagctcacct actctgccac ctttctacca   1080
```

```
ctttggctgt gctgtactct acctcactgc caccagccac agtgaggcga gccatgctgc   1140

tgcaggctca agcctccagc atgccaccgg tgacaactcc ttctctaatc tggggtcgga   1200

acagatgggc gggcagacgt agaagaacct ggaatggcaa gactctcgct tacaaaggtt   1260

atgcaaatta ggttcctgga ctacatgttc tgattggatg agagaaaaat ctctaggtct   1320

actatgattg ggctttattt tcgtgttgtg actggatgag aggaagtctt aggataacca   1380

atcagaacat gataacaaag tccaatcaga ctaggcctag aggtttctct tgtccaatca   1440

gaacatgtag tccaggaact tcatttgcat caactccaca tataaaggat gccaagtgag   1500

gcggctcctc attctaggct cttcagtgtc cactggtgta gctgctccat tccaggctta   1560

caggagaagg aggaggaggc acttgccacg cacgctggag actcgagcct gccttggctc   1620

cccttgctgc tgtggttggt ggtggcaagg aagacgacag tgcagccagg atggtaaaaa   1680

ggtggtggga taggttcgct atcccaggag gtactgcctg aggcatgggg ggtgggttgg   1740

ggtccctatc cagggcgtca ctgcccgtgt tgaggggctg gttgggtgtg ctatctgggg   1800

catcactgcc tgtggagggg agtgggttgg ggccctatct ggggtgtgct gcccgtggct   1860

gggggtgggt tggggcacta tcccaatctg tactgctagc ggcagtgggt ggttttgggg   1920

ggcactatct ggggatgcac tgcctgcggc cagggggtga gttgggagaa ctatcgggtg   1980

ctgcaatgcc cttgttgggc                                               2000
```

<210> SEQ ID NO 328
<211> LENGTH: 1001
<212> TYPE: DNA
<213> ORGANISM: Homo sapiens
<220> FEATURE:
<221> NAME/KEY: misc_feature
<222> LOCATION: (501)..(501)
<223> OTHER INFORMATION: n is a, c, g, or t

<400> SEQUENCE: 328

```
gttggaatca tttacttgca gagaggtgtg tgtgtgtgtg tgtgtattta tgtgtgtact     60

catgtgtata agaataggag aaacactttg tgggcatatc ctgctgaggt gagtaacgtg    120

ctgattagtg aactccagtc tcatcccatt taaacctgga ggagaaccac atcaagcaca    180

gaagcagcca aagcagcatt tcaacaggaa ggaaacatct attactgggg ctttgaagaa    240

acatgccatg aaggtgtact aatatcacaa agggaaggga aggactaaat tcagcatgat    300

aaacaaagtc cctttttgt aacggaagtg tttgatgatg tttgatcaat ggtggatcta    360

tctcttgaaa ggaaaatgca tttaaacccc aaatggagga ttcttatata aggtgcctag    420

cttgtaatga tatattcatg tttataggta gagtgactgg tttttagaga agaggttttt    480

ttttttcctt catttttgaa ngaaaacttg tctgtctcta ggctttgaaa tgtagaatta    540

tttacctttc cccaaaatga aatgtttcac tgaatctcct acaagcttgt ggaggccatg    600

aagcatgttg aataagagca caggctctgg aggccctgcc acccacaaag ggtgtgctaa    660

ggtaaacaac tgatagtatt ttgaaaatta gatgacttag aatccattca ataaatttta    720

gctattttta ttgtcttttt tttctaaatc tatttggaaa atattgcaga taaagtagat    780

aataccttc taaaacacag tgagaccagg cgcagtggct catgcctgta atcccagcac    840

tttcggaggc cgaggtatgc ggatcacgag gtcaggagat cgagaccatc ctggctaaca    900

cggtgaaatc ccgtctctac taaaaataca aaaattagcc aggcgtgggg gcatgcgcct    960

gtaatcccag ctactcagga ggctgaggca ggagaatggc g                       1001
```

<210> SEQ ID NO 329
<211> LENGTH: 1001
<212> TYPE: DNA
<213> ORGANISM: Homo sapiens

<400> SEQUENCE: 329
gatgggaaac aacaggccat gattttatgt ttttgttaaa ccagtataat tctttcaaag 60
cagtgtatat cacaactatt tctctgtgtt gaagagagta tcaagttctt aaagaaaaat 120
gtaatcccag cactttggga ggctgaggta ggaggagcac gaggtcagga gttggagagc 180
agacaggaga attgcttgaa tccgggaggt ggaggttgcg gtgagcagag atcgcgccac 240
tcactccgtc ctgggtgaca gagtgagact ccgtttcaaa aaaaaaaaaa aagaaagaaa 300
gaaagaacat tttctattct gcaggtggga ggaaatgaag aatgcaccta ttatttttgt 360
gttagtacaa cataaaaaaa atttgcattg taaagcaaac taccatcatc agctctttaa 420
tggacagcag cagacaggaa actgcctcca ccctgagact taaagactga gcaactgagt 480
tagatagcag gtgcgcaggc yaatcaagtc aattttctaa cacagagtag catgttgtgg 540
aacttgttct attagtcttt tttctctgtt aaggaagcaa ggatctctct gtatggaagc 600
agtgctgcta tttctagttt gaggaaaaaa atggtaaaga atttgataat taattgttgt 660
taaaacagca aattatattt taaacacaga ttgtccacac ctgtaggagg aggaatctca 720
agaatgcaca caattaataa aagctggttc tgaattaccc atacaagtgc gcactgcgtt 780
cagtaaacaa ctgatttgca aactatatcc tttctttccc agaaatagca ggaggaagtt 840
tttcaaatca aaaaaaaaat ctaactaaaa tattttatac gtgaaggcct gcagaatttt 900
acttcctttt gctgttgaaa aatcacaata gccaagagga gtaatgtatt ttattttaac 960
ttttaaaaag tcatgatggt taagggtaga gtggaggtgc a 1001

<210> SEQ ID NO 330
<211> LENGTH: 1001
<212> TYPE: DNA
<213> ORGANISM: Homo sapiens

<400> SEQUENCE: 330
tgttgcccag gcttgtctcc aactcctgag ctcaagagac ccacccactt ccgcctcgca 60
aagtgctggg attacaggtg tgagccaccg cacccagtca cattcctttt aacacttggg 120
ttacatctcc tgaactgaat ggctaggtaa ctaaagacat ctgagaaagt ttcttgcacc 180
tatacattaa gccctcttta ccaagtcata taacctatca ctatctattg aatcttccca 240
tatgagctct aaaggctatt gttatcacaa aacacaatgc caacttttga gtgattaagt 300
atccttctca tctataagag gatgttgccc agactaatct caaacttctg gtctcccgcc 360
ttggcctccc aaagtgccag gattacaggc ataataaaac tccttgatgc catcttccta 420
gaaagatatg cttagcctca ttcaatccaa atagttcctg catttctttt gcatgagatg 480
taagacattt tctgacataa mataaaccaa ataactcaac tacattcatt tttataacaa 540
cagctttttg aaatataatt cacatacaat aaattcatcc ttttaaagca tataattcag 600
tgggtttcag catattcaaa gagttgggca atcattacta tctaattata gaacattttc 660
atcatcacca aaagaaatct catacttatt aggagtcacc tccctcccat ccctagcccc 720
tagtaataac tagccaactt tctgtctcct tagatttgcc tattctggac gttacttaaa 780
attgaaagca tatcatatgt ggcctttctt gtgcctctca gattcaccta tgtgacagca 840
tttatcaata atccattcct ttatactact taataatatt tcactgtatg gatataccac 900
aatttgttta ttcactcatg acatgataga catctgggtt gtttccattt tttaccatta 960
ttaataatgc tgtaatgaac atttggctac aagttttcat g 1001

<210> SEQ ID NO 331
<211> LENGTH: 1001
<212> TYPE: DNA
<213> ORGANISM: Homo sapiens

<400> SEQUENCE: 331
tacacaatat aactagtatt gacttaaggg tactgtgatc accatgcagt gatcccataa 60
aagatgtgac caaaataccc acttaaaatt tgaacgtcag tcatgtaaga acatgtaaaa 120
gatgaaggga atatttcaaa aacgactatc tgacgtaata tgatacttac tatgactcat 180
atgggctttg ttcttcatct catcttcaaa taaaaagttg atgattagaa aaaggagcat 240
tagaaggggg aagtaacact actcggcaat agagaaaaac tccggtcaaa ggaagagcat 300
agttacagag ctccgaatgt cagggaaaat caagcatccg tcattcggaa ttagctctgt 360
atcggtcggt ttcttcatta cttaattgta cggggggaaa ctacttcaaa gtaagggctc 420
ttacgagagg caacttaagc atttgaaagt gcaggtttat ttcctcctag cgagaagtag 480
ggggtcacta gtgagaaacc yatttcaatc tgtgagacgc ccccttctac tcagcccacg 540
tggctaaagt aaacagaagg tgggccgggg cggggagaaa cagaactcgg tcaatttccc 600
agtttgtcgg gtctttaaaa atacaggccc ctaaagcact aagggcatgc cctcggtgaa 660
acaggggagc gcttctgctg aatgagatta aagcgacaga aaagggaaag gagagcgcgg 720
gcaacgggat ctaaagggag atagagacgc gggcctctga gggtaaggtg ggcgcaagcg 780
gaggtgtggt gcggggagag gtgccagtgg gtggaggcgg gggccagagc gagggcacgt 840
gcgggtacac tccggaggag gtgggtgcgc gcgggggcgt gtgcgcggga cctcgaagtg 900
gtggtggagt gcagaccagc aaaaagtttc aaagggaaat cttagatgtc acgtctttgt 960
ccaggcaccc gtgccatccc aacctcccac ctcgccccca a 1001

<210> SEQ ID NO 332
<211> LENGTH: 1001
<212> TYPE: DNA
<213> ORGANISM: Homo sapiens

<400> SEQUENCE: 332
acaaagatga ctctttccag cgatttgaaa ttgctagata agactatgaa attctattaa 60
aacaataaca acaaaaacaa tttaacttgc attagaagca attaaagcat aaaaagtaga 120
tctaagattt tctaaatatt agatattcta aaatattgac attatacaat gtctagcatc 180
cgtaactttt gaagatattt tatttcaagg taatttcata agaattcata agaatttacc 240
tactcagact ttgggcagga tggaaaatag agtttctgtg aggtgtgcct atgaatcata 300
agaagggctt cttaatgagg tcagtaatta aggaaataca tttcaatagt gacatttgac 360
ttacaacatt gtttgggggt ggagtcttag aagaattgat agggaacttt taacttcaac 420
aagtgaaact aaaacattaa ctccagttgt tgttacctaa tacaagacca gtgcccaata 480
aggactttgg aattctttca yaacaactcc ttggcaggtg cacttcactt gttctggaag 540
tgatattcac ttgccaatgt ctagtaggac catgtgccac tgcctcaaaa tcatatcaat 600
tcctccggct tctggcataa actggcacat cagacctaat taaagcctta agaagagttt 660
ggcaaatatg acaatttaaa caaagcaagg gatttctctc actgcaactt aatttctcat 720
tgatgattag ttcaataaga aaataagcaa aacaatgtca tagttaagaa aagctatcta 780
tcttgttatt gtccattatc atgttcctaa aattcaataa cccaagacag tcctatggaa 840
tttttggagc acctaggtag tatgatcaca tatatggtaa agaaagaact gaggttatgt 900
cttttattgt aaactacccc atacttatta aaataatttc tcttttccaa caaaggataa 960
agtgactaac atacacatct cttccttata atcactgaaa t 1001

<210> SEQ ID NO 333
<211> LENGTH: 1001
<212> TYPE: DNA
<213> ORGANISM: Homo sapiens

<400> SEQUENCE: 333
cagagagtaa agcctaaggg gaaagtttga caggctggtt gtatttatgt attcatcctg 60
ccacatcctc gaaaaaggta tttattgtta agtaggttca aaaacatctt caagaccaga 120
aaatgccttc ggacgccact gggctgttga attccttagt tattgattca ctaatgtcat 180
catgaaagaa tttatgattt tcccaatcca gtccaccagg agagggaagg ccttgataag 240
gatttagatg ataaggagaa gaattgccaa gattgaagac ccagagcaac agcaaagaat 300
tttggaaaag aaatttcacc aaagagtaaa gttagtgtta ttttggttat gtggaatatt 360
agagtgaatt aagtagagga ataaaatcac taataaaatt ggttagcaaa ggcgtcataa 420
aatcacacca atgagaaaca gagtgctaac ctagactttg tatatcttca gtttcctttc 480
aagcatttca aacctcccca rttagcttca agtttatcct taggtagatg tgtacaaaag 540
atttcttcaa ctactttcta gtattcaaga tattatttaa gggaaaaatc acatttattt 600
attcattaga tattttggta agtattctag gtgctggatt aaaagagaga aatggctcac 660
gcctgtaatc ctagcacttt gggaggccga gatgggcgga tcacttgaga tcagaagttt 720
gagaccagcc tggccaatgt gttgaaaccc tgtctctact aaaaatacaa aaattagccg 780
gaaatcacct gaacccggga ggtggaggtt gcagtgagcc gagattgtgt cactgcactc 840
tagcttgggc gacagagtga gactctttct taaaaaaaaa agttaaaaaa ataaaataga 900
taacatgtct tatttttcct caggctctgt ttaatggtgg tgatgatgac atgatggtca 960
tcactaccat ccattgagta catgcaccaa gtcatcatgt t 1001

<210> SEQ ID NO 334
<211> LENGTH: 10187
<212> TYPE: DNA
<213> ORGANISM: Homo sapiens

<400> SEQUENCE: 334
tgactgtcat gtgctaattc taacaatatt tgaaagaccc ctatcaaaat aaatatacct 60
tttagtagcc actttattag aaaatcaact ttaagttatt cccccatgtt tttttctaat 120
tgagatataa ttcacatacc ataaaattta cccttttaaa gtatacaatt cagttgtttc 180
agtacattca caaagctatg caaatgtcac ctctacctag tttcagaacg ttttcatcat 240
tcccagaagg aaaccctgta tttattaggc agtcacttcc ccttctcccc ttcttccttc 300
ctctaagtgg caaccacaaa taaacattca gtttctctgg atttacctat tctgggcatt 360
ttgtattagt gaaatcatgt atttggcctt tctctctggc ttctttcatg tacctcaatg 420
ttttcaagtc tcattcattt tattaaaaaa aaaaagtacc ttttttcttt ttcttttttt 480
tttttttgtc cacgtatata ttcacaccac attttttgag acagagtctc gctctgttgc 540
ccaggctagg gtgcaatggt gcaacctcag ctcactgcaa cctctgtctc ccgggttcaa 600

```
gtgattctca tgcctcagcc cccaagtagt tgggattaca gttgtgcacc accacaccca    660
gctaattttt gtatttttag tagagacagg gtttcaccat gttggctagg ctggtctcaa    720
actcagcctc aagtgatcct tctaccttag cctcctaaag tgctgggatt acaagcatga    780
gccactgtgc ccagccacat tttctttttc catttattag ttaattgaca tttggatcgt    840
ttctactttt tggcgattat aaattatgct gcaatgaaca tcggtgtaca agtttttgtg    900
tgaacatgtt ttcagttacc ttgggatata cacctaggag tgacattgtt agtaatatgg    960
taactttatg tttaactttt tgaagaactg ccaaactgtt ttccaaagta gctttatgct   1020
tttacatttc tgccaacaat gtatgaaggt tccagtgtat ctccacatcc tcaagaaaat   1080
gttattgtct ttttaattgt aaccatccaa gtgggtatga agtttatctc gtgattttga   1140
tttgcatttt cctaatggct gatattgggc atcttttcac gtgtgtattg accatgtatt   1200
tttttgagaa aagtctactt atatgttttt aattgtatta tttttagagt tgtaagaata   1260
tgttatgttg atacttgaac tttgtcaaat gcctggtttg cagatatttt ctcctatccc   1320
acaggttgtc gcttcacttt gataatgtcc ttaaagtaca aaagttttaa attgattttg   1380
atgaaactca atttcttttt aattggcagc ttgtgcattt ggggtcatat ttaagaaatc   1440
attgcctcat tcaagatctg aaagatttac acctatgctt tcttctcaga gtattataac   1500
tttagttctt acatttagat ttttaattaa tgttgagtta atttgatggt gagagataag   1560
agtccaactt cattcctttg caagtagctg tccagttttc tcagcaccat ttgttaaaag   1620
actgtttttt ttcaattaac tgaccaagat gtatgggttt atttctggac tcttaattct   1680
gttaatctgc atgacttttc ttatgccagt accacactgt gctgattcct gtagttttgt   1740
agtaaatttt gaaatcaaga caggtaagtc ttccaacttt gtacttttgc ctaccatgtt   1800
tcttgggttt ccatatgcat tttaagatca gcttctccgt ttcctttctg gatttttttt   1860
tttttttttt tttttttttt tttggtggag ctggagtctt actatattac ccaagctggt   1920
tttgaactcc tggctaaaga gatcctccct cctaggcttc ccagagagct ggggttacag   1980
gcatgagcca ccacatccaa ccccccttctg ggactttgac tggggttctg ttgaatctgt   2040
tggtcaattt ggagagtatt gatatcttaa cattaaagct tccaatttat gaacacaggc   2100
tatttttcca tttattctta aatttctttc agtaatgttt tggatgaaac atgtacaaag   2160
tcctgcactt tttatttttt ttaagacaga gtcttgctct gctgcccagt ccagagtgca   2220
gtgctgccat ctcagctcac tgcaacctcc acctccgggt tcaagtgatt ctcctgcctc   2280
agctggaact acaggtgcgc gccaccatgc ctggctaatt gttttgtgtt tttggtggag   2340
acagggtttc accatgttgg ccaggctggt ctcaaacacc tggcctcaag tgacctgact   2400
gccttggcct cccaaagtac tgggattaca ggcatgagcc accacgcctg gcctgtactt   2460
ctgttaaaat tttttctatg tatttttttt atcctattgc aaaatcaaat tttttgttga   2520
taatatatgg tcataaattt cattttttata tattggtctc atatcctacc aacttgctga   2580
actagcttat tagcactaac tttttttggt agattcctta ggatttgctg catacaagat   2640
tatgtcatct acaagtagag atagttttgt ttcttcactt ccaatctggg tggctttatg   2700
ttttttttctt gcctgattac ccagttagaa cttccagaaa atgtcaggta caattaacaa   2760
ctgcaaacat ccttgtctta ttcattttag aaagaaattt ttagtttttc accattaagt   2820
atgatactag ttgtaggttt tgtttaaaaa aagactgtgt caagttcaga agttcccttc   2880
tgttgctagt ttgttgaata attttatcac gaaagggtgt tgaacttttc tcaaatgctg   2940
```

tggctacatc taatgaaatg atcatgcgtt cttctccttt attctattaa tatggtatat 3000
tatattgatt catttttata cattagatta acattatatt tctggaataa atcccacttg 3060
gcctcagtgt gtattacttt ttatatattg ctggagtctg tttgcaggta tttcattgag 3120
gactttcgca tctctgttga taaggtatac tgatctttag ttctcttgtg atatctttgg 3180
ttttggtgtc agagtaattc tgagttcaca aaatgcattg ggaaatgttc ccttctctat 3240
cttttggaag agtttacaaa ggattggttt aactcttttt taaatgtttg aggaaattct 3300
ctacccctgg gctttccttt gtgggaattt ttaaacattt ttaaaataga ttatttttaa 3360
agcaatttta gggtaaaagc acattgaatg aaaggcacag agcttcctta agtacatgct 3420
gcccctgtat gtgcatagcc tccctcatta tcaacatcct ttaccagaat ggtacatttg 3480
ttgcagtcaa tgaacctgca ttgacaattg tcgmtgaaag ttcatagttt agagttcacc 3540
tttggtgtta tgtattctgt gagtctggat ccatgtttaa tgatactcat tcaccattac 3600
agtatcattc agagtaattt cactgcctta aaagtcctct gtaccctacc tatttttctc 3660
tcctacccca ctaaccctta gcaaccaatg atctttttat ctcaataatt ttgcctattc 3720
cagaatgtca tatagttgga atgatacagt atatggagcc ttttcagact ggtttttgtc 3780
acttagtaat aagcttttaa attttccacc atgtcatgat cgttcatttc ttttcagcat 3840
tgaataatat tccattgtct ggtttatcac agttgattta tccattcaca tagtgaaaga 3900
catcttagtt gcttccaagt tttgacaatt atgaataaag ctgttataaa agtatgtagg 3960
tttttgtgtg gacaaaagtt ttcagctcct ttgagtaaat aacacagagc acagtagctt 4020
gattgacagt aagagtaaga aatatttttt ctcagtctgt gtcttatttt ttcattcact 4080
tgacagtgcc atttgcagaa caaacagaaa gttttaattt taatgaagtc taggttatca 4140
gttaattcat gaataatgtt tttggtattg tatctaaaaa gtcaacacca aggtcatcta 4200
tatgttctgt gttatcttcc agaaatttta tagttctgca ttttacattt agggctgtga 4260
cccattttgc attaattttg caaaagctat aaagactatg tatagattca cttgtttgca 4320
tgtggagttg tccagttgtt cccgtaccat ttcttaaaga ctatctttgc tttattgtat 4380
tacctttgct actttgtcaa agatcagttg attataatta agtggtctgt ttctggactc 4440
tttattctgt tccattgata tatttgtcta gactttcacc aataccacac tatcttgtta 4500
acttaggctt tagagtaagt cttgcaatca tgtagtgtca gtcctctgac attgtttttc 4560
tccttcagta ttgagttggc tattcttttg cctattacta agtaaaaaaa gcagtctgaa 4620
aaggctatat atacagtcat ttattggtct tttgcctctt gatataaact ttaaaattac 4680
tttgtcagta tcctcaaaat cttgcaggaa ttttgataga ttgcactgca tttctagatt 4740
gagttagaaa tactgccatc ttgacaatac acatcttcct atccatgaac atggaacatc 4800
tctttcttgg atatccttca ttagaatttt gcattttccc catatagacc atgtacatat 4860
tagatttata cataaatatt tcatttgggg gggtgctaat ggtaatgtat ttttatctca 4920
gattctgctt gtacattgct ggtatgcaga aaagtgatca acttttgtat attaaacttg 4980
tttcctgcaa ccatgttata taatcacttt agatccagtt tttttttttt tggtcattct 5040
ttcatatttt ctaggtgatc atgtcatcta gcaaagacaa cttctttcta atctgtatac 5100
cttttatttt cttgtcttaa tgtattagct agcatttcca gtatgatgtt gaaaggcatt 5160
ggtgagaggc aacatacttg ccttgttcct gatctcagca ggaaatcttc aattttatgt 5220
tagctctatg gttttgtaga tattctttat ttacattaaa tatgttagct gtatggtttt 5280
gtatatattc tttatcaggt tcaggtagtt cccctctttt cctagtttac tgagaggctt 5340

```
ttgaaaatca ttaatcagtg ttggattttg taaatacttt ttttccacct attgatatta   5400
ccatatgatt tttctttagc ttattaacga aatggattac attaattgat tttcaaattt   5460
tgaactagac tggcatacct ggagcaaatc ccacatggtt gtgatacatt atttatgaat   5520
gcattcatgg tcatggttgc tattagtctg tagttatctt ttattgtaaa gactttggtg   5580
ttggtattaa ggtaatgctg ccctcataga ataagttatg aagtattttc tctgcttctg   5640
tcttaattga gattgtagag aattcatata atttcttcct taaaactttg gtagaaatca   5700
gaatgaacca tctgtgtctg gtactttgtt ttgaaaagtt attgctgatt caatttcttt   5760
catagatata ggcctattta gattattatt ttgcataaat attggtagtt gtgtccttca   5820
aggaattggt ccatttcacc ttgattatta aatgtgtggg cacatttgtt cataatattt   5880
ctttattatc ctttgttttt gagacagggt ctcactctgg ttgcccaggc tggagtgcag   5940
tagtatgatc tcagctcact gcagccttga cttcctgggc tcaagtgatt tacccacctc   6000
agcctcccaa gtagctcgga ctacaggcac atgccaccat gcctggctaa ttttttttatt  6060
attattagag atggagtttt cctatgttgc ccagtgtggt cttgaactcc tggactcaag   6120
caatctgcct gcctcagcct ccaaagagtg atgggattgc aggcatgagc catcacacct   6180
agcctgatgg cagaactttt taggaacaat agaatggtat atggcatttt caaaaattgt   6240
tttcccctcc tcctatggaa gcatgaaggg atttttctct agtattcatt gtgagaacct   6300
catctggctc ctgaatgtag aaaactcaca aaactgtgag gaacctatta tgactggatg   6360
cctttggagt tgttcacact gaacctccag caattcatca attatatttc agattttcct   6420
atcccaacac tggttcctac agaggtttct gctccagtaa gctgtaattc tttttatcca   6480
tctgcttcct tggttgtgag ggcagtgatt ttccctgtga cctcatttct ctgacagatc   6540
taagtagtct tgattacatc ttttaacctg ttgtaggtat attcagattt tctatttctt   6600
cttcagtcaa ttttagtagt ttgtgttttt ctagaagttt gttctctagc tctgctttag   6660
ctccatccaa taaaatatga gtatgtcgag ttttcattta caacaaggta ttttctaatt   6720
tctatcatgt ttttttgatt cctgactgta taggagtata tttttaccta ttacccaaat   6780
ttgcttgtta ttcatgtata attttatcag aaaacacact ttgcacaatt tttgcagtgt   6840
tacatttatt tagacttgtt ttataacttg acatacagtc catcctggag aatgtttcac   6900
gtgtgcttga gaagaatgtg tatattcagc tgttggtggg tggcatgttt tatagatgtc   6960
tgttagacct agttggttta tagtgttttt tacaacttct gttttctttt taatcttcta   7020
tctactttta gccattattg aaagtggatt agtaaattat ctatttattc ctttaattct   7080
gccatttttt gcttcatgta ttttggtgct ctgttgctta ttacatgtat gtttacattt   7140
gttacatcat tttaatggct tgaacttttt attataaaat gtgtatatct tgtagatatc   7200
gtatagttaa atctttttaa aaattgatat tgctagtctt tgccttttaa tttttcaatt   7260
tatatacatt taacataatt attgataagg taggatttgt ctgccatttt gtctgtatct   7320
tgtctttttt tgtgttcaat agatattttc tagtgtactg ttttaattcc cttgtctttt   7380
actaaatttt ttgatgttct taatggtttc cctggggatt acaactaact tataacagct   7440
agtctgaagt aataccaatt tcattacaat ataaggaaac tttgttccca tatagctaca   7500
ttccctcttt ttactctgtg ctattataca aattacattt tattttatgc ccattaacac   7560
agattatgtt ttttctttta aatcagattg atattgtcat ttaaatcaaa tatgagaaaa   7620
atagttacaa aaaaatacat atatgatttc atatttacct atgtaattat ctttactggt   7680
```

-continued

```
gctctttaag ttcttaggtg tatttgaggt actgtctagt gtcctttcct ttcagcctga   7740
agtatacatt tagtattttt tgtaggacat gcctgaaaac aataaactct tatttatcag   7800
agaatgtcct aatttattat ataatacatt tctgaaagat agttttgcaa aatacagaat   7860
tcttggttgg cagtcttttt cttgtggttc tatgtcattc tactgccttc tggtcttcat   7920
tgtttctgat cagagatcag ctattaatct tattgggaat cctgcataca tgataatcat   7980
acagttttca tgattttctt gtgttggctt tcagcagttt ggttatgatg tttatatgta   8040
tgcatatctt tgggtttatg ttacatggag ttagttgagc ttcttggaca tgtagattga   8100
tgttgttcat caaatttgag aagttttcgg ccattatttt tcaaatattc ttcctattct   8160
ttattcttca tcctctactt tggggacctg cattatgtct atgttggtat gctttatggt   8220
cttccacaga tctctgaggt tctgtttatg ttttcatttt tcagactgaa taatctcaat   8280
tgacttatct tcaagtccct ttttcccctc cttttcaact ctgctattga acccctctaa   8340
tttttactgc agttattaca ctttcagctt tagaattcta tttaataata tctttttctt   8400
gagtttatct catgtattta ataaaatgct gtagtcttac tttagttatt taaatacagt   8460
tttctttcat tatttgggca tacatgaaat agctgactta aagtctttgt ccagtggcct   8520
aacatctgga ctttttcagg aatagcctct attgactact ttataggggc catactttgt   8580
ttctgtttct cttaattgtt tagacatttt aaactaatgt aatggctgag agcagtggct   8640
cgtgcctgta atcccagcac gttgagaggc caaagcagga gcatcactta agcccaggag   8700
ttcaagacta gcctgggcag catagtgaga ccctgtctct acaaaaaataa aaataaataa   8760
aataatataa tctggtaaat ctgaaaatca gattctaccc cctgcccaga atatgttact   8820
gtttctggtg gttgttgttt atttcttttt aactactcct ataaagtttg tattgtttct   8880
catagatagc catcgaagtc tttgcttggt taacttagag gtcagctaag gattagacag   8940
aattccttag gtgcctgaga tcaataagtc agtctttgac aaaggggtct gtatgtgtgt   9000
tggggcatgc attcaacact cagccaggct atttgcagct ctggattagc ctttattccc   9060
tgcttgtgca gagtctcaag gttagactgt ggtgagagtt tagggctttc tgaggtcttt   9120
tgtgggccct acagttgcat gtggctttct aaattcccag gaatatattt tcaaagcctc   9180
ctgtggatca tctcatttcc caggtaattt acttttaagc ttttttagtt atcttatgtt   9240
ttgctccagt tattagctac acctgagtca gtgacaatat tcaacagctg cctatgatta   9300
tttgacaaat gcctctgtgg aaaaggtggt tcacactagg tgaactccaa gttagataaa   9360
gtaaagataa ccttactagt gggatcttcc aggaaactac caaacaggtc aaataatgta   9420
aggtctctgt gaatgggact ttagagtata tccaaccagt ctagagtata tccaaccaat   9480
ctggcctcct ctagtggcag cctggctgct gcttttcata ataaatgtgg gctgttttga   9540
tttgaaggct accatagagc tgtggggaaa gttaaaatac cacagagctc actcttctca   9600
ctgaaatcct gtcttttttt cccttgaaca aattctccct atattgctgc aagcttttttg   9660
ctaatttcca gatctgaaaa agctgattct gacaatattt atcagtactt ttattgcttt   9720
tatggaggat aaaattttca gagatcctta ttctgccatt tttgctgaca tgtgtaaagt   9780
gatcatttct aattgtaaaa ttccttttgc atttattagc tggaatactt tacaggactt   9840
ttcctcatca accgttagtt accatttaat atagtttgta agaatgatag aataaatgca   9900
tggcaagaat ctttacttct caaatttcag agattttgat gggaaattat atttagagat   9960
cacaatcagt gtctagatgt gctccctgct atggaggtgt cattactttt aggctttttt  10020
aatgggcaaa tacatgaagt aattattttt tagaaagaaa atctgagatt aactcaaatc  10080
```

attaattcat actgattttt cctattcata gttgacagag tattattatc ttttgttctg 10140
cttctcttgt acactgaaat tcttggtttt tgatattaac aattatt 10187

<210> SEQ ID NO 335
<211> LENGTH: 3249
<212> TYPE: DNA
<213> ORGANISM: Homo sapiens

<400> SEQUENCE: 335
gcatgagcca ctgcgcctgg acttacaatt tcttaaaata agacaacagt gaggtttacc 60
acatcaattg accctttctt tcatgagtga tttctctgtg gcatgcaatg ctgtttgata 120
gcattttact cacagtagaa cttgttttaa aattggagtc aattgtcttc agccctccca 180
ctgctttatc aggtaagttt acgaaatatt ctaaatcatt tgttatgact caagggacat 240
taaaaaaaaa agaaaaacaa tcttttattg tcatttcaac caggttcaca gtgtcttttt 300
tttttaaatt atattttaag ttctagggta catgtgcaca acatgcaggt ttgatacaaa 360
ggtatacatg tgccatgctg gtttgctaca cccatcaact catcatttac attaggtatt 420
tctcctaata ctatccctcc cccagccccc accgcccgac aggccccggt ttgtgatgtt 480
ccctgccctg tgtccaagtg atctcattgt tcaattccca cctttgagtg agaagatgcg 540
gtgtttggtt ttctgtcctt gtgatagttt gctgagaatg atggtttcca gcctcatcca 600
tgtccctgca aaggacatga attcatcctt ttttatggca gcatagtatt ccatggagta 660
tatgcactac attttcttaa tccagtctat cattgatgga catctggtat ggttccaagt 720
ctttgctatt gtgaatagtg ctgcaataaa catacatgtg catgtgtctt tatagtagca 780
ggatttataa tcctttgggt atatacccag taatgggatt gctgggtcaa atggtaattc 840
tagttctaga tccttgagga atcgccacac tgtcttccac aatggttgaa ctactttaca 900
ctcccaccaa cagtgtaaaa gtgttcctat ttctccacat cctctccagc atctgttgtt 960
ccctgacttt ttaatgattg ccattctaac tggcgtgaga tggtatctca ttgtggtttt 1020
gccttgcatt tctctgatga ccagcatgtt cacagtatct ttatcagaag tagattccat 1080
ctcaagaaac ttctttcttt gctcatccat aagaagcaac ttctcatttg ttaaaagttt 1140
tttcgtggat tacaacaatt cattcacatt ttcaggctcc acttttaatt ctaattctat 1200
tgctgttttc accatatctg cagttacttc ctccactaaa ctcttatacc cttcaaggtc 1260
atccatgagg tttggaatca actttttgg aactcctgtt gatgttgata ttttgacctc 1320
ttcccgtgag tcatgaatgt tctcaatggc atctatgatg gtgatttttt tctgaaggtt 1380
ttcaatttac tttgcccaga tgcatcagag gaatcactat ctatggctgc ttatattgcc 1440
ttacaaaata tatttctttt tttttttttt ttgagttgtt gtcttgctca gttacccagg 1500
ctggagtgca gtggcgtgat ctcggctcac tgcaagctcc gcctcccagg ttcatgccat 1560
tctcctgtct cagccttccg agtaactggg actacaggtg cccgccacca ggtccggcta 1620
attttttttt tgtattttta gtagagatgg ggtttcacca tgttagccgg gatggtctcg 1680
atctcctgac ctcgtgatcc acacgcctcg gctgggatta cagacacaaa atatatttct 1740
taataagact tgaaagtcaa acctattcct ggatccatgg gctgcagaat ggatattgaa 1800
ttagtaggca tgaaaacaac atggattttt ttgtacttct ccatcagaac tcttgtgtgg 1860
ccaggtgcat tgttaatgag cagtaacatt ttgacaggaa tctctttttc tgagcagtag 1920
gtctcaacag tgggcttaaa atattcagta aaccattctg taaatagatc tgctatcacc 1980
caggctttct tgttctattk tggagtgcaa gcagggagat ttagcatcat tcttaagggc 2040
cttgggtttt tggaatggaa catcagcact gattggcctc aacttagagt caccagctgc 2100
attagccact aacaagagag gcagcctgtc ctttgaagct ttgaagcctg ccattgactt 2160
ctccctagct aagaaagtgc tagatgacat cttcttccag taggaggctc tttcatctac 2220
attgaaaatc agttgtttag tgtagccatc ttcatcaatg atcttaacta tatcttctgg 2280
ataacttgct tcagcttctt catcagcact tgctccttca tcttgtactt ttacgttatg 2340
gagacaactt tccttaaacc tcatgaacca acgtttggta gcttccaact tcagcttcct 2400
cccctctctc agccttgata gaattgaaga gagttaaagc cttgttctgg attaggcttt 2460
ggcataggga atgtttcatt ccagaccact aaaactttct gcatctcagg gataaagttg 2520
tttcactttc tcatcattca catgttcatg gaagtagcgc ttttaacttc cttcaataac 2580
ttttcctttg catttgcaat tttgctaatt tttttgttgc aaaaggccta atttttagcc 2640
tgtcttggct ttccatgtgc ctttctcact aagcttgttt ctagcttttg atttaaaatg 2700
agagatgtgc gactattcct tttacttgaa cacttagagg ccattgcagg gttattaatt 2760
ggcctaattt caatattgtt gtgtctcaag taatgggctt ggtgaaaggg agagacagag 2820
aggaatggtt gtcagtggag cagtgagatc acacacactt ttaagtagct aagtttgctg 2880
tcttatatgg gtgtgattca tggtccccca aaatagttac aatagtaaca tcaaagatca 2940
ctgatcacgt caccaaaaca gatattataa taatgaggaa gtttgagata ttgtgagaat 3000
taccagaatg tggcacagag acaggaagtg agcacatgct gttggaaaaa tggcactgat 3060
agatttgctt aatgcaaggt tgccacaaag cttcaattgg caaaaaatgc aatacctgtg 3120
agtataatac aataaaatga ggtatgtcgg aacctgatta tgtcttagtc ataaaactta 3180
caaagaagta ggaggaatat tttccatgcc aacagaatgt atttaaatga tttgatatgt 3240
atttgaggt 3249

<210> SEQ ID NO 336
<211> LENGTH: 1001
<212> TYPE: DNA
<213> ORGANISM: Homo sapiens

<400> SEQUENCE: 336
aagtgtgttt ccaccatacc ttgttggtcc aaaacacctc tccccagctc cagcaactgc 60
tgcagctgtg cagggcagtc cctctccagg taggccctgt tctgcctggc ccgaatcttg 120
tgcctttccc actccagctt ggtgggccag gccctgggtt ctgctgctct ccaatccagt 180
gtgtcagggc agaattcaag gtggtcctgc ccatcatacc cgtacttcca gtagccctcg 240
gtactgttgt cttcttgcat ttcacagccc aggatgacct gcagggtgtg ggactctgga 300
aaaatcccca gccttgttaa ctgcaaccaa aggaataggt ccctatttcc accatcccca 360
aggaccaaat gatctcagga agcaaattcc ttccctcttc cctgctccca caagacctca 420
gacttccagc tgtttccttc aagatgcatg aaaagatgaa aagctctgac aacctcagga 480
aggtgaggcc ccctctccac rtacccttgc tgtggttgtg attttccata atagtccaga 540
agtcaacagt gaacatgtga tcccaccctt tcagactctg actcagctgc agccacatct 600
ggcttgaaat tctactggaa acccatggag ttcggggctc cacacggcga ctctcatgat 660
catagaacac gaacagctgg tcatccacgt agcccaaagc ttcaaacaag gaaagaccaa 720
ggtcctgctc tgaggcaccc atgaagaggt agtgcagaga gtgtgaacct ggagacagag 780
caacaggcct taaccatgtg tagtaggagg ggagcaggat gttgaggctc cacacacctg 840

```
catcaactca taccatcagc tgtgtctggt cctcattttg tgaagggtga gttgcagtcc     900

tgtctttctt ccatatgaca gtcctgggtg ctctttcctt gtgtgctttt ctctgccaca     960

cgtggctgcc accccctcac tgcccccaga tcctattcca a                        1001
```

<210> SEQ ID NO 337
<211> LENGTH: 1001
<212> TYPE: DNA
<213> ORGANISM: Homo sapiens

<400> SEQUENCE: 337

```
cagagccacc ctagccattg gtataataga aataattatt attgccactc ttataaatta      60

ctgcaccagc cagtctacat caatcccaga tggagatatt actgaccctc ttcctccagg     120

tcacccagtt ggtaaatgaa agagatgata tttgttcaga agccagtttg acctgcaaaa     180

ttttgctttt aaacacctcg caagagtgcc tatttcttgg aattatcttc catagctgct     240

actgtctcca ctagctagtt tcaaagcata tggatgatca gatacaaagc ttcagcttcc     300

tgccacttct ccctcacttt tgtcagtctt gttaatatgg atttttacat ttttcatttt     360

tatttttatc atatgaggaa acttggggtt ggggagtata taaaaattgt ccattgctat     420

acagaaaaga gttttggagg tcttcatctc aataccaaga gaagtgactt accgacttaa     480

tgtctgtgga agggcttcaa rttgaaccca gcgtttcctc caagcttact cccttggact     540

ttttggagca gagagatgag gattctttgc caccctaggg cttaagttgc taatcattaa     600

taaaagtcat caaactacaa agttgactca gaagggcttc ttgccaaata ggctttgaag     660

aagcattcgg aaatccagcc caatcccctc tgcagttctt tctgcttttt ggctgatgta     720

agcttctcca ccttcccctt gtgagtgtct cctcaggacc tcataggtgt cctctggttc     780

agacacttgc atatagctat tttgctttgc tttgtggtgt cttcaatgtc tttagtcttt     840

tttgaaaagg ttaaaaagag ataaattata attaaagagt tcagtatttt tgtgtttttt     900

actttgctat ttttgatttt ccccccttaat tgaaattttg ttaatttttt tcttctttga     960

aatatgtgaa ttgtaatatt atgggtaaac ttgaacttca t                        1001
```

<210> SEQ ID NO 338
<211> LENGTH: 2131
<212> TYPE: DNA
<213> ORGANISM: Homo sapiens

<400> SEQUENCE: 338

```
aaaaagtatc agcaagttat gtttggatgc caaattgctc tccacttccc ttccctgaca      60

ctggcatttc cagaacttag atgctcttac atgtaaaagc ctcctctagt gcaccatcga     120

gcttttcagg attggacatc agacttttta gttcctggac ctctagatat acggcagtct     180

ctgacaagaa gccctttttc tgttttaact tttttttttt ttaagttttg agacaacgtc     240

tgactcgctg tcacccaggc tggagtgagg tagcaccatc atagctcact gtatccttaa     300

acgcctgggt gcagggacta agggagcgtg ccaaccatgc ttgactaatt tacttttttg     360

taaaaccagt agtctccaac ctttttgaca caagagaccg ttttgtgtaa gacaattata     420

ccacggacca gggggtgcag gggctgggag caatgatttc cggactaaaa ctgctccaac     480

ctcagatcat caggcattag attgtcacaa ggagcctgaa acctagatcc cttgcatgtg     540

ccattcacaa tacagtttga gcttatgaga atctatctaa tgctgcagct aacctgacag     600

gcggtggagc tcagttggtt aatgttcgct caccccctcag ctgtgcggct caattcataa     660
```

-continued

```
cgtgccatgg acagggaccg gttaccggtc ggtggccggg graatgagga cccctggtat    720

agatggtagt ctggctatgt tgcccaggat ggtcttgaag cctggcctga attaattctc    780

caatctcaag ccttttcaac tcagctgcat cacaacttaa acctatagat aactgtcaca    840

gaaacttgtt tccagtgtta cgccatctta aaataatgtg ggtggctctt aaaagagcct    900

ttgggttctt tccaaattgg cctcccggaa agctctttac ttcttagatg tggcctttct    960

aacattaact tcatgatgtt gggtcaattt tgacttcgaa gcccttgcct tcactgggct   1020

cttctgctgt tgcttaccct tggctccttt agcctttctc ccgctcctaa cagttttagg   1080

agttgtcgct ctcggcttct tggctctctt attggtttta gcagtctttg gtgacttgga   1140

gtccctggat aaaaccagct tcttggtctt ggcagaaact gactttttag ccttgcttct   1200

ggtagattta ggaatcacct tcttactaag cttaaaggaa ccggaagcac cagtacccct   1260

ggtttgcacc aggattccct tgttcactaa gctcttgagg gacagtttga tgcggctgtt   1320

attcttctct acgtcgtagc cagcagcggc caatgccttc ttgagcgcaa ccaaagacat   1380

acctactcgt tcctgtgaca ctgaaagggc ctcggtgatc aacttggaca cagagaggtt   1440

cggcactttg cgacttgcac ttatcaagcc agccggcttc ctccctcgct tcttggttgg   1500

aagtttctcc atagcggcta caccagcact ggcagaagct gcaggcacgg tttcagacat   1560

aacaacagag aaacgcaaga tgtaataacc agcgaaaagc atgaaacacc cgggcggcct   1620

cggggcctta tatagggtag ggcgcgctgt gattggtgca tcacctaggc accgcccccg   1680

ccccttggag gaggagtatt tgtgtttgtt ttacccggaa aagttgagta taacaaaacc   1740

cctctttaca gaatctccca gggtctagtg ctgaataatc tgcggaaatt catatttgac   1800

atgacttttc tctttttaat gaaaaatgac cctggatgcc aaaactattc gagaaagccc   1860

tcgattttca atcaaattca cggagaggaa caaaacttcc ccttttcctt gtaaattaat   1920

aagtaatctt tggcagaaga cttatttcat ctcttcagag tggtcttcca aatggatagc   1980

ttcaaatcgg tagaggaaag aaattattca cgccatgatt tttatttaaa attatttata   2040

tatgtgaggg aagtaacaca gatctcttag ctgtctaatt gcggagtcag aagatgctta   2100

tagaattgtc aaaagactgc agaggatgtc t                                  2131
```

<210> SEQ ID NO 339
<211> LENGTH: 1001
<212> TYPE: DNA
<213> ORGANISM: Homo sapiens

<400> SEQUENCE: 339

```
tctctcagac ttttgcagaa aaatgagtca ttcaacaaat atttgaatcg agatagggaa     60

agtgacgagg aagaagtttg cacttatgag gttttaattt gcaattattt ggctaccttt    120

ttgccttccc aaaacatagg gtctttagga gtgaaacttc atagccaaac ttataccttg    180

tccagcacag agaaggccat caaaatgcct ggtttaaata aaaatattaa aatgattggg    240

agggtaaatc ccttgaccta taaatctgac ctcctttaaa cattatttgt atgttcccca    300

ataaactatt ccgtaattta ttagttagca agtggaaata aaaagaaatg tggaatgggg    360

ctatgcttag cgtcattaag ctgacaggaa tacagcgcat tcaacttgca aacacccttc    420

cactcccaca aagagcaagc tgtcactggc caatcaaaac aatgaaccat aatgaaacag    480

tttttcttgc tccacccact yggtgaccaa atttgaaaaa aaaaaaaaac cgcgccaact    540

catgttgttt tcaatcaggt ccgccaagtt tgtatttaag gaactgtttc agttcatacc    600

ttccactgcg ataggaatca tgtctggtcg cggcaaaggc ggaaaaggct tggggaaggg    660
```

```
tggtgctaag cgccatcgta aggtgctccg ggataacatc cagggcatta caaaaccggc    720

tattcgccgt ttggctcggc gcggtggcgt caagcgcatt tccggtctta tctatgagga    780

gactcgaggt gtgcttaagg ttttcttaga gaacgttatt cgagacgccg tcacctatac    840

ggagcacgcc aagcgcaaaa ctgtcacagc catggatgta gtatatgccc taaaacgtca    900

ggggcgcact ctgtatggct tcggcggctg aatctaagaa tacgcggtct cctgagaact    960

tcaaaaaaca aaaacaaaaa aacccaaagg cccttttcag g                       1001
```

<210> SEQ ID NO 340
<211> LENGTH: 1001
<212> TYPE: DNA
<213> ORGANISM: Homo sapiens

<400> SEQUENCE: 340

```
aatcattttt ttataacaac aaaggcattt gcactgagag tcaaggaagt accgaattat     60

tcctgttttt actgaattgt attaaaatat aaggaggata taataggaaa acacagcatg    120

tgttcatcaa tcacttctcc tgagtctcct cacttggtca aaaatttccg gagaaatttt    180

tgtttgtacc tgatttgaaa agaaaaacaa gggagcggtt ggaggggaag ggtggagaga    240

tgaggggagg gagtgcccta gtggaaacca cagcattaac accacctact acttctactt    300

cactaaaggc actgtcccga ttttttcttc agagatcact gttttgcctg ctgaattcaa    360

acctccaccc cagacacact gatgtcattg gaggcatcag gactgggggc ccaagtttta    420

ttatattaaa acgagttcat gctggggtaa attttaagat ctttagtgga cagaaaggca    480

gttcaaattc tttgatttta rtgacaaaat gctttaaact gacaatgcaa cctatcaaca    540

aaaggaccat attgagctgt gtgtgggctg cacagaaata cgccgcccca gaactctaag    600

tgctcccgga aaagctcgca attgttacaa cagagaatcc aattcttgtg gctaaagtat    660

ctcctggggg acttattaca aatgtggatt ctagaacccc tcgtgcaatg atcctgacta    720

aagcgattta ctatgggtcc caagaatctt aatcttacca agcaccctca agtaattcta    780

acttcaatag tctgctaaac ggcactcagt gaagggtgct aaagctgtca tggggaattt    840

aaaaactcat gaaataagct cgtagaaagg aagtttaggg tctggaggac acagagctga    900

aatgaaatcc tgaagtaggg ttggaatata attaatttat gtaacaatac tgaacaccta    960

gtgtgtggcg tgcccctttg tttttcaggt aatcagagga a                       1001
```

<210> SEQ ID NO 341
<211> LENGTH: 520
<212> TYPE: DNA
<213> ORGANISM: Homo sapiens

<400> SEQUENCE: 341

```
ccttgaagct acggaattac aattctcctt cacaaagaca gtcaaaggat gtgatctgat     60

gtgttagatt ttctctctcc tgttcaatat ggagttttgc atcttagttt ctttgggccg    120

ctataagaaa atacactaaa ctaggtgact aacaaataac aggattttac ttcttacagt    180

tctaaaggct aggaagtcta agatcaagga gacaccatat tctatgtcta atgaggctca    240

ctctctgctt catagatagc atcttcttgc tgcaacttcg tayggtacag ggggtgaaca    300

agctccctct tttatagggg tactaatccc attcatgagg acgccatcct tatgacctat    360

tcacctccca aaggccccac ctcttaatac caccataatg gggattatgc ttcaacacaa    420
```

-continued

```
gtatttgttt cttgtttttg ttttcaacat aaatatttgg agggtaacca ttcagatcat    480

agtagtacca gtatccaaaa ctgccaccaa atagtttgtt                          520
```